US012685726B2

(12) United States Patent
Muelbaier et al.

(10) Patent No.: US 12,685,726 B2
(45) Date of Patent: Jul. 21, 2026

(54) SULFOXIMINES AS INHIBITORS OF NaV1.8

(71) Applicant: Gruenenthal GmbH, Aachen (DE)

(72) Inventors: Marcel Muelbaier, Aachen (DE); Sebastian Krueger, Aachen (DE); Clemens Dialer, Aachen (DE); Mauro Marigo, Aachen (DE); Vipulkumar Patel, Aachen (DE)

(73) Assignee: Gruenenthal GmbH (DE)

( * ) Notice: Subject to any disclaimer, the term of this patent is extended or adjusted under 35 U.S.C. 154(b) by 232 days.

(21) Appl. No.: 18/540,502

(22) Filed: Dec. 14, 2023

(65) Prior Publication Data

US 2024/0252473 A1 Aug. 1, 2024

(30) Foreign Application Priority Data

Dec. 14, 2022 (EP) .................................... 22213333
Aug. 10, 2023 (EP) .................................... 23190960

(51) Int. Cl.
*A61K 31/44* (2006.01)
*A61K 31/415* (2006.01)
*A61P 29/00* (2006.01)

(52) U.S. Cl.
CPC ............ *A61K 31/44* (2013.01); *A61K 31/415* (2013.01); *A61P 29/00* (2018.01)

(58) Field of Classification Search
CPC .. A61K 31/44; A61K 31/415; A61K 31/4439; A61P 29/00; C07D 401/12; C07D 405/14; C07D 417/12; C07D 231/14; C07D 401/14; C07D 403/12; C07D 405/12; C07D 417/14
See application file for complete search history.

(56) References Cited

U.S. PATENT DOCUMENTS

| | | | |
|---|---|---|---|
| 8,519,137 | B2 | 8/2013 | Joshi et al. |
| 8,779,197 | B2 | 7/2014 | Chen et al. |
| 8,865,771 | B2 | 10/2014 | Chen et al. |
| 2021/0198241 | A1 | 7/2021 | Durrant |
| 2021/0387966 | A1 | 12/2021 | Arasappan et al. |
| 2022/0119363 | A1 | 4/2022 | Breslin et al. |

FOREIGN PATENT DOCUMENTS

| | | | |
|---|---|---|---|
| WO | 2009/049180 | A2 | 4/2009 |
| WO | 2009/049180 | A3 | 4/2009 |
| WO | 2009/049181 | A1 | 4/2009 |
| WO | 2009/049183 | A1 | 4/2009 |
| WO | 2020/092187 | A1 | 5/2020 |
| WO | 2020/092667 | A1 | 5/2020 |
| WO | 2020/092667 | A8 | 5/2020 |
| WO | 2021/113627 | A1 | 6/2021 |

OTHER PUBLICATIONS

Breslin et at., "2-Aminopyridines as Potent and Selective Nav1.8 Inhibitors Exhibiting Efficacy in a Nonhuman Primate Pain Model", ACS Medicinal Chemistry Letters, p. 1-7, Jun. 5, 2024.

*Primary Examiner* — Kamal A Saeed
*Assistant Examiner* — Meghan C Heasley
(74) *Attorney, Agent, or Firm* — Finnegan, Henderson, Farabow, Garrett & Dunner, LLP

(57) ABSTRACT

Compounds according to general formula (I)

(I)

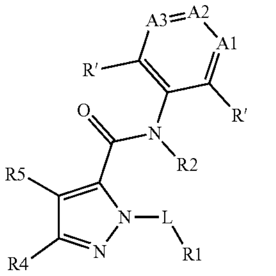

act as inhibitors of $Na_V1.8$ and can be used in the treatment of pain.

23 Claims, No Drawings

SULFOXIMINES AS INHIBITORS OF NaV1.8

The present application claims priority of European Patent Application No. 23190960.7 filed Aug. 10, 2023, and European Patent Application No. 22213333.2 filed Dec. 14, 2022, the disclosures of which patent applications are hereby incorporated herein by reference.

The invention relates to compounds according to general formula (I)

(I)

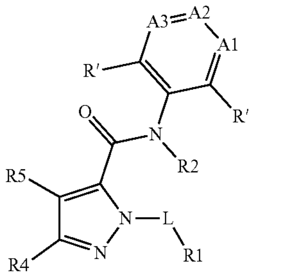

which act as inhibitors of $Na_V1.8$ and can be used in the treatment of pain.

Normal pain sensation (nociception) serves primarily as a survival mechanism, the body's way of self-protection, alerting against (further) tissue damage and disease from noxious stimuli. For instance, acute pain can arise when the external environment (temperature, pressure, chemicals) activates modality specific receptors (nociceptors) and ion channels within the skin. The peripheral terminals of pain-signaling neurons—whose cell bodies are found in the dorsal root ganglia [DRG] and trigeminal ganglia [TG]—convert the external stimuli into electrochemical generator potentials. Specific voltage-gated sodium channels (Nays) integrate and amplify these generator signals until the threshold for an action potential [AP] is reached. Thus, what starts as a noxious stimuli in the periphery eventually leads to action potential firing that travels towards the central nervous system, synapsing first onto neurons in the spinal cord and then towards the brain. Nays also function to support propagation of action potentials to the central terminals within the spinal cord. At the end of its travels along the somatosensory pathway, the action potential signal is interpreted as pain by the brain (Lumpkin and Caterina, Nature (2007), Vol. 445 pp 858-865; and Crawford and Catering Toxicologic Pathology (2020) 48(1)-174; Goodwin G and McMahon S. B. Nature Reviews Neuroscience (2021) Vol 22 pp 263-274; Bennett D. L. et al. Physiol Rev 99 (2019) Vol 99 pp 1079-1151).

Abnormal persistent neuropathic pain arises as a consequence of a lesion or disease of this somatosensory pathway. In response to nerve injury or inflammation, abnormal changes in ion channel expression can cause hyper-excitability of pain-signaling neurons and their nerves/axons, thus resulting in pathological pain.

The voltage-gated $Na_V1.8$ sodium channel is a therapeutic target for analgesia because of its restricted expression profile (almost exclusive to peripheral sensory tissues), its placement along the pain pathway (free nerve endings, sciatic nerve, and DRG), prominent physiological role in pain signaling (supports upstroke of AP and facilitates repetitive AP firing), and supporting genetic/pharmaco-phenotypic evidence (human/animal studies showing changes in $Na_V1.8$ function cause parallel changes in pain sensitivity).

Regarding its expression profile along the pain pathway, because $Na_V1.8$ was first found predominantly in peripheral sensory neurons of the dorsal root ganglia (DRG) and trigeminal ganglia (TG), it was originally termed SNS (sensory neuron specific) (Akopian A. N. et al Nature (1996) Vol 379 pp 257-261) or PN3 (peripheral nerve 3) (Sangameswaran L. et al J. Biol. Chem. (1996) Vol 271 pp 5953-5956). As well, $Na_V1.8$ is localized at free nerve endings, where pain signaling is initiated in the skin (Persson A. K. et al Mol. Pain. (2010) 6:84) and is diffusely localized along the entire length of non-myelinated axons of sciatic nerve (Rush A. M. et al. Eur. J. Neurosci (2005) Vol 22 pp 39-49).

In contrast, $Na_V1.8$ has minimal expression in nonneuronal tissue, such as heart and skeletal muscle, and in the CNS, including brain and spinal cord (9, 10, 338, 406) (Akopian A. N. op. cit.; Akopian A. N. et al. Nat. Neurosci (1999) Vol 2 pp 541-548; Novakovic S. D. et al. J. Neurosci. (1998) Vol 18, pp 2184-2187; and Sagameswaran L. op. cit.).

Regarding its physiological role, $Na_V1.8$ contributes the majority of the inward current during the rising phase of an all-or-none action potential in nociceptive sensory neurons (Blair N. T. et al. J. Neurosci. (2003) Vol 23 pp 10338-10350 and Renganathan M et al. J. Neurophysiol (2001) Vol 86 pp 629-640)—and also contributes most of the current in subsequent spikes during repetitive firing in DRG neurons (Choi J. S. J. Neurophysiol (2011) Vol 106 pp 3173-3184; and Tan Z. Y. et al. J. Neurosci. (2014) Vol 34 pp 7190-7197).

Regarding genetic and pharmacology studies, gain-of-function mutations in $Na_V1.8$ were found in patients with chronic neuropathic pain such as small fiber neuropathy (Faber C. G. et al. (2012) Ann. Neurol Vol 71 pp 26-39; Han C et al. J. Neurol Neurosurg Psychiatry (2014) Vol 85 pp 499-505; and, Kist A. M. et al. PLoS One (2016) Vol 11 e0161789); Eijkenboom I. et al J. NeurolNeurosurg Psychiatry (2019) 90 (3) pp 342-352); loss-of-function (gene knockout) studies in mice reduced pain sensitivity, notably in nociception (Laird J. M. et al. J. Neurosci (2002) J. Neurosci Vol 22 pp 8352-8356; Jarvis M. F. et al Proc Natl Acad Sci USA (2007) Vol 104 pp 8520-8525; Joshi S. K. et al Pain (2006) Vol 123 pp 75-82) and in neuropathic models (Roza C. et al J Physiol (2003) Vol 550 pp 921-926); $Na_V1.8$-selective small molecule inhibitors reduced pain in rodents, specifically in inflammatory and neuropathic models (Jarvis et al. op. cit.; Kort M. E. et al Bioorg Med Chem Lett (2010) Vol 20 pp 6812-6815; Scanio M. J. et al Bioorg Med Chem (2010) Vol 18 pp 7816-7825; Payne C. E. et al Br J Pharmacol (2015) Vol 172 pp 2654-2670).

Currently, non-selective Nay channel inhibitors are used to treat epilepsy, cardiac arrhythmia, and chronic pain (Hille, B. J. Gen. Physiol. (1977) Vol. 69 pp. 497-515; Hille. B, Ion Channels of Excitable Membranes (1992) pp. 391-421; Sunderland, Mass., Sinauer Associates, Inc. 3rd ed.; Hondeghem L. M. and Katzung B. G. Annu. Rev. Pharmacol. Toxicol. (1984) Vol. 24. Pp. 387-423; Catterall W. A. Trends Pharmacol. Sci. (1987) Vol. 8 pp. 57-65)—however, all of these analgesics have limited efficacy owing to dose-limiting adverse side-effects related to inhibiting $Na_V1.1/Na_V1.2/1.6$ (seizure liability), inhibiting $Na_V1.4$ (muscle weakness/paralysis), inhibiting $Na_V1.5$ (arrhythmia risk).

There is a need to develop a $Na_V1.8$-selective small molecule inhibitor as an effective and safe analgesic.

$Na_V1.8$ inhibitors are also known from WO 2020/092187, WO 2020/092667, WO 2009/049180, WO 2009/049183, WO 2009/049181 and WO 2021/113627.

It was an object of the invention to provide novel compounds which are inhibitors, preferably selective inhibitors, of $Na_V1.8$, and which preferably have advantages over the compounds of the prior art. The novel compounds should in particular be suitable for use in the treatment of pain.

This object has been achieved by the subject-matter of the patent claims.

It was surprisingly found that the compounds according to the invention are highly potent and selective inhibitors of the $Na_V1.8$ channel.

The invention relates to a compound according to general formula (I)

(I)

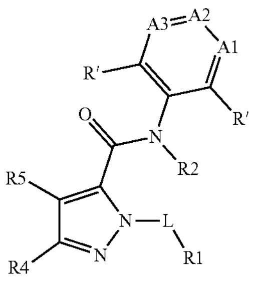

wherein one of A1, A2 and A3 represents C—R3 and the other two of A1, A2 and A3 independently from one another represent CR' or N;

R' independently represents H, F, $CH_3$, $CH_2F$, $CHF_2$, $CF_3$, or $OCH_3$;

L represents $CH_2$, $CH(CH_3)$ or $CH(CH_2CH_3)$;

R1 represents $C_{3-10}$-cycloalkyl, 4 to 11-membered bicycloalkyl, 5 to 11-membered spiroalkyl or dispiroalkyl, 4 to 10-membered heterocycloalkyl, or 5 to 11-membered heterobicycloalkyl;

R2 represents H or $C_{1-6}$-alkyl;

R3 represents S(O)(NR3a)R3b or $S(NR3a)_2R3b$;

R3a represents H, $C_{1-6}$-alkyl, $C(O)C_{1-5}$-alkyl, $C(O)C_{1-5}$-alkyl-$NH_2$, $C(O)C_{1-5}$-alkyl-NH—$CH_3$, $C(O)C_{1-5}$-alkyl-$N(CH_3)_2$, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl);

R3b represents $NH_2$, $C_{1-6}$-alkyl, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl);

or R3a and R3b mean $(CH_2)_{3-5}$ and together with the atoms to which they are attached form a ring;

R4 represents H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 11-membered bicycloalkyl, 5 to 11-membered spiroalkyl or bisspiroalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl);

R5 represents H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl);

wherein $C_{1-6}$-alkyl and $C_{1-6}$-alkylene in each case independently from one another is linear or branched;

wherein $C_{1-6}$-alkyl, $C_{1-6}$-alkylene, $C_{3-10}$-cycloalkyl, $C_{3-6}$-cycloalkyl, 4 to 11-membered bicycloalkyl, 5 to 11-membered spiroalkyl or dispiroalkyl, 4 to 10-membered heterocycloalkyl, 4 to 6-membered heterocycloalkyl, and 5 to 11-membered heterobicycloalkyl in each case independently from one another are unsubstituted or substituted with one, two, three, four or more substituents independently from one another selected from the group consisting of F, Cl, CN, $C_{1-6}$-alkyl, $C_{1-6}$-alkylene-OH, $C_{1-6}$-alkylene-$OCH_3$, $CF_3$, $CF_2H$, $CFH_2$, C(O)—$C_{1-6}$-alkyl, OH, =O, $OCF_3$, $OCF_2H$, $OCFH_2$, O—$C_{1-6}$-alkyl, $C_{1-4}$-alkylene-O—$C_{1-4}$-alkylene-O—$CH_3$, $C_{0-4}$-alkylene-O—($C_{1-4}$-alkylene-O$)_{1-4}$—$CH_3$, $NH_2$, NH—$C_{1-6}$-alkyl, $N(C_{1-6}$-alkyl$)_2$, or 4 to 6-membered heterocycloalkyl;

in the form of the free compound or a physiologically acceptable salt thereof.

In a preferred embodiment, the compound according to the invention is present in form of the free compound. For the purpose of specification, "free compound" preferably means that the compound according to the invention is not present in form of a salt. Methods to determine whether a chemical substance is present as the free compound or as a salt are known to the skilled artisan such as $^{14}N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the invention is present in form of a physiologically acceptable salt. For the purposes of this specification, the term "physiologically acceptable salt" preferably refers to a salt obtained from a compound according to the invention and a physiologically acceptable acid or base.

According to the invention, the compound according to the invention may be present in any possible form including solvates, cocrystals and polymorphs. For the purposes of this specification, the term "solvate" preferably refers to an adduct of (i) a compound according to the invention and/or a physiologically acceptable salt thereof with (ii) distinct molecular equivalents of one or more solvents.

Further, the compound according to the invention may be present in form of the racemate, enantiomers, diastereomers, tautomers or any mixtures thereof.

The compounds according to the invention may have one or more stereocenter. The person skilled in art knows by looking at a chemical structure whether the depicted compound has one or more stereocenters or not.

For some compounds according to the invention that have one or more stereocenters and which chemical structures are disclosed in the examples of the present application, the chemical structure includes bold bonds and/or hashed bonds to indicate the relative structural orientation of those substituents connected by the bold bonds and/or hashed bonds to the superior structure. If the bold bonds and/or hashed bonds are depicted in form of a wedge, the absolute stereochemical configuration of the compound is known and thereby indicated. If the bold bonds and/or hashed bonds are depicted as a straight bond (i.e. no wedge), the absolute stereochemical configuration of the compound has not been determined. In that case, the bold bonds and/or hashed bonds merely serve to indicate that this particular compound is present as one enantiomer or one diastereomer (e.g. cis-diastereomer (i.e. mixture of two cis-enantiomers) or trans-diastereomer (i.e. mixture of two trans-enantiomers)). All compounds according to the invention that have one or more stereocenters but which chemical structures disclosed in the examples of the present application do not include bold bonds and/or hashed bonds, are present as a mixture of the respective stereoisomers.

The invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2H$ (deuterium), $^3H$ (tritium), $^{13}C$ and $^{14}C$. Isotopic isomers of a compound of the invention can generally be prepared by conventional procedures known to a person skilled in the art.

According to the invention, the terms "$C_{1-6}$-alkyl" and "$C_{1-4}$-alkyl" preferably mean acyclic and preferably saturated hydrocarbon residues, which can be linear (i.e. unbranched) or branched and which can be unsubstituted or mono- or polysubstituted (e.g. di- or trisubstituted), and which contain 1 to 6 (i.e. 1, 2, 3, 4, 5 or 6) and 1 to 4 (i.e. 1, 2, 3 or 4) carbon atoms, respectively. Preferably, $C_{1-6}$-alkyl and $C_{1-4}$-alkyl are saturated. Preferred $C_{1-6}$-alkyl groups are selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl. Particularly preferred $C_{1-6}$-alkyl groups are selected from $C_{1-4}$-alkyl groups. Preferred $C_{1-4}$-alkyl groups are selected from the group consisting of methyl, ethyl, n-propyl, 2-propyl, n-butyl, isobutyl, sec-butyl and tert-butyl.

According to the invention, the terms "$C_{1-6}$-alkylene" and "$C_{1-4}$-alkylene" relate to linear or branched and preferably saturated aliphatic residues which can be unsubstituted or mono- or polysubstituted (e.g. di- or trisubstituted) and which are preferably selected from the group consisting of $CH_2$, $CH(CH_3)$, $CH_2CH_2$, $CH_2CH(CH_3)$, $CH(CH_3)CH_2$, $CH_2CH_2CH_2$, $CH(CH_3)CH_2CH_2$, $CH_2CH(CH_3)CH_2$, $CH_2CH_2CH(CH_3)$, $CH_2CH_2CH_2CH_2$, $CH(CH_3)CH_2CH_2CH_2$, $CH_2CH(CH_3)CH_2CH_2$, $CH_2CH_2CH(CH_3)CH_2$, $CH_2CH_2CH_2CH(CH_3)$, $CH_2CH_2CH_2CH_2CH_2$, $CH(CH_3)CH_2CH_2CH_2CH_2$, $CH_2CH(CH_3)CH_2CH_2CH_2$, $CH_2CH_2CH(CH_3)CH_2CH_2$, $CH_2CH_2CH_2CH(CH_3)CH_2$, $CH_2CH_2CH_2CH_2CH(CH_3)$, and $CH_2CH_2CH_2CH_2CH_2CH_2$; more preferably $CH_2$, $CH(CH_3)$, $CH_2CH_2$, $CH_2CH(CH_3)$ and $CH(CH_3)CH_2$, most preferably $CH_2$ and $CH(CH_3)$, and in particular $CH_2$. Preferably, $C_{1-6}$-alkylene is selected from $C_{1-4}$-alkylene.

According to the invention, the terms "$C_{3-10}$-cycloalkyl" and "$C_{3-6}$-cycloalkyl" preferably mean monocyclic aliphatic hydrocarbons containing 3, 4, 5, 6, 7, 8, 9 or 10 carbon atoms as ring members and 3, 4, 5 or 6 carbon atoms as ring members, respectively, wherein the hydrocarbons in each case can be saturated or unsaturated (but not aromatic), unsubstituted or mono- or polysubstituted.

Preferably, $C_{3-10}$-cycloalkyl and $C_{3-6}$-cycloalkyl are saturated. The $C_{3-10}$-cycloalkyl and $C_{3-6}$-cycloalkyl can be bound to the respective superordinate general structure via any desired and possible ring member of the cycloalkyl group. The $C_{3-10}$-cycloalkyl and $C_{3-6}$-cycloalkyl are not condensed with further ring systems and are not bridged.

Preferred $C_{3-10}$-cycloalkyl groups are selected from the group consisting of cyclopropyl, cyclobutyl, cyclopentyl, cyclohexyl, cycloheptyl, cyclooctyl, cyclononyl, and cyclodecyl. Preferred $C_{3-10}$-cycloalkyl groups are selected from $C_{3-6}$-cycloalkyl groups.

According to the invention, the term "4 to 11-membered bicycloalkyl" preferably means bicyclic aliphatic hydrocarbons containing 4, 5, 6, 7, 8, 9, 10 or 11 carbon atoms as ring members, wherein the hydrocarbons in each case can be saturated or unsaturated (but not aromatic), unsubstituted or mono- or polysubstituted. The bicyclic system may share a common bond (annealed rings) or may be bridged.

Preferably, 4 to 11-membered bicycloalkyl is saturated. The 4 to 11-membered bicycloalkyl can be bound to the respective superordinate general structure via any desired and possible ring member of the 4 to 11-membered bicycloalkyl group.

Preferred 4 to 11-membered bicycloalkyl groups are selected from the group consisting of bicyclo[1.1.0]butyl, bicylo[1.1.1]pentyl, bicyclo[2.1.0]pentyl, bicyclo[3.1.0]hexyl, bicyclo[2.2.0]hexyl, bicyclo[2.1.1]hexyl, bicyclo[4.1.0]heptyl, bicyclo[2.2.1]heptyl, and bicyclo[3.3.0]octyl.

According to the invention, the term "5 to 11-membered spiroalkyl or dispiroalkyl" means spirocyclic or dispirocyclic aliphatic hydrocarbons containing 5, 6, 7, 8, 9, 10 or 11 carbon atoms as ring members, wherein the hydrocarbons in each case can be saturated or unsaturated (but not aromatic), unsubstituted or mono- or polysubstituted. The spirocyclic system shares a common carbon atom connecting the rings. In case of a dispirocyclic system, there are three rings, whereas two of these three rings share a common carbon atom connecting these rings.

Preferably, 5 to 11-membered spiroalkyl or dispiroalkyl is saturated. The 5 to 11-membered spiroalkyl or dispiroalkyl can be bound to the respective superordinate general structure via any desired and possible ring member of the 5 to 11-membered spiroalkyl or dispiroalkyl group.

Preferred 5 to 11-membered spiroalkyl or dispiroalkyl groups are selected from the group consisting of spiro[2.2]pentyl, spiro[2.3]hexyl, spiro[3.3]heptyl, and dispiro[2.0.2.1]heptyl.

According to the invention, the terms "4 to 10-membered heterocycloalkyl" and "4 to 6-membered heterocycloalkyl" preferably mean monocyclic, heterocycloaliphatic saturated or unsaturated (but not aromatic) residues having 4 to 10, i.e. 4, 5, 6, 7, 8, 9 or 10 ring members and 4 to 6, i.e. 4, 5 or 6 ring members, respectively, wherein in each case at least one, if appropriate also two or three carbon atoms are replaced by a heteroatom or a heteroatom group each selected independently of one another from the group consisting of 0, S. S(═O), $S(═O)_2$, N, NH and N($C_{1-4}$-alkyl) such as $N(CH_3)$, wherein the carbon atoms of the ring can be unsubstituted or mono- or polysubstituted. Preferably, the 4 to 10-membered heterocycloalkyl and the 4 to 6-membered heterocycloalkyl contain only one heteroatom or heteroatom group within the ring.

Preferably, 4 to 10-membered heterocycloalkyl and 4 to 6-membered heterocycloalkyl are saturated. The 4 to 10-membered heterocycloalkyl and 4 to 6-membered heterocycloalkyl are not condensed with further ring systems and are not bridged.

The 4 to 10-membered heterocycloalkyl and the 4 to 6-membered heterocycloalkyl group can be bound to the superordinate general structure via any desired and possible ring member of the heterocycloaliphatic residue if not indicated otherwise. In a preferred embodiment, 4 to 10-membered heterocycloalkyl and 4 to 6-membered heterocycloalkyl are bound to the superordinate general structure via a carbon atom.

Preferred 4 to 10-membered heterocycloalkyl groups are selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, azepanyl, dioxepanyl, oxazepanyl, diazepanyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, piperazinyl, N-methylpyridinonyl, pyrazolidinyl, pyranyl; dihydroquinolinyl, dihydroisoquinolinyl, dihydroindolinyl, dihydroisoindolyl, tetrahydroquinolinyl, tetrahydroisoquinolinyl and tetrahydroindolinyl; more preferably oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl.

Preferred 4 to 6-membered heterocycloalkyl groups are selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, N-methylpyridinonyl, pyrazolidinyl, and pyranyl; more preferably oxetanyl, tetrahydrofuranyl, tetrahydropyranyl, morpholinyl, thiomorpholinyl, tetrahydrothiopyranyl, tetrahydrothiopyranyl 1,1-dioxide, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl.

According to the invention, the term "5 to 11-membered heterobicycloalkyl" preferably means bicyclic heteroaliphatic saturated or unsaturated (but not aromatic) hydrocarbons containing 5, 6, 7, 8, 9, 10 or 11 ring members, wherein in each case at least one, if appropriate also two or three carbon atoms are replaced by a heteroatom or a heteroatom group each selected independently of one another from the group consisting of O, S, S(═O), S(═O)$_2$, N, NH and N($C_{1-4}$-alkyl) such as N($CH_3$), wherein the carbon atoms of the ring can be unsubstituted or mono- or polysubstituted. The bicyclic system may share a common bond (annealed rings) or may be bridged.

Preferably, 5 to 11-membered heterobicycloalkyl is saturated. The 5 to 11-membered heterobicycloalkyl can be bound to the respective superordinate general structure via any desired and possible ring member of the 5 to 11-membered heterobicycloalkyl group.

A preferred 5 to 11-membered heterobicycloalkyl group is 2-oxa-bicyclo[2.1.1]hexyl.

In connection with the terms "$C_{1-6}$-alkyl", "$C_{1-4}$-alkyl", "$C_{1-6}$-alkylene", "$C_{1-4}$-alkylene", "$C_{3-10}$-cycloalkyl", "$C_{3-6}$-cycloalkyl", "4 to 11-membered bicycloalkyl", "5 to 11-membered spiroalkyl or dispiroalkyl", "4 to 10-membered heterocycloalkyl", "4 to 6-membered heterocycloalkyl", and "5 to 11-membered heterobicycloalkyl", the term "substituted" refers in the sense of the invention, with respect to the corresponding residues or groups, to the single substitution (monosubstitution) or multiple substitution (poly substitution), e.g. disubstitution, trisubstitution or tetrasubstitution; more preferably to mono substitution, disubstitution or trisubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of 1-chloro-3-fluorocyclohexyl. The multiple substitution can be carried out using the same or using different substituents.

If a residue occurs multiply within a molecule, then this residue can have respectively different meanings for various substituents: if, for example, both R4 and R5 denote $C_{1-6}$-alkyl, then $C_{1-6}$-alkyl can e.g. represent methyl for R4 and can represent 2-propyl for R5.

According to the invention, $C_{1-6}$-alkyl, $C_{1-4}$-alkyl, $C_{1-6}$-alkylene, $C_{1-4}$-alkylene, $C_{3-10}$-cycloalkyl, $C_{3-6}$-cycloalkyl, 4 to 11-membered bicycloalkyl, 5 to 11-membered spiroalkyl or dispiroalkyl, 4 to 10-membered heterocycloalkyl, 4 to 6-membered heterocycloalkyl, and 5 to 11-membered heterobicycloalkyl in each case independently from one another are unsubstituted or mono- or polysubstituted, more preferably unsubstituted or substituted with one, two, three, four or more substituents independently from one another selected from the group consisting of F, Cl, CN, $C_{1-6}$-alkyl, $C_{1-6}$-alkylene-OH, $C_{1-6}$-alkylene-$OCH_3$, $CF_3$, $CF_2H$, $CFH_2$, C(O)—$C_{1-6}$-alkyl, OH, ═O, $OCF_3$, $OCF_2H$, $OCFH_2$, O—$C_{1-6}$-alkyl, $C_{1-4}$-alkylene-O—$C_{1-4}$-alkylene-O—$CH_3$, $C_{0-4}$-alkylene-O—($C_{1-4}$-alkylene-O)$_{1-4}$—$CH_3$, $NH_2$, NH—$C_{1-6}$-alkyl, N($C_{1-6}$-alkyl)$_2$, or 4 to 6-membered heterocycloalkyl; preferably F, $CH_3$, $CF_3$, $CF_2H$, $CFH_2$, $OCH_3$, CN, ═O, OH, $NH_2$, N($CH_3$)$_2$, and oxetanyl; more preferably F, $CH_3$, $CF_3$, $CF_2H$, and $CFH_2$, and most preferably $CF_3$.

Preferably, $C_{1-6}$-alkylene groups are unsubstituted.

According to the invention, one of A1, A2 and A3 represents C—R3 and the other two of A1, A2 and A3 independently from one another represent CH or N.

In preferred embodiments, (i) A1 represents C—R3; A2 represents N; and A3 represents CR', preferably CH;

(ii) A1 represents C—R3; A2 represents CR', preferably CH; and A3 represents CR', preferably CH; or (iii) A1 represents C—R3; A2 represents N; and A3 represents N; or (iv) A1 represents C—R3; A2 represents CR', preferably CH; and A3 represents N; or (v) A1 represents CR', preferably CH; A2 represents C—R3; and A3 represent CR', preferably CH; or (vi) A1 represents N, A2 represents C—R3, and A3 represent CR', preferably CH, or (vii) A1 represents N, A2 represents C—R3, and A3 represent N.

According to the invention, R' independently represents H, F, $CH_3$, $CH_2F$, $CHF_2$, $CF_3$, or $OCH_3$.

In preferred embodiments, R' represents H.

According to the invention, L represents $CH_2$, CH($CH_3$) or CH($CH_2CH_3$).

In preferred embodiments, L represents $CH_2$.

According to the invention, R1 represents $C_{3-10}$-cycloalkyl, 4 to 11-membered bicycloalkyl, 5 to 11-membered spiroalkyl or dispiroalkyl, 4 to 10-membered heterocycloalkyl, or 5 to 11-membered heterobicycloalkyl.

In preferred embodiments, R1 represents $C_{3-10}$-cycloalkyl, unsubstituted or substituted with one, two, three, four, or more substituents independently from one another selected from F, $CH_3$, $OCH_3$, CN, $CHF_2$ and $CF_3$.

Preferably, R1 is selected from cyclopropyl, methyl cyclopropyl, dimethyl cyclopropyl, fluoro cyclopropyl, difluoro cyclopropyl, trifluoromethyl cyclopropyl, trifluoromethyl methyl cyclopropyl, methyl difluoro cyclopropyl, trifluoromethyl difluoro cyclopropyl, dimethyl difluoro cyclopropyl, cyclobutyl, methyl cyclobutyl, dimethyl cyclobutyl, fluoro cyclobutyl, difluoro cyclobutyl, trifluoromethyl cyclobutyl, trifluoromethyl methyl cyclobutyl, methyl difluoro cyclobutyl, trifluoromethyl difluoro cyclobutyl, dimethyl difluoro cyclobutyl, cyclopentyl, methyl cyclopentyl, dimethyl cyclopentyl, fluoro cyclopentyl, difluoro cyclopentyl, trifluoromethyl cyclopentyl, trifluoromethyl methyl cyclopentyl, methyl difluoro cyclopentyl, trifluoromethyl difluoro cyclopentyl, dimethyl difluoro cyclopentyl, cyclohexyl, methyl cyclohexyl, dimethyl cyclohexyl, fluoro cyclohexyl, difluoro cyclohexyl, trifluoromethyl cyclohexyl, trifluoromethyl methyl cyclohexyl, methyl difluoro cyclohexyl, trifluoromethyl difluoro cyclohexyl, dimethyl difluoro cyclohexyl, cycloheptyl, methyl cycloheptyl, dimethyl cycloheptyl, fluoro cycloheptyl, difluoro cycloheptyl, trifluoromethyl cycloheptyl, trifluoromethyl methyl cycloheptyl, methyl difluoro cycloheptyl, trifluoromethyl difluoro cycloheptyl, dimethyl difluoro cycloheptyl, cyclooctyl, methyl cyclooctyl, dimethyl cyclooctyl, fluoro cyclooctyl, difluoro cyclooctyl, trifluoromethyl cyclooctyl, trifluoromethyl methyl cyclooctyl, methyl difluoro cyclooctyl, trifluoromethyl difluoro cyclooctyl, dimethyl difluoro cyclooctyl, cyclononyl, methyl cyclononyl, dimethyl cyclononyl, fluoro cyclononyl, difluoro cyclononyl, trifluoromethyl cyclononyl, trifluoromethyl methyl cyclononyl, methyl difluoro cyclononyl, trifluoromethyl difluoro cyclononyl, dimethyl difluoro cyclononyl, cyclodecyl, methyl cyclodecyl, dimethyl cyclodecyl, fluoro cyclodecyl, difluoro cyclodecyl, trifluoromethyl cyclodecyl, trifluoromethyl methyl cyclodecyl, methyl difluoro cyclodecyl, trifluoromethyl difluoro cyclodecyl, and dimethyl difluoro cyclodecyl.

More preferably, R1 is selected from cyclopropyl, dimethyl cyclopropyl, trifluoromethyl methyl cyclopropyl, cyclobutyl, trifluoromethyl cyclobutyl, methyl trifluoromethyl cyclobutyl, difluoro cyclobutyl, methyl difluoro cyclobutyl, cyclopentyl, difluoro cyclopentyl, methyl difluoro cyclopentyl, trifluoromethyl cyclopentyl, trifluoromethyl difluoro cyclopentyl, cyclohexyl, difluoro cyclohexyl, and methyl difluoro cyclohexyl.

In preferred embodiments, R1 represents $C_{3-10}$-cycloalkyl, substituted with $CH_3$ and optionally substituted with one, two, three, four, or more substituents independently from one another selected from F, $OCH_3$, CN, $CHF_2$ and $CF_3$, wherein the carbon atom of $C_{3-10}$-cycloalkyl, which is substituted with $CH_3$, is linked to L. Preferred representatives include but are not limited to methyl difluoro cyclobutyl and methyl difluoro cyclopentyl.

In further preferred embodiments, R1 represents 4 to 11-membered bicycloalkyl, unsubstituted or substituted with one, two, three, four, or more substituents independently from one another selected from F, $CH_3$, $OCH_3$, CN, $CHF_2$ and $CF_3$.

Preferably, R1 is selected from bicylo[1.1.1]pentyl, methyl bicylo[1.1.1]pentyl, methoxy bicylo[1.1.1]pentyl, difluoromethyl bicylo[1.1.1]pentyl, trifluoromethyl bicylo[1.1.1]pentyl, fluoro bicylo[1.1.1]pentyl, difluoro bicylo[1.1.1]pentyl, methyl difluoro bicylo[1.1.1]pentyl, trifluoromethyl difluoro bicylo[1.1.1]pentyl, bicyclo[2.1.0]pentyl, methyl bicyclo[2.1.0]pentyl, trifluoromethyl bicyclo[2.1.0]pentyl, fluoro bicyclo[2.1.0]pentyl, difluoro bicyclo[2.1.0]pentyl, methyl difluoro bicyclo[2.1.0]pentyl, trifluoromethyl difluoro bicyclo[2.1.0]pentyl, bicyclo[3.1.0]hexyl, methyl bicyclo[3.1.0]hexyl, trifluoromethyl bicyclo[3.1.0]hexyl, fluoro bicyclo[3.1.0]hexyl, difluoro bicyclo[3.1.0]hexyl, methyl difluoro bicyclo[3.1.0]hexyl, trifluoromethyl difluoro bicyclo[3.1.0]hexyl, bicyclo[2.2.0]hexyl, methyl bicyclo[2.2.0]hexyl, trifluoromethyl bicyclo[2.2.0]hexyl, fluoro bicyclo[2.2.0]hexyl, difluoro bicyclo[2.2.0]hexyl, methyl difluoro bicyclo[2.2.0]hexyl, trifluoromethyl difluoro bicyclo[2.2.0]hexyl, bicyclo[2.1.1]hexyl, methyl bicyclo[2.1.1]hexyl, trifluoromethyl bicyclo[2.1.1]hexyl, fluoro bicyclo[2.1.1]hexyl, difluoro bicyclo[2.1.1]hexyl, fluoro bicyclo[2.1.1]hexyl, difluoro bicyclo[2.1.1]hexyl, methyl difluoro bicyclo[2.1.1]hexyl, trifluoromethyl difluoro bicyclo[2.1.1]hexyl, bicyclo[4.1.0]heptyl, methyl bicyclo[4.1.0]heptyl, trifluoromethyl bicyclo[4.1.0]heptyl, fluoro bicyclo[4.1.0]heptyl, difluoro bicyclo[4.1.0]heptyl, methyl difluoro bicyclo[4.1.0]heptyl, trifluoromethyl difluoro bicyclo[4.1.0]heptyl, bicyclo[2.2.1]heptyl, methyl bicyclo[2.2.1]heptyl, trifluoromethyl bicyclo[2.2.1]heptyl, fluoro bicyclo[2.2.1]heptyl, difluoro bicyclo[2.2.1]heptyl, methyl difluoro bicyclo[2.2.1]heptyl, trifluoromethyl difluoro bicyclo[2.2.1]heptyl, bicyclo[3.3.0]octyl, methyl bicyclo[3.3.0]octyl, trifluoromethyl bicyclo[3.3.0]octyl, fluoro bicyclo[3.3.0]octyl, difluoro bicyclo[3.3.0]octyl, methyl difluoro bicyclo[3.3.0]octyl, and trifluoromethyl difluoro bicyclo[3.3.0]octyl.

More preferably, R1 is selected from bicylo[1.1.1]pentyl, trifluoromethyl-bicylo[1.1.1]pentyl, bicyclo[2.1.0]pentyl, difluoro bicyclo[2.1.0]pentyl, bicyclo[3.1.0]hexyl, difluoro bicyclo[3.1.0]hexyl, methyl difluoro bicyclo[3.1.0]hexyl, trifluoromethyl difluoro bicyclo[3.1.0]hexyl, bicyclo[2.2.0]hexyl, methyl bicyclo[2.2.0]hexyl, bicyclo[2.1.1]hexyl, fluoro bicyclo[2.1.1]hexyl, difluoro bicyclo[2.1.1]hexyl, bicyclo[4.1.0]heptyl, difluoro bicyclo[4.1.0]heptyl, bicyclo[2.2.1]heptyl, fluoro bicyclo[2.2.1]heptyl, bicyclo[3.3.0]octyl, and fluoro bicyclo[3.3.0]octyl.

In other preferred embodiments, R1 represents 5 to 11-membered spiroalkyl or dispiroalkyl, unsubstituted or substituted with one, two, three, four, or more substituents independently from one another selected from F, $CH_3$, $OCH_3$, CN, $CHF_2$ and $CF_3$.

Preferably, R1 is selected from spiro[2.2]pentyl, methyl spiro[2.2]pentyl, fluoro spiro[2.2]pentyl, difluoro spiro[2.2]pentyl, methyl difluoro spiro[2.2]pentyl, spiro[2.3]hexyl, methyl spiro[2.3]hexyl, fluoro spiro[2.3]hexyl, difluoro spiro[2.3]hexyl, methyl difluoro spiro[2.3]hexyl, spiro[3.3]heptyl, methyl spiro[3.3]heptyl, fluoro spiro[3.3]heptyl, difluoro spiro[3.3]heptyl, methyl difluoro spiro[3.3]heptyl, and dispiro[2.0.2.1]heptyl.

More preferably, R1 is selected from spiro[2.2]pentyl, difluoro spiro[2.2]pentyl, spiro[2.3]hexyl, methyl spiro[2.3]hexyl, fluoro spiro[2.3]hexyl, methyl difluoro spiro[2.3]hexyl, spiro[3.3]heptyl, and dispiro[2.0.2.1]heptyl.

In still further preferred embodiments, R1 represents 4 to 10-membered heterocycloalkyl, unsubstituted or substituted with one, two, three, four, or more substituents independently from one another selected from F, $CH_3$, $OCH_3$, CN, $CHF_2$ and $CF_3$.

Preferably, R1 is selected from oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, azepanyl, dioxepanyl, oxazepanyl, diazepanyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, piperazinyl, N-methylpyridinonyl, pyrazolidinyl, pyranyl; dihydroquinolinyl, dihydroisoquinolinyl, dihydroindolinyl, dihydroisoindolyl, tetrahydroquinolinyl, tetrahydroisoquinolinyl and tetrahydroindolinyl.

In yet further preferred embodiments, R1 represents 5 to 11-membered heterobicycloalkyl, unsubstituted or substituted with one, two, three, four, or more substituents independently from one another selected from F, $CH_3$, $OCH_3$, CN, $CHF_2$ and $CF_3$.

Preferably, R1 represents 2-oxa-bicyclo[2.1.1]hexyl or methyl 2-oxa-bicyclo[2.1.1]hexyl.

According to the invention, R2 represents H or $C_{1-6}$-alkyl.

Preferably, R2 represents H.

According to the invention, R3 represents S(O)(NR3a)R3b or $S(NR3a)_2R3b$, preferably S(O)(NR3a)R3b. S(O)(NR3a)R3b defines sulfoximines or sulfonimidamides, whereas $S(NR3a)_2R3b$ defines thiodiimines.

According to the invention, R3a represents H, $C_{1-6}$-alkyl, $C(O)C_{1-5}$-alkyl, $C(O)C_{1-5}$-alkyl-$NH_2$, $C(O)C_{1-5}$-alkyl-NH—$CH_3$, $C(O)C_{1-5}$-alkyl-$N(CH_3)_2$, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl).

In preferred embodiments, R3a represents H, $C_{1-6}$-alkyl, $C(O)C_{1-5}$-alkyl, $C(O)C_{1-5}$-alkyl-$NH_2$, $C(O)C_{1-5}$-alkyl-NH—$CH_3$, $C(O)C_{1-5}$-alkyl-$N(CH_3)_2$. Preferably, R3a represents H, $CH_3$, $C(O)CH_3$ or $C(O)CH_2NHCH_3$.

According to the invention, R3b represents $NH_2$, $C_{1-6}$-alkyl, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl); In preferred embodiments, R3b represents $NH_2$, $C_{1-6}$-alkyl or $C_{3-10}$-cycloalkyl. Preferably, R3b represents $NH_2$, $CH_3$, $CH_2CH_3$, or cyclopropyl.

According to the invention, R3a and R3b may alternatively mean $(CH_2)_{3-5}$ and together with the atoms to which they are attached form a ring.

Preferably, R3a and R3b mean $(CH_2)_3$ and together with the atoms to which they are attached form a ring.

When R3 represents $S(NR3a)_2R3b$, R3a preferably represents H (i.e. $S(NH)_2R3b$), and R3b preferably represents $C_{1-6}$-alkyl (i.e. $S(NH)_2C_{1-6}$-alkyl).

According to the invention, R4 represents H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 11-membered bicycloalkyl, 5 to 11-membered spiroalkyl or bisspiroalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl).

In preferred embodiments, R4 represents $C_{1-6}$-alkyl.

Preferably, R4 is selected from $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$.

More preferably, R4 represents $CF_2CH_3$.

In other preferred embodiments, R4 represents $C_{3-10}$-cycloalkyl, unsubstituted or substituted with one, two, three, four, or more substituents independently from one another selected from F, $CH_3$, $OCH_3$, CN, $CHF_2$ and $CF_3$.

Preferably, R4 is selected from cyclopropyl, methyl cyclopropyl, difluoromethyl cyclopropyl, trifluoromethyl cyclopropyl, cyano cyclopropyl, methoxy cyclopropyl, fluoro cyclopropyl, difluoro cyclopropyl, trifluoro cyclopropyl, cyclobutyl, methyl cyclobutyl, difluoromethyl cyclobutyl, trifluoromethyl cyclobutyl, cyano cyclobutyl, methoxy cyclobutyl, fluoro cyclobutyl, difluoro cyclobutyl, trifluoro cyclobutyl, cyclopentyl, methyl cyclopentyl, difluoromethyl cyclopentyl, trifluoromethyl cyclopentyl, cyano cyclopentyl, methoxy cyclopentyl, fluoro cyclopentyl, difluoro cyclopentyl, trifluoro cyclopentyl, cyclohexyl, methyl cyclohexyl, difluoromethyl cyclohexyl, trifluoromethyl cyclohexyl, cyano cyclohexyl, methoxy cyclohexyl, fluoro cyclohexyl, difluoro cyclohexyl, and trifluoro cyclohexyl.

More preferably, R4 is selected from cyclopropyl, methyl cyclopropyl, difluoromethyl cyclopropyl, trifluoromethyl cyclopropyl, cyano cyclopropyl, methoxy cyclopropyl, fluoro cyclopropyl, difluoro cyclopropyl, trifluoro cyclopropyl, cyclobutyl, difluoro cyclobutyl, cyclopentyl, and difluoro cyclopentyl.

In still further preferred embodiments, R4 represents 4 to 11-membered bicycloalkyl, unsubstituted or substituted with one, two, three, four, or more substituents independently from one another selected from F, $CH_3$, $OCH_3$, CN, $CHF_2$ and $CF_3$.

Preferably, R4 represents bicyclo[1.1.1]pentyl.

In yet further preferred embodiments, R4 represents 5 to 11-membered spiroalkyl, unsubstituted or substituted with one, two, three, four, or more substituents independently from one another selected from F, $CH_3$, $OCH_3$, CN, $CHF_2$ and $CF_3$.

Preferably, R4 represents spiro[2.2]pentyl or spiro[2.3]hexyl.

In other preferred embodiments, R4 represents O—$C_{1-6}$-alkyl, unsubstituted or substituted with one, two, three, four, or more F. Preferably, R4 is selected from O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, or O—$CH(CH_3)_2$.

More preferably, R4 represents O—$CHF_2$.

According to the invention, R5 represents H, F, Cl, Br, CN, $CHF_2$, $CH_2F$, $CF_3$, $C_{1-6}$-alkyl, $C_{3-10}$-cycloalkyl, $C_{1-6}$alkylene-$C_{3-10}$-cycloalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl).

In preferred embodiments, R5 represents $C_{1-6}$-alkyl or Cl.

Preferably, R5 represents $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, or Cl.

More preferably, R5 represents $CF_3$, $CHF_2$, $CH_3$, or Cl.

In a particularly preferred embodiment, the compound according to the invention is selected from the group consisting of 1 3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 3 1-((3,3-difluorocyclobutyl)methyl)-3-(1,1-difluoroethyl)-N-(2-(S-methylsulfonimidoyl)pyridin-4-yl)-4-(trifluoromethyl)-1H-pyrazole-5-carboxamide 4 1-((3,3-difluorocyclopentyl)methyl)-3-(1,1-difluoroethyl)-4-methyl-N-(2-(S-methylsulfonimidoyl)pyridin-4-yl)-1H-pyrazole-5-carboxamide 5 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide 7 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide 9 1-((4,4-difluorocyclohexyl)methyl)-3-(1,1-difluoroethyl)-4-methyl-N-(2-(S-methylsulfonimidoyl)pyridin-4-yl)-1H-pyrazole-5-carboxamide 11 1-((4,4-difluoro-1-methylcyclohexyl)methyl)-3-(1,1-difluoroethyl)-4-methyl-N-(2-(S-methylsulfonimidoyl)pyridin-4-yl)-1H-pyrazole-5-carboxamide 13 3-(1,1-difluoroethyl)-4-methyl-N-(2-(S-methylsulfonimidoyl)pyridin-4-yl)-1-((2-(trifluoromethyl)cyclobutyl)methyl)-1H-pyrazole-5-carboxamide 15 3-(1,1-difluoroethyl)-4-methyl-N-(2-(S-methylsulfonimidoyl)pyridin-4-yl)-1-((3-(trifluoromethyl)bicyclo[1.1.1]pentan-1-yl)methyl)-1H-pyrazole-5-carboxamide 17 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide 21 3-cyclopropyl-1-((2-fluorospiro[3.3]heptan-2-yl)methyl)-N-(2-(S-methylsulfonimidoyl)pyridin-4-yl)-4-(trifluoromethyl)-1H-pyrazole-5-carboxamide 23 3-cyclopropyl-N-(2-(S-methylsulfonimidoyl)pyridin-4-yl)-4-(trifluoromethyl)-1-((3-(trifluoromethyl)bicyclo[1.1.1]pentan-1-yl)methyl)-1H-pyrazole-5-carboxamide 3-cyclopropyl-1-((3-fluorobicyclo[1.1.1]pentan-1-yl)methyl)-N-(2-(S-methylsulfonimidoyl)pyridin-4-yl)-4-(trifluoromethyl)-1H-pyrazole-5-carboxamide 27 3-cyclopropyl-1-((6,6-difluorospiro[3.3]heptan-2-yl)methyl)-N-(2-(S-methylsulfonimidoyl)pyridin-4-yl)-4-(trifluoromethyl)-1H-pyrazole-5-carboxamide 29 3-cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide 31 3-(1,1-difluoroethyl)-4-methyl-N-(2-(S-methylsulfonimidoyl)pyridin-4-yl)-1-((3-(trifluoromethyl)cyclobutyl)methyl)-1H-pyrazole-5-carboxamide 33 1-((3,3-difluorocyclopentyl)methyl)-3-(difluoromethoxy)-N-(2-(S-methylsulfonimidoyl)pyridin-4-yl)-4-(trifluoromethyl)-1H-pyrazole-5-carboxamide 34 1-((3,3-difluoro-1-methylcyclobutyl)methyl)-3-(1,1-difluoroethyl)-N-(2-(N, S-dimethylsulfonimidoyl)pyridin-4-yl)-4-methy 1-1H-pyrazole-5-carboxamide 36 3-cyclopropyl-1-((3,3-difluorocyclopentyl)methyl)-N-(2-(N,S-dimethylsulfonimidoyl)pyridin-4-yl)-4-(trifluoromethyl)-1H-pyrazole-5-carboxamide 44 1-((4,4-difluoro-1,2-dimethylcyclopentyl)methyl)-3-(1,1-difluoroethyl)-4-methyl-N-(2-(S-methylsulfonimidoyl)pyridin-4-yl)-1H-pyrazole-5-carboxamide 45 3-cyclopropyl-1-((3,3-difluoro-1-methylcyclobutyl)methyl)-N-(3-(S-methylsulfonimidoyl)phenyl)-4-(trifluoromethyl)-1H-pyrazole-5-carboxamide 46 3-cyclopropyl-1-((3,3-difluoro-1-methylcyclobutyl)methyl)-N-(5-(S-methylsulfonimidoyl)pyridin-3-yl)-4-(trifluoromethyl)-1H-pyrazole-5-carboxamide 47 3-cyclopropyl-1-((3,3-difluoro-1-methylcyclobutyl)methyl)-N-(6-(S-methylsulfonimidoyl)pyridazin-4-yl)-4-(trifluoromethyl)-1H-pyrazole-5-carboxamide 48 3-cyclopropyl-1-((3,3-difluoro-1-methylcyclobutyl)methyl)-N-(2-(ethylsulfonimidoyl)pyridin-4-yl)-4-(trifluoromethyl)-1H-pyrazole-5-carboxamide 49 N-(2-(cyclopropanesulfonimidoyl)pyridin-4-yl)-3-cyclopropyl-1-((3,3-difluoro-1-methylcyclobutyl)methyl)-4-(trifluoromethyl)-1H-pyrazole-5-carboxamide 50 3-cyclopropyl-1-((3,3-difluoro-1-methylcyclobutyl)methyl)-N-(2-methyl-6-(S-methylsulfonimidoyl)pyridin-4-yl)-4-(trifluoromethyl)-1H-pyrazole-5-carboxamide 51 3-cyclopropyl-1-((3,3-difluoro-1-methylcyclobutyl)methyl)-N-(2-(1-oxido-4,5-dihydro-3H-1λ$^{6}$-isothiazol-1-yl)pyridin-4-yl)-4-(trifluoromethyl)-1H-pyrazole-5-carboxamide 52 3-cyclopropyl-1-((3,3-difluoro-1-methylcyclobutyl)methyl)-N-(3-sulfamidimidoylphenyl)-4-(trifluoromethyl)-1H-pyrazole-5-carboxamide 53 3-cyclopropyl-1-((3,3-difluoro-1-methylcyclobutyl)methyl)-N-(3-(methyl(phenyl)-26-sulfanediimine))-4-(trifluoromethyl)-1H-pyrazole-5-carboxamide 54 N-(3-(N-acetyl-S-methylsulfonimidoyl)phenyl)-3-cyclopropyl-1-((3,3-difluoro-1-methylcyclobutyl)methyl)-4-(trifluoromethyl)-1H-pyrazole-5-carboxamide 55 3-cyclopropyl-1-((3,3-difluoro-1-methylcyclobutyl)methyl)-N-(3-(S-methyl-N-(methylglycyl)sulfonimidoyl)phenyl)-4-(trifluoromethyl)-1H-pyrazole-5-carboxamide 56 3-cyclobutyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 57 1-((3,3-difluoro-1-methylcyclobutyl)methyl)-3-(3,3-difluorocyclobutyl)-N-(2-(S-methylsulfonimidoyl)pyridin-4-yl)-4-(trifluoromethyl)-1H-pyrazole-5-carboxamide 58 3-(bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 59 3-cyclopentyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 60 1-((3,3-difluoro-1-methylcyclobutyl)methyl)-3-(3,3-difluorocyclopentyl)-N-(2-(S-methylsulfonimidoyl)pyridin-4-yl)-4-(trifluoromethyl)-1H-pyrazole-5-carboxamide 61 1-((3,3-difluoro-1-methylcyclobutyl)methyl)-N-(2-(S-methylsulfonimidoyl)pyridin-4-yl)-3-(spiro[2.3]hexan-5-yl)-4-(trifluoromethyl)-1H-pyrazole-5-carboxamide 62 1-((3,3-difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide 63 1-((3,3-difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide 64 1-((3,3-difluoro-1-methylcyclobutyl)methyl)-N-(2-(S-methylsulfonimidoyl)pyridin-4-yl)-3-(spiro[2.2]pentan-1-yl)-4-(trifluoromethyl)-1H-pyrazole-5-carboxamide 65 1-((3,3-difluoro-1-methylcyclobutyl)methyl)-3-(2-methylcyclopropyl)-N-(2-(S-methylsulfonimidoyl)pyridin-4-yl)-4-(trifluoromethyl)-1H-pyrazole-5-carboxamide 66 1-((3,3-difluoro-1-methylcyclobutyl)methyl)-3-(2-(difluoromethyl)cyclopropyl)-N-(2-(S-methylsulfonimidoyl)pyridin-4-yl)-4-(trifluoromethyl)-1H-pyrazole-5-carboxamide 67 1-((3,3-difluoro-1-methylcyclobutyl)methyl)-N-(2-(S-methylsulfonimidoyl)pyridin-4-yl)-4-(trifluoromethyl)-3-(2-(trifluoromethyl)cyclopropyl)-1H-pyrazole-5-carboxamide 68 3-(1-cyanocyclopropyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 69 1-((3,3-difluoro-1-methylcyclobutyl)methyl)-3-(1-methylcyclopropyl)-N-(2-(S-methylsulfonimidoyl)pyridin-4-yl)-4-(trifluoromethyl)-1H-pyrazole-5-carboxamide 70 1-((3,3-difluoro-1-methylcyclobutyl)methyl)-3-(1-fluorocyclopropyl)-N-(2-(S-methylsulfonimidoyl)pyridin-4-yl)-4-(trifluoromethyl)-1H-pyrazole-5-carboxamide 71 1-((3,3-difluoro-1-methylcyclobutyl)methyl)-3-(1-methoxycyclopropyl)-N-(2-(S-methylsulfonimidoyl)pyridin-4-yl)-4-(trifluoromethyl)-1H-pyrazole-5-carboxamide 72 1-((3,3-difluoro-1-methylcyclobutyl)methyl)-3-(2,3-difluorocyclopropyl)-N-(2-(S-methylsulfonimidoyl)pyridin-4-yl)-4-(trifluoromethyl)-1H-pyrazole-5-carboxamide 73 1-((3,3-difluoro-1-methylcyclobutyl)methyl)-N-(2-(S-methylsulfonimidoyl)pyridin-4-yl)-3-(1,2,2-trifluorocyclopropyl)-4-(trifluoromethyl)-1H-pyrazole-5-carboxamide 74 1-((3,3-difluoro-1-methylcyclobutyl)methyl)-3-(1,2-difluorocyclopropyl)-N-(2-(S-methylsulfonimidoyl)pyridin-4-yl)-4-(trifluoromethyl)-1H-pyrazole-5-carboxamide 75 1-((3,3-difluoro-1-methylcyclobutyl)methyl)-3-(1,1-difluoroethyl)-N-(2-(S-methylsulfonimidoyl)pyridin-4-yl)-4-(trifluoromethyl)-1H-pyrazole-5-carboxamide 76 4-chloro-1-((3,3-difluoro-1-methylcyclobutyl)methyl)-3-(1,1-difluoroethyl)-N-(2-(S-methylsulfonimidoyl)pyridin-4-yl)-1H-pyrazole-5-carboxamide 77 3-cyclopropyl-1-((3,3-difluoro-1-methylcyclobutyl)methyl)-4-(difluoromethyl)-N-(2-(S-methylsulfonimidoyl)pyridin-4-yl)-1H-pyrazole-5-carboxamide 78 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide 79 3-cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide 80 3-cyclopropyl-1-(dispiro[$2.0.2^4.1^3$]heptan-7-ylmethyl)-N-(2-(S-methylsulfonimidoyl)pyridin-4-yl)-4-(trifluoromethyl)-1H-pyrazole-5-carboxamide 81 3-cyclopropyl-1-((1,2-dimethylcyclopropyl)methyl)-N-(2-(S-methylsulfonimidoyl)pyridin-4-yl)-4-(trifluoromethyl)-1H-pyrazole-5-carboxamide 82 3-cyclopropyl-1-((1-methyl-2-(trifluoromethyl)cyclopropyl)methyl)-N-(2-(S-methylsulfonimidoyl)pyridin-4-yl)-4-(trifluoromethyl)-1H-pyrazole-5-carboxamide 83 1-(bicyclo[2.1.0]pentan-1-ylmethyl)-3-cyclopropyl-N-(2-(S-methylsulfonimidoyl)pyridin-4-yl)-4-(trifluoromethyl)-1H-pyrazole-5-carboxamide 84 3-cyclopropyl-N-(2-(S-methylsulfonimidoyl)pyridin-4-yl)-1-(spiro[2.3]hexan-5-ylmethyl)-4-(trifluoromethyl)-1H-pyrazole-5-carboxamide 85 3-cyclopropyl-1-((5-methylspiro[2.3]hexan-5-yl)methyl)-N-(2-(S-methylsulfonimidoyl)pyridin-4-yl)-4-(trifluoromethyl)-1H-pyrazole-5-carboxamide 86 3-cyclopropyl-1-((1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide 87 3-cyclopropyl-1-((1-fluorospiro[2.3]hexan-5-yl)methyl)-N-(2-(S-methylsulfonimidoyl)pyridin-4-yl)-4-(trifluoromethyl)-1H-pyrazole-5-carboxamide 88 3-cyclopropyl-N-(2-(S-methylsulfonimidoyl)pyridin-4-yl)-4-(trifluoromethyl)-1-((3-(trifluoromethyl)cyclobutyl)methyl)-1H-pyrazole-5-carboxamide 89 3-cyclopropyl-1-((3,3-difluorocyclobutyl)methyl)-N-(2-(S-methylsulfonimidoyl)pyridin-4-yl)-4-(trifluoromethyl)-1H-pyrazole-5-carboxamide 90 3-cyclopropyl-1-((5,5-difluorobicyclo[2.1.0]pentan-2-yl)methyl)-N-(2-(S-methylsulfonimidoyl)pyridin-4-yl)-4-(trifluoromethyl)-1H-pyrazole-5-carboxamide 91 3-cyclopropyl-N-(2-(S-methylsulfonimidoyl)pyridin-4-yl)-1-(spiro[2.3]hexan-4-ylmethyl)-4-(trifluoromethyl)-1H-pyrazole-5-carboxamide 92 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide 93 3-cyclopropyl-N-(2-(S-methylsulfonimidoyl)pyridin-4-yl)-1-(spiro[3.3]heptan-1-ylmethyl)-4-(trifluoromethyl)-1H-pyrazole-5-carboxamide 94 3-cyclopropyl-1-((2-methylbicyclo[2.2.0]hexan-2-yl)methyl)-N-(2-(S-methylsulfonimidoyl)pyridin-4-yl)-4-(trifluoromethyl)-1H-pyrazole-5-carboxamide 95 3-cyclopropyl-1-((3,3-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide 96 3-cyclopropyl-1-((4,4-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide 97 3-cyclopropyl-1-((5-fluorooctahydropentalen-2-yl)methyl)-N-(2-(S-methylsulfonimidoyl)pyridin-4-yl)-4-(trifluoromethyl)-1H-pyrazole-5-carboxamide 98 3-cyclopropyl-N-(2-(S-methylsulfonimidoyl)pyridin-4-yl)-4-(trifluoromethyl)-1-((1-(trifluoromethyl)cyclopentyl)methyl)-1H-pyrazole-5-carboxamide 99 3-cyclopropyl-1-((4,4-difluoro-2-methylcyclopentyl)methyl)-N-(2-(S-methylsulfonimidoyl)pyridin-4-yl)-4-(trifluoromethyl)-1H-pyrazole-5-carboxamide 100 3-cyclopropyl-1-((4,4-difluoro-2-(trifluoromethyl)cyclopentyl)methyl)-N-(2-(S-methylsulfonimidoyl)pyridin-4-yl)-4-(trifluoromethyl)-1H-pyrazole-5-carboxamide 101 3-cyclopropyl-1-((3,3-difluoro-5-methylbicyclo[3.1.0]hexan-1-yl)methyl)-N-(2-(S-methylsulfonimidoyl)pyridin-4-yl)-4-(trifluoromethyl)-1H-pyrazole-5-carboxamide 102 3-cyclopropyl-1-((3,3-difluoro-5-(trifluoromethyl)bicyclo[3.1.0]hexan-1-yl)methyl)-N-(2-(S-methylsulfonimidoyl)pyridin-4-yl)-4-(trifluoromethyl)-1H-pyrazole-5-carboxamide 103 3-cyclopropyl-1-((2,2-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide 104 3-cyclopropyl-1-((3,3-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide 105 3-cyclopropyl-1-((4-fluorobicyclo[2.1.1]hexan-1-yl)methyl)-N-(2-(S-methylsulfonimidoyl)pyridin-4-yl)-4-(trifluoromethyl)-1H-pyrazole-5-carboxamide 106 3-cyclopropyl-1-((4-fluorobicyclo[2.2.1]heptan-1-yl)methyl)-N-(2-(S-methylsulfonimidoyl)pyridin-4-yl)-4-(trifluoromethyl)-1H-pyrazole-5-carboxamide 107 3-cyclopropyl-1-((4,4-difluorobicyclo[4.1.0]heptan-1-yl)methyl)-N-(2-(S-methylsulfonimidoyl)pyridin-4-yl)-4-(trifluoromethyl)-1H-pyrazole-5-carboxamide 108 3-(bicyclo[1.1.1]pentan-1-yl)-1-((3,3-difluoro-1-methylcyclobutyl)methyl)-N-(3-(S-methylsulfonimidoyl)phenyl)-4-(trifluoromethyl)-1H-pyrazole-5-carboxamide 109 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide 110 1-((3,3-difluoro-1-methylcyclobutyl)methyl)-3-(3-fluorobicyclo[1.1.1]pentan-1-yl)-N-(2-(S-methylsulfonimidoyl)pyridin-4-yl)-4-(trifluoromethyl)-1H-pyrazole-5-carboxamide 111 1-((3,3-difluoro-1-methylcyclobutyl)methyl)-3-(3-fluorobicyclo[1.1.1]pentan-1-yl)-N-(3-(S-methylsulfonimidoyl)phenyl)-4-(trifluoromethyl)-1H-pyrazole-5-carboxamide 112 1-((3,3-difluoro-1-methylcyclobutyl)methyl)-4-(difluoromethyl)-3-(3-fluorobicyclo[1.1.1]pentan-1-yl)-N-(2-(S-methylsulfonimidoyl)pyridin-4-yl)-1H-pyrazole-5-carboxamide 113 1-((3,3-difluoro-1-methylcyclobutyl)methyl)-4-(difluoromethyl)-3-(3-fluorobicyclo[1.1.1]pentan-1-yl)-N-(3-(S-methylsulfonimidoyl)phenyl)-1H-pyrazole-5-carboxamide 114 1-((3,3-difluoro-1-methylcyclobutyl)methyl)-3-(2,2-difluorobicyclo[1.1.1]pentan-1-yl)-N-(2-(S-methylsulfonimidoyl)pyridin-4-yl)-4-(trifluoromethyl)-1H-pyrazole-5-carboxamide 115 1-((3,3-difluoro-1-methylcyclobutyl)methyl)-3-(2,2-difluorobicyclo[1.1.1]pentan-1-yl)-N-(3-(S-methylsulfonimidoyl)phenyl)-4-(trifluoromethyl)-1H-pyrazole-5-carboxamide 116 1-((3,3-difluoro-1-methylcyclobutyl)methyl)-3-(2,2-difluorobicyclo[1.1.1]pentan-1-yl)-4-(difluoromethyl)-N-(2-(S-methylsulfonimidoyl)pyridin-4-yl)-1H-pyrazole-5-carboxamide 117 1-((3,3-difluoro-1-methylcyclobutyl)methyl)-3-(2,2-difluorobicyclo[1.1.1]pentan-1-yl)-4-(difluoromethyl)-N-(3-(S-methylsulfonimidoyl)phenyl)-1H-pyrazole-5-carboxamide 118 1-((3,3-difluoro-1-methylcyclobutyl)methyl)-N-(2-(S-methylsulfonimidoyl)pyridin-4-yl)-3-(2,2,3-trifluorobicyclo[1.1.1]pentan-1-yl)-4-(trifluoromethyl)-1H-pyrazole-5-carboxamide 119 1-((3,3-difluoro-1-methylcyclobutyl)methyl)-N-(3-(S-methylsulfonimidoyl)phenyl)-3-(2,2,3-trifluorobicyclo[1.1.1]pentan-1-yl)-4-(trifluoromethyl)-1H-pyrazole-5-carboxamide 120 1-((3,3-difluoro-1-methylcyclobutyl)methyl)-4-(difluoromethyl)-N-(2-(S-methylsulfonimidoyl)pyridin-4-yl)-3-(2,2,3-trifluorobicyclo[1.1.1]pentan-1-yl)-1H-pyrazole-5-carboxamide 121 1-((3,3-difluoro-1-methylcyclobutyl)methyl)-4-(difluoromethyl)-N-(3-(S-methylsulfonimidoyl)phenyl)-3-(2,2,3-trifluorobicyclo[1.1.1]pentan-1-yl)-1H-pyrazole-5-carboxamide 122 1-((3,3-difluoro-1-methylcyclobutyl)methyl)-3-(3-methoxybicyclo[1.1.1]pentan-1-yl)-N-(2-(S-methylsulfonimidoyl)pyridin-4-yl)-4-(trifluoromethyl)-1H-pyrazole-5-carboxamide 123 1-((3,3-difluoro-1-methylcyclobutyl)methyl)-3-(3-methoxybicyclo[1.1.1]pentan-1-yl)-N-(3-(S-methylsulfonimidoyl)phenyl)-4-(trifluoromethyl)-1H-pyrazole-5-carboxamide 124 1-((3,3-difluoro-1-methylcyclobutyl)methyl)-4-(difluoromethyl)-3-(3-methoxybicyclo[1.1.1]pentan-1-yl)-N-(2-(S-methylsulfonimidoyl)pyridin-4-yl)-1H-pyrazole-5-carboxamide 125 1-((3,3-difluoro-1-methylcyclobutyl)methyl)-4-(difluoromethyl)-3-(3-methoxybicyclo[1.1.1]pentan-1-yl)-N-(3-(S-methylsulfonimidoyl)phenyl)-1H-pyrazole-5-carboxamide 126 1-((3,3-difluoro-1-methylcyclobutyl)methyl)-N-(4-fluoro-3-(S-methylsulfonimidoyl)phenyl)-3-(1-fluorocyclopropyl)-4-(trifluoromethyl)-1H-pyrazole-5-carboxamide 127 1-((3,3-difluoro-1-methylcyclobutyl)methyl)-N-(3-fluoro-5-(S-methylsulfonimidoyl)phenyl)-3-(1-fluorocyclopropyl)-4-(trifluoromethyl)-1H-pyrazole-5-carboxamide 128 1-((3,3-difluoro-1-methylcyclobutyl)methyl)-N-(2-fluoro-5-(S-methylsulfonimidoyl)phenyl)-3-(1-fluorocyclopropyl)-4-(trifluoromethyl)-1H-pyrazole-5-carboxamide 129 1-((3,3-difluoro-1-methylcyclobutyl)methyl)-N-(2-fluoro-3-(S-methylsulfonimidoyl)phenyl)-3-(1-fluorocyclopropyl)-4-(trifluoromethyl)-1H-pyrazole-5-carboxamide 130 1-((3,3-difluoro-1-methylcyclobutyl)methyl)-N-(3-(S-(difluoromethyl)sulfonimidoyl)phenyl)-3-(1-fluorocyclopropyl)-4-(trifluoromethyl)-1H-pyrazole-5-carboxamide 131 1-((3,3-difluoro-1-methylcyclobutyl)methyl)-3-(1-fluorocyclopropyl)-4-(trifluoromethyl)-N-(3-(S-(trifluoromethyl)sulfonimidoyl)phenyl)-1H-pyrazole-5-carboxamide 132 3-cyclopropyl-1-((3,3-difluoro-1-methylcyclobutyl)methyl)-N-(4-fluoro-3-(S-methylsulfonimidoyl)phenyl)-4-(trifluoromethyl)-1H-pyrazole-5-carboxamide 133 1-((3,3-difluoro-1-methylcyclobutyl)methyl)-4-(difluoromethyl)-N-(4-fluoro-3-(S-methylsulfonimidoyl)phenyl)-3-(1-fluorocyclopropyl)-1H-pyrazole-5-carboxamide 134 3-(1-fluorocyclopropyl)-N-(3-(S-methylsulfonimidoyl)phenyl)-4-(trifluoromethyl)-1-((2-(trifluoromethyl)cyclopropyl)methyl)-1H-pyrazole-5-carboxamide 135 1-((3,3-difluoro-1-methylcyclobutyl)methyl)-4-(difluoromethyl)-3-(1-fluorocyclopropyl)-N-(3-(S-methylsulfonimidoyl)phenyl)-1H-pyrazole-5-carboxamide 136 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide 137 3-(bicyclo[1.1.1]pentan-1-yl)-1-((3,3-difluoro-1-methylcyclobutyl)methyl)-4-(difluoromethyl)-N-(2-(S-methylsulfonimidoyl)pyridin-4-yl)-1H-pyrazole-5-carboxamide 138 1-((3,3-difluoro-1-methylcyclobutyl)methyl)-4-(difluoromethyl)-N-(4-fluoro-3-(S-methylsulfonimidoyl)phenyl)-3-(3-fluorobicyclo[1.1.1]pentan-1-yl)-1H-pyrazole-5-carboxamide 139 3-(bicyclo[1.1.1]pentan-1-yl)-1-((2-(difluoromethyl)cyclopropyl)methyl)-N-(3-(S-methylsulfonimidoyl)phenyl)-4-(trifluoromethyl)-1H-pyrazole-5-carboxamide 140 1-((2-acetyl-2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide 141 1-((3,3-difluoro-1-methylcyclobutyl)methyl)-N-(4-fluoro-3-(S-methylsulfonimidoyl)phenyl)-3-(3-fluorobicyclo[1.1.1]pentan-1-yl)-4-(trifluoromethyl)-1H-pyrazole-5-carboxamide 142 N-(2-(N-cyan-S-methylsulfonimidoyl)pyridin-4-yl)-3-cyclopropyl-1-((3,3-difluoro-1-methylcyclobutyl)methyl)-4-(trifluoromethyl)-1H-pyrazole-5-carboxamide 143 3-(tert-butyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide 144 1-((3,3-difluoro-1-methylcyclobutyl)methyl)-N-(2-(S-methylsulfonimidoyl)pyridin-4-yl)-4-(trifluoromethyl)-3-(1-(trifluoromethyl)cyclopropyl)-1H-pyrazole-5-carboxamide 145 1-((3,3-difluoro-1-methylcyclobutyl)methyl)-3-(1-(difluoromethyl)cyclopropyl)-N-(2-(S-methylsulfonimidoyl)pyridin-4-yl)-4-(trifluoromethyl)-1H-pyrazole-5-carboxamide 146 3-(bicyclo[1.1.1]pentan-1-yl)-1-((2-(difluoromethyl)cyclopropyl)methyl)-N-(2-(S-methylsulfonimidoyl)pyridin-4-yl)-4-(trifluoromethyl)-1H-pyrazole-5-carboxamide 147 3-(bicyclo[1.1.1]pentan-1-yl)-N-(2-(S-methylsulfonimidoyl)pyridin-4-yl)-4-(trifluoromethyl)-1-(((trans)-2-(trifluoromethyl)cyclopropyl)methyl)-1H-pyrazole-5-carboxamide 148 1-((3,3-difluoro-1-methylcyclobutyl)methyl)-3-(2-fluoropropan-2-yl)-N-(2-(S-methylsulfonimidoyl)pyridin-4-yl)-4-(trifluoromethyl)-1H-pyrazole-5-carboxamide 150 1-((3,3-difluoro-1-methylcyclobutyl)methyl)-3-(1-fluorocyclopropyl)-N-(3-(S-methyl-N-(oxetane-3-carbonyl) sulfonimidoyl)phenyl)-4-(trifluoromethyl)-1H-pyrazole-5-carboxamide 151 1-((3,3-difluoro-1-methylcyclobutyl)methyl)-3-(1-fluorocyclopropyl)-N-(3-(N-(2-hydroxyacetyl)-S-methylsulfonimidoyl)phenyl)-4-(trifluoromethyl)-1H-pyrazole-5-carboxamide 152 3-cyclopropyl-1-((3,3-difluoro-1-methylcyclobutyl) methyl)-N-(2-(N-(2,3-dihydroxypropyl)-S-methylsulfonimidoyl)pyridin-4-yl)-4-(trifluoromethyl)-1H-pyrazole-5-carboxamide 153 1-((2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide in the form of the free compound or a physiologically acceptable salt thereof.

In a preferred embodiment, the compound according to the invention is an inhibitor of $Na_V1.8$. In the sense of the invention, the term "inhibitor of $Na_V1.8$" preferably means that the respective compound exhibits in a patch clamp assay an IC50 value on $Na_V1.8$ of at most 10 μM ($10 \cdot 10^{-6}$ mol/L); more preferably at most 1 μM; still more preferably at most 500 nM ($10^{-9}$ mol/L); even more preferably at most 100 nM; and most preferably at most 10 nM.

A preferred assay for testing compounds for their potency and method for determining an IC50 on $Na_V1.8$ is described in the experimental part down below.

In a preferred embodiment, the compound according to the invention is a selective inhibitor of $Na_V1.8$. In the sense of the invention, the term "selective inhibitor of $Na_V1$ 0.8" preferably means that the respective compound preferably does not exhibit any inhibitory activity on $Na_V1.1$, $Na_V1.2$, $Na_V1.4$, $Na_V1.5$ and $Na_V1.6$. The skilled artisan knows suitable ways to determine whether a compound exhibits inhibitory effects on any of $Na_V1.1$, $Na_V1.2$, $Na_V1.4$, $Na_V1.5$ and $Na_V1.6$.

The invention therefore relates to a compound according to the invention for use in the inhibition of $Na_V1.8$.

Therefore, another aspect of the invention relates to a compound according to the invention for use in the treatment of pain. Still another aspect of the invention relates to a method of treatment of pain; comprising the administration of a therapeutically effective amount of a compound according to the invention to a subject in need thereof, preferably a human.

A further aspect of the invention relates to a compound according to the invention as medicament.

Another aspect of the invention relates to a pharmaceutical dosage form comprising a compound according to the invention. Preferably, the pharmaceutical dosage form comprises a compound according to the invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical dosage form according to the invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the invention is preferably prepared with the aid of conventional means, devices, methods and processes known in the art. The amount of the compound according to the invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the invention are administered per kg of the patient's body weight.

Therefore, another aspect of the invention relates to the pharmaceutical dosage form according to the invention for use in the treatment of pain. Still another aspect of the invention relates to a method of treatment of pain; comprising the administration of a pharmaceutical dosage form according to the invention to a subject in need thereof, preferably a human.

EXAMPLES

Experimental Protocols

The following abbreviations are used in the descriptions of the experimental protocols: ABPR=automatic back pressure regulator; ADDP=1'-(azodicarbonyl)dipiperidine, aq.=aqueous; Boc=tert-butyloxycarbonyl; Brettphos-Pd-G3=[(2-di-cyclohexylphosphino-3,6-dimethoxy-2',4',6'-tri-isopropyl-1,1'-biphenyl)-2-(2'-amino-1,1'-biphenyl)]palladium(II)-methansulfonat-methansulfonat; DAST=diethylaminosulfur trifluoride, DCE=dichloroethane, DCM=dichloromethane; DIAD=diisopropylazodicarboxylate; DIPEA=N,N-diisopropylethylamine; DMF=N,N-dimethylformamide; DMP=Dess-Martin periodinane, DMSO=dimethylsulfoxide; dppf=1,1'-bis(diphenylphosphin)ferrocene, EDC or EDCI=1-ethyl-3-(3-dimethylaminopropyl)carbodiimide, EtOAc=ethyl acetate; $Et_2O$=diethyl ether; EtOH=ethanol; h=hour; HATU=1-[bis(dimethylamino)methylene]-1H-1,2,3-triazolo[4,5-b]pyridinium 3-oxide hexafluorophosphate; Hex=hexane; HMPA=hexamethylphosphoramide, HPLC=high-performance liquid chromatography; HOBt=hydroxybenzotriazole; ITX=isopropylthioxanthone; KHMDS=potassium bis(trimethylsilyl)amid; LAH=lithium aluminium hydride, LCMS=liquid chromatography-mass spectrometry; LiHMDS=Lithium bis(trimethylsilyl)amide; MeCN=acetonitrile; MeI=methyl iodide; MeOH=methanol; $McSO_2Cl$=methanesulfonyl chloride; min=minute; Ms=methanesulfonyl; MTBE=methyl tert-butyl ether; NIS=N-iodosuccinimide; NMO=N-methylmorpholine N-oxide, NMR=nuclear magnetic resonance; NP=normal phase; PE=petroleum ether; PG=protection group; PIDA=(diacetoxyiodo)benzene; prep.=preparative; rt=room temperature; $R_t$=retention time; sat.=saturated; SEM=2-(trimethylsilyl)ethoxymethyl; SFC=supercritical fluid chromatography; SM=starting material; TBAF=tetra-n-butylammonium fluoride; TBDMS=tert-butyldimethylsilyl; TCFH=chloro-N,N,N',N'-tetramethylformamidinium hexafluorophosphate, TEA=triethylamine; Tf=trifluoromethylsulfonyl; TFA=trifluoroacetic acid, THF=tetrahydrofurane; $TMSCF_3$=trifluoromethyltrimethylsilane; Ts=p-toluenesulfonyl.

General Synthesis Schemes

As illustrated in Scheme 1, compounds of the invention can be prepared by N-alkylation of alkyl 1H-pyrazole-5-carboxylates of the general formula (A) with appropriately functionalized alkylation reagents of the general formula (B) (where Y is leaving group, such as Br, Cl, OTs, OMs, OTf) under basic conditions to afford compounds of general formula (C). Alternatively, intermediates of the general formula (C) can be prepared using a Mitsunobu reaction between alkyl 1H-pyrazole-5-carboxylates of type (A) and alcohols of the general formula (B) (where Y is OH) (*Chem. Rev.* 2009, 109, 6, 2551-2651). Alcohols of the general formula (B) with Y=OH are either commercially available or can be prepared as described in the present invention or synthesized according to the standard procedures known to the person skilled in the art. Intermediates of the general formula (C) can be hydrolized to carboxylic acids of the general formula (D).

Scheme 1: L, R1, R4, R5 are as defined in claim 1.

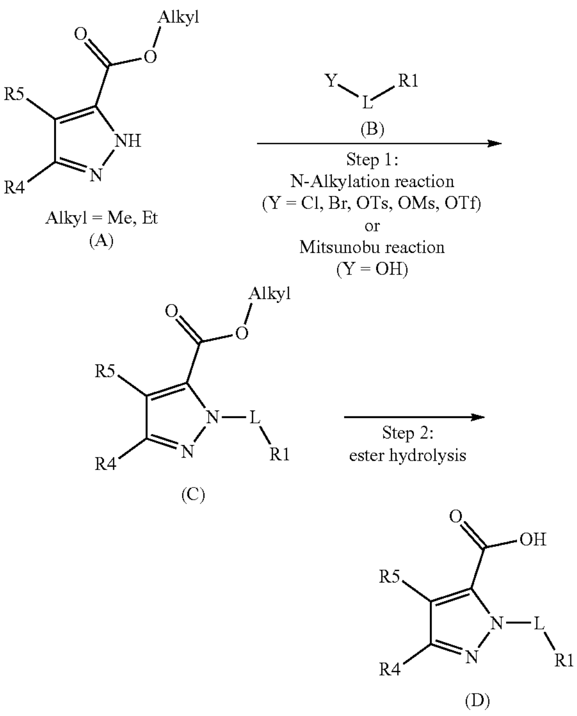

In some embodiments, intermediates need to bear one or more protecting groups, such as SEM (trimethylsilylethoxymethyl) or Bn (benzyl) which are deprotected after N-alkylation using standard deprotection protocols known in the art (T. W. Green, P. G. M. Wuts, *Protective Groups in Organic Synthesis*, Wiley-Interscience, New York, 1999). In some embodiments functional group interconversions are used such as fluorination using e.g. DAST (*Synthesis,* 2002, 2561-2578) or difluromethylation using sodium 2-chloro-2,2-difluoroacetate (*Chem. Soc. Rev,* 2021, 50, 8214-8247).

Scheme 2: L, R1, R4, R5 are as defined in claim 1.

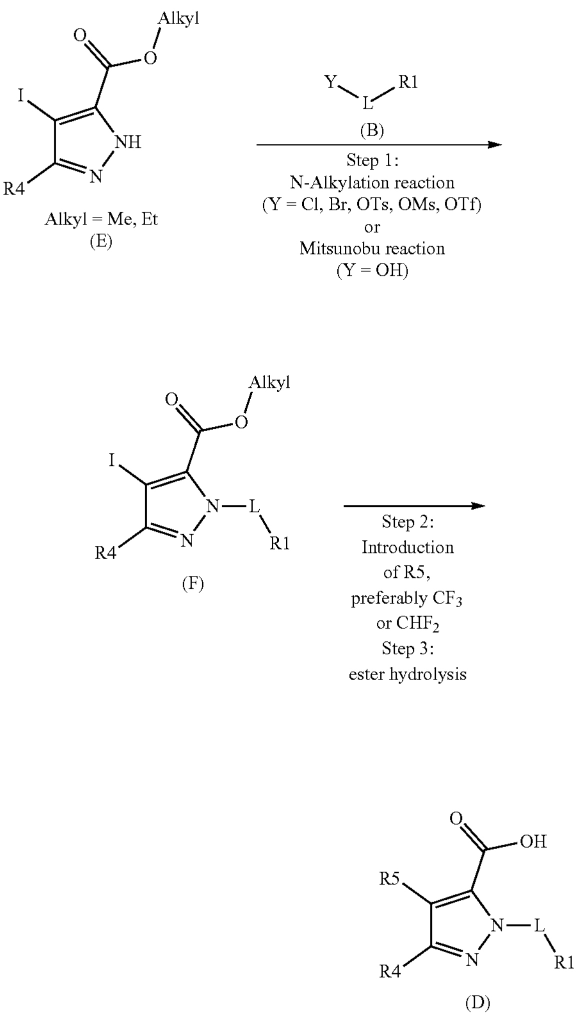

As illustrated in Scheme 2, intermediates of the general formula (F) can also be obtained by N-alkylation of alkyl 4-iodo-1H-pyrazole-5-carboxylates of the general formula (E) with appropriately functionalized alkylation reagents of the general formula (B) (Y is leaving group, such as Br, Cl, OTs, OMs, OTf) under basic conditions to give intermediates of the general formula (F). Introduction of the substituent R5 e.g. via trifluoromethylation with $TMSCF_3$ in the presence of CuI or Suzuki coupling followed by ester hydrolysis gives intermediates of the general formula (D). Furthermore, a reaction sequence of palladium-catalyzed vinylation, osmium-catalyzed dihydroxylation & diol cleavage (utilizing $NaIO_4$) followed by fluorination by e.g. DAST can be used to install a $CHF_2$ moiety, which after ester hydrolysis gives intermediates of the general formula (D) with R5=$CHF_2$. Alternatively, a Mitsunobu reaction between alkyl 4-iodo-1H-pyrazole-5-carboxylates of the general formula (E) and alcohols of the general formula (B) (where Y is OH) can be used to obtain intermediates of the general formula (F).

Scheme 3: R4, R5 are as defined in claim 1.

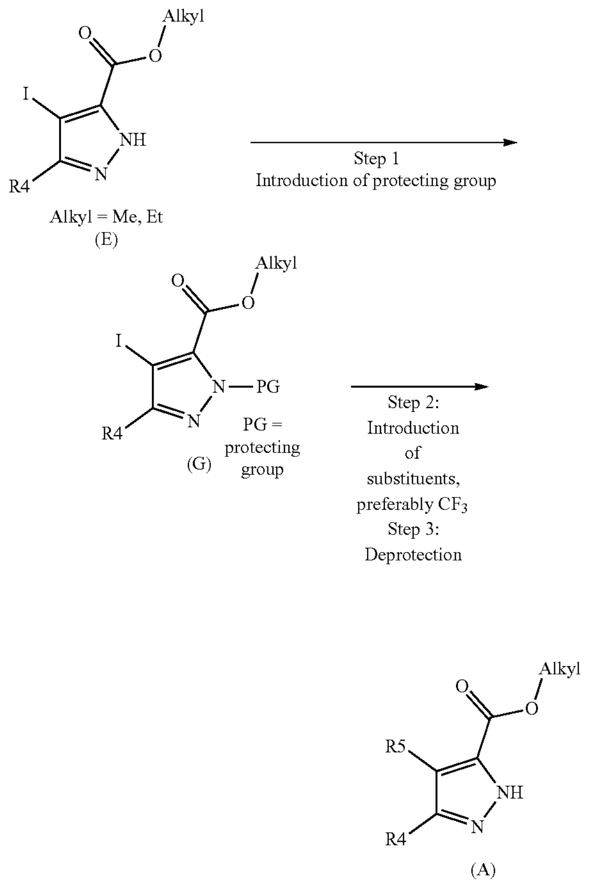

As illustrated in Scheme 3, alkyl 4-iodo-1H-pyrazole-5-carboxylates of the general formula (E) can also be used to obtain alkyl 1H-pyrazole-5-carboxylates of the general formula (A) using a sequence consisting of introduction of a protecting group followed by introduction of the substituent R5 e.g. via trifluoromethylation with $TMSCF_3$ in the presence of CuI or Suzuki coupling followed by deprotection. Suitable protecting groups are e.g. SEM (trimethylsilylethoxymethyl). Standard protection/deprotection protocols are known in the art (T. W. Green, P. G. M. Wuts, *Protective Groups in Organic Synthesis*, Wiley-Interscience, New York, 1999).

As illustrated in Scheme 4, intermediates of the general formula (D) can be converted to compounds of the general formula (I) using amide coupling with (hetero)arylamines of the general formula (H) in the presence of a carboxylic acid activating reagent, preferably HATU or $POCl_3$ and a base, preferably pyridine or DIPEA (March's Advanced Organic Chemistry, 2007, 6th Edition, page 1427-1474). Alternatively, intermediates of the general formula (I) can be synthesized from intermediates of the general formula (C) using (hetero)arylamines of the general formula (H) under basic conditions. Preferred bases include KHMDS. Compounds of the general formula (I) can be converted to compounds of the general formula (J) using further protocols known to the person skilled in the art, for example the preparation of an alkyl sulfonimidoyl group from a thioalkane (*Chem. Eur. J*, 2021, 27, 17293 17321).

Scheme 4: L, R1, R2, R4, R5, R′, A1, A2, A3 are as defined in claim 1. B1, B2, B3 independently from another can be CR′ or C-S-alkyl, with at least one of B1/B2/B3 being C-S-alkyl.

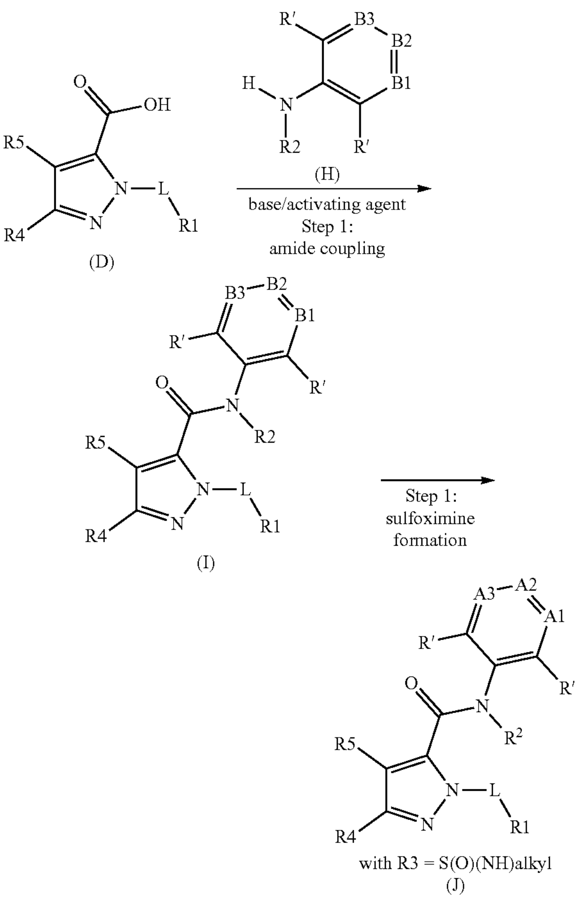

As illustrated in Scheme 5, acids of the general formula (K) can be converted to ketones of the general formula (M) via a standard functional group interconversion sequence. Preferred methods to achieved this transformation include e.g. first an activation step of the acid (e.g. Weinreb amide formation) and subsequent treatment with a carbon-nucleophile (e.g. organomagnesium compounds or organolithium compounds of the general formula (L)) (*Synthesis,* 2019, 51, 2792-2808). Ketones of the general formula (M) can be converted to compounds of the general formula (0) via deprotonation of (M) using a base (e.g. LiHMDS or KOtBu) and addition of the resulting enolate onto compounds of the general formula (N). Compounds of the general formula (0) can be treated with hydrazine or hydrazine hydrate to yield compounds of the general formula (A). Similar reaction sequences are well precedented in the literature (e.g. *Bioorg. & Medchem Lett.* 2007, 17, 5620-5623, *European Journal of Medicinal Chemistry,* 2016, 109, 350-359).

Scheme 5: R4, R5 are as defined in claim 1.

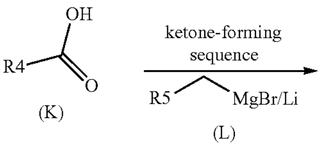

-continued

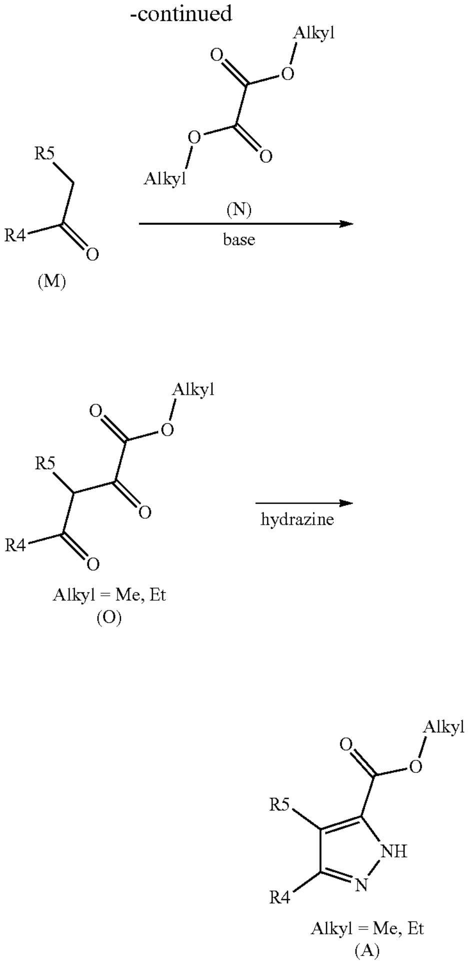

Alkyl 1H-pyrazole-5-carboxylates of the general formula (A), organomagnesium compounds or organolithium compounds of the general formula (L) and alkyl-oxalates of the general formula (N) are either commercially available or can be prepared as described in the present invention or synthesized according to the standard procedures known to the person skilled in the art.

As illustrated in Scheme 6, acids of the general formula (K) can be converted to ketones of the general formula (Q) via a standard functional group interconversion sequence. Preferred methods to achieved this transformation include e.g. first an activation step of the acid (e.g. Weinreb amide formation) and subsequent treatment with a carbon-nucleophile (e.g. organomagnesium compounds or organolithium compounds of the general formula (L)) (*Synthesis,* 2019, 51, 2792-2808). Ketones of the general formula (Q) can be converted to compounds of the general formula (R) via deprotonation of (Q) using a base (e.g. LiHMDS) and addition of the resulting enolate onto compounds of the general formula (R). Compounds of the general formula (R) can be treated with hydrazine or hydrazine hydrate to yield compounds of the general formula (S). Compounds of general formula (E) can be obtained by iodination (e.g. with NIS) of compounds of the general formula (S).

Similar reaction sequences are well precedented in the literature (e.g. *Bioorg. & Medchem Lett.* 2007, 17, 5620 5623, *European Journal of Medicinal Chemistry,* 2016, 109, 350-359).

Scheme 6: R4 is as defined in claim 1.

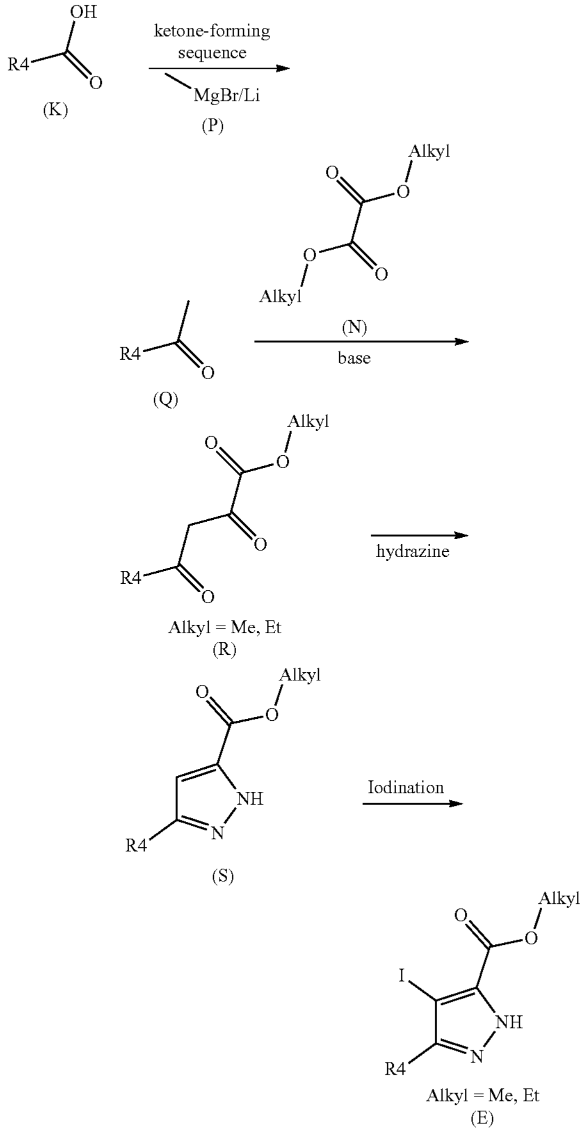

Alkyl 1H-pyrazole-5-carboxylates of the general formula (A), organomagnesium compounds or organolithium compounds of the general formula (P), ketones of the general formula (Q) and alkyl-oxalates of the general formula (N) are either commercially available or can be prepared as described in the present invention or synthesized according to the standard procedures known to the person skilled in the art.

As illustrated in Scheme 7, amides of the general formula (T) can be converted together with (hetero)arylhalides of the general formula (U) to compounds of the general formula (I) via transition-metal catalyzed couplings, employing e.g. copper or palladium based catalysts with appropriate ligands. Alternatively, amides of the general formula (T) can be converted together with arylhalides of the general formula (V) to compounds of the general formula (J) via transition-metal catalyzed couplings, employing e.g. copper or palladium based catalysts with appropriate ligands. Suitable catalysts and ligands include e.g. Brettphos-Pd-G3 or CuI/Cu(I) trifluoromethane sulphonate benzene complex in combination with either DMEDA, trans-1,2-diaminocyclohexane or trans-N,N'-dimethylcyclohexane-1,2-diamine. If arylhalides of the general formula (V) with R3═S(O)(NPG) alkyl are used in step 1, deprotection is required using methods known to the person skilled in the art to furnish compounds of the general formula (J). Suitable protecting groups include Boc, deprotection can be achieved under acidic conditions, using e.g. TFA. Amides of the general formula (T) can be prepared using standard methods used in the art, e.g. via amide coupling of acids of the general formula (D) or treatment of esters of the general formula (C) with the corresponding amines.

Scheme 7: L, R1, R2, R4, R5, R', A1, A2, A3 are as defined in claim 1. B1, B2, B3 independently from another can be CR' or N or C-S-alkyl, with at least one of B1/B2/B3 being C-S-alkyl. X = halide.

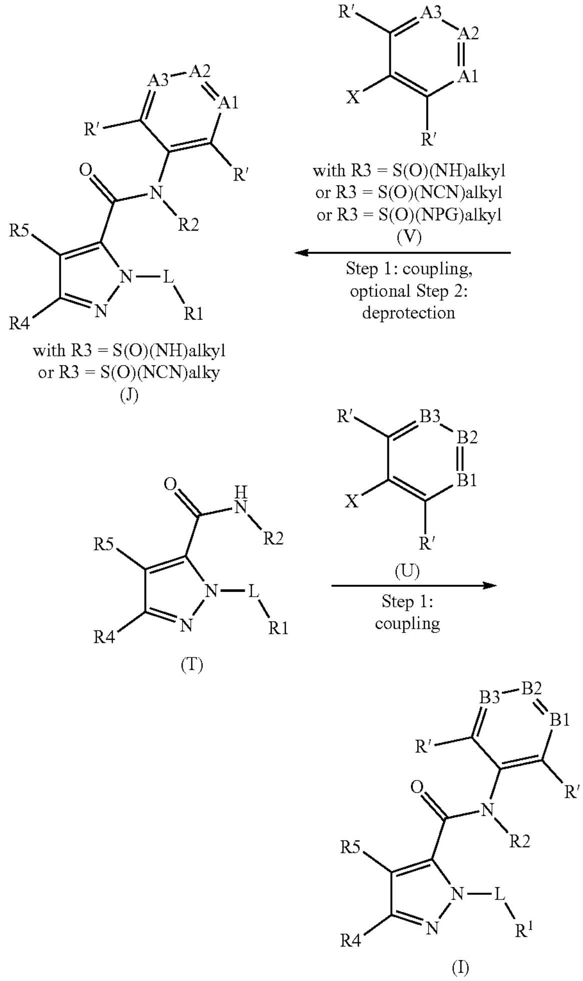

As illustrated in Scheme 8, compounds of the general formula (J) with R3═S(O)(NH)alkyl can be transformed into compounds of the general formula (J) with R3═S(O)(NRX)alkyl (RX=alkyl, acyl) via reactions known to the person skilled in the art. Alkylation can be achieved upon treatment with alkylating agents, e.g. epoxides under Lewis acid catalysis or Chan-Lam type couplings (*Chem. Eur. J*, 2021, 27, 17293-17321). Acylation can be achieved using standard amide coupling conditions known to the person skilled in the art. Protection/deprotection might be necessary and is known to the person skilled in the art.

Scheme 8: L, R1, R2, R4, R5, R¢, A1, A2, A3 are as defined in claim 1.. RX = alkyl, acyl.

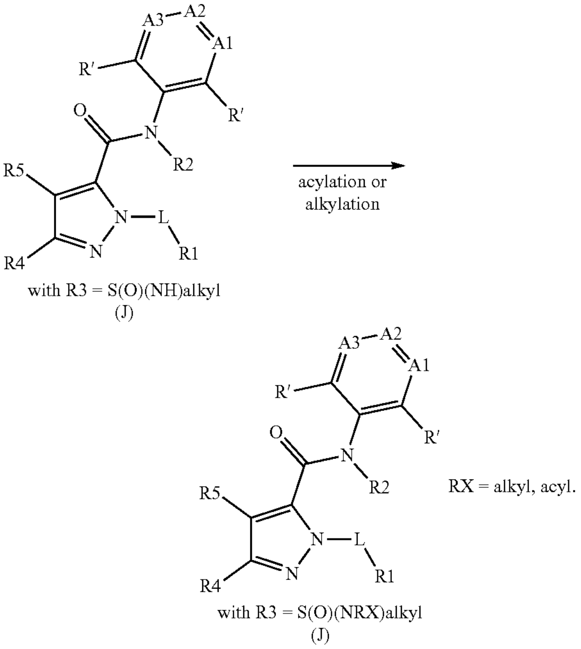

Intermediate 1

(3,3-Difluorocyclopentyl)methyl methanesulfonate

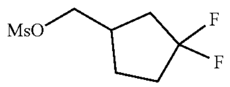 [SMILES: CS(=O)(=O)OCC1CCC(F)(F)C1]

To a stirred solution of (3,3-difluorocyclopentyl)methanol (1.20 g) in DCM (20 mL) were added TEA (2.90 mL) and MsCl (0.82 mL) at 0° C. and the resulting mixture was stirred for 2 h at rt. The reaction mixture was washed with ice-cold $NH_4Cl$ solution (100 mL) and extracted with EtOAc (3×100 mL). The combined organics were washed with brine (100 mL), dried ($Na_2SO_4$) and evaporated to dryness in vacuo to afford the title compound (1.5 g) which was used without further purification.

Intermediate 2

(3,3-Difluorocyclobutyl)methyl methanesulfonate

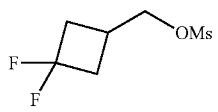 [SMILES: CS(=O)(=O)OCC1CC(F)(F)C1]

To a stirred solution of (3,3-difluorocyclobutyl)methanol (5.0 g) in DCM (100 mL) were added $Et_3N$ (12 g) and MsCl (12 g) at 0° C. and the mixture was stirred for 2 h at rt. The reaction mixture was quenched with water (80 mL) and extracted with DCM (2×50 mL). The combined organics were washed with water (50 mL), brine (50 mL), dried ($Na_2SO_4$) and concentrated under reduced pressure to afford the title compound (7.3 g, crude) which was used without further purification.

Intermediate 3

Benzyl 3,3-difluorocyclobutane-1-carboxylate

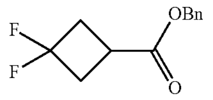 [SMILES: O=C(OCc1ccccc1)C1CC(F)(F)C1]

NaOH (2 M, 35 mL) was added at rt to a stirred solution of methyl 3,3-difluorocyclobutane-1-carboxylate (5.0 g) in MeOH (50 mL) and heated at 60° C. for 4 h. The reaction mixture was cooled to rt and concentrated under reduced pressure. The residue was acidified with saturated $KHSO_4$ solution to maintain pH-2. The precipitate was collected by filtration and co-evaporated with toluene under reduced pressure. The residue was dissolved in DMF (50 mL), $K_2CO_3$ (20.3 g) and BnBr (8.4 mL) were added sequentially at rt and the mixture was stirred for 16 h. The reaction mixture was quenched by addition of crushed ice and extracted with EtOAc (3×100 mL). The combined organics were washed with cold brine, dried ($Na_2SO_4$) and evaporated to dryness under reduced pressure and the residue was purified by CombiFlash chromatography ($SiO_2$, 0-10% EtOAc/Hex) to afford the title compound (6.5 g, 86%). $^1$H-NMR (400 MHz, $CDCl_3$): 7.39-7.30 (m, 5H), 5.15 (s, 2H), 3.00-2.80 (m, 5H).

Intermediate 4

Benzyl 3,3-difluoro-1-methylcyclobutane-1-carboxylate

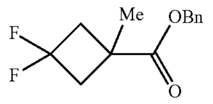 [SMILES: CC1(C(=O)OCc2ccccc2)CC(F)(F)C1]

To a stirred solution of benzyl 3,3-difluorocyclobutane-1-carboxylate (Intermediate 3, 2.0 g) in THE (60 mL) under Ar (g) were added 1 M KHMDS (17.7 mL) and MeI (2.2 mL) at −78° C. and the mixture was stirred for 8 h at −78° C. followed by 16 h at rt. The reaction mixture was quenched with aq. $NH_4Cl$ and extracted with EtOAc (3×100 mL). The combined organics were washed with $Na_2S_2O_3$ solution, cold brine, dried ($Na_2SO_4$) and concentrated under reduced pressure. The residue was purified by CombiFlash chromatography ($SiO_2$, 0-15% EtOAc/Hex) to afford the title compound (1.2 g, 57%). $^1$H-NMR (400 MHz, $CDCl_3$): 7.40-7.34 (m, 5H), 5.16 (s, 2H), 3.11-3.00 (q, 2H), 2.48-2.37 (m, 2H), 1.50 (t, 3H).

Intermediate 5

(3,3-Difluoro-1-methylcyclobutyl)methanol

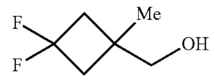

Part 1: To a stirred solution of benzyl 3,3-difluoro-1-methylcyclobutane-1-carboxylate (Intermediate 4, 0.40 g) in EtOH (2 mL) was added 5M NaOH (1.66 mL) portion wise at rt and the mixture was stirred for 16 h. The reaction mixture was concentrated under reduced pressure to give a residue which was diluted with water and washed with EtOAc (20 mL). The aqueous phase was acidified with $KHSO_4$ solution and extracted with EtOAc (3×100 mL). The combined organics were washed with brine, dried ($Na_2SO_4$) and concentrated under reduced pressure to give 3,3-difluoro-1-methylcyclobutane-1-carboxylic acid (0.25 g, crude).

Part 2: LAH (1M in THF, 3.65 mL) was added dropwise at 0° C. to a stirred solution of 3,3-difluoro-1-methylcyclobutane-1-carboxylic acid (Part 1, 0.25 g) in $Et_2O$ (10 mL) and the resulting mixture was allowed to stir for 2 h. The reaction mixture was cooled to 0° C. and ice-cold $Na_2SO_4$ was added dropwise. The aqueous phase was extracted with EtOAc (4×100 mL) and the combined organics were dried ($Na_2SO_4$) and concentrated to afford the title compound (0.16 g, crude).

Intermediate 100

Dispiro[2.0.2$^4$.1$^3$]heptan-7-ylmethanol

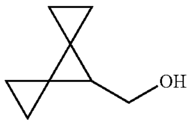

To a solution of dispiro[2.0.2$^4$.1$^3$]heptane-7-carboxylic acid (0.2 g) in $Et_2O$ (10.0 mL) was added LAH (2.4 M in THF, 1.2 mL) at 0° C. The resulting reaction mixture was stirred at rt for 16 h. The reaction mixture was again cooled to 0° C. and quenched with saturated $Na_2SO_4$ solution. The aqueous part was extracted with EtOAc (3×50 mL). The combined organic layers were dried ($Na_2SO_4$) and the organic layer was evaporated under reduced pressure to afford the title compound, which was used in next step without further purification (0.18 g, crude).

Intermediate 101

1-(Hydroxymethyl)bicyclo[2.1.1]hexan-2-one

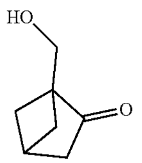

Part 1: To a solution of methyl 2-(hydroxymethyl)acrylate (10.0 g) in DCM (150 mL) were added benzyl trichloroacetimidate (32.2 mL) and triflic acid (catalytic) at rt. The reaction mixture was stirred at rt for 16 h. The reaction mixture was diluted with water and extracted with DCM. The combined organic layers were washed with brine, dried ($Na_2SO_4$), filtered and evaporated under reduced pressure to get the crude product, which was purified by column chromatography ($SiO_2$, 0-30% EtOAc/Hex) to afford methyl 2-((benzyloxy)methyl)acrylate (12.0 g, 68%).

Part 2: To a solution of methyl 2-((benzyloxy)methyl) acrylate (12.0 g) in a mixture of THF-$H_2O$ (8:1) (5 mL) was added LiOH—$H_2O$ (7.3 g) at rt. The reaction was stirred at rt for 4 h. The reaction mixture was concentrated under reduced pressure and diluted with water. The aqueous part was acidified with saturated $KHSO_4$ solution to pH-2 at 0° C. and extracted with EtOAc (3×25 mL). The combined organic layers were washed with brine, dried ($Na_2SO_4$) and evaporated under reduced pressure to get 2-((benzyloxy) methyl)acrylic acid, which was used for next step without further purification. Yield: (10.0 g, 89%).

Part 3: To a solution of 2-((benzyloxy)methyl) acrylic acid (10.0 g) in DCM (70 mL) were added EDC-HCl (15.0 g), DIPEA (27.3 mL) and N,O-dimethylhydroxylamine hydrochloride (9.42 g) at rt. The reaction was stirred at rt for 16 h. The reaction mixture was diluted with water and extracted with DCM. The combined organic layers were washed with brine, dried ($Na_2SO_4$), filtered and evaporated under reduced pressure to get the crude product, which was purified by column chromatography ($SiO_2$, 0-30% EtOAc/Hex) to afford 2-((benzyloxy)methyl)-N-methoxy-N-methyl acrylamide (8.0 g, 65%). LCMS m/z=236 $[M+H]^+$.

Part 4: To a solution of 2-((benzyloxy)methyl)-N-methoxy-N-methyl acrylamide (8.0 g) in THF (100.0 mL) was added allyl magnesium chloride (2M in THF, 34.0 mL) at 0° C. The reaction mixture was stirred at 0° C. for 2 h. The reaction mixture was quenched with $NH_4Cl$ solution and extracted with EtOAc. The combined organic layers were washed with brine, dried ($Na_2SO_4$), filtered and evaporated under reduced pressure to get the crude product, which was purified by CombiFlash column chromatography ($SiO_2$, 0-30% EtOAc/Hex) to afford 2-((benzyloxy)methyl)hexa-1,5-dien-3-one (5.0 g, 68%). LCMS m/z=217 $[M+H]^+$.

Part 5: A solution of 2-((benzyloxy)methyl)hexa-1,5-dien-3-one (2.5 g) in acetonitrile (100 mL) was degassed for 15 min followed by the addition of ITX (0.29 g) at rt. The reaction mixture was then placed under irradiation of 365 nm (UV lamp) for 16 h. The reaction mixture was evaporated under reduced pressure to get the crude product, which was purified by CombiFlash column chromatography ($SiO_2$, 0-30% EtOAc/Hex) to afford 1-((benzyloxy)methyl)bicyclo [2.1.1]hexan-2-one (1.5 g, 60%).

Part 6: To a solution of 1-((benzyloxy)methyl)bicyclo [2.1.1]hexan-2-one (1.0 g) in MeOH (30.0 mL) was added 10% Pd/C (50% wet, 0.1 g) at rt. The reaction mixture was then stirred under $H_2$-balloon pressure for 16 h. The reaction mixture was filtered through a sintered funnel and the filtrate was evaporated under reduced pressure to get the crude product, which was purified by CombiFlash column chromatography ($SiO_2$, 0-30% EtOAc/Hex) to to afford the title compound (0.38 g, 65%).

Intermediate 102

Spiro[2.2]pentan-1-ylmethanol

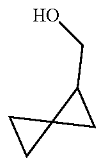

To a solution of spiro[2.2]pentane-1-carboxylic acid (0.9 g) in $Et_2O$ (30 mL) was added LAH (2.4 M in THF, 5.0 mL) at 0° C. The reaction mixture was stirred at rt for 16 h. The reaction mixture was cooled to 0° C. and quenched with saturated $Na_2SO_4$ solution. The mixture was then filtered through a celite bed sintered funnel and the filtrate was evaporated under reduced pressure to get the crude product, which was purified by column chromatography ($SiO_2$, 0-30% EtOAc/Hex) to afford the title compound (0.4 g, 51%). LCMS m/z=97 $[M-H]^-$.

Intermediate 103

(6,6-Difluoro-4-methylspiro[2.3]hexan-4-yl)methanol

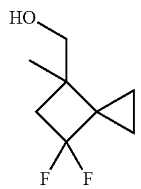

Part 1: To a stirred solution of 6-oxospiro[2.3]hexane-4-carboxylic acid (1.0 g) in DMF (15 mL) were added $K_2CO_3$ (1.5 g) and BnBr (0.9 mL) at rt. The reaction mixture was stirred for 16 h. The reaction mixture was diluted with ice water and was extracted with EtOAc (3×100 mL). The combined organic layers were washed with cold brine and dried over $Na_2SO_4$. The organic layer was concentrated under reduced pressure to get the crude compound which was purified by CombiFlash chromatography ($SiO_2$, 0-50% EtOAc/Hex) to obtain benzyl 6-oxospiro[2.3]hexane-4-carboxylate (1.5 g, 91%).

Part 2: To benzyl 6-oxospiro[2.3]hexane-4-carboxylate (1.7 g) was added DAST (4.4 mL) at 0° C. The reaction mixture was stirred at rt for 16 h. The reaction mixture was diluted with EtOAc and quenched by the addition of cold sat. $NaHCO_3$ solution and stirring for 30 minutes. The mixture was extracted with EtOAc (3×200 mL). The combined organic layers were dried over anhydrous $Na_2SO_4$ and concentrated under reduced pressure to get the crude product, which was purified by CombiFlash column chromatography ($SiO_2$, 0-10% EtOAc/Hex) to obtain benzyl 6,6-difluorospiro[2.3]hexane-4-carboxylate (1.4 g, 75%).

Part 3: To a stirred solution of benzyl 6,6-difluorospiro [2.3]hexane-4-carboxylate (2.5 g) in THF (50 mL) were added KHMDS (1 M, 30.0 mL) and MeI (2.5 mL) at −78° C. The reaction mixture was stirred for 16 h at rt. The reaction mixture was quenched by the addition of aqueous $NH_4Cl$ and extracted with EtOAc (3×500 mL). The combined organic layers were washed with cold brine and dried over $Na_2SO_4$. The organic layer was concentrated under reduced pressure to get the crude compound which was purified by CombiFlash chromatography ($SiO_2$, 0 10% EtOAc/Hex) to obtain benzyl 6,6-difluoro-4-methylspiro[2.3]hexane-4-carboxylate (1.6 g, 60%).

Part 4: Ta a solution of benzyl 6,6-difluoro-4-methylspiro[2.3]hexane-4-carboxylate (2.0 g) in EtOH (15 mL) was added 5N NaOH (8 mL) at rt. The reaction mixture was stirred at rt for 3 h. The reaction mixture was concentrated under reduced pressure and diluted with water. The aqueous part was acidified with 2N HCl to pH~2. The aqueous part was extracted with EtOAc (3×500 mL). The combined organic layers were washed with cold brine, dried over $Na_2SO_4$ and concentrated under reduced pressure to get 6,6-difluoro-4-methylspiro[2.3]hexane-4-carboxylic (1.0 g, 75%).

Part 5: To a stirred solution of 6,6-difluoro-4-methylspiro[2.3]hexane-4-carboxylic acid (1.5 g) in $Et_2O$ (75 mL), was added LAH (2M in THF, 9.0 mL) dropwise at 0° C. The reaction mixture was stirred at rt for 16 h. The reaction mixture was again cooled to 0° C. and ice-cold saturated solution of $Na_2SO_4$ was added dropwise. The aqueous part was extracted with $Et_2O$ (4×500 mL). The combined organic part was dried over $Na_2SO_4$ and concentrated. The residue was purified by CombiFlash column chromatography ($SiO_2$, 0-100% EtOAc/Hex) to obtain the title compound (1.1 g, 79%).

Intermediate 104

(2,2-Difluorospiro[2.2]pentan-1-yl)methanol

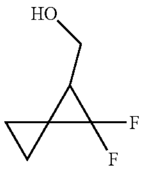

To a solution of 2,2-difluorospiro[2.2]pentane-1-carboxylic acid (0.2 g) in $Et_2O$ (15 mL) was added LAH (2.4 M in THF, 1.12 mL) at 0° C. The resulting reaction mixture was stirred at rt for 16 h. The reaction mixture was again cooled to 0° C. and quenched with saturated $Na_2SO_4$ solution. The reaction mixture was filtered off and the filtrate was diluted with EtOAc. The organic part was washed with water and brine, dried over $Na_2SO_4$ and evaporated under reduced pressure to get the crude product, which was purified by CombiFlash column chromatography ($SiO_2$, 0-50% EtOAc/Hex) to afford the title compound (0.12 g, 66%).

Intermediate 6

(3,3-Difluoro-1-methylcyclobutyl)methyl methanesulfonate

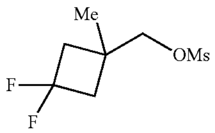 [SMILES: CC1(COS(C)(=O)=O)CC(F)(F)C1]

To a stirred solution of (3,3-difluoro-1-methylcyclobutyl)methanol (0.40 g) in DCM (15 mL) were added $Et_3N$ (0.88 mL) and MsCl (0.23 mL) at 0° C. The resulting mixture was stirred for 2 h at rt. The reaction mixture was then washed with ice-cold $NH_4Cl$ solution (30 mL) and extracted with EtOAc (3×50 mL). The combined organic layers were washed with brine (50 mL) and dried over $Na_2SO_4$. The solvent was evaporated under reduced pressure to get the title compound (0.16 g, crude).

Intermediate 7

(4-Fluorobicyclo[2.2.1]heptan-1-yl)methanol

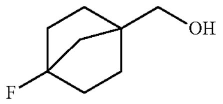

To a stirred solution of 4-fluorobicyclo[2.2.1]heptane-1-carboxylic acid (0.25 g) in THF (15 mL) was added borane dimethyl sulphide complex (0.3 mL) dropwise at rt. The reaction mixture was stirred for 16 h. The reaction mixture was quenched with methanol and concentrated under reduced pressure to get the crude product, which was purified by CombiFlash column chromatography ($SiO_2$, 0-30% EtOAc/Hex) to obtain the title compound (0.20 g, 88%).

Intermediate 105

Dispiro[$2.0.2^4$. $1^3$]heptan-7-ylmethyl methanesulfonate

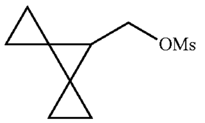 [SMILES: CS(=O)(=O)OCC1C2(CC2)C12CC2]

To a solution of dispiro[$2.0.2^4.1^3$]heptan-7-ylmethanol (Intermediate 100, 0.4 g) in DCM (15.0 mL) were added MsCl (0.4 mL) and $Et_3N$ (1.4 mL) at 0° C. The resulting reaction mixture was stirred at rt for 1 h. The reaction mixture was diluted with cold water and extracted with DCM (2×100 mL). The combined organic layers were dried over $Na_2SO_4$ and concentrated under reduced pressure to get the title compound, which was used in the next step without further purification (0.65 g, crude).

Intermediate 106

(3-Oxobicyclo[3.1.0]hexan-1-yl)methyl methanesulfonate

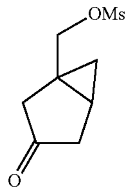 [SMILES: CS(=O)(=O)OCC12CC(=O)CC1C2]

Part 1: To a stirred solution of but-2-yne-1,4-diol (5.0 g) in DCM (100 mL) were added imidazole (7.9 g) and TBDMS chloride (10.53 g) portionwise at 0° C. The resulting reaction mixture was stirred at 0° C. for 2 h under an argon atmosphere. The reaction mixture was quenched with cold water (250 mL) and extracted with DCM (2×250 mL). The combined organic layers were washed with water (150 mL) and brine (150 mL), dried over anhydrous $Na_2SO_4$ and concentrated under reduced pressure to afford 4-((tert-butyldimethylsilyl)oxy)but-2-yn-1-ol (10.4 g, crude), which was directly used in the next step without further purification.

Part 2: To a stirred solution of 4-((tert-butyldimethylsilyl)oxy)but-2-yn-1-ol (10 g) in DCM (200 mL) was added DMP (42.4 g) portionwise at 0° C. The resulting reaction mixture was stirred at 0° C.—rt for 6 h under an argon atmosphere. The reaction mixture was filtered through a celite bed and the celite bed was washed with excess DCM (300 mL). The filtrate was concentrated under reduced pressure to get the crude product, which was purified by column chromatography ($SiO_2$, 3% EtOAc/PE) to afford 4-((tert-butyldimethylsilyl)oxy)but-2-ynal (7.1 g, 61% over 2 steps).

Part 3: To a stirred solution of 4-((tert-butyldimethylsilyl)oxy)but-2-ynal (7.0 g) in THF (105 mL) was added allyl magnesium chloride (1M in THF, 105.9 mL) dropwise at 0° C. The resulting reaction mixture was stirred at 0° C.—rt for 3 h under an argon atmosphere. The reaction mixture was quenched with sat. $NH_4Cl$ solution (250 mL) at 0° C. and was extracted with ethylacetate (2×200 mL). The combined organic layers were washed with water (200 mL) and brine (200 mL), dried over anhydrous $Na_2SO_4$ and concentrated under reduced pressure to get the crude product, which was purified by column chromatography ($SiO_2$, 7% EtOAc/PE) to afford 7-((tert-butyldimethylsilyl)oxy)hept-1-en-5-yn-4-ol (5.6 g, 66%).

Part 4: To a stirred solution of 7-((tert-butyldimethylsilyl)oxy)hept-1-en-5-yn-4-ol (3.5 g) in toluene (70 mL) was added $PtCl_2$ (194 mg) at rt. The resulting reaction mixture was stirred at 85° C. for 8 h under an argon atmosphere. The reaction mixture was concentrated under reduced pressure to obtain a residue. The residue was diluted with water (100 mL) and extracted with ethylacetate (2×100 mL). The combined organic layers were washed with water (75 mL) and brine (75 mL), dried over anhydrous $Na_2SO_4$ and concentrated under reduced pressure to get the crude product, which was purified by column chromatography ($SiO_2$, 2% EtOAc/PE) to afford 1-(((tert-butyldimethylsilyl)oxy)methyl)bicyclo[3.1.0]hexan-3-one (1.62 g, 46%).

Part 5: To a stirred solution of 1-(((tert-butyldimethylsilyl)oxy)methyl)bicyclo[3.1.0]hexan-3-one (1.6 g) in THF (32 mL) was added TBAF in THF (1M, 8.0 mL) at 0° C. The resulting reaction mixture was stirred at 0° C.—rt for 2 h under an argon atmosphere. The reaction mixture was quenched with sat. $NaHCO_3$ solution (50 mL) at 0° C. and was extracted with ethylacetate (2×50 mL). The combined organic layers were washed with water (40 mL) and brine (40 mL), dried over anhydrous $Na_2SO_4$ and concentrated under reduced pressure to afford 1-(hydroxymethyl)bicyclo[3.1.0]hexan-3-one (890 mg, crude), which was directly used in the next step without further purification.

Part 6: To a stirred solution of 1-(hydroxymethyl)bicyclo[3.1.0]hexan-3-one (0.8 g) in DCM (15 mL) was added TEA (0.961 g) followed by MsCl (1.08 g) dropwise at 0° C. under an argon atmosphere. The reaction mixture was stirred at 0° C.-rt for 4 h. The reaction mixture was quenched with cold water (20 mL) and extracted with DCM (2×25 mL). The combined organic layers were washed with water (20 mL) and brine (20 mL), dried over anhydrous $Na_2SO_4$ and concentrated under reduced pressure to afford the title compound (1.0 g, crude), which was used in the next step without further purification.

Intermediate 107

(3.3-Difluoro-1-methylcyclopentyl)methyl trifluoromethanesulfonate

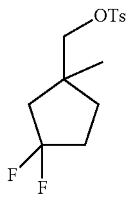 [SMILES: Cc1ccc(S(=O)(=O)OCC2(C)CCC(F)(F)C2)cc1]

Part 1: To a stirred solution of ethyl 3-oxocyclopentane-1-carboxylate (50 g) in DCM (750 mL) was added DAST (169 mL) at 0° C. under an argon atmosphere. The resulting reaction mixture was stirred at rt for 24 h. The reaction mixture was quenched with cold sat. $NaHCO_3$ solution (1.5 L) and extracted with DCM (2×1.0 L). The combined organic layers were washed with water (800 mL) and brine (800 mL), dried over anhydrous $Na_2SO_4$ and concentrated under reduced pressure to afford ethyl 3,3-difluorocyclopentane-1-carboxylate (52 g, crude), which was directly used in the next step without further purification.

Part 2: To a stirred solution of ethyl 3,3-difluorocyclopentane-1-carboxylate (50.0 g) in THF (70 mL) was added LiHMDS in THF (1M, 365 mL) at −5° C. and the mixture was stirred at 0° C. for 30 minutes under an argon atmosphere. To the reaction mixture was added a solution of methyl iodide (59.83 g) in THF (1.0 L) and the mixture was stirred at 0° C.—rt for 12 h. The reaction mixture was slowly quenched with saturated aq. $NH_4Cl$ solution (1.0 L) and extracted with EtOAc (2×1.0 L). The combined organic layers were washed with water (700 mL) and brine (700 mL), dried over anhydrous $Na_2SO_4$ and concentrated under reduced pressure to afford ethyl 3,3-difluoro-1-methylcyclopentane-1-carboxylate (51 g, crude), which was directly used in the next step without further purification.

Part 3: To a stirred solution of ethyl 3,3-difluoro-1-methylcyclopentane-1-carboxylate (51.0 g) in THF (1.02 L) was added LAH in THF (1M, 398.5 mL) at 0° C. under an argon atmosphere. The reaction mixture was stirred at 0° C. for 2 h. The reaction mixture was slowly poured into crushed ice (1 kg), the pH was adjusted with 1N aq. HCl solution to ~6. The mixture was stirred well and was then extracted with EtOAc (2×1.0 L). The combined organic layers were washed with water (700 mL) and brine (700 mL), dried over anhydrous $Na_2SO_4$ and concentrated under reduced pressure to gt the crude product, which was purified by column chromatography ($SiO_2$, 15% EtOAc/PE) to afford (3,3-difluoro-1-methylcyclopentyl)methanol (20.2 g, 42% over 3 steps).

Part 4: To a stirred solution of (3,3-difluoro-1-methylcyclopentyl)methanol (20 g) in DCM (400 mL) was added pyridine (21.06 g) followed by the addition of frifluoromethane sulfonic anhydride (48.88 g) dropwise at 0° C. under an argon atmosphere. The resulting reaction mixture was stirred at 0° C. for 2 h. The reaction mixture was quenched with water (500 mL) and extracted with DCM (2×500 mL). The combined organic layers were washed with water (300 mL) and brine (300 mL), dried over anhydrous $Na_2SO_4$ and concentrated under reduced pressure to afford the title compound (37.8 g, crude), which was directly used in the next step without further purification.

Intermediate 108

1-(Spiro[2.3]hexan-5-yl)ethan-1-one

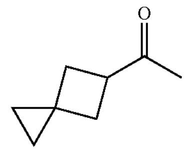

Part 1: To a stirred solution of 3-methylenecyclobutane-1-carboxylic acid (3.7 g) in MeCN (50 mL) were added $Cs_2CO_3$ (16.1 g) and iodo methane (3.0 mL) at 0° C. The reaction mixture was stirred at rt for 2 h. The reaction mixture was poured into ice water (100 mL) and extracted with $Et_2O$ (3×100 mL). The combined organic layers were washed with water (150 mL) and brine (150 mL), dried over anhydrous $Na_2SO_4$ and concentrated under reduced pressure to afford methyl 3-methylenecyclobutane-1-carboxylate (2.0 g, 48%).

Part 2: To a stirred solution of diethylzinc (43.6 mL) in DCM (40 mL) was added TFA (4.8 mL) in DCM (2 mL). Then, diiodomethane was added dropwise (5.2 mL) in DCM (2 mL) at 0° C. The reaction mixture was stirred at 0° C. for 1 h. Then, methyl 3-methylenecyclobutane-1-carboxylate (3.5 g) in DCM (5 mL) was added dropwise at 0° C. and the mixture was stirred at rt for 16 h. The reaction mixture was quenched with sat $NH_4Cl$ solution (50 mL) and extracted with EtOAc (3×50 mL). The combined organic layers were washed with water (50 mL) and brine (50 mL), dried over anhydrous $Na_2SO_4$ and concentrated under reduced pressure to get the crude material which was purified by column chromatography ($SiO_2$, 4-5% EtOAc/PE) to afford methyl spiro[2.3]hexane-5-carboxylate (3.5 g, 90%).

Part 3: To a stirred solution of methyl spiro[2.3]hexane-5-carboxylate (4.0 g) in $MeOH:H_2O$ (1:1, 40 mL) was added LiOH—$H_2O$ (3.6 g) at 0° C. The reaction mixture was stirred at rt for 2 h. The reaction mixture was concentrated under reduced pressure to obtain a residue. The residue was diluted with cold water (50 mL), the aqueous layer was acidified to pH~2 with 1N aq. HCl and extracted with ethylacetate (2×50 mL). The combined organic layers were washed with water (50 mL) and brine (50 mL), dried over anhydrous $Na_2SO_4$ and concentrated under reduced pressure to afford spiro[2.3]hexane-5-carboxylic acid (2.2 g, 61%).

Part 4: To a stirred solution of spiro[2.3]hexane-5-carboxylic acid (2.2 g) in $Et_2O$ (20 mL) was added MeLi (1.6 M in $Et_2O$, 3.6 mL) at −78° C. and the mixture was allowed to warm to rt over 2 h. The reaction mixture was poured into ice water (50 mL) and extracted with $Et_2O$ (3×50 mL). The combined organic layers were washed with water (50 mL) and brine (50 mL), dried over anhydrous $Na_2SO_4$ and concentrated under reduced pressure (bath temp below 30° C.) to afford the title compound (1.0 g, 47%).

Intermediate 109

1-(1-Methoxycyclopropyl)ethan-1-one

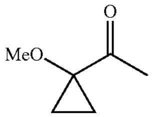

Part 1: To a stirred solution of 1-hydroxycyclopropanecarboxylic acid (5.0 g) in DMF (60 mL) was added NaH (60% in mineral oil, 5.9 g) at 0° C. The reaction mixture was stirred at 0° C. for 30 minutes followed by addition of MeI (10.0 mL) at 0° C. The reaction mixture was stirred at rt for 16 h. The reaction mixture was poured into sat. $NH_4Cl$ (50 mL) solution. The aqueous phase was extracted with MTBE (100 mL×3). The combined organic layers were washed with brine (50 mL), dried with anhydrous $Na_2SO_4$, filtered and concentrated under reduced pressure at low temperature to obtain methyl 1-methoxycyclopropanecarboxylate (6.1 g, 95%).

Part 2: A solution of methyl 1-methoxycyclopropanecarboxylate (6.4 g) in 50% aqueous NaOH solution (64 mL) and methanol (64 mL) was heated to 80° C. for 16 h in a sealed tube. The reaction mixture was cooled to rt and was concentrated under reduced pressure. The resulting crude was diluted with ice water (100 mL) and washed with MTBE (50 mL). The aqueous layer was acidified with NaH $SO_4$ solution to pH-4 and extracted with EtOAc (2×100 mL). The combined organic layers were washed with brine (50 mL), dried over $Na_2SO_4$ and concentrated at low temperature to obtain 1-methoxycyclopropane-1-carboxylic acid (5.2 g, 91%). LCMS m/z=115 $[M-H]^-$.

Part 3: To a stirred solution of 1-methoxycyclopropane-1-carboxylic acid (10.2 g) in DCM (500 mL) were added methoxy(methyl)amine hydrochloride (11.0 g), EDCI·HCl (24.0 g), HOBt (17.0 g) and $Et_3N$ (44 mL) at 0° C. The reaction mixture was stirred at rt for 16 h. The reaction mixture was diluted with ice cold aqueous 1 M HCl (100 mL) solution. The aqueous layer was extracted with DCM (3×500 mL). The combined organic layers were dried over $Na_2SO_4$, filtered and concentrated to get the crude product, which was purified by CombiFlash chromatography ($SiO_2$, 0-30% EtOAc/Hex) to obtain N,1-dimethoxy-N-methylcyclopropane-1-carboxamide (9.0 g, 64%).

Part 4: To a stirred solution of N,1-dimethoxy-N-methylcyclopropane-1-carboxamide (2.2 g) in $Et_2O$ (30 mL) was added MeMgBr (3M in $Et_2O$, 14 mL) at 0° C. The reaction mixture was stirred at rt for 16 h. The reaction mixture was quenched with saturated ammonium chloride solution (80 mL) and extracted with $Et_2O$ (2×80 mL). The combined organic layers were dried over $Na_2SO_4$, filtered through a silica bed and concentrated under reduced pressure at 20° C. to obtain the title compound (1.5 g, 95%).

Intermediate 110

1-(3-Fluorobicyclo[1.1.1]pentan-1-yl)ethan-1-one

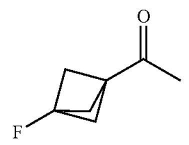

Part 1: To a stirred solution of 3-fluorobicyclo[1.1.1]pentane-1-carboxylic acid (50.0 g) in DMF (500 mL) were added HATU (219.17 g), DIPEA (148.71 g) and N,O-dimethylhydroxylamine hydrochloride (112.40 g) at rt and the resulting reaction mixture was stirred for 2 h at rt. The reaction mixture was diluted with water (500 mL) and extracted with EtOAc (2×250 mL). The combined organic layers were washed with water (150 mL) and brine (150 mL), dried over anhydrous $Na_2SO_4$ and concentrated under reduced pressure to get the crude product which was purified by column chromatography ($SiO_2$, 10-15% EtOAc/PE) to afford 3-fluoro-N-methoxy-N-methylbicyclo[1.1.1]pentane-1-carboxamide (50 g, 75%). LCMS m/z=174 $[M+H]^+$.

Part 2: To a stirred solution of 3-fluoro-N-methoxy-N-methylbicyclo[1.1.1]pentane-1-carboxamide (50 g) in THE (250 mL) was added MeMgBr (3M in $Et_2O$, 144.3 mL) at 0° C. and the mixture was stirred at 0° C. to rt for 4 h. The reaction mixture was quenched with saturated ammonium chloride solution (500 mL) and extracted with $Et_2O$ (2×250 mL). The combined organic layers were dried over anhydrous $Na_2SO_4$ and concentrated under reduced pressure to afford the title compound (50.0 g, crude), which was directly used in the next step without further purification.

Intermediates 111-112

The title compounds were prepared from the appropriate acid using an analogous method to that described for Intermediate 110.

| Intermediate | Structure/Name/Starting Materials/Data |
|---|---|
| 111 | 1-(1-(Trifluoromethyl)cyclopropyl)ethan-1-one<br>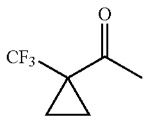<br>Acid: 1-(trifluoromethyl)cyclopropane-1-carboxylic acid<br>Yield: 2.0 g, crude. |
| 112 | 1-(Spiro[2.2]pentan-1-yl)ethan-1-one<br>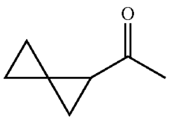<br>Acid: spiro[2.2]pentane-1-carboxylic acid<br>Yield: 1.0 g, 70%. |

Intermediate 113

1-((Trans)-2-methylcyclopropyl)ethan-1-one

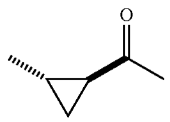

Part 1: To a solution of (trans)-2-methylcyclopropane-1-carboxylic acid (9.0 g) in DCM (250 mL) were added methoxy(methyl)amine hydrochloride (11.5 g), EDCI·HCl (24.2 g), HOBt (17.1 g) and $Et_3N$ (5.0 mL) at rt. The reaction mixture was stirred at rt for 16 h. The reaction was quenched with an ice cold aqueous (1M) HCl solution and the layers are separated. The aqueous layer was extracted with DCM (3×500 mL). The combined organic layers was dried over $Na_2SO_4$, filtered and evaporated under reduced pressure to get the crude product, which was purified by column chromatography ($SiO_2$, 0-35% EtOAc/Hex) to obtain (trans)-N-methoxy-N,2-dimethylcyclopropane-1-carboxamide (4.5 g, 35%).

Part 2: To a solution of (trans)-N-methoxy-N,2-dimethylcyclopropane-1-carboxamide (4.5 g) in $Et_2O$ (100 mL) was added MeMgBr (3M in $Et_2O$, 28.3 mL) at 0° C. The reaction mixture was stirred at rt for 16 h. The reaction mixture was quenched with sat. $NH_4Cl$ solution and extracted with $Et_2O$ (2×300 mL). The organic layer was dried over $Na_2SO_4$, filtered through a silica bed and concentrated at 20° C. to obtain the title compound (1.2 g, 43%), which was used in the next step without any purification.

Intermediate 114

1-(bicyclo[1.1.1]pentan-1-yl)ethan-1-one

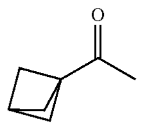

Part 1: To a stirred solution of bicyclo[1.1.1]pentane-1-carboxylic acid (4.0 g) in DCM (100 mL) were added oxalyl chloride (4.62 mL) and DMF (0.3 mL) at 0° C. The reaction mixture was stirred at rt for 2 h. A mixture of methoxy(methyl)amine hydrochloride (5.2 g) and DIPEA (17.7 mL) in DCM (20 mL) was then added dropwise to the reaction mixture at 0° C. The reaction mixture was stirred at rt for another 2 h. The reaction mixture was diluted with ice water and the resulting mixture was extracted with EtOAc. The combined organic layers were dried over $Na_t$ $SO_4$ and concentrated under reduced pressure to get the crude product, which was purified by column chromatography ($SiO_2$, 0-30% EtOAc/Hex) to get N-methoxy-N-methylbicyclo[1.1.1]pentane-1-carboxamide (3.0 g, 54%).

Part 2: To a stirred solution of N-methoxy-N-methylbicyclo[1.1.1]pentane-1-carboxamide (2.3 g) in $Et_2O$ (50 mL) was added MeMgBr (3M in $Et_2O$, 12.5 mL) at 0° C. and the mixture was stirred at rt for 16 h. The reaction mixture was quenched with saturated ammonium chloride solution and extracted with $Et_2O$ (3×70 mL). The combined organic layers were dried over $Na_2SO_4$ and concentrated under reduced pressure (at low temperature: −20° C.) to obtain the title compound (1.3 g, 80%), which was directly used in the next step without further purification.

Intermediate 115

1-(22-Difluorocyclopropyl)ethan-1-one

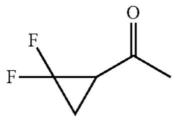

To a stirred solution of 2,2-difluorocyclopropane-1-carboxylic acid (5.0 g) in $Et_2O$ (50 mL) was added MeLi (1.6 M in $Et_2O$, 38.4 mL) at −78° C. and the mixture was slowly allowed to warm to rt over 2 h. The reaction mixture was poured into ice water (100 mL) and was extracted with $Et_2O$ (3×100 mL). The combined organic layers were washed with water (150 mL) and brine (150 mL), were dried over anhydrous $Na_2SO_4$ and concentrated under reduced pressure (bath temp. below 30° C.) to afford the title compound (2.0 g, crude), which was directly used in the next step without further purification.

Intermediate 116

1-(2-Fluorocyclopropyl ethan-1-one

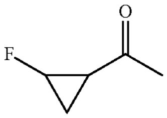

To a stirred solution of 2-fluorocyclopropane-1-carboxylic acid (4.0 g) in $Et_2O$ (40 mL) was added MeLi (1.6 M in $Et_2O$, 48 mL) at −78° C. and the mixture was slowly allowed to warm to rt over 2 h. The reaction mixture was poured into ice water (50 mL) and was extracted with MTBE (3×30 mL). The combined organic layers were washed with water (50 mL) and brine (50 mL), dried over anhydrous $Na_2SO_4$ and concentrated under reduced pressure (bath temp. below 30° C.) to yield the title compund (4.0 g, crude), which was directly used in next step without further purification.

Intermediate 18

Ethyl 3-acetyl-1H-pyrazole-5-carboxylate

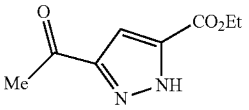 [SMILES: CCOC(=O)c1cc(C(C)=O)n[nH]1]

To a solution of $InCl_3$ (3.25 g) in water (200 mL) were added but-3-yn-2-one (5.0 g) and ethyl diazoacetate (9.31 mL) at rt and the reaction mixture was stirred at rt for 16 h. The reaction mixture was diluted with ice water and extracted with EtOAc (3×300 mL). The combined organics were washed with brine, dried ($Na_2SO_4$) and concentrated under reduced pressure. The residue was washed with hexane to afford the title compound (7.5 g 56%). LCMS m/z=183 $[M+H]^+$.

Intermediate 19

Ethyl 3-(11-difluoroethyl)-1H-pyrazole-5-carboxylate

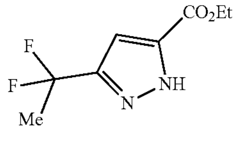 [SMILES: CCOC(=O)c1cc(C(C)(F)F)n[nH]1]

To a solution of ethyl 3-acetyl-1H-pyrazole-5-carboxylate (Intermediate 18, 6.0 g) in DCM (150 mL) was added DAST (17.4 mL) dropwise at 0° C. and the resulting mixture was stirred at rt for 16 h. The reaction was quenched with cold sat. $NaHCO_3$ solution and extracted with DCM (3×100 mL). The combined organics were dried ($Na_2SO_4$) and evaporated to dryness under reduced pressure. The residue was purified by CombiFlash chromatography ($SiO_2$, 0-40% EtOAc/Hex) to afford the title compound (6 g, 89%). LCMS m/z=205 $[M+H]^+$.

Intermediate 20

Methyl 3-(benzyloxy)-1H-pyrazole-5-carboxylate

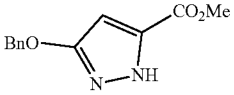

To a stirred solution of methyl 3-hydroxy-1H-pyrazole-5-carboxylate (10 g) in DMF (180 mL) were added $Cs_2CO_3$ (25.24 g) and benzyl bromide (8.36 mL) at rt and the mixture was stirred at rt for 1 h. The reaction was quenched with crushed ice and extracted with EtOAc (3×300 mL). The combined organics were washed with cold brine, dried ($Na_2SO_4$) and concentrated under reduced pressure. The residue was purified by CombiFlash chromatography ($SiO_2$, 0-20% EtOAc/Hex) to afford the title compound (12 g, 73%). LCMS m/z=233 $[M+H]^+$.

Intermediate 117

Methyl 3-(1-fluorocyclopropyl)-1H-pyrazole-5-carboxylate

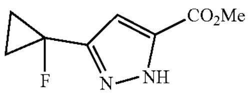 [SMILES: COC(=O)c1cc(C2(F)CC2)n[nH]1]

Part 1: To a stirred solution of 1-(1-fluorocyclopropyl) ethan-1-one (4.0 g) in THF (40 mL) was added LiHMDS (1M in THF, 58.7 mL) at −78° C. under nitrogen atmosphere and the mixture was stirred for 1 h. To the reaction mixture was then added dimethyl oxalate (6.93 g) at −78° C. and the resulting reaction mixture was stirred for 16 h at rt. The reaction mixture was quenched with sat $NH_4Cl$ solution (50 mL) and extracted with EtOAc (3×50 mL). The combined organic layers were washed with water (50 mL) and brine (50 mL), dried over anhydrous $Na_2SO_4$ and concentrated under reduced pressure to afford methyl 4-(1-fluorocyclopropyl)-2,4-dioxobutanoate (6.0 g, crude), which was directly used in the next step without further purification.

Part 2: To a stirred solution of methyl 4-(1-fluorocyclopropyl)-2,4-dioxobutanoate (6.0 g) in acetic acid (40 mL) was added $N_2H_4 \cdot H_2O$ (3.1 mL) at rt. The resulting reaction mixture was then heated to 80° C. for 16 h. The reaction mixture was cooled to rt, diluted with water (50 mL) and extracted with EtOAc (3×50 mL). The combined organic layers were washed with saturated $NaHCO_3$ solution (50 mL), water (15 mL) and brine (50 mL), dried over anhydrous $Na_2SO_4$ and concentrated under reduced pressure to get the crude material which was purified by column chromatography ($SiO_2$, 25% EtOAc/PE) to yield the title compound (2.9 g, 40% over two steps). LCMS m/z=185 $[M+H]^+$.

Intermediates 118-127

The title compounds were prepared from the appropriate ketones using an analogous method (at a suitable reaction time between 1-16 h for part 1 and a suitable reaction time between 4-16 h and a suitable reaction temperature between 80-100° C. for part 2) to that described for Intermediate 117.

| Intermediate | Structure/Name/Starting Materials/Data |
|---|---|
| 118 | Methyl 3-cyclopentyl-1H-pyrazole-5-carboxylate<br>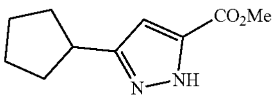 [SMILES: COC(=O)c1cc(C2CCCC2)n[nH]1]<br>Ketone: 1-cyclopentylethan-1-one<br>Yield: 7.0 g, 39% over two steps; LCMS m/z = 195 $[M + H]^+$. |
| 119 | Methyl 3-(spiro[2.3]hexan-5-yl)-1H-pyrazole-5-carboxylate<br>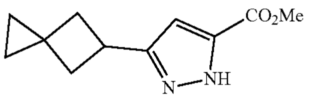 [SMILES: COC(=O)c1cc(C2CC3(CC3)C2)n[nH]1]<br>Ketone: 1-(spiro[2.3]hexan-5-yl)ethan-1-one (Intermediate 108)<br>Yield: 500 mg, 50% over two steps. |
| 120 | Methyl 3-(3,3-difluorocyclobutyl)-1H-pyrazole-5-carboxylate<br>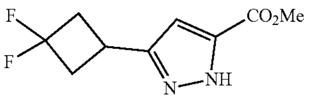 [SMILES: COC(=O)c1cc(C2CC(F)(F)C2)n[nH]1]<br>Ketone: 1-(3,3-difluorocyclobutyl)ethan-1-one<br>Yield: 1.8 g, crude; LCMS m/z = 217 $[M + H]^+$. |
| 121 | Methyl 3-(3-methoxybicyclo[1.1.1]pentan-1-yl)-1H-pyrazole-5-carboxylate<br>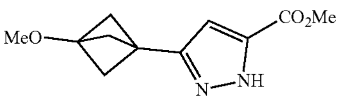 [SMILES: COC(=O)c1cc(C23CC(OC)(C2)C3)n[nH]1]<br>Ketone: 1-(3-methoxybicyclo[1.1.1]pentan-1-yl)ethan-1-one<br>Yield: 300 mg, crude; LCMS m/z = 223 $[M + H]^+$. |
| 122 | Methyl 3-(1-(difluoromethyl)cyclopropyl)-1H-pyrazole-5-carboxylate<br>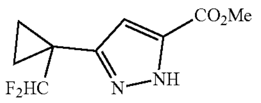<br>Ketone: 1-(1-(difluoromethyl)cyclopropyl)ethan-1-one<br>Yield: 2.9 g, 64% over two steps; LCMS m/z = 217 $[M + H]^+$. |
| 123 | Methyl 3-(1-(trifluoromethyl)cyclopropyl)-1H-pyrazole-5-carboxylate<br>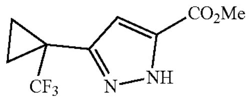 [SMILES: COC(=O)c1cc(C2(C(F)(F)F)CC2)n[nH]1]<br>Ketone: 1-(1-(trifluoromethyl)cyclopropyl)ethan-1-one (Intermediate 111)<br>Yield: 800 mg, 34% over three steps; LCMS m/z = 235 $[M + H]^+$. |
| 124 | Methyl 3-(3-fluorobicyclo[1.1.1]pentan-1-yl)-1H-pyrazole-5-carboxylate<br>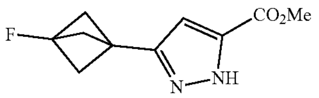 [SMILES: COC(=O)c1cc(C23CC(F)(C2)C3)n[nH]1]<br>Ketone: 1-(3-fluorobicyclo[1.1.1]pentan-1-yl)ethan-1-one (Intermediate 110)<br>Yield: 25.0 g, 41% over three steps; LCMS m/z = 211 $[M + H]^+$. |
| 125 | Methyl 3-(bicyclo[1.1.1]pentan-1-yl)-1H-pyrazole-5-carboxylate<br>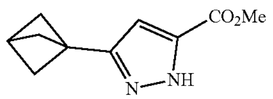 [SMILES: COC(=O)c1cc(C23CC(C2)C3)n[nH]1]<br>Ketone: 1-(bicyclo[1.1.1]pentan-1-yl)ethan-1-one (Intermediate 114)<br>Yield: 1.0 g, crude. |
| 126 | Methyl 3-(2,2-difluorocyclopropyl)-1H-pyrazole-5-carboxylate<br>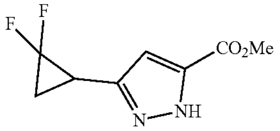 [SMILES: COC(=O)c1cc(C2CC2(F)F)n[nH]1]<br>Ketone: 1-(2,2-difluorocyclopropyl)ethan-1-one (Intermediate 115)<br>Yield: 1.5 g, 9% over three steps; LCMS m/z = 203 $[M + H]^+$. |
| 127 | Methyl 3-(2-fluorocyclopropyl)-1H-pyrazole-5-carboxylate<br>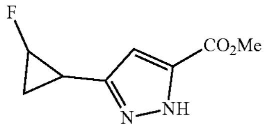 [SMILES: COC(=O)c1cc(C2CC2F)n[nH]1] |

-continued

-continued

| Intermediate | Structure/Name/Starting Materials/Data |
|---|---|
| | Ketone: 1-(2-fluorocyclopropyl)ethan-1-one (Intermediate 116)<br>Yield: 500 mg, 7% over three steps; LCMS m/z = 185 $[M + H]^+$. |

Intermediate 128

Methyl 3-cyclobutyl-1H-pyrazole-5-carboxylate

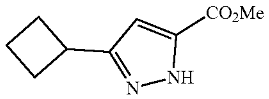 [SMILES: COC(=O)c1cc(C2CCC2)n[nH]1]

Part 1: To a stirred solution of 1-cyclobutylethan-1-one (4.0 g) and dimethyl oxalate (4.2 g) in toluene (30 mL) was added potassium tert-butoxide (5.4 g) portionwise in THE at 0° C. The resulting reaction mixture was stirred for 16 h at rt. The reaction mixture was quenched with sat 1N HCl solution (50 mL) and extracted with EtOAc (3×30 mL). The combined organic layers were washed with water (30 mL) and brine (30 mL), dried over anhydrous $Na_2SO_4$ and concentrated under reduced pressure to afford methyl 4-cyclobutyl-2,4-dioxobutanoate (4.2 g, 83%), which was directly used in the next step without further purification. LCMS m/z=185 $[M+H]^+$.

Part 2: To a stirred solution of methyl 4-cyclobutyl-2,4-dioxobutanoate (4.0 g) in acetic acid (6.0 mL) was added $N_2H_4{\cdot}H_2O$ (2.1 g) at 0° C. The resulting reaction mixture was stirred for 16 h at rt. The reaction mixture was quenched with sat. $NaHCO_3$ solution (50 mL) and extracted with EtOAc (3×30 mL). The combined organic layers were washed with water (50 mL) and brine (50 mL), dried over anhydrous $Na_2SO_4$ and concentrated under reduced pressure to give the crude product, which was purified by column chromatography ($SiO_2$, 25% EtOAc/PE) to afford the title compound (2.0 g, 81%). LCMS m/z=181 $[M+H]^+$.

Intermediate 129

Ethyl 3-(1-cyanocyclopropyl)-1H-pyrazole-5-carboxylate

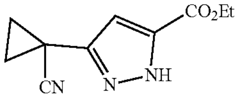 [SMILES: CCOC(=O)c1cc(C2(C#N)CC2)n[nH]1]

To a solution of 1-acetylcyclopropane-1-carbonitrile (4.2 g) in dry THF (80 mL) was added tBuOK (1M in THF, 46.2 mL) at rt and the mixture was stirred for 15 min followed by the addition of diethyl oxalate (5.6 mL). The reaction mixture was stirred at rt for 16 h. Then, $N_2H_4$-$H_2O$ (2.7 mL) and acetic acid (5.7 mL) were added to the reaction mixture. The mixture was heated to reflux for 4 h. The reaction mixture was concentrated and diluted with EtOAc (200 mL) The organic layer was basified (pH-8) with saturated $NaHCO_3$ solution and washed with water (100 mL) and brine (100 mL). The organic layer was dried over $Na_2SO_4$ and concentrated to get the crude product which was purified by column chromatography ($SiO_2$, 0-50% EtOAc/Hex) to yield the title compound (2.2 g, 28%). LCMS m/z=206 $[M+H]^+$.

Intermediates 130-134

The title compounds were prepared from the appropriate ketones using an analogous method (at a suitable reaction time between 2-4 h under reflux conditions) to that described for Intermediate 129.

| Intermediate | Structure/Name/Starting Materials/Data |
|---|---|
| 130 | Ethyl 3-(1-methylcyclopropyl)-1H-pyrazole-5-carboxylate<br>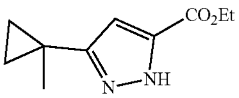<br>Ketone: 1-(1-methylcyclopropyl)ethan-1-one<br>Yield: 320 mg, 33% over two steps; LCMS m/z = 195 $[M + H]^+$. |
| 131 | Ethyl 3-(1-methoxycyclopropyl)-1H-pyrazole-5-carboxylate<br>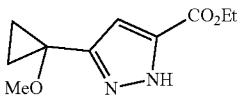 [SMILES: CCOC(=O)c1cc(C2(OC)CC2)n[nH]1]<br>Ketone: 1-(1-methoxycyclopropyl)ethan-1-one (Intermediate 109)<br>Yield: 1.5 g, 39%; LCMS m/z = 211 $[M + H]^+$. |
| 132 | Ethyl 3-((trans)-2-methylcyclopropyl)-1H-pyrazole-5-carboxylate<br>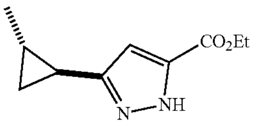<br>Ketone: 1-((trans)-2-methylcyclopropyl)ethan-1-one (Intermediate 113)<br>Yield: 0.9 g, 21%; LCMS m/z = 195 $[M + H]^+$. |
| 133 | Ethyl 3-(bicyclo[1.1.1]pentan-1-yl)-1H-pyrazole-5-carboxylate<br>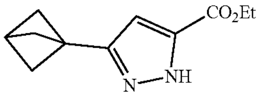 [SMILES: CCOC(=O)c1cc(C23CC(C2)C3)n[nH]1]<br>Ketone: 1-{bicyclo[1.1.1]pentan-1-yl}ethan-1-one (Intermedate 114)<br>Yield: 1.0 g, 33%; LCMS m/z = 207 $[M + H]^+$. |
| 134 | Ethyl 3-(spiro[2.2]pentan-1-yl)-1H-pyrazole-5-carboxylate<br>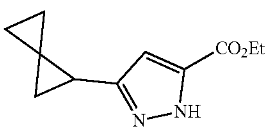 [SMILES: CCOC(=O)c1cc(C2CC23CC3)n[nH]1]<br>Ketone: 1-(spiro[2.2]pentan-1-yl)ethan-1-one (Intermediate 112)<br>Yield: 1.0 g, 70%. |

Intermediate 135

Ethyl 3-(2-hydroxypropan-2-yl)-1H-pyrazole-5-carboxylate

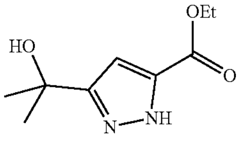

To a stirred solution of zinc trifluoromethanesulfonate (5.186 g), 2-methylbut-3-yn-2-ol (6.0 g) and $Et_3N$ (14.91 mL) was slowly added ethyl 2-diazoacetate (9.758 g) at rt. The resulting reaction mixture was heated to 100° C. for 8 h. The reaction mixture was slowly quenched with ice water (120 mL) and extracted with EtOAc (2×75 mL). The combined organic layers were washed with water (50 mL) and brine (50 mL), dried over anhydrous $Na_2SO_4$ and concentrated under reduced pressure to get the crude product, which was purified by column chromatography ($SiO_2$, 10-15% EtOAc/PE) to afford the title compound (2.0 g, 14%). LCMS m/z=199 $[M+H]^+$.

Intermediate 136

Ethyl 1-((3,3-difluoro-1-methylcyclobutyl)methyl)-3-(2,2-difluorobicyclo[1.1.1]pentan-1-yl)-1H-pyrazole-5-carboxylate

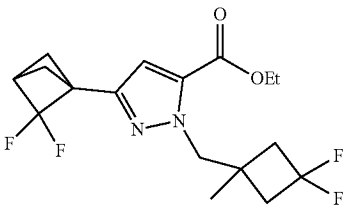 [SMILES: CCOC(=O)c1cc(C23CC(C2)C3(F)F)nn1CC1(C)CC(F)(F)C1]

Part 1: To 5-acetyl-2H-pyrazole-3-carboxylic acid ethyl ester (Intermediate 18, 1.50 g), (3,3-difluoro-1-methyl-cyclobutyl)methanol (1.35 g) and ADDP (2.49 g) in THE (80 mL) was added tributylphosphine (2.5 g) dropwise. The mixture was stirred at rt for 16 h. Then, EtOAc (100 mL) and sat. $NaHCO_3$ solution (30 mL) were added. The layers were separated and the aqueous layer was extracted with EtOAc (30 mL). The combined organic layers were washed with brine (20 mL), dried over anhydrous $Na_2SO_4$ and concentrated under reduced pressure to afford the crude product, which was purified by column chromatography ($SiO_2$, 5% EtOAc/Hex) to obtain ethyl 5-acetyl-2-[(3,3-difluoro-1-methyl-cyclobutyl)methyl]pyrazole-3-carboxylate (2.03 g, 82%). LCMS m/z=301 $[M+H]^+$.

Part 2: Ethyl 5-acetyl-2-[(3,3-difluoro-1-methyl-cyclobutyl)methyl]pyrazole-3-carboxylate (750 mg) and scandium(III) trifluoromethanesulfonate (61 mg) were dissolved in 15 mL of DCM. Then, 3,3-difluoroprop-2-en-1-amine hydrochloride (650 mg) and DIPEA (1.7 mL) in 10 mL DCE was added and the reaction mixture was heated to 60° C. for 16 h. The mixture was then cooled to 0° C. before the addition of DIPEA (1.7 mL) and (2,2,2-trifluoroacetyl) 2,2,2-trifluoroacetate (1.6 g). The reaction mixture was then stirred at rt for 1 h. The mixture was filtered through a sintered funnel, the funnel was washed with 100 mL of DCM. The organic layer was washed with sat. $NH_4Cl$ solution (30 mL). The layers were separated and the organic layer was concentrated under reduced pressure. The residue was purified by column chromatography to yield ethyl 5-[1-[3,3-difluoroallyl-(2,2,2-trifluoroacetyl)amino]vinyl]-2-[(3,3-difluoro-1-methyl-cyclobutyl)methyl]pyrazole-3-carboxylate (510 mg, 43%).

Part 3: Ethyl 5-[1-[3,3-difluoroallyl-(2,2,2-trifluoroacetyl)amino]vinyl]-2-[(3,3-difluoro-1-methyl-cyclobutyl)methyl]pyrazole-3-carboxylate (720 mg) was dissolved in MeCN (15 mL) under a nitrogen atmosphere. (4,4'-Di-t-butyl-2,2'-bipyridine)bis[3,5-difluoro-2-[5-trifluoromethyl-2-pyridinyl-kN)phenyl-kC]iridium(III) hexafluorophosphate (17 mg) dissolved in MeCN (1 mL) was then added and the resulting mixture was irradiated at 450 nm (95% intensity using a Lucent apparatus) for 16 h at rt. Another aliquot of (4,4'-di-t-butyl-2,2'-bipyridine)bis[3,5-difluoro-2-[5-trifluoromethyl-2-pyridinyl-kN)phenyl-kC]iridium(III) hexafluorophosphate (17 mg) dissolved in MeCN (1 mL) was added and the reaction was irradiated under the same conditions for 24 h. The reaction mixture was then diluted with EtOAc and was washed with sat. $NaHCO_3$ solution. The layers were separated, dried over $MgSO_4$ and the solvent was removed under reduced pressure. The residue was purified via column chromatography ($SiO_2$, 10% EtOAc/Hex) to yield ethyl 2-[(3,3-difluoro-1-methyl-cyclobutyl)methyl]-5-[5,5-difluoro-3-(2,2,2-trifluoroacetyl)-3-azabicyclo[2.1.1]hexan-4-yl]pyrazole-3-carboxylate (580 mg, 80%).

Part 4: To a solution of ethyl 2-[(3,3-difluoro-1-methyl-cyclobutyl)methyl]-5-[5,5-difluoro-3-(2,2,2-trifluoroacetyl)-3-azabicyclo[2.1.1]hexan-4-yl]pyrazole-3-carboxylate (580 mg) in EtOH (4 mL) was added NaOH (74 mg) and the mixture was stirred for 15 minutes. The mixture was diluted with EtOAc (30 mL) and was washed with water (5 mL). The organic layer was dried over $MgSO_4$ and the solvent was removed under reduced pressure. The residue was purified via column chromatography ($SiO_2$, 50% EtOAc/Hex) to yield ethyl 5-(5,5-difluoro-3-azabicyclo[2.1.1]hexan-4-yl)-2-[(3,3-difluoro-1-methyl-cyclobutyl)methyl]pyrazole-3-carboxylate (370 mg, 80%). LCMS m/z=376 $[M+H]^+$.

Part 5: Ethyl 5-(5,5-difluoro-3-azabicyclo[2.1.1]hexan-4-yl)-2-[(3,3-difluoro-1-methyl-cyclobutyl)methyl]pyrazole-3-carboxylate (270 mg) was dissolved in degassed THE (2 mL), followed by the addition of N-(benzyloxy)-1-[4-(trifluoromethyl)phenyl]formamido 2,2-dimethylpropanoate (528 mg) in 2 mL of degassed THF. The mixture was heated to 60° C. for 16 h. The mixture was diluted with EtOAc (50 mL) and was washed with sat. $NH_4Cl$ solution (10 mL). The layers were separated, and the aqueous layer was extracted with EtOAc (20 mL). The combined organic layers were dried over $MgSO_4$ and the solvent was removed under reduced pressure. The residue was purified by column chromatography ($SiO_2$, 5% EtOAc/Hex) to the title compound (80 mg, 31%). LCMS m/z=361 $[M+H]^+$.

Intermediate 21

Ethyl 3-cyclopropyl-4-iodo-1H-pyrazole-5-carboxylate

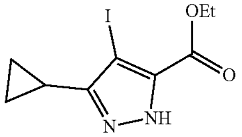 [SMILES: CCOC(=O)c1[nH]nc(C2CC2)c1I]

NIS (26.27 g) was added portion wise to a solution of ethyl 3-cyclopropyl-1H-pyrazole-5-carboxylate (15 g) in DCM (150 mL) at 0° C. and the reaction mixture was stirred for 2 h at rt. The reaction mixture was quenched with saturated sodium thiosulfate (200 mL) at 0° C. and extracted with DCM (2×250 mL). The combined organics were washed with saturated $NaHCO_3$ (250 mL), brine (200 mL), dried ($Na_2SO_4$) and evaporated to dryness under reduced pressure. The residue was purified by CombiFlash chromatography ($SiO_2$, 2-5% EtOAc/Hex) to afford the title compound (25 g, 90%). LCMS m/z=307 $[M+H]^+$.

Intermediate

The title compounds were prepared from the appropriate pyrazoles using an analogous method (at a suitable reaction time between 2-16 h and a suitable reaction temperature between 0° C.-rt) to that described for Intermediate 21.

| Intermediate | Structure/Name/Starting Materials/Data |
|---|---|
| 137 | Ethyl 4-iodo-3-(1-methylcyclopropyl)-1H-pyrazole-5-carboxylate 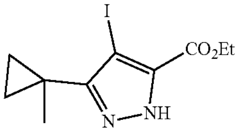 Pyrazole: ethyl 3-(1-methylcyclopropyl)-1H-pyrazole-5-carboxylate (Intermediate 130) Yield: 530 mg, 46%; LCMS m/z = 321 $[M + H]^+$. |
| 138 | Ethyl 4-iodo-3-(1-methoxycyclopropyl)-1H-pyrazole-5-carboxylate 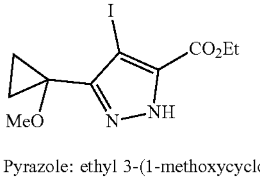 Pyrazole: ethyl 3-(1-methoxycyclopropyl)-1H-pyrazole-5-carboxylate (Intermediate 131) Yield: 200 mg, 3%; LCMS m/z = 337 $[M + H]^+$. |
| 139 | Ethyl 4-iodo-3-((trans)-2-methylcyclopropyl)-1H-pyrazole-5-carboxylate 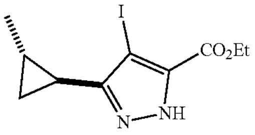 Pyrazole: ethyl 3-((trans)-2-methylcyclopropyl)-1H-pyrazole-5-carboxylate (Intermediate 132) Yield: 3.3 g, 91%; LCMS m/z = 321 $[M + H]^+$. |

-continued

| Intermediate | Structure/Name/Starting Materials/Data |
|---|---|
| 140 | Ethyl 3-(bicyclo[1.1.1]pentan-1-yl)-4-iodo-1H-pyrazole-5-carboxylate 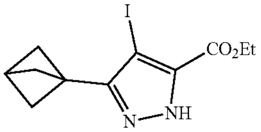 [SMILES: CCOC(=O)c1[nH]nc(C23CC(C2)C3)c1I] Pyrazole: ethyl 3-{bicyclo[1.1.1]pentan-1-yl}-1H-pyrazole-5-carboxylate (Intermediate 133) Yield: 1.3 g, 81%; LCMS m/z = 333 $[M + H]^+$. |
| 141 | Ethyl 4-iodo-3-(spiro[2.2]pentan-1-yl)-1H-pyrazole-5-carboxylate 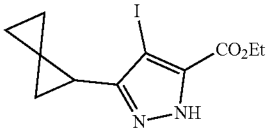 [SMILES: CCOC(=O)c1[nH]nc(C2CC23CC3)c1I] Pyrazole: ethyl 3-(spiro[2.2]pentan-1-yl)-1H-pyrazole-5-carboxylate (Intermediate 134) Yield: 2.5 g, 91%; LCMS m/z = 333 $[M + H]^+$. |

Intermediate 142

Methyl 3-(1-fluorocyclopropyl)-4-iodo-1H-pyrazole-5-carboxylate

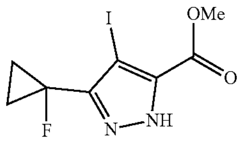 [SMILES: COC(=O)c1[nH]nc(C2(F)CC2)c1I]

To a stirred solution of methyl 3-(1-fluorocyclopropyl)-1H-pyrazole-5-carboxylate (Intermediate 117, 2.9 g) in MeCN (30 mL) were added NIS (5.314 g) and trifluoroacetic acid (1 mL) at rt. The resulting reaction mixture was stirred for 16 h at rt. The reaction mixture was quenched with water (50 mL) and extracted with EtOAc (3×50 mL). The combined organic layers were washed with hypo solution (saturated aqueous solution of $Na_2S_2O_3$, 50 mL), water (50 mL) and brine (50 mL), dried over anhydrous $Na_2SO_4$ and concentrated under reduced pressure to get the crude compound, which was purified by column chromatography ($SiO_2$, 4% EtOAc/PE) to obtain the title compound (4.0 g, 82%). LCMS m/z=311 $[M+H]^+$.

Intermediates 143-156

The title compounds were prepared from the appropriate pyrazoles using an analogous method (at a suitable reaction time between 2-16 h and a suitable reaction temperature between 0-80° C.) to that described for Intermediate 142.

| Intermediate | Structure/Name/Starting Materials/Data |
|---|---|
| 143 | Methyl 3-cyclobutyl-4-iodo-1H-pyrazole-5-carboxylate<br>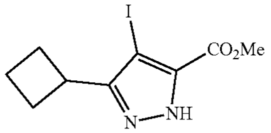 [SMILES: COC(=O)c1[nH]nc(C2CCC2)c1I]<br>Pyrazole: methyl 3-cyclobutyl-1H-pyrazole-5-carboxylate (Intermediate 128)<br>Yield: 2.2 g mg, 95%%; LCMS m/z = 307 [M + H]$^+$. |
| 144 | Methyl 3-cyclopentyl-4-iodo-1H-pyrazole-5-carboxylate<br>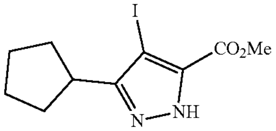 [SMILES: COC(=O)c1[nH]nc(C2CCCC2)c1I]<br>Pyrazole: ethyl 3-cyclopentyl-1H-pyrazole-5-carboxylate (Intermediate 118)<br>Yield: 5.0 g 60%. |
| 145 | Methyl 4-iodo-3-(spiro[2.3]hexan-5-yl)-1H-pyrazole-5-carboxylate<br>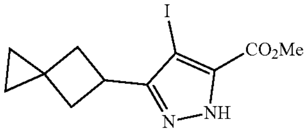 [SMILES: COC(=O)c1[nH]nc(C2CC3(CC3)C2)c1I]<br>Pyrazole: methyl 3-(spiro[2.3]hexan-5-yl)-1H-pyrazole-5-carboxylate (Intermediate 119)<br>Yield: 450 mg 55%; LCMS m/z = 333 [M + H]$^+$. |
| 146 | Methyl 3-(3,3-difluorocyclobutyl)-4-iodo-1H-pyrazole-5-carboxylate<br>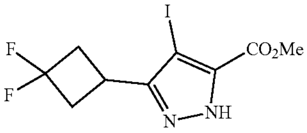 [SMILES: COC(=O)c1[nH]nc(C2CC(F)(F)C2)c1I]<br>Pyrazole: methyl 3-(3,3-difluorocyclobutyl)-1H-pyrazole-5-carboxylate (Intermediate 120)<br>Yield: 2.1 g, crude; LCMS m/z = 343 [M + H]$^+$. |
| 147 | Methyl 4-iodo-3-(3-methoxybicyclo[1.1.1]pentan-1-yl)-1H-pyrazole-5-carboxylate<br>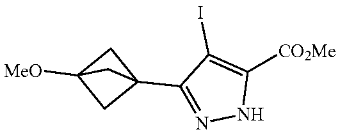 [SMILES: COC(=O)c1[nH]nc(C23CC(OC)(C2)C3)c1I]<br>Pyrazole: methyl 3-(3-methoxybicyclo[1.1.1]pentan-1-yl)-1H-pyrazole-5-carboxylate (Intermediate 121)<br>Yield: 250 mg, 16% over three steps; LCMS m/z = 349 [M + H]$^+$. |
| 148 | Ethyl 3-(tert-butyl)-4-iodo-1H-pyrazole-5-carboxylate<br>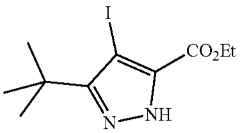<br>Pyrazole: ethyl 3-(tert-butyl)-1H-pyrazole-5-carboxylate<br>Yield: 4.2 g, 63% over three steps; LCMS m/z = 323 [M + H]$^+$. |

-continued

| Intermediate | Structure/Name/Starting Materials/Data |
|---|---|
| 149 | Methyl 3-(1-(difluoromethyl)cyclopropyl)-4-iodo-1H-pyrazole-5-carboxylate<br>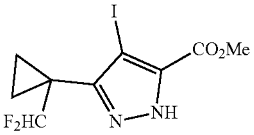 [SMILES: COC(=O)c1[nH]nc(C2(C(F)F)CC2)c1I]<br>Pyrazole: methyl 3-(1-(difluoromethyl)cyclopropyl)-1H-pyrazole-5-carboxylate (Intermediate 122)<br>Yield: 3.9 g, 91%. |
| 150 | Methyl 4-iodo-3-(1-(trifluoromethyl)cyclopropyl)-1H-pyrazole-5-carboxylate<br>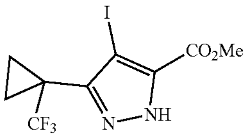 [SMILES: COC(=O)c1[nH]nc(C2(C(F)(F)F)CC2)c1I]<br>Pyrazole: methyl 3-(1-(trifluoromethyl)cyclopropyl)-1H-pyrazole-5-carboxylate (Intermediate 123)<br>Yield: 1.0 g, 94%; LCMS m/z = 361 [M + H]$^+$. |
| 151 | Ethyl 3-(2-hydroxypropan-2-yl)-4-iodo-1H-pyrazole-5-carboxylate<br>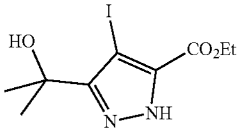<br>Pyrazole: ethyl 3-(2-hydroxypropan-2-yl)-1H-pyrazole-5-carboxylate (Intermediate 135)<br>Yield: 1.6 g, 49%; LCMS m/z = 325 [M + H]$^+$. |
| 152 | Methyl 3-(3-fluorobicyclo[1.1.1]pentan-1-yl)-4-iodo-1H-pyrazole-5-carboxylate<br>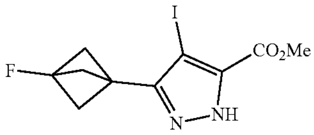 [SMILES: COC(=O)c1[nH]nc(C23CC(F)(C2)C3)c1I]<br>Pyrazole: methyl 3-(3-fluorobicyclo[1.1.1]pentan-1-yl)-1H-pyrazole-5-carboxylate (Intermediate 124)<br>Yield : 30.0 g, 75%; LCMS m/z = 335 [M − H]$^-$. |
| 153 | Methyl 3-(bicyclo[1.1.1]pentan-1-yl)-4-iodo-1H-pyrazole-5-carboxylate<br>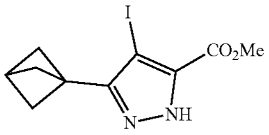 [SMILES: COC(=O)c1[nH]nc(C23CC(C2)C3)c1I]<br>Pyrazole: methyl 3-(bicyclo[1.1.1]pentan-1-yl)-1H-pyrazole-5-carboxylate (Intermediate 125)<br>Yield: 1.2 g, crude; LCMS m/z = 319 [M + H]$^+$. |
| 154 | Methyl 3-(2,2-difluorocyclopropyl)-4-iodo-1H-pyrazole-5-carboxylate<br>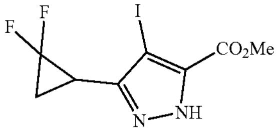 [SMILES: COC(=O)c1[nH]nc(C2CC2(F)F)c1I] |

-continued

| Intermediate | Structure/Name/Starting Materials/Data |
|---|---|
| | Pyrazole: methyl 3-(2,2-difluorocyclopropyl)-1H-pyrazole-5-carboxylate (Intermediate 126)<br>Yield: 1.3 g, crude; LCMS m/z = 329 $[M + H]^+$. |
| 155 | Methyl 3-(2-fluorocyclopropyl)-4-iodo-1H-pyrazole-5-carboxylate<br>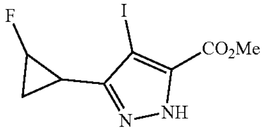 [SMILES: COC(=O)c1[nH]nc(C2CC2F)c1I]<br>Pyrazole: methyl 3-(2-fluorocyclopropyl)-1H-pyrazole-5-carboxylate (Intermediate 127)<br>Yield: 600 mg, 71%; LCMS m/z = 311 $[M + H]^+$. |
| 156 | Ethyl 1-((3,3-difluoro-1-methylcyclobutyl)methyl)-3-(2,2-difluorobicyclo[1.1.1]pentan-1-yl)-4-iodo-1H-pyrazole-5-carboxylate<br>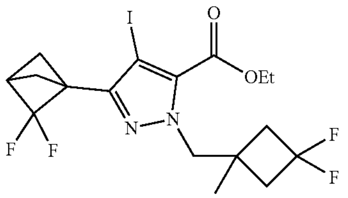 [SMILES: CCOC(=O)c1c(I)c(C23CC(C2)C3(F)F)nn1CC1(C)CC(F)(F)C1]<br>Pyrazole: ethyl 1-((3,3-difluoro-1-methylcyclobutyl)methyl)-3-(2,2-difluorobicyclo[1.1.1]pentan-1-yl)-1H-pyrazole-5-carboxylate (Intermediate 136)<br>Yield: 60 mg, 56%; LCMS m/z = 487 $[M + H]^+$. |

Intermediate 157

Ethyl 3-(1-cyanocyclopropyl)-4-iodo-1H-pyrazole-5-carboxylate

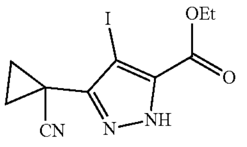 [SMILES: CCOC(=O)c1[nH]nc(C2(C#N)CC2)c1I]

To a solution of ethyl 3-(1-cyanocyclopropyl)-1H-pyrazole-5-carboxylate (Intermediate 129, 2.8 g) in DMF (30 mL) was added NIS (9.22 g) at 0° C. and the mixture was heated to 90° C. for 16 h. The reaction mixture was diluted with EtOAc (300 mL), washed with $Na_2S_2O_3$ solution (100 mL), water (100 mL) and brine (100 mL) and dried over $Na_2SO_4$. The organic layer was evaporated under reduced pressure to get the crude product which was purified by CombiFlash column chromatography ($SiO_2$, 30% EtOAc/Hex) to get the title compound (2.6 g, 57%).

Intermediate 22

Ethyl 3-cyclopropyl-4-iodo-1-((2-trimethylsilyl)ethoxy)methyl)-1H-pyrazole-5-carboxylate

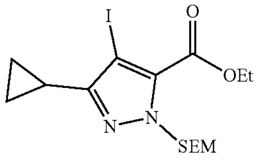 [SMILES: CCOC(=O)c1c(I)c(C2CC2)nn1COCC[Si](C)(C)C]

To a solution of ethyl 3-cyclopropyl-4-iodo-1H-pyrazole-5-carboxylate (Intermediate 21, 20 g) in DCM (200 mL) was added DIPEA (34.4 mL) at 0° C. and the solution was stirred for 30 min before a solution of SEM-Cl (15.6 mL) in DCM (100 mL) was added drop wise at 0° C. The reaction mixture was stirred at rt for 16 h. The reaction mixture was quenched with ice water and extracted with DCM (2×250 mL). The combined organics were washed with brine (250 mL), dried ($Na_2SO_4$) and evaporated to dryness under reduced pressure. The residue was purified by column chromatography ($SiO_2$, 5% EtOAc/Hex) to afford the title compound (22 g, 90%). $^1$H-NMR (400 MHz, DMSO-$d_6$): 5.61 (s, 2H), 4.33 (q, 2H), 3.45 (t, 2H), 1.89-1.85 (m, 1H), 1.34 (t, 3H), 0.96-0.90 (m, 2H), 0.78-0.73 (m, 4H), −0.09 (s, 9H).

Intermediate 158

The title compound was prepared from the appropriate pyrazole using an analogous method to that described for Intermediate 22.

| Intermediate | Structure/Name/Starting Materials/Data |
|---|---|
| 158 | Ethyl 4-iodo-3-(1-methylcyclopropyl)-1-((2-(trimethylsilyl)ethoxy)methyl)-1H-pyrazole-5-carboxylate<br>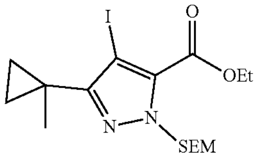 [SMILES: CCOC(=O)c1c(I)c(C2(C)CC2)nn1COCC[Si](C)(C)C]<br>Pyrazole: ethyl 4-iodo-3-(1-methylcyclopropyl)-1H-pyrazole-5-carboxylate (Intermediate137)<br>Yield: 1.0 g, 84%. |

Intermediate 23

Ethyl 3-cyclopropyl-4-(trifluoromethyl)-1-((2-(trimethylsilyl)ethoxy)methyl)-1H-pyrazole-5-carboxylate

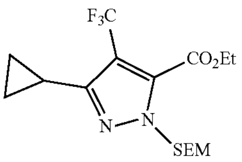 [SMILES: CCOC(=O)c1c(C(F)(F)F)c(C2CC2)nn1COCC[Si](C)(C)C]

To a solution of ethyl 3-cyclopropyl-4-iodo-1-((2-(trimethylsilyl)ethoxy)methyl)-1H-pyrazole-5-carboxylate (Intermediate 22, 10 g) in DMF (60 mL) at rt were added KF (4.0 g), $TMSCF_3$ (23.8 mL) and CuI (8.72 g) and the reaction mixture was heated at 90° C. in a sealed tube for 10 h. The reaction mixture was cooled to rt, diluted with cold-water (300 mL), filtered through celite and washed with EtOAc (800 mL). The filtrate was washed with water (3×100 mL), brine (200 mL), dried ($Na_2SO_4$) and evaporated to dryness under reduced pressure. The residue was purified by CombiFlash chromatography ($SiO_2$, 2-5% EtOAc/Hex) to give the title compound (7.8 g, 78%). $^1$H-NMR (400 MHz, DMSO-$d_6$): 5.57 (s, 2H), 4.35 (quin, 1H), 3.52-3.45 (m, 2H), 1.29 (q, 3H), 0.96-0.74 (m, 6H), −0.08 (s, 9H).

Intermediate 159

The title compound was prepared from the appropriate pyrazole using an analogous method to that described for Intermediate 23.

| Intermediate | Structure/Name/Starting Materials/Data |
|---|---|
| 159 | Ethyl 3-(1-methylcyclopropyl)-4-(trifluoromethyl)-1-((2-(trimethylsilyl)ethoxy)methyl)-1H-pyrazole-5-carboxylate 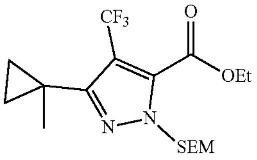 [SMILES: CCOC(=O)c1c(C(F)(F)F)c(C2(C)CC2)nn1COCC[Si](C)(C)C] Pyrazole: ethyl 4-iodo-3-(1-methylcyclopropyl)-1-((2-(trimethylsilyl)ethoxy)methyl)-1H-pyrazole-5-carboxylate (Intermediate 158) Yield: 850 mg, 97%. |

Intermediate 24

Ethyl 3-cyclopropyl-4-(trifluoromethyl)-1H-pyrazole-5-carboxylate

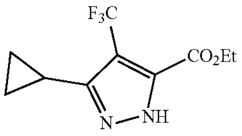 [SMILES: CCOC(=O)c1[nH]nc(C2CC2)c1C(F)(F)F]

To a solution of ethyl 3-cyclopropyl-4-(trifluoromethyl)-1-((2-(trimethylsilyl)ethoxy)methyl)-1H-pyrazole-5-carboxylate (Intermediate 23, 4.7 g) in EtOH (35 mL) was added 4M HCl in dioxane (25 mL) and the mixture was stirred at rt for 2 h. The reaction mixture was concentrated under reduced pressure and the residue was diluted with EtOAc (800 mL), washed with sat. $NaHCO_3$ (200 mL), water (2×100 mL), brine (250 mL), dried ($Na_2SO_4$) and evaporated under reduced pressure. The residue was purified by CombiFlash chromatography ($SiO_2$, 0-60% EtOAc/Hex) to afford the title compound (1.8 g, 58%). LCMS m/z=249 $[M+H]^+$.

Intermediate 160

The title compound was prepared from the appropriate pyrazole using an analogous method to that described for Intermediate 24.

| Intermediate | Structure/Name/Starting Materials/Data |
|---|---|
| 160 | Ethyl 3-(1-methylcyclopropyl)-4-(trifluoromethyl)-1H-pyrazole-5-carboxylate 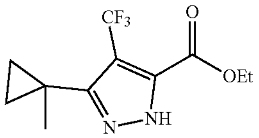 [SMILES: CCOC(=O)c1[nH]nc(C2(C)CC2)c1C(F)(F)F] Pyrazole: ethyl 3-(1-methylcyclopropyl)-4-(trifluoromethyl)-1-((2-(trimethylsilyl)ethoxy)methyl)-1H-pyrazole-5-carboxylate (Intermediate 159) Yield: 430 mg, 72%. |

Intermediate 25

Ethyl 3-(1,1-difluoroethyl)-4-iodo-1H-pyrazole-5-carboxylate

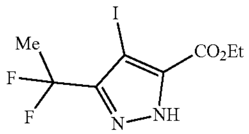 [SMILES: CCOC(=O)c1[nH]nc(C(C)(F)F)c1I]

The title compound was prepared (9 g, 92%) from ethyl 3-(1,1-difluoroethyl)-1H-pyrazole-5-carboxylate (Intermediate 19) using an analogous method to that described for Intermediate 21. LCMS m/z=331 $[M+H]^+$.

Intermediate 26

Ethyl 3-cyclopropyl-1-((3,3-difluorocyclopentyl)methyl)-4-iodo-1H-pyrazole-5-carboxylate

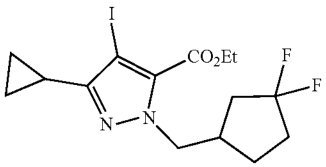 [SMILES: CCOC(=O)c1c(I)c(C2CC2)nn1CC1CCC(F)(F)C1]

To a solution of ethyl 3-cyclopropyl-4-iodo-1H-pyrazole-5-carboxylate (Intermediate 21, 1.8 g) in DMF (12 mL) were added (3,3-difluorocyclopentyl)methyl methanesulfonate (1.5 g) and $K_2CO_3$ (1.22 g) at rt and the resulting mixture was heated to 90° C. for 16 h. The reaction mixture was diluted with ice water (100 mL) and extracted with EtOAc (3×50 mL). The combined organics were washed with brine (100 mL), dried ($Na_2SO_4$) and evaporated to dryness under reduced pressure. The residue was purified by Combiflash chromatography ($SiO_2$, 0-30% EtOAc/Hex) to afford the title compound (1.5 g, 60%). LCMS m/z=425 $[M+H]^+$.

Intermediate 161

Ethyl 1-((3,3-difluoro-1-methylcyclobutyl)methyl)-3-(1-methylcyclopropyl)-4-(trifluoromethyl)-1H-pyrazole-5-carboxylate

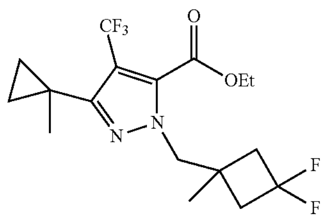 [SMILES: CCOC(=O)c1c(C(F)(F)F)c(C2(C)CC2)nn1CC1(C)CC(F)(F)C1]

To a solution of ethyl 3-(1-methylcyclopropyl)-4-(trifluoromethyl)-1H-pyrazole-5-carboxylate (Intermediate 160, 0.43 g) in DMF (10 mL) were added (3,3-difluoro-1-methylcyclobutyl)methyl methanesulfonate (0.42 g) and $Cs_2CO_3$ (1.34 g) at rt. The reaction mixture was heated to 90° C. for 1 h. The mixture was diluted with ice water and extracted with EtOAc (3×100 mL). The combined organic layers were dried over $Na_2SO_4$ and concentrated under reduced pressure to get the crude product, which was purified by CombiFlash column chromatography ($SiO_2$, 0-15% EtOAc/Hex) to get the title compound (0.35 g, 56%). LCMS m/z=381 $[M+H]^+$.

Intermediate 162

The title compound was prepared from the appropriate pyrazole and alkylating agent using an analogous method to that described for Intermediate 161.

| Intermediate | Structure/Name/Starting Materials/Data |
|---|---|
| 162 | Ethyl 3-cyclopropyl-1-((3,3-difluoro-1-methylcyclopentyl) methyl)-4-iodo-1H-pyrazole-5-carboxylate<br>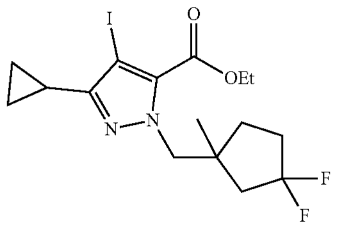 [SMILES: CCOC(=O)c1c(I)c(C2CC2)nn1CC1(C)CCC(F)(F)C1]<br>Pyrazole: ethyl 3-cyclopropyl-4-iodo-1H-pyrazole-5-carboxylate (Intermediate 21)<br>Alkylating agent: (3,3-difluoro-1-methylcyclopentyl) methyl trifluoromethanesulfonate (Intermediate 107)<br>Yield: 2.7 g, 77%. LCMS m/z = 439 $[M + H]^+$. |

Intermediate 163

Methyl 1-((3,3-difluoro-1-methylcyclobutyl) methyl)-3-(1-fluorocyclopropyl)-4-iodo-1H-pyrazole-5-carboxylate

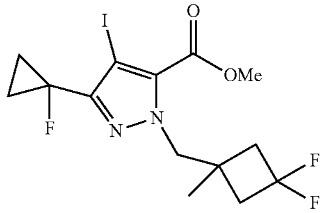 [SMILES: COC(=O)c1c(I)c(C2(F)CC2)nn1CC1(C)CC(F)(F)C1]

To a stirred solution of methyl 3-(1-fluorocyclopropyl)-4-iodo-1H-pyrazole-5-carboxylate (Intermediate 142, 4.0 g) in MeCN (40 mL) were added $K_2CO_3$ (5.341 g) and (3,3-difluoro-1-methylcyclobutyl)methyl methanesulfonate (Intermediate 6, 5.527 g) at rt. The reaction mixture was heated to 80° C. for 16 h. The reaction mixture was quenched with water (50 mL) and extracted with EtOAc (3×50 mL). The combined organic layers were washed with water (50 mL) and brine (50 mL), dried over anhydrous $Na_2SO_4$ and concentrated under reduced pressure to get the crude product, which was purified by column chromatography ($SiO_2$, 5% EtOAc/PE) to afford the title compound (3.0 g, 54%). LCMS m/z=429 $[M+H]^+$.

Intermediate 164-171

The title compounds were prepared from the appropriate pyrazoles and the appropriate mesylates (ROMs) using an analogous method to that described for Intermediate 163.

| Intermediate | Structure/Name/Starting Materials/Data |
|---|---|
| 164 | Methyl 3-cyclobutyl-1-((3,3-difluoro-1-methylcyclobutyl) methyl)-4-iodo-1H-pyrazole-5-carboxylate<br>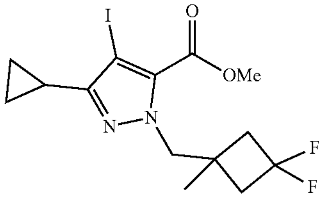<br>Pyrazole: methyl 3-cyclobutyl-4-iodo-1H-pyrazole-5-carboxylate (Intermediate 143)<br>ROMs: (3,3-difluoro-1-methylcyclobutyl)methyl methanesulfonate (Intermediate 6)<br>Yield: 2.6 g, 86%; LCMS m/z = 425 $[M + H]^+$. |
| 165 | Methyl 3-cyclopentyl-1-((3,3-difluoro-1-methylcyclobutyl) methyl)-4-iodo-1H-pyrazole-5-carboxylate<br>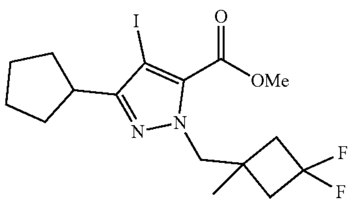 [SMILES: COC(=O)c1c(I)c(C2CCCC2)nn1CC1(C)CC(F)(F)C1] |

-continued

| Intermediate | Structure/Name/Starting Materials/Data |
|---|---|
| | Pyrazole: methyl 3-cyclopentyl-4-iodo-1H-pyrazole-5-carboxylate (Intermediate 144)<br>ROMs: (3,3-difluoro-1-methylcyclobutyl)methyl methanesulfonate (Intermediate 6)<br>Yield: 300 g, 14%, LCMS m/z = 439 [M + H]$^+$. |
| 166 | Methyl 1-((3,3-difluoro-1-methylcyclobutyl)methyl)-4-iodo-3-(spiro[2.3]hexan-5-yl)-1H-pyrazole-5-carboxylate<br>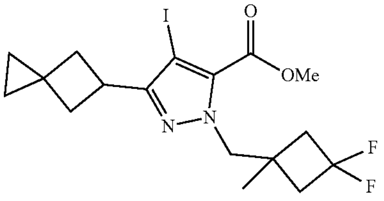 [SMILES: COC(=O)c1c(I)c(C2CC3(CC3)C2)nn1CC1(C)CC(F)(F)C1]<br>Pyrazole: methyl 4-iodo-3-(spiro[2.3]hexan-5-yl)-1H-pyrazole-5-carboxylate (Intermediate 145)<br>ROMs: (3,3-difluoro-1-methylcyclobutyl)methyl methanesulfonate (Intermediate 6)<br>Yield: 400 mg, 68%, LCMS m/z = 451 [M + H]$^+$. |
| 17 | Methyl 1-((3,3-difluoro-1-methylcyclobutyl)methyl)-3-(1-(difluoromethyl)cyclopropyl)-4-iodo-1H-pyrazole-5-carboxylate<br>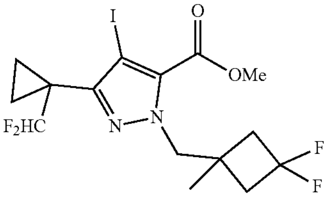 [SMILES: COC(=O)c1c(I)c(C2(C(F)F)CC2)nn1CC1(C)CC(F)(F)C1]<br>Pyrazole: methyl 3-(1-(difluoromethyl)cyclopropyl)-4-iodo-1H-pyrazole-5-carboxylate (Intermediate 149)<br>ROMs: (3,3-difluoro-1-methylcyclobutyl)methyl methanesulfonate (Intermediate 6)<br>Yield: 1.4 g, 44%, LCMS m/z = 461 [M + H]$^+$. |
| 168 | Methyl 1-((3,3-difluoro-1-methylcyclobutyl)methyl)-4-iodo-3-(1-(trifluoromethyl)cyclopropyl)-1H-pyrazole-5-carboxylate<br>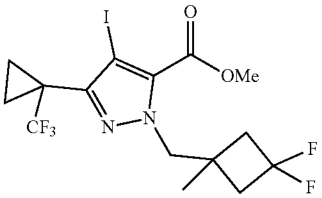 [SMILES: COC(=O)c1c(I)c(C2(C(F)(F)F)CC2)nn1CC1(C)CC(F)(F)C1]<br>Pyrazole: methyl 4-iodo-3-(1-(trifluoromethyl)cyclopropyl)-1H-pyrazole-5-carboxylate (Intermediate 150)<br>ROMs: (3,3-difluoro-1-methylcyclobutyl)methyl methanesulfonate (Intermediate 6)<br>Yield: 1.3 g, 61%, LCMS m/z = 479 [M + H]$^+$. |
| 169 | Methyl 1-((3,3-difluoro-1-methylcyclobutyl)methyl)-3-(3-fluorobicyclo[1.1.1]pentan-1-yl)-4-iodo-1H-pyrazole-5-carboxylate |

-continued

| Intermediate | Structure/Name/Starting Materials/Data |
|---|---|
| | 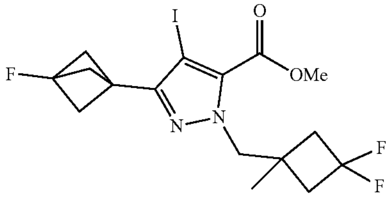 [SMILES: COC(=O)c1c(I)c(C23CC(F)(C2)C3)nn1CC1(C)CC(F)(F)C1]<br>Pyrazole: methyl 3-(3-fluorobicyclo[1.1.1]pentan-1-yl)-4-iodo-1H-pyrazole-5-carboxylate (Intermediate 152)<br>ROMs: (3,3-difluoro-1-methylcyclobutyl)methyl methanesulfonate (Intermediate 6)<br>Yield: 21.0 g, 51%, LCMS m/z = 455 [M + H]$^+$. |
| 170 | Methyl 1-((3,3-difluoro-1-methylcyclobutyl)methyl)-3-(2-fluorocyclopropyl)-4-iodo-1H-pyrazole-5-carboxylate<br>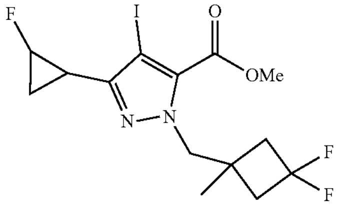 [SMILES: COC(=O)c1c(I)c(C2CC2F)nn1CC1(C)CC(F)(F)C1]<br>Pyrazole: methyl 3-(2-fluorocyclopropyl)-4-iodo-1H-pyrazole-5-carboxylate (Intermediate 155)<br>ROMs: (3,3-difluoro-1-methylcyclobutyl)methyl methanesulfonate (Intermediate 6)<br>Yield: 400 mg, 48%, LCMS m/z = 429 [M + H]$^+$. |
| 171 | Ethyl 3-cyclopropyl-4-iodo-1-((3-oxobicyclo[3.1.0]hexan-1-yl)methyl)-1H-pyrazole-5-carboxylate<br>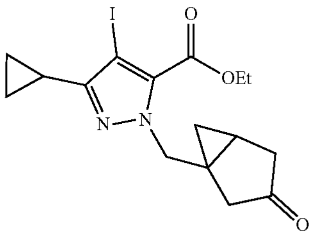 [SMILES: CCOC(=O)c1c(I)c(C2CC2)nn1CC12CC(=O)CC1C2]<br>Pyrazole: ethyl 3-cyclopropyl-4-iodo-1H-pyrazole-5-carboxylate (Intermediate 21)<br>ROMs: (3-oxobicyclo[3.1.0]hexan-1-yl)methyl methanesulfonate (Intermediate 106)<br>Yield: 0.4 g, 30%, LCMS m/z = 415 [M + H]$^+$. |

Intermediate 172

Ethyl 3-cyclopropyl-1-((3,3-difluorobicyclo[3.1.0]hexan-1-yl)methyl)-4-iodo-1H-pyrazole-5-carboxylate

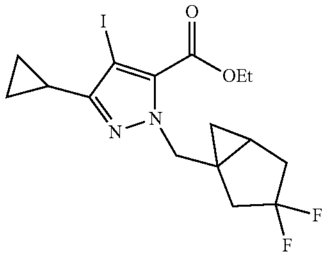 [SMILES: CCOC(=O)c1c(I)c(C2CC2)nn1CC12CC1CC(F)(F)C2]

To a stirred solution of ethyl 3-cyclopropyl-4-iodo-1-((3-oxobicyclo[3.1.0]hexan-1-yl)methyl)-1H-pyrazole-5-carboxylate (Intermediate 171, 400 mg) in DCM (5 mL) was added DAST (1.56 g) at 0° C. under an argon atmosphere. The resulting reaction mixture was stirred at 0° C.—rt for 48 h. The reaction mixture was quenched with sat. $NaHCO_3$ solution (30 mL) and extracted with DCM (2×30 mL). The combined organic layers were washed with water (30 mL) and brine (30 mL), dried over anhydrous $Na_2SO_4$ and concentrated under reduced pressure to get the crude product, which was purified by column chromatography ($SiO_2$, 5% EtOAc/PE) to afford the title compound (300 mg, 71%).

Intermediate 27

Ethyl 1-((3,3-difluorocyclobutyl)methyl)-3-(1,1-difluoroethyl)-4-iodo-1H-pyrazole-5-carboxylate

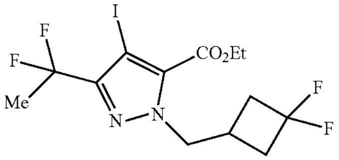 [SMILES: CCOC(=O)c1c(I)c(C(C)(F)F)nn1CC1CC(F)(F)C1]

The title compound was prepared (0.8 g, 60%) from ethyl 3-(1,1-difluoroethyl)-4-iodo-1H-pyrazole-5-carboxylate (Intermediate 25) and (3,3-difluorocyclobutyl)methyl methanesulfonate (Intermediate 2) using an analogous method to that described for Intermediate 26. LCMS m/z=435 $[M+H]^+$.

Intermediate 173

Ethyl 1-((3,3-difluoro-1-methylcyclobutyl)methyl)-3-(1,1-difluoroethyl)-4-iodo-1H-pyrazole-5-carboxylate

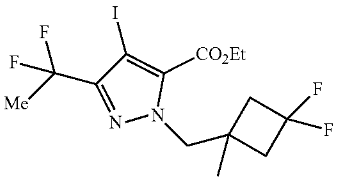 [SMILES: CCOC(=O)c1c(I)c(C(C)(F)F)nn1CC1(C)CC(F)(F)C1]

To a solution of ethyl 3-(1,1-difluoroethyl)-4-iodo-1H-pyrazole-5-carboxylate (Intermediate 25, 3.0 g) and (3,3-difluoro-1-methylcyclobutyl)methyl methanesulfonate (Intermediate 6, 2.5 g) in DMF (20 mL) was added $Cs_2CO_3$ (5.9 g) at rt and the reaction mixture was heated to 90° C. for 5 h. The reaction mixture was quenched with cold water (100 mL) and extracted with EtOAc (3×100 mL). The combined organic layers were washed with cold brine (100 mL) and dried over sodium sulfate. The solvent was evaporated under reduced pressure to get the crude material, which was purified by CombiFlash column chromatography ($SiO_2$, 0-5% EtOAc/Hex) to yield the title compound (1.4 g, 34%). LCMS m/z=449 $[M+H]^+$.

Intermediate 28

Ethyl 3-cyclopropyl-1-((3,3-difluorocyclopentyl)methyl)-4-(trifluoromethyl)-1H-pyrazole-5-carboxylate

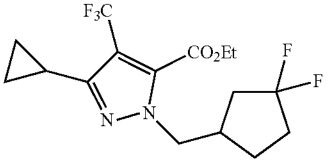 [SMILES: CCOC(=O)c1c(C(F)(F)F)c(C2CC2)nn1CC1CCC(F)(F)C1]

To a solution of ethyl 3-cyclopropyl-1-((3,3-difluorocyclopentyl)methyl)-4-iodo-1H-pyrazole-5-carboxylate (Intermediate 26, 1.25 g) in DMF (20 mL) were added KF (0.5 g), CuI (1.12 g) and $TMSCF_3$ (3.05 mL) at rt and the reaction mixture was heated at 90° C. in a sealed tube for 16 h. The mixture was cooled to rt and diluted with cold water (300 mL) and filtered through celite. The filtrate was extracted with EtOAc (3×100 mL), washed with brine (200 mL), dried ($Na_2SO_4$) and evaporated to dryness under reduced pressure. The residue was purified by CombiFlash chromatography ($SiO_2$, 0-5% EtOAc/Hex) to afford the title compound (0.9 g, 83%). LCMS m/z=367 $[M+H]^+$.

Intermediate 29

Ethyl 1-((3,3-difluorocyclobutyl)methyl)-3-(1,1-difluoroethyl)-4-(trifluoromethyl)-1H-pyrazole-5-carboxylate

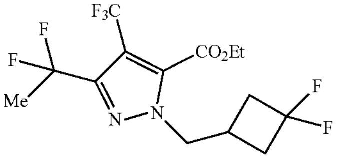 [SMILES: CCOC(=O)c1c(C(F)(F)F)c(C(C)(F)F)nn1CC1CC(F)(F)C1]

The title compound was prepared (0.2 g, 46%) from ethyl 1-((3,3-difluorocyclobutyl)methyl)-3-(1,1-difluoroethyl)-4-iodo-1H-pyrazole-5-carboxylate (Intermediate 27) using an analogous method to that described for Intermediate 28. LCMS m/z=377 $[M+H]^+$.

Intermediate 174

Methyl 1-((3,3-difluoro-1-methylcyclobutyl)methyl)-3-(1-fluorocyclopropyl)-4-(trifluoromethyl)-1H-pyrazole-5-carboxylate

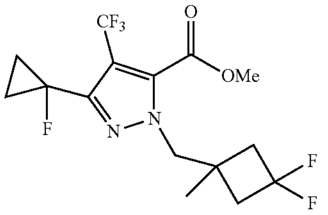 [SMILES: COC(=O)c1c(C(F)(F)F)c(C2(F)CC2)nn1CC1(C)CC(F)(F)C1]

To a stirred solution of methyl 1-((3,3-difluoro-1-methylcyclobutyl)methyl)-3-(1-fluorocyclopropyl)-4-iodo-1H-pyrazole-5-carboxylate (Intermediate 163, 3.0 g) in DMF (30 mL) in a sealed tube were added KF (0.614 g) and CuI (2.060 g) at rt. The mixture was degassed with argon for 15 minutes. To the reaction mixture was then added $CF_3Si(CH_3)_3$ (5.2 mL) at rt and the resulting reaction mixture was heated to 100° C. for 16 h. The reaction mixture was quenched with water (50 mL) and extracted with EtOAc (3x50 mL). The combined organic layers were washed with water (40 mL) and brine (40 mL), dried over anhydrous $Na_2SO_4$ and concentrated under reduced pressure to get the crude product, which was purified by column chromatography ($SiO_2$, 5% EtOAc/PE) to afford the title compound (1.5 g, 58%). LCMS m/z=371 $[M+H]^+$.

Intermediate 175-194

The title compounds were prepared from the appropriate pyrazoles using an analogous method (at a suitable reaction time between 16-20 h and a suitable reaction temperature between 90-100° C.) to that described for Intermediate 174.

| Intermediate | Structure/Name/Starting Materials/Data |
|---|---|
| 175 | Methyl 3-cyclobutyl-1-((3,3-difluoro-1-methylcyclobutyl)methyl)-4-(trifluoromethyl)-1H-pyrazole-5-carboxylate<br>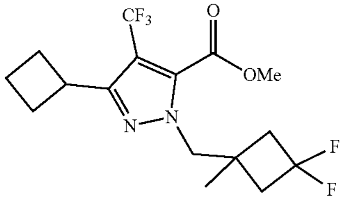 [SMILES: COC(=O)c1c(C(F)(F)F)c(C2CCC2)nn1CC1(C)CC(F)(F)C1]<br>Pyrazole: methyl 3-cyclobutyl-1-((3,3-difluoro-1-methylcyclobutyl)methyl)-4-iodo-1H-pyrazole-5-carboxylate (Intermediate 164)<br>Yield: 2.1 g, 57%; LCMS m/z = 367 $[M + H]^+$. |
| 176 | Methyl 3-cyclopentyl-1-((3,3-difluoro-1-methylcyclobutyl)methyl)-4-(trifluoromethyl)-1H-pyrazole-5-carboxylate<br>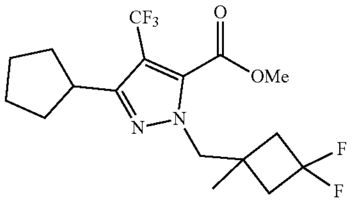 [SMILES: COC(=O)c1c(C(F)(F)F)c(C2CCCC2)nn1CC1(C)CC(F)(F)C1] |

-continued

| Intermediate | Structure/Name/Starting Materials/Data |
|---|---|
| | Pyrazole: methyl 3-cyclopentyl-1-((3,3-difluoro-1-methylcyclobutyl)methyl)-4-iodo-1H-pyrazole-5-carboxylate (Intermediate 165)<br>Yield: 400 mg, 93%; LCMS m/z = 381 $[M + H]^+$. |
| 177 | Methyl 1-((3,3-difluoro-1-methylcyclobutyl)methyl)-3-(spiro[2.3]hexan-5-yl)-4-(trifluoromethyl)-1H-pyrazole-5-carboxylate<br>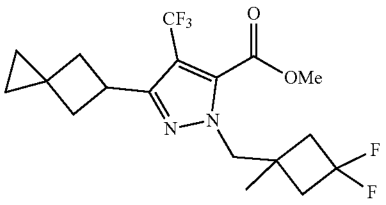 [SMILES: COC(=O)c1c(C(F)(F)F)c(C2CC3(CC3)C2)nn1CC1(C)CC(F)(F)C1]<br>Pyrazole: methyl 1-((3,3-difluoro-1-methylcyclobutyl)methyl)-4-iodo-3-(spiro[2.3]hexan-5-yl)-1H-pyrazole-5-carboxylate (Intermediate 166)<br>Yield: 320 mg, 91%; LCMS m/z = 393 $[M + H]^+$. |
| 178 | Ethyl 3-(1-cyanocyclopropyl)-1-((3,3-difluoro-1-methylcyclobutyl)methyl)-4-(trifluoromethyl)-1H-pyrazole-5-carboxylate<br>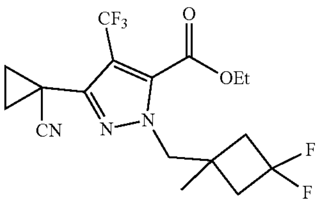 [SMILES: CCOC(=O)c1c(C(F)(F)F)c(C2(C#N)CC2)nn1CC1(C)CC(F)(F)C1]<br>Pyrazole: ethyl 3-(1-cyanocyclopropyl)-1-((3,3-difluoro-1-methylcyclobutyl)methyl)-4-iodo-1H-pyrazole-5-carboxylate (Intermediate 223)<br>Yield: 250 mg, 57%; LCMS m/z = 392 $[M + H]^+$. |
| 179 | Methyl 1-((3,3-difluoro-1-methylcyclobutyl)methyl)-3-(3,3-difluorocyclobutyl)-4-(trifluoromethyl)-1H-pyrazole-5-carboxylate<br>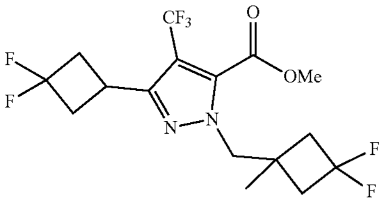 [SMILES: COC(=O)c1c(C(F)(F)F)c(C2CC(F)(F)C2)nn1CC1(C)CC(F)(F)C1]<br>Pyrazole: methyl 1-((3,3-difluoro-1-methylcyclobutyl)methyl)-3-(3,3-difluorocyclobutyl)-4-iodo-1H-pyrazole-5-carboxylate (Intermediate 224)<br>Yield: 1.04 g, 58%; LCMS m/z = 403 $[M + H]^+$. |
| 180 | Ethyl 1-((3,3-difluoro-1-methylcyclobutyl)methyl)-3-(1-methoxycyclopropyl)-4-(trifluoromethyl)-1H-pyrazole-5-carboxylate |

-continued

| Intermediate | Structure/Name/Starting Materials/Data |
|---|---|
| | 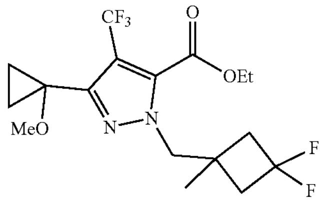 [SMILES: CCOC(=O)c1c(C(F)(F)F)c(C2(OC)CC2)nn1CC1(C)CC(F)(F)C1] Pyrazole: ethyl 1-((3,3-difluoro-1-methylcyclobutyl)methyl)-4-iodo-3-(1-methoxycyclopropyl)-1H-pyrazole-5-carboxylate (Intermediate 225) Yield: 150 mg, 55%; LCMS m/z = 397 $[M + H]^+$. |
| 181 | Methyl 1-((3,3-difluoro-1-methylcyclobutyl)methyl)-3-(3-methoxybicyclo[1.1.1]pentan-1-yl)-4-(trifluoromethyl)-1H-pyrazole-5-carboxylate 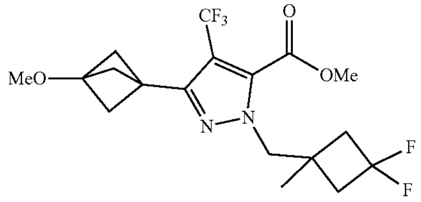 [SMILES: COC(=O)c1c(C(F)(F)F)c(C23CC(OC)(C2)C3)nn1CC1(C)CC(F)(F)C1] Pyrazole: methyl 1-((3,3-difluoro-1-methylcyclobutyl)methyl)-4-iodo-3-(3-methoxybicyclo[1.1.1]pentan-1-yl)-1H-pyrazole-5-carboxylate (Intermediate 226) Yield: 100 mg, 57%; LCMS m/z = 409 $[M + H]^+$. |
| 182 | Ethyl 1-((3,3-difluoro-1-methylcyclobutyl)methyl)-3-(1,1-difluoroethyl)-4-(trifluoromethyl)-1H-pyrazole-5-carboxylate 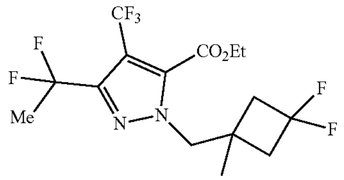 [SMILES: CCOC(=O)c1c(C(F)(F)F)c(C(C)(F)F)nn1CC1(C)CC(F)(F)C1] Pyrazole: ethyl 1-((3,3-difluoro-1-methylcyclobutyl)methyl)-3-(1,1-difluoroethyl)-4-iodo-1H-pyrazole-5-carboxylate (Intermediate 173) Yield: 390 mg, 37%. |
| 183 | Ethyl 3-(tert-butyl)-1-((3,3-difluoro-1-methylcyclobutyl)methyl)-4-(trifluoromethyl)-1H-pyrazole-5-carboxylate 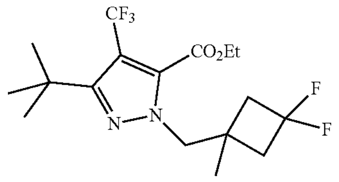 [SMILES: CCOC(=O)c1c(C(F)(F)F)c(C(C)(C)C)nn1CC1(C)CC(F)(F)C1] Pyrazole: ethyl 3-(tert-butyl)-1-((3,3-difluoro-1-methylcyclobutyl)methyl)-4-iodo-1H-pyrazole-5-carboxylate (Intermediate 173) Yield: 1.8 g, 66%; LCMS m/z = 383 $[M + H]^+$. |
| 184 | Methyl 1-((3,3-difluoro-1-methylcyclobutyl)methyl)-3-(1-(difluoromethyl)cyclopropyl)-4-(trifluoromethyl)-1H-pyrazole-5-carboxylate 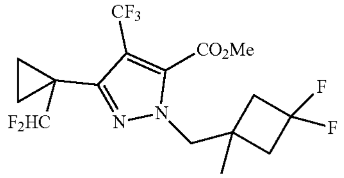 [SMILES: COC(=O)c1c(C(F)(F)F)c(C2(C(F)F)CC2)nn1CC1(C)CC(F)(F)C1] Pyrazole: methyl 1-((3,3-difluoro-1-methylcyclobutyl)methyl)-3-(1-(difluoromethyl)cyclopropyl)-4-iodo-1H-pyrazole-5-carboxylate (Intermediate 167) Yield: 900 mg, 51%; LCMS m/z = 403 $[M + H]^+$. |
| 185 | Ethyl 1-((3,3-difluoro-1-methylcyclobutyl)methyl)-3-((trans)-2-methylcyclopropyl)-4-(trifluoromethyl)-1H-pyrazole-5-carboxylate 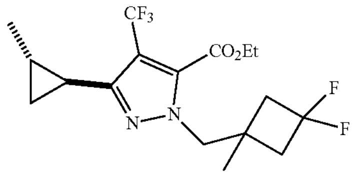 Pyrazole: ethyl 1-((3,3-difluoro-1-methylcyclobutyl)methyl)-4-iodo-3-((trans)-2-methylcyclopropyl)-1H-pyrazole-5-carboxylate (Intermediate 241) Yield: 1.0 g, 76%; LCMS m/z = 381 $[M + H]^+$. |
| 186 | Methyl 3-(bicyclo[1.1.1]pentan-1-yl)-1-(((trans)-2-(difluoromethyl)cyclopropyl)methyl)-4-(trifluoromethyl)-1H-pyrazole-5-carboxylate 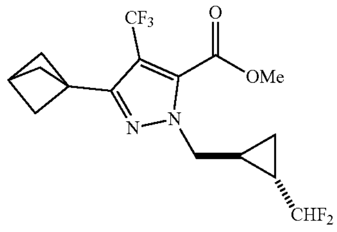 Pyrazole: methyl 3-(bicyclo[1.1.1]pentan-1-yl)-1-(((trans)-2-(difluoromethyl)cyclopropyl)methyl)-4-iodo-1H-pyrazole-5-carboxylate (Intermediate 234) Yield: 70 mg, 53%; LCMS m/z = 365 $[M + H]^+$. |
| 187 | Methyl 3-(bicyclo[1.1.1]pentan-1-yl)-4-(trifluoromethyl)-1-(((trans)-2-(trifluoromethyl)cyclopropyl)methyl)-1H-pyrazole-5-carboxylate 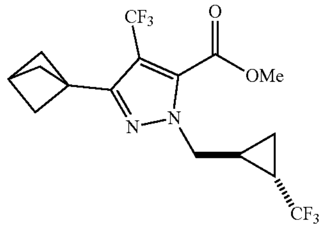 Pyrazole: methyl 3-(bicyclo[1.1.1]pentan-1-yl)-4-iodo-1-(((trans)-2-(trifluoromethyl)cyclopropyl)methyl)-1H-pyrazole-5-carboxylate (Intermediate 235) Yield: 320 mg, crude; LCMS m/z = 383 $[M + H]^+$. |
| 188 | Ethyl 1-((3,3-difluoro-1-methylcyclobutyl)methyl)-3-(spiro[2.2]pentan-1-yl)-4-(trifluoromethyl)-1H-pyrazole-5-carboxylate |

-continued

| Intermediate | Structure/Name/Starting Materials/Data |
| --- | --- |
| | 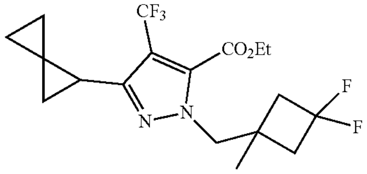 [SMILES: CCOC(=O)c1c(C(F)(F)F)c(C2CC23CC3)nn1CC1(C)CC(F)(F)C1]<br>Pyrazole: ethyl 1-[(3,3-difluoro-1-methylcyclobutyl) methyl]-4-iodo-3-{spiro[2.2]pentan-1-yl}-1H-pyrazole-5-carboxylate (Intermediate 248)<br>Yield: 640 mg, 52%; LCMS m/z = 393 $[M + H]^+$. |
| 189 | Methyl 1-((3,3-difluoro-1-methylcyclobutyl)methyl)-3-(2,2-difluorocyclopropyl)-4-(trifluoromethyl)-1H-pyrazole-5-carboxylate<br>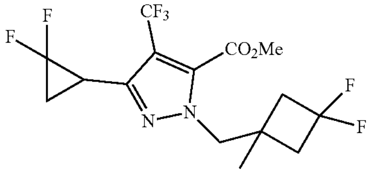 [SMILES: COC(=O)c1c(C(F)(F)F)c(C2CC2(F)F)nn1CC1(C)CC(F)(F)C1]<br>Pyrazole: methyl 1-((3,3-difluoro-1-methylcyclobutyl) methyl)-3-(2,2-difluorocyclopropyl)-4-iodo-1H-pyrazole-5-carboxylate (Intermediate 236)<br>Yield: 500 mg, crude; LCMS m/z = 389 $[M + H]^+$. |
| 190 | Methyl 1-((3,3-difluoro-1-methylcyclobutyl)methyl)-3-(2-fluorocyclopropyl)-4-(trifluoromethyl)-1H-pyrazole-5-carboxylate<br>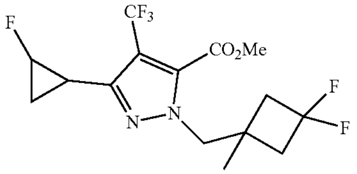 [SMILES: COC(=O)c1c(C(F)(F)F)c(C2CC2F)nn1CC1(C)CC(F)(F)C1]<br>Pyrazole: methyl 1-((3,3-difluoro-1-methylcyclobutyl) methyl)-3-(2-fluorocyclopropyl)-4-iodo-1H-pyrazole-5-carboxylate (Intermediate 170)<br>Yield: 200 mg, 57%. |
| 191 | Ethyl 3-cyclopropyl-1-((3,3-difluorobicyclo[3.1.0] hexan-1-yl)methyl)-4-(trifluoromethyl)-1H-pyrazole-5-carboxylate<br>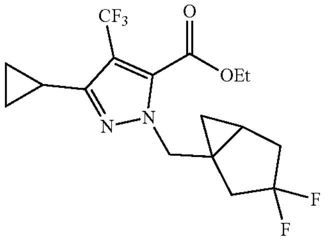 [SMILES: CCOC(=O)c1c(C(F)(F)F)c(C2CC2)nn1CC12CC1CC(F)(F)C2]<br>Pyrazole: ethyl 3-cyclopropyl-1-((3,3-difluorobicyclo [3.1.0]hexan-1-yl)methyl)-4-iodo-1H-pyrazole-5-carboxylate (Intermediate 172)<br>Yield: 200 mg, 77%. LCMS m/z = 379 $[M + H]^+$. |
| 192 | Ethyl 3-cyclopropyl-1-((3,3-difluoro-1-methylcyclopentyl) methyl)-4-(trifluoromethyl)-1H-pyrazole-5-carboxylate |

-continued

| Intermediate | Structure/Name/Starting Materials/Data |
| --- | --- |
| | 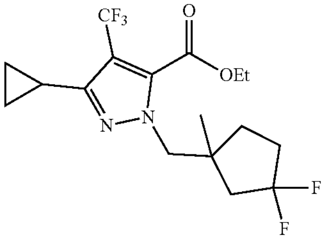 [SMILES: CCOC(=O)c1c(C(F)(F)F)c(C2CC2)nn1CC1(C)CCC(F)(F)C1]<br>Pyrazole: ethyl 3-cyclopropyl-1-((3,3-difluoro-1-methylcyclopentyl)methyl)-4-iodo-1H-pyrazole-5-carboxylate (Intermediate 162)<br>Yield: 2.3 g, 91%. LCMS m/z = 381 $[M + H]^+$. |
| 193 | Methyl 3-(bicyclo[1.1.1]pentan-1-yl)-1-((3,3-difluoro-1-methylcyclobutyl)methyl)-4-(trifluoromethyl)-1H-pyrazole-5-carboxylate<br>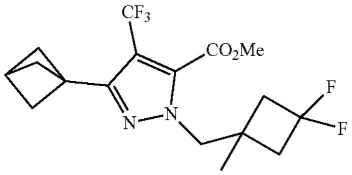 [SMILES: COC(=O)c1c(C(F)(F)F)c(C23CC(C2)C3)nn1CC1(C)CC(F)(F)C1]<br>Pyrazole: methyl 3-(bicyclo[1.1.1]pentan-1-yl)-1-((3,3-difluoro-1-methylcyclobutyl)methyl)-4-iodo-1H-pyrazole-5-carboxylate (Intermediate 238)<br>Yield: 0.5 g, 48%, LCMS m/z = 379 $[M + H]^+$. |
| 194 | Ethyl 1-((3,3-difluoro-1-methylcyclobutyl)methyl)-3-(2,2-difluorobicyclo[1.1.1]pentan-1-yl)-4-(trifluoromethyl)-1H-pyrazole-5-carboxylate<br>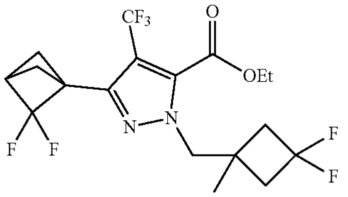 [SMILES: CCOC(=O)c1c(C(F)(F)F)c(C23CC(C2)C3(F)F)nn1CC1(C)CC(F)(F)C1]<br>Pyrazole: ethyl 1-((3,3-difluoro-1-methylcyclobutyl) methyl)-3-(2,2-difluorobicyclo[1.1.1]pentan-1-yl)-4-iodo-1H-pyrazole-5-carboxylate (Intermediate 156)<br>Yield: 60 mg, 55%; LCMS m/z = 429 $[M + H]^+$. |

Intermediate 195

Methyl 1-((3,3-difluoro-1-methylcyclobutyl) methyl)-4-(trifluoromethyl)-3-(1-(trifluoromethyl) cycloproyl)-1H-pyrazole-5-carboxylate

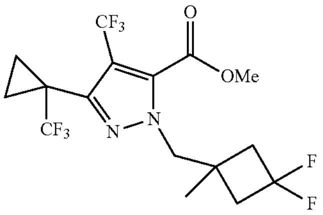 [SMILES: COC(=O)c1c(C(F)(F)F)c(C2(C(F)(F)F)CC2)nn1CC1(C)CC(F)(F)C1]

To a stirred solution of methyl 1-((3,3-difluoro-1-methylcyclobutyl)methyl)-4-iodo-3-(1-(trifluoromethyl)cyclopropyl)-1H-pyrazole-5-carboxylate (Intermediate 168, 1.2 g) in DMF (10 mL) in a sealed tube were added HMPA (2.25 g) and CuI (1.23 g) at rt and the mixture was degassed with argon for 5 minutes. To the reaction mixture was then added methyl 2,2-difluoro-2-(fluorosulfonyl)acetate (2.41 g) at rt. The resulting reaction mixture was heated to 100° C. for 16 h. The reaction mixture was cooled to rt, diluted with water (50 mL) and extracted with EtOAc (2×50 mL). The combined organic layers were washed with water (50 mL) and brine (50 mL), dried over anhydrous $Na_2SO_4$ and concentrated under reduced pressure to get the crude product, which was purified by column chromatography ($SiO_2$, 5-6% EtOAc/PE) to afford the title compound (830 mg, 78%). LCMS m/z=421 $[M+H]^+$.

Intermediate 196-198

The title compounds were prepared from the appropriate pyrazoles using an analogous method to that described for Intermediate 195.

| Intermediate | Structure/Name/Starting Materials/Data |
|---|---|
| 196 | Methyl 1-((3,3-difluoro-1-methylcyclobutyl)methyl)-3-(3-fluorobicyclo[1.1.1]pentan-1-yl)-4-(trifluoromethyl)-1H-pyrazole-5-carboxylate<br>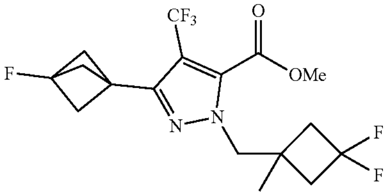 [SMILES: COC(=O)c1c(C(F)(F)F)c(C23CC(F)(C2)C3)nn1CC1(C)CC(F)(F)C1]<br>Pyrazole: methyl 1-((3,3-difluoro-1-methylcyclobutyl)methyl)-3-(3-fluorobicyclo[1.1.1]pentan-1-yl)-4-iodo-1H-pyrazole-5-carboxylate (Intermediate 170)<br>Yield: 3.0 g, 85%; LCMS m/z = 397 $[M + H]^+$. |
| 197 | Methyl 3-(1-fluorocyclopropyl)-4-(trifluoromethyl)-1-(((trans)-2-(trifluoromethyl)cyclopropyl)methyl)-1H-pyrazole-5-carboxylate<br>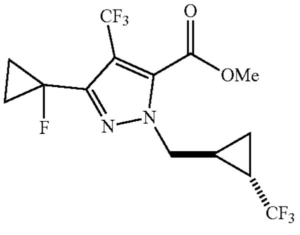<br>Pyrazole: methyl 3-(1-fluorocyclopropyl)-4-iodo-1-(((trans)-2-(trifluoromethyl)cyclopropyl)methyl)-1H-pyrazole-5-carboxylate (Intermediate 231)<br>Yield: 320 mg, 74%; LCMS m/z = 375 $[M + H]^+$. |
| 198 | Ethyl 1-((3,3-difluoro-1-methylcyclobutyl)methyl)-3-(2-fluoropropan-2-yl)-4-(trifluoromethyl)-1H-pyrazole-5-carboxylate |

-continued

| Intermediate | Structure/Name/Starting Materials/Data |
|---|---|
| | 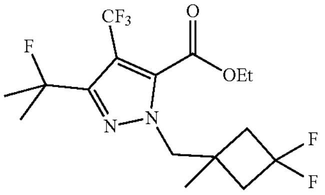 [SMILES: CCOC(=O)c1c(C(F)(F)F)c(C(C)(C)F)nn1CC1(C)CC(F)(F)C1]<br>Pyrazole: ethyl 1-((3,3-difluoro-1-methylcyclobutyl)methyl)-3-(2-fluoropropan-2-yl)-4-iodo-1H-pyrazole-5-carboxylate (Intermediate 245)<br>Yield: 750 mg, 86%; LCMS m/z = 387 $[M + H]^+$. |

1-((3,3-Difluoro-1-methylcyclobutyl)methyl)-3-(1-fluorocyclopropyl)-4-(trifluoromethyl)-1H-pyrazole-5-carboxylic acid

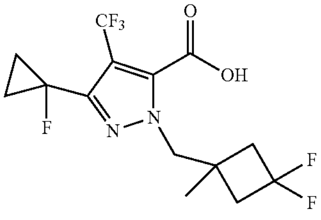 [SMILES: CC1(Cn2nc(C3(F)CC3)c(C(F)(F)F)c2C(=O)O)CC(F)(F)C1]

To a stirred solution of methyl 1-((3,3-difluoro-1-methylcyclobutyl)methyl)-3-(1-fluorocyclopropyl)-4-(trifluoromethyl)-1H-pyrazole-5-carboxylate (Intermediate 174, 1.5 g) in THE (6 mL), MeOH (6 mL) and water (6 mL) was added $LiOH \cdot H_2O$ (0.850 g) at 0° C. The resulting reaction mixture was then stirred for 2 h at rt. The mixture was concentrated under reduced pressure and diluted with water (30 mL). The pH was adjusted to ~4-5 with 1N aq. HCl solution (10 mL) and the mixture was extracted with EtOAc (3×30 mL). The combined organic layers were dried over anhydrous $Na_2SO_4$ and concentrated under reduced pressure to afford the title compound (1.4 g, 97%). LCMS m/z=355 $[M-H]^-$.

Intermediate 200-202, 204-218

The title compounds were prepared from the appropriate esters using an analogous method (at a suitable reaction time between 2-16 hand a suitable THF:MeOH:water mixture between 1:1:1 to 4:1:1 or 2.5:2.5:1) to that described for Intermediate 199.

| Intermediate | Structure/Name/Starting Materials/Data |
|---|---|
| 200 | 3-Cyclobutyl-1-((3,3-difluoro-1-methylcyclobutyl)methyl)-4-(trifluoromethyl)-1H-pyrazole-5-carboxylic acid<br>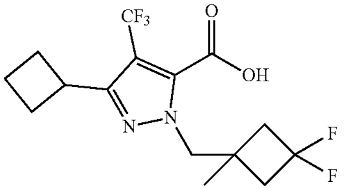 [SMILES: CC1(Cn2nc(C3CCC3)c(C(F)(F)F)c2C(=O)O)CC(F)(F)C1] |

-continued

| Intermediate | Structure/Name/Starting Materials/Data |
|---|---|
| | Ester: methyl 3-cyclobutyl-1-((3,3-difluoro-1-methylcyclobutyl)methyl)-4-iodo-1H-pyrazole-5-carboxylate (Intermediate 175)<br>Yield: 800 mg, 71%; LCMS m/z = 353 [M + H]$^+$. |
| 201 | 3-Cyclopentyl-1-((3,3-difluoro-1-methylcyclobutyl)methyl)-4-(trifluoromethyl)-1H-pyrazole-5-carboxylic acid<br>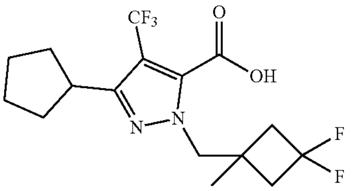 [SMILES: CC1(Cn2nc(C3CCCC3)c(C(F)(F)F)c2C(=O)O)CC(F)(F)C1]<br>Ester: methyl 3-cyclopentyl-1-((3,3-difluoro-1-methylcyclobutyl)methyl)-4-(trifluoromethyl)-1H-pyrazole-5-carboxylate (Intermediate 176)<br>Yield: 320 mg, 96%; LCMS m/z = 367 [M + H]$^+$. |
| 202 | 1-((3,3-Difluoro-1-methylcyclobutyl)methyl)-3-(spiro[2.3]hexan-5-yl)-4-(trifluoromethyl)-1H-pyrazole-5-carboxylic acid<br>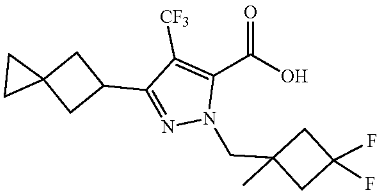 [SMILES: CC1(Cn2nc(C3CC4(CC4)C3)c(C(F)(F)F)c2C(=O)O)CC(F)(F)C1]<br>Ester: methyl 1-((3,3-difluoro-1-methylcyclobutyl)methyl)-3-(spiro[2.3]hexan-5-yl)-4-(trifluoromethyl)-1H-pyrazole-5-carboxylate (Intermediate 177)<br>Yield: 300 mg, crude; LCMS m/z = 379 [M + H]$^+$. |
| 204 | 1-((3,3-Difluoro-1-methylcyclobutyl)methyl)-3-(3,3-difluorocyclobutyl)-4-(trifluoromethyl)-1H-pyrazole-5-carboxylic acid<br>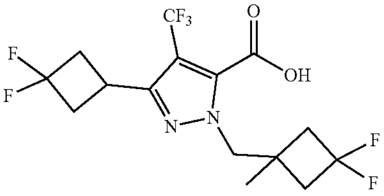 [SMILES: CC1(Cn2nc(C3CC(F)(F)C3)c(C(F)(F)F)c2C(=O)O)CC(F)(F)C1]<br>Ester: methyl 1-((3,3-difluoro-1-methylcyclobutyl)methyl)-3-(3,3-difluorocyclobutyl)-4-(trifluoromethyl)-1H-pyrazole-5-carboxylate (Intermediate 179)<br>Yield: 1.0 g, crude. |
| 205 | 1-((3,3-Difluoro-1-methylcyclobutyl)methyl)-3-(3-methoxybicyclo[1.1.1]pentan-1-yl)-4-(trifluoromethyl)-1H-pyrazole-5-carboxylic acid<br>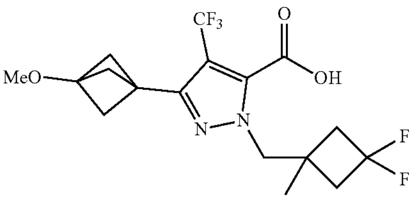 [SMILES: COC12CC(c3nn(CC4(C)CC(F)(F)C4)c(C(=O)O)c3C(F)(F)F)(C1)C2] |

-continued

| Intermediate | Structure/Name/Starting Materials/Data |
|---|---|
| | Ester: methyl 1-((3,3-difluoro-1-methylcyclobutyl)methyl)-3-(3-methoxybicyclo[1.1.1]pentan-1-yl)-4-(trifluoromethyl)-1H-pyrazole-5-carboxylate (Intermediate 181)<br>Yield: 90 mg, crude; LCMS m/z = 395 [M + H]$^+$. |
| 206 | 3-(Tert-butyl)-1-((3,3-difluoro-1-methylcyclobutyl)methyl)-4-(trifluoromethyl)-1H-pyrazole-5-carboxylic acid<br>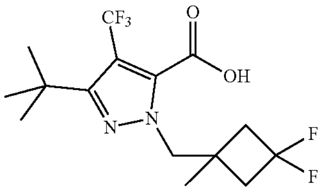 [SMILES: CC1(Cn2nc(C(C)(C)C)c(C(F)(F)F)c2C(=O)O)CC(F)(F)C1]<br>Ester: ethyl 3-(tert-butyl)-1-((3,3-difluoro-1-methylcyclobutyl)methyl)-4-(trifluoromethyl)-1H-pyrazole-5-carboxylate (Intermediate 183)<br>Yield: 1.5 g, crude; LCMS m/z = 355 [M + H]$^+$. |
| 207 | 1-((3,3-Difluoro-1-methylcyclobutyl)methyl)-3-(1-(difluoromethyl)cyclopropyl)-4-(trifluoromethyl)-1H-pyrazole-5-carboxylic acid<br>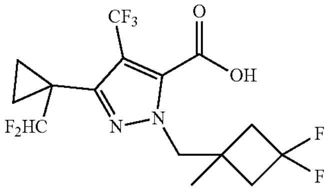 [SMILES: CC1(Cn2nc(C3(C(F)F)CC3)c(C(F)(F)F)c2C(=O)O)CC(F)(F)C1]<br>Ester: methyl 1-((3,3-difluoro-1-methylcyclobutyl)methyl)-3-(1-(difluoromethyl)cyclopropyl)-4-(trifluoromethyl)-1H-pyrazole-5-carboxylate (Intermediate 184)<br>Yield: 750 mg, 59%; LCMS m/z = 389 [M + H]$^+$. |
| 208 | 1-((3,3-Difluoro-1-methylcyclobutyl)methyl)-4-(trifluoromethyl)-3-(1-(trifluoromethyl)cyclopropyl)-1H-pyrazole-5-carboxylic acid<br>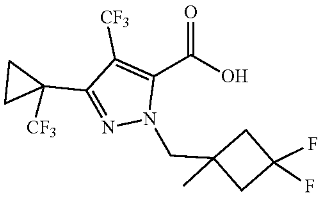 [SMILES: CC1(Cn2nc(C3(C(F)(F)F)CC3)c(C(F)(F)F)c2C(=O)O)CC(F)(F)C1]<br>Ester: methyl 1-((3,3-difluoro-1-methylcyclobutyl)methyl)-4-(trifluoromethyl)-3-(1-(trifluoromethyl)cyclopropyl)-1H-pyrazole-5-carboxylate (Intermediate 195)<br>Yield: 700 mg, 87%; LCMS m/z = 407 [M + H]$^+$. |
| 209 | 1-((3,3-Difluoro-1-methylcyclobutyl)methyl)-3-(2-fluoropropan-2-yl)-4-(trifluoromethyl)-1H-pyrazole-5-carboxylic acid<br>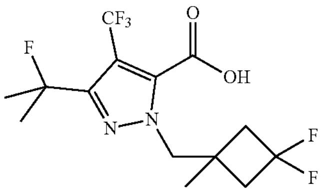 [SMILES: CC1(Cn2nc(C(C)(C)F)c(C(F)(F)F)c2C(=O)O)CC(F)(F)C1] |

-continued

| Intermediate | Structure/Name/Starting Materials/Data |
|---|---|
| | Ester: ethyl 1-((3,3-difluoro-1-methylcyclobutyl) methyl)-3-(2-fluoropropan-2-yl)-4-(trifluoromethyl)-1H-pyrazole-5-carboxylate (Intermediate 198)<br>Yield: 500 mg, crude; LCMS m/z = 359 [M + H]$^+$. |
| 210 | 1-((3,3-Difluoro-1-methylcyclobutyl)methyl)-3-(3-fluorobicyclo[1.1.1]pentan-1-yl)-4-(trifluoromethyl)-1H-pyrazole-5-carboxylic acid<br>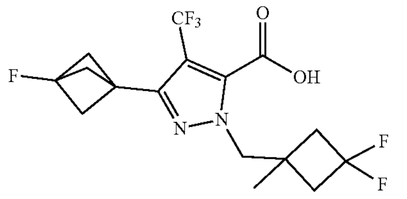 [SMILES: CC1(Cn2nc(C34CC(F)(C3)C4)c(C(F)(F)F)c2C(=O)O)CC(F)(F)C1]<br>Ester: methyl 1-((3,3-difluoro-1-methylcyclobutyl) methyl)-3-(3-fluorobicyclo[1.1.1]pentan-1-yl)-4-(trifluoromethyl)-1H-pyrazole-5-carboxylate (Intermediate 196)<br>Yield: 2.4 g, 99%; LCMS m/z = 381 [M − H]$^-$. |
| 211 | 3-(Bicyclo[1.1.1]pentan-1-yl)-1-(((trans)-2-(difluoromethyl)cyclopropyl)methyl)-4-(trifluoromethyl)-1H-pyrazole-5-carboxylic acid<br>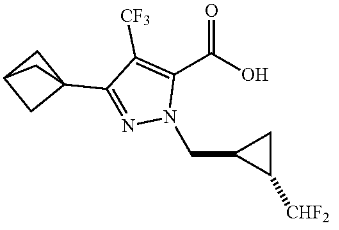<br>Ester: methyl 3-(bicyclo[1.1.1]pentan-1-yl)-1-(((trans)-2-(difluoromethyl)cyclopropyl)methyl)-4-(trifluoromethyl)-1H-pyrazole-5-carboxylate (Intermediate 186)<br>Yield: 55 mg, crude; LCMS m/z = 351 [M + H]$^+$. |
| 212 | 3-(Bicyclo[1.1.1]pentan-1-yl)-4-(trifluoromethyl)-1-(((trans)-2-(trifluoromethyl)cyclopropyl)methyl)-1H-pyrazole-5-carboxylic acid<br>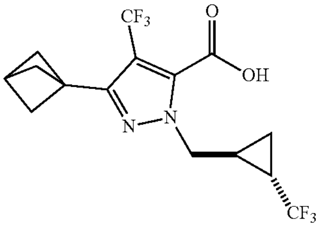<br>Ester: methyl 3-(bicyclo[1.1.1]pentan-1-yl)-4-(trifluoromethyl)-1-(((trans)-2-(trifluoromethyl) cyclopropyl)methyl)-1H-pyrazole-5-carboxylate (Intermediate 187)<br>Yield: 250 mg, crude; LCMS m/z = 369 [M + H]$^+$. |
| 213 | 1-((3,3-Difluoro-1-methylcyclobutyl)methyl)-3-(2,2-difluorocyclopropyl)-4-(trifluoromethyl)-1H-pyrazole-5-carboxylic acid |

-continued

| Intermediate | Structure/Name/Starting Materials/Data |
|---|---|
| | 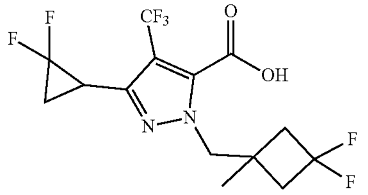 [SMILES: CC1(Cn2nc(C3CC3(F)F)c(C(F)(F)F)c2C(=O)O)CC(F)(F)C1]<br>Ester: methyl 1-((3,3-difluoro-1-methylcyclobutyl) methyl)-3-(2,2-difluorocyclopropyl)-4-(trifluoromethyl)-1H-pyrazole-5-carboxylate (Intermediate 189)<br>Yield: 300 mg, crude; LCMS m/z = 375 [M + H]$^+$. |
| 214 | 1-((3,3-Difluoro-1-methylcyclobutyl)methyl)-3-(2-fluorocyclopropyl)-4-(trifluoromethyl)-1H-pyrazole-5-carboxylic acid<br>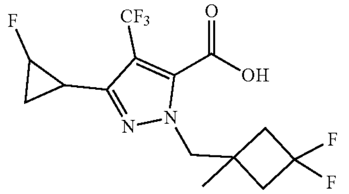 [SMILES: CC1(Cn2nc(C3CC3F)c(C(F)(F)F)c2C(=O)O)CC(F)(F)C1]<br>Ester: methyl 1-((3,3-difluoro-1-methylcyclobutyl) methyl)-3-(2-fluorocyclopropyl)-4-(trifluoromethyl)-1H-pyrazole-5-carboxylate (Intermediate 190)<br>Yield: 200 mg, 57%. |
| 215 | 3-Cyclopropyl-1-((3,3-difluoro-1-methylcyclopentyl) methyl)-4-(trifluoromethyl)-1H-pyrazole-5-carboxylic acid<br>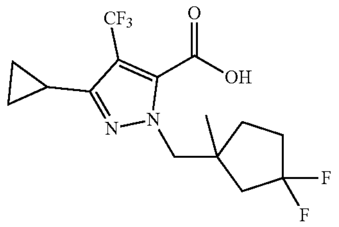 [SMILES: CC1(Cn2nc(C3CC3)c(C(F)(F)F)c2C(=O)O)CCC(F)(F)C1]<br>Ester: ethyl 3-cyclopropyl-1-((3,3-difluoro-1-methylcyclopentyl)methyl)-4-(trifluoromethyl)-1H-pyrazole-5-carboxylate (Intermediate 192)<br>Yield: 1.8 g, crude. |
| 216 | 3-Cyclopropyl-1-(((trans)-1-methyl-3-(trifluoromethyl) cyclobutyl)methyl)-4-(trifluoromethyl)-1H-pyrazole-5-carboxylic acid<br>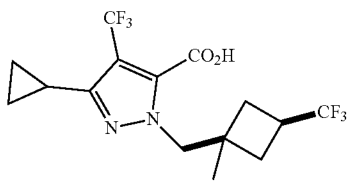<br>Ester: ethyl 3-cyclopropyl-1-(((trans)-1-methyl-3-(trifluoromethyl)cyclobutyl)methyl)-4-(trifluoromethyl)-1H-pyrazole-5-carboxylate (Intermediate 237a)<br>Yield: 0.22 g, 94%. LCMS m/z = 369 [M − H]$^-$. |
| 217 | 3-Cyclopropyl-1-(((cis)-1-methyl-3-(trifluoromethyl) cyclobutyl)methyl)-4-(trifluoromethyl)-1H-pyrazole-5-carboxylic acid |

-continued

| Intermediate | Structure/Name/Starting Materials/Data |
|---|---|
| | 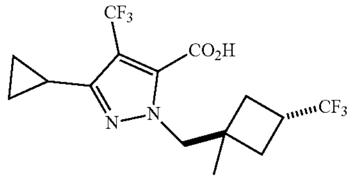<br>Ester: ethyl 3-cyclopropyl-1-(((cis)-1-methyl-3-(trifluoromethyl)cyclobutyl)methyl)-4-(trifluoromethyl)-1H-pyrazole-5-carboxylate (Intermediate 237b)<br>Yield: 0.22 g, 94%. LCMS m/z = 369 [M − H]⁻. |
| 218 | 3-(Bicyclo[1.1.1]pentan-1-yl)-1-((3,3-difluoro-1-methylcyclobutyl)methyl)-4-(trifluoromethyl)-1H-pyrazole-5-carboxylic acid<br>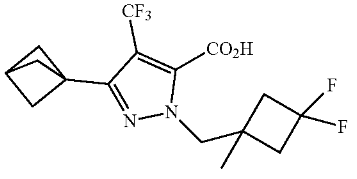 [SMILES: CC1(Cn2nc(C34CC(C3)C4)c(C(F)(F)F)c2C(=O)O)CC(F)(F)C1]<br>Ester: methyl 3-(bicyclo[1.1.1]pentan-1-yl)-1-((3,3-difluoro-1-methylcyclobutyl)methyl)-4-(trifluoromethyl)-1H-pyrazole-5-carboxylate (Intermediate 193)<br>Yield: 400 mg, 82%. LCMS m/z = 365 [M + H]⁺. |

Intermediate 219

1-((3,3-Difluoro-1-methylcyclobutyl)methyl)-3-(2,2-difluorobicyclo[1.1.1]pentan-1-yl)-4-(trifluoromethyl)-1H-pyrazole-5-carboxylic acid

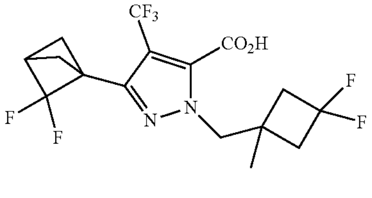 [SMILES: CC1(Cn2nc(C34CC(C3)C4(F)F)c(C(F)(F)F)c2C(=O)O)CC(F)(F)C1]

Ethyl 5-(2,2-difluoro-1-bicyclo[1.1.1]pentanyl)-2-[(3,3-difluoro-1-methyl-cyclobutyl)methyl]-4-(trifluoromethyl) pyrazole-3-carboxylate (Intermediate 194, 40 mg) was dissolved in EtOH (1 mL) followed by the addition of NaOH (2 mol/L) in $H_2O$ (0.056 mL). The mixture was heated to 50° C. for 30 minutes. The solvent was evaporated, the residue was taken up in DCM (10 mL) and was washed with 1M HCl (5 mL). The layers were separated and the organic phase was evaporated to dryness to yield the title compound (35 mg, 95%). LCMS m/z=402 [M+H]⁺.

Intermediate 30

3-Cyclopropyl-1-((3,3-difluorocyclopentyl)methyl)-4-(trifluoromethyl)-1H-pyrazole-5-carboxylic acid

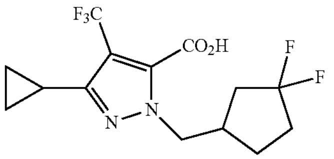 [SMILES: O=C(O)c1c(C(F)(F)F)c(C2CC2)nn1CC1CCC(F)(F)C1]

LiOH·$H_2O$ (0.12 g) was added to a solution of ethyl 3-cyclopropyl-1-((3,3-difluorocyclopentyl)methyl)-4-(trifluoromethyl)-1H-pyrazole-5-carboxylate (Intermediate 28, 0.7 g) in a mixture of THF/MeOH/$H_2O$ (2/2/1); 25 mL) at rt and the mixture was stirred for 16 h. The reaction mixture was concentrated under reduced pressure and diluted with water. The aqueous phase was acidified to pH 2 with saturated $KHSO_4$ solution at 0° C. and extracted with EtOAc (3×50 mL). The combined organics were washed with brine, dried ($Na_2SO_4$) and evaporated to dryness under reduced pressure to afford the title compound (0.6 g, 90%). LCMS m/z=339 [M+H]⁺.

Intermediate 220

1-((3,3-Difluoro-1-methylcyclobutyl)methyl)-3-(1-methylcyclopropyl)-4-(trifluoromethyl)-1H-pyrazole-5-carboxylic acid

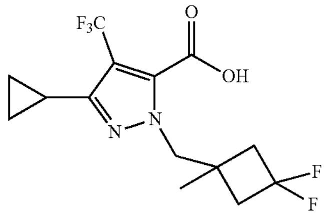 [SMILES: CC1(Cn2nc(C3CC3)c(C(F)(F)F)c2C(=O)O)CC(F)(F)C1]

To a solution of ethyl 1-[(3,3-difluoro-1-methylcyclobutyl)methyl]-3-(1-methylcyclopropyl)-4-(trifluoromethyl)-1H-pyrazole-5-carboxylate (Intermediate 161, 0.62 g) in a mixture of EtOH-THF-$H_2O$ (2:2:1) (25 mL) was added LiOH·$H_2O$ (0.27 g) at rt and the reaction mixture was stirred for 16 h. The reaction mixture was concentrated under reduced pressure and was acidified with saturated $NaHSO_4$ solution to pH~2. The resulting mixture was extracted with EtOAc (3×80 mL). The combined organic layers were dried over $Na_2SO_4$ and concentrated under reduced pressure to get the title compound (0.60 g, crude), which was used in the next step without further purification. Yield: Quantitative (0.60 g, crude).

Intermediate 221

The title compound was prepared from the appropriate ester using an analogous method to that described for Intermediate 220.

| Intermediate | Structure/Name/Starting Materials/Data |
|---|---|
| 221 | 3-(Bicyclo[1.1.1]pentan-1-yl)-1-((3,3-difluoro-1-methylcyclobutyl)methyl)-4-(difluoromethyl)-1H-pyrazole-5-carboxylic acid 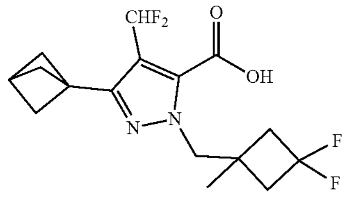 [SMILES: CC1(Cn2nc(C34CC(C3)C4)c(C(F)F)c2C(=O)O)CC(F)(F)C1] Ester: ethyl 3-{bicyclo[1.1.1]pentan-1-yl}-1-[(3,3-difluoro-1-methylcyclobutyl)methyl]-4-(difluoromethyl)-1H-pyrazole-5-carboxylate (Intermediate 284) Yield: 0.67 g, crude. |

Intermediate 222

1-((3,3-Difluoro-1-methylcyclobutyl)methyl)-3-(1,1-difluoroethyl)-4-(trifluoromethyl)-1H-pyrazole-5-carboxylic acid

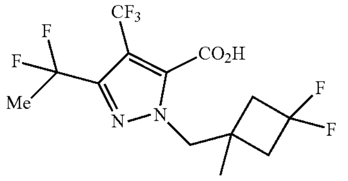

To a solution of ethyl 1-((3,3-difluoro-1-methylcyclobutyl)methyl)-3-(1,1-difluoroethyl)-4-(trifluoromethyl)-1H-pyrazole-5-carboxylate (Intermediate 182, 500 mg) in THE (8 mL) was added LiOH—$H_2O$ (97 mg) at rt and the mixture was stirred for 16 h. The reaction mixture was concentrated, diluted with water (50 mL) and washed with $Et_2O$ (2×50 mL). The aqueous layer was acidified with sat. $NaHSO_4$ solution to pH-5-6 and extracted with DCM (2×100 mL). The combined organic layers were dried over anhydrous $Na_2SO_4$ and concentrated under reduced pressure to yield the title compound (385 mg, 83%).

Intermediate 31

Methyl 3-(benzyloxy)-4-iodo-1H-pyrazole-5-carboxylate

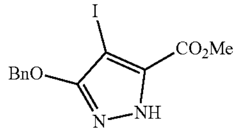 [SMILES: COC(=O)c1[nH]nc(OCc2ccccc2)c1I]

The title compound was prepared (2.8 g, 73%) from methyl 3-(benzyloxy)-1H-pyrazole-5-carboxylate (Intermediate 20) using an analogous method to that described for Intermediate 21. LCMS m/z=359 $[M+H]^+$.

Intermediate 32

Methyl 3-(benzyloxy)-4-iodo-1-((2-(trimethylsilyl)ethoxy)methyl)-1H-pyrazole-5-carboxylate

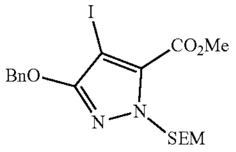 [SMILES: COC(=O)c1c(I)c(OCc2ccccc2)nn1COCC[Si](C)(C)C]

To a stirred solution of methyl 3-(benzyloxy)-4-iodo-1H-pyrazole-5-carboxylate (Intermediate 31, 2.7 g) in DCM (35 mL) at 0° C. was added DIPEA (3.75 mL) and the mixture was stirred at 0° C. for 0.5 h. SEM-Cl (1.6 mL) was added to the reaction mixture at 0° C. and stirred at rt for 1 h. The reaction was quenched with crushed ice and extracted with DCM (3×100 mL). The combined organics were washed with cold brine, dried ($Na_2SO_4$) and evaporated to dryness under reduced pressure. The residue was purified by CombiFlash chromatography ($SiO_2$, 0-15% EtOAc/Hex) to afford the title compound (3 g, 81%). LCMS m/z=489 $[M+H]^+$.

Intermediate 33

Methyl 3-(benzyloxy)-4-(trifluoromethyl)-1-((2-(trimethylsilyl)ethoxy)methyl)-1H-pyrazole-5-carboxylate

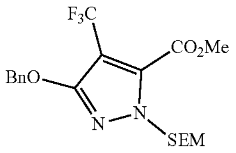 [SMILES: COC(=O)c1c(C(F)(F)F)c(OCc2ccccc2)nn1COCC[Si](C)(C)C]

To a stirred solution of methyl 3-(benzyloxy)-4-iodo-1-((2-(trimethylsilyl)ethoxy)methyl)-1H-pyrazole-5-carboxylate (Intermediate 32, 5 g) in DMF (70 mL) were added CuI (3.9 g), dry KF (1.78 g) and $TMSCF_3$ (10.6 mL) at rt. The reaction mixture was heated in a sealed tube at 90° C. for 16 h, diluted with ice water and extracted with EtOAc (3×150 mL). Combined organics were washed with cold brine, dried ($Na_2SO_4$) and evaporated to dryness in vacuo. The residue were purified by CombiFlash chromatography ($SiO_2$, 0-15% EtOAc/Hex) to afford the title compound (3.5 g, 79%).

Intermediate 34

Methyl 3-(benzyloxy)-4-(trifluoromethyl)-1H-pyrazole-5-carboxylate

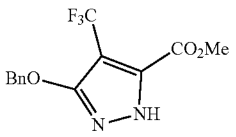 [SMILES: COC(=O)c1[nH]nc(OCc2ccccc2)c1C(F)(F)F]

To a stirred solution of methyl 3-(benzyloxy)-4-(trifluoromethyl)-1-((2-(trimethylsilyl)ethoxy)methyl)-1H-pyrazole-5-carboxylate (Intermediate 33, 6.7 g) in MeOH (30 mL) was added 4M dioxane/HCl (48 mL) at 0° C. and the reaction mixture stirred at rt for 2 h. The reaction mixture was concentrated under reduced pressure and the residue was quenched with sat. $NaHCO_3$ solution at 0° C. to maintain pH-8. The aqueous phase was extracted with EtOAc (3×200 mL). The combined organics were washed with brine, dried ($Na_2SO_4$) and evaporated to dryness in vacuo. The residue was purified by CombiFlash chromatography ($SiO_2$, 0-50% EtOAc/Hex) to afford the title compound (3.2 g, 68%). LCMS m/z=301 $[M+H]^+$.

Intermediate 35

Ethyl 3-acetyl-4-methyl-1H-pyrazole-5-carboxylate

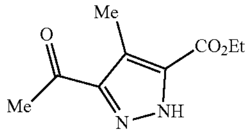 [SMILES: CCOC(=O)c1[nH]nc(C(C)=O)c1C]

To a stirred solution of KOH (112 g) in ethanol (15 vol), was added pentane-2,4-dione (200 g) at reflux temperature followed by addition of ethyl diazoacetate (258 g) and the resulting reaction mixture was stirred at 80° C. for 1 h. The reaction mixture was concentrated under reduced pressure, diluted with water (50 vol), adjusted the pH to ~2 with 3N aq. HCl solution at 15-20° C. The precipitated solid was collected by filtration, washed with water and dried to afford the title compound (150 g, 38%) which was used without further purification. LCMS m/z=197 $[M+H]^+$.

Intermediate 36

Ether 3-(1,1-difluoroethyl)-4-methyl-1H-pyrazole-5-carboxylate

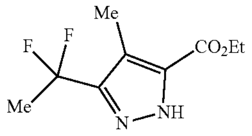 [SMILES: CCOC(=O)c1[nH]nc(C(C)(F)F)c1C]

To a stirred solution of ethyl 3-acetyl-4-methyl-1H-pyrazole-5-carboxylate (Intermediate 35, 100 g, 510 mmol) in DCM (1 L) was added DAST (164 g) at 0° C. and the reaction mixture was stirred at rt for 12 h. The reaction mixture was quenched with 50% aq. $NaHCO_3$ solution (500 mL), and extracted with DCM (2×200 mL). The combined organics were washed with water (150 mL), brine (150 mL), dried ($Na_2SO_4$) and evaporated to dryness in vacuo. The residue was purified by column chromatography ($SiO_2$, 10% EtOAc/PE) to afford the title compound (40 g, 35%). LCMS m/z=219 $[M+H]^+$.

Intermediate 37

Methyl 3-(benzyloxy)-1-((3,3-difluorocyclopentyl)methyl)-4-(trifluoromethyl)-1H-pyrazole-5-carboxylate

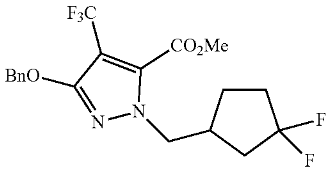 [SMILES: COC(=O)c1c(C(F)(F)F)c(OCc2ccccc2)nn1CC1CCC(F)(F)C1]

To a solution of methyl 3-(benzyloxy)-4-(trifluoromethyl)-1H-pyrazole-5-carboxylate (Intermediate 34, 1.0 g) and (3,3-difluorocyclopentyl)methanol (0.68 g) in THE (30 mL) was added $PPh_3$ (1.3 g) at 0° C. and after 5 min was added DIAD (1.0 mL) at 0° C. and the reaction was stirred at rt for 16 h. The reaction mixture was concentrated under reduced pressure and the residue was purified by CombiFlash chromatography ($SiO_2$; 0-20% EtOAc/Hex) to give the title compound (1 g, 72%). LCMS m/z=419 $[M+H]^+$.

Intermediate 38-52, 223-239

The title compounds were prepared from the appropriate pyrazole and alcohol (at a suitable temperature between 0-90° C.) using an analogous method to that described for Intermediate 37.

| Intermediate | Structure/Name/Starting Materials/Data |
|---|---|
| 38 | Ethyl 3-cyclopropyl-1-((4,4-difluorocyclohexyl)methyl)-4-(trifluoromethyl)-1H-pyrazole-5-carboxylate<br>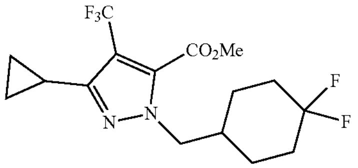 [SMILES: COC(=O)c1c(C(F)(F)F)c(C2CC2)nn1CC1CCC(F)(F)CC1]<br>ROH: (4,4-difluorocyclohexyl)methanol<br>Pyrazole: ethyl 3-cyclopropyl-4-(trifluoromethyl)-1H-pyrazole-5-carboxylate (Intermediate 24)<br>Yield: 450 mg, 73%; LCMS m/z = 381 $[M + H]^+$. |
| 39 | Ethyl 1-((4,4-difluorocyclohexyl)methyl)-3-(1,1-difluoroethyl)-4-methyl-1H-pyrazole-5-carboxylate<br>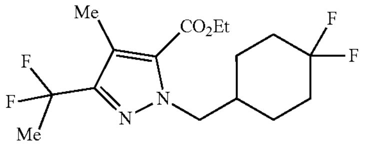 [SMILES: CCOC(=O)c1c(C)c(C(C)(F)F)nn1CC1CCC(F)(F)CC1]<br>ROH: (4,4-difluorocyclohexyl)methanol<br>Pyrazole: ethyl 3-(1,1-difluoroethyl)-4-methyl-1H-pyrazole-5-carboxylate (Intermediate 36)<br>Yield: 0.5 g, 62%; LCMS m/z = 351 $[M + H]^+$. |
| 40 | Ethyl 1-((4,4-difluoro-1-methylcyclohexyl)methyl)-3-(1,1-difluoroethyl)-4-methyl-1H-pyrazole-5-carboxylate |

-continued

| Intermediate | Structure/Name/Starting Materials/Data |
|---|---|
| | 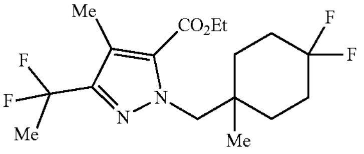 [SMILES: CCOC(=O)c1c(C)c(C(C)(F)F)nn1CC1(C)CCC(F)(F)CC1]<br>ROH: (4,4-difluoro-1-methylcyclohexyl)methanol<br>Pyrazole: ethyl 3-(1,1-difluoroethyl)-4-methyl-1H-pyrazole-5-carboxylate (Intermediate 36)<br>Yield: 0.5 g, 60%; LCMS m/z = 365 $[M + H]^+$. |
| 41 | Ethyl 3-(1,1-difluoroethyl)-4-methyl-1-((3-(trifluoromethyl)bicyclo[1.1.1]pentan-1-yl)methyl)-1H-pyrazole-5-carboxylate<br>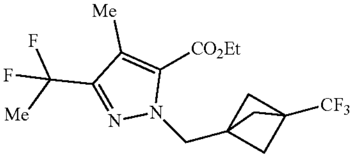 [SMILES: CCOC(=O)c1c(C)c(C(C)(F)F)nn1CC12CC(C(F)(F)F)(C1)C2]<br>ROH: (3-(trifluoromethyl)bicyclo[1.1.1]pentan-1-yl) methanol<br>Pyrazole: ethyl 3-(1,1-difluoroethyl)-4-methyl-1H-pyrazole-5-carboxylate (Intermediate 36)<br>Yield: 0.25 g, 60%; LCMS m/z = 367 $[M + H]^+$. |
| 43 | Ethyl (S)-3-cyclopropyl-1-((3,3-difluorocyclopentyl) methyl)-4-(trifluoromethyl)-1H-pyrazole-5-carboxylate<br>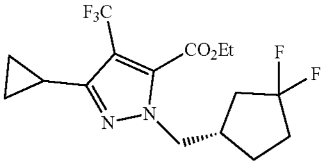 [SMILES: CCOC(=O)c1c(C(F)(F)F)c(C2CC2)nn1C[C@H]1CCC(F)(F)C1]<br>ROH: (S)-(3,3-difluorocyclopentyl)methanol<br>Pyrazole: ethyl 3-cyclopropyl-4-(trifluoromethyl)-1H-pyrazole-5-carboxy late (Intermediate 24)<br>Yield: 0.4 g, 77%; LCMS m/z = 367 $[M + H]^+$. |
| 44 | Ethyl (R)-3-cyclopropyl-1-((3,3-difluorocyclopentyl) methyl)-4-(trifluoromethyl)-1H-pyrazole-5-carboxylate<br>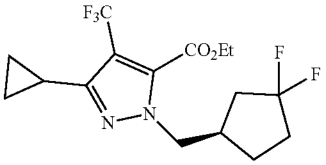 [SMILES: CCOC(=O)c1c(C(F)(F)F)c(C2CC2)nn1C[C@@H]1CCC(F)(F)C1]<br>ROH: (R)-(3,3-difluorocyclopentyl)methanol<br>Pyrazole: ethyl 3-cyclopropyl-4-(trifluoromethyl)-1H-pyrazole-5-carboxylate (Intermediate 24)<br>Yield: 0.4 g, 77%; LCMS m/z = 367 $[M + H]^+$. |
| 45 | Ethyl 3-cyclopropyl-1-((2-fluorospiro[3.3]heptan-2-yl) methyl)-4-(trifluoromethyl)-1H-pyrazole-5-carboxylate<br>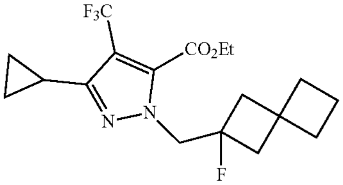 [SMILES: CCOC(=O)c1c(C(F)(F)F)c(C2CC2)nn1CC1(F)CC2(CCC2)C1]<br>ROH: (2-fluorospiro[3.3]heptan-2-yl)methanol<br>Pyrazole: ethyl 3-cyclopropyl-4-(trifluoromethyl)-1H-pyrazole-5-carboxylate (Intermediate 24)<br>Yield: 0.3 g, 78%; LCMS m/z = 375 $[M + H]^+$. |
| 46 | Ethyl 3-cyclopropyl-4-(trifluoromethyl)-1-((3-(trifluoromethyl)bicyclo[1.1.1]pentan-1-yl)methyl)-1H-pyrazole-5-carboxylate<br>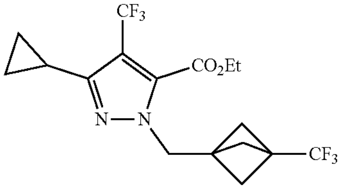 [SMILES: CCOC(=O)c1c(C(F)(F)F)c(C2CC2)nn1CC12CC(C(F)(F)F)(C1)C2]<br>ROH: (3-(trifluoromethyl)bicyclo[1.1.1]pentan-1-yl)methanol<br>Pyrazole: ethyl 3-cyclopropyl-4-(trifluoromethyl)-1H-pyrazole-5-carboxy late (Intermediate 24)<br>Yield: 0.35 g, 72%; LCMS m/z = 397 $[M + H]^+$. |
| 47 | Ethyl 3-cyclopropyl-1-((3-fluorobicyclo[1.1.1]pentan-1-yl)methyl)-4-(trifluoromethyl)-1H-pyrazole-5-carboxylate<br>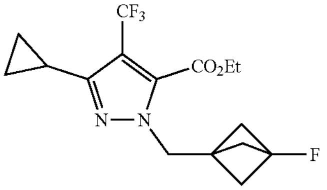 [SMILES: CCOC(=O)c1c(C(F)(F)F)c(C2CC2)nn1CC12CC(F)(C1)C2]<br>ROH: (3-fluorobicyclo[1.1.1]pentan-1-yl)methanol<br>Pyrazole: ethyl 3-cyclopropyl-4-(trifluoromethyl)-1H-pyrazole-5-carboxylate (Intermediate 24)<br>Yield: 0.43 g, 61%; LCMS m/z = 347 $[M + H]^+$. |
| 48 | Ethyl 3-cyclopropyl-1-((6,6-difluorospiro[3.3]heptan-2-yl) methyl)-4-(trifluoromethyl)-1H-pyrazole-5-carboxylate<br>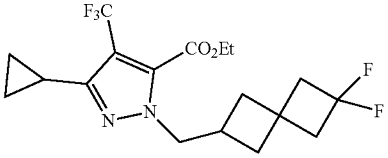 [SMILES: CCOC(=O)c1c(C(F)(F)F)c(C2CC2)nn1CC1CC2(C1)CC(F)(F)C2]<br>ROH: (6,6-difluorospiro[3.3]heptan-2-yl)methanol<br>Pyrazole: ethyl 3-cyclopropyl-4-(trifluoromethyl)-1H-pyrazole-5-carboxylate (Intermediate 24)<br>Yield: 0.2 g, 50%; LCMS m/z = 375 $[M + H]^+$. |
| 49 | Ethyl (S)-1-((3,3-difluorocyclopentyl)methyl)-3-(1,1-difluoroethyl)-4-methyl-1H-pyrazole-5-carboxylate<br>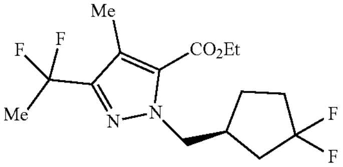 [SMILES: CCOC(=O)c1c(C)c(C(C)(F)F)nn1C[C@H]1CCC(F)(F)C1]<br>ROH: (S)-(3,3-difluorocyclopentyl)methanol<br>Pyrazole: ethyl 3-(1,1-difluoroethyl)-4-methyl-1H-pyrazole-5-carboxylate (Intermediate 36)<br>Yield: 4.5 g, 73%; LCMS: m/z = 337 $[M + H]^+$. |

-continued

| Intermediate | Structure/Name/Starting Materials/Data |
|---|---|
| 50 | Ethyl (R)-1-((3,3-difluorocyclopentyl)methyl)-3-(1,1-difluoroethyl)-4-methyl-1H-pyrazole-5-carboxylate<br>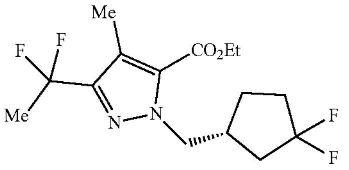 [SMILES: CCOC(=O)c1c(C)c(C(C)(F)F)nn1C[C@@H]1CCC(F)(F)C1]<br>ROH: (R)-(3,3-difluorocyclopentyl)methanol<br>Pyrazole: ethyl 3-(1,1-difluoroethyl)-4-methyl-1H-pyrazole-5-carboxylate (Intermediate 36)<br>Yield: 8 g, 65%; LCMS: m/z = 337 [M + H]$^+$. |
| 52 | Ethyl 3-(1,1-difluoroethyl)-4-methyl-1-(((cis)-3-(trifluoromethyl)cyclobutyl)methyl)-1H-pyrazole-5-carboxylate<br>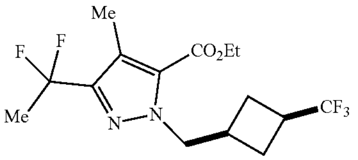<br>ROH: ((cis)-3-(trifluoromethyl)cyclobutyl)methanol<br>Pyrazole: Ethyl 3-(1,1-difluoroethyl)-4-methyl-1H-pyrazole-5-carboxylate (Intermediate 36)<br>Yield: 0.3 g, 46%; LCMS: m/z = 355 [M + H]$^+$. |
| 223 | Ethyl 3-(1-cyanocyclopropyl)-1-((3,3-difluoro-1-methylcyclobutyl)methyl)-4-iodo-1H-pyrazole-5-carboxylate<br>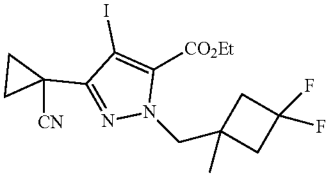 [SMILES: CCOC(=O)c1c(I)c(C2(C#N)CC2)nn1CC1(C)CC(F)(F)C1]<br>ROH: (3,3-difluoro-1-methylcyclobutyl)methanol (Intermediate 5)<br>Pyrazole: ethyl 3-(1-cyanocyclopropyl)-4-iodo-1H-pyrazole-5-carboxylate (Intermediate 157)<br>Yield: 1.4 g, 79%; LCMS m/z = 450 [M + H]$^+$. |
| 224 | Methyl 1-((3,3-difluoro-1-methylcyclobutyl)methyl)-3-(3,3-difluorocyclobutyl)-4-iodo-1H-pyrazole-5-carboxylate<br>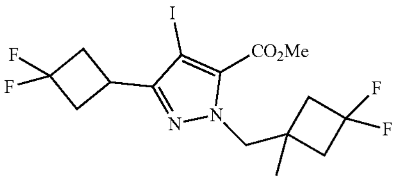 [SMILES: COC(=O)c1c(I)c(C2CC(F)(F)C2)nn1CC1(C)CC(F)(F)C1]<br>ROH: (3,3-difluoro-1-methylcyclobutyl)methanol (Intermediate 5)<br>Pyrazole: methyl 3-(3,3-difluorocyclobutyl)-4-iodo-1H-pyrazole-5-carboxylate (Intermediate 146)<br>Yield: 2.0 g, 29% over four steps; LCMS m/z = 461 [M + H]$^+$. |
| 225 | Ethyl 1-((3,3-difluoro-1-methylcyclobutyl)methyl)-4-iodo-3-(1-methoxycyclopropyl)-1H-pyrazole-5-carboxylate<br>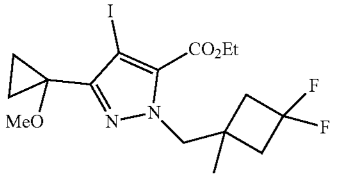 [SMILES: CCOC(=O)c1c(I)c(C2(OC)CC2)nn1CC1(C)CC(F)(F)C1]<br>ROH: (3,3-difluoro-1-methylcyclobutyl)methanol (Intermediate 5)<br>Pyrazole: ethyl 4-iodo-3-(1-methoxycyclopropyl)-1H-pyrazole-5-carboxylate (Intermediate 138)<br>Yield: 310 mg, 57%; LCMS m/z = 455 [M + H]$^+$. |
| 226 | Methyl 1-((3,3-difluoro-1-methylcyclobutyl)methyl)-4-iodo-3-(3-methoxybicyclo[1.1.1]pentan-1-yl)-1H-pyrazole-5-carboxylate<br>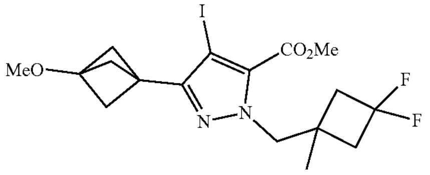 [SMILES: COC(=O)c1c(I)c(C23CC(OC)(C2)C3)nn1CC1(C)CC(F)(F)C1]<br>ROH: (3,3-difluoro-1-methylcyclobutyl)methanol (Intermediate 5)<br>Pyrazole: methyl 4-iodo-3-(3-methoxybicyclo[1.1.1]pentan-1-yl)-1H-pyrazole-5-carboxylate (Intermediate 147)<br>Yield: 180 mg, 54%; LCMS m/z = 467 [M + H]$^+$. |
| 227 | Ethyl 3-cyclopropyl-1-((2-oxobicyclo[2.1.1]hexan-1-yl)methyl)-4-(trifluoromethyl)-1H-pyrazole-5-carboxylate<br>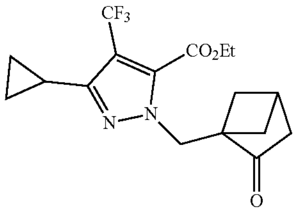 [SMILES: CCOC(=O)c1c(C(F)(F)F)c(C2CC2)nn1CC12CC(CC1=O)C2]<br>ROH: 1-(hydroxymethyl)bicyclo[2.1.1]hexan-2-one (Intermediate 101)<br>Pyrazole: ethyl 3-cyclopropyl-4-(trifluoromethyl)-1H-pyrazole-5-carboxylate (Intermediate 24)<br>Yield: 0.5 g, 62%; LCMS m/z = 357 [M + H]$^+$. |
| 228 | Ethyl 3-(tert-butyl)-1-((3,3-difluoro-1-methylcyclobutyl)methyl)-4-iodo-1H-pyrazole-5-carboxylate<br>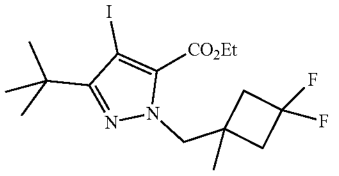 [SMILES: CCOC(=O)c1c(I)c(C(C)(C)C)nn1CC1(C)CC(F)(F)C1]<br>ROH: (3,3-difluoro-1-methylcyclobutyl)methanol (Intermediate 5)<br>Pyrazole: ethyl 3-(tert-butyl)-4-iodo-1H-pyrazole-5-carboxylate (Intermediate 148)<br>Yield: 4.2 g, 77%; LCMS m/z = 441 [M + H]$^+$. |
| 229 | Ethyl 1-((3,3-difluoro-1-methylcyclobutyl)methyl)-3-(2-hydroxypropan-2-yl)-4-iodo-1H-pyrazole-5-carboxylate |

-continued

| Intermediate | Structure/Name/Starting Materials/Data |
|---|---|
| | 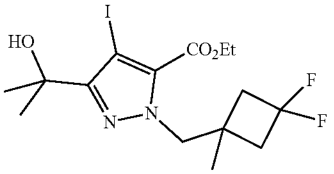 [SMILES: CCOC(=O)c1c(I)c(C(C)(C)O)nn1CC1(C)CC(F)(F)C1] ROH: (3,3-difluoro-1-methylcyclobutyl)methanol (Intermediate 5) Pyrazole: ethyl 3-(2-hydroxypropan-2-yl)-4-iodo-1H-pyrazole-5-carboxylate (Intermediate 151) Yield: 1.5 g, 68%. |
| 230 | Ethyl 3-cyclopropyl-1-(spiro[2.2]pentan-1-ylmethyl)-4-(trifluoromethyl)-1 H-pyrazole-5-carboxylate 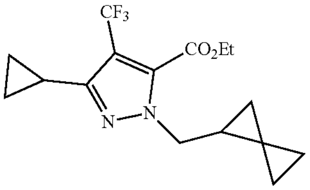 [SMILES: CCOC(=O)c1c(C(F)(F)F)c(C2CC2)nn1CC1CC12CC2] ROH: spiro[2.2]pentan-2-ylmethanol (Intermediate 102) Pyrazole: ethyl 3-cyclopropyl-4-(trifluoromethyl)-1H-pyrazole-5-carboxylate (Intermediate 24) Yield: 0.6 g, 70%; LCMS m/z = 329 [M + H]+. |
| 231 | Methyl 3-(1-fluorocyclopropyl)-4-iodo-1-(((trans)-2-(trifluoromethyl)cyclopropyl)methyl)-1H-pyrazole-5-carboxylate 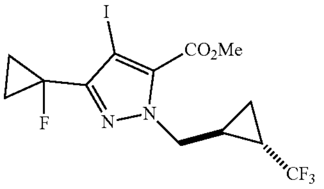 ROH: ((trans)-2-(trifluoromethyl)cyclopropyl)methanol Pyrazole: methyl 3-(1-fluorocyclopropyl)-4-iodo-1H-pyrazole-5-carboxylate (Intermediate 142) Yield: 500 mg, 59%; LCMS m/z = 433 [M + H]+. |
| 232 | Methyl 3-cyclopropyl-1-((2,2-difluorospiro[2.3]hexan-1-yl)methyl)-4-(trifluoromethyl)-1H-pyrazole-5-carboxylate 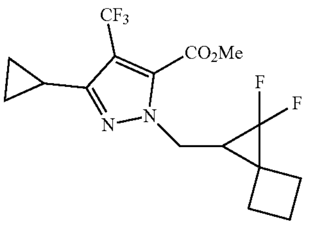 [SMILES: COC(=O)c1c(C(F)(F)F)c(C2CC2)nn1CC1C(F)(F)C12CCC2] ROH: {2,2-difluorospiro[2.3]hexan-1-yl} methanol Pyrazole: ethyl 3-cyclopropyl-4-(trifluoromethyl)-1H-pyrazole-5-carboxylate Yield: 0.6 g, 78%. |
| 233 | Ethyl 3-cyclopropyl-1-((2,2-difluorospiro[2.2]pentan-1-yl)methyl)-4-(trifluoromethyl)-1H-pyrazole-5-carboxylate 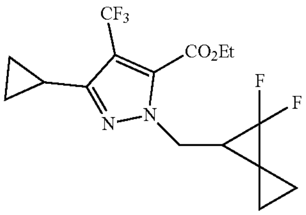 [SMILES: CCOC(=O)c1c(C(F)(F)F)c(C2CC2)nn1CC1C(F)(F)C12CC2] ROH: {2,2-difluorospiro[2.2]pentan-1-yl}methanol (Intermediate 104) Pyrazole: ethyl 3-cyclopropyl-4-(trifluoromethyl)-1H-pyrazole-5-carboxylate (Intermediate 24) Yield: 0.33 g, 89%; LCMS m/z = 365 [M + H]+. |
| 234 | Methyl 3-(bicyclo[1.1.1]pentan-1-yl)-1-(((trans)-2-(difluoromethyl)cyclopropyl)methyl)-4-iodo-1H-pyrazole-5-carboxylate 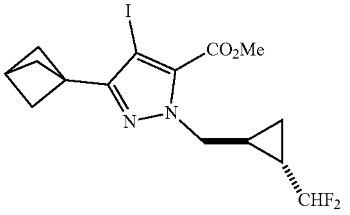 ROH: ((trans)-2-(difluoromethyl)cyclopropyl)methanol Pyrazole: methyl 3-(bicyclo[1.1.1]pentan-1-yl)-4-iodo-1H-pyrazole-5-carboxylate (Intermediate 153) Yield: 350 mg, 65%; LCMS m/z = 423 [M + H]+. |
| 235 | Methyl 3-(bicyclo[1.1.1]pentan-1-yl)-4-iodo-1-(((trans)-2-(trifluoromethyl)cyclopropyl)methyl)-1H-pyrazole-5-carboxylate 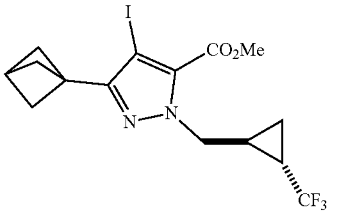 ROH: ((trans)-2-(trifluoromethyl)cyclopropyl)methanol Pyrazole: methyl 3-(bicyclo[1.1.1]pentan-1-yl)-4-iodo-1H-pyrazole-5-carboxylate (Intermediate 153) Yield: 520 mg, crude. |
| 236 | Methyl 1-((3,3-difluoro-1-methylcyclobutyl)methyl)-3-(2,2-difluorocyclopropyl)-4-iodo-1H-pyrazole-5-carboxylate 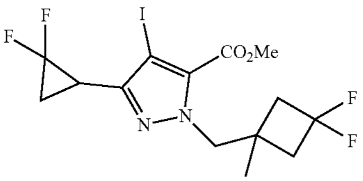 [SMILES: COC(=O)c1c(I)c(C2CC2(F)F)nn1CC1(C)CC(F)(F)C1] ROH: (3,3-difluoro-1-methylcyclobutyl)metanol (Intermediate 5) Pyrazole: methyl 3-(2,2-difluorocyclopropyl)-4-iodo-1H-pyrazole-5-carboxylate (Intermediate 154) Yield: 1.1 g, crude. LCMS m/z = 447 [M + H]+. |

-continued

| Intermediate | Structure/Name/Starting Materials/Data |
|---|---|
| 237a/237b | Ethyl 3-cyclopropyl-1-((1-methyl-3-(trifluoromethyl) cyclobutyl)methyl)-4-(trifluoromethyl)-1H-pyrazole-5-carboxylate 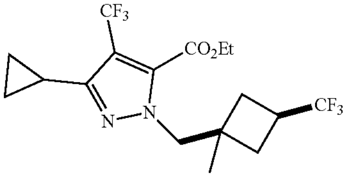 237a and 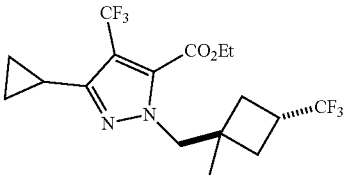 237b ROH: cis/trans [1-methyl-3-(trifluoromethyl)cyclobutyl] methanol Pyrazole: ethyl 3-cyclopropyl-4-(trifluoromethyl)-1H-pyrazole-5-carboxylate (Intermediate 24) Chiral-HPLC; YMC Actus Triart C18 (250 x 20 mm, 5 μm); A: 20 mM $NH_4HCO_3$ in water, B = 80:20 MeCN:THF; Gradient Profile: A/B 80/20, then A/B 25/75 in 3 min., then A/B 10/90 in 24 min, then A/B 0/100 in 25 min., held this composition up to 28 min. Peak 1, Intermediate 237a: 0.65 g, 68%. LCMS m/z = 399 $[M + H]^+$, first eluting. Peak 2, Intermediate 237b: 0.35 g, 36%. LCMS m/z = 399 $[M + H]^+$, second eluting. |
| 238 | Methyl 3-(bicyclo[1.1.1]pentan-1-yl)-1-((3,3-difluoro-1-methylcyclobutyl)methyl)-4-iodo-1H-pyrazole-5-carboxylate 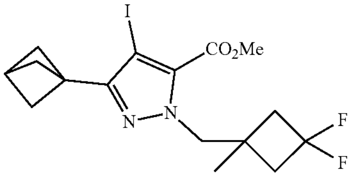 [SMILES: COC(=O)c1c(I)c(C23CC(C2)C3)nn1CC1(C)CC(F)(F)C1] ROH: (3,3-difluoro-1-methylcyclobutyl)methanol (Intermediate 5) Pyrazole: methyl 3-(bicyclo[1.1.1]pentan-1-yl)-4-iodo-1H-pyrazole-5-carboxylate (Intermediate 153) |

-continued

| Intermediate | Structure/Name/Starting Materials/Data |
|---|---|
| | Yield: 1.2 g, 10% over five steps; LCMS m/z = 437 $[M + H]^+$. |
| 239 | Ethyl 3-cyclopropyl-1-((4-fluorobicyclo[2.2.1]heptan-1-yl)methyl)-4-(trifluoromethyl)-1H-pyrazole-5-carboxylate 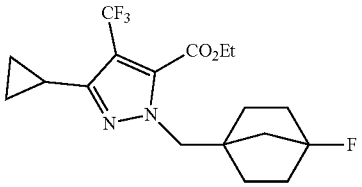 [SMILES: CCOC(=O)c1c(C(F)(F)F)c(C2CC2)nn1CC12CCC(F)(CC1)C2] ROH: {4-fluorobicyclo[2.2.1 ]heptan-1-yl} methanol (Intermediate 7) Pyrazole: ethyl 3-cyclopropyl-4-(trifluoromethyl)-1H-pyrazole-5-carboxylate (Intermediate 24) Yield: 0.35 g, 77%; LCMS m/z = 375 $[M + H]^+$. |

Intermediate 240

Ethyl 3-cyclopropyl-4-(trifluoromethyl)-1-((1-(trifluoromethyl)cyclopentyl)methyl)-1H-pyrazole-5-carboxylate

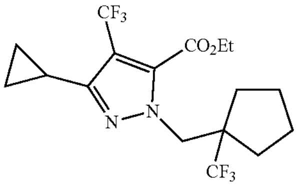 [SMILES: CCOC(=O)c1c(C(F)(F)F)c(C2CC2)nn1CC1(C(F)(F)F)CCCC1]

To a stirred solution of ethyl 3-cyclopropyl-4-(trifluoromethyl)-1H-pyrazole-5-carboxylate (Intemediate 24, 0.2 g) in toluene (4 mL) were added [1-(trifluoromethyl)cyclopentyl] methanol (0.16 g), $PPh_3$ (0.25 g) and DIAD (0.2 mL) at rt in a microwave vessel. The mixture was heated to 100° C. for 1.5 h under microwave irradiation. The reaction mixture was concentrated under reduced pressure to get the crude product, which was purified by column chromatography ($SiO_2$; 0-10% EtOAc/Hex) to yield the title compound (0.3 g, 93%). LCMS m/z=399 $[M+H]^+$.

Intermediate 241-244

The title compounds were prepared from the appropriate pyrazole and alcohol using an analogous method to that described for Intermediate 240.

| Intermediate | Structure/Name/Starting Materials/Data |
|---|---|
| 241 | Ethyl 1-((3,3-difluoro-1-methylcyclobutyl)methyl)-4-iodo-3-((trans)-2-methylcyclopropyl)-1H-pyrazole-5-carboxylate 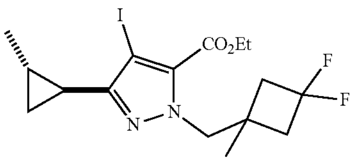 [SMILES: CCOC(=O)c1c(I)c([C@H]2C[C@@H]2C)nn1CC1(C)CC(F)(F)C1] |

-continued

| Intermediate | Structure/Name/Starting Materials/Data |
|---|---|
| | ROH: (3,3-difluoro-1-methylcyclobutyl)methanol (Intermediate 5)<br>Pyrazole: ethyl 4-iodo-3-((trans)-2-methylcyclopropyl)-1H-pyrazole-5-carboxylate (Intermediate 139)<br>Yield: 0.2 g, 73%. |
| 242 | Ethyl 3-(bicyclo[1.1.1]pentan-1-yl)-1-((3,3-difluoro-1-methylcyclobutyl)methyl)-4-iodo-1H-pyrazole-5-carboxylate<br>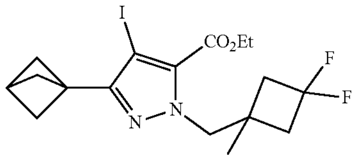 [SMILES: CCOC(=O)c1c(I)c(C23CC(C2)C3)nn1CC1(C)CC(F)(F)C1]<br>ROH: (3,3-difluoro-1-methylcyclobutyl)methanol (Intermediate 5)<br>Pyrazole: ethyl 3-{bicyclo[1.1.1]pentan-1-yl}-4-iodo-1H-pyrazole-5-carboxylate (Intermediate 140)<br>Yield: 0.7 g, 65%; LCMS m/z = 451 $[M + H]^+$. |
| 243 | Ethyl 3-cyclopropyl-1-((6,6-difluoro-4-methylspiro[2.3]hexan-4-yl)methyl)-4-(trifluoromethyl)-1H-pyrazole-5-carboxylate<br>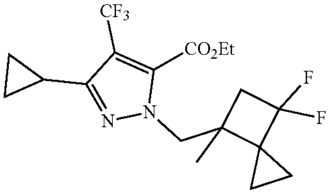 [SMILES: CCOC(=O)c1c(C(F)(F)F)c(C2CC2)nn1CC1(C)CC(F)(F)C12CC2]<br>ROH: {6,6-difluoro-4-methylspiro[2.3]hexan-4-yl}methanol (Intermediate 103)<br>Pyrazole: ethyl 3-cyclopropyl-4-(trifluoromethyl)-1H-pyrazole-5-carboxylate (Intermediate 24)<br>Yield: 1.5 g, 72%; LCMS m/z = 393 $[M + H]^+$. |
| 244 | Tert-butyl 5-((3-cyclopropyl-5-(ethoxycarbonyl)-4-(trifluoromethyl)-1H-pyrazol-1-yl)methyl)-2-azaspiro[3.3]heptane-2-carboxylate<br>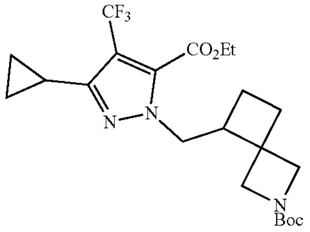 [SMILES: CCOC(=O)c1c(C(F)(F)F)c(C2CC2)nn1CC1CCC12CN(C(=O)OC(C)(C)C)C2]<br>ROH: tert-butyl 5-(hydroxymethyl)-2-azaspiro[3.3]heptane-2-carboxylate<br>Pyrazole: ethyl 3-cyclopropyl-4-(trifluoromethyl)-1H-pyrazole-5-carboxylate (Intermediate 24)<br>Yield: 0.35 g, 63%; LCMS m/z = 458 $[M + H]^+$. |

Intermediate 245

Ethyl 1-((3,3-difluoro-1-methylcyclobutyl)methyl)-3-(2-fluoropropan-2-yl)-4-iodo-1H-pyrazole-5-carboxylate

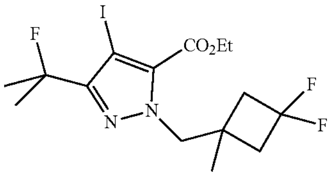 [SMILES: CCOC(=O)c1c(I)c(C(C)(C)F)nn1CC1(C)CC(F)(F)C1]

To a stirred solution ethyl 1-((3,3-difluoro-1-methylcyclobutyl)methyl)-3-(2-hydroxypropan-2-yl)-4-iodo-1H-pyrazole-5-carboxylate (Intermediate 229, 1.5 g) in DCM (15 mL) was added DAST (1.79 mL) at −20° C. and the mixture was allowed to warm to rt over 2 h. The reaction mixture was slowly quenched with ice water (100 mL) and extracted with DCM (2×65 mL). The combined organic layers were washed with water (25 mL) and brine (25 mL), dried over anhydrous $Na_2SO_4$ and concentrated under reduced pressure to get the crude product, which was purified by column chromatography ($SiO_2$, 8-10% EtOAc/PE) to yield the title compound (1.0 g, 66%). LCMS m/z=445 $[M+H]^+$.

Intermediate 246

Ethyl 3-cyclopropyl-1-((2,2-difluorobicyclo[2.1.1]hexan-1-yl)methyl)-4-(trifluoromethyl)-1H-pyrazole-5-carboxylate

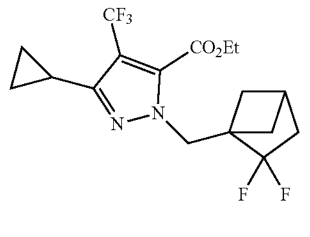 [SMILES: CCOC(=O)c1c(C(F)(F)F)c(C2CC2)nn1CC12CC(CC1(F)F)C2]

To a solution of ethyl 3-cyclopropyl-1-((2-oxobicyclo[2.1.1]hexan-1-yl)methyl)-4-(trifluoromethyl)-1H-pyrazole-5-carboxylate (Intermediate 227, 1.0 g) in DCM (15.0 mL) were added DAST (2.9 mL) and EtOH (0.1 mL) at 0° C. The reaction mixture was stirred at rt for 16 h. The reaction mixture was quenched with $NaHCO_3$ solution and extracted with DCM. The combined organic layers were washed with water and brine, dried over $Na_2SO_4$, filtered and evaporated under reduced pressure to get the crude product, which was purified by CombiFlash column chromatography ($SiO_2$, 0-40% EtOAc/Hex) to afford the title compound. LCMS m/z=379 $[M+H]^+$.

Intermediate 53

Methyl 1-((3,3-difluorocyclopentyl)methyl)-3-hydroxy-4-(trifluoromethyl)-1H-pyrazole-5-carboxylate

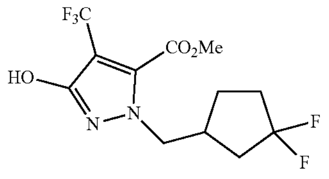 [SMILES: COC(=O)c1c(C(F)(F)F)c(O)nn1CC1CCC(F)(F)C1]

A solution of methyl 3-(benzyloxy)-1-((3,3-difluorocyclopentyl)methyl)-4-(trifluoromethyl)-1H-pyrazole-5-carboxylate (Intermediate 37, 1.0 g) in MeOH (30 mL) was degassed with $N_2$ for 15 min followed by the addition of 10% Pd—C(50% wet, 0.5 g) at rt. The reaction mixture was stirred at rt under 1.4 bar of pressure using a $H_2$-balloon for 16 h. The reaction mixture was filtered through a pad of celite, the filtrate was concentrated under reduced pressure and the residue was purified by Combiflash chromatography ($SiO_2$, 0-50% EtOAc/Hex) to afford the title compound (0.72 g, 92%). LCMS m/z=329 $[M+H]^+$.

Intermediate 54

Methyl 1-((3,3-difluorocyclopentyl)methyl)-3-(difluoromethoxy)-4-(trifluoromethyl)-1H-pyrazole-5-carboxylate

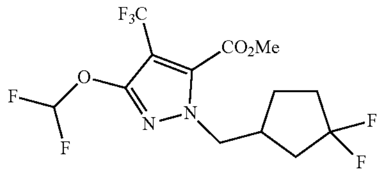 [SMILES: COC(=O)c1c(C(F)(F)F)c(OC(F)F)nn1CC1CCC(F)(F)C1]

To a stirred solution of methyl 1-((3,3-difluorocyclopentyl)methyl)-3-hydroxy-4-(trifluoromethyl)-1H-pyrazole-5-carboxylate (Intermediate 53, 0.3 g) in MeCN (16 mL) were added sodium 2-chloro-2,2-difluoroacetate (0.18 g) and $K_2CO_3$ (0.314 g) and the resulting mixture was heated to 80° C. for 2 h. The reaction mixture was concentrated under reduced pressure and the residue purified by CombiFlash chromatography ($SiO_2$; 0-20% EtOAc/Hex) to afford the title compound (0.24 g, 69%). LCMS m/z=379 $[M+H]^+$.

Intermediate 55

Ethyl 3-cyclopropyl-1-((3,3-difluoro-1-meth. 1H-pyrazole-5-carboxylate

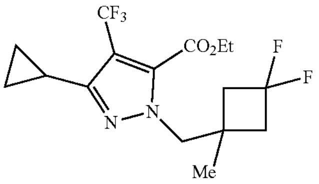 [SMILES: CCOC(=O)c1c(C(F)(F)F)c(C2CC2)nn1CC1(C)CC(F)(F)C1]

To a stirred solution of ethyl 3-cyclopropyl-4-(trifluoromethyl)-1H-pyrazole-5-carboxylate (Intermediate 24, 1.1 g) in DMF (20 mL) were added (3,3-difluoro-1-methylcyclobutyl)methyl methanesulfonate (Intermediate 6, 1.14 g) and $Cs_2CO_3$ (3.61 g) at rt and the reaction mixture was stirred at 90° C. for 1 h. The reaction mixture was diluted with ice water and extracted with EtOAc (3×200 mL). The combined organics were dried ($Na_2SO_4$) and concentrated under reduced pressure. The residue was purified by CombiFlash chromatography (0-15% EtOAc/hex) to afford the title compound (0.84 g, 56%). LCMS m/z=367 $[M+H]^+$.

Intermediate 56-57, 247-248

The title compounds were prepared from the appropriate pyrazole and mesylate (ROMs) using an analogous method (at a suitable reaction time between 1-16 h) to that described for Intermediate 55.

| Intermediate | Name/Structure/Starting Materials/Data |
|---|---|
| 56 | Ethyl 1-((3,3-difluorocyclopentyl)methyl)-3-(1,1-difluoroethyl)-4-iodo-1H-pyrazole-5-carboxylate<br>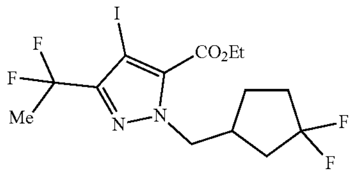 [SMILES: CCOC(=O)c1c(I)c(C(C)(F)F)nn1CC1CCC(F)(F)C1]<br>Alternative conditions: $K_2CO_3$/MeCN/80° C./16 h<br>ROMs: (3,3-difluorocyclopentyl)methyl methanesulfonate (Intermediate 1)<br>Pyrazole: ethyl 3-(1,1-difluoroethyl)-4-iodo-1H-pyrazole-5-carboxylate<br>Yield: 1 g, 61%; LCMS m/z = 449 $[M + H]^+$. |
| 57 | Ethyl 1-((3,3-difluoro-1-methylcyclobutyl)methyl)-3-(1,1-difluoroethyl)-4-methyl-1H-pyrazole-5-carboxylate<br>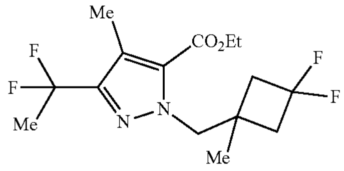 [SMILES: CCOC(=O)c1c(C)c(C(C)(F)F)nn1CC1(C)CC(F)(F)C1]<br>ROMs: (3,3-difluoro-1-methylcyclobutyl)methyl methanesulfonate (Intermediate 6)<br>Pyrazole: ethyl 3-(1,1-difluoroethyl)-4-methyl-1H-pyrazole-5-carboxylate (Intermediate 36)<br>Yield: 0.65 g, 65%; LCMS m/z = 337 $[M + H]^+$. |
| 247 | Ethyl 3-cyclopropyl-1-(dispiro[2.0.$2^4$.$1^3$]heptan-7-ylmethyl)-4-(trifluoromethyl)-1H-pyrazole-5-carboxylate<br>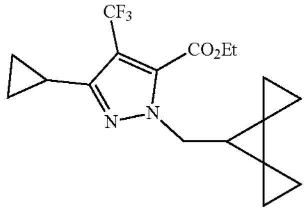<br>ROMs: {dispiro[2.0.$2^4$.$1^3$]heptan-7-yl} methyl methanesulfonate (Intermediate 105)<br>Pyrazole: ethyl 3-cyclopropyl-4-(trifluoromethyl)-1H-pyrazole-5-carboxylate (Intermediate 24)<br>Yield: 0.30 g, 27%; LCMS m/z = 355 $[M + H]^+$. |
| 248 | Ethyl 1-((3,3-difluoro-1-methylcyclobutyl)methyl)-4-iodo-3-(spiro[2.2]pentan-1-yl)-1H-pyrazole-5-carboxylate<br>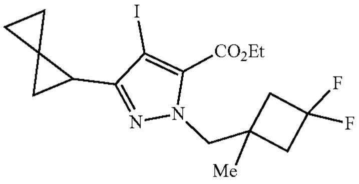 [SMILES: CCOC(=O)c1c(I)c(C2CC23CC3)nn1CC1(C)CC(F)(F)C1]<br>ROMs: (3,3-difluoro-1-methylcyclobutyl)methyl methanesulfonate (Intermediate 6)<br>Pyrazole: ethyl 4-iodo-3-{spiro[2.2]pentan-1-yl}-1H-pyrazole-5-carboxylate (Intermediate 141)<br>Yield: 2.2 g, 58%; LCMS m/z = 451 $[M + H]^+$. |

Intermediate 58

Ethyl 1-((3,3-difluorocyclopentyl)methyl)-3-(1,1-difluoroethyl)-4-methyl-1H-pyrazole-5-carboxylate

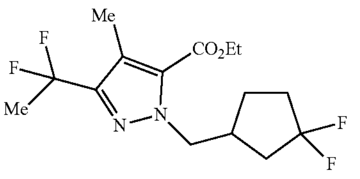 [SMILES: CCOC(=O)c1c(C)c(C(C)(F)F)nn1CC1CCC(F)(F)C1]

A mixture of ethyl 1-((3,3-difluorocyclopentyl)methyl)-3-(1,1-difluoroethyl)-4-iodo-1H-pyrazole-5-carboxylate (Intermediate 56, 0.57 g) and $Cs_2CO_3$ (0.82 g) in dioxane (13 mL) was degassed with Ar (g) for 15 min followed by the addition of trimethylboroxine (0.35 mL) and $PdCl_2$ (dppf)-DCM (52 mg) at rt and the resulting mixture was heated at 110° C. for 16 h in a sealed tube. The reaction mixture was cooled to rt, filtered through a pad of celite and washed with EtOAc. The filtrate was evaporated under reduced pressure and the residue purified by CombiFlash chromatography ($SiO_2$, 0-20% EtOAc/Hex) to afford the title compound (0.4 g, 93%). LCMS m/z $[M+H]^+$=337.

Intermediate 60

3-Cyclopropyl-1-((3,3-difluoro-1-methylcyclobutyl)methyl)-4-(trifluoromethyl)-1H-pyrazole-5-carboxylic acid

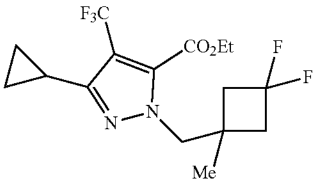 [SMILES: CCOC(=O)c1c(C(F)(F)F)c(C2CC2)nn1CC1(C)CC(F)(F)C1]

To a solution of ethyl 3-cyclopropyl-1-((3,3-difluoro-1-methylcyclobutyl)methyl)-4-(trifluoromethyl)-1H-pyrazole-5-carboxylate (Intermediate 55, 0.84 g) in a mixture of EtOH/THF/$H_2O$ (2:2:1, 25 mL) was added LiOH·$H_2O$ (0.144 g) at rt and the reaction mixture was stirred at rt for 16 h. The reaction mixture was concentrated under reduced pressure, acidified to approx. pH 2 with saturated $NaHSO_4$ solution and the aqueous phase extracted with EtOAc (3×80 mL). The combined organics were washed with cold brine, dried ($Na_2SO_4$) and evaporated to dryness under reduced pressure to afford the title compound (0.75 g, 96%). LCMS m/z=339 $[M+H]^+$.

Intermediate 62-77

The title compounds were prepared from the appropriate ester using an analogous method to that described for Intermediate 60.

| Intermediate | Name/Structure/Starting ester/Data |
| --- | --- |
| 62 | 1-((3,3-Difluorocyclopentyl)methyl)-3-(difluoromethoxy)-4-(trifluoromethyl)-1H-pyrazole-5-carboxylic acid 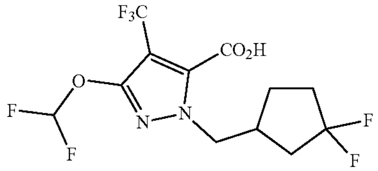 [SMILES: O=C(O)c1c(C(F)(F)F)c(OC(F)F)nn1CC1CCC(F)(F)C1] Ester: methyl 1-((3,3-difluorocyclopentyl)methyl)-3-(difluoromethoxy)-4-(trifluoromethyl)-1H-pyrazole-5-carboxylate (Intermediate 54) Yield: 200 mg, 85%; LCMS m/z = 363 $[M + H]^+$. |
| 63 | 1-((3,3-Difluorocyclobutyl)methyl)-3-(1,1-difluoroethyl)-4-(trifluoromethyl)-1H-pyrazole-5-carboxylic acid 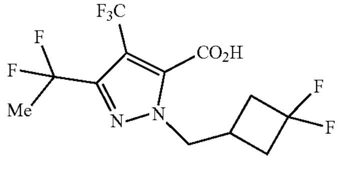 [SMILES: CC(F)(F)c1nn(CC2CC(F)(F)C2)c(C(=O)O)c1C(F)(F)F] Ester: ethyl 1-((3,3-difluorocyclobutyl)methyl)-3-(1,1-difluoroethyl)-4-(trifluoromethyl)-1H-pyrazole-5-carboxylate (Intermediate 29) Yield: 300 mg, 92%; LCMS m/z = 349 $[M + H]^+$. |
| 64 | 1-((3,3-Difluorocyclopentyl)methyl)-3-(1,1-difluoroethyl)-4-methyl-1H-pyrazole-5-carboxylic acid |

-continued

| Intermediate | Name/Structure/Starting ester/Data |
|---|---|
| | 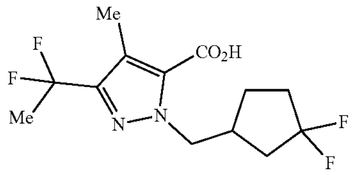 [SMILES: Cc1c(C(C)(F)F)nn(CC2CCC(F)(F)C2)c1C(=O)O] |
| | Ester: ethyl 1-((3,3-difluorocyclopentyl)methyl)-3-(1,1-difluoroethyl)-4-methyl-1H-pyrazole-5-carboxylate (Intermediate 58)<br>Yield: 300 mg, 81%; LCMS m/z = 309 $[M + H]^+$. |
| 65 | 1-((3,3-Difluoro-1-methylcyclobutyl)methyl)-3-(1,1-difluoroethyl)-4-methyl-1H-pyrazole-5-carboxylic acid |
| | 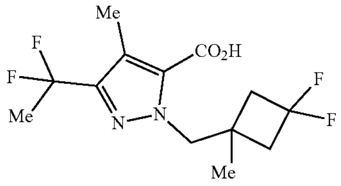 [SMILES: Cc1c(C(C)(F)F)nn(CC2(C)CC(F)(F)C2)c1C(=O)O] |
| | Ester: ethyl 1-((3,3-difluoro-1-methylcyclobutyl)methyl)-3-(1,1-difluoroethyl)-4-methyl-1H-pyrazole-5-carboxylate (Intermediate 57)<br>Yield: 80 mg, 80%; LCMS m/z = 309 $[M + H]^+$. |
| 66 | 1-((4,4-Difluorocyclohexyl)methyl)-3-(1,1-difluoroethyl)-4-methyl-1H-pyrazole-5-carboxylic acid |
| | 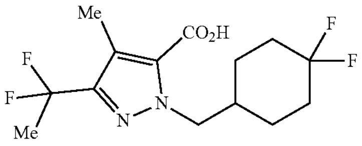 [SMILES: Cc1c(C(C)(F)F)nn(CC2CCC(F)(F)CC2)c1C(=O)O] |
| | Ester: ethyl 1-((4,4-difluorocyclohexyl)methyl)-3-(1,1-difluoroethyl)-4-methyl-1H-pyrazole-5-carboxylate (Intermediate 39)<br>Yield: 590 mg, 71%; LCMS m/z = 323 $[M + H]^+$. |
| 67 | 1-((4,4-Difluoro-1-methylcyclohexyl)methyl)-3-(1,1-difluoroethyl)-4-methyl-1H-pyrazole-5-carboxylic acid |
| | 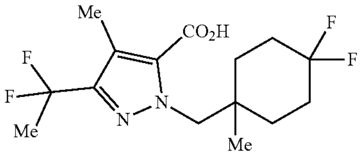 [SMILES: Cc1c(C(C)(F)F)nn(CC2(C)CCC(F)(F)CC2)c1C(=O)O] |
| | Ester: ethyl 1-((4,4-difluoro-1-methylcyclohexyl)methyl)-3-(1,1-difluoroethyl)-4-methyl-1H-pyrazole-5-carboxylate (Intermediate 40)<br>Yield: 330 mg, 66%; LCMS m/z = 337 $[M + H]^+$. |
| 68 | 3-(1,1-Difluoroethyl)-4-methyl-1-((3-(trifluoromethyl)bicyclo[1.1.1]pentan-1-yl)methyl)-1H-pyrazole-5-carboxylic acid |
| | 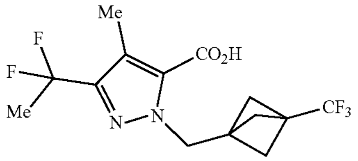 [SMILES: Cc1c(C(C)(F)F)nn(CC23CC(C(F)(F)F)(C2)C3)c1C(=O)O] |
| | Ester: ethyl 3-(1,1-difluoroethyl)-4-methyl-1-((3-(trifluoromethyl)bicyclo[1.1.1]pentan-1-yl)methyl)-1H-pyrazole-5-carboxylate (Intermediate 41)<br>Yield: 260 mg, 70%; LCMS m/z = 339 $[M + H]^+$. |
| 70 | (S)-3-Cyclopropyl-1-((3,3-difluorocyclopentyl)methyl)-4-(trifluoromethyl)-1H-pyrazole-5-carboxylic acid |

-continued

| Intermediate | Name/Structure/Starting ester/Data |
|---|---|
| | 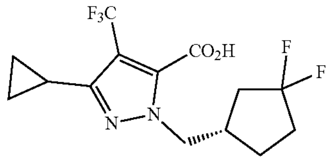 [SMILES: O=C(O)c1c(C(F)(F)F)c(C2CC2)nn1C[C@H]1CCC(F)(F)C1] |
| | Ester: ethyl (S)-3-cyclopropyl-1-((3,3-difluorocyclopentyl)methyl)-4-(trifluoromethyl)-1H-pyrazole-5-carboxylate (Intermediate 43)<br>Yield: 300 mg, 65%; LCMS m/z = 339 [M + H]$^+$. |
| 71 | (R)-3-Cyclopropyl-1-((3,3-difluorocyclopentyl)methyl)-4-(trifluoromethyl)-1H-pyrazole-5-carboxylic acid |
| | 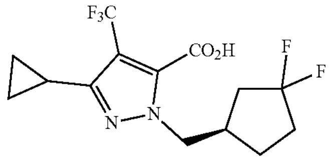 [SMILES: O=C(O)c1c(C(F)(F)F)c(C2CC2)nn1C[C@@H]1CCC(F)(F)C1] |
| | Ester: ethyl (R)-3-cyclopropyl-1-((3,3-difluorocyclopentyl)methyl)-4-(trifluoromethyl)-1H-pyrazole-5-carboxylate (Intermediate 44)<br>Yield: 300 mg, 65%; LCMS m/z = 339 [M + H]$^+$. |
| 72 | 3-Cyclopropyl-1-((2-fluorospiro[3.3]heptan-2-yl)methyl)-4-(trifluoromethyl)-1H-pyrazole-5-carboxylic acid |
| | 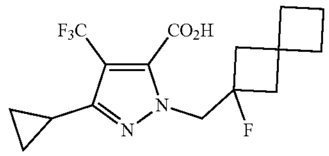 [SMILES: O=C(O)c1c(C(F)(F)F)c(C2CC2)nn1CC1(F)CC2(CCC2)C1] |
| | Ester: ethyl 3-cyclopropyl-1-((2-fluorospiro[3.3]heptan-2-yl)methyl)-4-(trifluoromethyl)-1H-pyrazole-5-carboxylate (Intermediate 45)<br>Yield: 250 mg, 77%; LCMS m/z = 347 [M + H]$^+$. |
| 73 | 3-Cyclopropyl-4-(trifluoromethyl)-1-((3-(trifluoromethyl)bicyclo[1.1.1]pentan-1-yl)methyl)-1H-pyrazole-5-carboxylic acid |
| | 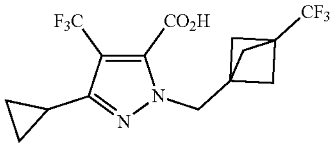 [SMILES: O=C(O)c1c(C(F)(F)F)c(C2CC2)nn1CC12CC(C(F)(F)F)(C1)C2] |
| | Ester: ethyl 3-cyclopropyl-4-(trifluoromethyl)-1-((3-(trifluoromethyl)bicyclo[1.1.1]pentan-1-yl)methyl)-1H-pyrazole-5-carboxylate (Intermediate 46)<br>Yield: 250 mg, 90%; LCMS m/z = 337 [M + H]$^+$. |
| 74 | 3-Cyclopropyl-1-((3-fluorobicyclo[1.1.1]pentan-1-yl)methyl)-4-(trifluoromethyl)-1H-pyrazole-5-carboxylic acid |
| | 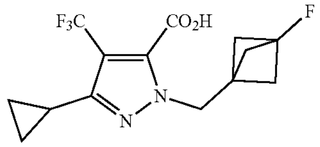 [SMILES: O=C(O)c1c(C(F)(F)F)c(C2CC2)nn1CC12CC(F)(C1)C2] |
| | Ester: ethyl 3-cyclopropyl-1-((3-fluorobicyclo[1.1.1]pentan-1-yl)methyl)-4-(trifluoromethyl)-1H-pyrazole-5-carboxylate (Intermediate 47)<br>Yield: 350 mg, 76%; LCMS m/z = 319 [M + H]$^+$. |
| 75 | 3-Cyclopropyl-1-((6,6-difluorospiro[3.3]heptan-2-yl)methyl)-4-(trifluoromethyl)-1H-pyrazole-5-carboxylic acid |
| | 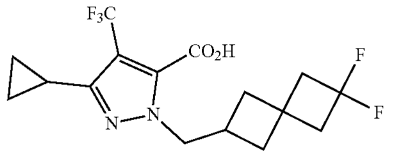 [SMILES: O=C(O)c1c(C(F)(F)F)c(C2CC2)nn1CC1CC2(C1)CC(F)(F)C2] |

-continued

| Intermediate | Name/Structure/Starting ester/Data |
|---|---|
| | Ester: ethyl 3-cyclopropyl-1-((6,6-difluorospiro[3.3]heptan-2-yl)methyl)-4-(trifluoromethyl)-1H-pyrazole-5-carboxylate (Intermediate 48) Yield: 120 mg, 92%; LCMS m/z = 363 $[M + H]^+$. |
| 77 | 3-(1,1-difluoroethyl)-4-methyl-1-(((cis)-3-(trifluoromethyl)cyclobutyl)methyl)-1H-pyrazole-5-carboxylic acid 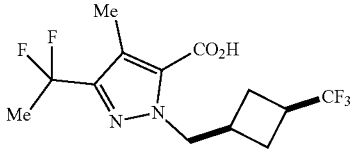 Ester: ethyl 3-(1,1-difluoroethyl)-4-methyl-1-(((cis)-3-(trifluoromethyl)cyclobutyl)methyl)-1H-pyrazole-5-carboxylate (Intermediate 52) Yield: 0.21 g, 99%; LCMS: m/z = 327 $[M + H]^+$. |

Intermediate 250

1-((3,3-Difluoro-1-methylcyclobutyl)methyl)-3-(1-methoxycyclopropyl)-4-(trifluoromethyl)-1H-pyrazole-5-carboxylic acid

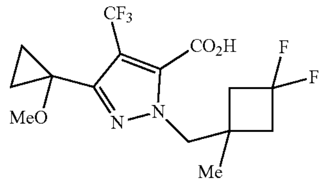 [SMILES: COC1(c2nn(CC3(C)CC(F)(F)C3)c(C(=O)O)c2C(F)(F)F)CC1]

To a solution of ethyl 1-[(3,3-difluoro-1-methylcyclobutyl)methyl]-3-(1-methoxycyclopropyl)-4-(trifluoromethyl)-1H-pyrazole-5-carboxylate (Intermediate 180, 0.15 g) in a mixture of THE-$H_2O$ (2:1) (9 mL) was added $LiOH{\cdot}H_2O$ (0.05 g) at rt and the reaction mixture was stirred for 16 h. The reaction mixture was concentrated under reduced pressure and acidified with saturated $NaHSO_4$ solution to pH~2. The aqueous part was extracted with EtOAc (3x30 mL). The combined organic layers were washed with cold brine, dried over $Na_2SO_4$ and concentrated under reduced pressure to obtain the title compound (0.13 g, 93%). LCMS m/z=369 $[M+H]^+$.

Intermediate 203, 251-261, 299

The title compounds were prepared from the appropriate ester using an analogous method (at a suitable reaction temperature between 0° C.-rt, a suitable reaction time between 4-16 h and a suitable THF:water mixture between 5:1 and 4:10) to that described for Intermediate 250.

| Intermediate | Name/Structure/Starting ester/Data |
|---|---|
| 203 | 3-(1-Cyanocyclopropyl)-1-((3,3-difluoro-1-methylcyclobutyl)methyl)-4-(trifluoromethyl)-1H-pyrazole-5-carboxylic acid 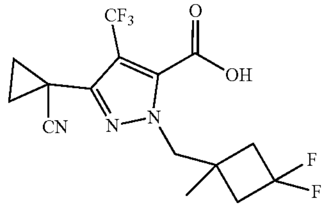 [SMILES: CC1(Cn2nc(C3(C#N)CC3)c(C(F)(F)F)c2C(=O)O)CC(F)(F)C1] Ester: ethyl 3-(1-cyanocyclopropyl)-1-((3,3-difluoro-1-methylcyclobutyl)methyl)-4-(trifluoromethyl)-1H-pyrazole-5-carboxylate (Intermediate 178) Yield: 500 mg, 70%; LCMS m/z = 364 $[M + H]^+$. |
| 251 | 3-Cyclopropyl-4-(trifluoromethyl)-1-((1-(trifluoromethyl)cyclopentyl)methyl)-1H-pyrazole-5-carboxylic acid 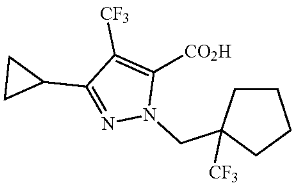 [SMILES: O=C(O)c1c(C(F)(F)F)c(C2CC2)nn1CC1(C(F)(F)F)CCCC1] |

-continued

| Intermediate | Name/Structure/Starting ester/Data |
|---|---|
| | Ester: ethyl 3-cyclopropyl-4-(trifluoromethyl)-1-{[1-(trifluoromethyl)cyclopentyl]methyl}-1H-pyrazole-5-carboxylate (Intermediate 240)<br>Yield: 790 mg, 96%; LCMS m/z = 371 [M + H]$^+$. |
| 252 | 3-Cyclopropyl-1-((2,2-difluorobicyclo[2.1.1]hexan-1-yl)methyl)-4-(trifluoromethyl)-1H-pyrazole-5-carboxylic acid<br>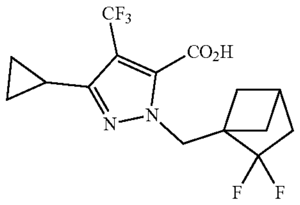 [SMILES: O=C(O)c1c(C(F)(F)F)c(C2CC2)nn1CC12CC(CC1(F)F)C2]<br>Ester: ethyl 3-cyclopropyl-1-((2,2-difluorobicyclo[2.1.1]hexan-1-yl)methyl)-4-(trifluoromethyl)-1H-pyrazole-5-carboxylate (Intermediate 246)<br>Yield: 0.3 mg, 92%; LCMS m/z = 351 [M + H]$^+$. |
| 253 | 3-Cyclopropyl-1-((4-fluorobicyclo[2.2.1]heptan-1-yl)methyl)-4-(trifluoromethyl)-1H-pyrazole-5-carboxylic acid<br>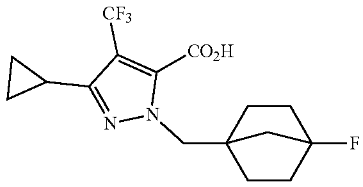 [SMILES: O=C(O)c1c(C(F)(F)F)c(C2CC2)nn1CC12CCC(F)(CC1)C2]<br>Ester: ethyl 3-cyclopropyl-1-({4-fluorobicyclo[2.2.1]heptan-1-yl}methyl)-4-(trifluoromethyl)-1H-pyrazole-5-carboxylate (Intermediate 239)<br>Yield: 0.30 g, 81%; LCMS m/z = 347 [M + H]$^+$. |
| 254 | 3-Cyclopropyl-1-(spiro[2.2]pentan-1-ylmethyl)-4-(trifluoromethyl)-1H-pyrazole-5-carboxylic acid<br>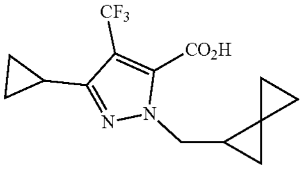 [SMILES: O=C(O)c1c(C(F)(F)F)c(C2CC2)nn1CC1CC12CC2]<br>Ester: ethyl 3-cyclopropyl-1-{spiro[2.2]pentan-1-ylmethyl}-4-(trifluoromethyl)-1H-pyrazole-5-carboxylate (Intermediate 230)<br>Yield: 0.6 g, 88%; LCMS m/z = 301 [M + H]$^+$. |
| 255 | 1-((3,3-Difluoro-1-methylcyclobutyl)methyl)-3-((trans)-2-methylcyclopropyl)-4-(trifluoromethyl)-1H-pyrazole-5-carboxylic acid<br>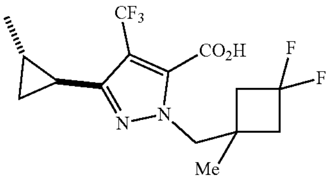 [SMILES: C[C@H]1C[C@@H]1c1nn(CC2(C)CC(F)(F)C2)c(C(=O)O)c1C(F)(F)F]<br>Ester: ethyl 1-((3,3-difluoro-1-methylcyclobutyl)methyl)-3-((trans)-2-methylcyclopropyl)-4-(trifluoromethyl)-1H-pyrazole-5-carboxylate (Intermediate 185)<br>Yield: 0.73 g, 98%; LCMS m/z = 353 [M + H]$^+$. |
| 256 | 3-Cyclopropyl-1-((2,2-difluorospiro[2.3]hexan-1-yl)methyl)-4-(trifluoromethyl)-1H-pyrazole-5-carboxylic acid |

-continued

| Intermediate | Name/Structure/Starting ester/Data |
|---|---|
| | 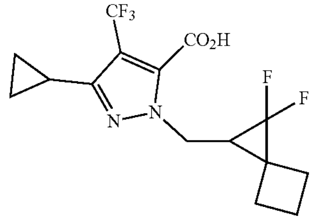 [SMILES: O=C(O)c1c(C(F)(F)F)c(C2CC2)nn1CC1C(F)(F)C12CCC2] |
| | Ester: ethyl 3-cyclopropyl-1-({2,2-difluorospiro[2.3]hexan-1-yl}methyl)-4-(trifluoromethyl)-1H-pyrazole-5-carboxylate (Intermediate 232) Yield: 0.73 g, 98%; LCMS m/z = 351 [M + H]$^+$. |
| 257 | 3-Cyclopropyl-1-((6,6-difluoro-4-methylspiro[2.3]hexan-4-yl)methyl)-4-(trifluoromethyl)-1H-pyrazole-5-carboxylic acid |
| | 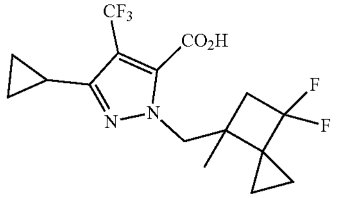 [SMILES: CC1(Cn2nc(C3CC3)c(C(F)(F)F)c2C(=O)O)CC(F)(F)C12CC2] |
| | Ester: ethyl 3-cyclopropyl-1-((6,6-difluoro-4-methylspiro[2.3]hexan-4-yl)methyl)-4-(trifluoromethyl)-1H-pyrazole-5-carboxylate (Intermediate 243) Yield: 1.7 g, 96%; LCMS m/z = 365 [M + H]$^+$. |
| 258 | 3-Cyclopropyl-1-((2,2-difluorospiro[2.2]pentan-1-yl)methyl)-4-(trifluoromethyl)-1H-pyrazole-5-carboxylic acid |
| | 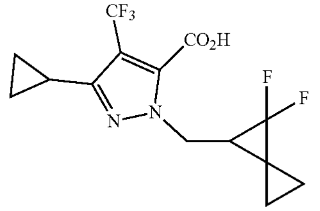 [SMILES: O=C(O)c1c(C(F)(F)F)c(C2CC2)nn1CC1C(F)(F)C12CC2] |
| | Ester: ethyl 3-cyclopropyl-1-({2,2-difluorospiro[2.2]pentan-1-yl}methyl)-4-(trifluoromethyl)-1H-pyrazole-5-carboxylate (Intermediate 233) Yield: 0.2 g, 94%; LCMS m/z = 337 [M + H]$^+$. |
| 259 | 1-((2-(Tert-butoxycarbonyl)-2-azaspiro[3.3]heptan-5-yl)methyl)-3-cyclopropyl-4-(trifluoromethyl)-1H-pyrazole-5-carboxylic acid |
| | 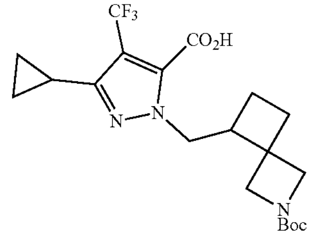 [SMILES: CC(C)(C)OC(=O)N1CC2(CCC2Cn2nc(C3CC3)c(C(F)(F)F)c2C(=O)O)C1] |
| | Ester: tert-butyl 5-{[3-cyclopropyl-5-(ethoxycarbonyl)-4-(trifluoromethyl)-1H-pyrazol-1-yl]methyl}-2-azaspiro[3.3]heptane-2-carboxylate (Intermediate 244) Yield: 1.4 g, 93%; LCMS m/z = 428 [M − H]$^-$. |
| 260 | 1-((3,3-Difluoro-1-methylcyclobutyl)methyl)-3-(spiro[2.2]pentan-1-yl)-4-(trifluoromethyl)-1H-pyrazole-5-carboxylic acid |
| | 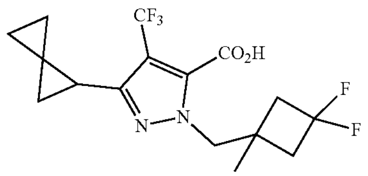 [SMILES: CC1(Cn2nc(C3CC34CC4)c(C(F)(F)F)c2C(=O)O)CC(F)(F)C1] |

-continued

| Intermediate | Name/Structure/Starting ester/Data |
|---|---|
| | Ester: ethyl 1-((3,3-difluoro-1-methylcyclobutyl)methyl)-3-(spiro[2.2]pentan-1-yl)-4-(trifluoromethyl)-1H-pyrazole-5-carboxylate (Intermediate 188) Yield: 720 mg, 83%; LCMS m/z = 365 $[M + H]^+$. |
| 261 | 3-Cyclopropyl-1-((3,3-difluorobicyclo[3.1.0]hexan-1-yl)methyl)-4-(trifluoromethyl)-1H-pyrazole-5-carboxylic acid 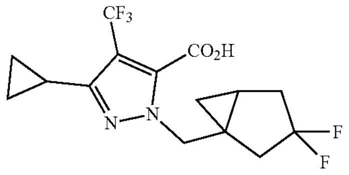 [SMILES: O=C(O)c1c(C(F)(F)F)c(C2CC2)nn1CC12CC1CC(F)(F)C2] Ester: ethyl 3-cyclopropyl-1-((3,3-difluorobicyclo[3.1.0]hexan-1-yl)methyl)-4-(trifluoromethyl)-1H-pyrazole-5-carboxylate (Intermediate 191) Yield: 160 mg, crude; LCMS m/z = 351 $[M + H]^+$. |
| 249 | 3-Cyclopropyl-1-(dispiro[$2.0.2^4.1^3$]heptan-7-ylmethyl)-4-(trifluoromethyl)-1H-pyrazole-5-carboxylic acid 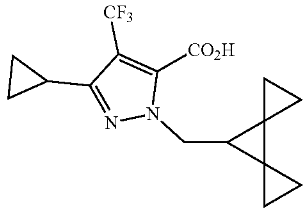 Ester: ethyl 3-cyclopropyl-1-({dispiro[$2.0.2^4.1^3$]heptan-7-yl}methyl)-4-(trifluoromethyl)-1H-pyrazole-5-carboxylate (Intermediate 247) Yield: 210 mg, 95%; LCMS m/z = 327 $[M + H]^+$. |

Intermediate 262

1-((3,3-Difluoro-1-methylcyclobutyl)methyl)-3-(1-fluorocyclopropyl)-4-(trifluoromethyl)-1H-pyrazole-5-carboxamide

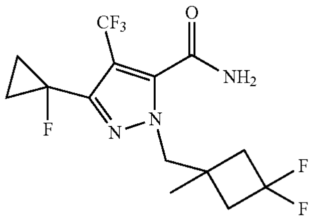 [SMILES: CC1(Cn2nc(C3(F)CC3)c(C(F)(F)F)c2C(N)=O)CC(F)(F)C1]

To a stirred solution of 1-((3,3-difluoro-1-methylcyclobutyl)methyl)-3-(1-fluorocyclopropyl)-4-(trifluoromethyl)-1H-pyrazole-5-carboxylic acid (Intermediate 199, 1.4 g) in DMF (20 mL) was added DIPEA (2.06 mL) followed by HATU (2.988 g) at 0° C. After 30 min, ammonium chloride (1.041 g) was added at 0° C. The resulting reaction mixture was stirred at rt for 2 h under an argon atmosphere. The reaction mixture was quenched with water (50 mL) and extracted with EtOAc (3x50 mL). The combined organic layers were washed with water (30 mL) and brine (30 mL), dried over anhydrous $Na_2SO_4$ and concentrated under reduced pressure to get the crude product, which was purified by column chromatography ($SiO_2$, 30% EtOAc/PE) to afford the title compound (300 mg, 21%). LCMS m/z=356 $[M+H]^+$.

Intermediate 263-281

The title compounds were prepared from the appropriate acids using an analogous method (at a suitable reaction temperature between 0° C.-rt and a suitable reaction time between 1-16 h) to that described for Intermediate 262.

| Intermediate | Structure/Name/Starting Materials/Data |
|---|---|
| 263 | 3-Cyclobutyl-1-((3,3-difluoro-1-methylcyclobutyl)methyl)-4-(trifluoromethyl)-1H-pyrazole-5-carboxamide 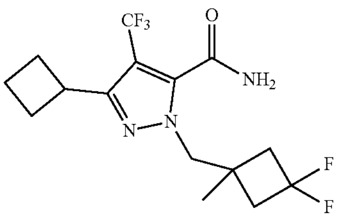 [SMILES: CC1(Cn2nc(C3CCC3)c(C(F)(F)F)c2C(N)=O)CC(F)(F)C1] |

-continued

| Intermediate | Structure/Name/Starting Materials/Data |
|---|---|
| | Acid: 3-cyclobutyl-1-((3,3-difluoro-1-methylcyclobutyl)methyl)-4-(trifluoromethyl)-1H-pyrazole-5-carboxylic acid (Intermediate 200) Yield: 289 mg, crude; LCMS m/z = 352 $[M + H]^+$. |
| 264 | 3-Cyclopentyl-1-((3,3-difluoro-1-methylcyclobutyl)methyl)-4-(trifluoromethyl)-1H-pyrazole-5-carboxamide 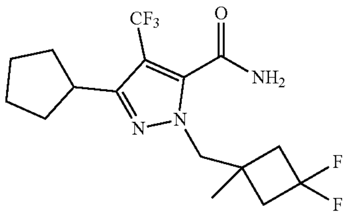 [SMILES: CC1(Cn2nc(C3CCCC3)c(C(F)(F)F)c2C(N)=O)CC(F)(F)C1] Acid: 3-cyclopentyl-1-((3,3-difluoro-1-methylcyclobutyl)methyl)-4-(trifluoromethyl)-1H-pyrazole-5-carboxylic acid (Intermediate 201) Yield: 410 mg, 66%; LCMS m/z = 366 $[M + H]^+$. |
| 265 | 1-((3,3-Difluoro-1-methylcyclobutyl)methyl)-3-(spiro[2.3]hexan-5-yl)-4-(trifluoromethyl)-1H-pyrazole-5-carboxamide 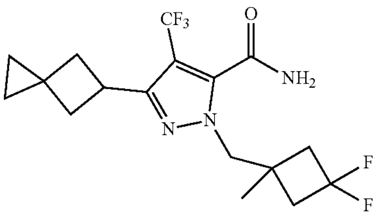 [SMILES: CC1(Cn2nc(C3CC4(CC4)C3)c(C(F)(F)F)c2C(N)=O)CC(F)(F)C1] Acid: 1-((3,3-difluoro-1-methylcyclobutyl)methyl)-3-(spiro[2.3]hexan-5-yl)-4-(trifluoromethyl)-1H-pyrazole-5-carboxylic acid (Intermediate 202) Yield: 180 mg, 46% over two steps; LCMS m/z = 378 $[M + H]^+$. |
| 266 | 1-((3,3-Difluoro-1-methylcyclobutyl)methyl)-3-(3,3-difluorocyclobutyl)-4-(trifluoromethyl)-1H-pyrazole-5-carboxamide 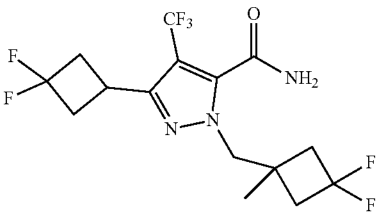 [SMILES: CC1(Cn2nc(C3CC(F)(F)C3)c(C(F)(F)F)c2C(N)=O)CC(F)(F)C1] Acid: 1-((3,3-difluoro-1-methylcyclobutyl)methyl)-3-(3,3-difluorocyclobutyl)-4-(trifluoromethyl)-1H-pyrazole-5-carboxylic acid (Intermediate 204) Yield: 410 mg, 21% over two steps; LCMS m/z = 388 $[M + H]^+$. |
| 267 | 1-((3,3-Difluoro-1-methylcyclobutyl)methyl)-3-(3-methoxybicyclo[1.1.1]pentan-1-yl)-4-(trifluoromethyl)-1H-pyrazole-5-carboxamide 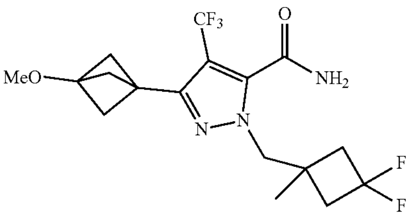 [SMILES: COC12CC(c3nn(CC4(C)CC(F)(F)C4)c(C(N)=O)c3C(F)(F)F)(C1)C2] Acid: 1-((3,3-difluoro-1-methylcyclobutyl)methyl)-3-(3-methoxybicyclo[1.1.1]pentan-1-yl)-4-(trifluoromethyl)-1H-pyrazole-5-carboxylic acid (Intermediate 205) Yield: 65 mg, crude; LCMS m/z = 394 $[M + H]^+$. |
| 268 | 3-(Tert-butyl)-1-((3,3-difluoro-1-methylcyclobutyl)methyl)-4-(trifluoromethyl)-1H-pyrazole-5-carboxamide |

-continued

| Intermediate | Structure/Name/Starting Materials/Data |
|---|---|
| | 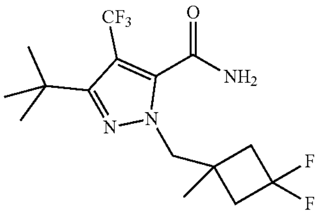 [SMILES: CC1(Cn2nc(C(C)(C)C)c(C(F)(F)F)c2C(N)=O)CC(F)(F)C1]<br>Acid: 3-(tert-butyl)-1-((3,3-difluoro-1-methylcyclobutyl)methyl)-4-(trifluoromethyl)-1H-pyrazole-5-carboxylic acid (Intermediate 206)<br>Yield: 750 mg, 45% over two steps; LCMS m/z = 354 $[M + H]^+$. |
| 269 | 1-((3,3-Difluoro-1-methylcyclobutyl)methyl)-3-(1-(difluoromethyl)cyclopropyl)-4-(trifluoromethyl)-1H-pyrazole-5-carboxamide<br>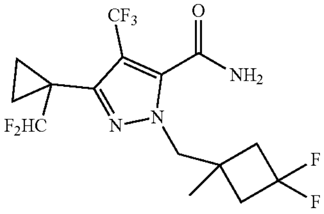 [SMILES: CC1(Cn2nc(C3(C(F)F)CC3)c(C(F)(F)F)c2C(N)=O)CC(F)(F)C1]<br>Acid: 1-((3,3-difluoro-1-methylcyclobutyl)methyl)-3-(1-(difluoromethyl)cyclopropyl)-4-(trifluoromethyl)-1H-pyrazole-5-carboxylic acid (Intermediate 207)<br>Yield: 500 mg, 45% over two steps; LCMS m/z = 388 $[M + H]^+$. |
| 270 | 1-((3,3-Difluoro-1-methylcyclobutyl)methyl)-4-(trifluoromethyl)-3-(1-(trifluoromethyl)cyclopropyl)-1H-pyrazole-5-carboxamide<br>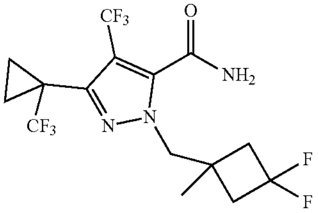 [SMILES: CC1(Cn2nc(C3(C(F)(F)F)CC3)c(C(F)(F)F)c2C(N)=O)CC(F)(F)C1]<br>Acid: 1-((3,3-difluoro-1-methylcyclobutyl)methyl)-4-(trifluoromethyl)-3-(1-(trifluoromethyl)cyclopropyl)-1H-pyrazole-5-carboxylic acid (Intermediate 208)<br>Yield: 280 mg, 58% over two steps; LCMS m/z = 406 $[M + H]^+$. |
| 271 | 1-((3,3-Difluoro-1-methylcyclobutyl)methyl)-3-(2-fluoropropan-2-yl)-4-(trifluoromethyl)-1H-pyrazole-5-carboxamide<br>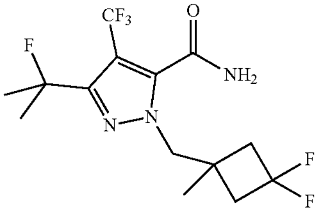 [SMILES: CC1(Cn2nc(C(C)(C)F)c(C(F)(F)F)c2C(N)=O)CC(F)(F)C1]<br>Acid: 1-((3,3-difluoro-1-methylcyclobutyl)methyl)-3-(2-fluoropropan-2-yl)-4-(trifluoromethyl)-1H-pyrazole-5-carboxylic acid (Intermediate 209)<br>Yield: 420 mg, crude; LCMS m/z = 358 $[M + H]^+$. |
| 272 | 3-Cyclopropyl-1-((6,6-difluoro-4-methylspiro[2.3]hexan-4-yl)methyl)-4-(trifluoromethyl)-1H-pyrazole-5-carboxamide |

-continued

| Intermediate | Structure/Name/Starting Materials/Data |
|---|---|
| | 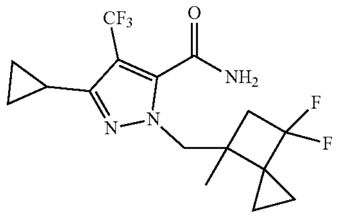 [SMILES: CC1(Cn2nc(C3CC3)c(C(F)(F)F)c2C(N)=O)CC(F)(F)C12CC2]<br>Acid: 3-cyclopropyl-1-((6,6-difluoro-4-methylspiro[2.3]hexan-4-yl)methyl)-4-(trifluoromethyl)-1H-pyrazole-5-carboxylic acid (Intermediate 257)<br>Yield: 1.6 g, 84%; LCMS m/z = 364 [M + H]$^+$. |
| 273 | 3-(Bicyclo[1.1.1]pentan-1-yl)-1-(((trans)-2-(difluoromethyl)cyclopropyl)methyl)-4-(trifluoromethyl)-1H-pyrazole-5-carboxamide<br>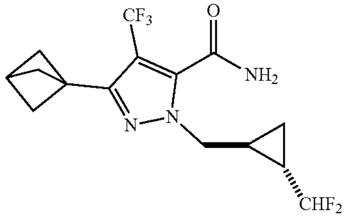<br>Acid: 3-(bicyclo[1.1.1]pentan-1-yl)-1-(((trans)-2-(difluoromethyl)cyclopropyl)methyl)-4-(trifluoromethyl)-1H-pyrazole-5-carboxylic acid (Intermediate 211)<br>Yield: 50 mg, crude; LCMS m/z = 350 [M + H]$^+$. |
| 274 | 3-(Bicyclo[1.1.1]pentan-1-yl)-4-(trifluoromethyl)-1-(((trans)-2-(trifluoromethyl)cyclopropyl)methyl)-1H-pyrazole-5-carboxamide<br>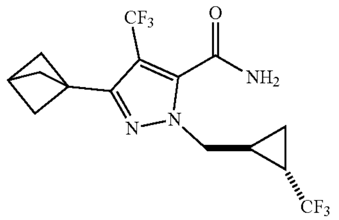<br>Acid: 3-(bicyclo[1.1.1]pentan-1-yl)-4-(trifluoromethyl)-1-(((trans)-2-(trifluoromethyl)cyclopropyl)methyl)-1H-pyrazole-5-carboxylic acid (Intermediate 212)<br>Yield: 210 mg, crude; LCMS m/z = 368 [M + H]$^+$. |
| 275 | Tert-butyl 5-((5-carbamoyl-3-cyclopropyl-4-(trifluoromethyl)-1H-pyrazol-1-yl)methyl)-2-azaspiro[3.3]heptane-2-carboxylate<br>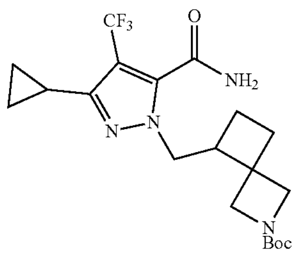 [SMILES: CC(C)(C)OC(=O)N1CC2(CCC2Cn2nc(C3CC3)c(C(F)(F)F)c2C(N)=O)C1]<br>Acid: 1-({2-[(tert-butoxy)carbonyl]-2-azaspiro[3.3]heptan-5-yl}methyl)-3-cyclopropyl-4-(trifluoromethyl)-1H-pyrazole-5-carboxylic acid (Intermediate 259)<br>Yield: 1.5 g, 93%; LCMS m/z = 429 [M + H]$^+$. |
| 276 | 1-((3,3-Difluoro-1-methylcyclobutyl)methyl)-3-(2,2-difluorocyclopropyl)-4-(trifluoromethyl)-1H-pyrazole-5-carboxamide |

-continued

| Intermediate | Structure/Name/Starting Materials/Data |
|---|---|
| | 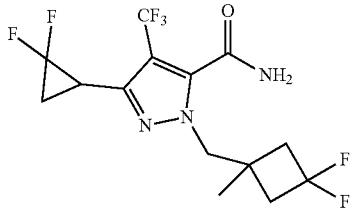 [SMILES: CC1(Cn2nc(C3CC3(F)F)c(C(F)(F)F)c2C(N)=O)CC(F)(F)C1] |
| | Acid: 1-((3,3-difluoro-1-methylcyclobutyl)methyl)-3-(2,2-difluorocyclopropyl)-4-(trifluoromethyl)-1H-pyrazole-5-carboxylic acid (Intermediate 213)<br>Yield: 240 mg, crude; LCMS m/z = 374 [M + H]$^+$. |
| 277 | 1-((3,3-Difluoro-1-methylcyclobutyl)methyl)-3-(2-fluorocyclopropyl)-4-(trifluoromethyl)-1H-pyrazole-5-carboxamide |
| | 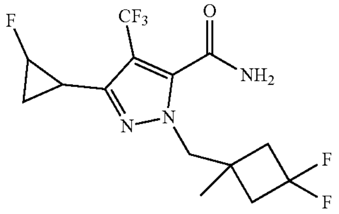 [SMILES: CC1(Cn2nc(C3CC3F)c(C(F)(F)F)c2C(N)=O)CC(F)(F)C1] |
| | Acid: 1-((3,3-difluoro-1-methylcyclobutyl)methyl)-3-(2-fluorocyclopropyl)-4-(trifluoromethyl)-1H-pyrazole-5-carboxylic acid (Intermediate 214)<br>Yield: 100 mg, 55%; LCMS m/z = 356 [M + H]$^+$. |
| 278 | 3-Cyclopropyl-1-((3,3-difluorobicyclo[3.1.0]hexan-1-yl)methyl)-4-(trifluoromethyl)-1H-pyrazole-5-carboxamide |
| | 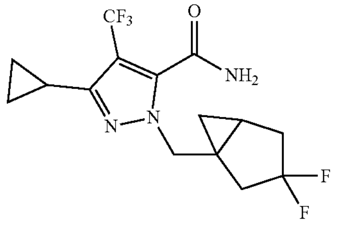 [SMILES: NC(=O)c1c(C(F)(F)F)c(C2CC2)nn1CC12CC1CC(F)(F)C2] |
| | Acid: 3-cyclopropyl-1-((3,3-difluorobicyclo[3.1.0]hexan-1-yl)methyl)-4-(trifluoromethyl)-1H-pyrazole-5-carboxylic acid (Intermediate 261)<br>Yield: 100 mg, 62% over two steps; LCMS m/z = 350 [M + H]$^+$. |
| 279 | 3-Cyclopropyl-1-((3,3-difluoro-1-methylcyclopentyl)methyl)-4-(trifluoromethyl)-1H-pyrazole-5-carboxamide |
| | 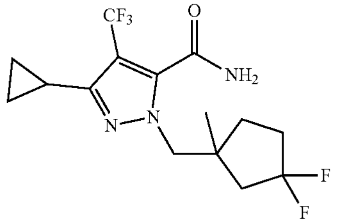 [SMILES: CC1(Cn2nc(C3CC3)c(C(F)(F)F)c2C(N)=O)CCC(F)(F)C1] |
| | Acid: 3-cyclopropyl-1-((3,3-difluoro-1-methylcyclopentyl)methyl)-4-(trifluoromethyl)-1H-pyrazole-5-carboxylic acid (Intermediate 215)<br>Yield: 1.5 g, 75%. |
| 280 | 3-(Bicyclo[1.1.1]pentan-1-yl)-1-((3,3-difluoro-1-methylcyclobutyl)methyl)-4-(trifluoromethyl)-1H-pyrazole-5-carboxamide |
| | 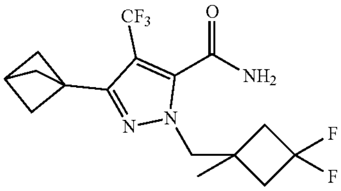 [SMILES: CC1(Cn2nc(C34CC(C3)C4)c(C(F)(F)F)c2C(N)=O)CC(F)(F)C1] |

-continued

| Intermediate | Structure/Name/Starting Materials/Data |
|---|---|
| | Acid: 3-(bicyclo[1.1.1]pentan-1-yl)-1-((3,3-difluoro-1-methylcyclobutyl)methyl)-4-(trifluoromethyl)-1H-pyrazole-5-carboxylic acid (Intermediate 218) Yield: 320 mg, 64%; LCMS m/z = 364 $[M + H]^+$. |
| 281 | 1-((3,3-Difluoro-1-methylcyclobutyl)methyl)-3-(2,2-difluorobicyclo[1.1.1]pentan-1-yl)-4-(trifluoromethyl)-1H-pyrazole-5-carboxamide 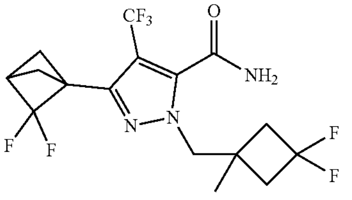 [SMILES: CC1(Cn2nc(C34CC(C3)C4(F)F)c(C(F)(F)F)c2C(N)=O)CC(F)(F)C1] Acid: 1-((3,3-difluoro-1-methylcyclobutyl)methyl)-3-(2,2-difluorobicyclo[1.1.1]pentan-1-yl)-4-(trifluoromethyl)-1H-pyrazole-5-carboxylic acid (Intermediate 219) Yield: 30 mg, 85%; LCMS m/z = 401 $[M + H]^+$. |

Intermediate 282

1-((3,3-Difluoro-1-methylcyclobutyl)methyl)-4-(difluoromethyl)-3-(1-fluorocyclopropyl)-1H-pyrazole-5-carboxamid

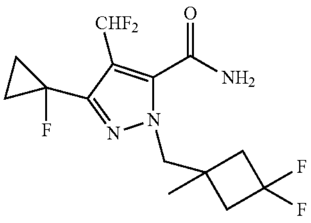 [SMILES: CC1(Cn2nc(C3(F)CC3)c(C(F)F)c2C(N)=O)CC(F)(F)C1]

Part 1: To a stirred solution of methyl 1-((3,3-difluoro-1-methylcyclobutyl)methyl)-3-(1-fluorocyclopropyl)-4-iodo-1H-pyrazole-5-carboxylate (Intermediate 163, 5.0 g) in 1,4-dioxane (50 mL)/$H_2O$ (10 mL) were added potassium vinyltrifluoroborate (3.128 g) and anhydrous sodium carbonate (3.713 g) at rt. The resulting reaction mixture was purged with argon gas for 5 minutes before the addition of $Pd(dppf)Cl_2 \cdot DCM$ (0.953 g). The resulting mixture was heated to 80° C. for 16 h. The reaction mixture was cooled to rt, quenched with cold water (100 mL) and extracted with EtOAc (2×50 mL). The combined organic layers were washed with water (50 mL) and brine (50 mL), dried over anhydrous $Na_2SO_4$ and concentrated under reduced pressure to get the crude product, which was purified by column chromatography ($SiO_2$, 10-20% EtOAc/Hex) to afford methyl 1-((3,3-difluoro-1-methylcyclobutyl)methyl)-3-(1-fluorocyclopropyl)-4-vinyl-1H-pyrazole-5-carboxylate (1.5 g, 48%). LCMS m/z=329 $[M+H]^+$.

Part 2: To a stirred solution of methyl 1-((3,3-difluoro-1-methylcyclobutyl)methyl)-3-(1-fluorocyclopropyl)-4-vinyl-1H-pyrazole-5-carboxylate (1.5 g) in THE (15.0 mL) and $H_2O$ (3.0 mL) were added osmium tetroxide (4 wt. % solution in water, 0.058 g) and sodium periodate (2.931 g) at 0° C. The resulting reaction mixture was stirred at rt for 4 h. The reaction mixture was quenched with $Na_2SO_3$ solution (50 mL) and extracted with EtOAc (2×40 mL). The combined organic layers were washed with water (30 mL) and brine (30 mL), dried over anhydrous $Na_2SO_4$ and concentrated under reduced pressure to afford methyl 1-((3,3-difluoro-1-methylcyclobutyl)methyl)-3-(1-fluorocyclopropyl)-4-formyl-1H-pyrazole-5-carboxylate (1.7 g, crude), which was used for next step without purification. LCMS m/z=331 $[M+H]^+$.

Part 3: To a stirred solution of methyl 1-((3,3-difluoro-1-methylcyclobutyl)methyl)-3-(1-fluorocyclopropyl)-4-formyl-1H-pyrazole-5-carboxylate (1.2 g) in DCM (10 mL) was added DAST (1.44 mL) at 0° C. and the mixture was stirred for 16 h at rt. The reaction mixture was slowly quenched with saturated $NaHCO_3$ solution (30 mL) and extracted with DCM (2×30 mL). The combined organic layers were washed with water (20 mL) and brine (20 mL), dried over anhydrous $Na_2SO_4$ and concentrated under reduced pressure to get the crude product, wich was purified by column chromatography ($SiO_2$, 10-20% EtOAc/Hex) to afford methyl 1-((3,3-difluoro-1-methylcyclobutyl)methyl)-4-(difluoromethyl)-3-(1-fluorocyclopropyl)-1H-pyrazole-5-carboxylate (700 mg, 62% over two steps). LCMS m/z=353 $[M+H]^+$.

Part 4: To a stirred solution of methyl 1-((3,3-difluoro-1-methylcyclobutyl)methyl)-4-(difluoromethyl)-3-(1-fluorocyclopropyl)-1H-pyrazole-5-carboxylate (500 mg) in methanol (5 mL) was added 7M $NH_3$ in methanol (10 mL). The resulting reaction mixture was heated to 100° C. for 16 h in a sealed tube. The excess volatiles were removed under reduced pressure, the obtained residue was washed with pentane (2×20 mL) and dried under vacuum to afford the title compound (480 mg, crude), which was used in next step without further purification. LCMS m/z=338 $[M+H]^+$.

Intermediate 283-284

The title compounds were prepared from the appropriate pyrazole using an analogous method to that described for part 1-3 of Intermediate 282. Suitable bases for part 1 are $K_2CO_3$ or $K_3PO_4$, reaction temperature 80-100° C. Suitable reaction times for part 2 are 1-4 h, with or without the addition of NMO.

| Intermediate | Structure/Name/Starting Materials/Data |
|---|---|
| 283 | Methyl 1-((3,3-difluoro-1-methylcyclobutyl)methyl)-4-(difluoromethyl)-3-(3-fluorobicyclo[1.1.1]pentan-1-yl)-1H-pyrazole-5-carboxylate<br>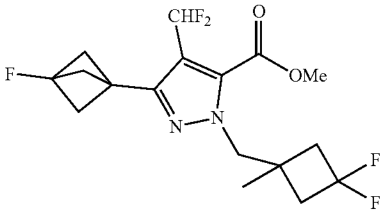 [SMILES: COC(=O)c1c(C(F)F)c(C23CC(F)(C2)C3)nn1CC1(C)CC(F)(F)C1]<br>Pyrazole: methyl 1-((3,3-difluoro-1-methylcyclobutyl)methyl)-3-(3-fluorobicyclo[1.1.1]pentan-1-yl)-4-iodo-1H-pyrazole-5-carboxylate (Intermediate 169)<br>Yield: 1.5 g, 60% over three steps; LCMS m/z = 379 [M + H]$^+$. |
| 284 | Ethyl 3-(bicyclo[1.1.1]pentan-1-yl)-1-((3,3-difluoro-1-methylcyclobutyl)methyl)-4-(difluoromethyl)-1H-pyrazole-5-carboxylate<br>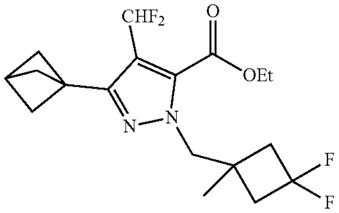 [SMILES: CCOC(=O)c1c(C(F)F)c(C23CC(C2)C3)nn1CC1(C)CC(F)(F)C1]<br>Pyrazole: ethyl 3-(bicyclo[1.1.1]pentan-1-yl)-1-((3,3-difluoro-1-methylcyclobutyl)methyl)-4-iodo-1H-pyrazole-5-carboxylate (Intermediate 242)<br>Yield: 0.58 g, 54% over three steps. |

Intermediate 285

1-((3,3-Difluoro-1-methylcyclobutyl)methyl)-4-(difluoromethyl)-3-(3-fluorobicyclo[1.1.1]pentan-1-yl)-1H-pyrazole-5-carboxamide

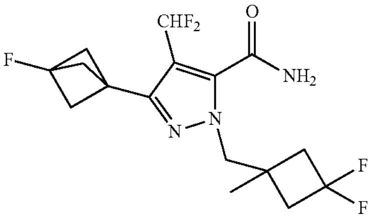 [SMILES: CC1(Cn2nc(C34CC(F)(C3)C4)c(C(F)F)c2C(N)=O)CC(F)(F)C1]

A stirred solution of methyl 1-((3,3-difluoro-1-methylcyclobutyl)methyl)-4-(difluoromethyl)-3-(3-fluorobicyclo[1.1.1]pentan-1-yl)-1H-pyrazole-5-carboxylate (Intermediate 283, 800 mg) in ammonia in methanol (7M, 5 mL) was heated to 80° C. for 16 h. The excess volatiles were removed under reduced pressure to get the crude product, which was purified by column chromatography ($SiO_2$, 15% EtOAc/PE) to afford the title compound (550 mg, 72%).

Intermediate 286

1-((3,3-Difluoro-1-methylcyclobutyl)methyl)-3-(3-fluorobicyclo[1.1.1]pentan-1-yl)-4-(trifluoromethyl)-1H-pyrazole-5-carboxamide

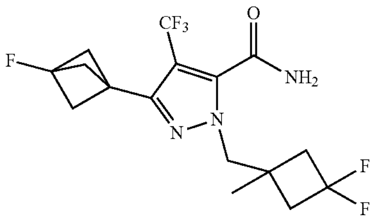 [SMILES: CC1(Cn2nc(C34CC(F)(C3)C4)c(C(F)(F)F)c2C(N)=O)CC(F)(F)C1]

To a stirred solution of 1-((3,3-difluoro-1-methylcyclobutyl)methyl)-3-(3-fluorobicyclo[1.1.1]pentan-1-yl)-4-(trifluoromethyl)-1H-pyrazole-5-carboxylic acid (Intermediate 210, 1.8 g) in toluene (7.5 mL) was added thionyl chloride (3.42 mL) at rt and the mixture was heated to 80° C. for 3 h. The reaction mixture was concentrated under reduced pressure, the residue was diluted with DCM and added to the solution of ammonium chloride (2514.22 mg) and DIPEA (3036.83 mg) in DCM (10 mL) at 0° C. The reaction mixture was stirred for 2 h at rt. The reaction mixture was diluted with water (100 mL) and extracted with DCM (2×75 mL). The combined organic layers were washed with water (50 mL) and brine (50 mL), dried over anhydrous $Na_2SO_4$ and concentrated under reduced pressure to yield the title compound (1.3 g, 72%). LCMS m/z=382 [M+H]$^+$.

Intermediate 287/287a/287b

287a

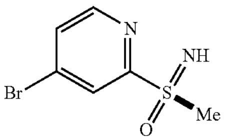

288b

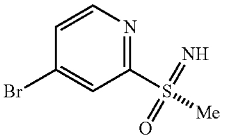

To a stirred solution of 4-bromo-2-(methylthio)pyridine (6.0 g) in MeOH (60 mL) were added (diacetoxyiodo) benzene (95.2 g) and $(NH_4)_2CO_3$ (28.4 g) at rt. The reaction mixture was stirred for 16 h at rt. The reaction mixture was diluted with water (100 mL) and extracted with EtOAc (2×100 mL). The combined organic layers were washed with water (100 mL) and brine (100 mL), dried over anhydrous $Na_2SO_4$ and concentrated under reduced pressure to get the crude product, which was purified by column chromatography ($SiO_2$, 50% EtOAc/PE) to afford the racemic title compound (Intermediate 287, 4.0 g, 57%). LCMS m/z=235 $[M+H]^+$.

4.0 g of the above racemic compound was separated by SFC (Chiral ART Cellulose—SC, 250×30 mm, 5 μm; 10% MeOH in $CO_2$) to obtain 1.8 g of the first eluting enantiomer of the title compound (Intermediate 287a) and 1.7 g of the second eluting enantiomer of the title compound (Intermediate 287b).

Peak 1, Intermediate 287a Chiral SFC: column: Chiralpak IC (4.6×250 mm) 5 hum, co-solvent: MeOH, flow: 3 mL/min; % of co-solvent: 10%; ABPR: 98 bar; T: 30° C.; $R_t$=13.25 min (first eluting).

Peak 2, Intermediate 287b Chiral SFC: column: Chiralpak IC (4.6×250 mm) 5 hum, co-solvent: MeOH, flow: 3 mL/min; % of co-solvent: 10%; ABPR: 98 bar; T: 30° C.; $R_t$=15.35 min (second eluting)

Intermediate 288

N-((4-Bromopyridin-2-yl)(methyl)(oxo)-16-sulfaneylidene)cyanamide

1a

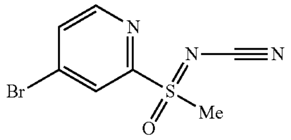

To a stirred solution of racemic (4-bromopyridin-2-yl)(imino)(methyl)-16-sulfanone (Intermediate 287, 500 mg) in DCM (20 mL) were added $Et_3N$ (430.5 mg) and cyanogen bromide (270.4 mg, 2.55 mmol) at 0° C. The resulting reaction mixture was stirred at rt for 16 h. The reaction mixture was diluted with water (20 mL) and extracted with $Et_2O$ (2×20 mL). The combined organic layers were washed with water (10 mL) and brine (10 mL), dried over anhydrous $Na_2SO_4$ and concentrated under reduced pressure to get the crude product, which was purified by column chromatography ($SiO_2$, 10-15% EtOAc/PE) to afford the title compound (300 mg, 54%).

Intermediate 289

2-(Ethylthio)pyridin-4-amine

1a

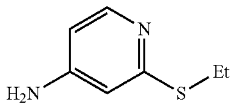

To a solution of 2-bromopyridin-4-amine (2.0 g) in DMSO (15 mL) were added $Cs_2CO_3$ (9.45 g) and sodium ethanethiolate (1.2 g) at rt and the mixture was then heated to 110° C. for 16 h. The reaction mixture was diluted with cold water (25 mL) and extracted with EtOAc (3×80 mL). The combined organic layers were washed with brine (30 mL), dried over $Na_2SO_4$ and evaporated under reduced pressure to get the crude product, which was purified by CombiFlash column chromatography ($SiO_2$, 0-70% EtOAc/Hex) to yield the title compound (1.4 g, 79%). LCMS m/z=155 $[M+H]^+$.

Intermediate 331

The title compounds were prepared from the appropriate arylbromide and the appropriate thiolate using an analogous method to that described for Intermediate 289.

| Intermediate | Structure/Name/Starting Materials/Data |
|---|---|
| 331 | 2-Methyl-6-(methylthio)pyridin-4-amine<br>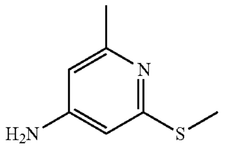<br>Arylbromide: 2-bromo-6-methylpyridin-4-amine<br>Thiolate: sodium methanethiolate<br>Yield: 0.6 g, 73%; LCMS m/z = 155 $[M + H]^+$. |

Intermediate 290a/290b

Tert-butyl ((4-bromopyridin-2-yl)methyl)(oxo)-16-sulfaneylidene)carbamate

290a

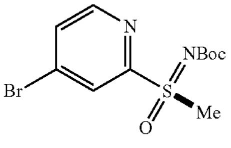

and

-continued

290b

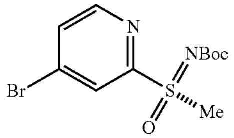

Part 1: 4-Bromo-2-methylsulfanyl-pyridine (100 g) was dissolved in EtOH (1.00 L) at 20° C. followed by the addition of PIDA (316 g). Then, $NH_4OAc$ (151 g) was added and the mixture was stirred at 30° C. for 16 h. The reaction mixture was concentrated under reduced pressure to give a residue, which was poured into 6.0 L sodium carbonate aqueous solution saturated with sodium chloride. The pH was then adjusted to 7-8 by the addition of sodium carbonate aqueous solution saturated with sodium chloride. The mixture was extracted with EtOAc (1.0 L×5). The combined organic layers were dried over $Na_2SO_4$, filtered and concentrated under reduced pressure to obtain a residue. The residue was purified by column chromatography ($SiO_2$, EtOAc/PE 1/50-100%). After concentration under reduced pressure, the residue was triturated with MTBE at 20° C. for 1 h to get 29 g of 4-bromo-2-(methylthio)pyridine (Intermediate 287).

17.0 g of the above racemic compound was separated by SFC (Chiralpak AS, 250×50 mm, 10 μm; 20% (0.1% $NH_3$ in MeOH) in $CO_2$) to obtain 5.85 g of the first eluting enantiomer and 7.54 g of the second eluting enantiomer.

Peak 1: LCMS m/z=235 $[M+H]^+$; Chiral SFC: column: Chiralpak IG-3 (4.6×50 mm) 3 hum, co-solvent: 0.05% diethylamine in MeOH, flow: 3 mL/min; % of co-solvent: 5-40%%; ABPR: 100 bar; T: 35° C.; $R_t$=1.88 min (first eluting enantiomer).

Peak 2: LCMS m/z=235 $[M+H]^+$; Chiral SFC: column: Chiralpak IG-3 (4.6×50 mm) 3 hum, co-solvent: 0.05% diethylamine in MeOH, flow: 3 mL/min; % of co-solvent: 5-40%%; ABPR: 100 bar; T: 35° C.; $R_t$=2.02 min (second eluting enantiomer)

Part 2: To a stirred solution of (4-bromopyridin-2-yl)(imino)(methyl)-16-sulfanone (first eluting enantiomer, Peak 1, 10 g) in THF (150 mL) were added potassium tert butoxide (1M in THF, 51.06 mL) and Boc anhydride (19.55 mL) at 0° C. The reaction mixture was stirred at rt for 2 h. The reaction mixture was diluted with ice water and the resulting mixture was extracted with EtOAc (3×200 mL). The combined organic layers were dried over $Na_2SO_4$ and concentrated under reduced pressure to get the crude product, which was purified by CombiFlash column chromatography ($SiO_2$, 0-50% EtOAc/Hex) to yield the title compound (Intermediate 290a, 12 g, 84%). LCMS m/z=335 $[M+H]^+$.

Intermediate 290b was prepared using an analogous method to that described for Intermediate 290a, using the second eluting enantiomer, Peak 2 from part 1. Yield: 1.8 g, 84%. LCMS m/z=335 $[M+H]^+$.

Intermediate 332

4-Fluoro-3-(methylthio)aniline

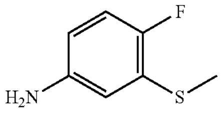

Part 1: A solution of 2-fluoro-5-nitroaniline (2.5 g) in dimethyldisulfide (75 mL) was heated to 100° C. followed by the addition of tert-butyl nitrite (technical grade, 90%, 2.64 mL). The mixture was stirred for 1 h at 100° C. The reaction mixture was concentrated to get the crude material, which was purified by CombiFlash column chromatography ($SiO_2$, 2-4% EtOAc/Hex) to afford 1-fluoro-2-(methylsulfanyl)-4-nitrobenzene (1.50 g, 50%).

Part 2: A solution of 1-fluoro-2-(methylsulfanyl)-4-nitrobenzene (550 mg) in ethanol (30 mL) was degassed with argon for 15 minutes followed by the addition of Pd/C (200 mg) at rt. The reaction mixture was stirred under $H_2$ balloon pressure for 16 h. The reaction mixture was filtered and washed with ethanol (50 mL). The crude product was purified by CombiFlash column chromatography ($SiO_2$, 35-45% EtOAc/Hex) to afford the title compound (200 mg, 43%). LCMS m/z=158 $[M+H]^+$.

Intermediate 79

3-Cyclopropyl-1-((3,3-difluoro-1-methylcyclobutyl)methyl)-N-(2-(methylthio)pyridin-4-yl)-4-(trifluoromethyl)-1H-pyrazole-5-carboxamide

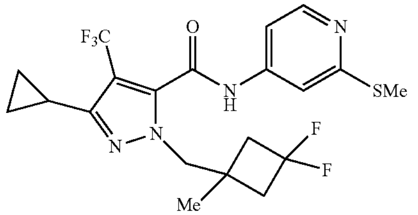 [SMILES: CSc1cc(NC(=O)c2c(C(F)(F)F)c(C3CC3)nn2CC2(C)CC(F)(F)C2)ccn1]

To a solution of 3-cyclopropyl-1-((3,3-difluoro-1-methylcyclobutyl)methyl)-4-(trifluoromethyl)-1H-pyrazole-5-carboxylic acid (Intermediate 60, 0.64 g) in pyridine (10 mL) were added $POCl_3$ (0.4 mL) and 2-(methylthio)pyridin-4-amine (0.53 g) at 0° C. and reaction mixture was stirred at rt for 2 h. The reaction mixture was concentrated under reduced pressure and the residue was diluted with cold water and extracted with EtOAc (3×100 mL). The combined organics were washed with brine, dried ($Na_2SO_4$) and evaporated to dryness under reduced pressure. The residue was dissolved in THE (10 mL) and 1N NaOH (4 mL) and the reaction mixture was stirred at 80° C. for 16 h. The reaction mixture was diluted with cold water and extracted with EtOAc (3×80 mL). The combined organics were washed with brine, dried ($Na_2SO_4$) and evaporated to dryness under reduced pressure. The residue was purified by CombiFlash chromatography ($SiO_2$, 0-50% EtOAc/Hex) to afford the title compound (0.8 g, 96%). LCMS m/z=461 $[M+H]^+$.

Intermediate 80-96, 291, 293-295, 296-297, 299, 306

The title compounds were prepared from the appropriate carboxylic acid and amines using an analogous method as described for Intermediate 79. Suitable conditions for the hydrolysis include NaOH concentrations between 1N-4M and temperatures of rt or 80° C.

| Intermediate | Name/Structure/Starting Materials/Data |
|---|---|
| 80 | 1-((3,3-Difluorocyclobutyl)methyl)-3-(1,1-difluoroethyl)-N-(2-(methylthio)pyridin-4-yl)-4-(trifluoromethyl)-1H-pyrazole-5-carboxamide<br>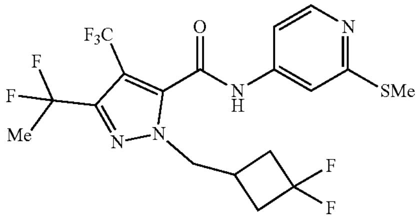 [SMILES: CSc1cc(NC(=O)c2c(C(F)(F)F)c(C(C)(F)F)nn2CC2CC(F)(F)C2)ccn1]<br>Acid: 1-((3,3-difluorocyclobutyl)methyl)-3-(1,1-difluoroethyl)-4-(trifluoromethyl)-1H-pyrazole-5-carboxylic acid (Intermediate 63)<br>Amine: 2-(methylthio)pyridin-4-amine hydrochloride<br>Yield: 140 mg, 46%; LCMS m/z = 471 $[M + H]^+$. |
| 81 | 1-((3,3-Difluorocyclopentyl)methyl)-3-(1,1-difluoroethyl)-4-methyl-N-(2-(methylthio)pyridin-4-yl)-1H-pyrazole-5-carboxamide<br>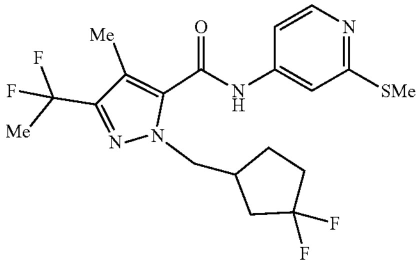 [SMILES: CSc1cc(NC(=O)c2c(C)c(C(C)(F)F)nn2CC2CCC(F)(F)C2)ccn1]<br>Acid: 1-((3,3-difluorocyclopentyl)methyl)-3-(1,1-difluoroethyl)-4-methyl-1H-pyrazole-5-carboxylic acid (Intermediate 64)<br>Amine: 2-(methylthio)pyridin-4-amine hydrochloride<br>Yield: 50 mg, 35%; LCMS m/z = 431 $[M + H]^+$. |
| 83 | 1-((3,3-Difluorocyclopentyl)methyl)-3-(difluoromethoxy)-N-(2-(methylthio)pyridin-4-yl)-4-(trifluoromethyl)-1H-pyrazole-5-carboxamide<br>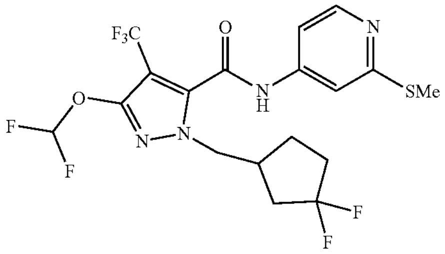 [SMILES: CSc1cc(NC(=O)c2c(C(F)(F)F)c(OC(F)F)nn2CC2CCC(F)(F)C2)ccn1]<br>Acid: 1-((3,3-difluorocyclopentyl)methyl)-3-(difluoromethoxy)-4-(trifluoromethyl)-1H-pyrazole-5-carboxylic acid (Intermediate 62)<br>Amine: 2-(methylthio)pyridin-4-amine hydrochloride<br>Yield: 150 mg, 56%; LCMS m/z = 487 $[M + H]^+$. |
| 84 | 1-((3,3-Difluoro-1-methylcyclobutyl)methyl)-3-(1,1-difluoroethyl)-4-methyl-N-(2-(methylthio)pyridin-4-yl)-1H-pyrazole-5-carboxamide<br>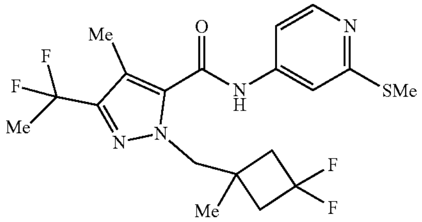 [SMILES: CSc1cc(NC(=O)c2c(C)c(C(C)(F)F)nn2CC2(C)CC(F)(F)C2)ccn1]<br>Acid: 1-((3,3-difluoro-1-methylcyclobutyl)methyl)-3-(1,1-difluoroethyl)-4-methyl-1H-pyrazole-5-carboxylic acid (Intermediate 65)<br>Amine: 2-(methylthio)pyridin-4-amine hydrochloride<br>Yield: 300 mg, 56%; LCMS m/z = 431 $[M + H]^+$. |
| 85 | 3-Cyclopropyl-1-((3,3-difluorocyclopentyl)methyl)-N-(2-(methylthio)pyridin-4-yl)-4-(trifluoromethyl)-1H-pyrazole-5-carboxamide |

-continued

| Intermediate | Name/Structure/Starting Materials/Data |
|---|---|
| | 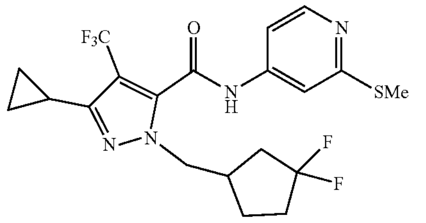 [SMILES: CSc1cc(NC(=O)c2c(C(F)(F)F)c(C3CC3)nn2CC2CCC(F)(F)C2)ccn1]<br>Acid: 3-cyclopropyl-1-((3,3-difluorocyclopentyl)methyl)-4-(trifluoromethyl)-1H-pyrazole-5-carboxylic acid (Intermediate 30)<br>Amine: 2-(methylthio)pyridin-4-amine hydrochloride<br>Yield: 250 mg, 39%; LCMS m/z = 461 $[M + H]^+$. |
| 86 | 1-((4,4-Difluorocyclohexyl)methyl)-3-(1,1-difluoroethyl)-4-methyl-N-(2-(methylthio)pyridin-4-yl)-1H-pyrazole-5-carboxamide<br>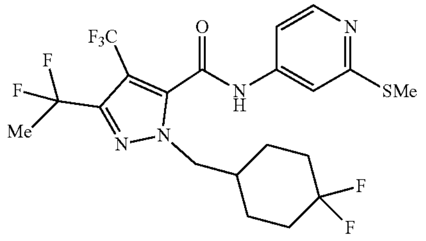 [SMILES: CSc1cc(NC(=O)c2c(C(F)(F)F)c(C(C)(F)F)nn2CC2CCC(F)(F)CC2)ccn1]<br>Acid: 1-((4,4-difluorocyclohexyl)methyl)-3-(1,1-difluoroethyl)-4-methyl-1H-pyrazole-5-carboxylic acid (Intermediate 66)<br>Amine: 2-(methylthio)pyridin-4-amine hydrochloride<br>Yield: 155 mg, 37%; LCMS m/z = 445 $[M + H]^+$. |
| 87 | 1-((4,4-Difluoro-1-methylcyclohexyl)methyl)-3-(1,1-difluoroethyl)-4-methyl-N-(2-(methylthio)pyridin-4-yl)-1H-pyrazole-5-carboxamide<br>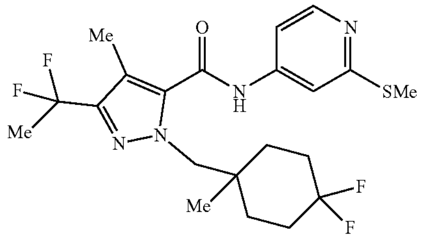 [SMILES: CSc1cc(NC(=O)c2c(C)c(C(C)(F)F)nn2CC2(C)CCC(F)(F)CC2)ccn1]<br>Acid: 1-((4,4-difluoro-1-methylcyclohexyl)methyl)-3-(1,1-difluoroethyl)-4-methyl-1H-pyrazole-5-carboxylic acid (Intermediate 67)<br>Amine: 2-(methylthio)pyridin-4-amine hydrochloride<br>Yield: 100 mg, 22%; LCMS m/z = 459 $[M + H]^+$. |
| 88 | 3-(1,1-Difluoroethyl)-4-methyl-N-(2-(methylthio)pyridin-4-yl)-1-((3-(trifluoromethyl)bicyclo[1.1.1]pentan-1-yl)methyl)-1H-pyrazole-5-carboxamide<br>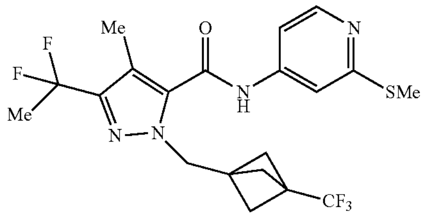 [SMILES: CSc1cc(NC(=O)c2c(C)c(C(C)(F)F)nn2CC23CC(C(F)(F)F)(C2)C3)ccn1]<br>Acid: 3-(1,1-difluoroethyl)-4-methyl-1-((3-(trifluoromethyl)bicyclo[1.1.1]pentan-1-yl)methyl)-1H-pyrazole-5-carboxylic acid (Intermediate 68)<br>Amine: 2-(methylthio)pyridin-4-amine hydrochloride<br>Yield: 150 mg, 27%; LCMS m/z = 461 $[M + H]^+$. |
| 89 | 3-(1,1-Difluoroethyl)-4-methyl-N-(2-(methylthio)pyridin-4-yl)-1-(((cis)-3-(trifluoromethyl)cyclobutyl)methyl)-1H-pyrazole-5-carboxamide |

-continued

| Intermediate | Name/Structure/Starting Materials/Data |
|---|---|
| | 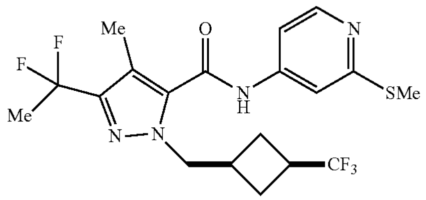<br>Acid: 3-(1,1-difluoroethyl)-4-methyl-1-(((cis)-3-(trifluoromethyl)cyclobutyl)methyl)-1H-pyrazole-5-carboxylic acid (Intermediate 77)<br>Amine: 2-(methylthio)pyridin-4-amine hydrochloride<br>Yield: 100 mg, 33%; LCMS m/z = 449 [M + H]$^+$. |
| 91 | (S)-3-Cyclopropyl-1-((3,3-difluorocyclopentyl)methyl)-N-(2-(methylthio)pyridin-4-yl)-4-(trifluoromethyl)-1H-pyrazole-5-carboxamide<br>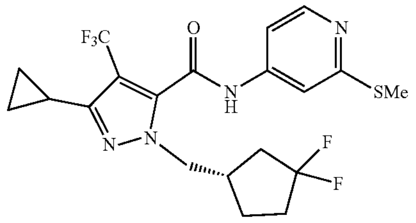 [SMILES: CSc1cc(NC(=O)c2c(C(F)(F)F)c(C3CC3)nn2C[C@H]2CCC(F)(F)C2)ccn1]<br>Acid: (S)-3-cyclopropyl-1-((3,3-difluorocyclopentyl)methyl)-4-(trifluoromethyl)-1H-pyrazole-5-carboxylic acid (Intermediate 70)<br>Amine: 2-(methylthio)pyridin-4-amine hydrochloride<br>Yield: 120 mg, 29%; LCMS m/z = 461 [M + H]$^+$. |
| 92 | (R)-3-Cyclopropyl-1-((3,3-difluorocyclopentyl)methyl)-N-(2-(methylthio)pyridin-4-yl)-4-(trifluoromethyl)-1H-pyrazole-5-carboxamide<br>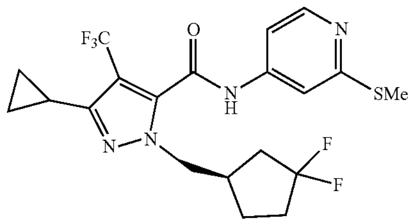 [SMILES: CSc1cc(NC(=O)c2c(C(F)(F)F)c(C3CC3)nn2C[C@@H]2CCC(F)(F)C2)ccn1]<br>Acid: (R)-3-cyclopropyl-1-((3,3-difluorocyclopentyl)methyl)-4-(trifluoromethyl)-1H-pyrazole-5-carboxylic acid (Intermediate 71)<br>Amine: 2-(methylthio)pyridin-4-amine hydrochloride<br>Yield: 120 mg, 29%; LCMS m/z = 461 [M + H]$^+$. |
| 93 | 3-Cyclopropyl-1-((2-fluorospiro[3.3]heptan-2-yl)methyl)-N-(2-(methylthio)pyridin-4-yl)-4-(trifluoromethyl)-1H-pyrazole-5-carboxamide<br>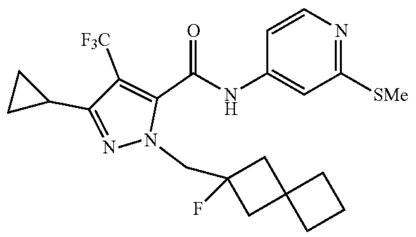 [SMILES: CSc1cc(NC(=O)c2c(C(F)(F)F)c(C3CC3)nn2CC2(F)CC3(CCC3)C2)ccn1]<br>Acid: 3-cyclopropyl-1-((2-fluorospiro[3.3]heptan-2-yl)methyl)-4-(trifluoromethyl)-1H-pyrazole-5-carboxylic acid (Intermediate 72)<br>Amine: 2-(methylthio)pyridin-4-amine hydrochloride<br>Yield: 85 mg, 24%; LCMS m/z = 469 [M + H]$^+$. |
| 94 | 3-Cyclopropyl-N-(2-(methylthio)pyridin-4-yl)-4-(trifluoromethyl)-1-((3-(trifluoromethyl)bicyclo[1.1.1]pentan-1-yl)methyl)-1H-pyrazole-5-carboxamide |

-continued

| Intermediate | Name/Structure/Starting Materials/Data |
|---|---|
| | 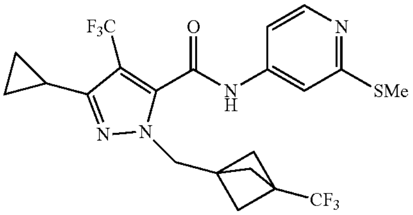 [SMILES: CSc1cc(NC(=O)c2c(C(F)(F)F)c(C3CC3)nn2CC23CC(C(F)(F)F)(C2)C3)ccn1]<br>Acid: 3-cyclopropyl-4-(trifluoromethyl)-1-((3-(trifluoromethyl)bicyclo[1.1.1]pentan-1-yl)methyl)-1H-pyrazole-5-carboxylic acid (Intermediate 73)<br>Amine: 2-(methylthio)pyridin-4-amine hydrochloride<br>Yield: 70 mg, 52%; LCMS m/z = 491 $[M + H]^+$. |
| 95 | 3-Cyclopropyl-1-((3-fluorobicyclo[1.1.1]pentan-1-yl)methyl)-N-(2-(methylthio)pyridin-4-yl)-4-(trifluoromethyl)-1H-pyrazole-5-carboxamide<br>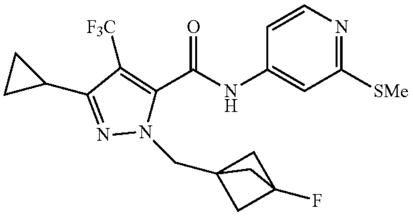 [SMILES: CSc1cc(NC(=O)c2c(C(F)(F)F)c(C3CC3)nn2CC23CC(F)(C2)C3)ccn1]<br>Acid: 3-cyclopropyl-1-((3-fluorobicyclo[1.1.1]pentan-1-yl)methyl)-4-(trifluoromethyl)-1H-pyrazole-5-carboxylic acid (Intermediate 74)<br>Amine: 2-(methylthio)pyridin-4-amine hydrochloride<br>Yield: 210 mg, 65%; LCMS m/z = 441 $[M + H]^+$. |
| 96 | 3-Cyclopropyl-1-((6,6-difluorospiro[3.3]heptan-2-yl)methyl)-N-(2-(methylthio)pyridin-4-yl)-4-(trifluoromethyl)-1H-pyrazole-5-carboxamide<br>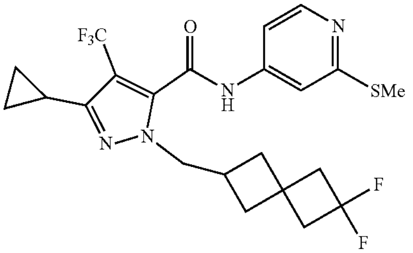 [SMILES: CSc1cc(NC(=O)c2c(C(F)(F)F)c(C3CC3)nn2CC2CC3(C2)CC(F)(F)C3)ccn1]<br>Acid: 3-cyclopropyl-1-((6,6-difluorospiro[3.3]heptan-2-yl)methyl)-4-(trifluoromethyl)-1H-pyrazole-5-carboxylic acid (Intermediate 75)<br>Amine: 2-(methylthio)pyridin-4-amine hydrochloride<br>Yield: 55 mg, 22%; LCMS m/z = 487 $[M + H]^+$. |
| 291 | 3-Cyclopropyl-1-((3,3-difluoro-1-methylcyclobutyl)methyl)-N-(3-(methylthio)phenyl)-4-(trifluoromethyl)-1H-pyrazole-5-carboxamide<br>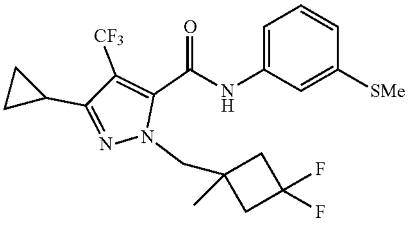 [SMILES: CSc1cccc(NC(=O)c2c(C(F)(F)F)c(C3CC3)nn2CC2(C)CC(F)(F)C2)c1]<br>Acid: 3-cyclopropyl-1-((3,3-difluoro-1-methylcyclobutyl)methyl)-4-(trifluoromethyl)-1H-pyrazole-5-carboxylic acid (Intermediate 60)<br>Amine: 3-(methylthio)aniline<br>Yield: 250 mg, 52%; LCMS m/z = 460 $[M + H]^+$. |
| 293 | 1-((3,3-Difluoro-1-methylcyclobutyl)methyl)-3-(1,1-difluoroethyl)-N-(2-(methylthio)pyridin-4-yl)-4-(trifluoromethyl)-1H-pyrazole-5-carboxamide |

-continued

| Intermediate | Name/Structure/Starting Materials/Data |
|---|---|
| | 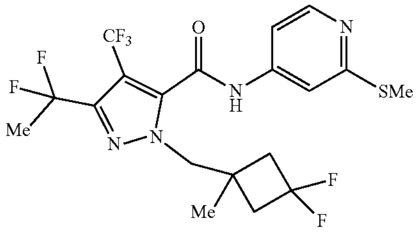 [SMILES: CSc1cc(NC(=O)c2c(C(F)(F)F)c(C(C)(F)F)nn2CC2(C)CC(F)(F)C2)ccn1] |
| | Acid: 1-((3,3-difluoro-1-methylcyclobutyl) methyl)-3-(1,1-difluoroethyl)-4-(trifluoromethyl)-1H-pyrazole-5-carboxylic acid (Intermediate 222)<br>Amine: 2-(methylthio)pyridin-4-amine<br>Yield: 90 mg, 19%; LCMS m/z = 485 $[M + H]^+$. |
| 294 | 3-Cyclopropyl-1-((4-fluorobicyclo[2.2.1]heptan-1-yl)methyl)-N-(2-(methylthio)pyridin-4-yl)-4-(trifluoromethyl)-1H-pyrazole-5-carboxamide |
| | 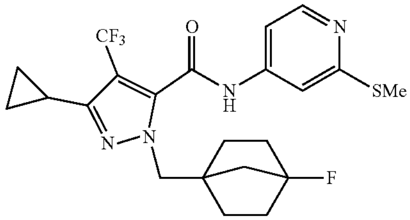 [SMILES: CSc1cc(NC(=O)c2c(C(F)(F)F)c(C3CC3)nn2CC23CCC(F)(CC2)C3)ccn1] |
| | Acid: 3-cyclopropyl-1-({4-fluorobicyclo[2.2.1]heptan-1-yl}methyl)-4-(trifluoromethyl)-1H-pyrazole-5-carboxylic acid (Intermediate 253)<br>Amine: 2-(methylthio)pyridin-4-amine<br>Yield: 0.2 g, crude; LCMS m/z = 469 $[M + H]^+$. |
| 295 | 3-Cyclopropyl-1-((3,3-difluoro-1-methylcyclobutyl)methyl)-N-(2-(ethylthio)pyridin-4-yl)-4-(trifluoromethyl)-1H-pyrazole-5-carboxamide |
| | 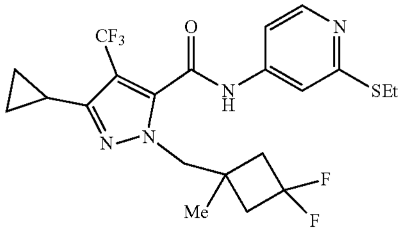 |
| | Acid: 3-cyclopropyl-1-((3,3-difluoro-1-methylcyclobutyl)methyl)-4-(trifluoromethyl)-1H-pyrazole-5-carboxylic acid (Intermediate 65)<br>Amine: 2-(ethylthio)pyridin-4-amine (Intermediate 289)<br>Yield: 180 mg, 51%; LCMS m/z = 475 $[M + H]^+$. |
| 297 | 1-((3,3-Difluoro-1-methylcyclobutyl)methyl)-N-(2-(methylthio)pyridin-4-yl)-3-(spiro[2.2]pentan-1-yl)-4-(trifluoromethyl)-1H-pyrazole-5-carboxamide |
| | 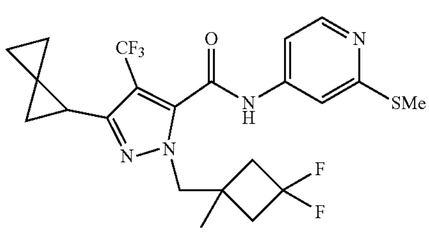 [SMILES: CSc1cc(NC(=O)c2c(C(F)(F)F)c(C3CC34CC4)nn2CC2(C)CC(F)(F)C2)ccn1] |
| | Acid: 1-((3,3-difluoro-1-methylcyclobutyl)methyl)-3-(spiro[2.2]pentan-1-yl)-4-(trifluoromethyl)-1H-pyrazole-5-carboxylic acid (Intermediate 260)<br>Amine: 2-(methylthio) pyridin-4-amine<br>Yield 85 mg, 32%; LCMS m/z = 487 $[M + H]^+$. |
| 299 | 3-(1-Cyanocyclopropyl)-1-((3,3-difluoro-1-methylcyclobutyl)methyl)-N-(2-(methylthio)pyridin-4-yl)-4-(trifluoromethyl)-1H-pyrazole-5-carboxamide |

-continued

| Intermediate | Name/Structure/Starting Materials/Data |
|---|---|
| | 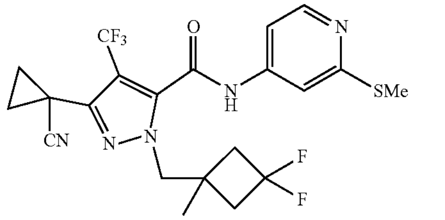 [SMILES: CSc1cc(NC(=O)c2c(C(F)(F)F)c(C3(C#N)CC3)nn2CC2(C)CC(F)(F)C2)ccn1]<br>Acid: 3-(1-cyanocyclopropyl)-1-((3,3-difluoro-1-methylcyclobutyl)methyl)-4-(trifluoromethyl)-1H-pyrazole-5-carboxylic acid (Intermediate 203)<br>Amine: 2-(methylthio)pyridin-4-amine<br>Yield: 120 mg, 26%; LCMS m/z = 486 $[M + H]^+$. |
| 306 | 3-(Bicyclo[1.1.1]pentan-1-yl)-1 -((3,3-difluoro-1-methylcyclobutyl)methyl)-4-(difluoromethyl)-N-(2-(methylthio)pyridin-4-yl)-1H-pyrazole-5-carboxamide<br>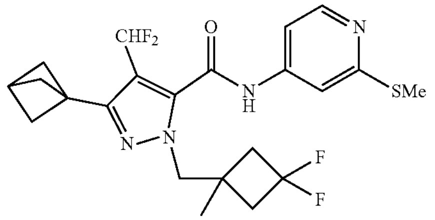 [SMILES: CSc1cc(NC(=O)c2c(C(F)F)c(C34CC(C3)C4)nn2CC2(C)CC(F)(F)C2)ccn1]<br>Acid: 3-(bicyclo[1.1.1]pentan-1-yl)-1-((3,3-difluoro-1-methylcyclobutyl)methyl)-4-(difluoromethyl)-1H-pyrazole-5-carboxylic acid (Intermediate 221)<br>Amine: 2-(methylthio)pyridin-4-amine<br>Yield: 0.17 g, 35%; LCMS m/z = 469 $[M + H]^+$. |

Intermediate 298

3-Cyclopropyl-1-(dispiro[2.0.2⁴.1³]heptan-7-ylmethyl)-N-(2-(methylthio)pyridin-4-yl)-4-(trifluoromethyl)-1H-pyrazole-5-carboxamide

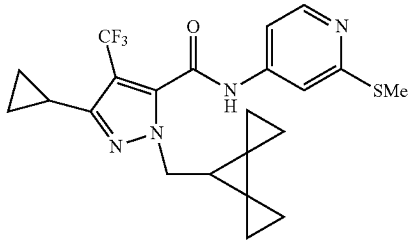 [SMILES: CSc1cc(NC(=O)c2c(C(F)(F)F)c(C3CC3)nn2CC2C3(CC3)C23CC3)ccn1]

To a solution of 3-cyclopropyl-1-({dispiro[$2.0.2^4.1^3$]heptan-7-yl}methyl)-4-(trifluoromethyl)-1H-pyrazole-5-carboxylic acid (Intermediate 249, 0.4 g) in pyridine (10 mL) were added $POCl_3$ (0.3 mL) and 2-(methylsulfanyl)pyridin-4-amine (0.344 g) at 0° C. The reaction mixture was stirred at rt for 2 h. The reaction mixture was concentrated under reduced pressure and diluted with cold water. The aqueous part was extracted with EtOAc (2×100 mL). The combined organic layers were washed with brine and dried over $Na_2SO_4$. The organic layer was concentrated under reduced pressure to get the crude product, which was purified by CombiFlash column chromatography ($SiO_2$, 0-40% EtOAc/Hex) to yield the title compound (0.18 g, 33%). LCMS m/z=449 $[M+H]^+$.

Intermediate 292, 305, 307-309

The title compounds were prepared from the appropriate carboxylic acid and amine (at a suitable reaction time between 2-3 hours) using an analogous method as described for Intermediate 298.

| Intermediate | Name/Structure/Starting Materials/Data |
|---|---|
| 292 | 1-((3,3-Difluoro-1-methylcyclobutyl)methyl)-3-(1-methoxycyclopropyl)-N-(2-(methylthio)pyridin-4-yl)-4-(trifluoromethyl)-1H-pyrazole-5-carboxamide<br>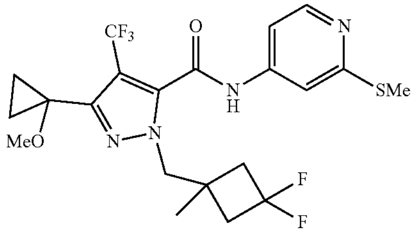 [SMILES: COC1(c2nn(CC3(C)CC(F)(F)C3)c(C(=O)Nc3ccnc(SC)c3)c2C(F)(F)F)CC1] |

-continued

| Intermediate | Name/Structure/Starting Materials/Data |
|---|---|
| | Acid: 1-[(3,3-difluoro-1-methylcyclobutyl)methyl]-3-(1-methoxycyclopropyl)-4-(trifluoromethyl)-1H-pyrazole-5-carboxylic acid (Intermediate 250)<br>Amine: 2-(methylthio)pyridin-4-amine<br>Yield: 70 mg, 40%; LCMS m/z = 491 $[M + H]^+$. |
| 300 | 1-((3,3-Difluoro-1-methylcyclobutyl)methyl)-3-(1-methylcyclopropyl)-N-(2-(methylthio)pyridin-4-yl)-4-(trifluoromethyl)-1H-pyrazole-5-carboxamide<br>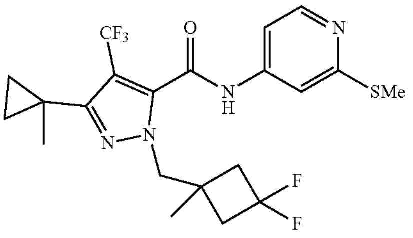<br>Acid: 1-((3,3-difluoro-1-methylcyclobutyl)methyl)-3-(1-methylcyclopropyl)-4-(trifluoromethyl)-1H-pyrazole-5-carboxylic acid (Intermediate 220)<br>Amine: 2-(methylthio)pyridin-4-amine<br>Yield: 400 mg, 48%; LCMS m/z = 475 $[M + H]^+$. |
| 301 | 3-Cyclopropyl-N-(2-(methylthio)pyridin-4-yl)-4-(trifluoromethyl)-1-((1-(trifluoromethyl)cyclopentyl)methyl)-1H-pyrazole-5-carboxamide<br>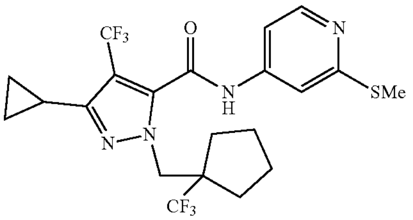 [SMILES: CSc1cc(NC(=O)c2c(C(F)(F)F)c(C3CC3)nn2CC2(C(F)(F)F)CCCC2)ccn1]<br>Acid: 3-cyclopropyl-4-(trifluoromethyl)-1-{[1-(trifluoromethyl)cyclopentyl]methyl}-1H-pyrazole-5-carboxylic acid (Intermediate 251)<br>Amine: 2-(methylthio)pyridin-4-amine<br>Yield: 250 mg, 46%; LCMS m/z = 493 $[M + H]^+$. |
| 302 | 3-Cyclopropyl-1-((2,2-difluorobicyclo[2.1.1]hexan-1-yl)methyl)-N-(2-(methylthio)pyridin-4-yl)-4-(trifluoromethyl)-1H-pyrazole-5-carboxamide<br>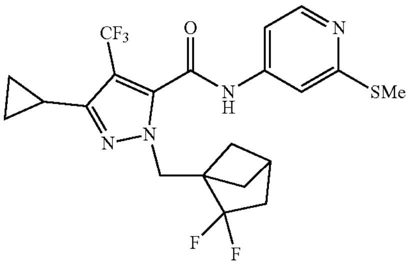 [SMILES: CSc1cc(NC(=O)c2c(C(F)(F)F)c(C3CC3)nn2CC23CC(CC2(F)F)C3)ccn1]<br>Acid: 3-cyclopropyl-1-((2,2-difluorobicyclo[2.1.1]hexan-1-yl)methyl)-4-(trifluoromethyl)-1H-pyrazole-5-carboxylic acid (Intermediate 252)<br>Amine: 2-(methylthio)pyridin-4-amine<br>Yield: 0.15 g, 62%; LCMS m/z = 473 $[M + H]^+$. |
| 303a/303b | 3-Cyclopropyl-N-(2-(methylthio)pyridin-4-yl)-1-(spiro[2.2]pentan-1-ylmethyl)-4-(trifluoromethyl)-1H-pyrazole-5-carboxamide<br>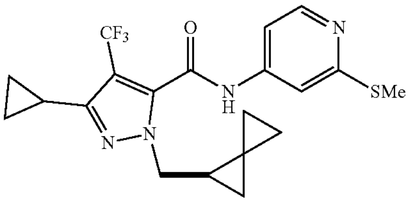<br>303a |

-continued

| Intermediate | Name/Structure/Starting Materials/Data |
|---|---|
| | and<br>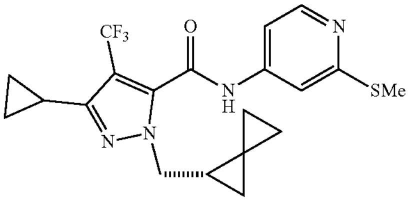<br>303b<br>Acid: 3-cyclopropyl-1-(spiro[2.2]pentan-1-ylmethyl)-4-(trifluoromethyl)-1H-pyrazole-5-carboxylic acid (Intermediate 254)<br>Amine: 2-(methylthio)pyridin-4-amine<br>Chiral-SFC (C Amylose A, 250 × 30 mm, 5 μm; 20% (hexane/MeOH/iPrOH 60/30/10) in $CO_2$)<br>Peak 1, Intermediate 303a (0.20 g, 20%). LCMS m/z = 423 $[M + H]^+$; Chiral SFC: column: C Amylose A (4.6 × 250 mm) 5 μm, mobile phase: 0.5% $iPrNH_2$ in iPrOH, flow: 4 mL/min; % of co-solvent: 35%; ABPR: 100 bar; T: 35° C.; $R_t$ = 2.79 min (first eluting).<br>Peak 2, Intermediate 303b (0.17 mg, 17%). LCMS m/z = 423 $[M + H]^+$; Chiral SFC: column: C Amylose A (4.6 × 250 mm) 5 μm, mobile phase: 0.5% $iPrNH_2$ in iPrOH, flow : 4 mL/min; % of co-solvent: 35%; ABPR: 100 bar; T: 35° C.; $R_t$ = 3.39 min (second eluting). |
| 304 | 1-((3,3-Difluoro-1-methylcyclobutyl)methyl)-3-((trans)-2-methylcyclopropyl)-N-(2-(methylthio)pyridin-4-yl)-4-(trifluoromethyl)-1H-pyrazole-5-carboxamide<br>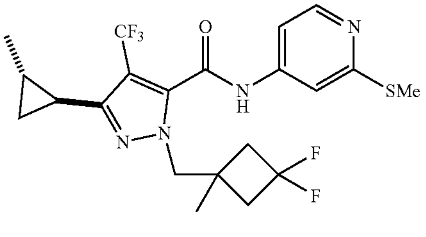<br>304a<br>and<br>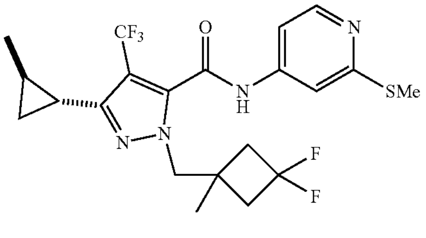<br>304b<br>Acid: 1-((3,3-difluoro-1-methylcyclobutyl)methyl)-3-((trans)-2-methylcyclopropyl)-4-(trifluoromethyl)-1H-pyrazole-5-carboxylic acid (Intermediate 255)<br>Amine: 2-(methylthio)pyridin-4-amine<br>Chiral-SFC (Ciralpak IG, 250 × 30 mm, 5 μm; 10% (hexane/iPrOH 60/40) in $CO_2$)<br>Peak 1, Intermediate 304a (0.33 g, 9%). LCMS m/z = 475 $[M + H]^+$; Chiral SFC: column: Chiralpak IG (4.6 × 250 mm) 5 μm, mobile phase: 0.3% $iPrNH_2$ in Hexane/iPrOH 60/40), flow: 3 mL/min; % of co-solvent: 20%; ABPR: 1500 psi; T: 35° C.; $R_t$ = 2.31 min (first eluting).<br>Peak 2, Intermediate 304b (0.34 g, 9%). LCMS m/z = 475 $[M + H]^+$; Chiral SFC: column: Chiralpak IG (4.6 × 250 mm) 5 μm, mobile phase: 0.3% $iPrNH_2$ in Hexane/iPrOH 60/40), flow: 3 mL/min; % of co-solvent: 20%; ABPR: 1500 psi; T: 35° C.; $R_t$ = 2.72 min (second eluting). |
| 305a/305b | 3-Cyclopropyl-1-((2,2-difluorospiro[2.3]hexan-1-yl)methyl)-N-(2-(methylthio)pyridin-4-yl)-4-(trifluoromethyl)-1H-pyrazole-5-carboxamide |

-continued

| Intermediate | Name/Structure/Starting Materials/Data |
|---|---|
| | 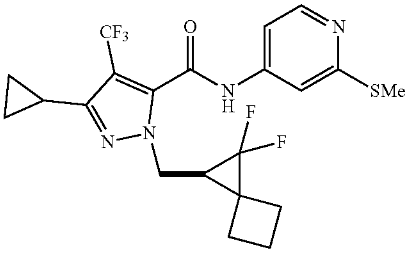<br>305a<br>and<br>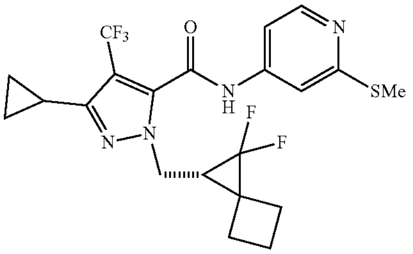<br>305b<br>Acid: 3-cyclopropyl-1-({2,2-difluorospiro[2.3]hexan-1-yl}methyl)-4-(trifluoromethyl)-1H-pyrazole-5-carboxylic acid (Intermediate 256)<br>Amine: 2-(methylthio)pyridin-4-amine<br>Chiral-SFC (C-Amylose-A, 250 x 30 mm, 5 μm; 15% (hexane/iPrOH 50/50) in $CO_2$)<br>Peak 1, Intermediate 305a (0.19 g, 19%). LCMS m/z = 473 $[M + H]^+$; Chiral SFC: column: C-Amylose-A (4.6 x 250 mm) 5 μm, mobile phase: hexae/iPrOH 50/50, flow: 3 mL/min; % of co-solvent: 20%; ABPR: 1500 psi; T: 35° C.; $R_t$ = 3.05 min (first eluting).<br>Peak 2, Intermediate 305b (0.19 g, 19%). LCMS m/z = 473 $[M + H]^+$; Chiral SFC: column: C-Amylose-A (4.6 x 250 mm) 5 μm, mobile phase: hexae/iPrOH 50/50, flow: 3 mL/min; % of co-solvent: 20%; ABPR: 1500 psi; T: 35° C.; $R_t$ = 3.64 min (second eluting) |
| 307a/307b | 3-Cyclopropyl-1-((2,2-difluorospiro[2.2]pentan-1-yl)methyl)-N-(2-(methylthio)pyridin-4-yl)-4-(trifluoromethyl)-1H-pyrazole-5-carboxamide<br>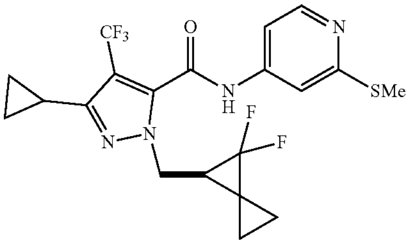<br>307a<br>and<br>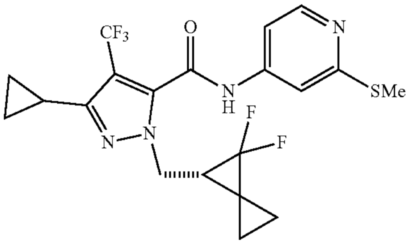<br>307b<br>Acid: 3-cyclopropyl-1-({2,2-difluorospiro[2.2]pentan-1-yl}methyl)-4-(trifluoromethyl)-1H-pyrazole-5-carboxylic acid (Intermediate 233) |

-continued

| Intermediate | Name/Structure/Starting Materials/Data |
|---|---|
| | Amine: 2-(methylthio)pyridin-4-amine<br>Chiral-SFC (Chiralpak IG, 250 x 30 mm, 5 μm; 15% (MeCN/iPrOH 50/50) in $CO_2$)<br>Peak 1, Intermediate 307a (0.08 g, 15%). LCMS m/z = 459 $[M + H]^+$; Chiral SFC: column: Chiralpak IG (4.6 x 250 mm) 5 μm, mobile phase: MeCN/iPrOH 50/50; flow: 2 mL/min; % of co-solvent: 20%; ABPR: 1500 psi; T: 35° C.; $R_t$ = 2.49 min (first eluting).<br>Peak 2, Intermediate 307b (0.07 g, 13%). LCMS m/z = 459 $[M + H]^+$; Chiral SFC: column: Chiralpak IG (4.6 x 250 mm) 5 μm, mobile phase: MeCN/iPrOH 50/50; flow: 2 mL/min; % of co-solvent: 20%; ABPR: 1500 psi; T: 35° C.; $R_t$ = 2.87 min (second eluting) |
| 308 | 3-Cyclopropyl-1-(((trans)-1-methyl-3-(trifluoromethyl)cyclobutyl)methyl)-N-(2-(methylthio)pyridin-4-yl)-4-(trifluoromethyl)-1H-pyrazole-5-carboxamide<br>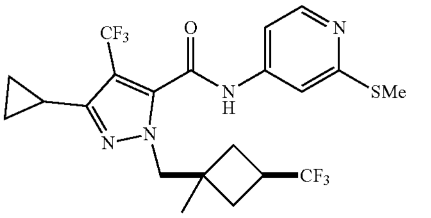<br>Acid: 3-cyclopropyl-1-(((trans)-1-methyl-3-(trifluoromethyl)cyclobutyl)methyl)-4-(trifluoromethyl)-1H-pyrazole-5-carboxylic acid (Intermediate 237a)<br>Amine: 2-(methylthio)pyridin-4-amine<br>Yield: 0.32 g, 69%; LCMS m/z = 491 $[M - H]^-$. |
| 309 | 3-Cyclopropyl-1-(((cis)-1-methyl-3-(trifluoromethyl)cyclobutyl)methyl)-N-(2-(methylthio)pyridin-4-yl)-4-(trifluoromethyl)-1H-pyrazole-5-carboxamide<br>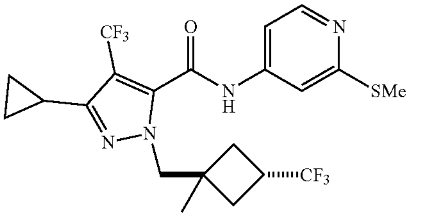<br>Acid: 3-cyclopropyl-1-(((cis)-1-methyl-3-(trifluoromethyl)cyclobutyl)methyl)-4-(trifluoromethyl)-1H-pyrazole-5-carboxylic acid (Intermediate 237b)<br>Amine: 2-(methylthio)pyridin-4-amine<br>Yield: 0.32 g, 69%; LCMS m/z = 491 $[M - H]^-$. |

Intermediate 310

3-Cyclopropyl-1-((3,3-difluoro-1-methylcyclobutyl) methyl)-N-(6-(methylthio)pyridazin-4-yl)-4-(trifluoromethyl)-1H-pyrazole-5-carboxamide

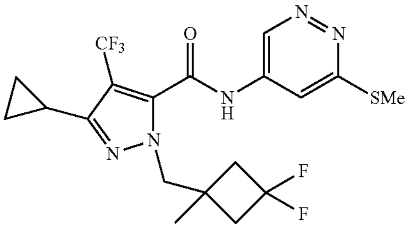 [SMILES: CSc1cc(NC(=O)c2c(C(F)(F)F)c(C3CC3)nn2CC2(C)CC(F)(F)C2)cnn1]

To a solution of 3-cyclopropyl-1-((3,3-difluoro-1-methylcyclobutyl)methyl)-4-(trifluoromethyl)-1H-pyrazole-5-carboxylic acid (Intermediate 65, 200 mg) in DCM (5.0 mL) were added DIPEA (0.26 mL) and HATU (340 mg) followed by 6-(methylthio)pyridazin-4-amine (100.0 mg) at rt. The reaction mixture was stirred at rt for 16 h. The reaction mixture was diluted with water (15 mL) and extracted with DCM (3x50 mL). The combined organic layers were washed with brine (20 mL), dried over $Na_2SO_4$ and evaporated under reduced pressure to get the crude product which was purified by CombiFlash column chromatography ($SiO_2$, 0-100% EtOAc/Hex) to yield the title compound (120 mg, 44%). LCMS m/z=462 $[M+H]^+$.

Intermediate 311

The title compounds were prepared from the appropriate carboxylic acid the appropriate amine using an analogous method as described for Intermediate 310.

| Intermediate | Name/Structure/Starting Materials/Data |
|---|---|
| 311 | 3-Cyclopropyl-1-((3,3-difluoro-1-methylcyclobutyl)methyl)-N-(4-fluoro-3-(methylthio)phenyl)-4-(trifluoromethyl)-1H-pyrazole-5-carboxamide 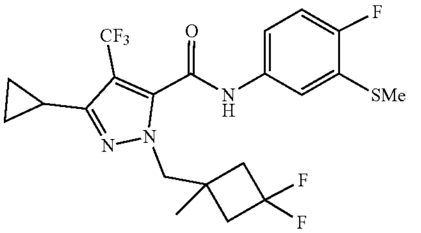 [SMILES: CSc1cc(NC(=O)c2c(C(F)(F)F)c(C3CC3)nn2CC2(C)CC(F)(F)C2)ccc1F] Acid: 3-cyclopropyl-1-((3,3-difluoro-1-methylcyclobutyl)methyl)-4-(trifluoromethyl)-1H-pyrazole-5-carboxylic acid (Intermediate 65) Amine: 4-fluoro-3-(methylthio)aniline (Intermediate 332) Yield: 180 mg, 85%; LCMS m/z = 478 $[M + H]^+$. |

Intermediate 312

3-Cyclopropyl-1-((3,3-difluoro-1-methylcyclobutyl)methyl)-N-(2-methyl-6-(methylthio)pyridin-4-yl)-4-(trifluoromethyl)-1H-pyrazole-5-carboxamide

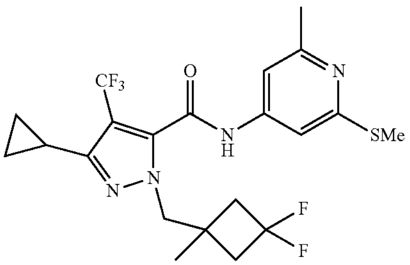 [SMILES: CSc1cc(NC(=O)c2c(C(F)(F)F)c(C3CC3)nn2CC2(C)CC(F)(F)C2)cc(C)n1]

To a solution of 3-cyclopropyl-1-((3,3-difluoro-1-methylcyclobutyl)methyl)-4-(trifluoromethyl)-1H-pyrazole-5-carboxylic acid (Intermediate 65, 0.44 g) in MeCN (5 ml) were added 2-methyl-6-(methylthio)pyridin-4-amine (Intermediate 331, 0.2 g), TCFH (581 mg) and DIPEA (1.35 mL) at rt. The resulting reaction mixture was stirred at rt for 16 h. The reaction mixture was quenched with cold water (20 mL) and extracted with EtOAc (2×70 mL). The combined organic layers were washed with brine (30 mL), dried over $Na_2SO_4$ and concentrated under reduced pressure to afford the crude product, which was purified by CombiFlash column chromatography ($SiO_2$, 10% EtOAc/Hex) to afford the title compound (0.16 g, 26%). LCMS m/z=475 $[M+H]^+$.

Intermediate 313

1-((3,3-Difluoro-1-methylcyclobutyl)methyl)-N-(4-fluoro-3-(methylthio)phenyl)-3-(1-fluorocyclopropyl)-4-(trifluoromethyl)-1H-pyrazole-5-carboxamide

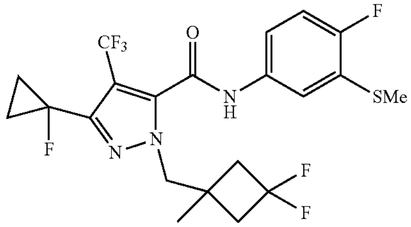 [SMILES: CSc1cc(NC(=O)c2c(C(F)(F)F)c(C3(F)CC3)nn2CC2(C)CC(F)(F)C2)ccc1F]

To a stirred solution of 1-((3,3-difluoro-1-methylcyclobutyl)methyl)-3-(1-fluorocyclopropyl)-4-(trifluoromethyl)-1H-pyrazole-5-carboxamide (Intermediate 262, 240 mg) in 1,4-dioxane (10 mL) in a sealed tube were added (5-bromo-2-fluorophenyl)(methyl)sulfane (164.22 mg), $K_2CO_3$ (111.87 mg) and CuI (12.8 mg). The mixture was degassed with argon gas for 10 minutes. To the reaction mixture was then added DMEDA (11.9 mg) at rt and the mixture was again degassed for 5 minutes. The resulting reaction mixture was heated to 100° C. for 16 h. The reaction mixture was cooled to rt, diluted with EtOAc (30 mL) and filtered through a celite bed. The filtrate was concentrated under reduced pressure to get the crude product, which was taken up in EtOAc (30 mL). The organic part layer was washed with water (30 mL) and brine (30 mL), dried over anhydrous $Na_2SO_4$ and concentrated under reduced pressure to get the crude product, which was purified by column chromatography ($SiO_2$, 20-25% EtOAc/PE) to yield the title compound (220 mg, 66%). LCMS m/z=496 $[M+H]^+$.

Intermediate 314-317

The title compounds were prepared from the appropriate amides and arylbromides (at a suitable reaction temperature between 90-100° C.) using an analogous method as described for Intermediate 313.

| Intermediate | Name/Structure/Starting Materials/Data |
|---|---|
| 314 | 1-((3,3-Difluoro-1-methylcyclobutyl)methyl)-N-(3-fluoro-5-(methylthio)phenyl)-3-(1-fluorocyclopropyl)-4-(trifluoromethyl)-1H-pyrazole-5-carboxamide 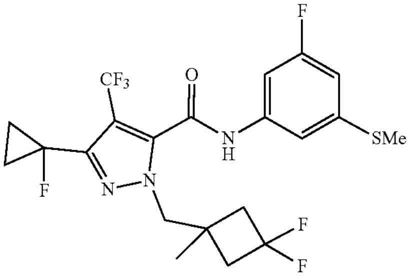 [SMILES: CSc1cc(F)cc(NC(=O)c2c(C(F)(F)F)c(C3(F)CC3)nn2CC2(C)CC(F)(F)C2)c1] Amide: 1-((3,3-difluoro-1-methylcyclobutyl)methyl)-3-(1-fluorocyclopropyl)-4-(trifluoromethyl)-1H-pyrazole-5-carboxamide (Intermediate 262) Arylbromide: (3-bromo-5-fluorophenyl)(methyl)sulfane Yield: 3.2 g, 91%. |
| 315 | 1-((3,3-Difluoro-1-methylcyclobutyl)methyl)-4-(difluoromethyl)-N-(4-fluoro-3-(methylthio)phenyl)-3-(1-fluorocyclopropyl)-1H-pyrazole-5-carboxamide 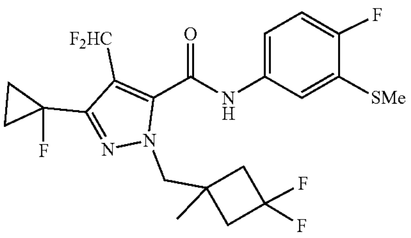 [SMILES: CSc1cc(NC(=O)c2c(C(F)F)c(C3(F)CC3)nn2CC2(C)CC(F)(F)C2)ccc1F] Amide: 1-((3,3-difluoro-1-methylcyclobutyl)methyl)-4-(difluoromethyl)-3-(1-fluorocyclopropyl)-1H-pyrazole-5-carboxamide (Intermediate 282) Arylbromide: (5-bromo-2-fluorophenyl)(methyl)sulfane Yield: 300 mg, 60%; LCMS m/z = 478 $[M + H]^+$. |
| 316 | 1-((3,3-Difluoro-1-methylcyclobutyl)methyl)-4-(difluoromethyl)-N-(4-fluoro-3-(methylthio)phenyl)-3-(3-fluorobicyclo[1.1.1]pentan-1-yl)-1H-pyrazole-5-carboxamide 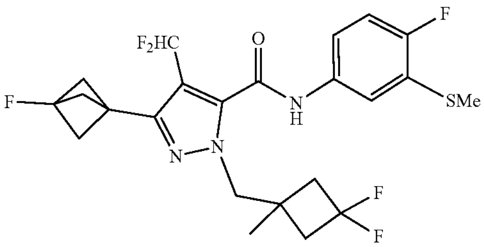 [SMILES: CSc1cc(NC(=O)c2c(C(F)F)c(C34CC(F)(C3)C4)nn2CC2(C)CC(F)(F)C2)ccc1F] Amide: 1-((3,3-difluoro-1-methylcyclobutyl)methyl)-4-(difluoromethyl)-3-(3-fluorobicyclo[1.1.1]pentan-1-yl)-1H-pyrazole-5-carboxamide (Intermediate 285) Arylbromide: (5-bromo-2-fluorophenyl)(methyl)sulfane Yield: 600 mg, 86%; LCMS m/z = 504 $[M + H]^+$. |
| 317 | 1-((3,3-Difluoro-1-methylcyclobutyl)methyl)-N-(4-fluoro-3-(methylthio)phenyl)-3-(3-fluorobicyclo[1.1.1]pentan-1-yl)-4-(trifluoromethyl)-1H-pyrazole-5-carboxamide 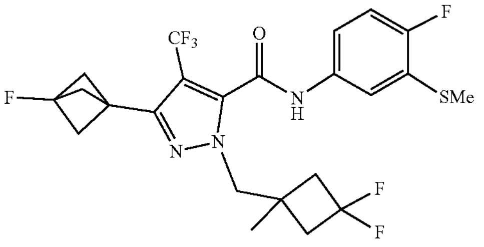 [SMILES: CSc1cc(NC(=O)c2c(C(F)(F)F)c(C34CC(F)(C3)C4)nn2CC2(C)CC(F)(F)C2)ccc1F] |

-continued

| Intermediate | Name/Structure/Starting Materials/Data |
|---|---|
| | Amide: 1-((3,3-difluoro-1-methylcyclobutyl)methyl)-3-(3-fluorobicyclo[1.1.1]pentan-1-yl)-4-(trifluoromethyl)-1H-pyrazole-5-carboxamide (Intermediate 286)<br>Arylbromide: (5-bromo-2-fluorophenyl)(methyl)sulfane<br>Yield: 200 mg, 68%; LCMS m/z = 521 [M − H]$^-$. |

Intermediate 318

3-Cyclopropyl-1-((3,3-difluoro-1-methylcyclobutyl)methyl)-N-(5-(methylthio)pyridin-3-yl)-4-(trifluoromethyl)-1H-pyrazole-5-carboxamide

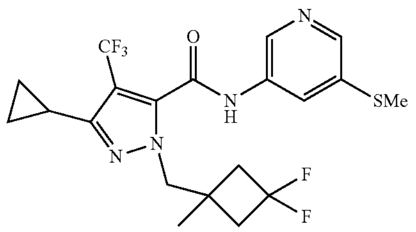 [SMILES: CSc1cncc(NC(=O)c2c(C(F)(F)F)c(C3CC3)nn2CC2(C)CC(F)(F)C2)c1]

A solution of 3-cyclopropyl-1-((3,3-difluoro-1-methylcyclobutyl)methyl)-4-(trifluoromethyl)-1H-pyrazole-5-carboxamide (350 mg, 1.04 mmol), 3-bromo-5-(methylthio)pyridine (252 mg) and $Cs_2CO_3$ (1.1 g) in 1,4-dioxane (25 mL) was degassed with argon for 15 min followed by the addition of CuI (99 mg) and trans-1,2-diaminocyclohexane (60 mg) at rt. The reaction mixture was heated to 90° C. for 16 h. The reaction mixture was cooled to rt, filtered through celite and the celite bed was washed with EtOAc (50 mL). The filtrate was diluted with water (75 mL) and extracted with EtOAc (2×50 mL). The combined organic layers were washed with brine (50 mL), dried over $Na_2SO_4$ and the solvent was evaporated under reduced pressure to get the crude product which was purified by reverse phase prep HPLC to yield the title compound (320 mg, 66%). LCMS m/z=461 $[M+H]^+$.

Intermediate 319

1-((3,3-Difluoro-1-methylcyclobutyl)methyl)-3-(1-fluorocyclopropyl)-N-(3-(methylthio)phenyl)-4-(trifluoromethyl)-1H-pyrazole-5-carboxamide

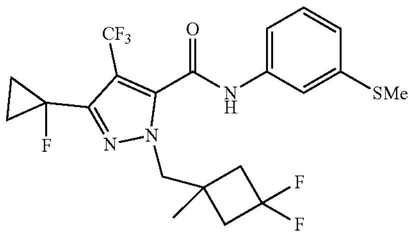 [SMILES: CSc1cccc(NC(=O)c2c(C(F)(F)F)c(C3(F)CC3)nn2CC2(C)CC(F)(F)C2)c1]

To a stirred solution of methyl 1-((3,3-difluoro-1-methylcyclobutyl)methyl)-3-(1-fluorocyclopropyl)-4-(trifluoromethyl)-1H-pyrazole-5-carboxylate (Intermediate 174, 300 mg) and 3-(methylthio)aniline (112.79 mg) in THF (10 mL) was added 1M KHMDS in THF (1.2 mL) at −78° C. The reaction mixture was stirred for 0.5 h at −78° C. The reaction mixture was quenched with sat $NH_4Cl$ solution (30 mL) and extracted with EtOAc (2×30 mL). The combined organic layers were washed with water (30 mL) and brine (30 mL), dried over anhydrous $Na_2SO_4$ and concentrated under reduced pressure to get the crude product. The crude product was triturated with pentane, filtered off and was dried under reduced pressure to afford the title compound (280 mg, 72%). LCMS m/z=478 $[M+H]^+$.

Intermediate 320-326

The title compounds were prepared from the appropriate ester and amine using an analogous method (at a suitable reaction time between 0.5-1 hours) as described for Intermediate 319.

| Intermediate | Name/Structure/Starting Materials/Data |
|---|---|
| 320 | 1-((3,3-Difluoro-1-methylcyclobutyl)methyl)-N-(3-((difluoromethyl)thio)phenyl)-3-(1-fluorocyclopropyl)-4-(trifluoromethyl)-1H-pyrazole-5-carboxamide<br>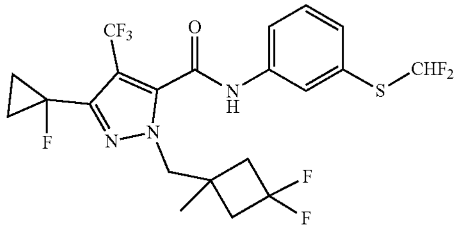 [SMILES: CC1(Cn2nc(C3(F)CC3)c(C(F)(F)F)c2C(=O)Nc2cccc(SC(F)F)c2)CC(F)(F)C1]<br>Ester: methyl 1-((3,3-difluoro-1-methylcyclobutyl)methyl)-3-(1-fluorocyclopropyl)-4-(trifluoromethyl)-1H-pyrazole-5-carboxylate (Intermediate 174)<br>Amine: 3-((difluoromethyl)thio)aniline<br>Yield: 240 mg, 57%; LCMS m/z = 514 [M + H]$^+$. |

-continued

| Intermediate | Name/Structure/Starting Materials/Data |
|---|---|
| 321 | 1-((3,3-Difluoro-1-methylcyclobutyl)methyl)-3-(1-fluorocyclopropyl)-4-(trifluoromethyl)-N-(3-((trifluoromethyl)thio)phenyl)-1H-pyrazole-5-carboxamide<br>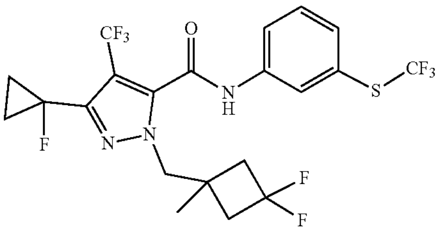 [SMILES: CC1(Cn2nc(C3(F)CC3)c(C(F)(F)F)c2C(=O)Nc2cccc(SC(F)(F)F)c2)CC(F)(F)C1]<br>Ester: methyl 1-((3,3-difluoro-1-methylcyclobutyl)methyl)-3-(1-fluorocyclopropyl)-4-(trifluoromethyl)-1H-pyrazole-5-carboxylate (Intermediate 174)<br>Amine: 3-((trifluoromethyl)thio)aniline<br>Yield: 280 mg, 61%; LCMS m/z = 530 $[M-H]^-$. |
| 322 | 1-((3,3-Difluoro-1-methylcyclobutyl)methyl)-3-(3-fluorobicyclo[1.1.1]pentan-1-yl)-N-(3-(methylthio)phenyl)-4-(trifluoromethyl)-1H-pyrazole-5-carboxamide<br>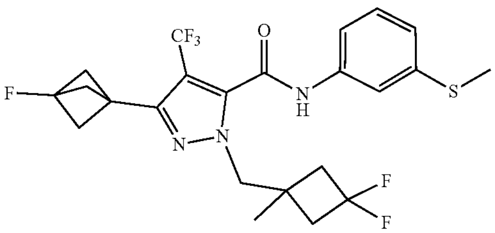 [SMILES: CSc1cccc(NC(=O)c2c(C(F)(F)F)c(C34CC(F)(C3)C4)nn2CC2(C)CC(F)(F)C2)c1]<br>Ester: methyl 1-((3,3-difluoro-1-methylcyclobutyl)methyl)-3-(3-fluorobicyclo[1.1.1]pentan-1-yl)-4-(trifluoromethyl)-1H-pyrazole-5-carboxylate (Intermediate 196)<br>Amine: 3-(methylthio)aniline<br>Yield: 1.9 g, 99%; LCMS m/z = 504 $[M+H]^+$. |
| 323 | 1-((3,3-Difluoro-1-methylcyclobutyl)methyl)-4-(difluoromethyl)-3-(3-fluorobicyclo[1.1.1]pentan-1-yl)-N-(3-(methylthio)phenyl)-1H-pyrazole-5-carboxamide<br>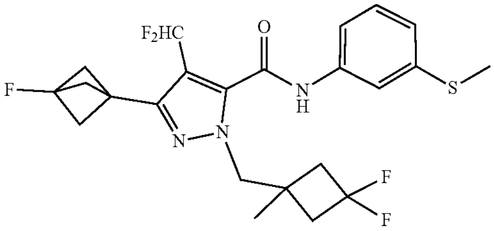 [SMILES: CSc1cccc(NC(=O)c2c(C(F)F)c(C34CC(F)(C3)C4)nn2CC2(C)CC(F)(F)C2)c1]<br>Ester: methyl 1-((3,3-difluoro-1-methylcyclobutyl)methyl)-4-(difluoromethyl)-3-(3-fluorobicyclo[1.1.1]pentan-1-yl)-1H-pyrazole-5-carboxylate (Intermediate 283)<br>Amine: 3-(methylthio)aniline<br>Yield: 220 mg, 57%; LCMS m/z = 486 $[M+H]^+$. |
| 324 | 3-(1-Fluorocyclopropyl)-N-(3-(methylthio)phenyl)-4-(trifluoromethyl)-1-(((trans)-2-(trifluoromethyl)cyclopropyl)methyl)-1H-pyrazole-5-carboxamide<br>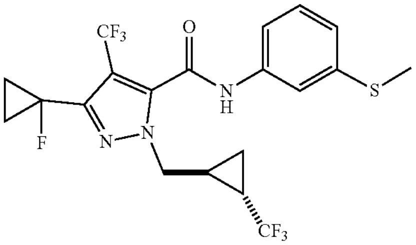 [SMILES: CSc1cccc(NC(=O)c2c(C(F)(F)F)c(C3(F)CC3)nn2C[C@H]2C[C@@H]2C(F)(F)F)c1]<br>Ester: methyl 3-(1-fluorocyclopropyl)-4-(trifluoromethyl)-1-(((trans)-2-(trifluoromethyl)cyclopropyl)methyl)-1H-pyrazole-5-carboxylate (Intermediate 197)<br>Amine: 3-(methylthio)aniline<br>Yield: 400 mg, crude; LCMS m/z = 482 $[M+H]^+$. |

-continued

| Intermediate | Name/Structure/Starting Materials/Data |
|---|---|
| 325 | 1-((3,3-Difluoro-1-methylcyclobutyl)methyl)-4-(difluoromethyl)-3-(1-fluorocyclopropyl)-N-(3-(methylthio)phenyl)-1H-pyrazole-5-carboxamide 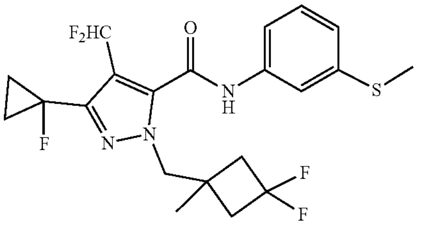 [SMILES: CSc1cccc(NC(=O)c2c(C(F)F)c(C3(F)CC3)nn2CC2(C)CC(F)(F)C2)c1] Ester: methyl 1-((3,3-difluoro-1-methylcyclobutyl)methyl)-4-(difluoromethyl)-3-(1-fluorocyclopropyl)-1H-pyrazole-5-carboxylate (Intermediate 282, after part 3) Amine: 3-(methylthio)aniline Yield: 250 mg, 63%; LCMS m/z = 460 $[M + H]^+$. |
| 326 | 3-(Bicyclo[1.1.1]pentan-1-yl)-1-(((1S,2S)-2-(difluoromethyl)cyclopropyl)methyl)-N-(3-(methylthio)phenyl)-4-(trifluoromethyl)-1H-pyrazole-5-carboxamide 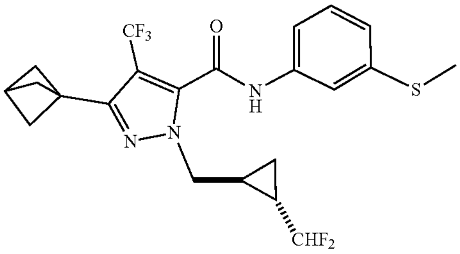 [SMILES: CSc1cccc(NC(=O)c2c(C(F)(F)F)c(C34CC(C3)C4)nn2C[C@H]2C[C@@H]2C(F)F)c1] Ester: methyl 3-(bicyclo[1.1.1]pentan-1-yl)-1-(((trans)-2-(difluoromethyl)cyclopropyl)methyl)-4-(trifluoromethyl)-1H-pyrazole-5-carboxylate (Intermediate 186) Amine: 3-(methylthio)aniline Yield: 80 mg, crude; LCMS m/z = 472 $[M + H]^+$. |

Intermediate 327a/327b

3-C propyl-1-((6,6-difluoro-4-methylspiro[2.3]hexan-4-yl)methyl)-N-(2-(methylthio)pyridin-4-yl)-4-(trifluoromethyl)-1H-pyrazole-5-carboxamide 327a

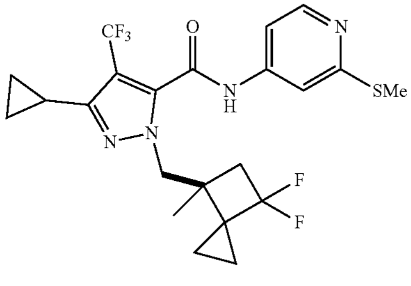

and

-continued

327b

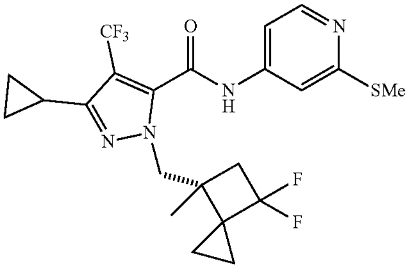

To a stirred solution of 3-cyclopropyl-1-({6,6-difluoro-4-methylspiro[2.3]hexan-4-yl}methyl)-4-(trifluoromethyl)-1H-pyrazole-5-carboxamide (Intermediate 272, 1.0 g) in 1,4-dioxane (30 mL) were added 4-iodo-2-(methylthio)pyridine (1.0 g) and $Cs_2CO_3$ (1.8 g) at rt. The reaction mixture was degassed with argon for 10 min. Then, Brettphos-Pd-G3 (0.3 g) was added and the mixture was heated to 110° C. for 16 h in a sealed tube. The reaction mixture was cooled to rt, filtered through a celite bed and the celite bed was washed with 10% MeOH in DCM. The filtrate was concentrated to get the crude product, which was purified by CombiFlash column chromatography ($SiO_2$, 0-50% EtOAc/Hex) followed by chiral SFC purification to yield the title compound.

Chiral-SFC (C-Amylose-A, 250×30 mm, 5 μm; 20% (0.1% $iPrNH_2$ in hexane/iPrOH 60/40) in $CO_2$)

Peak 1, Intermediate 327a (0.285 g, 21%). LCMS m/z=487 $[M+H]^+$; Chiral SFC: column: C-Amylose-A (4.6×250 mm) 5 hum, mobile phase: (0.1% $iPrNH_2$ in hexane/iPrOH 60/40), flow: 3 mL/min; % of co-solvent: 20%; ABPR: 1500 psi; T: 35° C.; $R_t$=3.14 min (first eluting).

Peak 2, Intermediate 327b (0.19 g, 19%). LCMS m/z=473 $[M+H]^+$; Chiral SFC: column: C-Amylose-A (4.6×250 mm) 5 hum, mobile phase: (0.1% $iPrNH_2$ in hexane/iPrOH 60/40), flow: 3 mL/min; % of co-solvent: 20%; ABPR: 1500 psi; T: 35° C.; $R_t$=3.71 min (second eluting)

Intermediate 328

The title compounds were prepared from the appropriate amide and aryliodide using an analogous method as described for Intermediate 327.

| Intermediate | Name/Structure/Starting Materials/Data |
|---|---|
| 328 | Tert-butyl 5-((3-cyclopropyl-5-((2-(methylthio)pyridin-4-yl)carbamoyl)-4-(trifluoromethyl)-1H-pyrazol-1-yl)methyl)-2-azaspiro[3.3]heptane-2-carboxylate<br>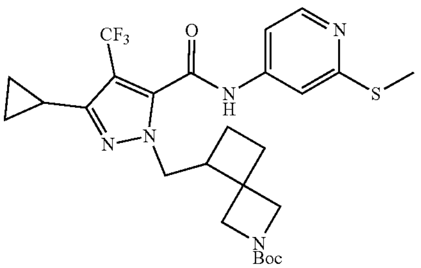 [SMILES: CSc1cc(NC(=O)c2c(C(F)(F)F)c(C3CC3)nn2CC2CCC23CN(C(=O)OC(C)(C)C)C3)ccn1]<br>Amide: tert-butyl 5-{[5-carbamoyl-3-cyclopropyl-4-(trifluoromethyl)-1H-pyrazol-1-yl]methyl}-2-azaspiro[3.3]heptane-2-carboxylate (Intermediate 275)<br>Aryliodide: 4-iodo-2-(methylthio)pyridine<br>Yield: 1.0 g, 97%; LCMS m/z = 552 $[M + H]^+$. |

Intermediate 329a/329b 1-((2-Acetyl-2-azaspiro[3.3]heptan-5-yl)methyl)-3-cyclopropyl-N-(2-(methylthio)pyridin-4-yl)-4-(trifluoromethyl)-1H-pyrazole-5-carboxamide 329a

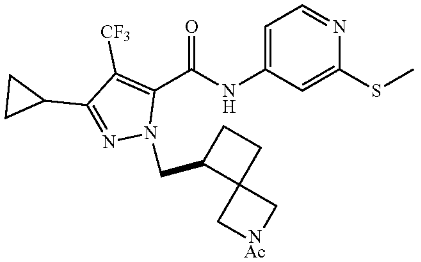

and

-continued

329b

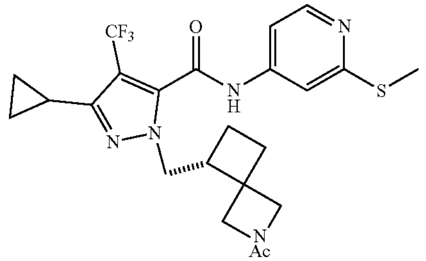

Part 1: To a stirred solution of tert-butyl 5-[(3-cyclopropyl-5-{[2-(methylsulfanyl)pyridin-4-yl]carbamoyl}-4-(trifluoromethyl)-1H-pyrazol-1-yl)methyl]-2-azaspiro[3.3]heptane-2-carboxylate (Intermediate 328, 0.8 g) in DCM (20 mL) was added 4M TFA in DCM (20 mL) at 0° C. The reaction mixture was stirred at rt for 2 h. The reaction mixture was concentrated under reduced pressure to get the crude mixture, which was basified with saturated $K_2CO_3$ solution and extracted with EtOAc (3×100 mL). The combined organic layers were washed with cold brine and dried over $Na_2SO_4$. The organic layer was concentrated under reduced pressure to get 1-({2-azaspiro[3.3]heptan-5-yl}methyl)-3-cyclopropyl-N-[2-(methylsulfanyl)pyridin-4-yl]-4-(trifluoromethyl)-1H-pyrazole-5-carboxamide (0.55 g, 84%). LCMS m/z=452 $[M+H]^+$.

Part 2: To a stirred solution of 1-({2-azaspiro[3.3]heptan-5-yl}methyl)-3-cyclopropyl-N-[2-(methylsulfanyl)pyridin-4-yl]-4-(trifluoromethyl)-1H-pyrazole-5-carboxamide (0.6 g) in DCM (25 mL) were added TEA (0.4 mL) and acetyl chloride (0.2 mL) at 0° C. The resulting mixture was stirred at rt for 16 h. The reaction mixture was diluted with ice water and extracted with EtOAc (3×50 mL). The combined organic layers were washed with brine, dried over $Na_2SO_4$ and concentrated to get the crude product, which was purified by CombiFlash column chromatography ($SiO_2$, 0-100% EtOAc/Hex) followed by chiral SFC purification to yield the title compound.

Chiral-SFC (Chiralpak IG, 250×30 mm, 5 μm; 30% iPrOH in $CO_2$)

Peak 1, Intermediate 329a (0.12 g, 18%). LCMS m/z=494 $[M+H]^+$; Chiral SFC: column: Chiralpak IG (4.6×250 mm)

5 hum, mobile phase: 0.5% $iPrNH_2$ in iPrOH, flow: 3 mL/min; % of co-solvent: 40%; ABPR: 1500 psi; T: 35° C.; $R_t$=1.81 min (first eluting).

Peak 2, Intermediate 329b (0.17 g, 25%). LCMS m/z=494 $[M+H]^+$; Chiral SFC: column: Chiralpak IG (4.6×250 mm) 5 hum, mobile phase: 0.5% $iPrNH_2$ in iPrOH, flow: 3 mL/min; % of co-solvent: 40%; ABPR: 1500 psi; T: 35° C.; $R_t$=2.04 min (second eluting)

Example 1a/1b

3-Cyclopropyl-1-((3,3-difluoro-1-methylcyclobutyl) methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (1a) and enantiomer 2 of 3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (1 b)

1a

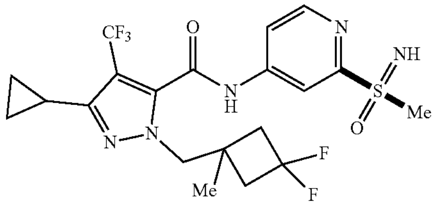

and

1b

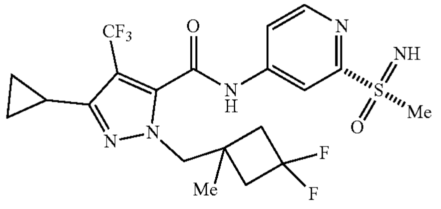

Part 1. To a stirred solution of 3-cyclopropyl-1-((3,3-difluoro-1-methylcyclobutyl)methyl)-N-(2-(methylthio) pyridin-4-yl)-4-(trifluoromethyl)-1H-pyrazole-5-carboxamide (Intermediate 79, 0.8 g) in MeOH (25 mL) were added diacetoxyiodobenzene (5.59 g) and ammonium carbonate (1.66 g) at rt and the mixture was stirred for 2 h. The reaction mixture was washed with water and extracted with EtOAc (3×100 mL). The combined organics were washed with cold brine, dried ($Na_2SO_4$) and evaporated to dryness under reduced pressure. The residue was purified by CombiFlash chromatography ($SiO_2$, 0-100% EtOAc/Hex) to afford (rac)-3-cyclopropyl-1-((3,3-difluoro-1-methylcyclobutyl) methyl)-N-(2-(S-methylsulfonimidoyl)pyridin-4-yl)-4-(trifluoromethyl)-1H-pyrazole-5-carboxamide.

Part 2. (rac)-3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (Part 1) was separated by chiral-HPLC (Chiralpak IC, 250×21 mm, 5 μm; 80/10/10 Hexane/DCM/EtOH) to afford:

Peak 1, Example 1a (0.16 g. 19%). LCMS m/z=492 $[M+H]^+$; $^1H$-NMR (400 MHz, DMSO-$d_6$): 11.73 (s, 1H), 8.66 (d, 1H), 8.36 (s, 1H), 7.79-7.77 (m, 1H), 4.42 (s, 1H), 4.17 (s, 2H), 3.15 (s, 3H), 2.78-2.67 (m, 2H), 2.33-2.24 (m, 2H), 1.96-1.93 (m, 1H), 1.05 (s, 3H), 1.00-0.96 (m, 2H), 0.86-0.82 (m, 2H). Chiral HPLC: column: Chiralpak IC (4.6×250 mm) 5 hum, mobile phase: hexane/DCM/EtOH/$iPrNH_2$ 60/20/20/0.1, flow rate: 1.0 mL/min, $R_t$=4.74 min (first eluting).

Peak 2, Example 1b (0.15 g, 17%). LCMS m/z=492 $[M+H]^+$; $^1H$-NMR (400 MHz, DMSO-$d_6$): 11.73 (s, 1H), 8.66 (d, 1H), 8.36 (s, 1H), 7.79-7.77 (m, 1H), 4.42 (s, 1H), 4.17 (s, 2H), 3.15 (s, 3H), 2.78-2.66 (m, 2H), 2.33-2.24 (m, 2H), 1.96-1.93 (m, 1H), 1.05 (s, 3H), 1.00-0.96 (m, 2H), 0.86-0.84 (m, 2H). Chiral HPLC: column: Chiralpak IC (4.6×250 mm) 5 hum, mobile phase: hexane/DCM/EtOH/$iPrNH_2$ 60/20/20/0.1, flow rate: 1.0 mL/min, $R_t$=5.47 min (second eluting).

Example 3-31, 46-48, 50, 64-65, 68-69, 71, 75, 78-80, 96, 92, 98, 103, 111, 113, 126-127, 130-141

The title compounds were prepared from the appropriate methylthioaryl (ArSMe) or alkylthioaryl (ArSalkyl) using an analogous method (at a suitable reaction time between 0.5-16 hours and a suitable reaction temperature between 0° C. to rt) to that described for Example 1 with or without chiral separation as Part 2.

| Example | Name/Structure/Starting Material/Data |
|---|---|
| 3 | 1-((3,3-Difluorocyclobutyl)methyl)-3-(1,1-difluoroethyl)-N-(2-(S-methylsulfonimidoyl)pyridin-4-yl)-4-(trifluoromethyl)-1H-pyrazole-5-carboxamide<br>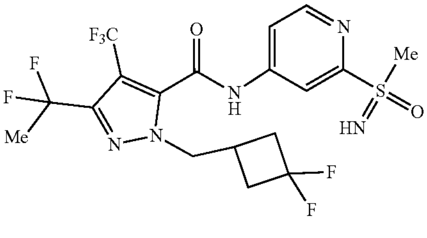 [SMILES: CC(F)(F)c1nn(CC2CC(F)(F)C2)c(C(=O)Nc2ccnc(S(C)(=N)=O)c2)c1C(F)(F)F]<br>ArSMe: 1-((3,3-difluorocyclobutyl)methyl)-3-(1,1-difluoroethyl)-N-(2-(methylthio)pyridin-4-yl)-4-(trifluoromethyl)-1H-pyrazole-5-carboxamide (Intermediate 80).<br>Prep-HPLC (YMC Actus C18, 250 x 20 mm, 5 μm; 30-70% $MeCN/H_2O$ (20 mM $NH_4HCO_3$)) Yield (27 mg, 42%); LCMS m/z = 502 $[M + H]^+$; $^1H$-NMR (400 MHz, DMSO-$d_6$): 11.91 (brs, 1H), 8.69 (d, 1H), 8.37 (s, 1H), 7.78 (d, 1H), 4.43 (brs, 1H), 4.38 (d, 2H), 3.16 (s, 3H), 2.66 (brs, 3H), 2.50-2.42 (m, 2H), 2.08 (t, 3H). |

-continued

| Example | Name/Structure/Starting Material/Data |
|---|---|
| 4 | 1-((3,3-Difluorocyclopentyl)methyl)-3-(1,1-difluoroethyl)-4-methyl-N-(2-(S-methylsulfonimidoyl)pyridin-4-yl)-1H-pyrazole-5-carboxamide 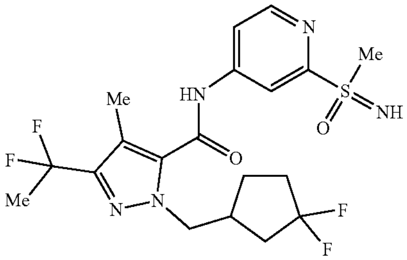 [SMILES: Cc1c(C(C)(F)F)nn(CC2CCC(F)(F)C2)c1C(=O)Nc1ccnc(S(C)(=N)=O)c1] ArSMe: 1-((3,3-difluorocyclopentyl)methyl)-3-(1,1-difluoroethyl)-4-methyl-N-(2-(methylthio)pyridin-4-yl)-1H-pyrazole-5-carboxamide (Intermediate 81). Prep-HPLC (YMC Actus C18, 250 x 20 mm, 5 µm; 30-80% $MeCN/H_2O$ (20 mM $NH_4HCO_3$)) Yield (24 mg, 37%); LCMS m/z = 462 $[M + H]^+$; $^1$H-NMR (400 MHz, DMSO-$d_6$): 11.24 (brs, 1H), 8.64 (d, 1H), 8.44 (s, 1H), 7.82 (t, 1H), 4.37 (s, 1H), 4.27 (d, 2H), 3.15 (s, 3H), 2.63-2.59 (m, 1H), 2.23 (s, 3H), 2.16-1.98 (m, 6H), 1.93-1.87 (m, 1H), 1.81-1.77 (m, 1H), 1.54-1.49 (m, 1H). |
| 5a/5b | 1-((3,3-Difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide, synthesized in the form of enantiomer 1 of 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide (5a) and enantiomer 2 of 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide (5b) 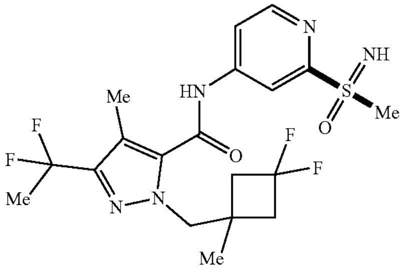 5a and 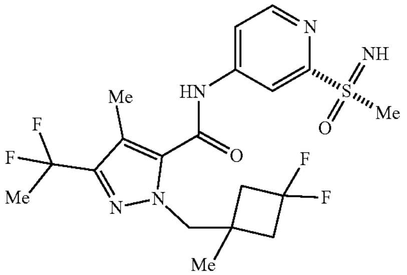 5b ArSMe: 1-((3,3-difluoro-1-methylcyclobutyl)methyl)-3-(1,1-difluoroethyl)-4-methyl-N-(2-(methylthio)pyridin-4-yl)-1H-pyrazole-5-carboxamide (Intermediate 84) Chiral-HPLC (Chiralpak IC 250 x 20 mm, 5 µm; 70% Hex/15% EtOAc/15% EtOH/0.1% $iPrNH_2$) Peak 1, Example 5a (105 mg, 32%). LCMS m/z = 462 $[M + H]^+$; $^1$H-NMR (400 MHz, DMSO-$d_6$): 11.28 (s, 1H), 8.64 (d, 1H), 8.42 (s, 1H), 7.84 (d, 1H), 4.36 (s, 3H), 3.15 (s, 3H), 2.73-2.66 (m, 2H), 2.30-2.24 (m, 5H), 2.08-1.98 (m, 3H), 1.07 (s, 3H). Chiral HPLC: column: Chiralpak IC (4.6 x 250 mm) 5 µm, mobile phase: hexane/EtOAc/EtOH/$iPrNH_2$ 70/15/15/0.1, flow rate: 1.0 mL/min, $R_t$ = 5.69 min (first eluting). Peak 2, Example 5b (75 mg, 23%). LCMS m/z = 462 $[M + H]^+$; $^1$H-NMR (400 MHz, DMSO-$d_6$): 11.27 (s, 1H), 8.64 (d, 1H), 8.42 (s, 1H), 7.84 (d, 1H), 4.36 (s, 2H), 3.15 (s, 3H), 2.76-2.66 (m, 2H), 2.30-2.24 (m, 5H), 2.08-1.98 (m, 3H), 1.07 (s, 3H). Chiral HPLC: column: Chiralpak IC (4.6 x 250 mm) 5 um, mobile phase: hexane/EtOAc/EtOH/$iPrNH_2$ 70/15/15/0.1, flow rate: 1.0 mL/min, $R_t$ = 6.76 min (second eluting). |
| 7a/7b | 3-Cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide, synthesized in form of diastereomeric pair |

-continued

| Example | Name/Structure/Starting Material/Data |
|---|---|
| | 1 of 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide (7a) and diastereomeric pair 2 of 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide (7b)<br>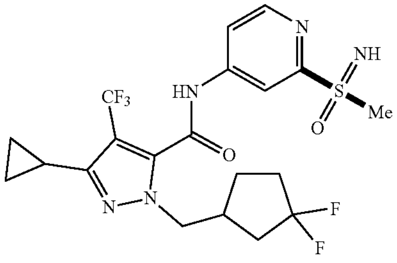<br>7a<br>and<br>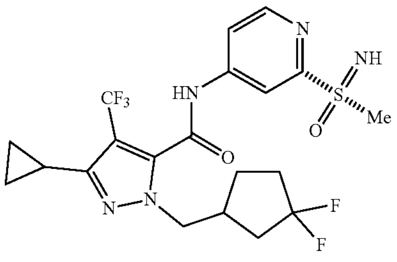<br>7b<br>ArSMe: 3-cyclopropyl-1-((3,3-difluorocyclopentyl)methyl)-N-(2-(methylthio)pyridin-4-yl)-4-(trifluoromethyl)-1H-pyrazole-5-carboxamide (Intermediate 85).<br>Chiral-HPLC (Reflect-I Cellulose-C 250 x 21.1 mm, 5 μm; 20-95% $MeCN/H_2O$ (10 mM $NH_4OAc$))<br>Peak 1, Example 7a (50 mg, 31%). LCMS m/z = 492 $[M + H]^+$; $^1H$-NMR (400 MHz, DMSO-$d_6$): 10.96 (s, 1H), 8.64-8.62 (m, 1H), 8.35 (s, 1H), 7.75-7.74 (m, 1H), 4.39 (s, 1H), 4.11-4.09 (d, 2H), 3.14 (s, 3H), 2.66-2.53 (m, 1H), 2.16-2.00 (m, 3H), 1.98-1.86 (m, 2H), 1.81-1.73 (m, 1H), 1.54-1.47 (m, 1H), 0.98-0.84 (m, 4H). Chiral HPLC: column: Reflect-I Cellulose-C (4.6 x 250 mm) 5 μm, mobile phase: A: MeCN, B: 0.05% TFA in water, A/B 10/90 for 0.01 min, 20/80 for 1.5 min, 35/65 for 6.5 min, 85/15 for 22 min, 95/5 for 23 min to 25 min, flow rate: 0.8 mL/min, $R_t$ = 11.06 min (first eluting).<br>Peak 2, Example 7b (40 mg, 25%). LCMS m/z = 492 $[M + H]^+$; $^1H$-NMR (400 MHz, DMSO-$d_6$): 11.71 (s, 1H), 8.65-8.63 (m, 1H), 8.36 (s, 1H), 7.76-7.74 (m, 1H), 4.40 (s, 1H), 4.11-4.09 (d, 2H), 3.15 (s, 3H), 2.66-2.53 (m, 1H), 2.16-2.00 (m, 3H), 1.98-1.86 (m, 2H), 1.81-1.73 (m, 1H), 1.52-1.47 (m, 1H), 0.98-0.84 (m, 4H). Chiral HPLC: column: Reflect-I Cellulose-C (4.6 x 250 mm) 3 μm, mobile phase: A: MeCN, B: 0.05% TFA in water, A/B 10/90 for 0.01 min, 20/80 for 1.5 min, 35/65 for 6.5 min, 85/15 for 22 min, 95/5 for 23 min to 25 min, flow rate: 0.8 mL/min, $R_t$ = 11.56 min (second eluting). |
| 9a/9b | 1-((4,4-Difluorocyclohexyl)methyl)-3-(1,1-difluoroethyl)-4-methyl-N-(2-(S-methylsulfonimidoyl)pyridin-4-yl)-1H-pyrazole-5-carboxamide, synthesized in the form of enantiomer 1 of 1-((4,4-difluorocyclohexyl)methyl)-3-(1,1-difluoroethyl)-4-methyl-N-(2-(S-methylsulfonimidoyl)pyridin-4-yl)-1H-pyrazole-5-carboxamide (9a) and enantiomer 2 of 1-((4,4-difluorocyclohexyl)methyl)-3-(1,1-difluoroethyl)-4-methyl-N-(2-(S-methylsulfonimidoyl)pyridin-4-yl)-1H-pyrazole-5-carboxamide (9b)<br>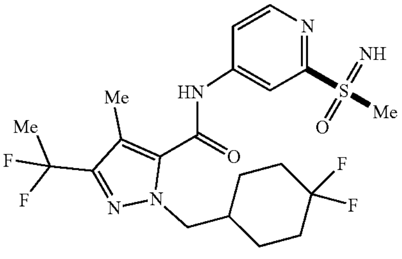<br>9a<br>and |

-continued

| Example | Name/Structure/Starting Material/Data |
|---|---|
| | 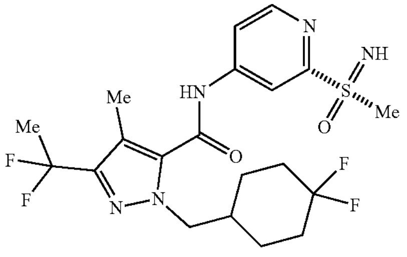<br>9b<br>ArSMe: 1-((4,4-difluorocyclohexyl)methyl)-3-(1,1-difluoroethyl)-4-methyl-N-(2-(methylthio)pyridin-4-yl)-1H-pyrazole-5-carboxamide (Intermediate 86)<br>Chiral-HPLC (Chiralpak IC 250 × 21 mm, 5 μm; 80/10/10 Hex/EtOAc/EtOH)<br>Peak 1, Example 9a (34 mg, 21%). LCMS m/z = 476 $[M + H]^+$; $^1$H-NMR (400 MHz, DMSO-$d_6$): 11.24 (s, 1H), 8.64 (d, 1H), 8.44 (s, 1H), 7.83-7.81 (m, 1H), 4.38 (s, 1H), 4.20-4.18 (m, 2H), 3.15 (s, 3H), 2.23 (s, 3H), 2.07-1.98 (m, 6H), 1.83-1.71 (m, 2H), 1.59-1.56 (m, 2H), 1.25-1.16 (m, 2H). Chiral HPLC: column: Chiralpak IC (4.6 × 250 mm) 5 μm, mobile phase: hexane/EtOAc/EtOH/iPrNH$_2$ 70/15/15/0.1, flow rate: 1.0 mL/min, $R_t$ = 5.81 min (first eluting).<br>Peak 2, Example 9b (29 mg, 18%). LCMS m/z = 476 $[M + H]^+$; $^1$H-NMR (400 MHz, DMSO-$d_6$): 11.24 (s, 1H), 8.64 (d, 1H), 8.44 (s, 1H), 7.83-7.81 (m, 1H), 4.38 (s, 1H), 4.19-4.18 (m, 2H), 3.15 (s, 3H), 2.23 (s, 3H), 2.07-1.96 (m, 6H), 1.83-1.68 (m, 2H), 1.59-1.56 (m, 2H), 1.25-1.15 (m, 2H). Chiral HPLC: column: Chiralpak IC (4.6 x 250 mm) 5 μm, mobile phase: hexane/EtOAc/EtOH/iPrNH$_2$ 70/15/15/0.1, flow rate: 1.0 mL/min, $R_t$ = 6.92 min (second eluting). |
| 11a/11b | 1-((4,4-Difluoro-1-methylcyclohexyl)methyl)-3-(1,1-difluoroethyl)-4-methyl-N-(2-(S-methylsulfonimidoyl)pyridin-4-yl)-1H-pyrazole-5-carboxamide, synthesized in the form of enantiomer 1 of 1-((4,4-difluoro-1-methylcyclohexyl)methyl)-3-(1,1-difluoroethyl)-4-methyl-N-(2-(S-methylsulfonimidoyl)pyridin-4-yl)-1H-pyrazole-5-carboxamide (11a) and enantiomer 2 of 1-((4,4-difluoro-1-methylcyclohexyl)methyl)-3-(1,1-difluoroethyl)-4-methyl-N-(2-(S-methylsulfonimidoyl)pyridin-4-yl)-1H-pyrazole-5-carboxamide (11b)<br>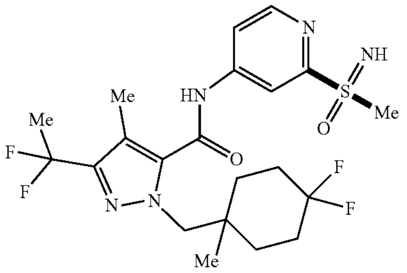<br>11a<br>and<br>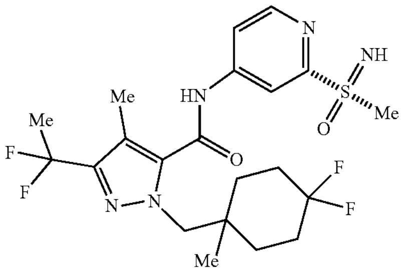<br>11b<br>ArSMe: 1-((4,4-difluoro-1-methylcyclohexyl)methyl)-3-(1,1-difluoroethyl)-4-methyl-N-(2-(methylthio)pyridin-4-yl)-1H-pyrazole-5-carboxamide (Intermediate 87)<br>Chiral-SFC (Chiralcelox-H, 250 × 21 mm, 5 mm; 20% MeOH in CO$_2$)<br>Peak 1, Example 11a (19 mg, 17%). LCMS m/z = 490 $[M + H]^+$; $^1$H-NMR (400 MHz, DMSO-$d_6$): 11.29 (s, 1H), 8.64 (d, 1H), 8.42 (s, 1H), 7.84-7.82 (m, 1H), 4.40 (s, 1H), 4.26 (s, 2H), 3.15 (s, 3H), 2.24 (s, 3H), 2.07-1.85 (m, 7H), 1.49-1.33 (m, 4H), 0.84 (s, 3H). Chiral SFC: column: Chiracel OX-H (4.6 × 150 mm) 3 μm; co-solvent: 0.3% iPrNH$_2$ in MeOH, flow: 3 mL/min; % of co-solvent: 35%; ABPR: 100 bar T: 35° C.; $R_t$ = 3.40 min (first eluting).<br>Peak 2, Example 11b (16 mg, 14%). LCMS m/z = 490 $[M + H]^+$; $^1$H-NMR (400 MHz, DMSO- |

-continued

| Example | Name/Structure/Starting Material/Data |
|---|---|
| | d6): 11.28 (s, 1H), 8.64 (d, 1H), 8.41 (s, 1H), 7.84-7.82 (m, 1H), 4.38 (s, 1H), 4.26 (s, 2H), 3.15 (s, 3H), 2.24 (s, 3H), 2.07-1.94 (m, 7H), 1.47-1.34 (m, 4H), 0.84 (s, 3H). Chiral SFC: column: Chiracel OX-H (4.6 x 150 mm) 3 μm; co-solvent : 0.3% $iPrNH_2$ in MeOH, flow: 3 mL/min; % of co-solvent: 35%; ABPR: 100 bar T: 35° C.; $R_t$ = 3.77 min (second eluting). |
| 15a/15b | 3-(1,1-Difluoroethyl)-4-methyl-N-(2-(S-methylsulfonimidoyl)pyridin-4-yl)-1-((3-(trifluoromethyl)bicyclo[1.1.1]pentan-1-yl)methyl)-1H-pyrazole-5-carboxamide, synthesized in the form of enantiomer 1 of 3-(1,1-difluoroethyl)-4-methyl-N-(2-(S-methylsulfonimidoyl)pyridin-4-yl)-1-((3-(trifluoromethyl)bicyclo[1.1.1]pentan-1-yl)methyl)-1H-pyrazole-5-carboxamide (15a) and enantiomer 2 of 3-(1,1-difluoroethyl)-4-methyl-N-(2-(S-methylsulfonimidoyl)pyridin-4-yl)-1-((3-(trifluoromethyl)bicyclo[1.1.1]pentan-1-yl)methyl)-1H-pyrazole-5-carboxamide (15b)<br>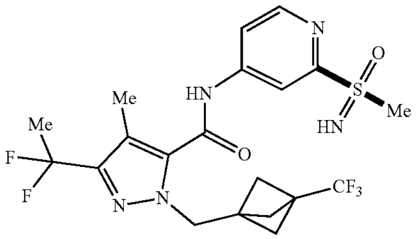<br>15a<br>and<br>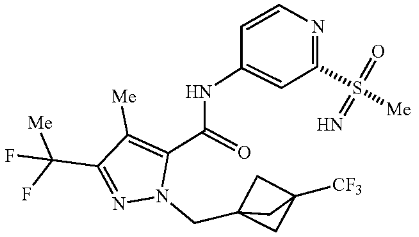<br>15b<br>ArSMe: 3-(1,1-difluoroethyl)-4-methyl-N-(2-(methylthio)pyridin-4-yl)-1-((3-(trifluoromethyl)bicyclo[1.1.1]pentan-1-yl)methyl)-1H-pyrazole-5-carboxamide (Intermediate 88)<br>Chiral-HPLC (Chiralpak IC, 250 x 21 mm, 5 μm; 80/10/10 Hex/EtOAc/EtOH)<br>Peak 1, Example 15a (34 mg, 26%). LCMS m/z = 492 $[M + H]^+$; $^1$H-NMR (400 MHz, DMSO-$d_6$): 11.17 (s, 1H), 8.65-8.63 (m, 1H), 8.43-8.42 (m, 1H), 7.84-7.83 (m, 1H), 4.48 (s, 2H), 4.39 (s, 1H), 3.15 (s, 3H), 2.25 (s, 3H), 2.08-1.98 (t, 3H), 1.83 (s, 6H). Chiral HPLC: column: Chiralpak IC (4.6 x 250 mm) 5 μm, mobile phase: hexane/DCM/EtOH/$iPrNH_2$ 70/15/15/0.1, flow rate: 1.0 mL/min, $R_t$ = 5.58 min (first eluting).<br>Peak 2, Example 15b (32 mg, 25%). LCMS m/z = 492 $[M + H]^+$; $^1$H-NMR (400 MHz, DMSO-$d_6$): 11.17 (s, 1H), 8.65-8.63 (m, 1H), 8.43-8.42 (m, 1H), 7.85-7.83 (m, 1H), 4.48 (s, 2H), 4.39 (s, 1H), 3.15 (s, 3H), 2.25 (s, 3H), 2.08-1.98 (t, 3H), 1.83 (s, 6H). Chiral HPLC: column: Chiralpak IC (4.6 x 250 mm) 5 μm, mobile phase: hexane/DCM/EtOH/$iPrNH_2$ 70/15/15/0.1, flow rate: 1.0 mL/min, $R_t$ = 6.63 min (second eluting). |
| 17a/17b | 3-Cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide (17a) and diastereomer 2 of 3-cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide (17b)<br>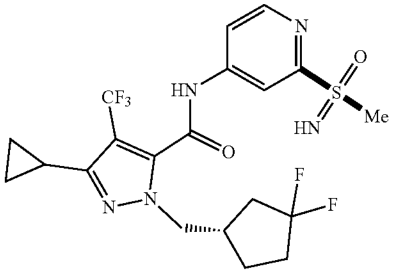<br>17a<br>and |

-continued

| Example | Name/Structure/Starting Material/Data |
|---|---|
| | 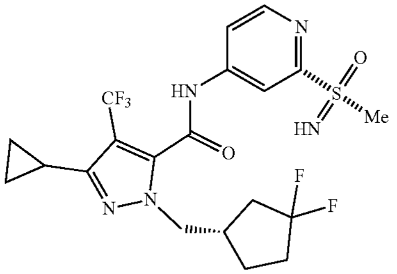<br>17b<br>ArSMe: (S)-3-cyclopropyl-1-((3,3-difluorocyclopentyl)methyl)-N-(2-(methylthio)pyridin-4-yl)-4-(trifluoromethyl)-1H-pyrazole-5-carboxamide (Intermediate 91).<br>Chiral HPLC (Chiralpak IC, 250 × 20 mm, 5 μm; 80/10/10 Hex/EtOAc/EtOH + 0.1% $iPrNH_2$)<br>Peak 1, Example 17a (26 mg, 20%). LCMS m/z = 492 $[M + H]^+$; $^1$H-NMR (400 MHz, DMSO-$d_6$): 11.73 (s, 1H), 8.66-8.65 (m, 1H), 8.37 (s, 1H), 7.78-7.77 (m, 1H), 4.40 (s, 1H), 4.11-4.10 (m, 2H), 3.15 (s, 3H), 2.60-2.50 (m, 1H), 2.13-2.01 (m, 3H), 1.99-1.86 (m, 2H), 1.82-1.77 (m, 1H), 1.52-1.47 (m, 1H), 0.98-0.85 (m, 4H). Chiral HPLC: column: Chiralpak IC (4.6 x 250 mm) 5 μm, mobile phase: hexane/DCM/EtOH/$iPrNH_2$ 60/20/20/0.1, flow rate: 1.0 mL/min $R_t$ = 4.83 min (first eluting).<br>Peak 2, Example 17b (31 mg, 24%). LCMS m/z = 492 $[M + H]^+$; $^1$H-NMR (400 MHz, DMSO-$d_6$): 11.73 (s, 1H), 8.67-8.65 (m, 1H), 8.38 (s, 1H), 7.78-7.76 (m, 1H), 4.42 (s, 1H), 4.11-4.09 (m, 2H), 3.15 (s, 3H), 2.59-2.50 (m, 1H), 2.14-2.03 (m, 3H), 1.96-1.88 (m, 2H), 1.82-1.76 (m, 1H), 1.52-1.47 (m, 1H), 0.98-0.84 (m, 4H). Chiral HPLC: column: Chiralpak IC (4.6 x 250 mm) 5 μm, mobile phase: hexane/DCM/EtOH/$iPrNH_2$ 60/20/20/0.1, flow rate: 1.0 mL/min $R_t$ = 5.64 min (second eluting). |
| 17c/17d | 3-Cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide, synthesized in the form of diastereomer 3 of 3-cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide (17c) and diastereomer 4 of 3-cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide (17d)<br>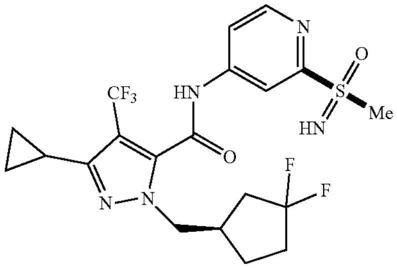<br>17c<br>and<br>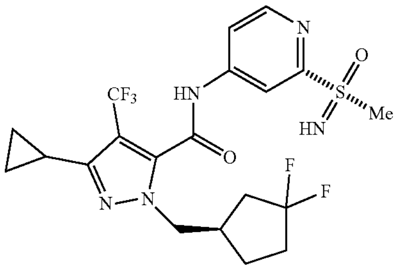<br>17d<br>ArSMe: (R)-3-cyclopropyl-1-((3,3-difluorocyclopentyl)methyl)-N-(2-(methylthio)pyridin-4-yl)-4-(trifluoromethyl)-1H-pyrazole-5-carboxamide (Intermediate 92).<br>Chiral HPLC (Chiralpak IC, 250 × 20 mm, 5 μm; 80/10/10 Hex/EtOAc/EtOH + 0.1% $iPrNH_2$)<br>Peak 1, Example 17c (40 mg, 15%). LCMS m/z = 492 $[M + H]^+$; $^1$H-NMR (400 MHz, DMSO-$d_6$): 11.73 (s, 1H), 8.67-8.65 (m, 1H), 8.38 (s, 1H), 7.78-7.76 (m, 1H), 4.42 (s, 1H), 4.11-4.09 (m, 2H), 3.15 (s, 3H), 2.61-2.57 (m, 2H), 2.14-2.07 (m, 3H), 1.96-1.90 (m, 2H), 1.79-1.77 (m, 1H), 1.52-1.47 (m, 1H), 1.00-0.85 (m, 4H). Chiral HPLC: column: Chiralpak IC (4.6 x 250 mm) |

-continued

| Example | Name/Structure/Starting Material/Data |
|---|---|
| | 5 μm, mobile phase: hexane/DCM/EtOH/iPrNH$_2$ 60/20/20/0.1, flow rate: 1.0 mL/min, $R_t$ = 4.82 min (first eluting). Peak 2, Example 17d (38 mg, 14%). LCMS m/z = 492 $[M + H]^+$; $^1$H-NMR (400 MHz, DMSO-$d_6$): 11.73 (s, 1H), 8.67-8.65 (m, 1H), 8.38-8.37 (m, 1H), 7.78-7.76 (m, 1H), 4.42 (s, 1H), 4.11-4.09 (m, 2H), 3.15 (s, 3H), 2.59-2.49 (m, 1H), 2.13-2.11 (m, 3H), 1.94-1.92 (m, 2H), 1.84-1.75 (m, 1H), 1.52-1.49 (m, 1H), 0.99-0.83 (m, 4H). Chiral HPLC: column: Chiralpak IC (4.6 x 250 mm) 5 μm, mobile phase: hexane/DCM/EtOH/iPrNH$_2$ 60/20/20/0.1, flow rate: 1.0 mL/min, $R_t$ = 5.58 min (second eluting). |
| 21a/21b | 3-Cyclopropyl-1-((2-fluorospiro[3.3]heptan-2-yl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((2-fluorospiro[3.3]heptan-2-yl)methyl)-N-(2-(S-methylsulfonimidoyl)pyridin-4-yl)-4-(trifluoromethyl)-1H-pyrazole-5-carboxamide (21a) and enantiomer 2 of 3-cyclopropyl-1-((2-fluorospiro[3.3]heptan-2-yl)methyl)-N-(2-(S-methylsulfonimidoyl)pyridin-4-yl)-4-(trifluoromethyl)-1H-pyrazole-5-carboxamide (21b) 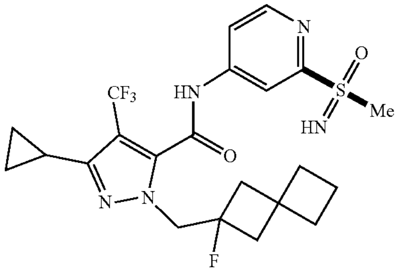 21a and 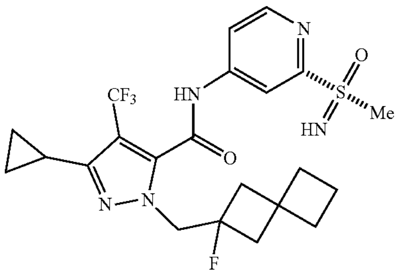 21b ArSMe: 3-cyclopropyl-1-((2-fluorospiro[3.3]heptan-2-yl)methyl)-N-(2-(methylthio)pyridin-4-yl)-4-(trifluoromethyl)-1H-pyrazole-5-carboxamide (Intermediate 93). Chiral SFC (Chiralpak IC, 250 x 20 mm, 5 μm; 30% (iPrOH + 0.5% iPrNH$_2$) in CO$_2$) Peak 1, Example 21a (21 mg, 23%). LCMS m/z = 500 $[M + H]^+$; $^1$H-NMR (400 MHz, DMSO-$d_6$): 11.70 (s, 1H), 8.64-8.63 (m, 1H), 8.37 (s, 1H), 7.76-7.75 (m, 1H), 4.39-4.32 (m,3H), 3.14 (s, 3H), 2.43-2.37 (m, 2H), 2.17-2.07 (m, 2H), 2.01-1.96 (m, 5H), 1.81-1.73 (m, 2H), 1.00-0.87 (m, 4H). Chiral HPLC: column: Chiralpak IC (4.6 x 250 mm) 5 μm, mobile phase: hexane/DCM/EtOH/iPrNH$_2$ 60/20/20/0.1, flow rate: 1.0 mL/min, $R_t$ = 4.37 min (first eluting). Peak 2, Example 21b (24 mg, 26%). LCMS m/z = 500 $[M + H]^+$; $^1$H-NMR (400 MHz, DMSO-$d_6$): 11.70 (s, 1H), 8.59 (bs, 1H), 8.33 (s, 1H), 7.72 (s, 1H), 4.40-4.34 (m,3H), 3.13 (s, 3H), 2.43-2.37 (m, 2H), 2.17-2.07 (m, 2H), 1.99-1.95 (m, 5H), 1.79-1.74 (m, 2H), 0.98-0.85 (m, 4H). Chiral HPLC: column: Chiralpak IC (4.6 x 250 mm) 5 μm, mobile phase: hexane/DCM/EtOH/iPrNH$_2$ 60/20/20/0.1, flow rate: 1.0 mL/min, $R_t$ = 4.93 min (second eluting). |
| 23a/23b | 3-Cyclopropyl-N-(2-(S-methylsulfonimidoyl)pyridin-4-yl)-4-(trifluoromethyl)-1-((3-(trifluoromethyl)bicyclo[1.1.1]pentan-1-yl)methyl)-1H-pyrazole-5-carboxamide, synthesized in the form of enantiomer 1 of 3-cyclopropyl-N-(2-(S-methylsulfonimidoyl)pyridin-4-yl)-4-(trifluoromethyl)-1-((3-(trifluoromethyl)bicyclo[1.1.1]pentan-1-yl)methyl)-1H-pyrazole-5-carboxamide (23a) and enantiomer 2 of 3-cyclopropyl-N-(2-(S-methylsulfonimidoyl)pyridin-4-yl)-4-(trifluoromethyl)-1-((3-(trifluoromethyl)bicyclo[1.1.1]pentan-1-yl)methyl)-1H-pyrazole-5-carboxamide (23b) |

-continued

| Example | Name/Structure/Starting Material/Data |
|---|---|
| | 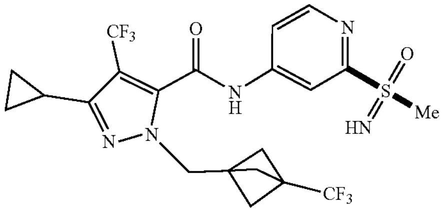 23a and 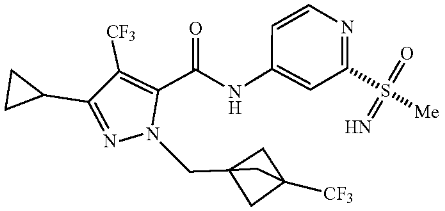 23b ArSMe: 3-cyclopropyl-N-(2-(methylthio)pyridin-4-yl)-4-(trifluoromethyl)-1-((3-(trifluoromethyl)bicyclo[1.1.1]pentan-1-yl)methyl)-1H-pyrazole-5-carboxamide (Intermediate 94). Chiral HPLC (Chiralart Cellulose SC, 250 x 20 mm, 5 μm; 80/10/10 Hex/DCM/EtOH) Peak 1, Example 23a (82 mg, 25%). LCMS m/z = 522 $[M + H]^+$; $^1$H-NMR (400 MHz, DMSO-$d_6$): 11.61 (s, 1H), 8.65-8.64 (m, 1H), 8.36 (s, 1H), 7.77-7.75 (m, 1H), 4.28-4.27 (m, 2H), 3.15 (s, 3H), 1.96-1.89 (m, 1H), 1.83 (s, 6H), 0.97-0.95 (m, 2H), 0.84-0.83 (m, 2H). Chiral HPLC: column: Chiralpak IC (4.6 x 250 mm) 5 μm, mobile phase: hexane/DCM/EtOH/iPrNH$_2$ 60/20/20/0.1, flow rate: 1.0 mL/min, $R_t$ = 4.37 min (first eluting). Peak 2, Example 23b (80 mg, 25%). LCMS m/z = 522 $[M + H]^+$; $^1$H-NMR (400 MHz, DMSO-$d_6$): 11.66 (s, 1H), 8.68-8.66 (m, 1H), 8.38 (s, 1H), 7.79-7.78 (m, 1H), 4.31-4.30 (m, 2H), 3.18 (s, 3H), 1.95-1.94 (m, 1H), 1.84 (s, 6H), 0.99-0.97 (m, 2H), 0.85-0.84 (m, 2H). Chiral HPLC: column: Chiralpak IC (4.6 x 250 mm) 5 μm, mobile phase: hexane/DCM/EtOH/iPrNH$_2$ 60/20/20/0.1, flow rate: 1.0 mL/min, $R_t$ = 4.93 min (second eluting). |
| 25a/25b | 3-Cyclopropyl-1-((3-fluorobicyclo[1.1.1]pentan-1-yl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((3-fluorobicyclo[1.1.1]pentan-1-yl)methyl)-N-(2-(S-methylsulfonimidoyl)pyridin-4-yl)-4-(trifluoromethyl)-1H-pyrazole-5-carboxamide (25a) and enantiomer 2 of 3-cyclopropyl-1-((3-fluorobicyclo[1.1.1]pentan-1-yl)methyl)-N-(2-(S-methylsulfonimidoyl)pyridin-4-yl)-4-(trifluoromethyl)-1H-pyrazole-5-carboxamide (25b) 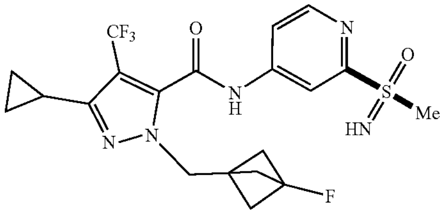 25a and 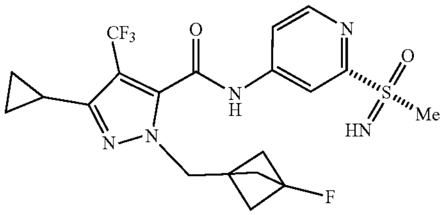 25b ArSMe: 3-cyclopropyl-1-((3-fluorobicyclo[1.1.1]pentan-1-yl)methyl)-N-(2-(methylthio)pyridin-4-yl)-4-(trifluoromethyl)-1H-pyrazole-5-carboxamide (Intermediate 95). |

-continued

| Example | Name/Structure/Starting Material/Data |
|---|---|
| | Chiral HPLC (Chiralart Cellulose SC, 250 x 20 mm, 5 μm; 80/20 Hex/EtOH)<br>Peak 1, Example 25a (28 mg, 13%). LCMS m/z = 472 $[M + H]^+$; $^1$H-NMR (400 MHz, DMSO-$d_6$): 11.63 (s, 1H), 8.67 (d, 1H), 8.36 (s, 1H), 7.79 (d, 1H), 4.44 (s, 3H), 3.15 (s, 3H), 2.22 (s, 1H), 1.93-1.92 (m, 6H), 1.00-0.96 (m, 2H), 0.85-0.84 (m, 2H). Chiral HPLC: column: Chiralpak IC (4.6 x 250 mm) 5 μm, mobile phase: hexane/DCM/EtOH/iPrN$H_2$60/20/20/0.1, flow rate: 1.0 mL/min, $R_t$ = 4.78 min (first eluting).<br>Peak 2, Example 25b (25 mg, 11%). LCMS m/z = 472 $[M + H]^+$; $^1$H-NMR (400 MHz, DMSO-$d_6$): 11.63 (s, 1H), 8.67 (d, 1H), 8.36 (s, 1H), 7.79 (d, 1H), 4.44 (s, 3H), 3.15 (s, 3H), 2.22 (s, 1H), 1.93-1.92 (m, 6H), 0.98-0.97 (m, 2H), 0.85-0.84 (m, 2H). Chiral HPLC: column: Chiralpak IC (4.6 x 250 mm) 5 μm, mobile phase: hexane/DCM/EtOH/iPrN$H_2$60/20/20/0.1, flow rate: 1.0 mL/min, $R_t$ = 5.68 min (second eluting). |
| 27a/27b | 3-Cyclopropyl-1-((6,6-difluorospiro[3.3]heptan-2-yl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((6,6-difluorospiro[3.3]heptan-2-yl)methyl)-N-(2-(S-methylsulfonimidoyl)pyridin-4-yl)-4-(trifluoromethyl)-1H-pyrazole-5-carboxamide (27a) and enantiomer 2 of 3-cyclopropyl-1-((6,6-difluorospiro[3.3]heptan-2-yl)methyl)-N-(2-(S-methylsulfonimidoyl)pyridin-4-yl)-4-(trifluoromethyl)-1H-pyrazole-5-carboxamide (27b)<br>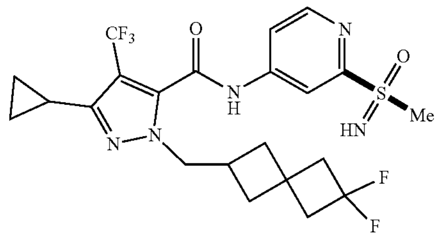<br>27a<br>and<br>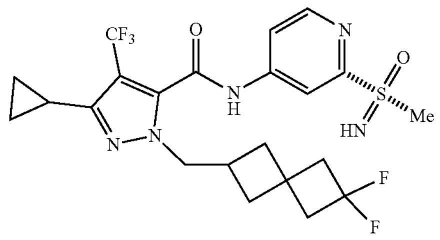<br>27b<br>ArSMe: 3-cyclopropyl-1-((6,6-difluorospiro[3.3]heptan-2-yl)methyl)-N-(2-(methylthio)pyridin-4-yl)-4-(trifluoromethyl)-1H-pyrazole-5-carboxamide (Intermediate 96).<br>Chiral HPLC (Chiralart Cellulose SC, 250 x 20 mm, 5 μm; 80/20 Hex/EtOH)<br>Peak 1, Example 27a (40 mg, 31%). LCMS m/z = 518 $[M + H]^+$; $^1$H-NMR (400 MHz, DMSO-$d_6$): 11.72 (s, 1H), 8.67 (d, 1H), 8.38 (s, 1H), 7.78 (d, 1H), 4.41 (s, 1H), 4.08 (d, 1H), 3.15 (s, 3H), 2.60-2.55 (m, 3H), 2.50-2.47 (m, 2H), 2.11-2.08 (m, 2H), 1.95-1.89 (m, 3H), 0.98-0.96 (m, 2H), 0.95-0.83 (m, 2H). Chiral HPLC: column: Chiralart Cellulose SC (4.6 x 250 mm) 5 μm, mobile phase: hexane/EtOH/iPrN$H_2$ 70/30/0.1, flow rate: 1.0 mL/min, $R_t$ = 6.29 min (first eluting).<br>Peak 2, Example 27b (43 mg, 33%). LCMS m/z = 518 $[M + H]^+$; $^1$H-NMR (400 MHz, DMSO-$d_6$): 11.72 (s, 1H), 8.67 (d, 1H), 8.38 (s, 1H), 7.78 (d, 1H), 4.40 (s, 1H), 4.09 (d, 1H), 3.15 (s, 3H), 2.60-2.50 (m, 3H), 2.45-2.42 (m, 2H), 2.11-2.08 (m, 2H), 1.95-1.90 (m, 3H), 0.97-0.95 ( m, 2H), 0.84-0.83 (m, 2H). Chiral HPLC: column: Chiralart Cellulose SC (4.6 x 250 mm) 5 μm, mobile phase: hexane/EtOH/iPrN$H_2$ 70/30/0.1, flow rate: 1.0 mL/min, $R_t$ = 7.40 min (second eluting). |
| 31a/31b | 3-(1,1-Difluoroethyl)-4-methyl-N-(2-(S-methylsulfonimidoyl)pyridin-4-yl)-1-(((cis)-3-(trifluoromethyl)cyclobutyl)methyl)-1H-pyrazole-5-carboxamide, synthesized in the form of enantiomer 1 of 3-(1,1-difluoroethyl)-4-methyl-N-(2-(S-methylsulfonimidoyl)pyridin-4-yl)-1-(((cis)-3-(trifluoromethyl)cyclobutyl)methyl)-1H-pyrazole-5-carboxamide (31a) and enantiomer 2 of 3-(1,1-difluoroethyl)-4-methyl-N-(2-(S-methylsulfonimidoyl)pyridin-4-yl)-1-(((cis)-3-(trifluoromethyl)cyclobutyl)methyl)-1H-pyrazole-5-carboxamide (31b) |

-continued

| Example | Name/Structure/Starting Material/Data |
|---|---|
| | 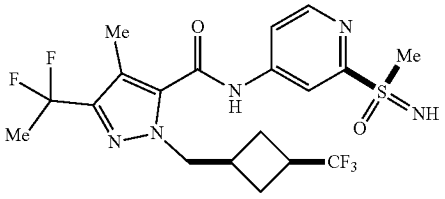 31a and 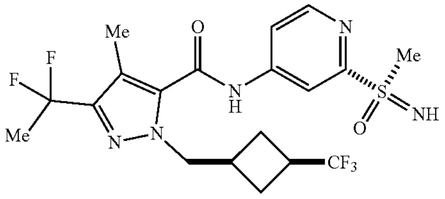 31b ArSMe: 3-(1,1-difluoroethyl)-4-methyl-N-(2-(methylthio)pyridin-4-yl)-1-(((cis)-3-(trifluoromethyl)cyclobutyl)methyl)-1H-pyrazole-5-carboxamide (Intermediate 89). Chiral-SFC ((R,R)-WHELK-01, 250 × 21.1 mm, 5 μm; 25% (0.5% $iPrNH_2$/MeOH) in $CO_2$) Peak 1, Example 31a (26 mg, 24%). LCMS m/z = 480 $[M + H]^+$; $^1$H-NMR (400 MHz, DMSO-$d_6$): 11.23 (s, 1H), 8.64-8.63 (m, 1H), 8.44-8.43 (m, 1H), 7.84-7.83 (m, 1H), 4.38 (s, 1H), 4.27-4.25 (m, 2H), 3.14 (s, 3H), 3.08-3.01 (m, 1H), 2.75-2.71 (m, 1H), 2.23 (s, 3H), 2.17-2.10 (m, 2H), 2.07-1.97 (m, 3H), 1.92-1.89 (m, 2H). Chiral SFC: column: I-Cellulose C (4.6 mm × 250 mm), 5 μm; co-solvent: 0.3% $iPrNH_2$ in MeOH, flow: 3 mL/min; % of co-solvent: 30%; ABPR: 100 bar T: 35° C.; $R_t$ = 1.42 min (first eluting). Peak 2, Example 31b (20 mg, 19%). LCMS m/z = 480 $[M + H]^+$; $^1$H-NMR (400 MHz, DMSO-$d_6$): 11.23 (s, 1H), 8.65-8.63 (m, 1H), 8.43 (s, 1H), 7.85-7.83 (m, 1H), 4.37 (s, 1H), 4.27-4.25 (m, 2H), 3.15 (s, 3H), 3.08-3.01 (m, 1H), 2.76-2.72 (m, 1H), 2.23 (s, 3H), 2.17-2.10 (m, 2H), 2.07-1.97 (m, 3H), 1.92-1.84 (m, 2H). Chiral SFC: column: I-Cellulose C (4.6 mm × 250 mm), 5 μm; co-solvent: 0.3% $iPrNH_2$ in MeOH, flow: 3 mL/min; % of co-solvent: 30%; ABPR: 100 bar T: 35° C.; $R_t$ = 1.43 min (second eluting). |
| 45a/45b | 3-Cyclopropyl-1-((3,3-difluoro-1-methylcyclobutyl)methyl)-N-(3-(S-methylsulfonimidoyl)phenyl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(3-(S-methylsulfonimidoyl)phenyl)-4-(trifluoromethyl)-1H-pyrazole-5-carboxamide (45a) and enantiomer 2 of 3-cyclopropyl-1-((3,3-difluoro-1-methylcyclobutyl)methyl)-N-(3-(S-methylsulfonimidoyl)phenyl)-4-(trifluoromethyl)-1H-pyrazole-5-carboxamide (45b) 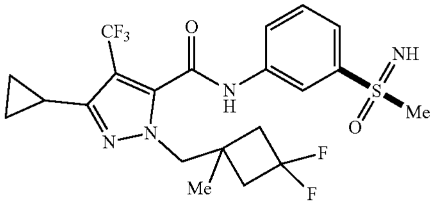 45a and 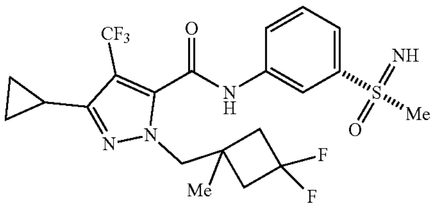 45b ArSMe: 3-cyclopropyl-1-[(3,3-difluoro-1-methylcyclobutyl)methyl]-N-[3-(methylsulfanyl)phenyl]-4-(trifluoromethyl)-1H-pyrazole-5-carboxamide (Intermediate 291). Chiral-SFC ((R,R)-WHELK-01, 250 × 21.1 mm, 5 μm; 25% (0.5% $iPrNH_2$ in iPrOH) in $CO_2$) |

-continued

| Example | Name/Structure/Starting Material/Data |
| --- | --- |
| | Peak 1, Example 45a (26 mg, 10%). LCMS m/z = 491 $[M + H]^+$; $^1$H-NMR (400 MHz, DMSO-$d_6$): 11.32 (s, 1H), 8.28 (s, 1H), 7.86 (d, 1H), 7.72 (d, 1H), 7.64-7.60 (m, 1H), 4.26-4.16 (m, 3H), 3.06 (s, 3H), 2.76-2.67 (m, 2H), 2.31-2.25 (m, 2H), 1.95-1.94 (m, 1H), 1.07 (m, 3H), 1.00-0.97 (m, 2H), 0.84-0.85 (m, 2H). Chiral SFC: column: ((R,R)-WHELK-01, 250 × 4.6 mm, 5 μm; co-solvent: 0.5% $iPrNH_2$ in iPrOH, flow: 3 mL/min; % of co-solvent: 25%; ABPR: 100 bar; T: 35° C.; $R_t$ = 4.01 min (first eluting). |
| | Peak 2, Example 45b (28 mg, 10%). LCMS m/z = 491 $[M + H]^+$; $^1$H-NMR (400 MHz, DMSO-$d_6$): 11.32 (s, 1H), 8.28 (s, 1H), 7.86 (d, 1H), 7.72 (d, 1H), 7.63-7.60 (m, 1H), 4.26-4.16 (m, 3H), 3.06 (s, 3H), 2.76-2.67 (m, 2H), 2.31-2.25 (m, 2H), 1.95-1.94 (m, 1H), 1.07 (m, 3H), 1.00-0.97 (m, 2H), 0.84-0.85 (m, 2H). Chiral SFC: column: ((R,R)-WHELK-01, 250 × 4.6 mm, 5 μm; co-solvent: 0.5% $iPrNH_2$ in iPrOH, flow: 3 mL/min; % of co-solvent: 25%; ABPR: 100 bar; T: 35° C.; $R_t$ = 4.62 min (second eluting). |
| 46a/46b | 3-Cyclopropyl-1-((3,3-difluoro-1-methylcyclobutyl)methyl)-N-(5-(S-methylsulfonimidoyl)pyridin-3-yl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(5-(S-methylsulfonimidoyl)pyridin-3-yl)-4-(trifluoromethyl)-1H-pyrazole-5-carboxamide (46a) and enantiomer 2 of 3-cyclopropyl-1-((3,3-difluoro-1-methylcyclobutyl)methyl)-N-(5-(S-methylsulfonimidoyl)pyridin-3-yl)-4-(trifluoromethyl)-1H-pyrazole-5-carboxamide (46b)<br>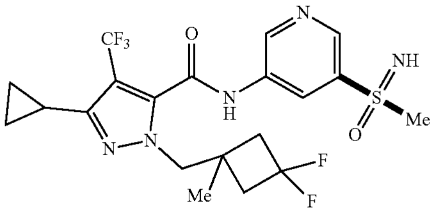<br>46a<br>and<br>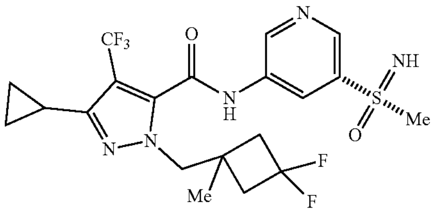<br>46b<br>ArSMe: 3-cyclopropyl-1-((3,3-difluoro-1-methylcyclobutyl)methyl)-N-(5-(methylthio)pyridin-3-yl)-4-(trifluoromethyl)-1H-pyrazole-5-carboxamide (Intermediate 318).<br>Chiral-SFC (Chiralpak IG; 250 × 30 mm, 5 μm; 30% (0.3% $iPrNH_2$ in hexane/MeOH/iPrOH 60/03/10) in $CO_2$)<br>Peak 1, Example 46a (67 mg, 21%). LCMS m/z = 492 $[M + H]^+$; $^1$H-NMR (400 MHz, DMSO-$d_6$): 11.56 (s, 1H), 8.94 (d, 1H), 8.84 (d, 1H), 8.61 (s, 1H), 4.56 (s, 1H), 4.16 (s, 2H), 3.15 (s, 3H), 2.77-2.64 (m, 2H), 2.32-2.22 (m, 2H), 1.93 (s, 1H), 1.04 (s, 3H), 0.98-0.94 (m, 2H), 0.82-0.81 (m, 2H); Chiral SFC: column: Chiralpak IG, 250 × 4.6 mm, 5 μm; co-solvent: 0.3% $iPrNH_2$ in hexane/MeOH/iPrOH 60/03/10; flow: 3 mL/min; % of co-solvent: 20%; ABPR: 100 bar; T: 35° C.; $R_t$ = 4.50 min (first eluting).<br>Peak 2, Example 46b (65 mg, 19%). LCMS m/z = 492 $[M + H]^+$; $^1$H-NMR (400 MHz, DMSO-$d_6$): 11.56 (s, 1H), 8.97 (d, 1H), 8.86 (d, 1H), 8.64 (s, 1H), 4.59 (s, 1H), 4.19 (s, 2H), 3.18 (s, 3H), 2.79-2.67 (m, 2H), 2.34-2.25 (m, 2H), 1.97-194 (m, 1H), 1.07 (s, 3H), 1.00-0.96 (m, 2H), 087-0.84 (m, 2H); Chiral SFC: column: Chiralpak IG, 250 × 4.6 mm, 5 μm; co-solvent: 0.3% $iPrNH_2$ in hexane/MeOH/iPrOH 60/03/10; flow: 3 mL/min; % of co-solvent: 20%; ABPR: 100 bar; T: 35° C.; $R_t$ = 5.08 min (second eluting). |
| 47a/47b | 3-Cyclopropyl-1-((3,3-difluoro-1-methylcyclobutyl)methyl)-N-(6-(S-methylsulfonimidoyl)pyridazin-4-yl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(6-(S-methylsulfonimidoyl)pyridazin-4-yl)-4-(trifluoromethyl)-1H-pyrazole-5-carboxamide (47a) and enantiomer 2 of 3-cyclopropyl-1-((3,3-difluoro-1-methylcyclobutyl)methyl)-N-(6-(S-methylsulfonimidoyl)pyridazin-4-yl)-4-(trifluoromethyl)-1H-pyrazole-5-carboxamide (47b) |

-continued

| Example | Name/Structure/Starting Material/Data |
|---|---|
| | 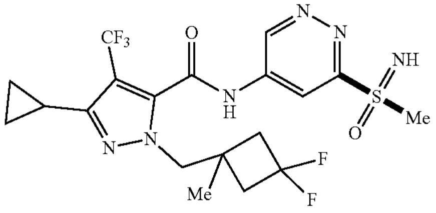<br>47a<br>and<br>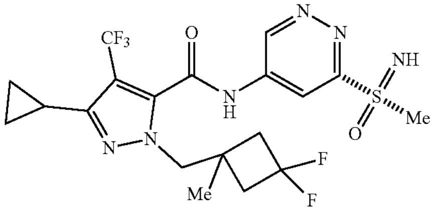<br>47b<br>ArSMe: 3-cyclopropyl-1-((3,3-difluoro-1-methylcyclobutyl)methyl)-N-(6-(methylthio)pyridazin-4-yl)-4-(trifluoromethyl)-1H-pyrazole-5-carboxamide (Intermediate 310).<br>Chiral-SFC ((R,R)-WHELK-01, 250 × 21.1 mm, 5 μm; 25% hexane/iPrOH/MeOH 50/40/10) in $CO_2$)<br>Peak 1, Example 47a (18 mg, 17%). LCMS m/z = 493 $[M + H]^+$; $^1$H-NMR (400 MHz, DMSO-$d_6$): 12.09 (s, 1H), 9.40 (s, 1H), 8.63-8.62 (m, 1H), 4.93 (s, 1H), 4.21 (s, 2H), 2.77-2.67 (m, 2H), 2.30-2.28 (m, 2H), 1.95 (br. s, 1H), 1.04-0.98 (m, 5H), 0.85 (s, 2H), 3H omitted by water. Chiral SFC: column: ((R,R)-WHELK-01, 250 × 4.6 mm, 5 μm; co-solvent: hexane/iPrOH/MeOH/iPr$NH_2$ 50/40/10/0.3, flow: 3 mL/min; % of co-solvent: 30%; ABPR: 100 bar T: 35° C.; $R_t$ = 3.45 min (first eluting).<br>Peak 2, Example 47b (19 mg, 18%). LCMS m/z = 493 $[M + H]^+$; $^1$H-NMR (400 MHz, DMSO-$d_6$): 12.10 (s, 1H), 9.40 (s, 1H), 8.62 (s, 1H), 4.93 (s, 1H), 4.21 (s, 2H), 2.77-2.67 (m, 2H), 2.30-2.27 (m, 2H), 1.95 (br.s, 1H), 1.04-0.98 (m, 5H), 0.84 (s, 2H), 3H omitted by water. Chiral SFC: column: ((R,R)-WHELK-01, 250 × 4.6 mm, 5 μm; co-solvent: 0.3% iPr$NH_2$ in iPrOH, flow: 3 mL/min; % of co-solvent: 30%; ABPR: 100 bar T: 35° C.; $R_t$ = 3.82 min (second eluting). |
| 48a/48b | 3-Cyclopropyl-1-((3,3-difluoro-1-methylcyclobutyl)methyl)-N-(2-(ethylsulfonimidoyl)pyridin-4-yl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(2-(ethylsulfonimidoyl)pyridin-4-yl)-4-(trifluoromethyl)-1H-pyrazole-5-carboxamide (48a) and enantiomer 2 of 3-cyclopropyl-1-((3,3-difluoro-1-methylcyclobutyl)methyl)-N-(2-(ethylsulfonimidoyl)pyridin-4-yl)-4-(trifluoromethyl)-1H-pyrazole-5-carboxamide (48b)<br>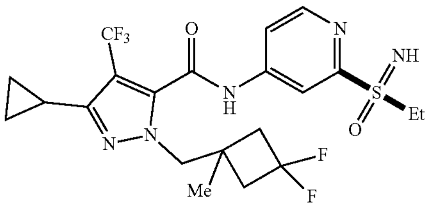<br>48a<br>and<br>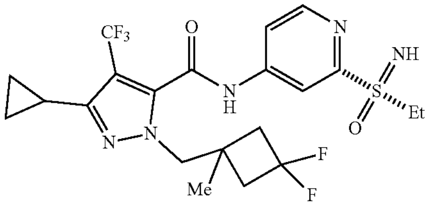<br>48b<br>ArSalkyl: 3-cyclopropyl-1-((3,3-difluoro-1-methylcyclobutyl)methyl)-N-(2-(ethylthio)pyridin-4-yl)-4-(trifluoromethyl)-1H-pyrazole-5-carboxamide (Intermediate 295). |

-continued

| Example | Name/Structure/Starting Material/Data |
|---|---|
| | Chiral-SFC (Chiralpak IC; 250 x 21.1 mm, 5 μm; 25% (0.3% $iPrNH_2$ in MeOH) in $CO_2$)<br>Peak 1, Example 48a (17 mg, 9%). LCMS m/z = 506 $[M + H]^+$; $^1H$-NMR (400 MHz, DMSO-$d_6$): 11.74 (s, 1H), 8.67 (d, 1H), 8.37 (d, 1H), 7.80-7.78 (m, 1H), 4.39 (s, 1H), 4.18 (s, 2H), 3.38-3.28 (m, 2H), 2.78-2.68 (m, 2H), 2.34-2.24 (m, 2H), 1.96-194 (m, 1H), 1.23 (m, 3H), 1.12-1.05 (m, 3H), 0.9-0.85 (m, 4H); Chiral SFC: column: Chiralpak IG, 250 x 4.6 mm, 5 μm; co-solvent: 0.5% $iPrNH_2$ in iPrOH; flow: 3 mL/min; % of co-solvent: 30%; ABPR: 100 bar; T: 35° C.; $R_t$ = 2.78 min (first eluting).<br>Peak 2, Example 48b (29 mg, 15%). LCMS m/z = 506 $[M + H]^+$; $^1H$-NMR (400 MHz, DMSO-$d_6$): 11.74 (s, 1H), 8.67 (d, 1H), 8.37 (s, 1H), 7.80 (d, 1H), 4.38 (s, 1H), 4.17 (s, 2H), 3.38-3.28 (m, 2H), 2.75-2.68 (m, 2H), 2.32-2.28 (m, 2H), 1.96 (s, 1H), 1.23 (s, 3H), 1.12-1.05 (m, 3H), 0.99-0.84 (m, 4H); Chiral SFC: column: Chiralpak IG, 250 x 4.6 mm, 5 μm; co-solvent: 0.3% $iPrNH_2$ in hexane/MeOH/iPrOH 60/03/10; flow: 3 mL/min; % of co-solvent: 20%; ABPR: 100 bar; T: 35° C.; $R_t$ = 3.45 min (second eluting). |
| 50a/50b | 3-Cyclopropyl-1-((3,3-difluoro-1-methylcyclobutyl)methyl)-N-(2-methyl-6-(S-methylsulfonimidoyl)pyridin-4-yl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(2-methyl-6-(S-methylsulfonimidoyl)pyridin-4-yl)-4-(trifluoromethyl)-1H-pyrazole-5-carboxamide (50a) and enantiomer 2 of 3-cyclopropyl-1-((3,3-difluoro-1-methylcyclobutyl)methyl)-N-(2-methyl-6-(S-methylsulfonimidoyl)pyridin-4-yl)-4-(trifluoromethyl)-1H-pyrazole-5-carboxamide (50b)<br>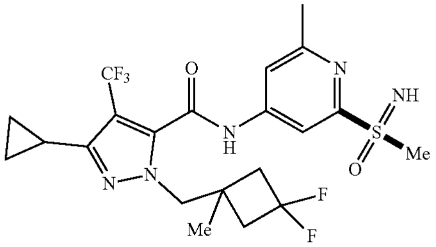<br>50a<br>and<br>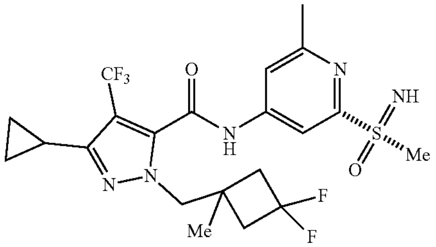<br>50b<br>ArSMe: 3-cyclopropyl-1-((3,3-difluoro-1-methylcyclobutyl)methyl)-N-(2-methyl-6-(methylthio)pyridin-4-yl)-4-(trifluoromethyl)-1H-pyrazole-5-carboxamide (Intermediate 312).<br>Chiral-SFC ((R,R)-WHELK-01, 250 x 21.1 mm, 5 μm; 25% (hexane/iPrOH/MeOH 50/40/10) in $CO_2$)<br>Peak 1, Example 50a (18 mg, 17%). LCMS m/z = 506 $[M + H]^+$; $^1H$-NMR (400 MHz, DMSO-$d_6$): 11.65 (s, 1H), 8.15 (s, 1H), 7.68 (s, 1H), 4.36 (s, 1H), 4.16 (s, 2H), 3.12 (s, 3H), 2.74-2.67 (m, 2H), 2.54 (s, 3H), 2.33-2.27 (m, 2H), 1.94 (m, 1H), 1.05 (s, 3H), 1.00-0.95 (m, 2H), 0.86-0.85 (m, 2H). Chiral SFC: column: ((R,R)-WHELK-01, 250 x 4.6 mm, 5 μm; co-solvent: 0.3% $iPrNH_2$ in iPrOH, flow: 3 mL/min; % of co-solvent: 30%; ABPR: 100 bar; T: 35° C.; $R_t$ = 3.97 min (first eluting).<br>Peak 2, Example 50b (19 mg, 18%). LCMS m/z = 506 $[M + H]^+$; $^1H$-NMR (400 MHz, DMSO-$d_6$): 11.65 (s, 1H), 8.15 (s, 1H), 7.68 (s, 1H), 4.36 (s, 1H), 4.16 (s, 2H), 3.12 (s, 3H), 2.74-2.67 (m, 2H), 2.54 (s, 3H), 2.33-2.27 (m, 2H), 1.94 (m, 1H), 1.05 (s, 3H), 1.00-0.95 (m, 2H), 0.86-0.85 (m, 2H). Chiral SFC: column: ((R,R)-WHELK-01, 250 x 4.6 mm, 5 μm; co-solvent: 0.3% $iPrNH_2$ in iPrOH, flow: 3 mL/min; % of co-solvent: 30%; ABPR: 100 bar; T: 35° C.; $R_t$ = 4.57 min (second eluting). |
| 64a/64b | 1-((3,3-Difluoro-1-methylcyclobutyl)methyl)-N-(2-(S-methylsulfonimidoyl)pyridin-4-yl)-3-(spiro[2.2]pentan-1-yl)-4-(trifluoromethyl)-1H-pyrazole-5-carboxamide, synthesized in the form of diastereomer 1 of 1-((3,3-difluoro-1-methylcyclobutyl)methyl)-N-(2-(S-methylsulfonimidoyl)pyridin-4-yl)-3-(spiro[2.2]pentan-1-yl)-4-(trifluoromethyl)-1H-pyrazole-5-carboxamide (64a) and diastereomer 2 of 1-((3,3-difluoro-1-methylcyclobutyl)methyl)-N-(2-(S-methylsulfonimidoyl)pyridin-4-yl)-3-(spiro[2.2]pentan-1-yl)-4-(trifluoromethyl)-1H-pyrazole-5-carboxamide (64b) |

-continued

| Example | Name/Structure/Starting Material/Data |
|---|---|
| | 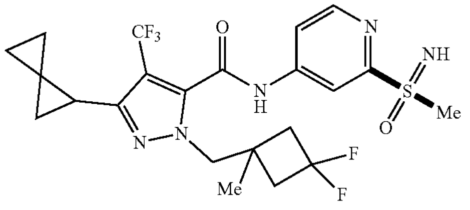<br>64a<br>and<br>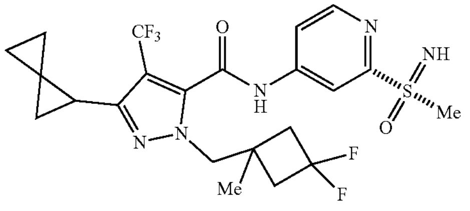<br>64b<br>ArSMe: 1-((3,3-difluoro-1-methylcyclobutyl)methyl)-N-(2-(methylthio)pyridin-4-yl)-3-(spiro[2.2]pentan-1-yl)-4-(trifluoromethyl)-1H-pyrazole-5-carboxamide (Intermediate 297).<br>Yield for racemic: (80 mg, 38%), then chiral-SFC (Chiralpak IC; 250 × 21 mm, 5 μm; 20% (0.3% iPrNH$_2$ in MeOH) in CO$_2$)<br>Peak 1, Example 64a LCMS m/z = 518 [M + H]$^+$; $^1$H-NMR (400 MHz, DMSO-d$_6$): 11.71 (s, 1H), 8.65 (d, 1H), 8.36 (s, 1H), 7.79 (d, 1H), 4.41 (bs, 1H), 4.24-4.16 (m, 2H), 3.15 (s, 3H), 2.81-2.70 (m, 2H), 2.32-2.24 (m, 3H), 1.50-1.45 (m, 2H), 1.23 (s, 1H), 1.05 (s, 3H), 0.93-0.90 (m, 2H), 0.85-0.77 (m, 1H), 0.65-0.61 (m, 1H); Chiral SFC: column: Chiralpak IC, 250 × 4.6 mm, 5 μm; co-solvent: 0.3% iPrNH$_2$ in MeOH; flow: 3 mL/min; % of co-solvent: 25%; ABPR: 100 bar; T: 35° C.; R$_t$ = 1.87 min (first eluting).<br>Peak 2, Example 64b LCMS m/z = 518 [M + H]$^+$; $^1$H-NMR (400 MHz, DMSO-d$_6$): 11.71 (s, 1H), 8.65 (d, 1H), 8.36 (s, 1H), 7.79 (d, 1H), 4.42 (bs, 1H), 4.20 (s, 2H), 3.15 (s, 3H), 2.78-2.75 (m, 2H), 2.32-2.27 (m, 2H), 1.51-1.45 (m, 2H), 1.05 (s, 3H), 0.93-0.90 (m, 2H), 0.81-0.79 (m, 1H), 0.65-0.61 (m, 1H); Chiral SFC: column: Chiralpak IC, 250 × 4.6 mm, 5 μm; co-solvent: 0.3% iPrNH$_2$ in MeOH; flow: 3 mL/min; % of co-solvent: 25%; ABPR: 100 bar;; R$_t$ = 2.06 (second eluting). |
| 65a/65b | 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide, synthesized in the form of diastereomer 1 of 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide (65a) and diastereomer 2 of 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide (65b)<br>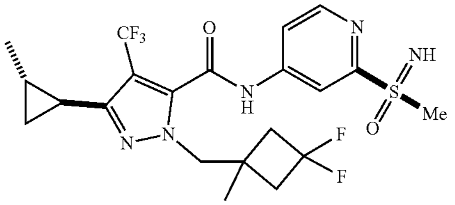<br>65a<br>and<br>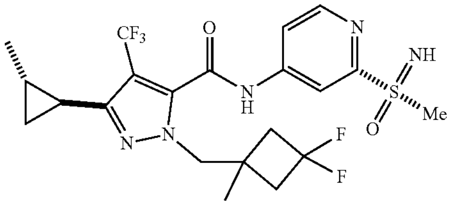<br>65b |

-continued

| Example | Name/Structure/Starting Material/Data |
|---|---|
| | ArSMe: 1-((3,3-difluoro-1-methylcyclobutyl)methyl)-3-((trans)-2-methylcyclopropyl)-N-(2-(methylthio)pyridin-4-yl)-4-(trifluoromethyl)-1H-pyrazole-5-carboxamide (Intermediate 304a). Chiral-HPLC (Chiralpak IC; 250 × 20 mm, 5 μm; hexane/DCM/EtOH 80/10/10)<br>Peak 1, Example 65a (3 mg, 9%). LCMS m/z =506 $[M + H]^+$; $^1$H-NMR (400 MHz, DMSO-$d_6$): 11.72 (s, 1H), 8.66 (d, 1H), 8.36 (s, 1H), 7.78 (d, 1H), 4.42 (s, 1H), 4.16 (s, 2H), 3.15 (s, 3H), 2.77-2.67 (m, 2H), 2.33-2.24 (m, 2H), 1.63 (s, 1H), 1.15-1.05 (m, 8H), 0.80-0.78 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 4.48 min (first eluting).<br>Peak 2, Example 65b (2 mg, 8%). LCMS m/z = 506 $[M + H]^+$; $^1$H-NMR (400 MHz, DMSO-$d_6$): 11.72 (s, 1H), 8.66 (d, 1H), 8.36 (s, 1H), 7.78 (d, 1H), 4.42 (s, 1H), 4.16 (s, 2H), 3.15 (s, 3H), 2.77-2.67 (m, 2H), 2.33-2.24 (m, 2H), 1.63 (s, 1H), 1.15-1.05 (m, 8H), 0.80-0.78 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.22 min (second eluting). |
| 65c/65d | 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide, synthesized in the form of diastereomer 3 of 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide (65c) and diastereomer 4 of 1-((3,3-Difluoro-1-methylcyclobutyl)methyl)-3-((trans)-2-methylcyclopropyl)-N-(2-(S-methylsulfonimidoyl)pyridin-4-yl)-4-(trifluoromethyl)-1H-pyrazole-5-carboxamide (65d)<br>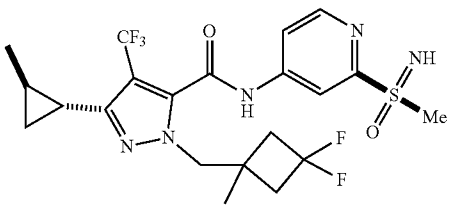<br>65c<br>and<br>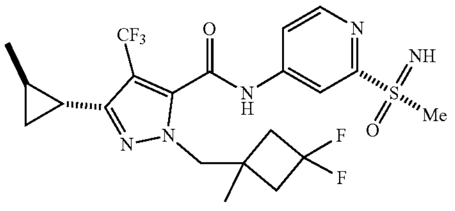<br>65d<br>ArSMe: 1-((3,3-difluoro-1-methylcyclobutyl)methyl)-3-((trans)-2-methylcyclopropyl)-N-(2-(methylthio)pyridin-4-yl)-4-(trifluoromethyl)-1H-pyrazole-5-carboxamide (Intermediate 304b). Chiral-HPLC (Chiralpak IC; 250 × 20 mm, 5 μm; hexane/DCM/EtOH 80/10/10)<br>Peak 1, Example 65c (4 mg, 12%). LCMS m/z = 506 $[M + H]^+$; $^1$H-NMR (400 MHz, DMSO-$d_6$): 11.72 (s, 1H), 8.66 (d, 1H), 8.36 (s, 1H), 7.78 (d, 1H), 4.42 (s, 1H), 4.16 (s, 2H), 3.15 (s, 3H), 2.74-2.67 (m, 2H), 2.32-2.24 (m, 2H), 1.63 (s, 1H), 1.15-1.05 (m, 8H), 0.85-0.78 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 4.44 min (first eluting).<br>Peak 2, Example 65d (2 mg, 6%). LCMS m/z = 506 $[M + H]^+$; $^1$H-NMR (400 MHz, DMSO-$d_6$): 11.72 (s, 1H), 8.66 (d, 1H), 8.36 (s, 1H), 7.78 (d, 1H), 4.43 (s, 1H), 4.16 (s, 2H), 3.15 (s, 2H), 2.77-2.67 (m, 2H), 2.30-2.24 (m, 2H), 1.63 (s, 1H), 1.14-1.05 (m, 8H), 0.80-0.79 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.10 min (second eluting). |
| 68a/68b | 3-(1-Cyanocyclopropyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-(1-cyanocyclopropyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (68a) and enantiomer 2 of 3-(1-cyanocyclopropyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (68b) |

-continued

| Example | Name/Structure/Starting Material/Data |
|---|---|
| | 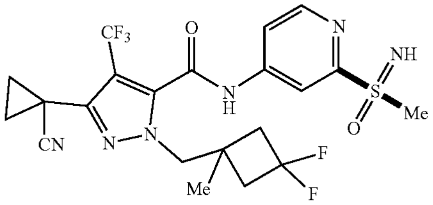 68a and 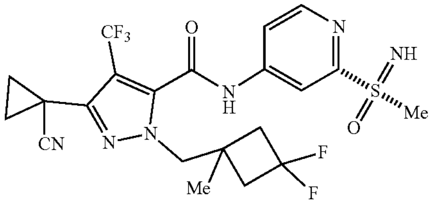 68b ArSMe: 3-(1-cyanocyclopropyl)-1-((3,3-difluoro-1-methylcyclobutyl)methyl)-N-(2-(methylthio)pyridin-4-yl)-4-(trifluoromethyl)-1H-pyrazole-5-carboxamide (Intermediate 299). Chiral-SFC (Chiralpak IC, 250 x 21 mm, 5 μm; 20% (0.3% $iPrNH_2$ in MeOH) in $CO_2$) Peak 1, Example 68a (19 mg, 9%). LCMS m/z = 517 $[M + H]^+$; $^1H$-NMR (400 MHz, DMSO-$d_6$): 11.85 (s, 1H), 8.67 (d, 1H), 8.36 (s, 1H), 7.78 (d, 1H), 4.44 (bs, 1H), 4.28 (s, 2H), 3.15 (s, 3H), 2.79-2.66 (m, 2H), 2.37-2.28 (m, 2H), 1.80 (s, 2H), 1.54 (s, 2H), 1.06 (s, 3H); Chiral SFC: column: Chiralpak IC, 250 x 4.6 mm, 5 μm; co-solvent: 0.5% $iPrNH_2$ in iPrOH, flow: 4 mL/min; % of co-solvent: 10%; ABPR: 100 bar; T: 35° C.; $R_t$ = 1.78 min (first eluting). Peak 2, Example 68b (17 mg, 8%). LCMS m/z = 517 $[M + H]^+$; $^1H$-NMR (400 MHz, DMSO-$d_6$): 11.85 (s, 1H), 8.67 (d, 1H), 8.36 (s, 1H), 7.78 (s, 1H), 4.48 (s, 1H), 4.28 (s, 2H), 3.15 (s, 3H), 2.80-2.66 (m, 2H), 2.37-2.28 (m, 2H), 1.80 (s, 2H), 1.54 (s, 2H), 1.06 (s, 3H); Chiral SFC: column: Chiralpak IC, 250 x 4.6 mm, 5 μm; co-solvent: 0.5% $iPrNH_2$ in iPrOH, flow: 4 mL/min; % of co-solvent: 10%; ABPR: 100 bar; T: 35° C.; $R_t$ = 2.14 min (second eluting). |
| 69a/69b | 1-((3,3-Difluoro-1-methylcyclobutyl)methyl)-3-(1-methylcyclopropyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(1-methylcyclopropyl)-N-(2-(S-methylsulfonimidoyl)pyridin-4-yl)-4-(trifluoromethyl)-1H-pyrazole-5-carboxamide (69a) and enantiomer 2 of 1-((3,3-difluoro-1-methylcyclobutyl)methyl)-3-(1-methylcyclopropyl)-N-(2-(S-methylsulfonimidoyl)pyridin-4-yl)-4-(trifluoromethyl)-1H-pyrazole-5-carboxamide (69b) 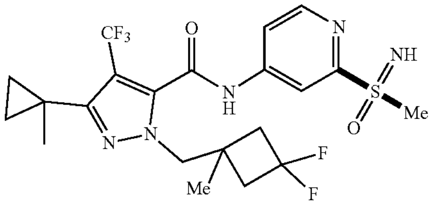 69a and 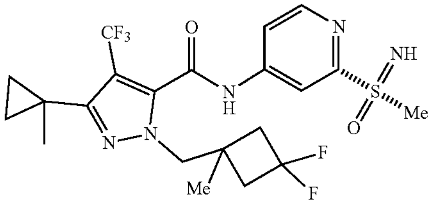 69b ArSMe: 1-((3,3-difluoro-1-methylcyclobutyl)methyl)-3-(1-methylcyclopropyl)-N-(2-(methylthio)pyridin-4-yl)-4-(trifluoromethyl)-1H-pyrazole-5-carboxamide (Intermediate 300). Chiral-HPLC (Chiralpak IC, 250 x 21 mm, 5 μm; 80/10/10 hexane/DCM/EtOH) Peak 1, Example 69a (55 mg, 26%). LCMS m/z = 506 $[M + H]^+$; $^1H$-NMR (400 MHz, DMSO- |

-continued

| Example | Name/Structure/Starting Material/Data |
|---|---|
| | $d_6$): 11.75 (s, 1H), 8.66 (d, 1H), 8.36 (s, 1H), 7.79-7.77 (m, 1H), 4.42 (s, 1H), 4.17 (s, 2H), 3.15 (s, 3H), 2.80-2.70 (m, 2H), 2.35-2.26 (m, 2H), 1.34 (s, 3H), 1.07 (s, 3H), 0.90-0.87 (m, 2H), 0.75-0.72 (m, 2H); Chiral HPLC: column: Chiralpak IC, 250 x 4.6 mm, 5 μm; solvent: DCM/iPrOH/TFA 50/50/0.1; flow: 1 mL/min; $R_t$ = 4.46 min (first eluting). Peak 2, Example 69b (52 mg, 24%). LCMS m/z = 506 $[M + H]^+$; $^1$H-NMR (400 MHz, DMSO-$d_6$): 11.75 (s, 1H), 8.66 (d, 1H), 8.36 (s, 1H), 7.79-7.77 (m, 1H), 4.42 (s, 1H), 4.17 (s, 2H), 3.15 (s, 3H), 2.80-2.70 (m, 2H), 2.35-2.26 (m, 2H), 1.34 (s, 3H), 1.07 (s, 3H), 0.90-0.87 (m, 2H), 0.75-0.72 (m, 2H); Chiral HPLC: column: Chiralpak IC, 250 x 4.6 mm, 5 μm; solvent: DCM/iPrOH/TFA 50/50/0.1; flow: 1 mL/min; $R_t$ = 5.20 min (second eluting). |
| 71a/71b | 1-((3,3-Difluoro-1-methylcyclobutyl)methyl)-3-(1-methoxycyclopropyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(1-methoxycyclopropyl)-N-(2-(S-methylsulfonimidoyl)pyridin-4-yl)-4-(trifluoromethyl)-1H-pyrazole-5-carboxamide (71a) and enantiomer 2 of 1-((3,3-difluoro-1-methylcyclobutyl)methyl)-3-(1-methoxycyclopropyl)-N-(2-(S-methylsulfonimidoyl)pyridin-4-yl)-4-(trifluoromethyl)-1H-pyrazole-5-carboxamide (71b)<br>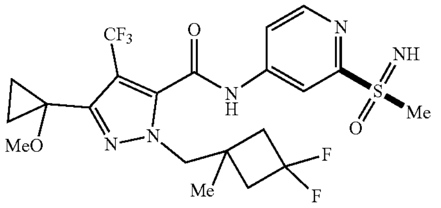<br>71a<br>and<br>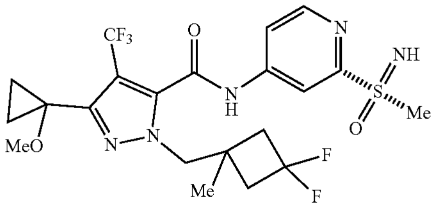<br>71b<br>ArSMe: 1-[(3,3-difluoro-1-methylcyclobutyl)methyl]-3-(1-methoxycyclopropyl)-N-[2-(methylsulfanyl)pyridin-4-yl]-4-(trifluoromethyl)-1H-pyrazole-5-carboxamide (Intermediate 292).<br>Chiral-SFC ((R,R)-Whelk-O-1, 250 x 21 mm, 5 μm; 20% (0.3% $iPrNH_2$in iPrOH) in $CO_2$)<br>Peak 1, Example 71a (17 mg, 14%). LCMS m/z = 522 $[M + H]^+$; $^1$H-NMR (400 MHz, DMSO-$d_6$): 11.78 (s, 1H), 8.68 (d, 1H), 8.37 (s, 1H), 7.82-7.80 (m, 1H), 4.42 (s, 1H), 4.24 (s, 2H), 3.15 (s, 3H), 3.12 (s, 3H), 2.78-2.74 (m, 2H), 2.32-2.30 (m, 2H), 1.11-1.10 (m, 2H), 1.08 (s, 3H), 1.00-0.97 (m, 2H); Chiral SFC: column: (R,R)-Whelk-O-1, 150 x 4.6 mm, 3.5 μm; co-solvent: (0.5% $iPrNH_2$ in iPrOH), flow: 3 mL/min; % of co-solvent: 20%; ABPR: 1500 psi; T: 35° C.; $R_t$ = 5.79 min (first eluting).<br>Peak 2, Example 71b (16 mg, 14%). LCMS m/z = 522 $[M + H]^+$; $^1$H-NMR (400 MHz, DMSO-$d_6$): 11.78 (s, 1H), 8.68 (d, 1H), 8.37-8.36 (m, 1H), 7.82-7.80 (m, 1H), 4.42 (s, 1H), 4.24 (s, 2H), 3.15 (s, 3H), 3.12 (s, 3H), 2.78-2.74 (m, 2H), 2.32-2.30 (m, 2H), 1.11-1.10 (m, 2H), 1.08 (s, 3H), 1.00-0.97 (m, 2H); Chiral SFC: column: (R,R)-Whelk-O-1, 150 x 4.6 mm, 3.5 μm; co-solvent: (0.5% $iPrNH_2$ in iPrOH), flow: 3 mL/min; % of co-solvent: 20%; ABPR: 1500 psi; T: 35° C.; $R_t$ = 7.21 min (second eluting). |
| 75a/75b | 1-((3,3-Difluoro-1-methylcyclobutyl)methyl)-3-(1,1-difluoroethyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(1,1-difluoroethyl)-N-(2-(S-methylsulfonimidoyl)pyridin-4-yl)-4-(trifluoromethyl)-1H-pyrazole-5-carboxamide (75a) and enantiomer 2 of 1-((3,3-difluoro-1-methylcyclobutyl)methyl)-3-(1,1-difluoroethyl)-N-(2-(S-methylsulfonimidoyl)pyridin-4-yl)-4-(trifluoromethyl)-1H-pyrazole-5-carboxamide (75b) |

-continued

| Example | Name/Structure/Starting Material/Data |
|---|---|
| | 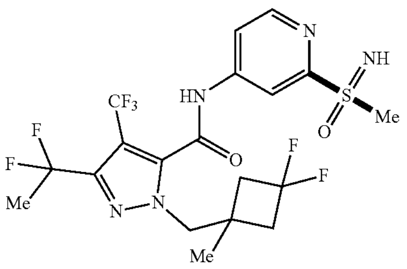 75a and 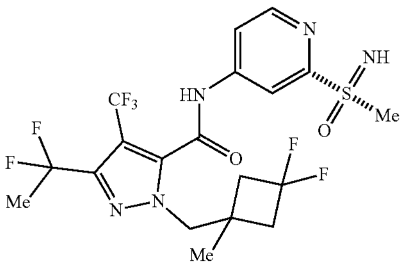 75b ArSMe: 1-((3,3-difluoro-1-methylcyclobutyl) methyl)-3-(1,1-difluoroethyl)-N-(2-(methylthio) pyridin-4-yl)-4-(trifluoromethyl)-1H-pyrazole-5-carboxamide (Intermediate 293) Chiral-SFC (Chiralpak IC 250 x 21 mm, 5 μm); 20% (0.3% $iPrNH_2$ in hexane/MeOH/iPrOH (50/40/10) in $CO_2$) Peak 1, Example 75a (105 mg, 32%). LCMS m/z = 516 $[M + H]^+$; $^1H$-NMR (400 MHz, DMSO-$d_6$): 11.90 (s, 1H), 8.68 (s, 1H), 8.35 (s, 1H), 7.78 (s, 1H), 4.44 (bs, 1H), 4.34 (s, 2H), 3.16 (s, 3H), 2.84-2.66 (m, 2H), 2.40-2.34 (m, 2H), 2.08 (t, 3H), 1.10 (s, 3H). Chiral SFC: column: Chiralpak IC (250 x 4.6 mm, 5 μm); 250 x 21 mm, 5 μm; co-solvent: (0.3% $iPrNH_2$ in hexane/MeOH/iPrOH (50/40/10), flow: 3 mL/min; % of co-solvent: 25%; ABPR: 100 bar; T: 35° C.; $R_t$ = 1.82 min (first eluting). Peak 2, Example 75b (75 mg, 23%). LCMS m/z = 516 $[M + H]^+$; $^1H$-NMR (400 MHz, DMSO-$d_6$): 11.88 (s, 1H), 8.68 (d, 1H), 8.35 (s, 1H), 7.78 (d, 1H), 4.43 (bs, 1H), 4.34 (s, 2H), 3.16 (s, 3H), 2.81-2.77 (m, 2H), 2.37-2.32 (m, 2H), 2.08 (t, 3H), 1.17 (s, 3H); Chiral SFC: column: Chiralpak IC (250 x 4.6 mm, 5 μm); 250 x 21 mm, 5 μm; co-solvent: (0.3% $iPrNH_2$ in hexane/MeOH/iPrOH (50/40/10), flow: 3 mL/min; % of co-solvent: 25%; ABPR: 100 bar; T: 35° C.; $R_t$ = 2.30 min (second eluting). |
| 78a/78b | 3-Cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide, synthesized in the form of diastereomer 1 of 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide (78a) and diastereomer 2 of 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide (78b) 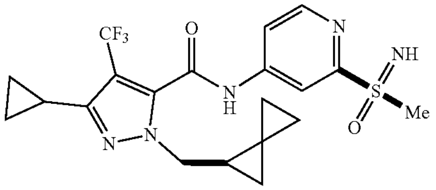 78a and |

-continued

| Example | Name/Structure/Starting Material/Data |
|---|---|
| | 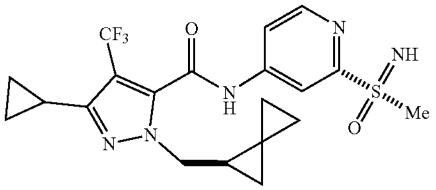<br>78b<br>ArSMe: 3-cyclopropyl-N-(2-(methylthio) pyridin-4-yl)-1-(spiro[2.2]pentan-1-ylmethyl)-4-(trifluoromethyl)-1H-pyrazole-5-carboxamide (Intermediate 303a).<br>Chiral-SFC (Chiralpak IC; 250 x 21 mm, 5 μm; 30% (0.3% $iPrNH_2$ in iPrOH) in $CO_2$)<br>Peak 1, Example 78a (47 mg, 22%). LCMS m/z = 454 $[M + H]^+$; $^1$H-NMR (400 MHz, DMSO-$d_6$): 11.78 (s, 1H), 8.66 (d, 1H), 8.39 (s, 1H), 7.77 (d, 1H), 4.45 (bs, 1H), 4.08-4.00 (m, 2H), 3.15 (s, 3H), 1.93 (bs, 1H), 1.50-1.48 (m, 1H), 1.01-0.96 (m, 3H), 0.84-0.82 (m, 3H), 0.73-0.66 (m, 4H); Chiral SFC: column: Chiralpak IC, 250 x 4.6 mm, 5 μm; co-solvent: 0.5% $iPrNH_2$ in iPrOH; flow: 4 mL/min; % of co-solvent: 35%; ABPR: 100 bar; T: 35° C.; $R_t$ = 2.02 min (first eluting).<br>Peak 2, Example 78b (45 mg, 21%). LCMS m/z = 454 $[M + H]^+$; $^1$H-NMR (400 MHz, DMSO-$d_6$): 11.79 (s, 1H), 8.66 (d, 1H), 8.39 (s, 1H), 7.77 (d, 1H), 4.43 (s, 1H), 4.06-4.00 (m, 2H), 3.15 (s, 3H), 1.98-1.93 (m, 1H), 1.49-1.48 (m, 1H), 1.01-0.96 (m, 3H), 0.83 (m, 3H), 0.73-0.66 (m, 4H); Chiral SFC: column: Chiralpak IC, 250 x 4.6 mm, 5 μm; co-solvent : 0.5% $iPrNH_2$ in iPrOH; flow: 4 mL/min; % of co-solvent: 35%; ABPR: 100 bar; T: 35° C.; $R_t$ = 2.72 min (second eluting). |
| 78c/78d | 3-Cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide, synthesized in the form of diastereomer 3 of 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide (78c) and diastereomer 4 of 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide (78d)<br>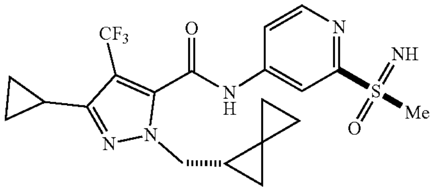<br>78c<br>and<br>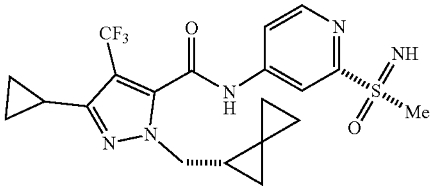<br>78d<br>ArSMe: 3-cyclopropyl-N-(2-(methylthio) pyridin-4-yl)-1-(spiro[2.2]pentan-1-ylmethyl)-4-(trifluoromethyl)-1H-pyrazole-5-carboxamide (Intermediate 303b).<br>Chiral-SFC (Chiralpak IC; 250 x 21 mm, 5 μm; 30% (0.3% $iPrNH_2$ in iPrOH) in $CO_2$)<br>Peak 1, Example 78c (27 mg, 15%). LCMS m/z = 454 $[M + H]^+$; 1H-NMR (400 MHz, DMSO-d6): 11.78 (s, 1H), 8.66 (d, 1H), 8.39 (s, 1H), 7.77 (d, 1H), 4.42 (s, 1H), 4.08-3.97 (m, 2H), 3.15 (s, 3H), 1.93 (bs, 1H), 1.50-1.48 (m, 1H), 1.01-0.96 (m, 3H), 0.83 (m, 3H), 0.73-0.66 (m, 4H); Chiral SFC: column: Chiralpak IC, 250 x 4.6 mm, 5 um; co-solvent : 0.5% iPrNH2 in iPrOH; flow : 4 mL/min; % of co-solvent : 35%; ABPR : 100 bar; T: 35 °C; Rt = 2.06 min (first eluting).<br>Peak 2, Example 78d (42 mg, 23%). LCMS m/z = 454 $[M + H]^+$; 1H-NMR (400 MHz, DMSO-d6): 11.78 (s, 1H), 8.66 (d, 1H), 8.39 (s, 1H), 7.77 (d, 1H), 4.42 (s, 1H), 4.10-3.97 (m, 2H), 3.15 (s, 3H), 1.94-1.92 (m, 1H), 1.50-1.46 (m, 1H), 1.01-0.96 (m, 3H), 0.85-0.82 (m, 3H), 0.74-0.69 (m, 4H); Chiral SFC: column: Chiralpak IC, 250 x 4.6 mm, 5 μm; co-solvent: 0.5% $iPrNH_2$ in iPrOH; flow: 4 mL/min; % of co-solvent: 35%; ABPR: 100 bar; T: 35° C.; $R_t$ = 2.77 min (second eluting). |
| 79a/79b | 3-Cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide (79a) and diastereomer 2 of 3-cyclopropyl-1-((2,2-difluorospiro[2.2]pentan-1- |

-continued

| Example | Name/Structure/Starting Material/Data |
|---|---|
| | yl)methyl)-N-(2-(S-methylsulfonimidoyl)pyridin-4-yl)-4-(trifluoromethyl)-1H-pyrazole-5-carboxamide (79b) |
| | 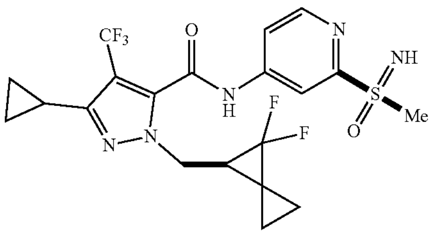<br>79a<br>and<br>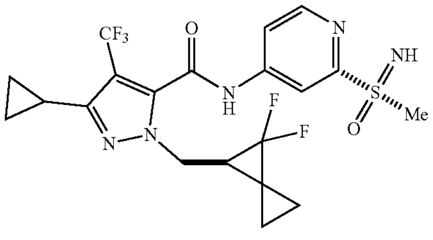<br>79b |
| | ArSMe: 3-cyclopropyl-1-((2,2-difluorospiro[2.2]pentan-1-yl)methyl)-N-(2-(methylthio)pyridin-4-yl)-4-(trifluoromethyl)-1H-pyrazole-5-carboxamide (Intermediate 307a). Chiral-HPLC (Chiralpak IC; 250 × 20 mm, 5 μm; 0.1% $iPrNH_2$ in hexane/DCM/EtOH 70/15/15)<br>Peak 1, Example 79a (26 mg, 12%). LCMS m/z = 490 $[M + H]^+$; $^1$H-NMR (400 MHz, DMSO-$d_6$): 11.77 (s, 1H), 8.66-8.65 (m, 1H), 8.37 (s, 1H), 7.77-7.76 (m, 1H), 4.42 (s, 1H), 4.25-4.23 (m, 2H), 3.15 (s, 3H), 2.38-2.36 (m, 1H), 1.95-1.94 (m, 1H), 1.16-0.84 (m, 8H); Chiral HPLC: column: Chiralpak IC, 250 × 4.6 mm, 5 μm; mobile phase: hexane/DCM/EtOH/$iPrNH_2$ 60/20/20/0.1; flow: 1 mL/min; $R_t$ = 4.90 min (first eluting).<br>Peak 2, Example 79b (26 mg, 12%). LCMS m/z = 490 $[M + H]^+$; $^1$H-NMR (400 MHz, DMSO-$d_6$): 11.77 (s, 1H), 8.66-8.65 (m, 1H), 8.37 (s, 1H), 7.77-7.76 (m, 1H), 4.42 (s, 1H), 4.25-4.23 (m, 2H), 3.15 (s, 3H), 2.40-2.32 (m, 1H), 1.96-1.93 (m, 1H), 1.80-0.84 (m, 8H); Chiral HPLC: column: Chiralpak IC, 250 × 4.6 mm, 5 μm; mobile phase: hexane/DCM/EtOH/$iPrNH_2$ 60/20/20/0.1; flow: 1 mL/min; $R_t$ = 5.70 min (second eluting). |
| 79c/79d | 3-Cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide, synthesized in the form of diastereomer 3 of 3-cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide (79c) and diastereomer 4 of 3-cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide (79d)<br>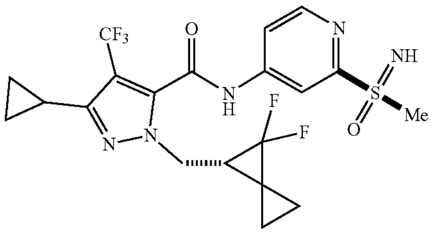<br>79c<br>and |

-continued

| Example | Name/Structure/Starting Material/Data |
|---|---|
| | 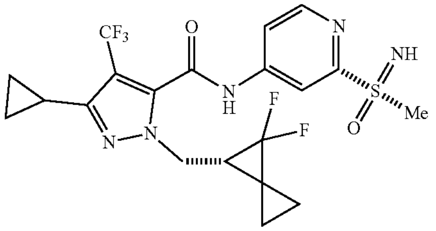<br>79d<br>ArSMe: 3-cyclopropyl-1-((2,2-difluorospiro[2.2]pentan-1-yl)methyl)-N-(2-(methylthio)pyridin-4-yl)-4-(trifluromethyl)-1H-pyrazole-5-carboxamide (Intermediate 307b).<br>Chiral-HPLC (Chiralpak IC; 250 × 20 mm, 5 μm; 0.1% $iPrNH_2$ in hexane/DCM/EtOH 70/15/15)<br>Peak 1, Example 79c (60 mg, 29%). LCMS m/z = 490 $[M + H]^+$; $^1$H-NMR (400 MHz, DMSO-$d_6$): 11.81 (s, 1H), 8.65-8.64 (m, 1H), 8.36 (s, 1H), 7.76-7.75 (m, 1H), 4.42 (s, 1H), 4.29-4.23 (m, 2H), 3.14 (s, 3H), 2.40-2.32 (m, 1H), 1.94-1.90 (m, 1H), 1.16-0.83 (m, 8H); Chiral HPLC: column: Chiralpak IC, 250 × 4.6 mm, 5 μm; mobile phase: hexane/DCM/EtOH/$iPrNH_2$ 60/20/20/0.1; flow: 1 mL/min; $R_t$ = 4.87 min (frst eluting).<br>Peak 2, Example 79d (53 mg, 26%). LCMS m/z = 490 $[M + H]^+$; $^1$H-NMR (400 MHz, DMSO-$d_6$): 11.79 (s, 1H), 8.66-8.64 (m, 1H), 8.37 (s, 1H), 7.76-7.75 (m, 1H), 4.43 (s, 1H), 4.25-4.23 (m, 2H), 3.15 (s, 3H), 2.40-2.32 (m, 1H), 1.94-1.90 (m, 1H), 1.16-0.84 (m, 8H); Chiral HPLC: column: Chiralpak IC, 250 × 4.6 mm, 5 μm; mobile phase: hexane/DCM/EtOH/$iPrNH_2$ 60/20/20/0.1; flow: 1 mL/min; $R_t$ = 5.84 min (second eluting). |
| 80a/80b | 3-Cyclopropyl-1-(dispiro[2.0.24.13]heptan-7-ylmethyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-(dispiro[2.0.24.13]heptan-7-ylmethyl)-N-(2-(S-methylsulfonimidoyl)pyridin-4-yl)-4-(trifluoromethyl)-1H-pyrazole-5-carboxamide (80a) and enantiomer 2 of 3-cyclopropyl-1-(dispiro[2.0.24.13]heptan-7-ylmethyl)-N-(2-(S-methylsulfonimidoyl)pyridin-4-yl)-4-(trifluoromethyl)-1H-pyrazole-5-carboxamide (80b)<br>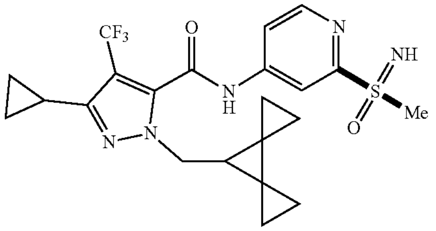<br>80a<br>and<br>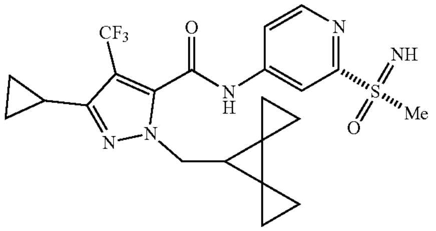<br>80b<br>ArSMe: 3-cyclopropyl-1-({dispiro[2.0.24.13]heptan-7-yl}methyl)-N-[2-(methylsulfanyl)pyridin-4-yl]-4-(trifluoromethyl)-1H-pyrazole-5-carboxamide (Intermediate 298).<br>Chiral HPLC (Chiralart Cellulose SC, 250 × 20 mm, 5 μm; 80/10/10 Hex/EtOH/DCM)<br>Peak 1, Example 80a (37 mg, 19%). LCMS m/z = 480 $[M + H]^+$; $^1$H-NMR (400 MHz, DMSO-$d_6$): 11.76 (s, 1H), 8.63 (s, 1H), 8.37 (s, 1H), 7.75 (s, 1H), 4.40 (s, 1H), 4.10-4.09 (m, 2H), 3.15 (s, 3H), 1.92-1.89 (m, 1H), 1.76-1.73 (m, 1H), 0.97-0.96 (m, 2H), 0.90-0.89 (m, 2H), 0.81-0.80 (m, 4H), 0.65-0.63 (m, 2H), 0.53-0.52 (m, 2H). Chiral HPLC: column: Chiralpak IC, 250 × 4.6 mm, 5 μm; mobile phase: hexane/DCM/EtOH/$iPrNH_2$ 60/20/20/0.1, flow rate: 1.0 mL/min, $R_t$ = 5.07 min (first eluting).<br>Peak 2, Example 80b (22 mg, 11%). LCMS m/z = 480 $[M + H]^+$; $^1$H-NMR (400 MHz, DMSO-$d_6$): 11.73 (s, 1H), 8.66-8.65 (m, 1H), 8.38 (s, 1H), 7.77-7.76 (m, 1H), 4.42 (s, 1H), 4.01-4.08 (m, 2H), 3.15 (s, 3H), 1.93-1.92 (m, 1H), 1.76-1.73 (m, 1H), 1.00-0.95 (m, 2H), 0.92-0.88 (m, 2H), 0.83-0.77 (m, 6H), 0.69-0.67 (m, 2H). Chiral HPLC: column: Chiralpak IC, 250 × 4.6 mm, |

-continued

| Example | Name/Structure/Starting Material/Data |
|---|---|
| | 5 μm; mobile phase: hexane/DCM/EtOH/iPrNH$_2$ 60/20/20/0.1, flow rate: 1.0 mL/min, $R_t$ = 6.15 min (second eluting). |
| 86a/86b | 3-Cyclopropyl-1-((1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-(((trans)-1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide (86a) and enantiomer 2 of 3-cyclopropyl-1-(((trans)-1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide (86b) 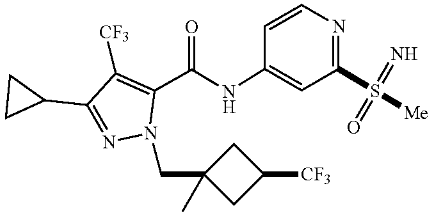 86a and 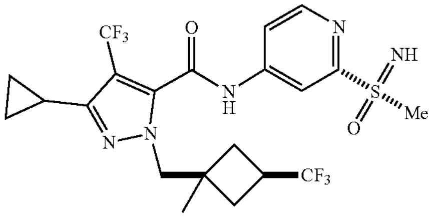 86b ArSMe: 3-cyclopropyl-1-(((trans)-1-methyl-3-(trifluoromethyl)cyclobutyl)methyl)-N-(2-(methylthio)pyridin-4-yl)-4-(trifluoromethyl)-1H-pyrazole-5-carboxamide (Intermediate 308). Chiral-HPLC (Chiralpak IC; 250 × 21 mm, 5 μm; hexane/EtOH 90/10) Peak 1, Example 86a (36 mg, 15%). LCMS m/z = 524 [M + H]$^+$; $^1$H-NMR (400 MHz, DMSO-d$_6$): 11.72 (s, 1H), 8.66 (d, 1H), 8.35 (s, 1H), 7.79 (d, 1H), 4.42 (s, 1H), 4.00 (s, 2H), 3.18-3.14 (m, 4H), 2.17-2.11 (m, 2H), 1.96-1.95 (m, 1H), 1.79-1.74 (m, 2H), 1.05-0.96 (m, 5H), 0.85-0.83 (m, 2H); Chiral HPLC: column: Chiralpak IC, 250 × 4.6 mm, 5 μm; mobile phase: hexane/EtOH/iPrNH$_2$ 70/30/0.1; flow: 1 mL/min; $R_t$ = 5.16 min (first eluting). Peak 2, Example 86b (36 mg, 15%). LCMS m/z = 524 [M + H]$^+$; $^1$H-NMR (400 MHz, DMSO-d$_6$): 11.71 (s, 1H), 8.66 (d, 1H), 8.35 (s, 1H), 7.79 (d, 1H), 4.42 (s, 1H), 4.00 (s, 2H), 3.18-3.14 (m, 3H), 2.17-2.11 (m, 2H), 1.96-1.95 (m, 1H), 1.79-1.74 (m, 3H), 1.05-0.96 (m, 5H), 0.85-0.83 (m, 2H); Chiral HPLC: column: Chiralpak IC, 250 × 4.6 mm, 5 μm; mobile phase: hexane/EtOH/iPrNH$_2$ 70/30/0.1; flow: 1 mL/min; $R_t$ = 5.98 min (second eluting). |
| 86c/86d | 3-Cyclopropyl-1-((1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-(((cis)-1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide (86c) and enantiomer 2 of 3-cyclopropyl-1-(((cis)-1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide (86d) 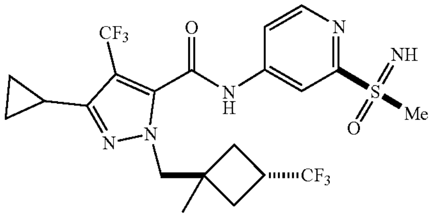 86c and |

-continued

| Example | Name/Structure/Starting Material/Data |
|---|---|
| | 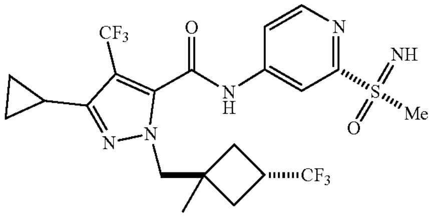 86d ArSMe: 3-cyclopropyl-1-(((cis)-1-methyl-3-(trifluoromethyl)cyclobutyl)methyl)-N-(2-(methylthio)pyridin-4-yl)-4-(trifluoromethyl)-1H-pyrazole-5-carboxamide (Intermediate 309). Chiral-HPLC (Chiralpak IC; 250 x 21 mm, 5 μm; hexane/EtOH/DCM 80/10/10) Peak 1, Example 86c (50 mg, 21%). LCMS m/z = 524 $[M + H]^+$; $^1$H-NMR (400 MHz, DMSO-$d_6$): 11.73 (s, 1H), 8.66 (d, 1H), 8.37 (s, 1H), 7.79 (d, 1H), 4.43 (s, 1H), 4.18 (s, 2H), 3.15 (s, 3H), 3.10-3.06 (m, 1H), 2.37-2.31 (m, 2H), 1.96-1.95 (m, 1H), 1.83-1.78 (m, 2H), 1.00-0.94 (m, 5H), 0.85-0.83 (m, 2H); Chiral HPLC: column: Chiralpak IC, 250 x 4.6 mm, 5 μm; mobile phase: hexane/DCM/EtOH/iPrNH$_2$ 60/20/20/0.1; flow: 1 mL/min; $R_t$ = 4.32 min (frst eluting). Peak 2, Example 86d (60 mg, 28%). LCMS m/z = 524 $[M + H]^+$; $^1$H-NMR (400 MHz, DMSO-$d_6$): 11.73 (s, 1H), 8.66 (d, 1H), 8.37 (s, 1H), 7.79 (d, 1H), 4.43 (s, 1H), 4.18 (s, 2H), 3.15-3.08 (m, 4H), 2.37-2.31 (m, 2H), 1.96-1.95 (m, 1H), 1.83-1.78 (m, 2H), 0.99-0.94 (m, 5H), 0.84-0.80 (m, 2H); Chiral HPLC: column: Chiralpak IC, 250 x 4.6 mm, 5 μm; mobile phase: hexane/DCM/EtOH/iPrNH$_2$ 60/20/20/0.1; flow: 1 mL/min; $R_t$ = 4.91 min (second eluting). |
| 92a/92b | 3-Cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide (92a) and diastereomer 2 of 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide (92b) 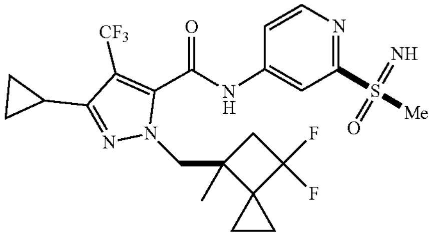 92a and 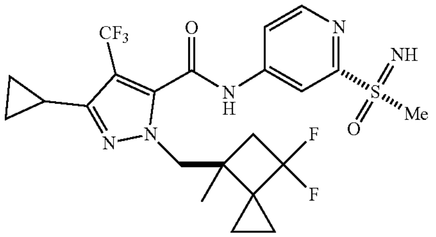 92b ArSMe: 3-cyclopropyl-1-{[(4S)-6,6-difluoro-4-methylspiro[2.3]hexan-4-yl]methyl}-N-[2-(methylsulfanyl)pyridin-4-yl]-4-(trifluoromethyl)-1H-pyrazole-5-carboxamide (Intermediate 327a). Chiral-HPLC (Chiralpak IC; 250 x 20 mm, 5 μm; hexane/DCM/EtOH 80/10/10) Peak 1, Example 92a (67 mg, 22%). LCMS m/z = 518 $[M + H]^+$; $^1$H-NMR (400 MHz, DMSO-$d_6$): 11.69 (s, 1H), 8.66 (d, 1H), 8.36 (s, 1H), 7.78-7.77 (m, 1H), 4.42 (s, 1H), 4.14-4.10 (m, 1H), 4.05-4.02 (m, 1H), 3.15 (s, 3H), 2.94-2.84 (m, 1H), 2.45-2.36 (m, 1H), 1.95-1.93 (m, 1H), 1.23-1.18 (m, 1H), 1.00-0.97 (m, 2H), 0.90 (s, 3H), 0.87-0.77 (m, 4H), 0.71-0.70 (m, 1H), Chiral HPLC: column: Chiralpak IC, 250 x 4.6 mm, 5 μm; mobile phase: hexane/DCM/EtOH/iPrNH$_2$ 60/20/20/0.1; flow: 1 mL/min; $R_t$ = 4.50 min (first eluting). Peak 2, Example 92b (65 mg, 21%). LCMS m/z = 518 $[M + H]^+$; $^1$H-NMR (400 MHz, DMSO-$d_6$): 11.69 (s, 1H), 8.66 (d, 1H), 8.36 (s, 1H), 7.78-7.77 (m, 1H), 4.42 (s, 1H), 4.14-4.10 (m, 1H), 4.05-4.02 (m, 1H), 3.15 (s, 3H), 2.94-2.84 (m, 1H), 2.45-2.32 (m, 1H), 1.95-1.93 (m, 1H), 1.23-1.19 (m, 1H), 1.00-0.97 (m, 2H), 0.90 (s, 3H), 0.87-0.77 (m, 4H), 0.71-0.70 (m, 1H); Chiral |

-continued

| Example | Name/Structure/Starting Material/Data |
|---|---|
| | HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.23 min (second eluting). |
| 92c/92d | 3-Cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide, synthesized in the form of diastereomer 3 of 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide (92c) and diastereomer 4 of 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide (92d) 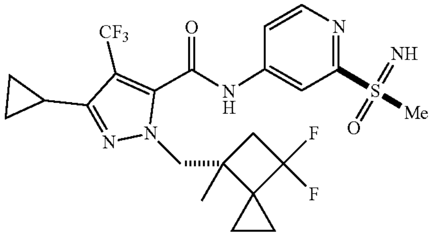 92c and 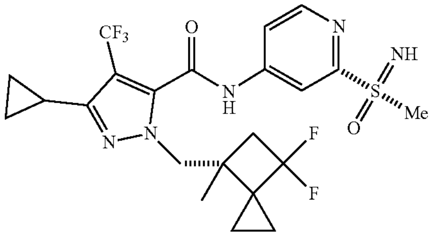 92d ArSMe: 3-cyclopropyl-1-{[(4S)-6,6-difluoro-4-methylspiro[2.3]hexan-4-yl]methyl}-N-[2-(methylsulfanyl)pyridin-4-yl]-4-(trifluoromethyl)-1H-pyrazole-5-carboxamide (Intermediate 327b). Chiral-HPLC (Chiralpak IC; 250 × 20 mm, 5 μm; hexane/DCM/EtOH 80/10/10) Peak 1, Example 92c (45 mg, 21%). LCMS m/z = 518 [M + H]$^+$; $^1$H-NMR (400 MHz, DMSO-d$_6$): 11.69 (s, 1H), 8.66 (d, 1H), 8.36 (s, 1H), 7.79-7.77 (m, 1H), 4.42 (s, 1H), 4.14-4.02 (m, 2H), 3.15 (s, 3H), 2.94-2.84 (m, 1H), 2.45-2.32 (m, 1H), 1.95-1.93 (m, 1H), 1.23-1.18 (m, 1H), 1.00-0.97 (m, 2H), 0.90 (s, 3H), 0.87-0.77 (m, 4H), 0.71-0.70 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 4.55 min (first eluting). Peak 2, Example 92d (45 mg, 21%). LCMS m/z = 518 [M + H]$^+$; $^1$H-NMR (400 MHz, DMSO-d$_6$): 11.69 (s, 1H), 8.66 (d, 1H), 8.36 (s, 1H), 7.79-7.77 (m, 1H), 4.42 (s, 1H), 4.14-4.10 (m, 1H), 4.05-4.02 (m, 1H), 3.15 (s, 3H), 2.94-2.84 (m, 1H), 2.45-2.36 (m, 1H), 1.95-1.93 (m, 1H), 1.23-1.19 (m, 1H), 1.00-0.97 (m, 2H), 0.90 (s, 3H), 0.87-0.77 (m, 4H), 0.71-0.70 (m, 1H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.22 min (second eluting). |
| 98a/98b | 3-Cyclopropyl-N-(2-(S-methylsulfonimidoyl)pyridin-4-yl)-4-(trifluoromethyl)-1-((1-(trifluoromethyl)cyclopentyl)methyl)-1H-pyrazole-5-carboxamide, synthesized in the form of enantiomer 1 of 3-cyclopropyl-N-(2-(S-methylsulfonimidoyl)pyridin-4-yl)-4-(trifluoromethyl)-1-((1-(trifluoromethyl)cyclopentyl)methyl)-1H-pyrazole-5-carboxamide (98a) and enantiomer 2 3-cyclopropyl-N-(2-(S-methylsulfonimidoyl)pyridin-4-yl)-4-(trifluoromethyl)-1-((1-(trifluoromethyl)cyclopentyl)methyl)-1H-pyrazole-5-carboxamide (98b) 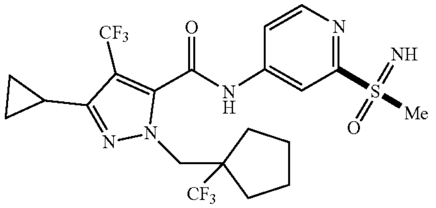 98a and |

-continued

| Example | Name/Structure/Starting Material/Data |
|---|---|
| | 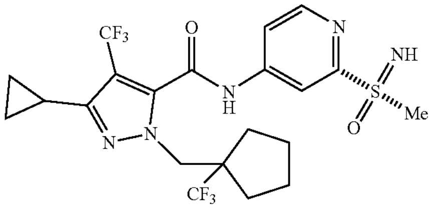<br>98b<br>ArSMe: 3-cyclopropyl-N-[2-(methylsulfanyl)pyridin-4-yl]-4-(trifluoromethyl)-1-{[1-(trifluoromethyl)cyclopentyl] methyl}-1H-pyrazole-5-carboxamide (Intermediate 301).<br>Chiral-HPLC (Chiralpak-IC, 250 x 20 mm, 5 μm; hexane/DCM/EtOH 70/15/15)<br>Peak 1, Example 98a (69 mg, 25%). LCMS m/z = 524 $[M + H]^+$; $^1$H-NMR (400 MHz, DMSO-$d_6$): 11.74 (s, 1H), 8.67-8.65 (m, 1H), 8.35 (s, 1H), 7.82-7.81 (m, 1H), 4.30 (s, 2H), 3.16 (s, 3H), 1.96-1.91 (m, 3H), 1.78-1.74 (m, 2H), 1.58-1.50 (m, 4H), 1.00-0.98 (m, 2H), 0.84-0.83 (m, 2H); Chiral HPLC: column: Chiralpak IC (4.6 x 250 mm) 5 μm, mobile phase: hexane/DCM/EtOH/iPr$NH_2$ 50/25/25/0.1, flow rate: 1.0 mL/min, $R_t$ = 4.13 min (first eluting).<br>Peak 2, Example 98b (73 mg, 27%). LCMS m/z = 524 $[M + H]^+$; $^1$H-NMR (400 MHz, DMSO-$d_6$): 11.75 (s, 1H), 8.68-8.67 (m, 1H), 8.36 (s, 1H), 7.82-7.81 (m, 1H), 4.30 (s, 2H), 3.18 (s, 3H), 1.96-1.91 (m, 3H), 1.78-1.73 (m, 2H), 1.58-1.50 (m, 4H), 1.00-0.98 (m, 2H), 0.84-0.83 (m, 2H); Chiral HPLC: column: Chiralpak IC (4.6 x 250 mm) 5 μm, mobile phase: hexane/DCM/EtOH/iPr$NH_2$ 50/25/25/0.1, flow rate: 1.0 mL/min, $R_t$ = 4.67 min (second eluting). |
| 103a/103b | 3-Cyclopropyl-1-((2,2-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((2,2-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide (103a) and enantiomer 2 of 3-cyclopropyl-1-((2,2-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide (103b)<br>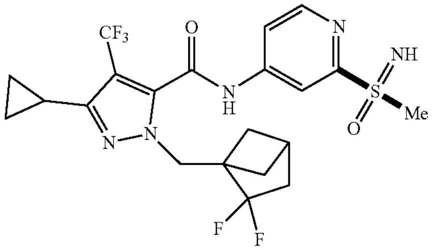<br>103a<br>and<br>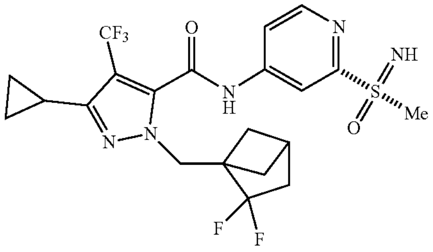<br>103b<br>ArSMe: 3-cyclopropyl-1-((2,2-difluorobicyclo[2.1.1]hexan-1-yl)methyl)-N-(2-(methylthio)pyridin-4-yl)-4-(trifluoromethyl)-1H-pyrazole-5-carboxamide (Intermediate 302).<br>Chiral-HPLC (Chiralpak-IC, 250 x 20 mm, 5 μm; hexane/DCM/iPrOH 70/15/15)<br>Peak 1, Example 103a (32 mg, 20%). LCMS m/z = 504 $[M + H]^+$; $^1$H-NMR (400 MHz, DMSO-$d_6$): 11.68 (s, 1H), 8.65 (d, 1H), 8.35 (s, 1H), 7.79 (d, 1H), 4.32 (s, 2H), 3.16 (s, 3H), 2.39 (bs, 1H), 2.08 (t, 2H), 1.95-1.94 (m, 1H), 1.64 (bs, 2H), 1.45-1.44 (m, 2H), 1.01-0.96 (m, 2H), 0.87-0.83 (m, 2H); Chiral HPLC: column: Chiralpak IC (4.6 x 250 mm) 5 μm, mobile phase: hexane/DCM/EtOH/ iPr$NH_2$ 60/20/20/0.1, flow rate: 1.0 mL/min, $R_t$ = 6.84 min (first eluting).<br>Peak 2, Example 103b (30 mg, 19%). LCMS m/z = 504 $[M + H]^+$; $^1$H-NMR (400 MHz, DMSO-$d_6$): 11.68 (s, 1H), 8.66 (d, 1H), 8.35 (s, 1H), 7.78 (d, 1H), 4.32 (s, 2H), 3.16 (s, 3H), 2.39 (bs, 1H), 2.08 (t, 2H), 1.95-1.94 (m, 1H), 1.64 (bs, 2H), 1.46-1.44 (m, 2H), 1.01-0.96 (m, 2H), 0.87-0.83 (m, 2H); Chiral HPLC: column: Chiralpak IC (4.6 x 250 mm) 5 μm, mobile phase: hexane/DCM/EtOH/iPr$NH_2$ 60/20/20/0.1, flow rate: 1.0 mL/min, $R_t$ = 7.71 min (second eluting). |

-continued

| Example | Name/Structure/Starting Material/Data |
|---|---|
| 106a/106b | 3-Cyclopropyl-1-((4-fluorobicyclo[2.2.1]heptan-1-yl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopropyl-1-((4-fluorobicyclo[2.2.1 ]heptan-1-yl)methyl)-N-(2-(S-methylsulfonimidoyl)pyridin-4-yl)-4-(trifluoromethyl)-1H-pyrazole-5-carboxamide (106a) and enantiomer 2 of 3-cyclopropyl-1-((4-fluorobicyclo[2.2.1 ]heptan-1-yl)methyl)-N-(2-(S-methylsulfonimidoyl)pyridin-4-yl)-4-(trifluoromethyl)-1H-pyrazole-5-carboxamide (106b)<br>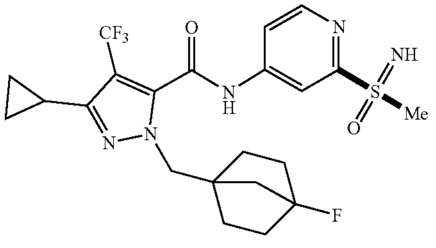<br>160a<br>and<br>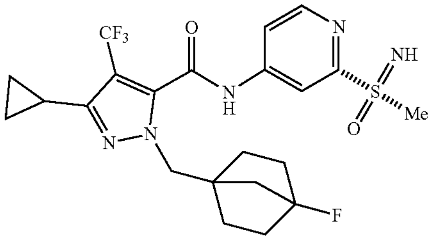<br>160b<br>ArSMe: 3-cyclopropyl-1-({4-fluorobicyclo[2.2.1]heptan-1-yl}methyl)-N-[2-(methylsulfanyl)pyridin-4-yl]-4-(trifluoromethyl)-1H-pyrazole-5-carboxamide (Intermediate 294).<br>Chiral-HPLC (Chiralart Cellulose SC, 250 x 20 mm, 5 μm; hexane/DCM/EtOH 80/10/10)<br>Peak 1, Example 106a (38 mg, 24%). LCMS m/z = 500 $[M + H]^+$; $^1H$-NMR (400 MHz, DMSO-$d_6$): 11.66 (s, 1H), 8.66 (d, 1H), 8.37 (s, 1H), 7.77 (d, 1H), 4.41 (s, 1H), 4.17 (s, 2H), 3.15 (s, 3H), 1.95 (s, 1H), 1.82-1.63 (m, 6H), 1.57 (s, 2H), 1.37-1.35 (m, 2H), 0.98-0.96 (m, 2H), 0.85-0.84 (m, 2H); Chiral HPLC: column: Chiralpak IC (4.6 x 250 mm) 5 μm, mobile phase: hexane/DCM/EtOH/ $iPrNH_2$ 60/20/20/0.1, flow rate: 1.0 mL/min, $R_t$ = 4.95 min (first eluting).<br>Peak 2, Example 106b (37 mg, 23%). LCMS m/z = 500 $[M + H]^+$; $^1H$-NMR (400 MHz, DMSO-$d_6$): 11.66 (s, 1H), 8.66 (d, 1H), 8.37 (s, 1H), 7.77 (d, 1H), 4.42 (s, 1H), 4.17 (s, 2H), 3.15 (s, 3H), 1.94 (s, 1H), 1.76-1.63 (m, 6H), 1.57 (s, 2H), 1.37-1.35 (m, 2H), 0.98-0.96 (m, 2H), 0.85-0.84 (m, 2H); Chiral HPLC: column: Chiralpak IC (4.6 x 250 mm) 5 μm, mobile phase: hexane/DCM/EtOH/$iPrNH_2$ 60/20/20/0.1, flow rate: 1.0 mL/min, $R_t$ = 5.90 min (second eluting). |
| 111a/111b | 1-((3,3-Difluoro-1-methylcyclobutyl)methyl)-3-(3-fluorobicyclo[1.1.1]pentan-1-yl)-N-(3-(S-methylsulfonimidoyl)phenyl)-4-(trifluoromethyl)-1H-pyrazole-5-carboxamide, synthesized in the form of enantiomer 1 of 1-((3,3-difluoro-1-methylcyclobutyl)methyl)-3-(3-fluorobicyclo[1.1.1]pentan-1-yl)-N-(3-(S-methylsulfonimidoyl)phenyl)-4-(trifluoromethyl)-1H-pyrazole-5-carboxamide (111a) and enantiomer 2 of 1-((3,3-difluoro-1-methylcyclobutyl)methyl)-3-(3-fluorobicyclo[1.1.1]pentan-1-yl)-N-(3-(S-methylsulfonimidoyl)phenyl)-4-(trifluoromethyl)-1H-pyrazole-5-carboxamide (111b)<br>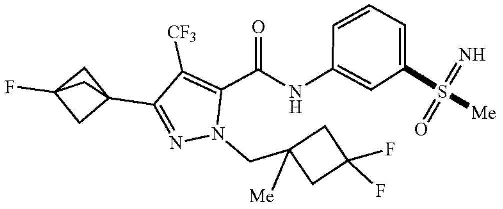<br>111a<br>and |

-continued

| Example | Name/Structure/Starting Material/Data |
|---|---|
| | 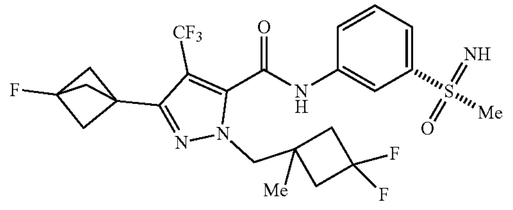<br>111b<br>ArSMe: 1-((3,3-difluoro-1-methylcyclobutyl)methyl)-N-(4-fluoro-3-(methylthio)phenyl)-3-(1-fluorocyclopropyl)-4-(trifluoromethyl)-1H-pyrazole-5-carboxamide (Intermediate 322).<br>Chiral-SFC (Chiral ART Cellulose-SC; 250 x 30 mm, 5 μm; 10% (0.5% $NH_3$ in iPrOH) in $CO_2$)<br>Peak 1, Example 111a (185 mg, 6%). LCMS m/z = 535 $[M + H]^+$; $^1$H-NMR (400 MHz, DMSO-$d_6$): 11.36 (s, 1H), 8.27 (t, 1H), 7.86 (dd, 1H), 7.73 (d, 1H), 7.62 (t, 1H), 4.25 (s, 1H), 4.22 (s, 2H), 3.06 (s, 3H), 2.79-2.76 (m, 2H), 2.44 (d, 6H), 2.35-2.29 (m, 2H), 1.11 (s, 3H); Chiral SFC: column: Chiralpak IC, 250 x 4.6 mm, 5 μm; co-solvent: iPrOH; flow: 3 mL/min; % of co-solvent: 10%; ABPR: 1500 psi; T: 30° C.; $R_t$ = 3.07 min (first eluting).<br>Peak 2, Example 111b (155 mg, 5%). LCMS m/z = 535 $[M + H]^+$; $^1$H-NMR (400 MHz, DMSO-$d_6$): 11.36 (s, 1H), 8.27 (t, 1H), 7.86 (d, 1H), 7.73 (d, 1H), 7.64 (t, 1H), 4.25 (s, 1H), 4.22 (s, 2H), 3.06 (s, 3H), 2.82-2.71 (m, 2H), 2.44 (d, 6H), 2.36-2.26 (m, 2H), 1.11 (s, 3H); Chiral SFC: column: Chiralpak IC, 250 x 4.6 mm, 5 μm; co-solvent: iPrOH; flow: 3 mL/min; % of co-solvent: 10%; ABPR: 1500 psi; T: 30° C.; $R_t$ = 4.41 min (second eluting). |
| 113a/113b | 1-((3,3-Difluoro-1-methylcyclobutyl)methyl)-4-(difluoromethyl)-3-(3-fluorobicyclo[1.1.1]pentan-1-yl)-N-(3-(S-methylsulfonimidoyl)phenyl)-1H-pyrazole-5-carboxamide, synthesized in the form of enantiomer 1 of 1-((3,3-difluoro-1-methylcyclobutyl)methyl)-4-(difluoromethyl)-3-(3-fluorobicyclo[1.1.1]pentan-1-yl)-N-(3-(S-methylsulfonimidoyl)phenyl)-1H-pyrazole-5-carboxamide (113a) and enantiomer 2 01-((3,3-difluoro-1-methylcyclobutyl)methyl)-4-(difluoromethyl)-3-(3-fluorobicyclo[1.1.1]pentan-1-yl)-N-(3-(S-methylsulfonimidoyl)phenyl)-1H-pyrazole-5-carboxamide (113b)<br>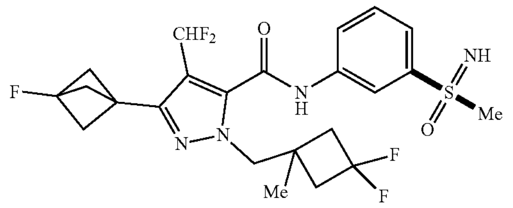<br>113a<br>and<br>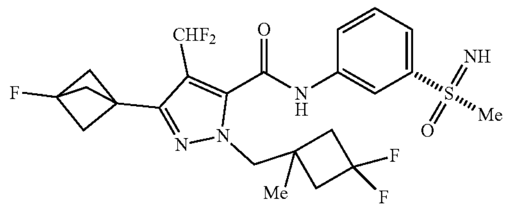<br>113b<br>ArSMe: 1-((3,3-difluoro-1-methylcyclobutyl)methyl)-4-(difluoromethyl)-3-(3-fluorobicyclo[1.1.1]pentan-1-yl)-N-(3-(methylthio)phenyl)-1H-pyrazole-5-carboxamide (Intermediate 323).<br>Chiral-SFC (Chiralpak AS-H; 250 x 30 mm, 5 μm; 30% iPrOH in $CO_2$)<br>Peak 1, Example 113a (13 mg, 6%). LCMS m/z = 517 $[M + H]^+$; $^1$H-NMR (400 MHz, DMSO-$d_6$): 11.21 (brs, 1H), 8.30 (t, 1H), 7.84 (d, 1H), 7.72 (dd, 1H), 7.60 (t, 1H), 7.07 (t, 1H), 4.26 (s, 3H), 3.06 (s, 3H), 2.79-2.68 (m, 2H), 2.43 (d, 6H), 2.35-2.23 (m, 2H), 1.08 (s, 3H); Chiral SFC: column: Chiralpak AS-H, 150 x 4.6 mm, 3 μm; co-solvent: MeCN; flow: 3 mL/min; % of co-solvent: 20%; ABPR: 1500 psi; T: 30° C.; $R_t$ = 1.07 min (first eluting).<br>Peak 2, Example 113b (10 mg, 45%). LCMS m/z = 535 $[M + H]^+$; $^1$H-NMR (400 MHz, DMSO-$d_6$): 11.19 (s, 1H), 8.30 (s, 1H), 7.85 (d, 1H), 7.71 (d, 1H), 7.60 (t, 1H), 7.07 (t, 1H), 4.27 (s, 2H), 4.23 (s, 1H), 3.06 (s, 3H), 2.79-2.66 (m, 2H), 2.43 (s, 6H), 2.35-2.24 (m, 2H), 1.08 (s, 3H), Chiral SFC: column: Chiralpak AS-H, 150 x 4.6 mm, 3 μm; co-solvent: MeCN; flow: 3 mL/min; % of co-solvent: 20%; ABPR: 1500 psi; T: 30° C.; $R_t$ = 4.30 min (second eluting). |

-continued

| Example | Name/Structure/Starting Material/Data |
|---|---|
| 126a/126b | 1-((3,3-Difluoro-1-methylcyclobutyl)methyl)-N-(4-fluoro-3-(S-methylsulfonimidoyl)phenyl)-3-(1-fluorocyclopropyl)-4-(trifluoromethyl)-1H-pyrazole-5-carboxamide, synthesized in the form of enantiomer 1 of 1-((3,3-difluoro-1-methylcyclobutyl)methyl)-N-(4-fluoro-3-(S-methylsulfonimidoyl)phenyl)-3-(1-fluorocyclopropyl)-4-(trifluoromethyl)-1H-pyrazole-5-carboxamide (126a) and enantiomer 2 of 1-((3,3-difluoro-1-methylcyclobutyl)methyl)-N-(4-fluoro-3-(S-methylsulfonimidoyl)phenyl)-3-(1-fluorocyclopropyl)-4-(trifluoromethyl)-1H-pyrazole-5-carboxamide (126b) 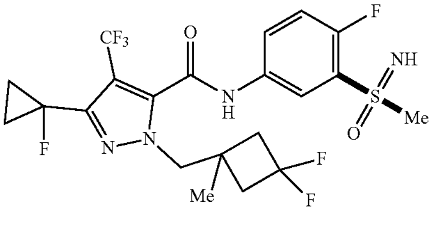 126a and 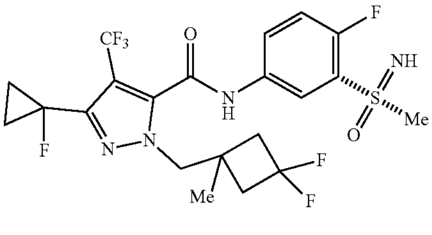 126b ArSMe: 1-((3,3-difluoro-1-methylcyclobutyl)methyl)-N-(4-fluoro-3-(methylthio)phenyl)-3-(1-fluorocyclopropyl)-4-(trifluoromethyl)-1H-pyrazole-5-carboxamide (Intermediate 313). Chiral-SFC (Chiralpak AD-H, 250 x 30 mm, 5 μm; 10% MeOH in $CO_2$) Peak 1, Example 126a (22 mg, 9%). LCMS m/z = 527 $[M + H]^+$; $^1$H-NMR (400 MHz, DMSO-$d_6$): 11.43 (s, 1H), 8.23-8.21 (m, 1H), 7.94-7.90 (m, 1H), 7.47 (t, 1H), 4.75 (s, 1H), 4.26 (s, 2H), 3.20 (s, 3H), 2.82-2.71 (m, 2H), 2.39-2.28 (m, 2H), 1.51-1.43 (m, 2H), 1.20-1.18 (m, 2H), 1.10 (s, 3H). Chiral SFC: column: Chiralpak AD-H, 250 x 4.6 mm, 5 μm; co-solvent: MeOH, flow: 3 mL/min; % of co-solvent : 10%; ABPR: 1500 psi; T: 30° C.; $R_t$ = 2.02 min (first eluting). Peak 2, Example 126b (22 mg, 9%). LCMS m/z = 527 $[M + H]^+$; $^1$H-NMR (400 MHz, DMSO-$d_6$): 11.43 (s, 1H), 8.23-8.21 (m, 1H), 7.94-7.91 (m, 1H), 7.47 (t, 1H), 4.74 (s, 1H), 4.25 (s, 2H), 3.20 (s, 3H), 2.82-2.71 (m, 2H), 2.35-2.28 (m, 2H), 1.51-1.43 (m, 2H), 1.20-1.14 (m, 2H), 1.09 (s, 3H). Chiral SFC: column: Chiralpak AD-H, 250 x 4.6 mm, 5 μm; co-solvent: MeOH, flow: 3 mL/min; % of co-solvent: 10%; ABPR: 1500 psi; T: 30° C.; $R_t$ = 2.81 min (second eluting). |
| 127a/127b | 1-((3,3-Difluoro-1-methylcyclobutyl)methyl)-N-(3-fluoro-5-(S-methylsulfonimidoyl)phenyl)-3-(1-fluorocyclopropyl)-4-(trifluoromethyl)-1H-pyrazole-5-carboxamide, synthesized in the form of enantiomer 1 of 1-((3,3-difluoro-1-methylcyclobutyl)methyl)-N-(3-fluoro-5-(S-methylsulfonimidoyl)phenyl)-3-(1-fluorocyclopropyl)-4-(trifluoromethyl)-1H-pyrazole-5-carboxamide (127a) and enantiomer 2 of 1-((3,3-difluoro-1-methylcyclobutyl)methyl)-N-(3-fluoro-5-(S-methylsulfonimidoyl)phenyl)-3-(1-fluorocyclopropyl)-4-(trifluoromethyl)-1H-pyrazole-5-carboxamide (127b) 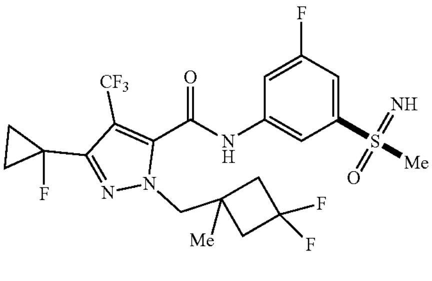 127a and |

-continued

| Example | Name/Structure/Starting Material/Data |
|---|---|
| | 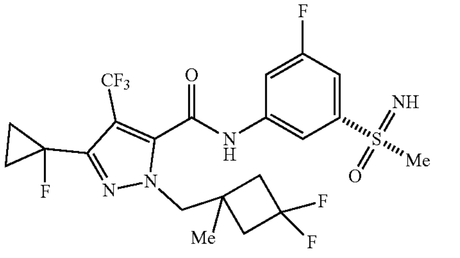<br>127b<br>ArSMe: 1-((3,3-difluoro-1-methylcyclobutyl)methyl)-N-(3-fluoro-5-(methylthio)phenyl)-3-(1-fluorocyclopropyl)-4-(trifluoromethyl)-1H-pyrazole-5-carboxamide (Intermediate 314).<br>Chiral-SFC (Chiralpak AD-H, 250 × 30 mm, 5 μm; 10% MeOH in $CO_2$)<br>Peak 1, Example 127a (435 mg, 16%). LCMS m/z = 527 $[M + H]^+$; $^1$H-NMR (400 MHz, DMSO-$d_6$): 11.63 (s, 1H), 8.02 (s, 1H), 7.82 (d, 1H), 7.56 (d, 1H), 4.43 (s, 1H), 4.27 (s, 2H), 3.11 (s, 3H), 2.81-2.67 (m, 2H), 2.38-2.28 (m, 2H), 1.52-1.44 (m, 2H), 1.20-1.14 (m, 2H), 1.09 (m, 3H). Chiral SFC: column: Chiralpak AS-H, 150 × 4.6 mm, 5 μm; co-solvent: MeOH, flow: 3 mL/min; % of co-solvent: 10%; ABPR: 1500 psi; T: 30° C.; $R_t$ = 1.05 min (first eluting).<br>Peak 2, Example 127b (430 mg, 16%). LCMS m/z = 527 $[M + H]^+$; $^1$H-NMR (400 MHz, DMSO-$d_6$): 11.63 (s, 1H), 8.02 (s, 1H), 7.84-7.81 (m, 1H), 7.56 (d, 1H), 4.43 (s, 1H), 4.27 (s, 2H), 3.17 (s, 3H), 2.82-2.71 (m, 2H), 2.38-2.28 (m, 2H), 1.52-1.44 (m, 2H), 1.20-1.14 (m, 2H), 1.09 (m, 3H). Chiral SFC: column: Chiralpak AD-H, 250 × 4.6 mm, 5 μm; co-solvent: MeOH, flow: 3 mL/min; % of co-solvent: 10%; ABPR: 1500 psi; T: 30° C.; $R_t$ = 3.18 min (second eluting). |
| 130a/130b | 1-((3,3-Difluoro-1-methylcyclobutyl)methyl)-N-(3-(S-(difluoromethyl)sulfonimidoyl)phenyl)-3-(1-fluorocyclopropyl)-4-(trifluoromethyl)-1H-pyrazole-5-carboxamide, synthesized in the form of enantiomer 1 of 1-((3,3-difluoro-1-methylcyclobutyl)methyl)-N-(3-(S-(difluoromethyl)sulfonimidoyl)phenyl)-3-(1-fluorocyclopropyl)-4-(trifluoromethyl)-1H-pyrazole-5-carboxamide (130a) and enantiomer 2 of 1-((3,3-difluoro-1-methylcyclobutyl)methyl)-N-(3-(S-(difluoromethyl)sulfonimidoyl)phenyl)-3-(1-fluorocyclopropyl)-4-(trifluoromethyl)-1H-pyrazole-5-carboxamide (130b)<br>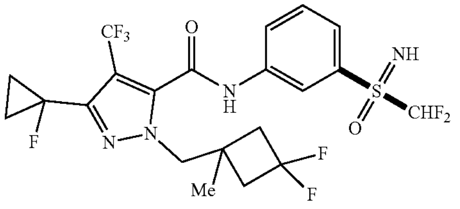<br>130a<br>and<br>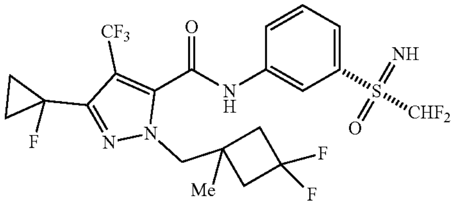<br>130b<br>ArSalkyl: 1-((3,3-difluoro-1-methylcyclobutyl)methyl)-N-(3-((difluoromethyl)thio)phenyl)-3-(1-fluorocyclopropyl)-4-(trifluoromethyl)-1H-pyrazole-5-carboxamide (Intermediate 320).<br>Chiral-SFC (Ciralpak AS-H, 250 × 30 mm, 5 μm; 10% MeOH in $CO_2$)<br>Peak 1, Example 130a (45 mg, 21%). LCMS m/z = 545 $[M + H]^+$; $^1$H-NMR (400 MHz, DMSO-$d_6$): 11.52 (s, 1H), 8.35 (s, 1H), 8.01 (d, 1H), 7.77-7.70 (m, 2H), 6.91 (t, 1H), 5.69 (s, 1H), 4.27 (s, 2H), 2.82-2.67 (m, 2H), 2.38-2.28 (m, 2H), 1.52-1.43 (m, 2H), 1.23-1.16 (m, 2H), 1.09 (s, 3H); Chiral SFC: column: Chiralpak AS-H, 150 × 4.6 mm, 5 μm; co-solvent: MeOH, flow: 3 mL/min; % of co-solvent: 10%; ABPR: 1500 psi; T: 30° C.; $R_t$ = 1.10 min (first eluting).<br>Peak 2, Example 130b (55 mg, 26%). LCMS m/z = 545 $[M + H]^+$; $^1$H-NMR (400 MHz, DMSO-$d_6$): 11.52 (s, 1H), 8.36 (s, 1H), 8.02-7.99 (m, 1H), 7.78-7.71 (m, 2H), 6.91 (t, 1H), 5.70 (s, 1H), 4.27 (s, 2H), 2.81-2.71 (m, 2H), 2.38-2.28 (m, 2H), 1.52-1.41 (m, 2H), 1.22-1.15 (m, 2H), 1.10 (s, 3H); Chiral SFC: column: Chiralpak AS-H, 150 × 4.6 mm, 5 μm; co-solvent: MeOH, flow: 3 mL/min; % of co-solvent: 10%; ABPR: 1500 psi; T: 30° C.; $R_t$ = 2.57 min (second eluting). |

-continued

| Example | Name/Structure/Starting Material/Data |
|---|---|
| 131 | 1-((3,3-Difluoro-1-methylcyclobutyl)methyl)-3-(1-fluorocyclopropyl)-4-(trifluoromethyl)-N-(3-(S-(trifluoromethyl)sulfonimidoyl)phenyl)-1H-pyrazole-5-carboxamide 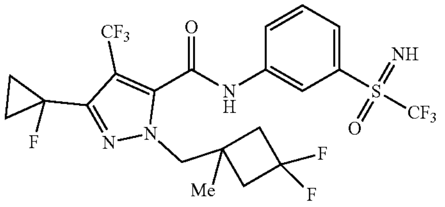 131 ArSalkyl: 1-((3,3-difluoro-1-methylcyclobutyl)methyl)-3-(1-fluorocyclopropyl)-4-(trifluoromethyl)-N-(3-((trifluoromethyl)thio)phenyl)-1H-pyrazole-5-carboxamide Intermediate 321). Example 131 (25 mg, 18%). LCMS m/z = 563 [M + H]$^+$; $^1$H-NMR (400 MHz, DMSO-$d_6$): 11.59 (s, 1H), 8.48 (s, 1H), 8.05 (d, 1H), 7.78 (d, 1H), 7.78 (t, 1H), 6.96 (s, 1H), 4.28 (s, 2H), 2.81-2.66 (m, 2H), 2.37-2.28 (m, 2H), 1.52-1.44 (m, 2H), 1.20-1.14 (m, 2H), 1.09 (s, 3H). |
| 132a/132b | 3-Cyclopropyl-1-((3,3-difluoro-1-methylcyclobutyl)methyl)-N-(4-fluoro-3-(S-methylsulfonimidoyl)phenyl)-4-(trifluoromethyl)-1H-pyrazole-5-carboxamide, synthesized in the form of enantiomer 1 of 3-cyclopropyl-1-((3,3-difluoro-1-methylcyclobutyl)methyl)-N-(4-fluoro-3-(S-methylsulfonimidoyl)phenyl)-4-(trifluoromethyl)-1H-pyrazole-5-carboxamide (132a) and enantiomer 2 of 3-cyclopropyl-1-((3,3-difluoro-1-methylcyclobutyl)methyl)-N-(4-fluoro-3-(S-methylsulfonimidoyl)phenyl)-4-(trifluoromethyl)-1H-pyrazole-5-carboxamide (132b) 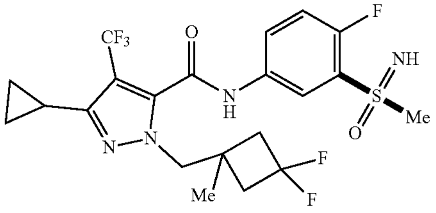 132a and 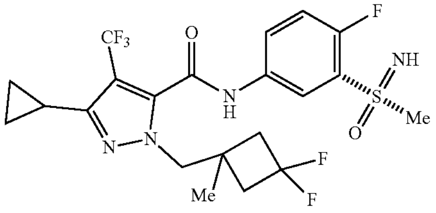 132b ArSMe: 3-cyclopropyl-1-((3,3-difluoro-1-methylcyclobutyl)methyl)-N-(4-fluoro-3-(methylthio)phenyl)-4-(trifluoromethyl)-1H-pyrazole-5-carboxamide (Intermediate 311). Chiral-SFC (Ciralpak IG, 250 x 30 mm, 5 µm; 25% (hexane/iPrOH/MeOH 50/40/10) in $CO_2$) Peak 1, Example 132a (43 mg, 22%). LCMS m/z = 509 [M + H]$^+$; $^1$H-NMR (400 MHz, DMSO-$d_6$): 11.31 (s, 1H), 8.20 (d, 1H), 7.90 (d, 1H), 7.46 (t, 1H), 4.73 (s, 1H ), 4.14 (s, 2H), 3.19 (s, 3H), 2.75-2.64 (m, 2H), 2.32-2.28 (m, 2H), 1.94 (bs, 1H), 1.06 (s, 3H), 0.98-0.83 (m, 4H); Chiral SFC: column: Chiralpak IG, 250 x 4.6 mm, 5 µm; co-solvent: 0.3% $iPrNH_2$ in hexane/MeOH/iPrOH 60/30/10, flow: 3 mL/min; % of co-solvent: 25%; ABPR: 100 bar; T: 35° C.; $R_t$ = 2.44 min (first eluting). Peak 2, Example 132b (47 mg, 25%). LCMS m/z = 509 [M + H]$^+$; $^1$H-NMR (400 MHz, DMSO-$d_6$): 11.31 (s, 1H), 8.23-8.21 (dd, 1H), 7.93-7.89 (m, 1H), 7.46 (t, 1H), 4.73 (s, 1H ), 4.14 (s, 2H), 3.19 (s, 3H), 2.79-2.66 (m, 2H), 2.33-2.24 (m, 2H), 1.95-1.91 (m, 1H), 1.06 (s, 3H), 0.98-0.95 (m, 2H), 0.85-0.82 (m, 2H); Chiral SFC: column: Chiralpak IG, 250 x 4.6 mm, 5 µm; co-solvent: 0.3% $iPrNH_2$ in hexane/MeOH/iPrOH 60/30/10, flow: 3 mL/min; % of co-solvent: 25%; ABPR: 100 bar; T: 35° C.; $R_t$ = 2.92 min (second eluting). |
| 133a/133b | 1-((3,3-Difluoro-1-methylcyclobutyl)methyl)-4-(difluoromethyl)-N-(4-fluoro-3-(S-methylsulfonimidoyl)phenyl)-3-(1-fluorocyclopropyl)-1H-pyrazole-5-carboxamide, synthesized in the form of enantiomer 1 of 1-((3,3-difluoro-1-methylcyclobutyl)methyl)-4-(difluoromethyl)-N-(4-fluoro-3-(S-methylsulfonimidoyl)phenyl)-3-(1-fluorocyclopropyl)-1H- |

-continued

| Example | Name/Structure/Starting Material/Data |
|---|---|

pyrazole-5-carboxamide (133a) and enantiomer 2 of 1-((3,3-difluoro-1-methylcyclobutyl)methyl)-4-(difluoromethyl)-N-(4-fluoro-3-(S-methylsulfonimidoyl)phenyl)-3-(1-fluorocyclopropyl)-1H-pyrazole-5-carboxamide (133b)

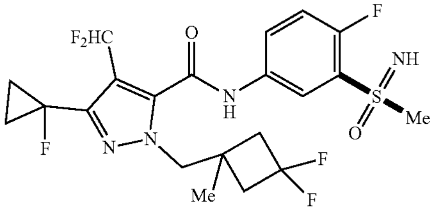

133a and

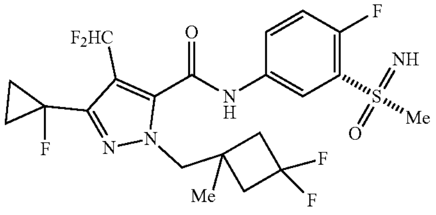

133b

ArSMe: 1-((3,3-difluoro-1-methylcyclobutyl)methyl)-4-(difluoromethyl)-N-(4-fluoro-3-(methylthio)phenyl)-3-(1-fluorocyclopropyl)-1H-pyrazole-5-carboxamide (Intermediate 315).
Chiral-SFC (Ciralpak AS-H, 250 × 30 mm, 5 μm; 50% MeOH in $CO_2$)
Peak 1, Example 133a (35 mg, 23%). LCMS m/z = 509 $[M + H]^+$; $^1H$-NMR (400 MHz, DMSO-$d_6$): 11.23 (bs, 1H), 8.26-8.23 (m, 1H), 7.95-7.91 (m, 1H), 7.46 (t, 1H), 7.17 (t, 1H), 4.72 (s, 1H), 4.28 (s, 2H), 3.19 (s, 3H), 2.85-2.66 (m, 2H), 2.36-2.25 (m, 2H) 1.49-1.40 (m, 2H), 1.17-1.10 (m, 2H), 1.07 (m, 3H); Chiral SFC: column: Chiralpak AS-H, 150 × 4.6 mm, 5 μm; co-solvent: MeOH; flow: 3 mL/min; % of co-solvent: 20%; ABPR: 1500 psi; T: 30° C.; $R_t$ = 0.88 min (first eluting).
Peak 2, Example 133b (46 mg, 30%). LCMS m/z = 509 $[M + H]^+$; $^1H$-NMR (400 MHz, DMSO-$d_6$): 11.23 (bs, 1H), 8.26-8.23 (m, 1H), 7.95-7.91 (m, 1H), 7.46 (t, 1H), 7.17 (t, 1H), 4.72 (s, 1H), 4.28 (s, 2H), 3.19 (s, 3H), 2.85-2.66 (m, 2H), 2.36-2.25 (m, 2H) 1.49-1.40 (m, 2H), 1.19-1.13 (m, 2H), 1.11 (m, 3H); Chiral SFC: column: Chiralpak AS-H, 150 × 4.6 mm, 5 μm; co-solvent: MeOH; flow: 3 mL/min; % of co-solvent: 20%; ABPR: 1500 psi; T: 30° C.; $R_t$ = 6.04 min (second eluting).

134a/134b 134c/134d 3-(1-Fluorocyclopropyl)-N-(3-(S-methylsulfonimidoyl)phenyl)-4-(trifluoromethyl)-1-(((trans)-2-(trifluoromethyl)cyclopropyl)methyl)-1H-pyrazole-5-carboxamide, synthesized in the form of diastereomer 1 of 3-(1-fluorocyclopropyl)-N-(3-(S-methylsulfonimidoyl)phenyl)-4-(trifluoromethyl)-1-(((trans)-2-(trifluoromethyl)cyclopropyl)methyl)-1H-pyrazole-5-carboxamide (134a), diastereomer 2 of 3-(1-fluorocyclopropyl)-N-(3-(S-methylsulfonimidoyl)phenyl)-4-(trifluoromethyl)-1-(((trans)-2-(trifluoromethyl)cyclopropyl)methyl)-1H-pyrazole-5-carboxamide (134b), diastereomer 3 of 3-(1-fluorocyclopropyl)-N-(3-(S-methylsulfonimidoyl)phenyl)-4-(trifluoromethyl)-1-(((trans)-2-(trifluoromethyl)cyclopropyl)methyl)-1H-pyrazole-5-carboxamide (134c) and diastereomer 4 of 3-(1-fluorocyclopropyl)-N-(3-(S-methylsulfonimidoyl)phenyl)-4-(trifluoromethyl)-1-(((trans)-2-(trifluoromethyl)cyclopropyl)methyl)-1H-pyrazole-5-carboxamide (134d)

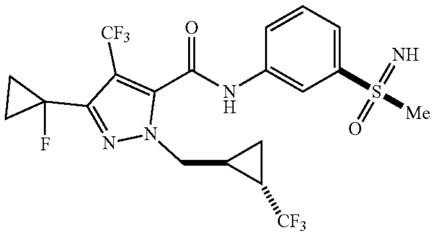

134a and

-continued

| Example | Name/Structure/Starting Material/Data |
| --- | --- |
| | 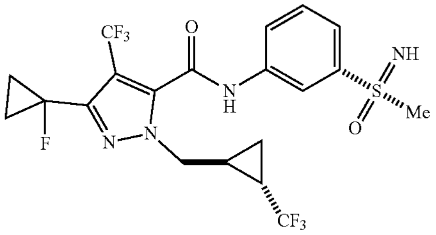<br>134b<br>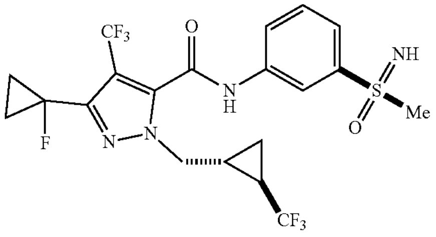<br>134c<br>and<br>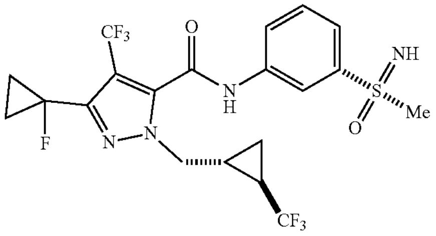<br>134d<br>ArSMe: 3-(1-fluorocyclopropyl)-N-(3-(methylthio)phenyl)-4-(trifluoromethyl)-1-(((trans)-2-(trifluoromethyl)cyclopropyl)methyl)-1H-pyrazole-5-carboxamide (Intermediate 324).<br>Chiral-SFC (Chiralpak AS-H; 250 × 30 mm, 5 μm; 10% MeOH in $CO_2$)<br>Peak 1, Example 134a (16 mg, 4% over two steps). LCMS m/z = 513 $[M + H]^+$; $^1H$-NMR (400 MHz, DMSO-$d_6$): 11.46 (s, 1H), 8.31 (t, 1H), 7.87 (dd, 1H), 7.74 (d, 1H), 7.63 (t, 1H), 4.26 (s, 1H), 4.18 (d, 2H), 3.07 (s, 3H), 2.07-2.00 (m, 1H), 1.71-1.66 (m, 1H), 1.52-1.44 (m, 2H), 1.21-1.16 (m, 2H), 1.07-0.95 (s, 2H); Chiral SFC: column: LUX Cellulose-4, 150 × 4.6 mm, 3 μm; co-solvent: iPrOH; flow: 3 mL/min; % of co-solvent: 10%; ABPR: 1500 psi; T: 30° C.; $R_t$ = 3.63 min (first eluting).<br>Peak 2, Example 134b (18 mg, 4% over two steps). LCMS m/z = 513 $[M + H]^+$; $^1H$-NMR (400 MHz, DMSO-$d_6$): 11.46 (s, 1H), 8.31 (s, 1H), 7.86 (d, 1H), 7.74 (d, 1H), 7.63 (t, 1H), 4.26 (s, 1H), 4.18 (d, 2H), 3.07 (s, 3H), 2.07-2.01 (m, 1H), 1.72-1.64 (m, 1H), 1.50-1.44 (m, 2H), 1.20-1.15 (m, 2H), 1.07-0.95 (s, 2H); Chiral SFC: column: LUX Cellulose-4, 150 × 4.6 mm, 3 μm; co-solvent: iPrOH; flow: 3 mL/min; % of co-solvent: 10%; ABPR: 1500 psi; T: 30° C.; $R_t$ = 4.54 min (second eluting).<br>Peak 3, Example 134c (20 mg, 5% over two steps). LCMS m/z = 513 $[M + H]^+$; $^1H$-NMR (400 MHz, DMSO-$d_6$): 11.46 (s, 1H), 8.30 (s, 1H), 7.85 (d, 1H), 7.72 (s, 1H), 7.63 (d, 1H), 4.25 (s, 1H), 4.19 (d, 2H), 3.07 (s, 3H), 2.06-2.00 (m, 1H), 1.71-1.66 (m, 1H), 1.50-1.45 (m, 2H), 1.20-1.16 (m, 2H), 1.04-0.95 (s, 2H); Chiral SFC: column: Chiralpak AS-H, 150 × 4.6 mm, 5 μm; co-solvent: 0.5% $iPrNH_2$ in iPrOH; flow: 3 mL/min; % of co-solvent: 10%; ABPR: 1500 psi; T: 30° C.; $R_t$ = 8.26 min (first eluting).<br>Peak 4, Example 134d (18 mg, 4% over two steps). LCMS m/z = 513 $[M + H]^+$; $^1H$-NMR (400 MHz, DMSO-$d_6$): 11.46 (s, 1H), 8.30 (s, 1H), 7.85 (d, 1H), 7.72 (s, 1H), 7.62 (d, 1H), 4.24 (s, 1H), 4.19 (d, 2H), 3.06 (s, 3H), 2.07-2.00 (m, 1H), 1.71-1.66 (m, 1H), 1.50-1.45 (m, 2H), 1.19-1.16 (m, 2H), 1.04-0.99 (s, 2H); Chiral SFC: column: Chiralpak AS-H, 150 × 4.6 mm, 5 μm; co-solvent: 0.5% $iPrNH_2$ in iPrOH; flow: 3 mL/min; % of co-solvent: 10%; ABPR: 1500 psi; T: 30° C.; $R_t$ = 11.16 min (secondeluting). |
| 135a/135b | 1-((3,3-Difluoro-1-methylcyclobutyl)methyl)-4-(difluoromethyl)-3-(1-fluorocyclopropyl)-N-(3-(S-methylsulfonimidoyl)phenyl)-1H-pyrazole-5-carboxamide, synthesized in the form of enantiomer 1 of 1-((3,3-difluoro-1-methylcyclobutyl)methyl)-4-(difluoromethyl)-3-(1-fluorocyclopropyl)-N-(3-(S-methylsulfonimidoyl)phenyl)-1H-pyrazole-5-carboxamide (135a) and enantiomer 2 of 1-((3,3-difluoro-1-methylcyclobutyl)methyl)-4-(difluoromethyl)-3-(1-fluorocyclopropyl)-N-(3-(S-methylsulfonimidoyl)phenyl)-1H-pyrazole-5-carboxamide (135b) |

-continued

| Example | Name/Structure/Starting Material/Data |
|---|---|
| | 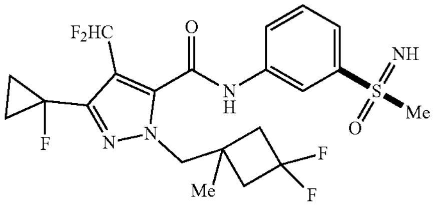<br>135a<br>and<br>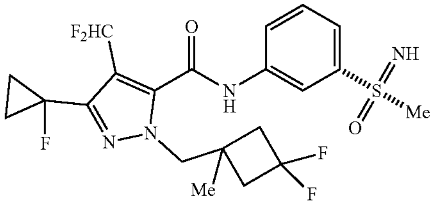<br>135b<br>ArSMe: 1-((3,3-difluoro-1-methylcyclobutyl)methyl)-4-(difluoromethyl)-N-(4-fluoro-3-(methylthio)phenyl)-3-(1-fluorocyclopropyl)-1H-pyrazole-5-carboxamide (Intermediate 325). Chiral-SFC (Cellulose-SC (118), 10% iPrOH in $CO_2$)<br>Peak 1, Example 135a (34 mg, 27%). LCMS m/z = 491 $[M + H]^+$; $^1$H-NMR (400 MHz, DMSO-$d_6$): 11.23 (bs, 1H), 8.30 (t, 1H), 7.87 (d, 1H), 7.72 (d, 1H), 7.61 (t, 1H), 7.31-7.04 (m, 1H), 4.29 (s, 2H), 4.24 (s, 1H), 3.06 (s, 3H), 2.79-2.67 (m, 2H), 2.36-2.25 (m, 2H) 1.50-1.41 (m, 2H), 1.18-1.07 (m, 5H); Chiral SFC: column: Chiralpak IC, 250 × 4.6 mm, 5 μm; co-solvent: iPrOH; flow: 3 mL/min; % of co-solvent: 10%; ABPR: 1500 psi; T: 30° C.; $R_t$ = 9.81 min (first eluting).<br>Peak 2, Example 135b (32 mg, 26%). LCMS m/z = 491 $[M + H]^+$; $^1$H-NMR (400 MHz, DMSO-$d_6$): 11.23 (bs, 1H), 8.30 (t, 1H), 7.87 (d, 1H), 7.72 (d, 1H), 7.61 (t, 1H), 7.31-7.04 (m, 1H), 4.29 (s, 2H), 4.24 (s, 1H), 3.06 (s, 3H), 2.79-2.67 (m, 2H), 2.36-2.25 (m, 2H) 1.50-1.41 (m, 2H), 1.18-1.07 (m, 5H); Chiral SFC: column: Chiralpak IC, 250 × 4.6 mm, 5 μm; co-solvent: iPrOH; flow: 3 mL/min; % of co-solvent: 10%; ABPR: 1500 psi; T: 30° C.; $R_t$ = 16.09 min (second eluting). |
| 136a/136b | 3-Cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide (136a) and diastereomer 2 of 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide (136b)<br>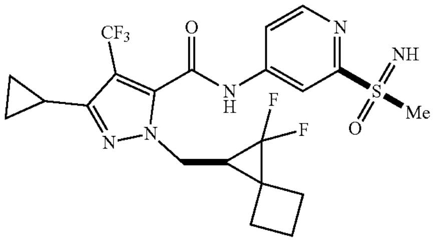<br>136a<br>and |

-continued

| Example | Name/Structure/Starting Material/Data |
|---|---|
| | 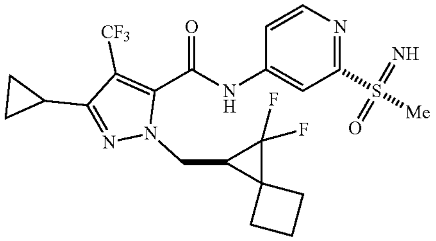<br>136b<br><br>ArSMe: 3-cyclopropyl-1-((2,2-difluorospiro[2.3]hexan-1-yl)methyl)-N-(2-(methylthio)pyridin-4-yl)-4-(trifluoromethyl)-1H-pyrazole-5-carboxamide (Intermediate 307a).<br>Chiral-HPLC (Chiralpak IC; 250 × 20 mm, 5 μm; hexane/DCM/EtOH 80/10/10)<br>Peak 1, Example 136a (55 mg, 27%). LCMS m/z = 504 $[M + H]^+$; $^1$H-NMR (400 MHz, DMSO-$d_6$): 11.76 (s, 1H), 8.66-8.65 (m, 1H), 8.37 (s, 1H), 7.77-7.76 (m, 1H), 4.42 (s, 1H), 4.15-4.06 (m, 2H), 3.15 (s, 3H), 2.21-2.15 (m, 2H), 2.10-1.97 (m, 5H), 1.90-1.83 (m, 1H), 1.01-0.88 (m, 4H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 4.76 min (frst eluting).<br>Peak 2, Example 136b (53 mg, 26%). LCMS m/z = 504 $[M + H]^+$; $^1$H-NMR (400 MHz, DMSO-$d_6$): 11.76 (s, 1H), 8.66-8.65 (m, 1H), 8.37 (s, 1H), 7.77-7.76 (m, 1H), 4.42 (s, 1H), 4.19-4.06 (m, 2H), 3.15 (s, 3H), 2.21-2.17 (m, 2H), 2.11-1.97 (m, 5H), 1.90-1.83 (m, 1H), 1.01-0.88 (m, 4H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.72 min (second eluting). |
| 136c/136d | 3-Cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide, synthesized in the form of diastereomer 3 of 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide (136c) and diastereomer 4 of 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide (136d)<br>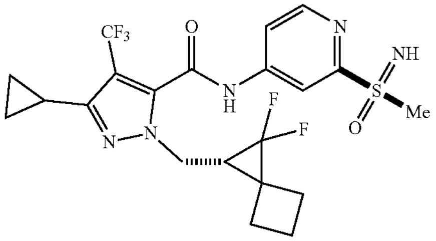<br>136c<br><br>and<br>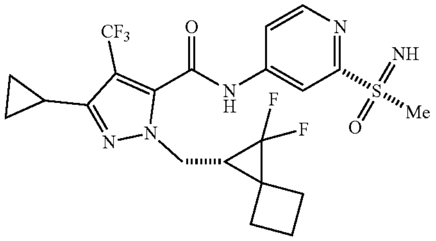<br>136d<br><br>ArSMe: 3-cyclopropyl-1-((2,2-difluorospiro[2.3]hexan-1-yl)methyl)-N-(2-(methylthio)pyridin-4-yl)-4-(trifluoromethyl)-1H-pyrazole-5-carboxamide (Intermediate 307b).<br>Chiral-HPLC (Chiralpak IC; 250 × 20 mm, 5 μm; hexane/DCM/EtOH 80/10/10)<br>Peak 1, Example 136c (61 mg, 30%). LCMS m/z = 504 $[M + H]^+$; $^1$H-NMR (400 MHz, DMSO-$d_6$): 11.76 (s, 1H), 8.66-8.65 (m, 1H), 8.37 (s, 1H), 7.77-7.76 (m, 1H), 4.42 (s, 1H), 4.15-4.10 (m, 2H), 3.15 (s, 3H), 2.21-2.15 (m, 2H), 2.11-1.97 (m, 5H), 1.88-1.85 (m, 1H), 1.01-0.88 (m, 4H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 4.75 min (frst eluting).<br>Peak 2, Example 136d (50 mg, 25%). LCMS m/z = 504 $[M + H]^+$; $^1$H-NMR (400 MHz, DMSO-$d_6$): 11.76 (s, 1H), 8.66-8.65 (m, 1H), 8.37 (s, 1H), 7.77-7.76 (m, 1H), 4.42 (s, 1H), 4.15-4.06 (m, 2H), 3.15 (s, 3H), 2.21-2.15 (m, 2H), 2.10-1.83 (m, 6H), 1.01-0.88 (m, 4H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.51 min (second eluting). |

-continued

| Example | Name/Structure/Starting Material/Data |
|---|---|
| 137a/137b | 3-(Bicyclo[1.1.1]pentan-1-yl)-1-((3,3-difluoro-1-methylcyclobutyl)methyl)-4-(difluoromethyl)-N-(2-(S-methylsulfonimidoyl)pyridin-4-yl)-1H-pyrazole-5-carboxamide, synthesized in the form of enantiomer 1 of 3-(bicyclo[1.1.1]pentan-1-yl)-1-((3,3-difluoro-1-methylcyclobutyl)methyl)-4-(difluoromethyl)-N-(2-(S-methylsulfonimidoyl)pyridin-4-yl)-1H-pyrazole-5-carboxamide (137a) and enantiomer 2 of 3-(bicyclo[1.1.1]pentan-1-yl)-1-((3,3-difluoro-1-methylcyclobutyl)methyl)-4-(difluoromethyl)-N-(2-(S-methylsulfonimidoyl)pyridin-4-yl)-1H-pyrazole-5-carboxamide (137b) 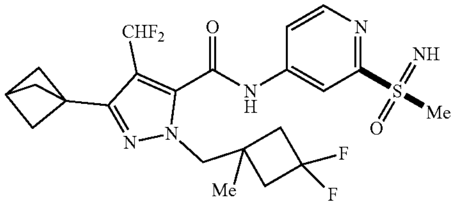 137a and 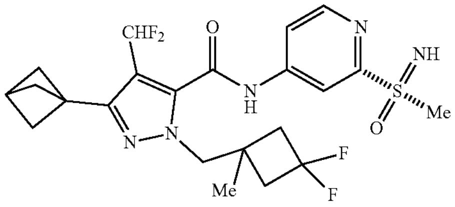 137b ArSMe: 3-(bicyclo[1.1.1]pentan-1-yl)-1-((3,3-difluoro-1-methylcyclobutyl)methyl)-4-(difluoromethyl)-N-(2-(methylthio)pyridin-4-yl)-1H-pyrazole-5-carboxamide (Intermediate 306). Chiral-HPLC (Chiralpak IC; 250 × 20 mm, 5 μm; hexane/DCM/EtOH 80/10/10) Peak 1, Example 137a (37 mg, 44%). LCMS m/z = 500 $[M + H]^+$; $^1H$-NMR (400 MHz, DMSO-$d_6$): 11.56 (s, 1H), 8.65 (d, 1H), 8.37 (s, 1H), 7.78-7.77 (m, 1H), 7.22-6.95 (m, 1H), 4.44 (s, 1H), 4.25 (s, 2H), 3.15 (s, 3H), 2.74-2.67 (m, 2H), 2.53-2.49 (m, 1H), 2.33-2.23 (m, 2H), 2.14 (s, 6H), 1.07 (s, 3H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 5.12 min (first eluting). Peak 2, Example 137b (30 mg, 35%). LCMS m/z = 500 $[M + H]^+$; $^1H$-NMR (400 MHz, DMSO-$d_6$): 11.56 (s, 1H), 8.65 (d, 1H), 8.37 (s, 1H), 7.78-7.77 (m, 1H), 7.22-6.95 (m, 1H), 4.40 (s, 1H), 4.25 (s, 2H), 3.15 (s, 3H), 2.78-2.67 (m, 2H), 2.53-2.49 (m, 1H), 2.33-2.23 (m, 2H), 2.14 (s, 6H), 1.07 (s, 3H); Chiral HPLC: column: Chiralpak IC, 250 × 4.6 mm, 5 μm; mobile phase: hexane/DCM/EtOH/iPrNH$_2$ 60/20/20/0.1; flow: 1 mL/min; $R_t$ = 6.36 min (second eluting). |
| 138a/138b | 1-((3,3-Difluoro-1-methylcyclobutyl)methyl)-4-(difluoromethyl)-N-(4-fluoro-3-(S-methylsulfonimidoyl)phenyl)-3-(3-fluorobicyclo[1.1.1]pentan-1-yl)-1H-pyrazole-5-carboxamide, synthesized in the form of enantiomer 1 of 1-((3,3-difluoro-1-methylcyclobutyl)methyl)-4-(difluoromethyl)-N-(4-fluoro-3-(S-methylsulfonimidoyl)phenyl)-3-(3-fluorobicyclo[1.1.1]pentan-1-yl)-1H-pyrazole-5-carboxamide (138a) and enantiomer 2 of 1-((3,3-difluoro-1-methylcyclobutyl)methyl)-4-(difluoromethyl)-N-(4-fluoro-3-(S-methylsulfonimidoyl)phenyl)-3-(3-fluorobicyclo[1.1.1]pentan-1-yl)-1H-pyrazole-5-carboxamide (138b) 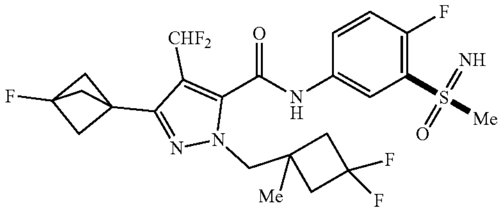 138a and |

-continued

| Example | Name/Structure/Starting Material/Data |
|---|---|
| | 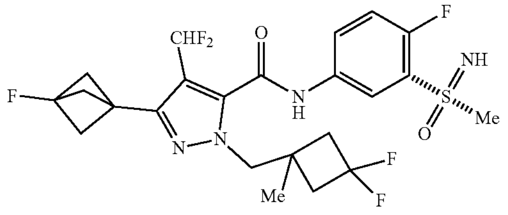<br>138b<br><br>ArSMe: 1-((3,3-difluoro-1-methylcyclobutyl)methyl)-4-(difluoromethyl)-N-(4-fluoro-3-(methylthio)phenyl)-3-(3-fluorobicyclo[1.1.1]pentan-1-yl)-1H-pyrazole-5-carboxamide (Intermediate 316).<br>Chiral-SFC (Chiral ART Cellulose-SC; 250 x 30 mm, 5 μm; 20% MeOH in $CO_2$)<br>Peak 1, Example 138a (80 mg, 12%). LCMS m/z = 535 $[M + H]^+$; $^1$H-NMR (400 MHz, DMSO-$d_6$): 11.19 (s, 1H), 8.24 (dd, 1H), 7.93-7.89 (m, 1H), 7.45 (t, 1H), 7.07 (t, 1H), 4.71 (s, 1H), 4.26 (s, 2H), 3.19 (s, 3H), 2.78-2.66 (m, 2H), 2.42 (d, 6H), 2.34-2.24 (m, 2H), 1.08 (s, 3H); Chiral SFC: column: Chiralcel OJ-H, 250 x 4.6 mm, 5 μm; co-solvent: MeOH; flow: 3 mL/min; % of co-solvent: 20%; ABPR: 1500 psi; T: 30° C.; $R_t$ = 1.70 min (first eluting).<br>Peak 2, Example 138b (85 mg, 13%). LCMS m/z = 535 $[M + H]^+$; $^1$H-NMR (400 MHz, DMSO-$d_6$): 11.19 (s, 1H), 8.24 (dd, 1H), 7.93-7.87 (m, 1H), 7.45 (t, 1H), 7.07 (t, 1H), 4.71 (s, 1H), 4.26 (s, 2H), 3.19 (s, 3H), 2.78-2.66 (m, 2H), 2.42 (d, 6H), 2.34-2.24 (m, 2H), 1.08 (s, 3H); Chiral SFC: column: Chiralcel OJ-H, 250 x 4.6 mm, 5 μm; co-solvent: MeOH; flow: 3 mL/min; % of co-solvent: 20%; ABPR: 1500 psi; T: 30° C.; $R_t$ = 2.77 min (second eluting). |
| 139 | 3-(Bicyclo[1.1.1]pentan-1-yl)-1-(((trans)-2-(difluoromethyl)cyclopropyl)methyl)-N-(3-(S-methylsulfonimidoyl)phenyl)-4-(trifluoromethyl)-1H-pyrazole-5-carboxamide<br>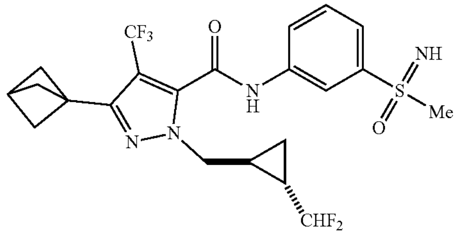<br>139<br><br>ArSMe: 3-(bicyclo[1.1.1]pentan-1-yl)-1-(((trans)-2-(difluoromethyl)cyclopropyl)methyl)-N-(3-(methylthio)phenyl)-4-(trifluoromethyl)-1H-pyrazole-5-carboxamide (Intermediate 326).<br>Peak 1, Example 139 (13 mg, 19% over two steps). LCMS m/z = 503 $[M + H]^+$; $^1$H-NMR (400 MHz, DMSO-$d_6$): 11.35 (s, 1H), 8.33-8.30 (m, 1H), 7.87-7.81(m, 1H), 7.75-7.71 (m, 1H), 7.64-7.58 (m, 1H), 5.75 (td, 1H), 4.24 (s, 1H), 4.21-4.15 (m, 1H), 4.05-3.95 (m, 1H), 3.06 (s, 3H), 2.54 (s, 1H), 2.15 (s, 6H), 1.60-1.45 (m, 2H), 0.85-0.70 (m, 2H). |
| 140a/140b | 1-((2-Acetyl-2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide, synthesized in the form of diastereomer 1 of 1-((2-acetyl-2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (140a) and diastereomer 2 of 1-((2-acetyl-2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (140b)<br>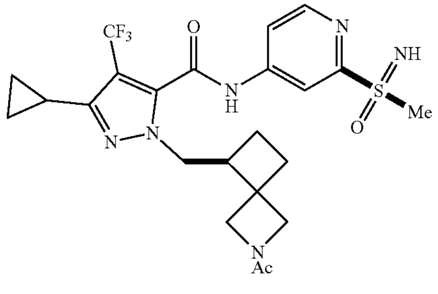<br>140a<br><br>and |

-continued

| Example | Name/Structure/Starting Material/Data |
|---|---|
| | 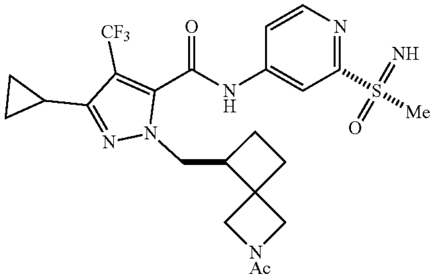<br>140b<br>ArSMe: 1-((2-acetyl-2-azaspiro[3.3]heptan-5-yl)methyl)-3-cyclopropyl-N-(2-(methylthio)pyridin-4-yl)-4-(trifluoromethyl)-1H-pyrazole-5-carboxamide (Intermediate 329a). Chiral-HPLC (Chiralpak IC; 250 × 20 mm, 5 μm; hexane/DCM/EtOH 60/20/20)<br>Peak 1, Example 140a (28 mg, 22%). LCMS m/z = 525 $[M + H]^+$; $^1$H-NMR (400 MHz, DMSO-$d_6$): 11.31 (bs, 1H), 8.65 (d, 1H), 8.36 (s, 1H), 7.81-7.80 (m, 1H), 4.32-4.27 (m, 1H), 4.15-4.07 (m, 2H), 3.88-3.66 (m, 4H), 3.17 (s, 3H), 2.81-2.76 (m, 1H), 2.08-2.05 (m, 2H), 1.93-1.84 (m, 2H), 1.69 (s, 3H), 1.65-1.56 (m, 1H), 0.98-0.85 (m, 4H); Chiral HPLC: column: Chiralpak IC, 250 × 4.6 mm, 5 μm; mobile phase: hexane/EtOAc/EtOH/iPrNH$_2$ 50/25/25/0.1; flow: 1 mL/min; $R_t$ = 6.59 min (first eluting).<br>Peak 2, Example 140b (25 mg, 20%). LCMS m/z = 525 $[M + H]^+$; $^1$H-NMR (400 MHz, DMSO-$d_6$): 11.40 (bs, 1H), 8.65 (d, 1H), 8.36 (s, 1H), 7.81-7.80 (m, 1H), 4.32-4.26 (m, 1H), 4.14-4.07 (m, 2H), 3.88-3.65 (m, 4H), 3.17 (s, 3H), 2.83-2.75 (m, 1H), 2.07-2.05 (m, 2H), 1.93-1.84 (m, 2H), 1.69 (s, 3H), 1.65-1.56 (m, 1H), 0.98-0.85 (m, 4H); Chiral HPLC: column: Chiralpak IC, 250 × 4.6 mm, 5 μm; mobile phase: hexane/EtOAc/EtOH/iPrNH$_2$ 50/25/25/0.1; flow: 1 mL/min; $R_t$ = 7.88 min (second eluting). |
| 141a/141b | 1-((3,3-Difluoro-1-methylcyclobutyl)methyl)-N-(4-fluoro-3-(S-methylsulfonimidoyl)phenyl)-3-(3-fluorobicyclo[1.1.1]pentan-1-yl)-4-(trifluoromethyl)-1H-pyrazole-5-carboxamide, synthesized in the form of enantiomer 1 of 1-((3,3-difluoro-1-methylcyclobutyl)methyl)-N-(4-fluoro-3-(S-methylsulfonimidoyl)phenyl)-3-(3-fluorobicyclo[1.1.1]pentan-1-yl)-4-(trifluoromethyl)-1H-pyrazole-5-carboxamide (141a) and enantiomer 2 of 1-((3,3-difluoro-1-methylcyclobutyl)methyl)-N-(4-fluoro-3-(S-methylsulfonimidoyl)phenyl)-3-(3-fluorobicyclo[1.1.1]pentan-1-yl)-4-(trifluoromethyl)-1H-pyrazole-5-carboxamide (141b)<br>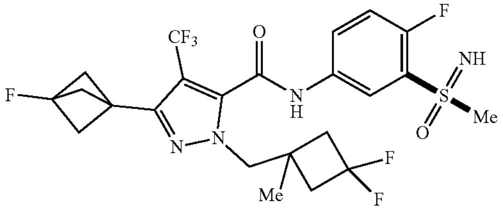<br>141a<br>and<br>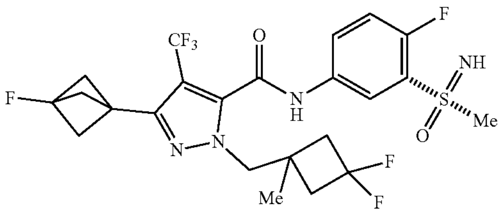<br>141b<br>ArSMe: 1-((3,3-difluoro-1-methylcyclobutyl)methyl)-N-(4-fluoro-3-(methylthio)phenyl)-3-(3-fluorobicyclo[1.1.1]pentan-1-yl)-4-(trifluoromethyl)-1H-pyrazole-5-carboxamide (Intermediate 317).<br>Chiral-SFC (Chiralpak AS-H; 250 × 4.6 mm, 5 μm; 25% MeOH in $CO_2$)<br>Peak 1, Example 141a (80 mg, 12%). LCMS m/z = 553 $[M + H]^+$; $^1$H-NMR (400 MHz, DMSO-$d_6$): 11.37 (s, 1H), 8.21 (dd, 1H), 7.93-7.87 (m, 1H), 7.47 (t, 1H), 4.74 (s, 1H), 4.21 (s, 2H), 3.19 (s, 3H), 2.83-2.65 (m, 2H), 2.44 (d, 6H), 2.37-2.26 (m, 2H), 1.10 (s, 3H); Chiral SFC: column: Chiralpak AS-H, 150 × 4.6 mm, 5 μm; co-solvent: MeOH; flow: 3 mL/min; % of co-solvent: 15%; ABPR: 1500 psi; T: 30° C.; $R_t$ = 0.85 min (first eluting).<br>Peak 2, Example 141b (85 mg, 13%). LCMS m/z = 553 $[M + H]^+$; $^1$H-NMR (400 MHz, DMSO- |

-continued

| Example | Name/Structure/Starting Material/Data |
|---|---|
| | $d_6$): 11.37 (s, 1H), 8.20 (d, 1H), 7.93-7.87 (m, 1H), 7.46 (t, 1H), 4.74 (s, 1H), 4.22 (s, 2H), 3.19 (s, 3H), 2.83-2.65 (m, 2H), 2.44 (d, 6H), 2.37-2.26 (m, 2H), 1.11 (s, 3H); Chiral SFC: column: Chiralpak AS-H, 150 × 4.6 mm, 5 μm; co-solvent: MeOH; flow: 3 mL/min; % of co-solvent: 15%; ABPR: 1500 psi; T: 30° C.; $R_t$ = 7.51 min (second eluting). |

Example 33

1-((3,3-Difluorocyclopentyl)methyl)-3-(difluoromethoxy)-N-(2-(S-methylsulfonimidoyl)pyridin-4-yl)-4-(trifluoromethyl)-1H-pyrazole-5-carboxamide

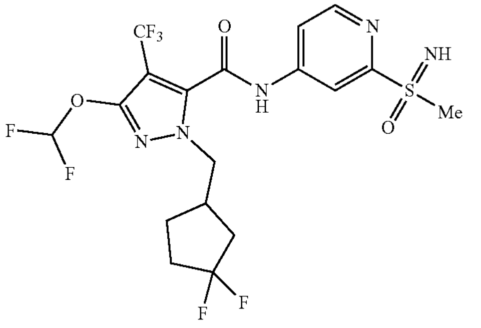 [SMILES: CS(=N)(=O)c1cc(NC(=O)c2c(C(F)(F)F)c(OC(F)F)nn2CC2CCC(F)(F)C2)ccn1]

The title compound was prepared (25 mg, 31%) from 1-((3,3-difluorocyclopentyl)methyl)-3-(difluoromethoxy)-N-(2-(methylthio)pyridin-4-yl)-4-(trifluoromethyl)-1H-pyrazole-5-carboxamide (Intermediate 83) using an analogous method to that described for Example 1. LCMS m/z=418 $[M+H]^+$; $^1$H-NMR (400 MHz, DMSO-$d_6$): 11.87 (s, 1H), 8.68 (d, 1H), 8.36 (s, 1H), 7.78 (d, 1H), 7.50 (t, 1H), 4.44 (s, 1H), 4.17 (d, 2H), 3.16 (s, 3H), 2.67-2.50 (m, 1H), 2.18-1.96 (m, 6H), 1.56-1.51 (m, 1H).

Example 34a/34b 1-((3,3-Difluoro-1-methylcyclobutyl)methyl)-3-(1,1-difluoroethyl)-N-(2-(N,S-dimethylsulfonimidoyl)pyridin-4-yl)-4-methyl-1H-pyrazole-5-carboxamide, synthesized in the form of enantiomer 1 of 1-((3,3-difluoro-1-methylcyclobutyl)methyl)-3-(1,1-difluoroethyl)-N-(2-(N,S-dimethylsulfonimidoyl)pyridin-4-yl)-4-methyl-1H-pyrazole-5-carboxamide (34a) and enantiomer 2 of 1-((3,3-difluoro-1-methylcyclobutyl)methyl)-3-(1,1-difluoroethyl)-N-(2-(N,S-dimethylsulfonimidoyl)pyridin-4-yl)-4-methyl-1H-pyrazole-5-carboxamide (34b)

34a

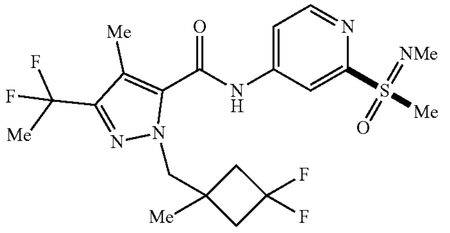

and

-continued

34b

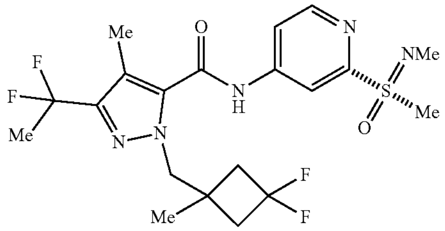

Part 1. To a stirred solution of 1-((3,3-difluoro-1-methylcyclobutyl)methyl)-3-(1,1-difluoroethyl)-4-methyl-N-(2-(methylthio)pyridin-4-yl)-1H-pyrazole-5-carboxamide (Intermediate 84, 0.30 g) in MeOH (10 mL) were added diacetoxyiodobenzene (2.25 g) and ammonium carbonate (0.672 g) at rt and the mixture was stirred for 2 h. The reaction mixture was washed with water and extracted with EtOAc (3×100 mL). The combined organics were washed with cold brine, dried ($Na_2SO_4$) and evaporated to dryness under reduced pressure. The residue was purified by CombiFlash chromatography ($SiO_2$, 0-50% EtOAc/Hex) to afford 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide (105 mg, 32%). LCMS m/z=462 $[M+H]^+$.

Part 2. To a stirred solution of 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide (0.17 g) in dioxane (10 mL) were added pyridine (0.07 mL) and methyl boronic acid (0.04 g) at rt and the mixture was degassed with $O_2$ for 15 min followed by addition of $Cu(OAc)_2$ (0.1 g) and was then heated in a sealed tube at 100° C. for 4 h. The reaction mixture was cooled and filtered through celite and the filtrate was diluted with ice water and extracted with EtOAc (3×100 mL). The combined organics were washed with brine, dried ($Na_2SO_4$) and evaporated to dryness under reduced pressure. The residue was purified by CombiFlash chromatography ($SiO_2$, 0-5% MeOH/DCM) followed by chiral-HPLC (Chiralpak IC, 250×20 mm, 5 μm; 70/15/15/0.1 Hex/EtOAc/EtOH/$iPrNH_2$) to afford: Peak 1, Example 34a (20 mg, 11%). LCMS m/z=476 $[M+H]^+$; $^1$H-NMR (400 MHz, DMSO-$d_6$): 11.28 (s, 1H), 8.69 (d, 1H), 8.39 (s, 1H), 7.85-7.84 (m, 1H), 4.36 (s, 2H), 3.18 (s, 3H), 2.73-2.66 (m, 2H), 2.32-2.28 (m, 2H), 2.23 (s, 3H), 2.08-1.98 (m, 3H), 1.07 (s, 3H). Chiral HPLC: column: Chiralpak IC (4.6×250 mm) 5 hum, mobile phase: hexane/DCM/EtOH/$iPrNH_2$ 60/20/20/0.1, flow rate: 1.0 mL/min, $R_t$=4.28 min (first eluting).

Peak 2, Example 34b (12 mg, 7%). LCMS m/z=476 $[M+H]^+$; $^1$H-NMR (400 MHz, DMSO-$d_6$): 11.28 (s, 1H), 8.69 (d, 1H), 8.39 (s, 1H), 7.85-7.84 (m, 1H), 4.36 (s, 2H), 3.18 (s, 3H), 2.73-2.66 (m, 2H), 2.32-2.28 (m, 2H), 2.23 (s, 3H), 2.08-1.98 (m, 3H), 1.07 (s, 3H). Chiral HPLC: column: Chiralpak IC (4.6×250 mm) 5 hum, mobile phase: hexane/DCM/EtOH/$iPrNH_2$ 60/20/20/0.1, flow rate: 1.0 mL/min, $R_t$=5.64 min (second eluting).

Example 36-39

The title compounds were prepared from the appropriate methylthiopyridine (ArSMe) using an analogous method to that described for Example 34.

| Example | Name/Structure/Starting Material/Data |
|---|---|
| 36a/36b | 3-Cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide (36a) and diastereomer 2 of 3-cyclopropyl-1-(((S)-3,3-difluorocyclopentyl)methyl)-N-(2-(S-methylsulfonimidoyl)pyridin-4-yl)-4-(trifluoromethyl)-1H-pyrazole-5-carboxamide (36b)<br>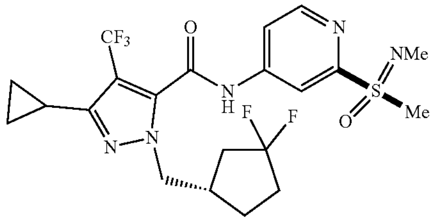 and 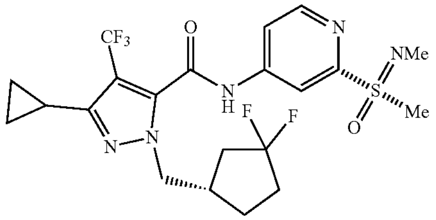<br>36a 36b<br>ArSMe: (S)-3-cyclopropyl-1-((3,3-difluorocyclopentyl)methyl)-N-(2-(methylthio)pyridin-4-yl)-4-(trifluoromethyl)-1H-pyrazole-5-carboxamide (Intermediate 91)<br>Chiral-HPLC (Chiralpak IC 250 × 20 mm, 5 μm; 90% Hex/5% EtOAc/5% EtOH)<br>Peak 1, Example 36a (26 mg, 21%). LCMS m/z = 506 $[M + H]^+$; $^1$H-NMR (400 MHz, DMSO-$d_6$): 11.73 (s, 1H), 8.71-8.70 (m, 1H), 8.32 (s, 1H), 7.81-7.80 (m, 1H), 4.11-4.10 (m, 2H), 3.19 (s, 3H), 2.62-2.58 (m, 1H), 2.15-2.07 (m, 3H), 2.04-2.01 (m, 2H), 1.99-1.76 (m, 1H), 1.52-1.47 (m, 1H), 1.00-0.95 (m, 2H), 0.86-0.83 (m, 2H). Chiral HPLC: column: Chiralpak IC (4.6 x 250 mm) 5 μm, mobile phase: hexane/DCM/EtOH/ iPrNH2 70/15/15/0.1, flow rate: 1.0 mL/min $R_t$ = 4.39 min (first eluting).<br>Peak 2, Example 36b (26 mg, 21%). LCMS m/z = 506 $[M + H]^+$; $^1$H-NMR (400 MHz, DMSO-$d_6$): 11.73 (s, 1H), 8.71-8.70 (m, 1H), 8.32 (s, 1H), 7.81-7.80 (m, 1H), 4.11-4.10 (m, 2H), 3.19 (s, 3H), 2.60-2.58 (m, 1H), 2.13-2.07 (m, 2H), 1.96-1.77 (m, 4H), 1.52-1.47 (m, 1H), 0.99-0.86 (m, 4H). Chiral HPLC: column: Chiralpak IC (4.6 x 250 mm) 5 μm, mobile phase: hexane/DCM/EtOH/ $iPrNH_2$ 70/15/15/0.1, flow rate: 1.0 mL/min $R_t$ = 5.79 min (second eluting). |
| 36c/36d | 3-Cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide, synthesized in the form of diastereomer 1 of 3-cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide (36c) and diastereomer 2 of 3-cyclopropyl-1-(((R)-3,3-difluorocyclopentyl)methyl)-N-(2-(S-methylsulfonimidoyl)pyridin-4-yl)-4-(trifluoromethyl)-1H-pyrazole-5-carboxamide (36d)<br>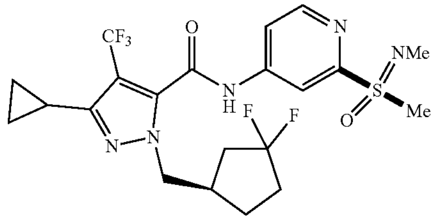 and 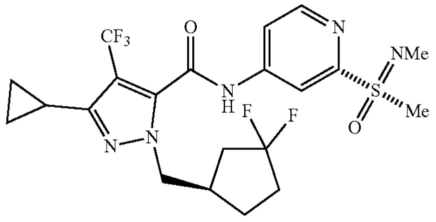<br>36c 36d<br>ArSMe: (S)-3-cyclopropyl-1-((3,3-difluorocyclopentyl)methyl)-N-(2-(methylthio)pyridin-4-yl)-4-(trifluoromethyl)-1H-pyrazole-5-carboxamide (Intermediate 91)<br>Chiral-HPLC (Chiralpak IC 250 × 20 mm, 5 μm; 70% Hex/15% DCM/15% EtOH)<br>Peak 1, Example 36c LCMS m/z = 506 $[M + H]^+$; $^1$H-NMR (400 MHz, DMSO-$d_6$): 11.73 (s, 1H), 8.71-8.70 (m, 1H), 8.32 (s, 1H), 7.81-7.80 (m, 1H), 4.11-4.10 (m, 2H), 3.19 (s, 3H), 2.62-2.58 (m, 1H), 2.15-2.07 (m, 3H), 1.96-1.92 (m, 3H), 1.79-1.77 (m, 1H), 1.53-1.47 (m, 1H), 0.99-0.96 (m, 2H), 0.86-0.85 (m, 2H). Chiral HPLC: column: Chiralpak IC (4.6 x 250 mm) 5 μm, mobile phase: hexane/DCM/EtOH/ $iPrNH_2$ 60/20/20/0.1, flow rate: 1.0 mL/min $R_t$ = 4.14 min (first eluting).<br>Peak 2, Example 36d (16 mg, 10%). LCMS m/z = 506 $[M + H]^+$; $^1$H-NMR (400 MHz, DMSO-$d_6$): 11.72 (s, 1H), 8.71-8.70 (m, 1H), 8.32 (s, 1H), 7.81-7.80 (m, 1H), 4.11-4.10 (m, 2H), 3.18 (s, 3H), 2.62-2.58 (m, 1H), 2.13-2.01 (m, 2H), 1.99-1.76 (m, 4H), 1.79-1.76 (m, 1H), 1.53-1.47 (m, 1H), 0.99-0.96 (m, 2H), 0.86-0.85 (m, 2H). Chiral HPLC: column: Chiralpak IC (4.6 x 250 mm) 5 μm, mobile phase: hexane/DCM/EtOH/ $iPrNH_2$ 60/20/20/0.1, flow rate: 1.0 mL/min $R_t$ = 5.28 min (second eluting). |

Example 70b 1-((3,3-Difluoro-1-methylcyclobutyl)methyl)-3-(1-fluorocyclopropyl)-N-(2-(S-methylsulfonimidoyl) pyridin-4-yl)-4-(trifluoromethyl)-1H-pyrazole-5-carboxamide, synthesized in the form of enantiomer 2 of 1-((3,3-difluoro-1-methylcyclobutyl)methyl)-3-(1-fluorocyclopropyl)-N-(2-(S-methylsulfonimidoyl)pyridin-4-yl)-4-(trifluoromethyl)-1H-pyrazole-5-carboxamide (70b)

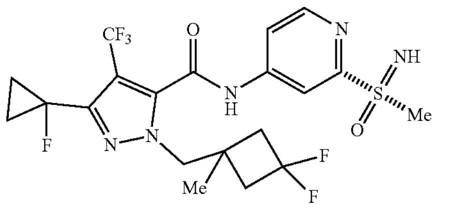

70b

To a stirred solution of 1-((3,3-difluoro-1-methylcyclobutyl)methyl)-3-(1-fluorocyclopropyl)-4-(trifluoromethyl)-1H-pyrazole-5-carboxamide (Intermediate 262, 250 mg) in 1,4-dioxane (10 mL) in a sealed tube were added (4-bromopyridin-2-yl)(imino)(methyl)-16-sulfanone (Intermediate 287b) (199 mg) and caesium carbonate (573 mg). The mixture was degassed with argon gas for 10 minutes. To the reaction mixture were then added trans-N,N'-dimethylcyclohexane-1,2-diamine (30 mg) and Cu(I) trifluoromethane sulphonate benzene complex (44 mg) at rt, and the mixture was again degassed for 5 minutes. The resulting reaction mixture was heated to 100° C. for 16 h. The reaction mixture was cooled to rt, diluted with EtOAc (15 mL) and filtered through a celite bed. The filtrate was concentrated under reduced pressure to get the crude product, which was dissolved in EtOAc (50 mL). The organic layer was washed with water (30 mL) and brine (30 mL), dried over anhydrous $Na_2SO_4$ and concentrated under reduced pressure to get the crude product, which was purified by prep-HPLC to afford the title compound.

Peak 2, Example 70b (75 mg, 21%). LCMS m/z=510 $[M+H]^+$; $^1H$-NMR (400 MHz, DMSO-$d_6$): 11.85 (s, 1H), 8.67 (d, 1H), 8.37 (s, 1H), 7.79 (d, 1H), 4.43 (s, 1H), 4.29 (s, 2H), 3.16 (s, 3H), 2.81-2.67 (m, 2H), 2.38-2.29 (m, 2H), 1.53-1.44 (m, 2H), 1.21-1.15 (m, 2H), 1.09 (s, 3H); Chiral SFC: column: (RR)Whelk-01 (150×4.6 mm, 3.5 μm); co-solvent: MeOH, flow: 3 mL/min; % of co-solvent: 20%; ABPR: 1500 psi; T: 30° C.; $R_t$=2.24 min (second eluting).

Examples 29, 56-59, 61-63, 70a, 95, 142-145

The title compounds were prepared from the appropriate amides and arylbromides (at a suitable reaction time between 12-16 hours and a suitable reaction temperature between 80-100° C.) using an analogous method to that described for Example 70b, with or without chiral separation.

| Example | Name/Structure/Starting Material/Data |
|---|---|
| 29a | 3-Cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide, synthesized in the form of diasteromeric mixture 1 of 3-cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide (29a)<br>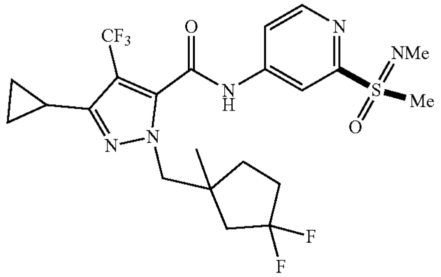<br>29a<br>Amide: 3-cyclopropyl-1-((3,3-difluoro-1-methylcyclopentyl)methyl)-4-(trifluoromethyl)-1H-pyrazole-5-carboxamide (Intermediate 279)<br>Arylbromide: (4-bromopyridin-2-yl)(imino)(methyl)-16-sulfanone (Intermediate 287a)<br>Example 29a (200 mg, 34%). LCMS m/z = 506 $[M + H]^+$; $^1H$-NMR (400 MHz, DMSO-$d_6$): 11.71 (s, 1H), 8.65 (d, 1H), 8.35 (s, 1H), 7.78 (d, 1H), 4.41 (s, 1H), 4.06 (s, 2H), 3.15 (s, 3H), 2.42-2.31 (m, 1H), 2.25-2.01 (m, 2H), 1.99-1.91 (m, 1H), 1.89-1.80 (m, 2H), 1.55-1.49 (m, 1H), 1.01-0.97 (m, 2H), 0.94 (s, 3H), 0.86-0.83 (m, 2H). |
| 29b | 3-Cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide, synthesized in the form of diasteromeric mixture 2 of 3-cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide (29b) |

-continued

| Example | Name/Structure/Starting Material/Data |
|---|---|
| | 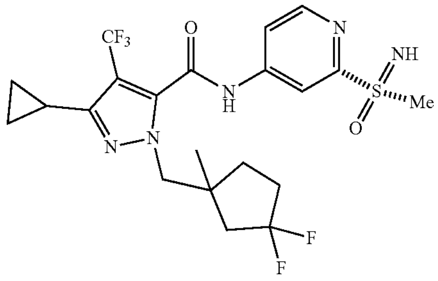<br>29b<br>Amide: 3-cyclopropyl-1-((3,3-difluoro-1-methylcyclopentyl)methyl)-4-(trifluoromethyl)-1H-pyrazole-5-carboxamide (Intermediate 279)<br>Arylbromide (4-bromopyridin-2-yl)(imino)(methyl)-16-sulfanone (Intermediate 287b)<br>Example 29b (130 mg, 22%). LCMS m/z = 506 $[M + H]^+$; $^1H$-NMR (400 MHz, DMSO-$d_6$): 11.71 (s, 1H), 8.66 (d, 1H), 8.36 (s, 1H), 7.77 (d, 1H), 4.42 (s, 1H), 4.06 (s, 2H), 3.15 (s, 3H), 2.42-2.39 (m, 1H), 2.25-2.01 (m, 2H), 1.99-1.81 (m, 3H), 1.55-1.49 (m, 1H), 1.01-0.96 (m, 2H), 0.94 (s, 3H), 0.86-0.83 (m, 2H) |
| 56a/56b | 3-Cyclobutyl-1-((3,3-difluoro-1-methylcyclobutyl)methyl)-N-(2-(S-synthesized in the form of enantiomer 1 of 3-cyclobutyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (56a) and enantiomer 2 of 3-cyclobutyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (56b)<br>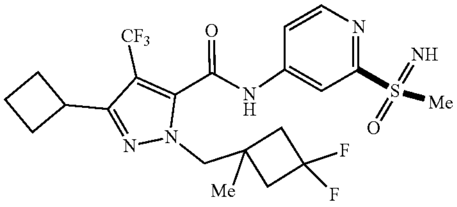 and 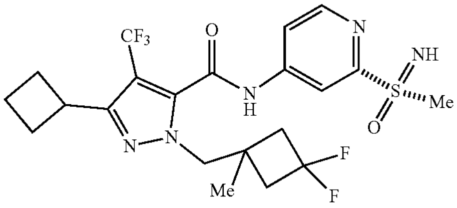<br>56a 56b<br>Amide: 3-cyclobutyl-1-((3,3-difluoro-1-methylcyclobutyl)methyl)-4-(trifluoromethyl)-1H-pyrazole-5-carboxamide (Intermediate 263)<br>Arylbromide: (4-bromopyridin-2-yl)(imino)(methyl)-16-sulfanone, racemate (Intermediate 287)<br>Trans-1,2-diaminocyclohexane was used instead of trans-N,N'-dimethylcyclohexane-1,2-diamine.<br>Chiral-SFC (Chiralpak AS-H, 250 x 30 mm, 5 μm; 20% (30 mM $NH_3$ in MeOH) in $CO_2$)<br>Peak 1, Example 56a (10 mg, 7%). LCMS m/z = 506 $[M + H]^+$; $^1H$-NMR (400 MHz, DMSO-$d_6$): 11.73 (s, 1H), 8.65 (d, 1H), 8.36 (s, 1H), 7.78 (s, 1H), 4.41 (s, 1H), 4.25 (s, 2H), 3.62-358 (m, 1H), 3.25 (s, 3H), 2.85-2.75 (m, 2H), 2.40-2.25 (m, 6H), 2.09-1.98 (m, 1H), 1.90-1.80 (m, 1H), 1.10 (s, 3H); Chiral SFC: column: Chiralpak AS-3 (150 x 4.6 mm, 3 μm); co-solvent: 0.5% diethylamine in MeOH, flow: 3 mL/min; % of co-solvent: 10%; ABPR: 1500 psi; T: 30° C.; $R_t$ = 1.38 min (first eluting).<br>Peak 2, Example 56b (7 mg, 5%). LCMS m/z = 506 $[M + H]^+$; $^1H$-NMR (400 MHz, DMSO-$d_6$): 11.73 (s, 1H), 8.66 (d, 1H), 8.36 (s, 1H), 7.78 (d, 1H), 4.41 (s, 1H), 4.25 (s, 2H), 3.62-3.5 1H), 3.15 (s, 3H), 2.85-2.75 (m, 2H), 2.37-2.25 (m, 6H), 2.06-2.01 (m, 1H), 1.90-1.83 (m, 1H), 1.10 (s, 3H); Chiral SFC: column: Chiralpak AS-3 (150 x 4.6 mm, 3 μm); co-solvent: 0.5% diethylamine in MeOH, flow: 3 mL/min; % of co-solvent: 10%; ABPR: 1500 psi; T: 30° C.; $R_t$ = 3.53 min (second eluting). |
| 57a/57b | 1-((3,3-Difluoro-1-methylcyclobutyl)methyl)-3-(3,3-difluorocyclobutyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(3,3-difluorocyclobutyl)-N-(2-(S-methylsulfonimidoyl)pyridin-4-yl)-4-(trifluoromethyl)-1H-pyrazole-5-carboxamide (57a) and enantiomer 2 of 1-((3,3-difluoro-1-methylcyclobutyl)methyl)-3-(3,3-difluorocyclobutyl)-N-(2-(S-methylsulfonimidoyl)pyridin-4-yl)-4-(trifluoromethyl)-1H-pyrazole-5-carboxamide (57b) |

-continued

| Example | Name/Structure/Starting Material/Data |
|---|---|
| | 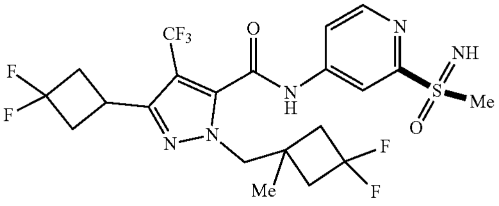 and 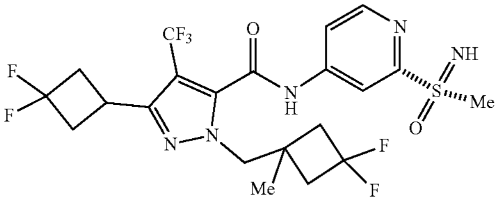<br>57a 57b<br>Amide: 1-((3,3-difluoro-1-methylcyclobutyl)methyl)-3-(3,3-difluorocyclobutyl)-4-(trifluoromethyl)-1H-pyrazole-5-carboxamide (Intermediate 266)<br>Arylbromide: (4-bromopyridin-2-yl)(imino)(methyl)-16-sulfanone, racemate (Intermediate 287)<br>Trans-1,2-diaminocyclohexane was used instead of trans-N,N'-dimethylcyclohexane-1,2-diamine.<br>Chiral-SFC (Chiralpak AS-H, 250 x 30 mm, 5 μm; 30% (30 mM $NH_3$ in MeOH) in $CO_2$)<br>Peak 1, Example 57a (20 mg, 8%). LCMS m/z = 540 $[M - H]^-$; $^1$H-NMR (400 MHz, DMSO-$d_6$): 11.78 (s, 1H), 8.66 (d, 1H), 8.36 (s, 1H), 7.78 (d, 1H), 4.42 (s, 1H), 4.29 (s, 2H), 3.54-3.50 (m, 1H), 3.16 (s, 3H), 3.11-3.00 (m, 2H), 2.95-2.75 (m, 4H), 2.42-2.28 (m, 2H), 1.09 (s, 3H); Chiral SFC: column: Chiralpak AS-H (150 x 4.6 mm, 5 μm); co-solvent : 0.5% $iPrNH_2$ in iPrOH; flow: 3 mL/min; % of co-solvent: 15%; ABPR: 1500 psi; T: 30° C.; $R_t$ = 1.31 min (first eluting).<br>Peak 2, Example 57b (18 mg, 7%). LCMS m/z = 540 $[M - H]^-$; $^1$H-NMR (400 MHz, DMSO-$d_6$): 11.78 (s, 1H), 8.65 (s, 1H), 8.35 (s, 1H), 7.78 (s, 1H), 4.41 (s, 1H), 4.28 (s, 2H), 3.53-3.49 (m, 1H), 3.15 (s, 3H), 3.11-3.00 (m, 2H), 2.93-2.77 (m, 4H), 2.39-2.28 (m, 2H), 1.09 (s, 3H); Chiral SFC: column: Chiralpak AS-H (150 x 4.6 mm, 5 μm); co-solvent: 0.5% $iPrNH_2$ in iPrOH; flow: 3 mL/min; % of co-solvent: 15%; ABPR: 1500 psi; T: 30° C.; $R_t$ = 5.27 min (second eluting). |
| 58a | 3-(Bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-(bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (58a)<br>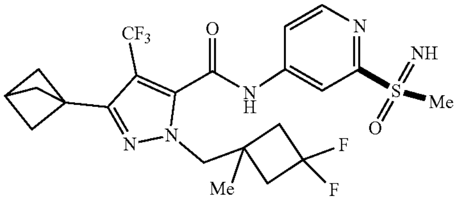<br>58a<br>Amide: 3-(bicyclo[1.1.1]pentan-1-yl)-1-((3,3-difluoro-1-methylcyclobutyl)methyl)-4-(trifluoromethyl)-1H-pyrazole-5-carboxamide (Intermediate 280)<br>Arylbromide: (4-bromopyridin-2-yl)(imino)(methyl)-16-sulfanone (Intermediate 287a)<br>Trans-1,2-diaminocyclohexane was used instead of trans-N,N'-dimethylcyclohexane-1,2-diamine.<br>Peak 1, Example 58a (8 mg, 6%). LCMS m/z = 516 $[M - H]^-$; $^1$H-NMR (400 MHz, DMSO-$d_6$): 11.75 (s, 1H), 9.00-8.00 (m, 2H), 8.00-7.40 (m, 1H), 4.70-4.00 (m, 3H), 3.12 (s, 3H), 2.85-2.70 (m, 2H), 2.60-2.50 (m, 1H), 2.35-2.20 (m, 2H), 2.13 (s, 6H), 1.10 (s, 3H); Chiral SFC: column: (R,R)Whelk-01 (150 x 4.6 mm, 3.5 μm); co-solvent : 0.5% $iPrNH_2$ in iPrOH; flow: 3 mL/min; % of co-solvent: 20%; ABPR: 1500 psi; T: 30° C.; $R_t$ = 2.33 min (first eluting). |
| 58b | 3-(Bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide, synthesized in the form of enantiomer 2 of 3-(bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (58b)<br>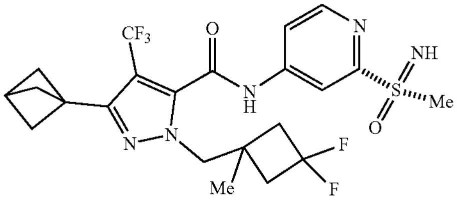<br>58b<br>Amide: 3-(bicyclo[1.1.1]pentan-1-yl)-1-((3,3-difluoro-1-methylcyclobutyl)methyl)-4-(trifluoromethyl)-1H-pyrazole-5-carboxamide (Intermediate 280)<br>Arylbromide: (4-bromopyridin-2-yl)(imino)(methyl)-16-sulfanone (Intermediate 287b) |

-continued

| Example | Name/Structure/Starting Material/Data |
|---|---|
| | Trans-1,2-diaminocyclohexane was used instead of trans-N,N'-dimethylcyclohexane-1,2-diamine. Peak 1, Example 58a (9 mg, 6%). LCMS m/z = 516 [M − H]$^-$; $^1$H-NMR (400 MHz, DMSO-$d_6$): 11.76 (s, 1H), 9.00-8.00 (m, 2H), 8.00-7.40 (m, 1H), 4.24 (s, 3H), 3.11 (s, 3H), 2.90-2.70 (m, 2H), 2.60-2.50 (m, 1H), 2.35-2.20 (m, 2H), 2.18-2.05 (s, 6H), 1.11 (s, 3H); Chiral SFC: column: (R,R)Whelk-01 (150 × 4.6 mm, 3.5 μm); co-solvent: 0.5% iPrNH$_2$ in iPrOH; flow: 3 mL/min; % of co-solvent: 20%; ABPR: 1500 psi; T: 30° C.; $R_t$ = 2.64 min (seond eluting). |
| 59a/59b | 3-Cyclopentyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-cyclopentyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (59a) and enantiomer 2 of 3-cyclopentyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (59b)<br>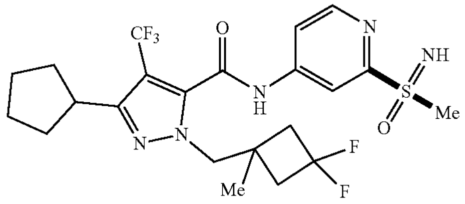 and 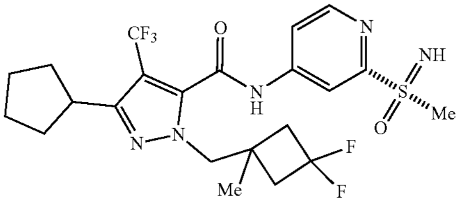<br>59a 59b<br>Amide: 3-cyclopentyl-1-((3,3-difluoro-1-methylcyclobutyl)methyl)-4-(trifluoromethyl)-1H-pyrazole-5-carboxamide (Intermediate 264)<br>Arylbromide: (4-bromopyridin-2-yl)(imino)(methyl)-16-sulfanone, racemate (Intermediate 287)<br>Trans-1,2-diaminocyclohexane was used instead of trans-N,N'-dimethylcyclohexane-1,2-diamine.<br>Chiral-SFC (Chiralpak AS-H, 250 × 30 mm, 5 μm; 20% (30 mM NH$_3$ in MeOH) in CO$_2$)<br>Peak 1, Example 59a (11 mg, 4%). LCMS m/z = 520 [M + H]$^+$; $^1$H-NMR (400 MHz, DMSO-$d_6$): 11.74 (s, 1H), 8.65 (s, 1H), 8.36 (s, 1H), 7.78 (s, 1H), 4.41 (s, 1H), 4.21 (s, 2H), 3.20-3.10 (m, 4H), 2.88-2.72 (m, 2H), 2.36-2.21 (m, 2H), 2.03-1.90 (m, 2H), 1.83-1.60 (m, 6H), 1.08 (s, 3H); Chiral SFC: column: Chiralpak AS-H (150 × 4.6 mm, 3 μm); co-solvent: 0.5% diethylamine in MeOH, flow: 3 mL/min; % of co-solvent: 10%; ABPR: 1500 psi; T: 30° C.; $R_t$ = 1.11 min (first eluting).<br>Peak 2, Example 59b (10 mg, 4%). LCMS m/z = 520 [M + H]$^+$; $^1$H-NMR (400 MHz, DMSO-$d_6$): 11.74 (s, 1H), 8.65 (s, 1H), 8.36 (s, 1H), 7.78 (s, 1H), 4.41 (s, 1H), 4.21 (s, 2H), 3.20-3.10 (m, 4H), 2.88-2.72 (m, 2H), 2.36-2.21 (m, 2H), 2.03-1.90 (m, 2H), 1.83-1.60 (m, 6H), 1.08 (s, 3H); Chiral SFC: column: Chiralpak AS-H (150 × 4.6 mm, 3 μm); co-solvent: 0.5% diethylamine in MeOH, flow: 3 mL/min; % of co-solvent: 10%; ABPR: 1500 psi; T: 30° C.; $R_t$ = 3.98 min (second eluting). |
| 61a/61b | 1-((3,3-Difluoro-1-methylcyclobutyl)methyl)-N-(2-(S-methylsulfonimidoyl)pyridin-4-yl)-3-(spiro[2.3]hexan-5-yl)-4-(trifluoromethyl)-1H-pyrazole-5-carboxamide, synthesized in the form of enantiomer 1 of 1-((3,3-difluoro-1-methylcyclobutyl)methyl)-N-(2-(S-methylsulfonimidoyl)pyridin-4-yl)-3-(spiro[2.3]hexan-5-yl)-4-(trifluoromethyl)-1H-pyrazole-5-carboxamide (61a) and enantiomer 2 of 1-((3,3-difluoro-1-methylcyclobutyl)methyl)-N-(2-(S-methylsulfonimidoyl)pyridin-4-yl)-3-(spiro[2.3]hexan-5-yl)-4-(trifluoromethyl)-1H-pyrazole-5-carboxamide (61b)<br>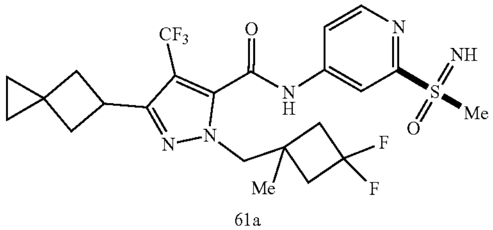 and 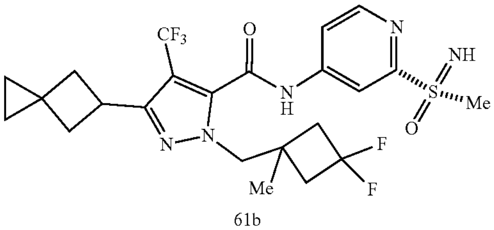<br>61a 61b<br>Amide: 1-((3,3-difluoro-1-methylcyclobutyl)methyl)-3-(spiro[2.3]hexan-5-yl)-4-(trifluoromethyl)-1H-pyrazole-5-carboxamide (Intermediate 265)<br>Arylbromide: (4-bromopyridin-2-yl)(imino)(methyl)-16-sulfanone, racemate (Intermediate 287)<br>Chiral-SFC (Chiralpak IK, 250 × 30 mm, 5 μm; 25% (30 mM NH$_3$ in MeOH) in CO$_2$)<br>Peak 1, Example 61a (20 mg, 8%). LCMS m/z = 532 [M + H]$^+$; $^1$H-NMR (400 MHz, DMSO-$d_6$): 11.82 (s, 1H), 8.63 (s, 1H), 8.33 (s, 1H), 7.76 (s, 1H), 4.38 (brs, 1H), 4.27 (s, 2H), 3.74 (t, 1H), 3.14 (s, 3H), 2.87-2.76 (m, 2H), 2.66-2.51 (m, 2H), 2.49-2.27 (m, 4H), 1.11 (s, 3H), 0.54-0.50 (m, 2H), 0.42-0.41 (m, 2H); Chiral SFC: column: Chiralpak IK (150 × 4.6 mm, 3 μm); co-solvent: 0.5% (7N methanolic ammonia) in iPrOH; flow: 3 mL/min; % of co-solvent: 10%; ABPR: 1500 psi; T: 30° C.; $R_t$ = 2.82 min (first eluting).<br>Peak 2, Example 61b (18 mg, 7%). LCMS m/z = 532 [M + H]$^+$; $^1$H-NMR (400 MHz, DMSO-$d_6$): 11.74 (s, 1H), 8.65 (s, 1H), 8.36 (s, 1H), 7.78 (s, 1H), 4.41 (brs, 1H), 4.26 (s, 2H), 3.74 (t, |

-continued

| Example | Name/Structure/Starting Material/Data |
| --- | --- |
| | 1H), 3.15 (s, 3H), 2.86-2.76 (m, 2H), 2.51-2.49 (m, 2H), 2.38-2.28 (m, 4H), 1.11 (s, 3H), 0.54-0.50 (m, 2H), 0.42-0.41 (m, 2H); Chiral SFC: column: Chiralpak IK (150 × 4.6 mm, 3 μm); co-solvent: 0.5% (7N methanolic ammonia) in iPrOH; flow: 3 mL/min; % of co-solvent: 10%; ABPR: 1500 psi; T: 30° C.; $R_t$ = 3.90 min (second eluting). |
| 62a | 1-((3,3-Difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide, synthesized in the form of diasteromeric mixture 1 of 1-((3,3-difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide (62a)<br>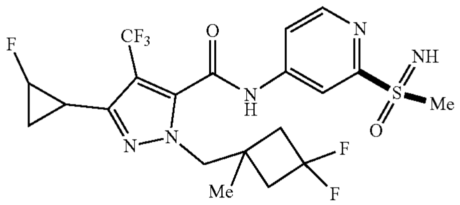<br>62a<br>Amide: 1-((3,3-difluoro-1-methylcyclobutyl)methyl)-3-(2-fluorocyclopropyl)-4-(trifluoromethyl)-1H-pyrazole-5-carboxamide (Intermediate 277)<br>Arylbromide: (4-bromopyridin-2-yl)(imino)(methyl)-16-sulfanone (Intermediate 287a)<br>Example 62a (18 mg, 25%). LCMS m/z = 510 $[M + H]^+$; $^1$H-NMR (400 MHz, DMSO-$d_6$): 11.77 (s, 1H), 8.66 (d, 1H), 8.35 (s, 1H), 7.76 (s, 1H), 4.96-4.79 (m, 1H), 4.42 (s, 1H), 4.19 (s, 2H), 3.15 (s, 3H), 2.79-2.65 (m, 2H), 2.36-2.24 (m, 2H), 1.70-1.60 (m, 1H), 1.35-1.22 (m, 2H), 1.04 (s, 3H); Chiral SFC: column: Chiralcel OX-H (250 × 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 10.57 and 11.04 min. |
| 62b | 1-((3,3-Difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide, synthesized in the form of diasteromeric mixture 2 of 1-((3,3-difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide (62b)<br>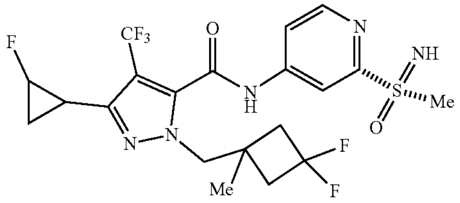<br>62b<br>Amide: 1-((3,3-difluoro-1-methylcyclobutyl)methyl)-3-(2-fluorocyclopropyl)-4-(trifluoromethyl)-1H-pyrazole-5-carboxamide (Intermediate 277)<br>Arylbromide: (4-bromopyridin-2-yl)(imino)(methyl)-16-sulfanone (Intermediate 287b)<br>Example 287b (15 mg, 21%). LCMS m/z = 510 $[M + H]^+$; $^1$H-NMR (400 MHz, DMSO-$d_6$): 11.77 (s, 1H), 8.65 (s, 1H), 8.35 (s, 1H), 7.77 (s, 1H), 4.96-4.79 (m, 1H), 4.42 (s, 1H), 4.19 (s, 2H), 3.15 (s, 3H), 2.78-2.66 (m, 2H), 2.34-2.29 (m, 2H), 1.69-1.60 (m, 1H), 1.35-1.22 (m, 2H), 1.04 (s, 3H), Chiral SFC: column: Chiralcel OX-H (250 × 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 6.74 and 8.65. |
| 63a/63b/63c | 1-((3,3-Difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide, synthesized in the form of diasteromeric mixture 1 of 1-((3,3-difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide (63a), diastereomer 2 of 1-((3,3-difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide (63b) and diastereomer 3 of 1-((3,3-difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide (63c) |

-continued

| Example | Name/Structure/Starting Material/Data |
|---|---|
| | 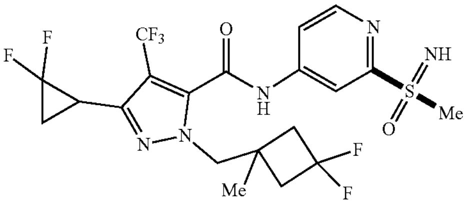 and 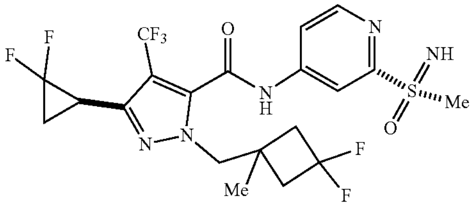<br>63a 63b<br>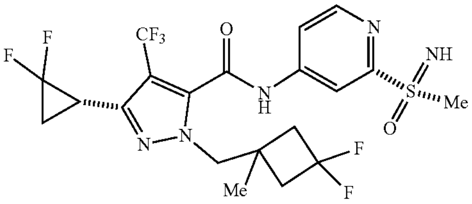<br>63c<br>Amide: 1-((3,3-difluoro-1-methylcyclobutyl)methyl)-3-(2,2-difluorocyclopropyl)-4-(trifluoromethyl)-1H-pyrazole-5-carboxamide (Intermediate 276)<br>Arylbromide: (4-bromopyridin-2-yl)(imino)(methyl)-16-sulfanone, racemic (Intermediate 287)<br>Chiral-SFC (Chiralpak AS-H, 250 × 10 mm, 5 μm; 10% EtOH in $CO_2$)<br>Peak 1, Example 63a (21 mg, 1% over six steps). LCMS m/z = 528 $[M + H]^+$; $^1H$-NMR (400 MHz, DMSO-$d_6$): 11.82 (s, 1H), 8.66 (s, 1H), 8.35 (s, 1H), 7.79 (s, 1H), 4.41 (s, 1H), 4.28 (s, 2H), 3.18-3.00 (m, 4H), 2.82-2.65 (m, 2H), 2.40-2.20 (m, 2H), 2.18-2.00 (m, 2H), 1.05 (s, 3H), Chiral SFC: column: Chiralpak AS-H (250 × 4.6 mm, 5 μm); co-solvent : 0.5% diethylamine in EtOH; flow: 3 mL/min; % of co-solvent: 10%; ABPR: 100 bar; T: 30° C.; $R_t$ = 2.86-3.04 min (first eluting).<br>Peak 2, Example 63b (14 mg, 1% over six steps). LCMS m/z = 528 $[M + H]^+$; $^1H$-NMR (400 MHz, DMSO-$d_6$): 11.82 (s, 1H), 8.64 (s, 1H), 8.33 (s, 1H), 7.77 (s, 1H), 4.50-4.30 (m, 3H), 3.20-3.00 (m, 4H), 2.82-2.65 (m, 2H), 2.40-2.20 (m, 2H), 2.18-2.00 (m, 2H), 1.05 (s, 3H), Chiral SFC: column: Chiralpak AS-H (250 × 4.6 mm, 5 μm); co-solvent: 0.5% diethylamine in EtOH; flow: 3 mL/min; % of co-solvent: 10%; ABPR: 100 bar; T: 30° C.; $R_t$ = 14.60 min (second eluting).<br>Peak 3, Example 63c (15 mg, 1% over six steps). LCMS m/z = 528 $[M + H]^+$; $^1H$-NMR (400 MHz, DMSO-$d_6$): 11.82 (s, 1H), 8.60 (s, 1H), 8.35 (s, 1H), 7.74 (s, 1H), 4.31 (s, 3H), 3.20-3.00 (m, 4H), 2.82-2.65 (m, 2H), 2.35-2.20 (m, 2H), 2.15-2.00 (m, 2H), 1.06 (s, 3H), Chiral SFC: column: Chiralpak AS-H (250 × 4.6 mm, 5 μm); co-solvent : 0.5% diethylamine in EtOH; flow: 3 mL/min; % of co-solvent: 10%; ABPR: 100 bar; T: 30° C.; $R_t$ = 18.78 min (third eluting). |
| 70a | 1-((3,3-Difluoro-1-methylcyclobutyl)methyl)-3-(1-fluorocyclopropyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(1-fluorocyclopropyl)-N-(2-(S-methylsulfonimidoyl)pyridin-4-yl)-4-(trifluoromethyl)-1H-pyrazole-5-carboxamide (70a)<br>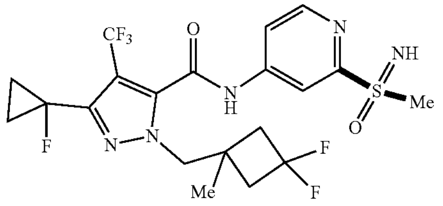<br>70a<br>Amide: 1-((3,3-difluoro-1-methylcyclobutyl)methyl)-3-(1-fluorocyclopropyl)-4-(trifluoromethyl)-1H-pyrazole-5-carboxamide (Intermediate 262)<br>Arylbromide: (4-bromopyridin-2-yl)(imino)(methyl)-16-sulfanone (Intermediate 287a)<br>Peak 1, Example 70a (105 mg, 29%). LCMS m/z = 510 $[M + H]^+$; $^1H$-NMR (400 MHz, DMSO-$d_6$): 11.88 (s, 1H), 8.63 (s, 1H), 8.34 (s, 1H), 7.76 (s, 1H), 4.39 (s, 1H), 4.30 (s, 2H), 3.15 (s, 3H), 2.82-2.67 (m, 2H), 2.37-2.28 (m, 2H), 1.52-1.43 (m, 2H), 1.20-1.14 (m, 2H), 1.09 (s, 3H); Chiral SFC: column: (R,R)Whelk-01 (150 × 4.6 mm, 3.5 μm); co-solvent: MeOH, flow: 3 mL/min; % of co-solvent: 20%; ABPR: 1500 psi; T: 30° C.; $R_t$ = 2.01 min (first eluting). |
| 95a/95b/95c | 3-Cyclopropyl-1-((3,3-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide, synthesized in the form of diasteromeric mixture 1 of 3-cyclopropyl-1-((3,3-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide (95a), diastereomer 2 of 3-cyclopropyl-1-((3,3-difluorobicyclo[3.1.0]hexan-1-yl)methyl)-N-(2-(S-methylsulfonimidoyl)pyridin-4-yl)-4- |

-continued

| Example | Name/Structure/Starting Material/Data |
|---|---|
| | (trifluoromethyl)-1H-pyrazole-5-carboxamide (95b) and diastereomer 3 of 3-cyclopropyl-1-((3,3-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide (95c) |

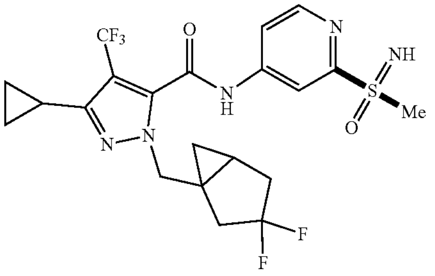

and

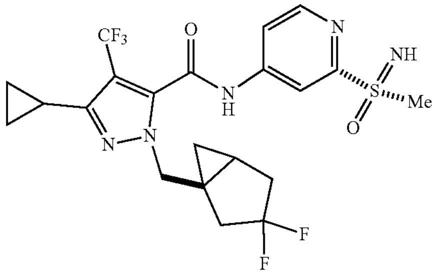

95a

95b

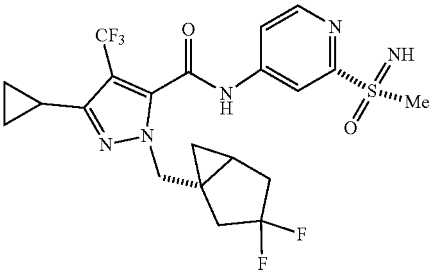

95c

Amide: 3-cyclopropyl-1-((3,3-difluorobicyclo[3.1.0]hexan-1-yl)methyl)-4-(trifluoromethyl)-1H-pyrazole-5-carboxamide (Intermediate 278)
Arylbromide: (4-bromopyridin-2-yl)(imino)(methyl)-16-sulfanone, racemic (Intermediate 287)
Chiral-SFC (Chiralpak AS-H, 250 x 10 mm, 5 μm; 10% (30 mM $NH_3$ in MeOH) in $CO_2$)
Peak 1, Example 95a (12 mg, 8%). LCMS m/z = 504 $[M + H]^+$; $^1$H-NMR (400 MHz, DMSO-$d_6$): 11.76 (s, 1H), 8.58 (s, 1H), 8.31 (s, 1H), 7.71 (s, 1H), 4.32-4.15 (m, 3H), 3.13 (s, 3H), 2.45-2.05 (m, 4H), 1.95 (bs, 1H), 1.45 (bs, 1H), 0.97 (d, 2H), 0.90-0.75 (m, 3H), 0.47 (bs, 1H); Chiral SFC: column: Chiralcel OJ-H (250 x 4.6 mm, 5 μm); co-solvent: 0.5% diethylamine in MeOH; flow: 3 mL/min; % of co-solvent: 10%; ABPR: 99 bar; T: 30° C.; $R_t$ = 2.76 and 3.06
Peak 2, Example 95b (7 mg, 5%). LCMS m/z = 504 $[M + H]^+$; $^1$H-NMR (400 MHz, DMSO-$d_6$): 11.75 (s, 1H), 8.63 (s, 1H), 8.34 (s, 1H), 7.75 (s, 1H), 4.39 (s, 1H), 4.28 (d, 1H), 4.18 (d, 1H), 3.19-3.12 (m, 3H), 2.45-2.05 (m, 4H), 1.95 (bs, 1H), 1.45 (bs, 1H), 0.97 (d, 2H), 0.90-0.75 (m, 3H), 0.45 (bs, 1H), Chiral SFC: column: Chiralpak AS-3 (150 x 4.6 mm, 5 μm); co-solvent: 0.5% diethylamine in MeOH; flow: 3 mL/min; % of co-solvent: 10%; ABPR: 1500 psi; T: 30° C.; $R_t$ = 2.72 min (second eluting).
Peak 3, Example 95c (17 mg, 5%). LCMS m/z = 504 $[M + H]^+$; $^1$H-NMR (400 MHz, DMSO-$d_6$): 11.75 (s, 1H), 8.62 (s, 1H), 8.34 (s, 1H), 7.74 (s, 1H), 4.38 (s, 1H), 4.28 (d, 1H), 4.18 (d, 1H), 3.19-3.12 (m, 3H), 2.45-2.05 (m, 4H), 1.95 (bs, 1H), 1.45 (bs, 1H), 0.97 (d, 2H), 0.90-0.75 (m, 3H), 0.46 (bs, 1H), Chiral SFC: column: Chiralpak AS-3 (150 x 4.6 mm, 5 μm); co-solvent: 0.5% diethylamine in MeOH; flow: 3 mL/min; % of co-solvent: 10%; ABPR: 1500 psi; T: 30° C.;; $R_t$ = 3.72 min (third eluting).

142a/142b N-(2-(N-Cyano-S-methylsulfonimidoyl)pyridin-4-yl)-3-cyclopropyl-1-((3,3-difluoro-1-methylcyclobutyl)methyl)-4-(trifluoromethyl)-1H-pyrazole-5-carboxamide, synthesized in the form of enantiomer 1 of N-(2-(N-cyano-S-methylsulfonimidoyl)pyridin-4-yl)-3-cyclopropyl-1-((3,3-difluoro-1-methylcyclobutyl)methyl)-4-(trifluoromethyl)-1H-pyrazole-5-carboxamide (142a) and enantiomer 2 of N-(2-(N-cyano-S-methylsulfonimidoyl)pyridin-4-yl)-3-cyclopropyl-1-((3,3-difluoro-1-methylcyclobutyl)methyl)-4-(trifluoromethyl)-1H-pyrazole-5-carboxamide (142b)

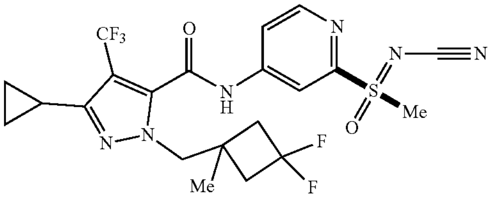

and

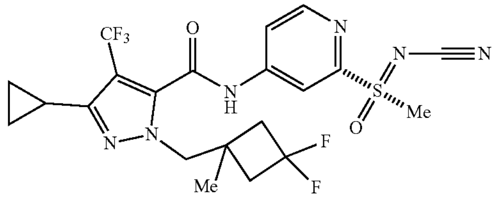

142a

142b

Amide: 3-cyclopropyl-1-((3,3-difluoro-1-methylcyclobutyl)methyl)-4-(trifluoromethyl)-1H-pyrazole-5-carboxamide, made from Intermediate 60 using an analogous method to that -continued

| Example | Name/Structure/Starting Material/Data |
|---|---|
| | described for Intermediate 262 (synthesized 2.0 g, 87%, LCMS m/z = 338 [M + H]$^+$).<br>Arylbromide: N-((4-bromopyridin-2-yl)(methyl)(oxo)-16-sulfaneylidene)cyanamide, racemate (Intermediate 288)<br>Trans-1,2-diaminocyclohexane was used instead of trans-N,N'-dimethylcyclohexane-1,2-diamine.<br>Yield for racemic: (250 mg, 80%), then chiral-SFC ((R,R) Whelk-01, 250 × 30 mm, 5 μm; 15% (30 mM $NH_3$ in iPrOH) in $CO_2$)<br>Peak 1, Example 142a LCMS m/z = 517 [M + H]$^+$; $^1$H-NMR (400 MHz, DMSO-$d_6$): 11.98 (s, 1H), 8.84 (d, 1H), 8.48 (d, 1H), 7.99 (d, 1H), 4.20 (s, 2H), 3.73 (s, 3H), 2.80-2.65 (m, 2H), 2.35-2.24 (m, 2H), 1.98-1.92 (m, 1H), 1.05 (s, 3H), 1.01-0.96 (m, 2H), 0.86-0.81 (m, 2H); Chiral SFC: column: (R,R) whelk-01 (250 × 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 11.13 min (first eluting).<br>Peak 2, Example 142b LCMS m/z = 540 [M + H]$^+$; $^1$H-NMR (400 MHz, DMSO-$d_6$): 11.98 (s, 1H), 8.84 (d, 1H), 8.48 (d, 1H), 7.99 (d, 1H), 4.20 (s, 2H), 3.73 (s, 3H), 2.80-2.65 (m, 2H), 2.35-2.24 (m, 2H), 1.98-1.92 (m, 1H), 1.05 (s, 3H), 1.01-0.96 (m, 2H), 0.86-0.81 (m, 2H), Chiral SFC: column: (R,R) whelk-01 (250 × 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 12.07 min (second eluting). |
| 143a/143b | 3-(Tert-butyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide, synthesized in the form of enantiomer 1 of 3-(tert-butyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (143a) and enantiomer 2 of 3-(tert-butyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (143b)<br>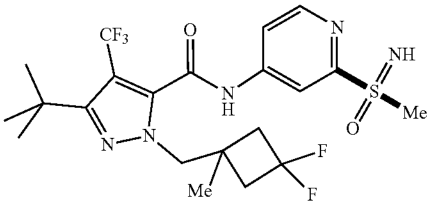 and 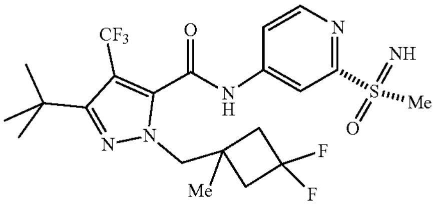<br>143a 143b<br>Amide: 3-(tert-butyl)-1-((3,3-difluoro-1-methylcyclobutyl)methyl)-4-(trifluoromethyl)-1H-pyrazole-5-carboxamide (Intermediate 268)<br>Arylbromide: (4-bromopyridin-2-yl)(imino)(methyl)-16-sulfanone, racemate (Intermediate 287)<br>Trans-1,2-diaminocyclohexane was used instead of trans-N,N'-dimethylcyclohexane-1,2-diamine.<br>Chiral-SFC (Chiralpak ART Cellulose - SC, 250 × 30 mm, 5 μm; 15% (30 mM $NH_3$ in iPrOH) in $CO_2$)<br>Peak 1, Example 143a (19 mg, 3%). LCMS m/z = 508 [M + H]$^+$; $^1$H-NMR (400 MHz, DMSO-$d_6$): 11.76 (s, 1H), 8.66 (d, 1H), 8.37 (s, 1H), 7.79 (d, 1H), 4.41 (s, 1H), 4.17 (s, 2H), 3.15 (s, 3H), 2.86-2.73 (m, 2H), 2.38-2.27 (m, 2H), 1.34 (s, 9H), 1.09 (s, 3H); Chiral SFC: column: Chiralpak IC (150 × 4.6 mm, 5 μm); co-solvent: 0.5% $iPrNH_2$ in iPrOH; flow: 3 mL/min; % of co-solvent: 10%; ABPR: 1500 psi; T: 30° C.; $R_t$ = 3.54 min (first eluting).<br>Peak 2, Example 143b (20 mg, 3%). LCMS m/z = 508 [M + H]$^+$; $^1$H-NMR (400 MHz, DMSO-$d_6$): 11.76 (s, 1H), 8.66 (d, 1H), 8.37 (s, 1H), 7.79 (d, 1H), 4.41 (s, 1H), 4.17 (s, 2H), 3.15 (s, 3H), 2.86-2.73 (m, 2H), 2.38-2.27 (m, 2H), 1.34 (s, 9H), 1.09 (s, 3H); Chiral SFC: column: Chiralpak IC (150 × 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 6.28 min (second eluting). |
| 145a/145b | 1-((3,3-Difluoro-1-methylcyclobutyl)methyl)-3-(1-(difluoromethyl)cyclopropyl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(1-(difluoromethyl)cyclopropyl)-N-(2-(S-methylsulfonimidoyl)pyridin-4-yl)-4-(trifluoromethyl)-1H-pyrazole-5-carboxamide (145a) and enantiomer 2 of 1-((3,3-difluoro-1-methylcyclobutyl)methyl)-3-(1-(difluoromethyl)cyclopropyl)-N-(2-(S-methylsulfonimidoyl)pyridin-4-yl)-4-(trifluoromethyl)-1H-pyrazole-5-carboxamide (145b)<br>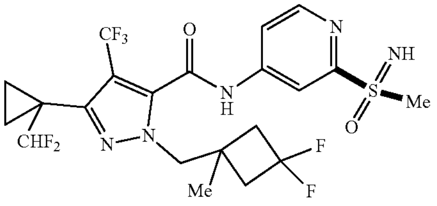 and 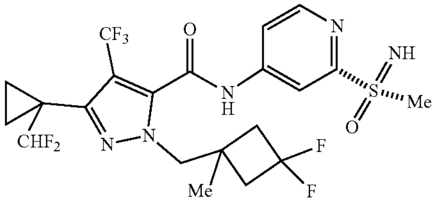<br>145a 145b<br>Amide: 1-((3,3-difluoro-1-methylcyclobutyl)methyl)-3-(1-(difluoromethyl)cyclopropyl)-4-(trifluoromethyl)-1H-pyrazole-5-carboxamide (Intermediate 269)<br>Arylbromide: (4-bromopyridin-2-yl)(imino)(methyl)-16-sulfanone, racemic (Intermediate 287) |

-continued

| Example | Name/Structure/Starting Material/Data |
|---|---|
| | Trans-1,2-diaminocyclohexane was used instead of trans-N,N'-dimethylcyclohexane-1,2-diamine. Chiral-SFC ((R,R)Whelk-01, 250 x 4.6 mm, 5 μm; 15% (30 mM $NH_3$ in iPrOH) in $CO_2$) Peak 1, Example 145a (55 mg, 9%). LCMS m/z = 542 $[M + H]^+$; $^1$H-NMR (400 MHz, DMSO-$d_6$): 11.81 (s, 1H), 8.67 (d, 1H), 8.36 (s, 1H), 7.79 (d, 1H), 5.83 (t, 1H), 4.42 (s, 1H), 4.28 (s, 2H), 3.15 (s, 3H), 2.80-2.66 (m, 2H), 2.35-2.25 (m, 2H), 1.26-1.23 (s, 2H), 1.11-1.03 (m, 5H); Chiral SFC: column: (R,R) whelk-01 (250 x 4.6 mm, 5 μm); co-solvent : 0.5% iPrOH in iPrOH; flow: 3 mL/min; % of co-solvent: 10%; ABPR: 1500 psi; T: 30° C.; $R_t$ = 4.76 min (first eluting). Peak 2, Example 145b (65 mg, 10%). LCMS m/z = 542 $[M + H]^+$; $^1$H-NMR (400 MHz, DMSO-$d_6$): 11.81 (s, 1H), 8.67 (d, 1H), 8.36 (s, 1H), 7.79 (d, 1H), 5.83 (t, 1H), 4.42 (s, 1H), 4.28 (s, 2H), 3.15 (s, 3H), 2.80-2.67 (m, 2H), 2.35-2.25 (m, 2H), 1.27-1.22 (m, 2H), 1.09-1.04 (m, 5H); Chiral SFC: column: (R,R) whelk-01 (150 x 4.6 mm, 5 μm); co-solvent : 0.5% $iPrNH_2$ in iPrOH; flow: 3 mL/min; % of co-solvent: 10%; ABPR: 1500 psi; T: 30° C.; $R_t$ = 5.71 min (second eluting). |

Example 109a/109b 1-((3,3-Difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide, synthesized in the form of enantiomer 1 of 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide (109a) and enantiomer 2 of 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide (109b)

109a

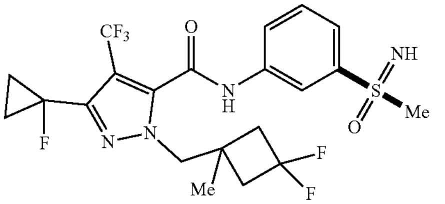

and

109b

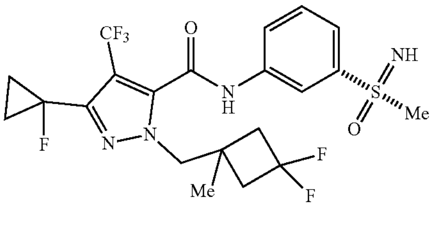

To a stirred solution of 1-((3,3-difluoro-1-methylcyclobutyl)methyl)-3-(1-fluorocyclopropyl)-N-(3-(methylthio)phenyl)-4-(trifluoromethyl)-1H-pyrazole-5-carboxamide (Intermediate 319, 260 mg) in MeOH (10 mL) were added diacetoxy iodo benzene (0.877 g) and ammonium carbonate (0.478 g) at rt. The resulting reaction mixture was stirred at rt for 2 h under an argon atmosphere. The reaction mixture was quenched with water (30 mL) and extracted with EtOAc (2×30 mL). The combined organic layers were washed with water (30 mL) and brine (30 mL), dried over anhydrous $Na_2SO_4$ and concentrated under reduced pressure to get the crude product, which was triturated with pentane, filtered and dried under reduced pressure to afford the racemic title compound (240 mg, 87%).

The residue was purified by Chiral-SFC: Chiral ART cellulose-SC (250×30 mm, 5 μm), 10% iPrOH in $CO_2$ to afford:

Peak 1, Example 109a (100 mg, 36%). LCMS m/z=509 $[M+H]^+$; $^1$H-NMR (400 MHz, DMSO-$d_6$): 11.43 (s, 1H), 8.29 (t, 1H), 7.89-7.86 (m, 1H), 7.74 (d, 1H), 7.63 (t, 1H), 4.27 (s, 3H), 3.07 (s, 3H), 2.82-2.65 (m, 2H), 2.40-2.28 (m, 2H), 1.52-1.44 (m, 2H), 1.21-1.15 (m, 2H), 1.10 (s, 3H), Chiral SFC: column: Chiralpak IC 250×4.6 mm, 5 μm; co-solvent: iPrOH, flow: 3 mL/min; % of co-solvent: 10%; ABPR: 1500 psi; T: 30° C.; $R_t$=4.57 min (first eluting).

Peak 2, Example 109b (75 mg, 27%). LCMS m/z=509 $[M+H]^+$; $^1$H-NMR (400 MHz, DMSO-$d_6$): 11.43 (s, 1H), 8.29 (t, 1H), 7.89-7.86 (m, 1H), 7.76-7.73 (m, 1H), 7.63 (t, 1H), 4.27 (s, 3H), 3.07 (s, 3H), 2.82-2.66 (m, 2H), 2.38-2.28 (m, 2H), 1.52-1.40 (m, 2H), 1.20-1.16 (m, 2H), 1.10 (s, 3H), Chiral SFC: column: Chiralpak IC 250×4.6 mm, 5 μm; co-solvent: iPrOH, flow: 3 mL/min; % of co-solvent: 10%; ABPR: 1500 psi; T: 30° C.; $R_t$=6.78 min (second eluting).

Example 122

1-((3,3-Difluoro-1-methylcyclobutyl)methyl)-3-(3-methoxybicyclo[1.1.1]pentan-1-yl)-N-(2-(S-methylsulfonimidoyl)pyridin-4-yl)-4-(trifluoromethyl)-1H-pyrazole-5-carboxamide

122

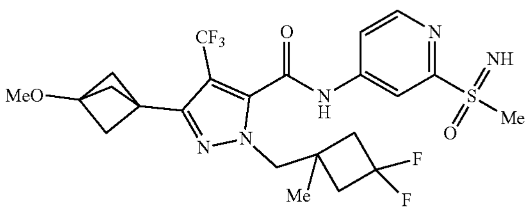

To a solution of 1-((3,3-difluoro-1-methylcyclobutyl)methyl)-3-(3-methoxybicyclo[1.1.1]pentan-1-yl)-4-(trifluoromethyl)-1H-pyrazole-5-carboxamide (Intermediate 267, 60 mg) and racemic (4-bromopyridin-2-yl)(imino)(methyl)-16-sulfanone (Intermediate 287, 43.03 mg) in 1,4 dioxane (5 mL) in a sealed tube were added CuI (2.89 mg) and potassium carbonate (31.57 mg) at rt and the mixture was degassed with argon for 10 min. To the reaction mixture was then added DMEDA (2.68 mg) at rt and the mixture was again degassed for 5 min. The resulting reaction mixture was heated to 90° C. for 16 h. The reaction mixture was cooled to rt, diluted with EtOAc (10 mL) and filtered through a celite pad. The filtrate was washed with water (10 mL) and brine (10 mL), dried over anhydrous sodium sulfate and concentrated under reduced pressure to get the crude product, which was purified by prep-HPLC to afford the title compound (4 mg, 3% over 3 steps).

Example 122 (4 mg, 3% over three steps). LCMS m/z=548 $[M+H]^+$; $^1$H-NMR (400 MHz, DMSO-$d_6$): 11.77 (s, 1H), 8.65 (d, 1H), 8.35 (s, 1H), 7.77 (d, 1H), 4.42 (s, 1H), 4.22 (s, 2H), 3.25 (s, 3H), 3.15 (s, 3H), 2.85-2.65 (m, 2H), 2.40-2.25 (m, 2H), 2.20 (s, 6H), 1.10 (s, 3H).

Example 144, 146-147

The title compounds were prepared from the appropriate amides and arylbromides using an analogous method to that described for Example 122.

| Example | Name/Structure/Starting Material/Data |
| --- | --- |
| 144a/144b | 1-((3,3-Difluoro-1-methylcyclobutyl)methyl)-N-(2-(S-methylsulfonimidoyl)pyridin-4-yl)-4-(trifluoromethyl)-3-(1-(trifluoromethyl)cyclopropyl)-1H-pyrazole-5-carboxamide, synthesized in the form of enantiomer 1 of 1-((3,3-difluoro-1-methylcyclobutyl)methyl)-N-(2-(S-methylsulfonimidoyl)pyridin-4-yl)-4-(trifluoromethyl)-3-(1-(trifluoromethyl)cyclopropyl)-1H-pyrazole-5-carboxamide (144a) and enantiomer 2 of 1-((3,3-difluoro-1-methylcyclobutyl)methyl)-N-(2-(S-methylsulfonimidoyl)pyridin-4-yl)-4-(trifluoromethyl)-3-(1-(trifluoromethyl)cyclopropyl)-1H-pyrazole-5-carboxamide (144b)<br>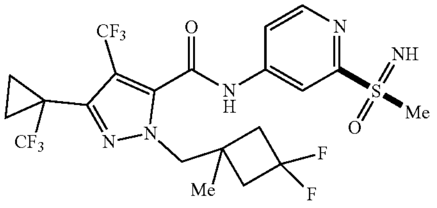 and<br>144a<br>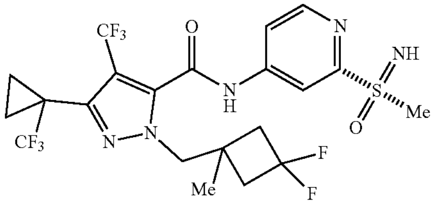<br>144a<br>Amide: 1-((3,3-difluoro-1-methylcyclobutyl)methyl)-4-(trifluoromethyl)-3-(1-(trifluoromethyl)cyclopropyl)-1H-pyrazole-5-carboxamide (Intermediate 270)<br>Arylbromide: (4-bromopyridin-2-yl)(imino)(methyl)-l6-sulfanone (Intermediate 287a) for example 144a, (4-bromopyridin-2-yl)(imino)(methyl)-l6-sulfanone, (Intermediate 287b) for example 144b<br>Peak 1, Example 144a (35 mg, 18%). LCMS m/z = 560 $[M + H]^+$; $^1$H-NMR (400 MHz, DMSO-$d_6$): 11.83 (s, 1H), 8.67 (d, 1H), 8.36 (s, 1H), 7.79 (d, 1H), 4.42 (s, 1H), 4.31 (s, 2H), 3.15 (s, 3H), 2.81-2.67 (m, 2H), 2.35-2.26 (m, 2H), 1.52-1.48 (m, 2H), 1.25-1.23 (m, 2H), 1.08 (s, 3H); Chiral SFC: column: (R,R) whelk-01 (250 × 4.6 mm, 5 μm); co-solvent: 0.5% diethylamine in iPrOH; flow: 3 mL/min; % of co-solvent: 10%; ABPR: 1500 psi; T: 30° C.; $R_t$ = 6.61 min (first eluting).<br>Peak 2, Example 144b (50 mg, 80%). LCMS m/z = 560 $[M + H]^+$; $^1$H-NMR (400 MHz, DMSO-$d_6$): 11.83 (s, 1H), 8.67 (d, 1H), 8.36 (s, 1H), 7.79 (d, 1H), 4.42 (s, 1H), 4.31 (s, 2H), 3.15 (s, 3H), 2.77-2.67 (m, 2H), 2.35-2.30 (m, 2H), 1.50-1.46 (m, 2H), 1.25-1.23 (m, 2H), 1.08 (s, 3H); Chiral SFC: column: (R,R) whelk-01 (150 × 4.6 mm, 5 μm); co-solvent: 0.5% $iPrNH_2$ in iPrOH; flow: 3 mL/min; % of co-solvent: 10%; ABPR: 1500 psi; T: 30° C.; $R_t$ = 7.32 min (second eluting). |
| 146 | 3-(Bicyclo[1.1.1]pentan-1-yl)-1-(((trans)-2-(difluoromethyl)cyclopropyl)methyl)-N-(2-(S-methylsulfonimidoyl)pyridin-4-yl)-4-(trifluoromethyl)-1H-pyrazole-5-carboxamide<br>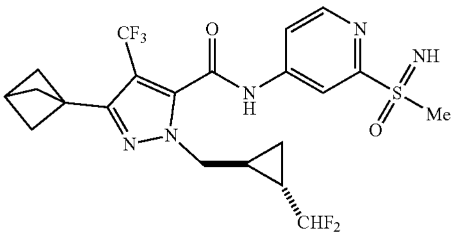<br>146 |

-continued

| Example | Name/Structure/Starting Material/Data |
|---|---|
| | Amide: 3-(bicyclo[1.1.1]pentan-1-yl)-1-(((trans)-2-(difluoromethyl)cyclopropyl)methyl)-4-(trifluoromethyl)-1H-pyrazole-5-carboxamide (Intermediate 273) Arylbromide: (4-bromopyridin-2-yl)(imino)(methyl)-16-sulfanone, racemate (Intermediate 287) Example 146 (13 mg, 13%). LCMS m/z = 504 [M + H]$^+$; $^1$H-NMR (400 MHz, DMSO-$d_6$): 11.78 (s, 1H), 8.69-8.60 (m, 1H), 8.36 (s, 1H), 7.78-7.70 (m, 1H), 5.75 (td, 1H), 4.40 (s, 1H), 4.25-4.15 (m, 1H), 4.05-3.95 (m, 1H), 3.15 (s, 3H), 2.52 (s, 1H), 2.15 (s, 6H), 1.60-1.48 (m, 2H), 0.85-0.70 (m, 2H). |
| 147 | 3-(Bicyclo[1.1.1]pentan-1-yl)-N-(2-(S-methylsulfonimidoyl)pyridin-4-yl)-4-(trifluoromethyl)-1-(((trans-2-(trifluoromethyl)cyclopropyl)methyl)-1H-pyrazole-5-carboxamide 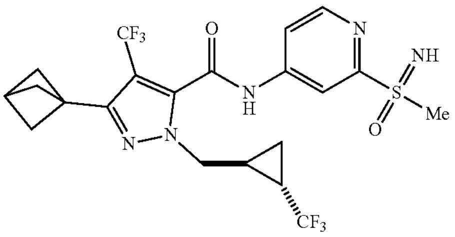 147 Amide: 3-(bicyclo[1.1.1]pentan-1-yl)-4-(trifluoromethyl)-1-(((trans)-2-(trifluoromethyl)cyclopropyl)methyl)-1H-pyrazole-5-carboxamide (Intermediate 274) Arylbromide: (4-bromopyridin-2-yl)(imino)(methyl)-16-sulfanone, racemate (Intermediate 287) Example 147 (13 mg, 2% over four steps). LMCS m/z = 522 [M + H]$^+$; $^1$H-NMR (400 MHz, DMSO-$d_6$): 11.55 (bs, 1H), 8.65 (d, 1H), 8.36 (d, 1H), 7.75 (dd, 1H), 4.40 (s, 1H), 4.25-4.15 (m, 2H), 3.15 (s, 3H), 2.55 (s, 1H), 2.15 (s, 6H), 2.05-1.95 (m, 1H), 1.70-1.60 (m, 1H), 1.05-0.90 (m, 2H). |

Example 148a

1-((3,3-Difluoro-1-methylcyclobutyl)methyl)-3-(2-fluoropropan-2-yl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(2-fluoropropan-2-yl)-N-(2-(S-methylsulfonimidoyl)pyridin-4-yl)-4-trifluoromethyl)-1H-pyrazole-5-carboxamide (148a)

148a

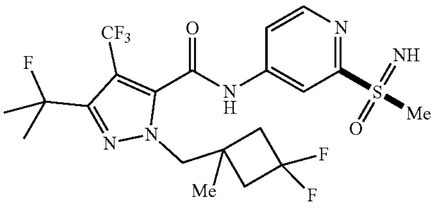

To a stirred solution of 1-((3,3-difluoro-1-methylcyclobutyl)methyl)-3-(2-fluoropropan-2-yl)-4-(trifluoromethyl)-1H-pyrazole-5-carboxamide (Intermediate 271, 200 mg) in 1,4-dioxane (20 mL) were added (4-bromopyridin-2-yl)(imino)(methyl)-16-sulfanone (Intermediate 287a, 157.92 mg), CuI (10.64 mg and $K_2CO_3$ (84.97 mg) and the mixture was degassed with argon for 10 minutes. To the reaction mixture was then added DMEDA (9.852 mg) at rt. The resulting reaction mixture was then heated to 100° C. for 16 h. The reaction mixture was diluted with water (50 mL) and extracted with EtOAc (2×20 mL). The combined organic layers were washed with water (15 mL) and brine (15 mL), dried over anhydrous $Na_2SO_4$ and concentrated under reduced pressure to get the crude product, which was purified by prep-HPLC to afford the title compound (100 mg, 35%).

Peak 1, Example 148a LCMS m/z=512 [M+H]$^+$; $^1$H-NMR (400 MHz, DMSO-$d_6$): 11.81 (bs, 1H), 8.67 (d, 1H), 8.36 (d, 1H), 7.79 (dd, 1H), 4.42 (s, 1H), 4.24 (s, 2H), 3.15 (s, 3H), 2.84-2.67 (m, 2H), 2.39-2.27 (m, 2H), 1.75 (s, 3H), 1.69 (s, 3H), 1.09 (s, 3H), Chiral SFC: column: Chiralpak IC (250×4.6 mm, 5 μm); co-solvent: MeOH; flow: 3 mL/min; % of co-solvent: 10%; ABPR: 1500 psi; T: 30° C.; $R_t$=3.38 min (first eluting).

Example 110, 148b

The title compounds were prepared from the appropriate amides and arylbromides (at a heating time between 3 16 hours) using an analogous method to that described for Example 148a.

| Example | Name/Structure/Starting Material/Data |
|---|---|
| 110a/110b | 1-((3,3-Difluoro-1-methylcyclobutyl)methyl)-3-(3-fluorobicyclo[1.1.1]pentan-1-yl)-N-(2-(S-methylsulfonimidoyl)pyridin-4-yl)-4-(trifluoromethyl)-1H-pyrazole-5-carboxamide, synthesized in the form of enantiomer 1 of 1-((3,3-difluoro-1-methylcyclobutyl)methyl)-3-(3-fluorobicyclo[1.1.1]pentan-1-yl)-N-(2-(S-methylsulfonimidoyl)pyridin-4-yl)-4-(trifluoromethyl)-1H-pyrazole-5-carboxamide (110a) and enantiomer 2 of 1-((3,3-difluoro-1-methylcyclobutyl)methyl)-3-(3-fluorobicyclo[1.1.1]pentan-1-yl)-N-(2-(S-methylsulfonimidoyl)pyridin-4-yl)-4-(trifluoromethyl)-1H-pyrazole-5-carboxamide (110b)<br>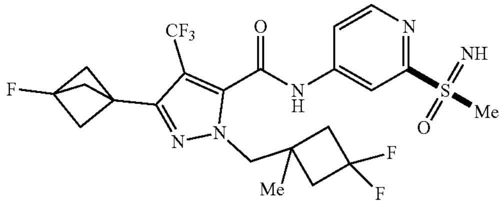 and<br>110a<br>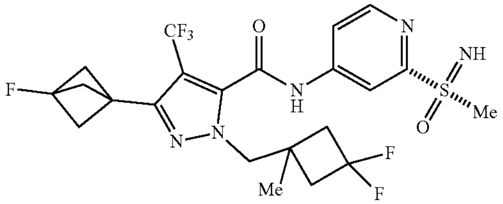<br>110b<br>Amide: 1-((3,3-difluoro-1-methylcyclobutyl)methyl)-3-(3-fluorobicyclo[1.1.1]pentan-1-yl)-4-(trifluoromethyl)-1H-pyrazole-5-carboxamide (Intermediate 286)<br>Arylbromide: (4-bromopyridin-2-yl)(imino)(methyl)-l6-sulfanone (Intermediate 287a) for Example 110a and (4-bromopyridin-2-yl)(imino)(methyl)-l6-sulfanone (Intermediate 287b) for Example 110b<br>Peak 1, Example 110a (50 mg, 17%). LCMS m/z = 536 $[M + H]^+$; $^1$H-NMR (400 MHz, DMSO-$d_6$): 11.78 (s, 1H), 8.66 (d, 1H), 8.34 (d, 1H), 7.77 (dd, 1H), 4.42 (s, 1H), 4.24 (s, 2H), 3.15 (s, 3H), 2.82-2.65 (m, 2H), 2.44 (d, 6H), 2.36-2.27 (m, 2H), 1.09 (s, 3H), Chiral SFC: column: Chiralpak AS-H (150 × 4.6 mm, 5 μm); co-solvent: 0.5% diethylamne in MeOH; flow: 3 mL/min; % of co-solvent: 10%; ABPR: 1500 psi; T: 30° C.; $R_t$ = 0.89 min (first eluting).<br>Peak 2, Example 110b (190 mg, 22%). LCMS m/z = 536 $[M + H]^+$; $^1$H-NMR (400 MHz, DMSO-$d_6$): 11.78 (s, 1H), 8.67 (d, 1H), 8.34 (s, 1H), 7.77 (d, 1H), 4.42 (s, 1H), 4.24 (s, 2H), 3.15 (s, 3H), 2.78-2.74 (m, 2H), 2.44 (d, 6H), 2.36-2.28 (m, 2H), 1.09 (s, 3H), Chiral SFC: column: Chiralpak AS-H (150 × 4.6 mm, 5 μm); co-solvent: 0.5% diethylamne in MeOH; flow: 3 mL/min; % of co-solvent: 10%; ABPR: 1500 psi; T: 30° C.; $R_t$ = 2.05 min (second eluting). |
| 148b | 1-((3,3-Difluoro-1-methylcyclobutyl)methyl)-3-(2-fluoropropan-2-yl)-N-(2-(S-methylsulfonimidoyl)pyridin-4-yl)-4-(trifluoromethyl)-1H-pyrazole-5-carboxamide, synthesized in the form of enantiomer 2 of 1-((3,3-difluoro-1-methylcyclobutyl)methyl)-3-(2-fluoropropan-2-yl)-N-(2-(S-methylsulfonimidoyl)pyridin-4-yl)-4-(trifluoromethyl)-1H-pyrazole-5-carboxamide (148b)<br>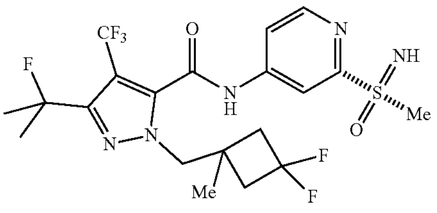<br>148b<br>Amide: 1-((3,3-difluoro-1-methylcyclobutyl)methyl)-3-(2-fluoropropan-2-yl)-4-(trifluoromethyl)-1H-pyrazole-5-carboxamide (Intermediate 271)<br>Arylbromide: (4-bromopyridin-2-yl)(imino)(methyl)-l6-sulfanone (Intermediate 287b)<br>Peak 2, Example 148b (105 mg, 29%). LCMS m/z = 512 $[M + H]^+$; $^1$H-NMR (400 MHz, DMSO-$d_6$): 11.82 (bs, 1H), 8.67 (d, 1H), 8.36 (d, 1H), 7.79 (dd, 1H), 4.42 (s, 1H), 4.24 (s, 2H), 3.15 (s, 3H), 2.83-2.67 (m, 2H), 2.39-2.27 (m, 2H), 1.75 (s, 3H), 1.69 (s, 3H), 1.09 (s, 3H), Chiral SFC: column: Chiralpak IC (250 × 4.6 mm, 5 μm); co-solvent: MeOH; flow: 3 mL/min; % of co-solvent: 10%; ABPR: 1500 psi; T: 30° C.; $R_t$ = 4.30 min (second eluting) |

Example 150a 1-((3,3-Difluoro-1-methylcyclobutyl)methyl)-3-(1-fluorocyclopropyl)-N-(3-(S-methyl-N-(oxetane-3-carbonyl)sulfonimidoyl)phenyl)-4-(trifluoromethyl)-1H-pyrazole-5-carboxamide, synthesized in the form of enantiomer 1 of 1-((3,3-difluoro-1-methylcyclobutyl)methyl)-3-(1-fluorocyclopropyl)-N-(3-(S-methyl-N-(oxetane-3-carbonyl)sulfonimidoyl)phenyl)-4-(trifluoromethyl)-1H-pyrazole-5-carboxamide (150a)

150a

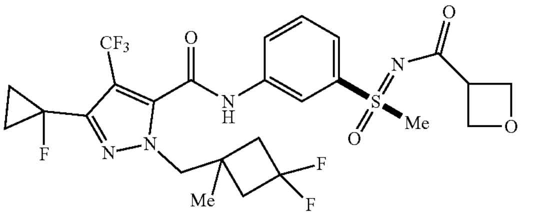

To a stirred solution of oxetane-3-carboxylic acid (20.078 mg) in DMF (10 mL) were added HATU (112.17 mg) and DIPEA (0.103 mL) followed by 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide (Example 109b, 100 mg) at rt and the mixture was stirred for 2 h. The reaction mixture was then diluted with water (20 mL) and extracted with EtOAc (3×10 mL). The combined organic layers were washed with water (25 mL) and brine (25 mL), dried over sodium sulfate and concentrated under reduced pressure to get the crude product, which was purified by prep-HPLC to yield the title compound (19 mg, 16%).

Peak 1, Example 150a (19 mg, 16%). LCMS m/z=593 $[M+H]^+$; $^1H$-NMR (400 MHz, DMSO-$d_6$): 11.54 (s, 1H), 8.33 (s, 1H), 7.92 (d, 1H), 7.80-7.69 (m, 2H), 4.75-4.55 (m, 4H), 4.27 (s, 2H), 3.90-3.75 (m, 1H), 3.49 (s, 3H), 2.85-2.70 (m, 2H), 2.40-2.25 (m, 2H), 1.55-1.40 (m, 2H), 1.20-1.13 (m, 2H), 1.10 (s, 3H); Chiral SFC: column: Chiralpak OX-H (250×4.6 mm, 5 μm); co-solvent: 0.5% $iPrNH_2$ in MeOH; flow: 3 mL/min; % of co-solvent: 20%; ABPR: 1500 psi; T: 30° C.; $R_t$=2.19 min (first eluting).

Example 150b

The title compounds were prepared from the appropriate sulfoximines using an analogous method to that described for Example 150a.

| Example | Name/Structure/Starting Material/Data |
|---|---|
| 150b | 1-((3,3-Difluoro-1-methylcyclobutyl)methyl)-3-(1-fluorocyclopropyl)-N-(3-(S-methyl-N-(oxetane-3-carbonyl)sulfonimidoyl)phenyl)-4-(trifluoromethyl)-1H-pyrazole-5-carboxamide, synthesized in the form of enantiomer 2 of 1-((3,3-difluoro-1-methylcyclobutyl)methyl)-3-(1-fluorocyclopropyl)-N-(3-(S-methyl-N-(oxetane-3-carbonyl)sulfonimidoyl)phenyl)-4-(trifluoromethyl)-1H-pyrazole-5-carboxamide (150b)<br>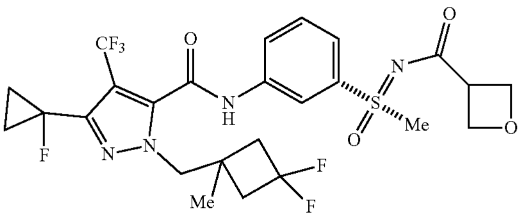<br>150b<br>Sulfoximine: 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide (Example 109a). Peak 2, Example 150b (40 mg, 34%). LCMS m/z = 593 $[M + H]^+$; $^1H$-NMR (400 MHz, DMSO-$d_6$): 11.53 (bs, 1H), 8.35-8.31 (m, 1H), 7.93 (d, 1H), 7.80-7.69 (m, 2H), 4.70-4.58 (m, 4H), 4.27 (s, 2H), 3.85-3.75 (m, 1H), 3.49 (s, 3H), 2.85-2.70 (m, 2H), 2.40-2.25 (m, 2H), 1.55-1.40 (m, 2H), 1.20-1.13 (m, 2H), 1.10 (s, 3H); Chiral SFC: column: Chiralpak OX-H (250 x 4.6 mm, 5 μm); co-solvent: 0.5% $iPrNH_2$ in MeOH; flow: 3 mL/min; % of co-solvent: 20%; ABPR: 1500 psi; T: 30° C.; $R_t$ = 2.84 min (second eluting). |

Example 151a/151b 1-((3,3-Difluoro-1-methylcyclobutyl)methyl)-3-(1-fluorocyclonronvl)-N-(3-(N-(2-hvdroxyacetvl)-S methylsulfonimidoyl)phenyl)-4-(trifluoromethyl)-1H-pyrazole-5-carboxamide, synthesized in the form of enantiomer 1 of 1-((3,3-difluoro-1-methyl-cyclobutyl)methyl)-3-(1-fluorocyclopropyl)-N-(3-(N-(2-hydroxettyl)-S-methylsulfonimidoyl)phenyl)-4-(trifluoromethyl)-1H-pyrazole-5-carboxamide (151a) and enantiomer 2 of 1-((3,3-difluoro-1-methylcyclobutyl)methyl)-3-(1-fluorocyclopropyl)-N-(3-(N-(2-hydroxettyl)-S-methylsulfonimidoyl) phenyl)-4-(trifluoromethyl)-1H-pyrazole-5-carboxamide (151b)

151a

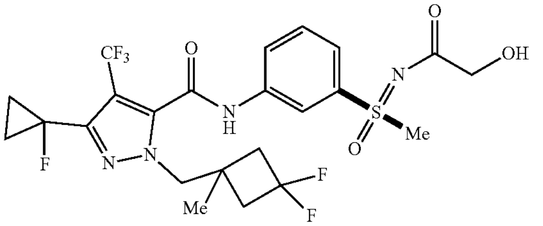

and

151b

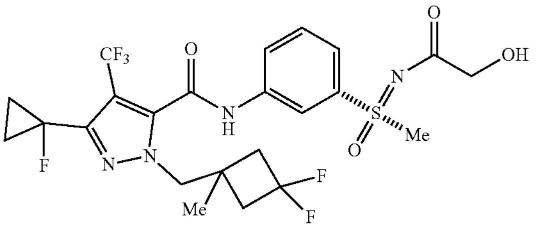

Part 1: To a stirred solution of 2-((tert-butyldiphenylsilyl) oxy)acetic acid (500 mg) in DMF (5 mL) were added DIPEA (0.83 mL) and HATU (900 mg) at 0° C. The resulting reaction mixture was stirred at 0° C. for 10 min. Then, 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide (Example 109, 800 mg) was added at 0° C. The reaction mixture was stirred at rt for 1 h. The reaction mixture was quenched with water (50 mL) and extracted with DCM (3×20 mL). The combined organic layers were washed with brine (20 mL), dried over anhydrous $Na_2SO_4$ and concentrated under reduced pressure to afford N-(3-(N-(2-((tert-butyldiphenyl-silyl)oxy)acetyl)-S-methylsulfonimidoyl)phenyl)-1-((3,3-difluoro-1-methylcyclobutyl)methyl)-3-(1-fluorocyclopropyl)-4-(trifluoromethyl)-1H-pyrazole-5-carboxamide (550 mg, 43%).

Part 2: To a stirred solution of N-(3-(N-(2-((tert-butyldiphenylsilyl)oxy)acetyl)-S-methylsulfonimidoyl)phenyl)-1-((3,3-difluoro-1-methylcyclobutyl)methyl)-3-(1-fluorocyclopropyl)-4-(trifluoromethyl)-1H-pyrazole-5-carboxamide (500 mg) in THF (5 mL) was added TBAF in THF (1M, 2 mL) at 0° C. The reaction mixture was then stirred at rt for 2 h. The reaction mixture was quenched with water (50 mL) and extracted with DCM (3×20 mL). The combined organic layers were washed with brine (20 mL), dried over anhydrous $Na_2SO_4$ and concentrated under reduced pressure to afford the crude product, which was purified by prep-HPLC separation to obtain the racemic title compound (130 mg, 36%).

The residue was purified by Chiral-SFC (Cellulose-4 (250×30 mm, 5 μm), 10% MeOH in $CO_2$) to afford:

Peak 1, Example 151a (35 mg, 9%). LCMS m/z=567 $[M+H]^+$; $^1$H-NMR (400 MHz, DMSO-$d_6$): 11.53 (s, 1H), 8.28 (s, 1H), 7.96 (d, 1H), 7.77-7.68 (m, 2H), 4.78 (t, 1H), 4.28 (s, 2H), 3.94 (d, 2H), 3.47 (s, 3H), 2.83-2.73 (m, 2H), 2.39-2.27 (m, 2H), 1.53-1.43 (m, 2H), 1.24-1.14 (m, 2H), 1.10 (s, 3H); Chiral SFC: column: Chiracel OX-H 150×4.6 mm, 5 μm; co-solvent: MeOH, flow: 3 mL/min; % of co-solvent: 15%; ABPR: 1500 psi; T: 30° C.; $R_t$=2.30 min (first eluting).

Peak 2, Example 151b (45 mg, 12%). LCMS m/z=567 $[M+H]^+$; $^1$H-NMR (400 MHz, DMSO-$d_6$): 11.53 (s, 1H), 8.27 (s, 1H), 7.98-7.91 (m, 1H), 7.78-7.64 (m, 2H), 4.78 (t, 1H), 4.28 (s, 2H), 3.95 (d, 2H), 3.47 (s, 3H), 2.83-2.73 (m, 2H), 2.38-2.27 (m, 2H), 1.51-1.42 (m, 2H), 1.24-1.14 (m, 2H), 1.05 (s, 3H); Chiral SFC: column: Chiracel OX-H 150×4.6 mm, 5 μm; co-solvent: MeOH, flow: 3 mL/min; % of co-solvent: 15%; ABPR: 1500 psi; T: 30° C.; $R_t$=2.94 min (second eluting).

Example 152

3-Cyclopropyl-1-((3,3-difluoro-1-methylcyclobutyl) methyl)-N-(2-(N—((R)-2,3-dihydroxypropyl)-S-methylsulfonimidoyl)pyridin-4-yl)-4-(trifluoromethyl)-1H-pyrazole-5-carboxamide

152

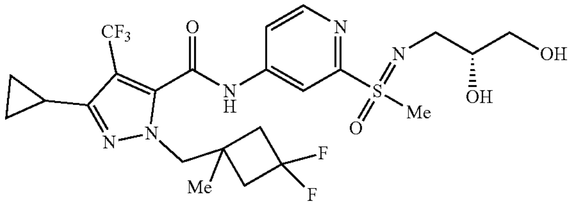

Part 1: To a solution of racemic 3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide (Example 1, 80 mg) in 2-MeTHF in (7.0 mL) were added (R)-trimethyl(oxiran-2-ylmethoxy)silane (119 mg) and $Ca(NTf_2)_2$ (49 mg). The reaction mixture was heated to 70° C. for 16 h. The reaction mixture was concentrated under reduced pressure to get the crude product, which was purified by reverse phase prep HPLC to yield the title compound (17 mg, 18%).

Example 152 LCMS m/z=566 $[M+H]^+$; $^1$H-NMR (400 MHz, DMSO-$d_6$): 11.75 (s, 1H), 8.69 (d, 1H), 8.31 (s, 1H), 7.80 (d, 1H), 4.14 (s, 2H), 3.69 (s, 1H), 3.19-3.17 (m, 2H), 2.70-2.50 (m, 2H), 2.33-226 (m, 3H), 1.93 (s, 1H), 1.26-1.14 (m, 6H), 1.04-0.96 (m, 2H), 0.83-0.73 (m, 4H)

Examples 153a/153b/153c/153d 1-((2-Azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide, synthesized in the form of diastereomer 1 of 1-((2-Azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (153a), diastereomer 2 of 1-((2-Azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (153b), diastereomer 3 of 1-((2-Azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (153c) and diastereomer 4 of 1-((2-Azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide (153d)

153a

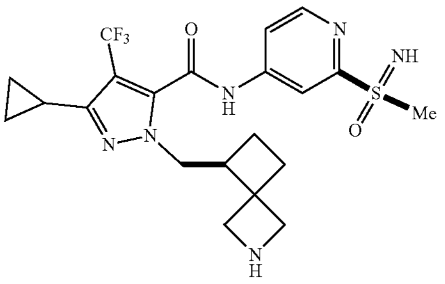

and

153b

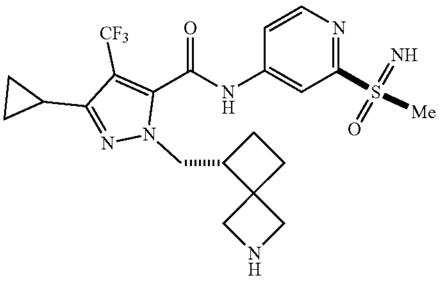

153c

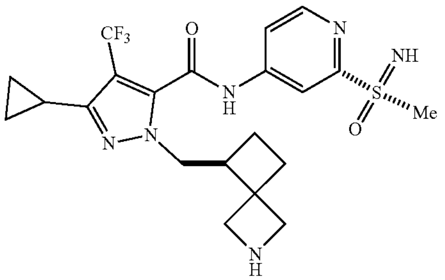

and

-continued

153d

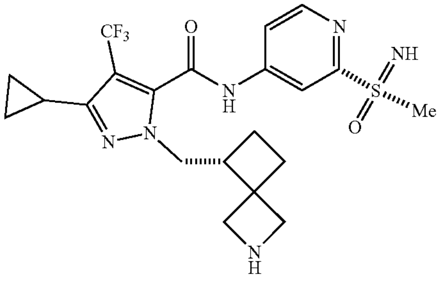

Part 1: To the stirred solution of tert-butyl 5-{[5-carbamoyl-3-cyclopropyl-4-(trifluoromethyl)-1H-pyrazol-1-yl]methyl}-2-azaspiro[3.3]heptane-2-carboxylate (Intermediate 275, 0.5 g) in 1,4-dioxane (15 mL) were added tert-butyl ((4-bromopyridin-2-yl)(methyl)(oxo)-16-sulfaneylidene) carbamate (Intermediate 290b, 0.5 g) and $Cs_2CO_3$ (0.42 g) at rt. The reaction mixture was purged with argon gas for 10 min, followed by the addition of CuI (0.022 g) and DMEDA (0.033 g) at rt. The reaction mixture was heated to 110° C. for 8 h in a sealed tube. The reaction mixture was cooled to rt and filtered through a celite bed. The filtrate was concentrated under reduced pressure to get the crude product, which was purified by CombiFlash column chromatography ($SiO_2$, 0-80% EtOAc/Hex) and chiral NP purification to afford tert-butyl 5-((5-((2-(N-(tert-butoxycarbonyl)-S-methylsulfonimidoyl)pyridin-4-yl)carbamoyl)-3-cyclopropyl-4-(trifluoromethyl)-1H-pyrazol-1-yl)methyl)-2-azaspiro[3.3]heptane-2-carboxylate, which was separated into the individual diastereomers by chiral HPLC.

Chiral-HPLC (Chiralpak IG 250×30 mm, 5 μm; Hex/EtOH 80/20)

Peak 1, Intermediate 330a (0.34 g, 42%). LCMS m/z=683 $[M+H]^+$; Chiral HPLC: column: Chiralpak IG (250×4.6 mm, 5 μm); mobile phase: Hexane/EtOH/iPrNH$_2$ 70/30/0.1, flow rate: 1.0 mL/min; $R_t$=6.24 min (first eluting).

Peak 2, Intermediate 330b (0.27 mg, 33%). LCMS m/z=683 $[M+H]^+$; Chiral HPLC: column: Chiralpak IG (250×4.6 mm, 5 μm); mobile phase: hexane/EtOH/iPrNH$_2$ 70/30/0.1, flow rate: 1.0 mL/min; $R_t$=7.91 min (second eluting).

Intermediates 330c/330d were prepared using an analogous method to that described for Intermediates 330a/330b, using Intermediate 290a in part 1.

Chiral-HPLC (Chiralpak IG 250×30 mm, 5 μm; Hex/EtOH 90/10)

Peak 1, Intermediate 330c (0.256 g, 33%). LCMS m/z=683 $[M+H]^+$; Chiral HPLC: column: Chiralpak IG (250×4.6 mm, 5 μm); mobile phase: hexane/EtOH/iPrNH$_2$ 70/30/0.1, flow rate: 1.0 mL/min; Rc=5.70 min (first eluting).

Peak 2, Intermediate 330d (0.245 mg, 30%). LCMS m/z=683 $[M+H]^+$; Chiral HPLC: column: Chiralpak IG (250×4.6 mm, 5 μm); mobile phase: Hexane/EtOH/iPrNH$_2$ 70/30/0.1, flow rate: 1.0 mL/min; $R_t$=6.43 min (second eluting).

Part 2: To a stirred solution of tert-butyl 5-((5-((2-(N-(tert-butoxycarbonyl)-S-methylsulfonimidoyl)pyridin-4-yl)carbamoyl)-3-cyclopropyl-4-(trifluoromethyl)-1H-pyrazol-1-yl)methyl)-2-azaspiro[3.3]heptane-2-carboxylate (Intermediate 330a, 0.15 g) in DCM (10 mL) was added TFA (4 M in DCM; 5 mL) at 0° C. The reaction mixture was stirred at 0° C. for 1 h. The reaction mixture was concentrated under reduced pressure to get the crude product, which was basified with saturated $NaHCO_3$ solution and extracted with EtOAc (3×80 mL). The combined organic part was washed with cold brine and dried over $Na_2SO_4$. The organic layer was concentrated under reduced pressure to get the crude product, which was purified by RP prep HPLC to the title compound (153a).

Example 153a (17 mg, 16%). LCMS m/z=483 $[M+H]^+$; $^1$H-NMR (400 MHz, DMSO-$d_6$): 8.64-8.63 (m, 1H), 8.43 (s, 1H), 7.83-7.82 (m, 1H), 4.40-4.35 (m, 1H), 4.18-4.13 (m, 1H), 4.09-4.07 (m, 1H), 3.68-3.66 (m, 1H), 3.60-3.55 (m, 2H), 3.27 (s, 3H), 2.84-2.80 (m, 1H), 2.18-2.12 (m, 2H), 2.02-1.99 (m, 1H), 1.91-1.90 (m, 1H), 1.66-1.64 (m, 1H), 1.00-0.91 (m, 4H).

Example 153b was prepared using an analogous method to that described for Example 153a, part 2, using Intermediate 330b.

Example 153b (16 mg, 15%). LCMS m/z=483 $[M+H]^+$; $^1$H-NMR (400 MHz, DMSO-$d_6$): 8.58-8.57 (m, 1H), 8.33 (s, 1H), 7.69-7.68 (m, 1H), 4.31-4.30 (m, 1H), 4.13-4.08 (m, 1H), 3.81-3.74 (m, 4H), 3.14 (s, 3H), 2.66-2.65 (m, 1H), 1.98-1.92 (m, 3H), 1.77-1.76 (m, 1H), 1.57-1.52 (m, 1H), 0.95-0.84 (m, 4H).

Example 153c was prepared using an analogous method to that described for Example 153a, part 2, using Intermediate 330c.

Example 153c (24 mg, 22%). LCMS m/z=483 $[M+H]^+$; $^1$H-NMR (400 MHz, DMSO-$d_6$): 8.58-8.57 (m, 1H), 8.33 (s, 1H), 7.71-7.70 (m, 1H), 4.31-4.24 (m, 1H), 4.13-4.08 (m, 2H), 3.74-3.73 (m, 1H), 3.41-3.40 (m, 2H), 3.14 (s, 3H), 2.66-2.65 (m, 1H), 1.98-1.92 (m, 3H), 1.76-1.74 (m, 1H), 1.56-1.52 (m, 1H), 0.95-0.84 (m, 4H).

Example 153d was prepared using an analogous method to that described for Example 153a, part 2, using Intermediate 330d.

Example 153d (18 mg, 17%). LCMS m/z=483 $[M+H]^+$; $^1$H-NMR (400 MHz, DMSO-$d_6$): 8.58-8.57 (m, 1H), 8.33 (s, 1H), 7.71-7.70 (m, 1H), 4.31-4.24 (m, 1H), 4.13-4.08 (m, 2H), 3.74-3.73 (m, 2H), 3.41-3.34 (m, 2H), 3.14 (s, 3H), 2.66-2.65 (m, 1H), 1.98-1.92 (m, 3H), 1.76-1.74 (m, 1H), 1.56-1.52 (m, 1H), 0.95-0.84 (m, 4H).

Example 114

The title compounds were prepared from the appropriate amides and arylbromides using an analogous method to that described for Example 153.

| Example | Name/Structure/Starting Material/Data |
|---|---|
| 114 | 1-((3,3-Difluoro-1-methylcyclobutyl)methyl)-3-(2,2-difluorobicyclo[1.1.1]pentan-1-yl)-N-(2-(S-methylsulfonimidoyl)pyridin-4-yl)-4-(trifluoromethyl)-1H-pyrazole-5-carboxamide<br>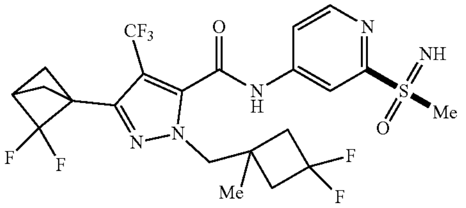<br>114<br>Amide: 1-((3,3-difluoro-1-methylcyclobutyl)methyl)-3-(2,2-difluorobicyclo[1.1.1]pentan-1-yl)-4-(trifluoromethyl)-1H-pyrazole-5-carboxamide (Intermediate 281)<br>Arylbromide: tert-butyl ((4-bromopyridin-2-yl)(methyl)(oxo)-l6-sulfaneylidene)carbamate (Intermediate 290b)<br>Example 114 (35 mg, 53%). LCMS m/z = 554 $[M + H]^+$; $^1$H-NMR (600 MHz, DMSO-$d_6$): 8.68 (d, 1H), 8.36 (d, 1H), 7.79 (dd, 1H), 4.41 (s, 1H), 4.29 (s, 2H), 3.23 (d, 1H), 3.16 (d, 3H), 2.84-2.73 (m, 2H), 2.33 (d, 4H), 2.03-1.96 (m, 2H), 1.12 (s, 3H). |

The following prophetic examples could be synthesized according to the general schemes and by analogy to the synthetic procedures described above:

| Structure | Prophetic example number | Chemical name |
|---|---|---|
| 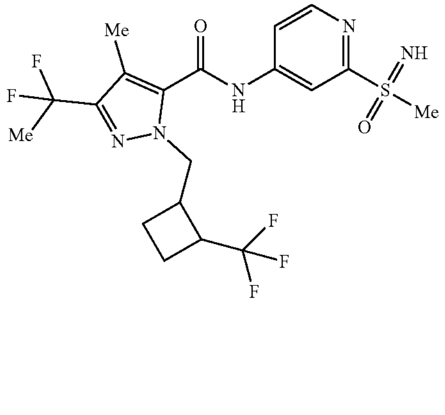 [SMILES: Cc1c(C(C)(F)F)nn(CC2CCC2C(F)(F)F)c1C(=O)Nc1ccnc(S(C)(=N)=O)c1] | 13 | 3-(1,1-difluoroethyl)-4-methyl-N-(2-(S-methylsulfonimidoyl)pyridin-4-yl)-1-((2-(trifluoromethyl)cyclobutyl)methyl)-1H-pyrazole-5-carboxamide |

-continued

| Structure | Prophetic example number | Chemical name |
|---|---|---|
| 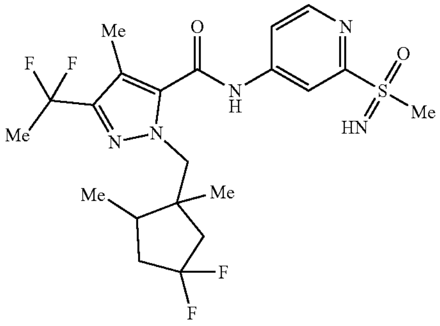 [SMILES: Cc1c(C(C)(F)F)nn(CC2(C)CC(F)(F)CC2C)c1C(=O)Nc1ccnc(S(C)(=N)=O)c1] | 44 | 1-((4,4-difluoro-1,2-dimethylcyclopentyl)methyl)-3-(1,1-difluoroethyl)-4-methyl-N-(2-(S-methylsulfonimidoyl)pyridin-4-yl)-1H-pyrazole-5-carboxamide |
| 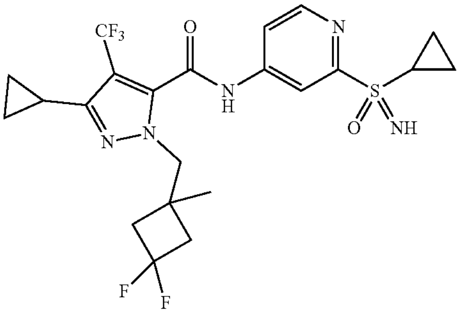 [SMILES: CC1(Cn2nc(C3CC3)c(C(F)(F)F)c2C(=O)Nc2ccnc(S(=N)(=O)C3CC3)c2)CC(F)(F)C1] | 49 | N-(2-(cyclopropanesulfonimidoyl)pyridin-4-yl)-3-cyclopropyl-1-((3,3-difluoro-1-methylcyclobutyl)methyl)-4-(trifluoromethyl)-1H-pyrazole-5-carboxamide |
| 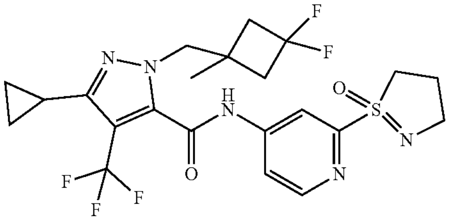 [SMILES: CC1(Cn2nc(C3CC3)c(C(F)(F)F)c2C(=O)Nc2ccnc(S3(=O)=NCCC3)c2)CC(F)(F)C1] | 51 | 3-cyclopropyl-1-((3,3-difluoro-1-methylcyclobutyl)methyl)-N-(2-(1-oxido-4,5-dihydro-3H-1λ$^6$-isothiazol-1-yl)pyridin-4-yl)-4-(trifluoromethyl)-1H-pyrazole-5-carboxamide |
| 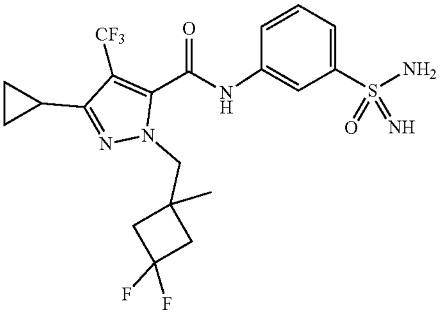 [SMILES: CC1(Cn2nc(C3CC3)c(C(F)(F)F)c2C(=O)Nc2cccc(S(=N)(N)=O)c2)CC(F)(F)C1] | 52 | 3-cyclopropyl-1-((3,3-difluoro-1-methylcyclobutyl)methyl)-N-(3-sulfamidimidoylphenyl)-4-(trifluoromethyl)-1H-pyrazole-5-carboxamide |
| 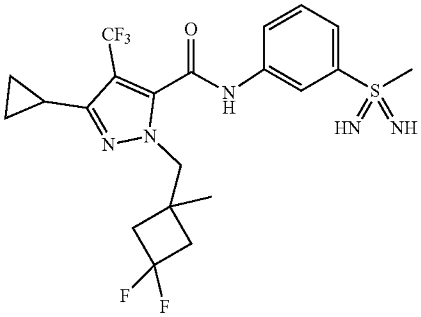 [SMILES: CC1(Cn2nc(C3CC3)c(C(F)(F)F)c2C(=O)Nc2cccc(S(C)(=N)=N)c2)CC(F)(F)C1] | 53 | 3-cyclopropyl-1-((3,3-difluoro-1-methylcyclobutyl)methyl)-N-(3-(methyl(phenyl)-λ6-sulfanediimine))-4-(trifluoromethyl)-1H-pyrazole-5-carboxamide |

-continued

| Structure | Prophetic example number | Chemical name |
| --- | --- | --- |
| 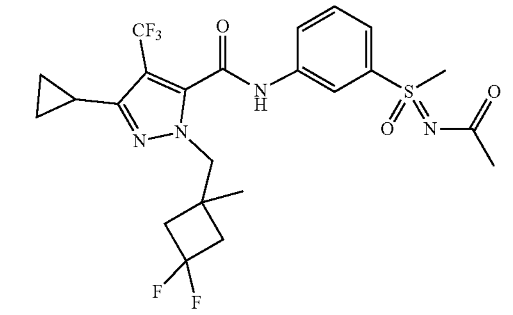 [SMILES: CC(=O)N=S(C)(=O)c1cccc(NC(=O)c2c(C(F)(F)F)c(C3CC3)nn2CC2(C)CC(F)(F)C2)c1] | 54 | N-(3-(N-acetyl-S-methylsulfonimidoyl)phenyl)-3-cyclopropyl-1-((3,3-difluoro-1-methylcyclobutyl)methyl)-4-(trifluoromethyl)-1H-pyrazole-5-carboxamide |
| 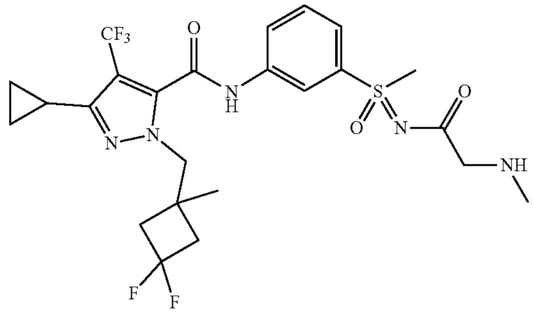 [SMILES: CNCC(=O)N=S(C)(=O)c1cccc(NC(=O)c2c(C(F)(F)F)c(C3CC3)nn2CC2(C)CC(F)(F)C2)c1] | 55 | 3-cyclopropyl-1-((3,3-difluoro-1-methylcyclobutyl)methyl)-N-(3-(S-methyl-N-(methylglycyl)sulfonimidoyl)phenyl)-4-(trifluoromethyl)-1H-pyrazole-5-carboxamide |
| 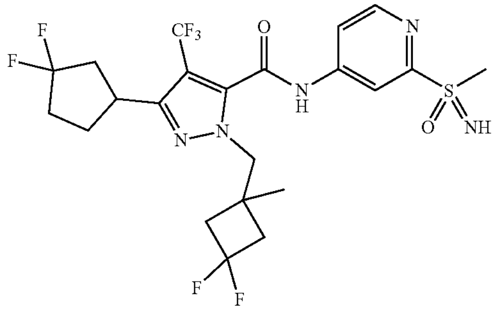 [SMILES: CC1(Cn2nc(C3CCC(F)(F)C3)c(C(F)(F)F)c2C(=O)Nc2ccnc(S(C)(=N)=O)c2)CC(F)(F)C1] | 60 | 1-((3,3-difluoro-1-methylcyclobutyl)methyl)-3-(3,3-difluorocyclopentyl)-N-(2-(S-methylsulfonimidoyl)pyridin-4-yl)-4-(trifluoromethyl)-1H-pyrazole-5-carboxamide |
| 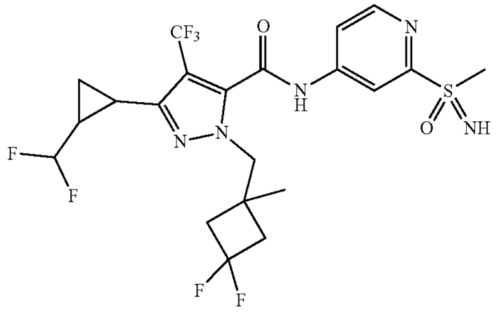 [SMILES: CC1(Cn2nc(C3CC3C(F)F)c(C(F)(F)F)c2C(=O)Nc2ccnc(S(C)(=N)=O)c2)CC(F)(F)C1] | 66 | 1-((3,3-difluoro-1-methylcyclobutyl)methyl)-3-(2-(difluoromethyl)cyclopropyl)-N-(2-(S-methylsulfonimidoyl)pyridin-4-yl)-4-(trifluoromethyl)-1H-pyrazole-5-carboxamide |

-continued

| Structure | Prophetic example number | Chemical name |
|---|---|---|
| 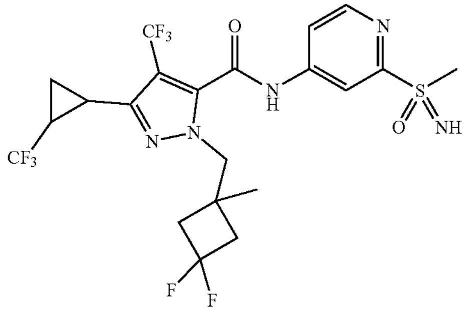 [SMILES: CC1(Cn2nc(C3CC3C(F)(F)F)c(C(F)(F)F)c2C(=O)Nc2ccnc(S(C)(=N)=O)c2)CC(F)(F)C1] | 67 | 1-((3,3-difluoro-1-methylcyclobutyl)methyl)-N-(2-(S-methylsulfonimidoyl)pyridin-4-yl)-4-(trifluoromethyl)-3-(2-(trifluoromethyl)cyclopropyl)-1H-pyrazole-5-carboxamide |
| 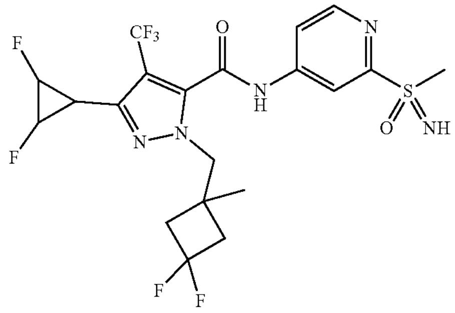 [SMILES: CC1(Cn2nc(C3C(F)C3F)c(C(F)(F)F)c2C(=O)Nc2ccnc(S(C)(=N)=O)c2)CC(F)(F)C1] | 72 | 1-((3,3-difluoro-1-methylcyclobutyl)methyl)-3-(2,3-difluorocyclopropyl)-N-(2-(S-methylsulfonimidoyl)pyridin-4-yl)-4-(trifluoromethyl)-1H-pyrazole-5-carboxamide |
| 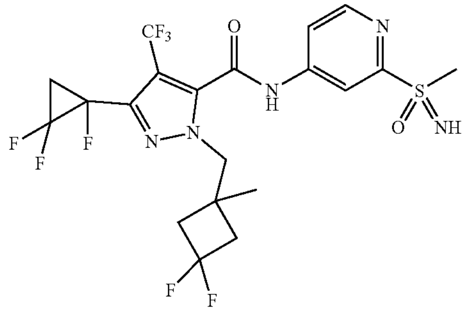 [SMILES: CC1(Cn2nc(C3(F)CC3(F)F)c(C(F)(F)F)c2C(=O)Nc2ccnc(S(C)(=N)=O)c2)CC(F)(F)C1] | 73 | 1-((3,3-difluoro-1-methylcyclobutyl)methyl)-N-(2-(S-methylsulfonimidoyl)pyridin-4-yl)-3-(1,2,2-trifluorocyclopropyl)-4-(trifluoromethyl)-1H-pyrazole-5-carboxamide |
| 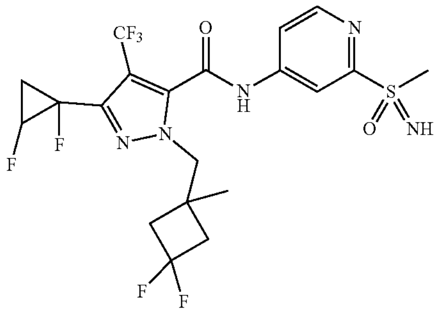 [SMILES: CC1(Cn2nc(C3(F)CC3F)c(C(F)(F)F)c2C(=O)Nc2ccnc(S(C)(=N)=O)c2)CC(F)(F)C1] | 74 | 1-((3,3-difluoro-1-methylcyclobutyl)methyl)-3-(1,2-difluorocyclopropyl)-N-(2-(S-methylsulfonimidoyl)pyridin-4-yl)-4-(trifluoromethyl)-1H-pyrazole-5-carboxamide |

-continued

| Structure | Prophetic example number | Chemical name |
|---|---|---|
| 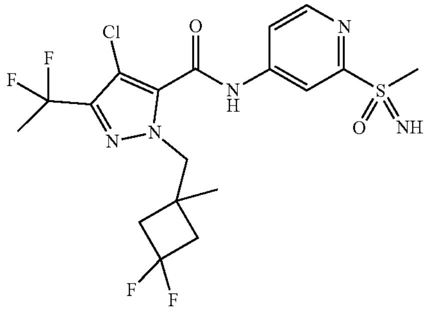 [SMILES: CC1(Cn2nc(C(C)(F)F)c(Cl)c2C(=O)Nc2ccnc(S(C)(=N)=O)c2)CC(F)(F)C1] | 76 | 4-chloro-1-((3,3-difluoro-1-methylcyclobutyl)methyl)-3-(1,1-difluoroethyl)-N-(2-(S-methylsulfonimidoyl)pyridin-4-yl)-1H-pyrazole-5-carboxamide |
| 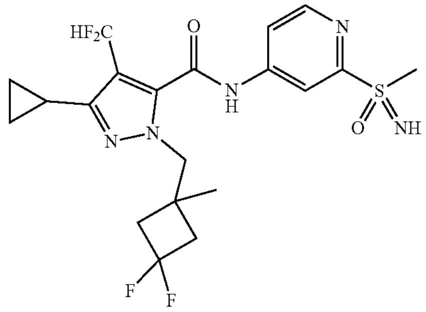 | 77 | 3-cyclopropyl-1-((3,3-difluoro-1-methylcyclobutyl)methyl)-4-(difluoromethyl)-N-(2-(S-methylsulfonimidoyl)pyridin-4-yl)-1H-pyrazole-5-carboxamide |
| 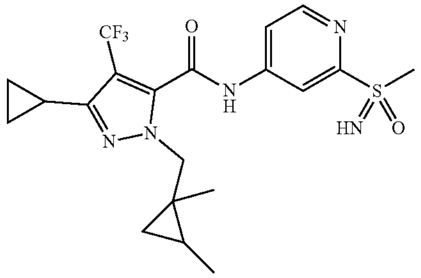 [SMILES: CC1CC1(C)Cn1nc(C2CC2)c(C(F)(F)F)c1C(=O)Nc1ccnc(S(C)(=N)=O)c1] | 81 | 3-cyclopropyl-1-((1,2-dimethylcyclopropyl)methyl)-N-(2-(S-methylsulfonimidoyl)pyridin-4-yl)-4-(trifluoromethyl)-1H-pyrazole-5-carboxamide |
| 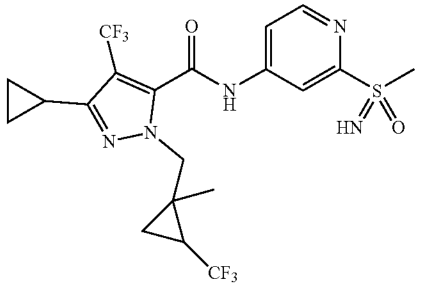 [SMILES: CC1(Cn2nc(C3CC3)c(C(F)(F)F)c2C(=O)Nc2ccnc(S(C)(=N)=O)c2)CC1C(F)(F)F] | 82 | 3-cyclopropyl-1-((1-methyl-2-(trifluoromethyl)cyclopropyl)methyl)-N-(2-(S-methylsulfonimidoyl)pyridin-4-yl)-4-(trifluoromethyl)-1H-pyrazole-5-carboxamide |
| 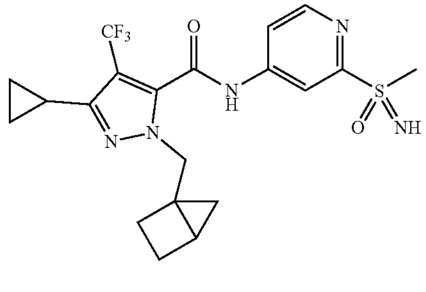 [SMILES: CS(=N)(=O)c1cc(NC(=O)c2c(C(F)(F)F)c(C3CC3)nn2CC23CCC2C3)ccn1] | 83 | 1-(bicyclo[2.1.0]pentan-1-ylmethyl)-3-cyclopropyl-N-(2-(S-methylsulfonimidoyl)pyridin-4-yl)-4-(trifluoromethyl)-1H-pyrazole-5-carboxamide |

-continued

| Structure | Prophetic example number | Chemical name |
|---|---|---|
| 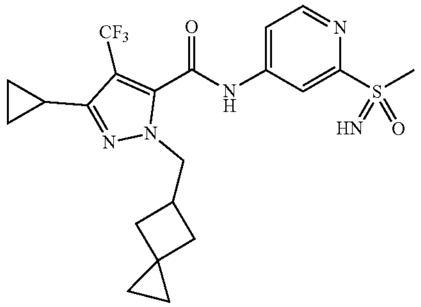 [SMILES: CS(=N)(=O)c1cc(NC(=O)c2c(C(F)(F)F)c(C3CC3)nn2CC2CC3(CC3)C2)ccn1] | 84 | 3-cyclopropyl-N-(2-(S-methylsulfonimidoyl)pyridin-4-yl)-1-(spiro[2.3]hexan-5-ylmethyl)-4-(trifluoromethyl)-1H-pyrazole-5-carboxamide |
| 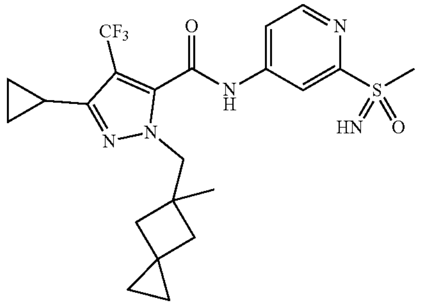 [SMILES: CC1(Cn2nc(C3CC3)c(C(F)(F)F)c2C(=O)Nc2ccnc(S(C)(=N)=O)c2)CC2(CC2)C1] | 85 | 3-cyclopropyl-1-((5-methylspiro[2.3]hexan-5-yl)methyl)-N-(2-(S-methylsulfonimidoyl)pyridin-4-yl)-4-(trifluoromethyl)-1H-pyrazole-5-carboxamide |
| 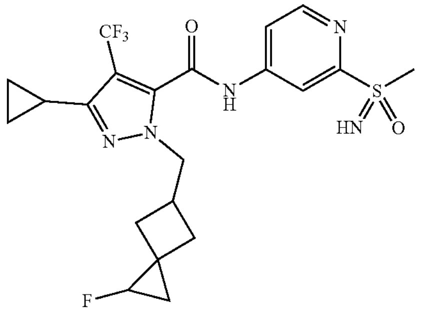 [SMILES: CS(=N)(=O)c1cc(NC(=O)c2c(C(F)(F)F)c(C3CC3)nn2CC2CC3(C2)CC3F)ccn1] | 87 | 3-cyclopropyl-1-((1-fluorospiro[2.3]hexan-5-yl)methyl)-N-(2-(S-methylsulfonimidoyl)pyridin-4-yl)-4-(trifluoromethyl)-1H-pyrazole-5-carboxamide |
| 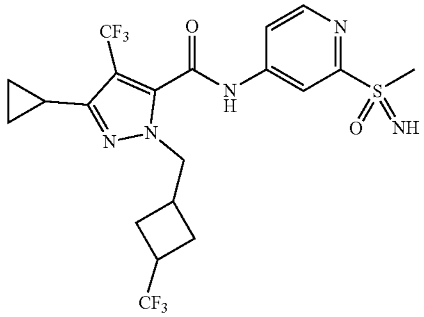 [SMILES: CS(=N)(=O)c1cc(NC(=O)c2c(C(F)(F)F)c(C3CC3)nn2CC2CC(C(F)(F)F)C2)ccn1] | 88 | 3-cyclopropyl-N-(2-(S-methylsulfonimidoyl)pyridin-4-yl)-4-(trifluoromethyl)-1-((3-(trifluoromethyl)cyclobutyl)methyl)-1H-pyrazole-5-carboxamide |

-continued

| Structure | Prophetic example number | Chemical name |
|---|---|---|
| 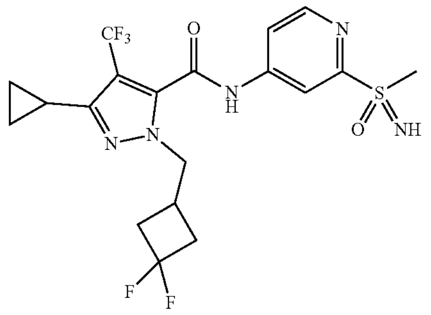 [SMILES: CS(=N)(=O)c1cc(NC(=O)c2c(C(F)(F)F)c(C3CC3)nn2CC2CC(F)(F)C2)ccn1] | 89 | 3-cyclopropyl-1-((3,3-difluorocyclobutyl)methyl)-N-(2-(S-methylsulfonimidoyl)pyridin-4-yl)-4-(trifluoromethyl)-1H-pyrazole-5-carboxamide |
| 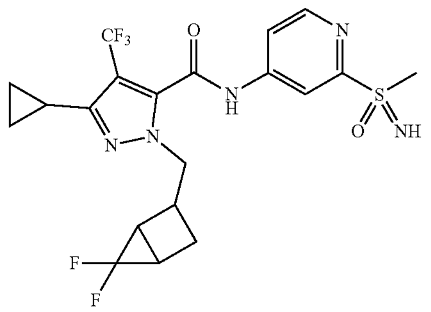 [SMILES: CS(=N)(=O)c1cc(NC(=O)c2c(C(F)(F)F)c(C3CC3)nn2CC2CC3C2C3(F)F)ccn1] | 90 | 3-cyclopropyl-1-((5,5-difluorobicyclo[2.1.0]pentan-2-yl)methyl)-N-(2-(S-methylsulfonimidoyl)pyridin-4-yl)-4-(trifluoromethyl)-1H-pyrazole-5-carboxamide |
| 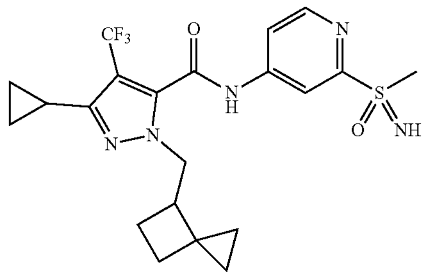 [SMILES: CS(=N)(=O)c1cc(NC(=O)c2c(C(F)(F)F)c(C3CC3)nn2CC2CCC23CC3)ccn1] | 91 | 3-cyclopropyl-N-(2-(S-methylsulfonimidoyl)pyridin-4-yl)-1-(spiro[2.3]hexan-4-ylmethyl)-4-(trifluoromethyl)-1H-pyrazole-5-carboxamide |
| 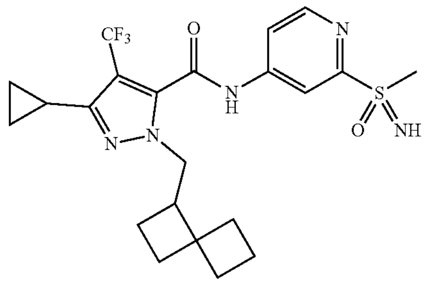 [SMILES: CS(=N)(=O)c1cc(NC(=O)c2c(C(F)(F)F)c(C3CC3)nn2CC2CCC23CCC3)ccn1] | 93 | 3-cyclopropyl-N-(2-(S-methylsulfonimidoyl)pyridin-4-yl)-1-(spiro[3.3]heptan-1-ylmethyl)-4-(trifluoromethyl)-1H-pyrazole-5-carboxamide |
| 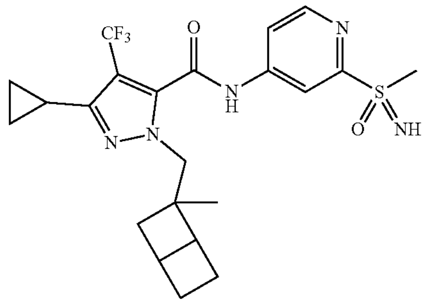 [SMILES: CC1(Cn2nc(C3CC3)c(C(F)(F)F)c2C(=O)Nc2ccnc(S(C)(=N)=O)c2)CC2CCC21] | 94 | 3-cyclopropyl-1-((2-methylbicyclo[2.2.0]hexan-2-yl)methyl)-N-(2-(S-methylsulfonamidoyl)pyridin-4-yl)-4-(trifluoromethyl)-1H-pyrazole-5-carboxamide |

-continued

| Structure | Prophetic example number | Chemical name |
|---|---|---|
| 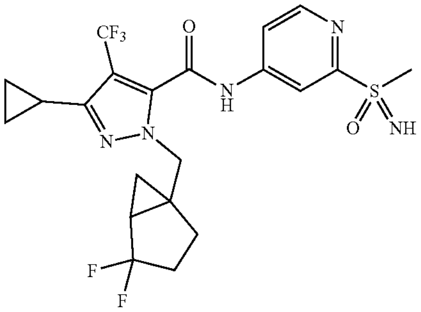 [SMILES: CS(=N)(=O)c1cc(NC(=O)c2c(C(F)(F)F)c(C3CC3)nn2CC23CCC(F)(F)C2C3)ccn1] | 96 | 3-cyclopropyl-1-((4,4-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide |
| 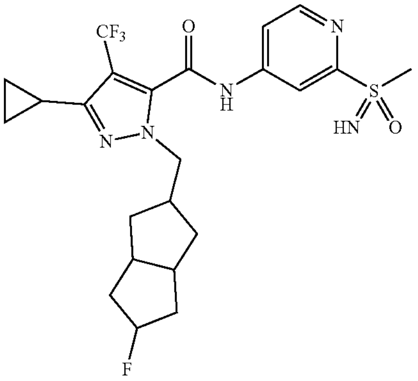 [SMILES: CS(=N)(=O)c1cc(NC(=O)c2c(C(F)(F)F)c(C3CC3)nn2CC2CC3CC(F)CC3C2)ccn1] | 97 | 3-cyclopropyl-1-((5-fluorooctahydropentalen-2-yl)methyl)-N-(2-(S-methylsulfonimidoyl)pyridin-4-yl)-4-(trifluoromethyl)-1H-pyrazole-5-carboxamide |
| 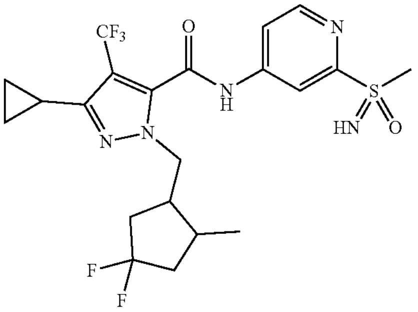 [SMILES: CC1CC(F)(F)CC1Cn1nc(C2CC2)c(C(F)(F)F)c1C(=O)Nc1ccnc(S(C)(=N)=O)c1] | 99 | 3-cyclopropyl-1-((4,4-difluoro-2-methylcyclopentyl)methyl)-N-(2-(S-methylsulfonimidoyl)pyridin-4-yl)-4-(trifluoromethyl)-1H-pyrazole-5-carboxamide |
| 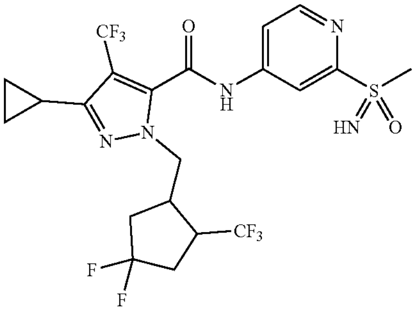 [SMILES: CS(=N)(=O)c1cc(NC(=O)c2c(C(F)(F)F)c(C3CC3)nn2CC2CC(F)(F)CC2C(F)(F)F)ccn1] | 100 | 3-cyclopropyl-1-((4,4-difluoro-2-(trifluoromethyl)cyclopentyl)methyl)-N-(2-(S-methylsulfonimidoyl)pyridin-4-yl)-4-(trifluoromethyl)-1H-pyrazole-5-carboxamide |

-continued

| Structure | Prophetic example number | Chemical name |
| --- | --- | --- |
| 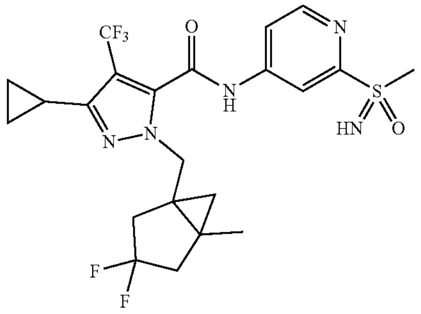 [SMILES: CC12CC(F)(F)CC1(Cn1nc(C3CC3)c(C(F)(F)F)c1C(=O)Nc1ccnc(S(C)(=N)=O)c1)C2] | 101 | 3-cyclopropyl-1-((3,3-difluoro-5-methylbicyclo[3.1.0]hexan-1-yl)methyl)-N-(2-(S-methylsulfonimidoyl)pyridin-4-yl)-4-(trifluoromethyl)-1H-pyrazole-5-carboxamide |
| 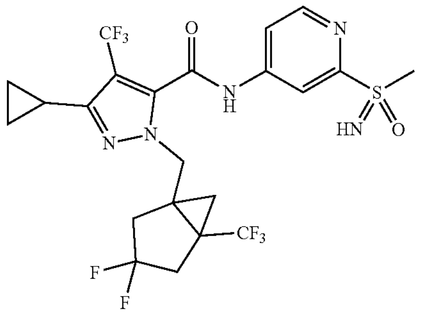 [SMILES: CS(=N)(=O)c1cc(NC(=O)c2c(C(F)(F)F)c(C3CC3)nn2CC23CC(F)(F)CC2(C(F)(F)F)C3)ccn1] | 102 | 3-cyclopropyl-1-((3,3-difluoro-5-(trifluoromethyl)bicyclo[3.1.0]hexan-1-yl)methyl)-N-(2-(S-methylsulfonimidoyl)pyridin-4-yl)-4-(trifluoromethyl)-1H-pyrazole-5-carboxamide |
| 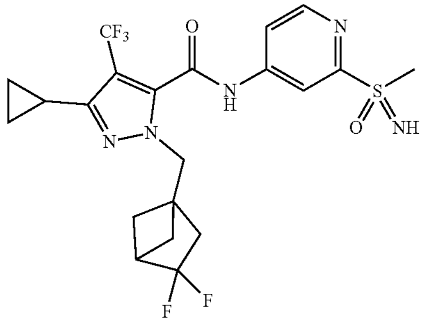 [SMILES: CS(=N)(=O)c1cc(NC(=O)c2c(C(F)(F)F)c(C3CC3)nn2CC23CC(C2)C(F)(F)C3)ccn1] | 104 | 3-cyclopropyl-1-((3,3-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide |
| 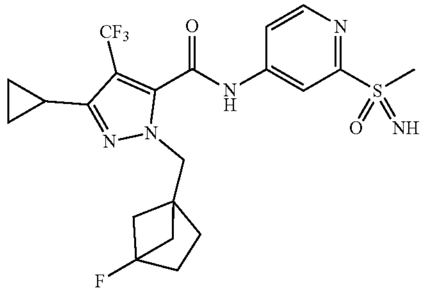 [SMILES: CS(=N)(=O)c1cc(NC(=O)c2c(C(F)(F)F)c(C3CC3)nn2CC23CCC(F)(C2)C3)ccn1] | 105 | 3-cyclopropyl-1-((4-fluorobicyclo[2.1.1]hexan-1-yl)methyl)-N-(2-(S-methylsulfonimidoyl)pyridin-4-yl)-4-(trifluoromethyl)-1H-pyrazole-5-carboxamide |

-continued

| Structure | Prophetic example number | Chemical name |
|---|---|---|
| 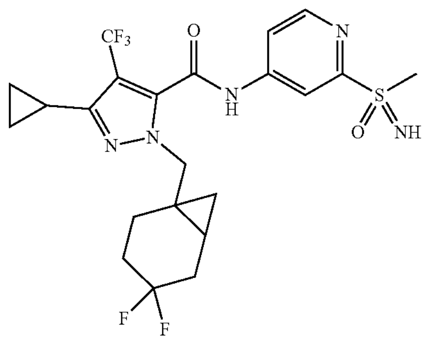 [SMILES: CS(=N)(=O)c1cc(NC(=O)c2c(C(F)(F)F)c(C3CC3)nn2CC23CCC(F)(F)CC2C3)ccn1] | 107 | 3-cyclopropyl-1-((4,4-difluorobicyclo[4.1.0]heptan-1-yl)methyl)-N-(2-(S-methylsulfonimidoyl)pyridin-4-yl)-4-(trifluoromethyl)-1H-pyrazole-5-carboxamide |
| 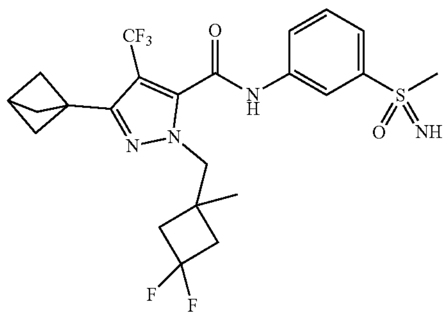 [SMILES: CC1(Cn2nc(C34CC(C3)C4)c(C(F)(F)F)c2C(=O)Nc2cccc(S(C)(=N)=O)c2)CC(F)(F)C1] | 108 | 3-(bicyclo[1.1.1]pentan-1-yl)-1-((3,3-difluoro-1-methylcyclobutyl)methyl)-N-(3-(S-methylsulfonimidoyl)phenyl)-N-(trifluoromethyl)-1H-pyrazole-5-carboxamide |
| 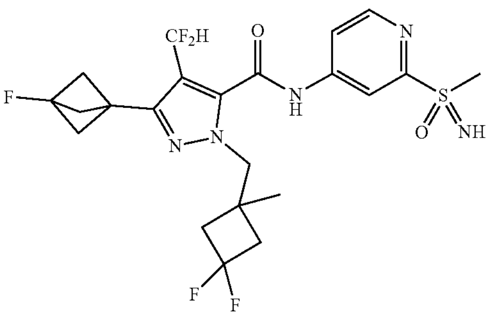 [SMILES: CC1(Cn2nc(C34CC(F)(C3)C4)c(C(F)F)c2C(=O)Nc2ccnc(S(C)(=N)=O)c2)CC(F)(F)C1] | 112 | 1-((3,3-difluoro-1-methylcyclobutyl)methyl)-4-(difluoromethyl)-3-(3-fluorobicyclo[1.1.1]pentan-1-yl)-N-(2-(2-methylsulfonimidoyl)pyridin-4-yl)-1H-pyrazole-5-carboxamide |
| 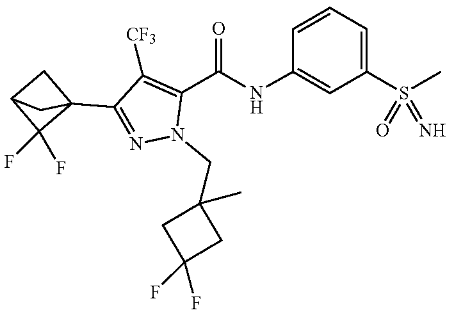 [SMILES: CC1(Cn2nc(C34CC(C3)C4(F)F)c(C(F)(F)F)c2C(=O)Nc2cccc(S(C)(=N)=O)c2)CC(F)(F)C1] | 115 | 1-((3,3-difluoro-1-methylcyclobutyl)methyl)-3-(2,2-difluorobicyclo[1.1.1]pentan-1-yl)-N-(3-(S-methylsulfonimidoyl)phenyl)-4-(trifluoromethyl)-1H-pyrazole-5-carboxamide |

-continued

| Structure | Prophetic example number | Chemical name |
|---|---|---|
| 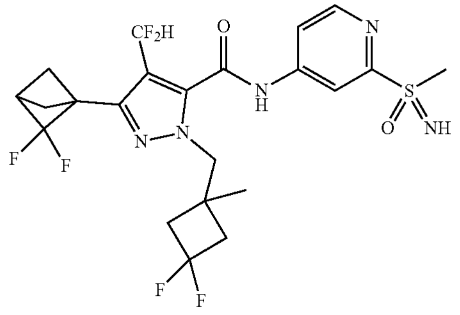 [SMILES: CC1(Cn2nc(C34CC(C3)C4(F)F)c(C(F)F)c2C(=O)Nc2ccnc(S(C)(=N)=O)c2)CC(F)(F)C1] | 116 | 1-((3,3-difluoro-1-methylcyclobutyl)methyl)-N-(2,2-difluorobicyclo[1.1.1]pentan-1-yl)-4-(difluoromethyl)-N-(2-(S-methylsulfonimidoyl)pyridin-4-yl)-1H-pyrazole-5-carboxamide |
| 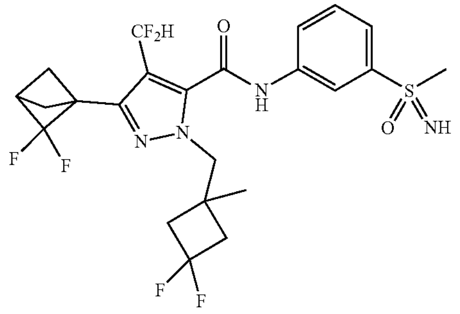 [SMILES: CC1(Cn2nc(C34CC(C3)C4(F)F)c(C(F)F)c2C(=O)Nc2cccc(S(C)(=N)=O)c2)CC(F)(F)C1] | 117 | 1-((3,3-difluoro-1-methylcyclobutyl)methyl)-3-(2,2-difluorobicyclo[1.1.1]pentan-1-yl)-4-(difluoromethyl)-N-(3-(S-methylsulfonimidoyl)phenyl)-1H-pyrazole-5-carboxamide |
| 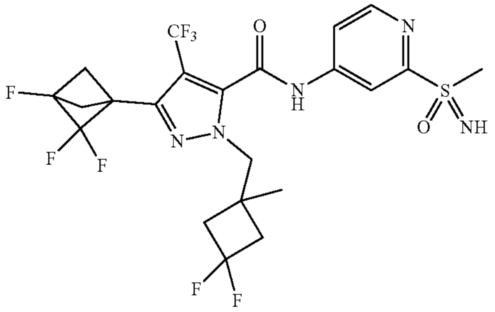 [SMILES: CC1(Cn2nc(C34CC(F)(C3)C4(F)F)c(C(F)(F)F)c2C(=O)Nc2ccnc(S(C)(=N)=O)c2)CC(F)(F)C1] | 118 | 1-((3,3-difluoro-1-methylcyclobutyl)methyl)-N-(2-(S-methylsulfonimidoyl)pyridin-4-yl)-3-(2,2,3-trifluorobicyclo[1.1.1]pentan-1-yl)-4-(trifluoromethyl)-1H-pyrazole-5-carboxamide |
| 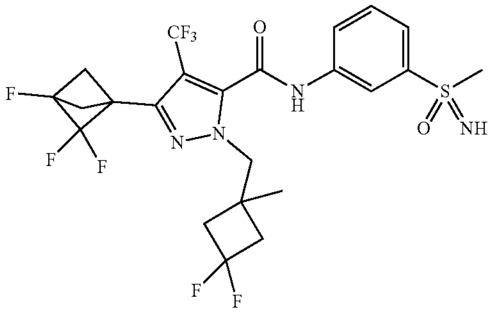 [SMILES: CC1(Cn2nc(C34CC(F)(C3)C4(F)F)c(C(F)(F)F)c2C(=O)Nc2cccc(S(C)(=N)=O)c2)CC(F)(F)C1] | 119 | 1-((3,3-difluoro-1-methylcyclobutyl)methyl)-N-(3-(S-methylsulfonimidoyl)phenyl)-3-(2,2,3-trifluorobicyclo[1.1.1]pentan-1-yl)-4-(trifluoromethyl)-1H-pyrazole-5-carboxamide |

-continued

| Structure | Prophetic example number | Chemical name |
|---|---|---|
| 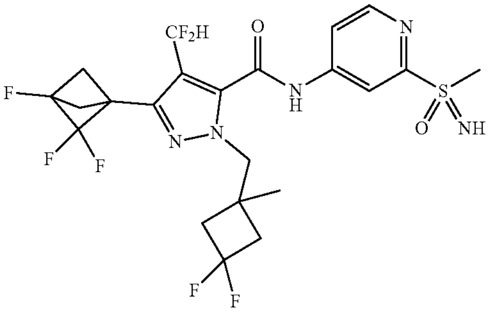 [SMILES: CC1(Cn2nc(C34CC(F)(C3)C4(F)F)c(C(F)F)c2C(=O)Nc2ccnc(S(C)(=N)=O)c2)CC(F)(F)C1] | 120 | 1-((3,3-difluoro-1-methylcyclobutyl)methyl)-4-(difluoromethyl)-N-(2-(S-methylsulfonimidoyl)pyridin-4-yl)-3-(2,2,3-trifluorobicyclo[1.1.1]pentan-3-yl)-1H-pyrazole-5-carboxamide |
| 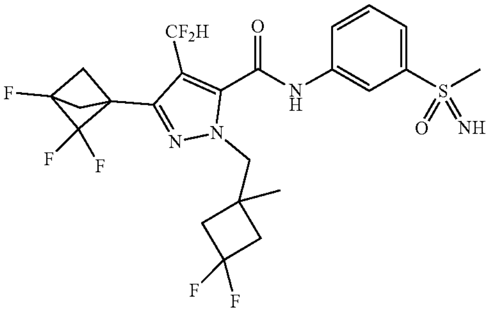 [SMILES: CC1(Cn2nc(C34CC(F)(C3)C4(F)F)c(C(F)F)c2C(=O)Nc2cccc(S(C)(=N)=O)c2)CC(F)(F)C1] | 121 | 1-((3,3-difluoro-1-methylcyclobutyl)methyl)-4-(difluoromethyl)-N-(3-(S-methylsulfonimidoyl)phenyl)-3-(2,2,3-trifluorobicyclo[1.1.1]pentan-1-yl)-1H-pyrazole-5-carboxamide |
| 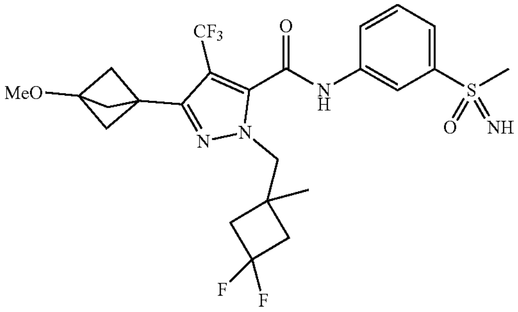 [SMILES: COC12CC(c3nn(CC4(C)CC(F)(F)C4)c(C(=O)Nc4cccc(S(C)(=N)=O)c4)c3C(F)(F)F)(C1)C2] | 123 | 1-((3,3-difluoro-1-methylcyclobutyl)methyl)-3-(3-methoxybicyclo[1.1.1]pentan-1-yl)-N-(3-(S-methylsulfonimidoyl)phenyl)-4-(trifluoromethyl)-1H-pyrazole-5-carboxamide |
| 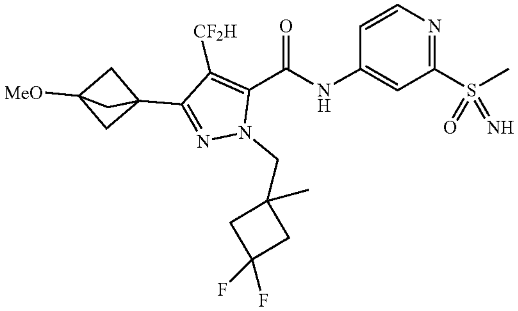 [SMILES: COC12CC(c3nn(CC4(C)CC(F)(F)C4)c(C(=O)Nc4ccnc(S(C)(=N)=O)c4)c3C(F)F)(C1)C2] | 124 | 1-((3,3-difluoro-1-methylcyclobutyl)methyl)-4-(difluoromethyl)-3-(3-methoxybicyclo[1.1.1]pentan-1-yl)-N-(2-(S-methylsulfonimidoyl)pyridin-4-yl)-1H-pyrazole-5-carboxamide |

-continued

| Structure | Prophetic example number | Chemical name |
|---|---|---|
| 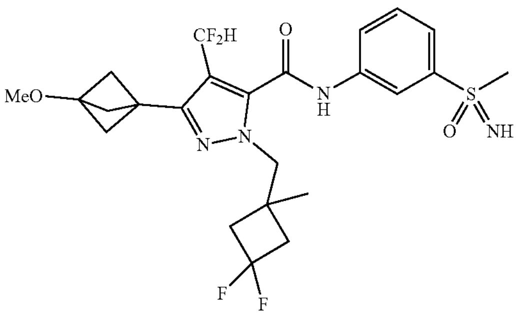 [SMILES: COC12CC(c3nn(CC4(C)CC(F)(F)C4)c(C(=O)Nc4cccc(S(C)(=N)=O)c4)c3C(F)F)(C1)C2] | 125 | 1-((3,3-difluoro-1-methylcyclobutyl)methyl)-4-(difluoromethyl)-3-(3-methoxybicyclo[1.1.1]pentan-1-yl)-N-(3-(S-methylsulfonimidoyl)phenyl)-1H-pyrazole-5-carboxamide |
| 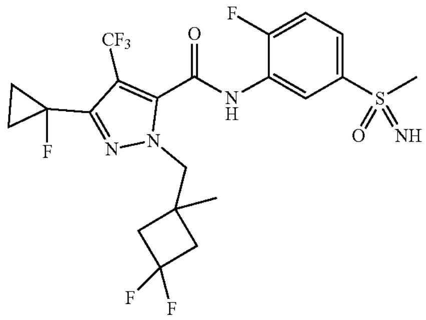 [SMILES: CC1(Cn2nc(C3(F)CC3)c(C(F)(F)F)c2C(=O)Nc2cc(S(C)(=N)=O)ccc2F)CC(F)(F)C1] | 128 | 1-((3,3-difluoro-1-methylcyclobutyl)methyl)-N-(2-fluoro-5-(S-methylsulfonimidoyl)phenyl)-3-(1-fluorocyclopropyl)-4-(trifluoromethyl)-1H-pyrazole-5-carboxamide |
| 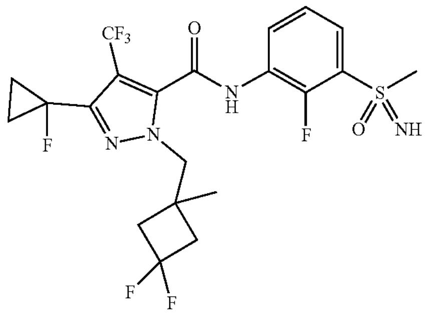 [SMILES: CC1(Cn2nc(C3(F)CC3)c(C(F)(F)F)c2C(=O)Nc2cccc(S(C)(=N)=O)c2F)CC(F)(F)C1] | 129 | 1-((3,3-difluoro-1-methylcyclobutyl)methyl)-N-(2-fluoro-3-(S-methylsulfonimidoyl)phenyl)-3-(1-fluorocyclopropyl)-4-(trifluoromethyl)-1H-pyrazole-5-carboxamide |

Electrophysiology: Voltage-Clamp Recordings

The following $Na_V1.8$ recombinant cell line was used for recordings: HEK-$Na_V1.8$ (NM_006514.1) with b3 (NM_018400.3).

Sodium currents were measured using the patch clamp technique in the whole-cell configuration using the Qube384 (Sophion A/S, Copenhagen, Denmark) automated voltage clamp platform. "Multi hole" plates were used for the cell line expressing $Na_V1.8$ while "single hole" plates were used for the recombinant cell lines expressing the other subtypes. Appropriate filters (for minimum seal resistance and minimum current size) and series resistance compensation (for high quality sodium channel recordings) were applied. Data was collected at ambient room temperature or 19° C.

The recording extracellular solution contained (in mM): NaCl 145 mM, KCl 4 mM, $CaCl_2$ 2 mM, $MgCl_2$ 1 mM, HEPES 10 mM, Glucose 10 mM, pH 7.4 (NaOH). The intracellular recording solution contained (in mM): CsF 120 mM, CsCl 20 mM, NaCl 10 mM, EGTA 10 mM, HEPES 10 mM, pH 7.2 (CsOH). Currents were recorded at 25 kHz sampling frequency and filtered at 5 kHz. Series resistance compensation was applied at 65%.

Vehicle (VEH) is the control condition where cells are exposed to 0.3% DMSO without compound. All runs include VEH controls being exposed to the same voltage protocols to assess non-compound related phenomena such as run down and then used to isolate compound dependent effects on currents.

To check for state-dependent inhibition, the following voltage-sequence was applied every 20 seconds:

From a resting membrane potential of −120 mV, the first test pulse (P1; 20 ms to −10 mV) was applied to check for channels in the Resting State followed by a brief recovery (100 ms to −120 mV), then holding the membrane voltage to $V_{1/2}$ (4 seconds at voltage to obtain half the channel at Rest and half Inactivated) with a subsequent second test pulse (P2; 20 ms to −10 mV) to check for channels in the Inactivated State, followed by another brief recovery (20 ms to −120 mV) and a final third test pulse (P3; 20 ms to −10 mV) to check for recovered channels.

To check for frequency-dependent inhibition, a 10 Hz protocol and a 20 Hz protocol were applied; namely, From a resting membrane potential of −120 mV, 40-pulses (10 ms to −10 mV) was applied at 10 Hz (at 100 ms between pulses) and then at 20 Hz (at 50 ms between pulses).

Each parameter was recorded (P1, P2, P3, P40 from 10 Hz and P40 from 20 Hz) during a control period (lasting 5 minutes) when establishing the baseline and during compound period (lasting ~12 minutes) when test compound (or vehicle) was applied. For each parameter, the value at the end of the compound period was normalized to the vehicle baseline; as follows $$\text{Normalized Inhibition } (Norm_{CPD}) = \frac{CPD \text{ Value}_{end\ CPD\ period}}{VEH \text{ Value}_{end\ Control\ Period}}$$

To adjust for any variance in the $Na^+$ current signal during the compound period (owing to cumulative inactivation independent of compound or shifts in biophysics over time), a dedicated segment of the recording wells in each 384 plate were dedicated to having only vehicle exposure. These vehicle-only recordings were used to correct for any apparent "run-up" or "run-down" in the experiment.

$$\text{Normalized Inhibition } (Norm_{VEH}) = \frac{VEH \text{ Value}_{end\ CPD\ period}}{VEH \text{ Value}_{end\ Control\ Period}}$$

The adjusted inhibition was calculated as follows:

$$\% \text{ Inhibition}_{corrected} = 100 \times \frac{Norm_{CPD} - Norm_{VEH}}{100 - Norm_{VEH}}$$

Percent inhibition was determined and $IC_{50}$ values were calculated using a 4 parameter logistic model within XLFit Software (IDBS, Boston MA): F $$\% \text{ Inhibition}_{corrected} = A + \frac{(B - A)}{(1 + \left(\frac{x}{C}\right)^D}$$

where A and B are the maximal and minimum inhibition respectively, C is the $IC_{50}$ concentration and D is the (Hill) slope.

The potency data of the example compounds are summarized in the table below (category A: human NaV 1.8 $IC_{50} \leq 0.1$ μM; category B: 0.1 μM<human NaV 1.8 $IC_{50} \leq 1$ μM; category C: 1 μM<human NaV 1.8 $IC_{50} \leq 10$ μM; "n.d.": not determined):

| Example | Potency category |
|---|---|
| 1a | A |
| 1b | A |
| 3 | A |
| 4 | A |
| 5a | A |
| 5b | A |
| 7a | A |
| 7b | A |
| 9a | A |
| 9b | A |
| 11a | A |
| 11b | A |
| 15a | A |
| 15b | A |
| 17a | A |
| 17b | A |
| 17c | A |
| 17d | A |

-continued

| Example | Potency category |
|---|---|
| 21a | A |
| 21b | A |
| 23a | A |
| 23b | A |
| 25a | A |
| 25b | B |
| 27a | A |
| 27b | A |
| 29a | A |
| 29b | A |
| 31a | A |
| 31b | A |
| 33 | A |
| 34a | A |
| 34b | A |
| 36a | A |
| 36b | A |
| 36c | A |
| 36d | A |
| 45a | A |
| 45b | A |
| 46a | A |
| 46b | A |
| 47a | A |
| 47b | A |
| 48a | A |
| 48b | A |
| 50a | A |
| 50b | A |
| 56a | A |
| 56b | A |
| 57a | A |
| 57b | A |
| 58a | A |
| 58b | A |
| 59a | A |
| 59b | A |
| 61a | A |
| 61b | A |
| 62a | A |
| 62b | A |
| 63a | A |
| 63b | A |
| 63c | A |
| 64a | A |
| 64b | A |
| 65a | A |
| 65b | A |
| 65c | A |
| 65d | A |
| 68a | A |
| 68b | A |
| 69a | A |
| 69b | A |
| 70a | A |
| 70b | A |
| 71a | B |
| 71b | A |
| 75a | A |
| 75b | A |
| 78a | A |
| 78b | A |
| 78c | A |
| 78d | A |
| 79a | A |
| 79b | A |
| 79c | A |
| 79d | A |
| 80a | A |
| 80b | A |
| 86a | A |
| 86b | A |
| 86c | A |
| 86d | A |
| 92a | A |
| 92b | A |
| 92c | A |

-continued

| Example | Potency category |
|---|---|
| 92d | A |
| 95a | A |
| 95b | A |
| 95c | A |
| 98a | A |
| 98b | A |
| 103a | A |
| 103b | A |
| 106a | A |
| 106b | A |
| 109a | A |
| 109b | A |
| 110a | A |
| 110b | A |
| 111a | A |
| 111b | A |
| 113a | A |
| 113b | A |
| 114 | A |
| 122 | A |
| 126a | A |
| 126b | A |
| 127a | A |
| 127b | A |
| 130a | A |
| 130b | A |
| 131 | A |
| 132a | A |
| 132b | A |
| 133a | A |
| 133b | A |
| 134a | A |
| 134b | A |
| 134c | A |
| 134d | A |
| 135a | A |
| 135b | A |
| 136a | A |
| 136b | A |
| 136c | A |
| 136d | A |
| 137a | A |
| 137b | A |
| 138a | A |
| 138b | A |
| 139 | A |
| 140a | B |
| 140b | B |
| 141a | A |
| 141b | A |
| 142a | A |
| 142b | A |
| 143a | A |
| 143b | A |
| 144a | A |
| 144b | A |
| 145a | A |
| 145b | A |
| 146 | A |
| 147 | A |
| 148a | A |
| 148b | A |
| 150a | A |
| 150b | A |
| 151a | A |
| 151b | A |
| 152 | A |
| 153a | C |
| 153b | C |
| 153c | C |
| 153d | C |

The invention claimed is:

1. A compound according to formula (I):

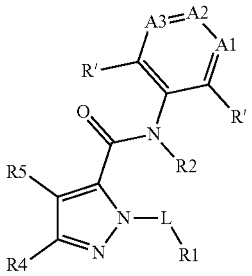

(I)

wherein one of A1, A2 and A3 represents C—R3 and another two of A1, A2 and A3 independently from one another represent CR' or N;

R' independently represents H, F, $CH_3$, $CH_2F$, $CHF_2$, $CF_3$, or $OCH_3$;

L represents $CH_2$, $CH(CH_3)$ or $CH(CH_2CH_3)$;

R1 represents $C_{3-10}$-cycloalkyl, 4 to 11-membered bicycloalkyl, 5 to 11-membered spiroalkyl or dispiroalkyl, 4 to 10-membered heterocycloalkyl, or 5 to 11-membered heterobicycloalkyl;

R2 represents H or $C_{1-6}$-alkyl;

R3 represents S(O)(NR3a)R3b or $S(NR3a)_2R3b$;

R3a represents H, $C_{1-6}$-alkyl, $C(O)C_{1-5}$-alkyl, $C(O)C_{1-5}$-alkyl-$NH_2$, $C(O)C_{1-5}$-alkyl-NH—$CH_3$, $C(O)C_{1-5}$-alkyl-$N(CH_3)_2$, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl);

R3b represents $NH_2$, $C_{1-6}$-alkyl, $C_{3-10}$-cycloalkyl, $C_{1-6}$-alkylene-$C_{3-10}$-cycloalkyl, 4 to 10-membered heterocycloalkyl, or $C_{1-6}$-alkylene-(4 to 10-membered heterocycloalkyl);

or R3a and R3b mean $(CH_2)_{3-5}$ and together with the atoms to which they are attached form a ring;

R4 represents H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 11-membered bicycloalkyl, 5 to 11-membered spiroalkyl or bisspiroalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl);

R5 represents H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl$)_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl);

wherein $C_{1-6}$-alkyl and $C_{1-6}$-alkylene in each case independently from one another is linear or branched;

wherein $C_{1-6}$-alkyl, $C_{1-6}$-alkylene, $C_{3-10}$-cycloalkyl, 4 to 11-membered bicycloalkyl, 5 to 11-membered spiroalkyl or dispiroalkyl, 4 to 10-membered heterocycloalkyl, 4 to 6-membered heterocycloalkyl, and 5 to 11-membered heterobicycloalkyl in each case independently from one another are unsubstituted or substituted with one, two, three, four or more substituents independently from one another selected from the group consisting of F, Cl, CN, $C_{1-6}$-alkyl, $C_{1-6}$-alkylene-OH, $C_{1-6}$-alkylene-$OCH_3$, $CF_3$, $CF_2H$, $CFH_2$, C(O)—$C_{1-6}$-alkyl, OH, =O, $OCF_3$, $OCF_2H$, $OCFH_2$, O—$C_{1-6}$-alkyl, $C_{1-4}$-alkylene-O—$C_{1-4}$-alkylene-O—$CH_3$, $C_{0-4}$-alkylene-O—($C_{1-4}$-alkylene-O)$_{1-4}$—$CH_3$, $NH_2$, NH—$C_{1-6}$-alkyl, N($C_{1-6}$-alkyl)$_2$, or 4 to 6-membered heterocycloalkyl;

in the form of a free compound or a physiologically acceptable salt thereof.

2. The compound according to claim 1, wherein (i) A1 represents C—R3, A2 represents N, and A3 represents CH;

(ii) A1 represents C—R3, A2 represents CH, and A3 represents CH; or (iii) A1 represents C—R3, A2 represents N, and A3 represents N; or (iv) A1 represents C—R3, A2 represents CH, and A3 represents N; or (v) A1 represents CH, A2 represents C—R3, and A3 represent CH; or (vi) A1 represents N, A2 represents C—R3, and A3 represent CH; or (vii) A1 represents N, A2 represents C—R3, and A3 represent N.

3. The compound according to claim 1, wherein L represents $CH_2$.

4. The compound according to claim 1, wherein R1 represents $C_{3-10}$-cycloalkyl, unsubstituted or substituted with one, two, three, four, or more substituents independently from one another selected from F, $CH_3$, $OCH_3$, CN, $CHF_2$ and $CF_3$;

4 to 11-membered bicycloalkyl, unsubstituted or substituted with one, two, three, four, or more substituents independently from one another selected from F, $CH_3$, $OCH_3$, CN, $CHF_2$ and $CF_3$;

5 to 11-membered spiroalkyl or dispiroalkyl, unsubstituted or substituted with one, two, three, four, or more substituents independently from one another selected from F, $CH_3$, $OCH_3$, CN, $CHF_2$ and $CF_3$;

4 to 10-membered heterocycloalkyl, unsubstituted or substituted with one, two, three, four, or more substituents independently from one another selected from F, $CH_3$, $OCH_3$, CN, $CHF_2$ and $CF_3$; or 5 to 11-membered heterobicycloalkyl, unsubstituted or substituted with one, two, three, four, or more substituents independently from one another selected from F, $CH_3$, $OCH_3$, CN, $CHF_2$ and $CF_3$.

5. The compound according to claim 4, wherein R1 represents cyclopropyl, methyl cyclopropyl, dimethyl cyclopropyl, fluoro cyclopropyl, difluoro cyclopropyl, trifluoromethyl cyclopropyl, trifluoromethyl methyl cyclopropyl, methyl difluoro cyclopropyl, trifluoromethyl difluoro cyclopropyl, dimethyl difluoro cyclopropyl, cyclobutyl, methyl cyclobutyl, dimethyl cyclobutyl, fluoro cyclobutyl, difluoro cyclobutyl, trifluoromethyl cyclobutyl, trifluoromethyl methyl cyclobutyl, methyl difluoro cyclobutyl, trifluoromethyl difluoro cyclobutyl, dimethyl difluoro cyclobutyl, cyclopentyl, methyl cyclopentyl, dimethyl cyclopentyl, fluoro cyclopentyl, difluoro cyclopentyl, trifluoromethyl cyclopentyl, trifluoromethyl methyl cyclopentyl, methyl difluoro cyclopentyl, trifluoromethyl difluoro cyclopentyl, dimethyl difluoro cyclopentyl, cyclohexyl, methyl cyclohexyl, dimethyl cyclohexyl, fluoro cyclohexyl, difluoro cyclohexyl, trifluoromethyl cyclohexyl, trifluoromethyl methyl cyclohexyl, methyl difluoro cyclohexyl, trifluoromethyl difluoro cyclohexyl, dimethyl difluoro cyclohexyl, cycloheptyl, methyl cycloheptyl, dimethyl cycloheptyl, fluoro cycloheptyl, difluoro cycloheptyl, trifluoromethyl cycloheptyl, trifluoromethyl methyl cycloheptyl, methyl difluoro cycloheptyl, trifluoromethyl difluoro cycloheptyl, dimethyl difluoro cycloheptyl, cyclooctyl, methyl cyclooctyl, dimethyl cyclooctyl, fluoro cyclooctyl, difluoro cyclooctyl, trifluoromethyl cyclooctyl, trifluoromethyl methyl cyclooctyl, methyl difluoro cyclooctyl, trifluoromethyl difluoro cyclooctyl, dimethyl difluoro cyclooctyl, cyclononyl, methyl cyclononyl, dimethyl cyclononyl, fluoro cyclononyl, difluoro cyclononyl, trifluoromethyl cyclononyl, trifluoromethyl methyl cyclononyl, methyl difluoro cyclononyl, trifluoromethyl difluoro cyclononyl, dimethyl difluoro cyclononyl, cyclodecyl, methyl cyclodecyl, dimethyl cyclodecyl, fluoro cyclodecyl, difluoro cyclodecyl, trifluoromethyl cyclodecyl, trifluoromethyl methyl cyclodecyl, methyl difluoro cyclodecyl, trifluoromethyl difluoro cyclodecyl, or dimethyl difluoro cyclodecyl; or bicylo[1.1.1]pentyl, methyl bicylo[1.1.1]pentyl, methoxy bicylo[1.1.1]pentyl, difluoromethyl bicylo[1.1.1]pentyl, trifluoromethyl bicylo[1.1.1]pentyl, fluoro bicylo [1.1.1]pentyl, difluoro bicylo[1.1.1]pentyl, methyl difluoro bicylo[1.1.1]pentyl, trifluoromethyl difluoro bicylo[1.1.1]pentyl, bicyclo[2.1.0]pentyl, methyl bicyclo[2.1.0]pentyl, trifluoromethyl bicyclo[2.1.0]pentyl, fluoro bicyclo[2.1.0]pentyl, difluoro bicyclo[2.1.0]pentyl, methyl difluoro bicyclo[2.1.0]pentyl, trifluoromethyl difluoro bicyclo[2.1.0]pentyl, bicyclo[3.1.0]hexyl, methyl bicyclo[3.1.0]hexyl, trifluoromethyl bicyclo[3.1.0]hexyl, fluoro bicyclo[3.1.0]hexyl, difluoro bicyclo[3.1.0]hexyl, methyl difluoro bicyclo [3.1.0]hexyl, trifluoromethyl difluoro bicyclo[3.1.0]hexyl, bicyclo[2.2.0]hexyl, methyl bicyclo[2.2.0]hexyl, trifluoromethyl bicyclo[2.2.0]hexyl, fluoro bicyclo[2.2.0]hexyl, difluoro bicyclo[2.2.0]hexyl, methyl difluoro bicyclo[2.2.0]hexyl, trifluoromethyl difluoro bicyclo[2.2.0]hexyl, bicyclo[2.1.1]hexyl, methyl bicyclo[2.1.1]hexyl, trifluoromethyl bicyclo [2.1.1]hexyl, fluoro bicyclo[2.1.1]hexyl, difluoro bicyclo[2.1.1]hexyl, fluoro bicyclo[2.1.1]hexyl, difluoro bicyclo[2.1.1]hexyl, methyl difluoro bicyclo[2.1.1]hexyl, trifluoromethyl difluoro bicyclo[2.1.1]hexyl, bicyclo[4.1.0]heptyl, methyl bicyclo[4.1.0]heptyl, trifluoromethyl bicyclo[4.1.0]heptyl, fluoro bicyclo[4.1.0]heptyl, difluoro bicyclo[4.1.0]heptyl, methyl difluoro bicyclo[4.1.0]heptyl, trifluoromethyl difluoro bicyclo [4.1.0]heptyl, bicyclo[2.2.1]heptyl, methyl bicyclo [2.2.1]heptyl, trifluoromethyl bicyclo[2.2.1]heptyl, fluoro bicyclo[2.2.1]heptyl, difluoro bicyclo[2.2.1]heptyl, methyl difluoro bicyclo[2.2.1]heptyl, trifluoromethyl difluoro bicyclo[2.2.1]heptyl, bicyclo[3.3.0]octyl, methyl bicyclo[3.3.0]octyl, trifluoromethyl bicyclo [3.3.0]octyl, fluoro bicyclo[3.3.0]octyl, difluoro bicyclo[3.3.0]octyl, methyl difluoro bicyclo[3.3.0]octyl, or trifluoromethyl difluoro bicyclo[3.3.0]octyl; or spiro[2.2]pentyl, methyl spiro[2.2]pentyl, fluoro spiro [2.2]pentyl, difluoro spiro[2.2]pentyl, methyl difluoro spiro[2.2]pentyl, spiro[2.3]hexyl, methyl spiro[2.3]hexyl, fluoro spiro[2.3]hexyl, difluoro spiro[2.3]hexyl, methyl difluoro spiro[2.3]hexyl, spiro[3.3]heptyl, methyl spiro[3.3]heptyl, fluoro spiro[3.3]heptyl, difluoro spiro[3.3]heptyl, methyl difluoro spiro[3.3]heptyl, or dispiro[2.0.2.1]heptyl; or oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, azepanyl, dioxepanyl, oxazepanyl, diazepanyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, piperazinyl, N-methylpyridinonyl, pyrazolidinyl, pyranyl; dihydroquinolinyl, dihydroisoquinolinyl, dihydroindolinyl, dihydroisoindolyl, tetrahydroquinolinyl, tetrahydroisoquinolinyl or tetrahydroindolinyl;

or 2-oxa-bicyclo[2.1.1]hexyl or methyl 2-oxa-bicyclo[2.1.1]hexyl.

6. The compound according to claim 5, wherein R1 represents cyclopropyl, dimethyl cyclopropyl, trifluoromethyl methyl cyclopropyl, cyclobutyl, trifluoromethyl cyclobutyl, methyl trifluoromethyl cyclobutyl, difluoro cyclobutyl, methyl difluoro cyclobutyl, cyclopentyl, difluoro cyclopentyl, methyl difluoro cyclopentyl, trifluoromethyl cyclopentyl, trifluoromethyl difluoro cyclopentyl, cyclohexyl, difluoro cyclohexyl, or methyl difluoro cyclohexyl; or bicylo[1.1.1]pentyl, trifluoromethyl-bicylo[1.1.1]pentyl, bicyclo[2.1.0]pentyl, difluoro bicyclo[2.1.0]pentyl, bicyclo[3.1.0]hexyl, difluoro bicyclo[3.1.0]hexyl, methyl difluoro bicyclo[3.1.0]hexyl, trifluoromethyl difluoro bicyclo[3.1.0]hexyl, bicyclo[2.2.0]hexyl, methyl bicyclo[2.2.0]hexyl, bicyclo[2.1.1]hexyl, fluoro bicyclo[2.1.1]hexyl, difluoro bicyclo[2.1.1]hexyl, bicyclo[4.1.0]heptyl, difluoro bicyclo[4.1.0]heptyl, bicyclo[2.2.1]heptyl, fluoro bicyclo[2.2.1]heptyl, bicyclo[3.3.0]octyl, or fluoro bicyclo[3.3.0]octyl; or spiro[2.2]pentyl, difluoro spiro[2.2]pentyl, spiro[2.3]hexyl, methyl spiro[2.3]hexyl, fluoro spiro[2.3]hexyl, methyl difluoro spiro[2.3]hexyl, spiro[3.3]heptyl, or dispiro[2.0.2.1]heptyl.

7. The compound according to claim 1, wherein R2 represents H.

8. The compound according to claim 1, wherein R3a represents H, $C_{1-6}$-alkyl, $C(O)C_{1-5}$-alkyl, $C(O)C_{1-5}$-alkyl-$NH_2$, $C(O)C_{1-5}$-alkyl-NH—$CH_3$, $C(O)C_{1-5}$-alkyl-$N(CH_3)_2$.

9. The compound according to claim 8, wherein R3a represents H, $CH_3$, $C(O)CH_3$ or $C(O)CH_2NHCH_3$.

10. The compound according to claim 1, wherein R3b represents $NH_2$, $C_{1-6}$-alkyl or $C_{3-10}$-cycloalkyl.

11. The compound according to claim 10, wherein R3b represents $NH_2$, $CH_3$, $CH_2CH_3$, or cyclopropyl.

12. The compound according to claim 1, wherein R3a and R3b mean $(CH_2)_3$ and together with the atoms to which they are attached form a ring.

13. The compound according to claim 1, wherein R4 represents $C_{1-6}$-alkyl;

$C_{3-10}$-cycloalkyl, unsubstituted or substituted with one, two, three, four, or more substituents independently from one another selected from F, $CH_3$, $OCH_3$, CN, $CHF_2$ and $CF_3$;

4 to 11-membered bicycloalkyl, unsubstituted or substituted with one, two, three, four, or more substituents independently from one another selected from F, $CH_3$, $OCH_3$, CN, $CHF_2$ and $CF_3$;

5 to 11-membered spiroalkyl, unsubstituted or substituted with one, two, three, four, or more substituents independently from one another selected from F, $CH_3$, $OCH_3$, CN, $CHF_2$ and $CF_3$; or O—$C_{1-6}$-alkyl, unsubstituted or substituted with one, two, three, four, or more F.

14. The compound according to claim 13, wherein R4 represents $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, or $CH(CH_3)_2$, or cyclopropyl, methyl cyclopropyl, difluoromethyl cyclopropyl, trifluoromethyl cyclopropyl, cyano cyclopropyl, methoxy cyclopropyl, fluoro cyclopropyl, difluoro cyclopropyl, trifluoro cyclopropyl, cyclobutyl, methyl cyclobutyl, difluoromethyl cyclobutyl, trifluoromethyl cyclobutyl, cyano cyclobutyl, methoxy cyclobutyl, fluoro cyclobutyl, difluoro cyclobutyl, trifluoro cyclobutyl, cyclopentyl, methyl cyclopentyl, difluoromethyl cyclopentyl, trifluoromethyl cyclopentyl, cyano cyclopentyl, methoxy cyclopentyl, fluoro cyclopentyl, difluoro cyclopentyl, trifluoro cyclopentyl, cyclohexyl, methyl cyclohexyl, difluoromethyl cyclohexyl, trifluoromethyl cyclohexyl, cyano cyclohexyl, methoxy cyclohexyl, fluoro cyclohexyl, difluoro cyclohexyl, or trifluoro cyclohexyl; or bicyclo[1.1.1]pentyl; or spiro[2.2]pentyl or spiro[2.3]hexyl; or O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, or O—$CH(CH_3)_2$.

15. The compound according to claim 14, wherein R4 represents $CF_2CH_3$; or cyclopropyl, methyl cyclopropyl, difluoromethyl cyclopropyl, trifluoromethyl cyclopropyl, cyano cyclopropyl, methoxy cyclopropyl, fluoro cyclopropyl, difluoro cyclopropyl, trifluoro cyclopropyl, cyclobutyl, difluoro cyclobutyl, cyclopentyl, or difluoro cyclopentyl; or

O—$CHF_2$.

16. The compound according to claim 1, wherein R5 represents $C_{1-6}$-alkyl or Cl.

17. The compound according to claim 16, wherein R5 represents $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, or Cl.

18. The compound according to claim 17, wherein R5 represents $CF_3$, $CHF_2$, $CH_3$, or Cl.

19. The compound according to claim 1, which is selected from the group consisting of:

1 3-cyclopropyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide;

3 1-((3,3-difluorocyclobutyl)methyl)-3-(1,1-difluoroethyl)-N-(2-(S-methylsulfonimidoyl)pyridin-4-yl)-4-(trifluoromethyl)-1H-pyrazole-5-carboxamide;

4 1-((3,3-difluorocyclopentyl)methyl)-3-(1,1-difluoroethyl)-4-methyl-N-(2-(S-methylsulfonimidoyl)pyridin-4-yl)-1H-pyrazole-5-carboxamide;

5 1-((3,3-difluoro-1-methylcyclobutyl)methyl)-3-(1,1-difluoroethyl)-4-methyl-N-(2-(S-methylsulfonimidoyl)pyridin-4-yl)-1H-pyrazole-5-carboxamide;

7 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide;

9 1-((4,4-difluorocyclohexyl)methyl)-3-(1,1-difluoroethyl)-4-methyl-N-(2-(S-methylsulfonimidoyl)pyridin-4-yl)-1H-pyrazole-5-carboxamide;

11 1-((4,4-difluoro-1-methylcyclohexyl)methyl)-3-(1,1-difluoroethyl)-4-methyl-N-(2-(S-methylsulfonimidoyl)pyridin-4-yl)-1H-pyrazole-5-carboxamide;

13 3-(1,1-difluoroethyl)-4-methyl-N-(2-(S-methylsulfonimidoyl)pyridin-4-yl)-1-((2-(trifluoromethyl)cyclobutyl)methyl)-1H-pyrazole-5-carboxamide;

15 3-(1,1-difluoroethyl)-4-methyl-N-(2-(S-methylsulfonimidoyl)pyridin-4-yl)-1-((3-(trifluoromethyl)bicyclo[1.1.1]pentan-1-yl)methyl)-1H-pyrazole-5-carboxamide;

17 3-cyclopropyl-1-((3,3-difluorocyclopentyl)methyl)-N-(2-(S-methylsulfonimidoyl)pyridin-4-yl)-4-(trifluoromethyl)-1H-pyrazole-5-carboxamide;

21 3-cyclopropyl-1-((2-fluorospiro[3.3]heptan-2-yl)methyl)-N-(2-(S-methylsulfonimidoyl)pyridin-4-yl)-4-(trifluoromethyl)-1H-pyrazole-5-carboxamide;

23 3-cyclopropyl-N-(2-(S-methylsulfonimidoyl)pyridin-4-yl)-4-(trifluoromethyl)-1-((3-(trifluoromethyl)bicyclo[1.1.1]pentan-1-yl)methyl)-1H-pyrazole-5-carboxamide;

25 3-cyclopropyl-1-((3-fluorobicyclo[1.1.1]pentan-1-yl)methyl)-N-(2-(S-methylsulfonimidoyl)pyridin-4-yl)-4-(trifluoromethyl)-1H-pyrazole-5-carboxamide;

27 3-cyclopropyl-1-((6,6-difluorospiro[3.3]heptan-2-yl)methyl)-N-(2-(S-methylsulfonimidoyl)pyridin-4-yl)-4-(trifluoromethyl)-1H-pyrazole-5-carboxamide;

29 3-cyclopropyl-1-((3,3-difluoro-1-methylcyclopentyl)methyl)-N-(2-(S-methylsulfonimidoyl)pyridin-4-yl)-4-(trifluoromethyl)-1H-pyrazole-5-carboxamide;

31 3-(1,1-difluoroethyl)-4-methyl-N-(2-(S-methylsulfonimidoyl)pyridin-4-yl)-1-((3-(trifluoromethyl)cyclobutyl)methyl)-1H-pyrazole-5-carboxamide;

33 1-((3,3-difluorocyclopentyl)methyl)-3-(difluoromethoxy)-N-(2-(S-methylsulfonimidoyl)pyridin-4-yl)-4-(trifluoromethyl)-1H-pyrazole-5-carboxamide;

34 1-((3,3-difluoro-1-methylcyclobutyl)methyl)-3-(1,1-difluoroethyl)-N-(2-(N, S-dimethylsulfonimidoyl)pyridin-4-yl)-4-methyl-1H-pyrazole-5-carboxamide;

36 3-cyclopropyl-1-((3,3-difluorocyclopentyl)methyl)-N-(2-(N,S-dimethylsulfonimidoyl)pyridin-4-yl)-4-(trifluoromethyl)-1H-pyrazole-5-carboxamide;

44 1-((4,4-difluoro-1,2-dimethylcyclopentyl)methyl)-3-(1,1-difluoroethyl)-4-methyl-N-(2-(S-methylsulfonimidoyl)pyridin-4-yl)-1H-pyrazole-5-carboxamide;

45 3-cyclopropyl-1-((3,3-difluoro-1-methylcyclobutyl)methyl)-N-(3-(S-methylsulfonimidoyl)phenyl)-4-(trifluoromethyl)-1H-pyrazole-5-carboxamide;

46 3-cyclopropyl-1-((3,3-difluoro-1-methylcyclobutyl)methyl)-N-(5-(S-methylsulfonimidoyl)pyridin-3-yl)-4-(trifluoromethyl)-1H-pyrazole-5-carboxamide;

47 3-cyclopropyl-1-((3,3-difluoro-1-methylcyclobutyl)methyl)-N-(6-(S-methylsulfonimidoyl)pyridazin-4-yl)-4-(trifluoromethyl)-1H-pyrazole-5-carboxamide;

48 3-cyclopropyl-1-((3,3-difluoro-1-methylcyclobutyl)methyl)-N-(2-(ethylsulfonimidoyl)pyridin-4-yl)-4-(trifluoromethyl)-1H-pyrazole-5-carboxamide;

49 N-(2-(cyclopropanesulfonimidoyl)pyridin-4-yl)-3-cyclopropyl-1-((3,3-difluoro-1-methylcyclobutyl)methyl)-4-(trifluoromethyl)-1H-pyrazole-5-carboxamide;

50 3-cyclopropyl-1-((3,3-difluoro-1-methylcyclobutyl)methyl)-N-(2-methyl-6-(S-methylsulfonimidoyl)pyridin-4-yl)-4-(trifluoromethyl)-1H-pyrazole-5-carboxamide;

51 3-cyclopropyl-1-((3,3-difluoro-1-methylcyclobutyl)methyl)-N-(2-(1-oxido-4,5-dihydro-3H-11$\lambda^6$-isothiazol-1-yl)pyridin-4-yl)-4-(trifluoromethyl)-1H-pyrazole-5-carboxamide;

52 3-cyclopropyl-1-((3,3-difluoro-1-methylcyclobutyl)methyl)-N-(3-sulfamidimidoylphenyl)-4-(trifluoromethyl)-1H-pyrazole-5-carboxamide;

53 3-cyclopropyl-1-((3,3-difluoro-1-methylcyclobutyl)methyl)-N-(3-(methyl(phenyl)-26-sulfanediimine))-4-(trifluoromethyl)-1H-pyrazole-5-carboxamide;

54 N-(3-(N-acetyl-S-methylsulfonimidoyl)phenyl)-3-cyclopropyl-1-((3,3-difluoro-1-methylcyclobutyl)methyl)-4-(trifluoromethyl)-1H-pyrazole-5-carboxamide;

55 3-cyclopropyl-1-((3,3-difluoro-1-methylcyclobutyl)methyl)-N-(3-(S-methyl-N-(methylglycyl)sulfonimidoyl)phenyl)-4-(trifluoromethyl)-1H-pyrazole-5-carboxamide;

56 3-cyclobutyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide;

57 1-((3,3-difluoro-1-methylcyclobutyl)methyl)-3-(3,3-difluorocyclobutyl)-N-(2-(S-methylsulfonimidoyl)pyridin-4-yl)-4-(trifluoromethyl)-1H-pyrazole-5-carboxamide;

58 3-(bicyclo[1.1.1]pentan-1-yl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide;

59 3-cyclopentyl-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide;

60 1-((3,3-difluoro-1-methylcyclobutyl)methyl)-3-(3,3-difluorocyclopentyl)-N-(2-(S-methylsulfonimidoyl)pyridin-4-yl)-4-(trifluoromethyl)-1H-pyrazole-5-carboxamide;

61 1-((3,3-difluoro-1-methylcyclobutyl)methyl)-N-(2-(S-methylsulfonimidoyl)pyridin-4-yl)-3-(spiro[2.3]hexan-5-yl)-4-(trifluoromethyl)-1H-pyrazole-5-carboxamide;

62 1-((3,3-difluoro-1-methylcyclobutyl)methyl)-3-(2-fluorocyclopropyl)-N-(2-(S-methylsulfonimidoyl)pyridin-4-yl)-4-(trifluoromethyl)-1H-pyrazole-5-carboxamide;

63 1-((3,3-difluoro-1-methylcyclobutyl)methyl)-3-(2,2-difluorocyclopropyl)-N-(2-(S-methylsulfonimidoyl)pyridin-4-yl)-4-(trifluoromethyl)-1H-pyrazole-5-carboxamide;

64 1-((3,3-difluoro-1-methylcyclobutyl)methyl)-N-(2-(S-methylsulfonimidoyl)pyridin-4-yl)-3-(spiro[2.2]pentan-1-yl)-4-(trifluoromethyl)-1H-pyrazole-5-carboxamide;

65 1-((3,3-difluoro-1-methylcyclobutyl)methyl)-3-(2-methylcyclopropyl)-N-(2-(S-methylsulfonimidoyl)pyridin-4-yl)-4-(trifluoromethyl)-1H-pyrazole-5-carboxamide;

66 1-((3,3-difluoro-1-methylcyclobutyl)methyl)-3-(2-(difluoromethyl)cyclopropyl)-N-(2-(S-methylsulfonimidoyl)pyridin-4-yl)-4-(trifluoromethyl)-1H-pyrazole-5-carboxamide;

67 1-((3,3-difluoro-1-methylcyclobutyl)methyl)-N-(2-(S-methylsulfonimidoyl)pyridin-4-yl)-4-(trifluoromethyl)-3-(2-(trifluoromethyl)cyclopropyl)-1H-pyrazole-5-carboxamide;

68 3-(1-cyanocyclopropyl)-1-((3,3-difluoro-1-methylcyclobutyl)methyl)-N-(2-(S-methylsulfonimidoyl)pyridin-4-yl)-4-(trifluoromethyl)-1H-pyrazole-5-carboxamide;

69 1-((3,3-difluoro-1-methylcyclobutyl)methyl)-3-(1-methylcyclopropyl)-N-(2-(S-methylsulfonimidoyl)pyridin-4-yl)-4-(trifluoromethyl)-1H-pyrazole-5-carboxamide;

70 1-((3,3-difluoro-1-methylcyclobutyl)methyl)-3-(1-fluorocyclopropyl)-N-(2-(S-methylsulfonimidoyl)pyridin-4-yl)-4-(trifluoromethyl)-1H-pyrazole-5-carboxamide;

71 1-((3,3-difluoro-1-methylcyclobutyl)methyl)-3-(1-methoxycyclopropyl)-N-(2-(S-methylsulfonimidoyl)pyridin-4-yl)-4-(trifluoromethyl)-1H-pyrazole-5-carboxamide;

72 1-((3,3-difluoro-1-methylcyclobutyl)methyl)-3-(2,3-difluorocyclopropyl)-N-(2-(S-methylsulfonimidoyl)pyridin-4-yl)-4-(trifluoromethyl)-1H-pyrazole-5-carboxamide;

73 1-((3,3-difluoro-1-methylcyclobutyl)methyl)-N-(2-(S-methylsulfonimidoyl)pyridin-4-yl)-3-(1,2,2-trifluorocyclopropyl)-4-(trifluoromethyl)-1H-pyrazole-5-carboxamide;

74 1-((3,3-difluoro-1-methylcyclobutyl)methyl)-3-(1,2-difluorocyclopropyl)-N-(2-(S-methylsulfonimidoyl)pyridin-4-yl)-4-(trifluoromethyl)-1H-pyrazole-5-carboxamide;

75 1-((3,3-difluoro-1-methylcyclobutyl)methyl)-3-(1,1-difluoroethyl)-N-(2-(S-methylsulfonimidoyl)pyridin-4-yl)-4-(trifluoromethyl)-1H-pyrazole-5-carboxamide;

76 4-chloro-1-((3,3-difluoro-1-methylcyclobutyl)methyl)-3-(1,1-difluoroethyl)-N-(2-(S-methylsulfonimidoyl)pyridin-4-yl)-1H-pyrazole-5-carboxamide;

77 3-cyclopropyl-1-((3,3-difluoro-1-methylcyclobutyl)methyl)-4-(difluoromethyl)-N-(2-(S-methylsulfonimidoyl)pyridin-4-yl)-1H-pyrazole-5-carboxamide;

78 3-cyclopropyl-N-(2-(S-methylsulfonimidoyl)pyridin-4-yl)-1-(spiro[2.2]pentan-1-ylmethyl)-4-(trifluoromethyl)-1H-pyrazole-5-carboxamide;

79 3-cyclopropyl-1-((2,2-difluorospiro[2.2]pentan-1-yl)methyl)-N-(2-(S-methylsulfonimidoyl)pyridin-4-yl)-4-(trifluoromethyl)-1H-pyrazole-5-carboxamide;

80 3-cyclopropyl-1-(dispiro[2.0.2$^{4}$.1$^{3}$]heptan-7-ylmethyl)-N-(2-(S-methylsulfonimidoyl)pyridin-4-yl)-4-(trifluoromethyl)-1H-pyrazole-5-carboxamide;

81 3-cyclopropyl-1-((1,2-dimethylcyclopropyl)methyl)-N-(2-(S-methylsulfonimidoyl)pyridin-4-yl)-4-(trifluoromethyl)-1H-pyrazole-5-carboxamide;

82 3-cyclopropyl-1-((1-methyl-2-(trifluoromethyl)cyclopropyl)methyl)-N-(2-(S-methylsulfonimidoyl)pyridin-4-yl)-4-(trifluoromethyl)-1H-pyrazole-5-carboxamide;

83 1-(bicyclo[2.1.0]pentan-1-ylmethyl)-3-cyclopropyl-N-(2-(S-methylsulfonimidoyl)pyridin-4-yl)-4-(trifluoromethyl)-1H-pyrazole-5-carboxamide;

84 3-cyclopropyl-N-(2-(S-methylsulfonimidoyl)pyridin-4-yl)-1-(spiro[2.3]hexan-5-ylmethyl)-4-(trifluoromethyl)-1H-pyrazole-5-carboxamide;

85 3-cyclopropyl-1-((5-methylspiro[2.3]hexan-5-yl)methyl)-N-(2-(S-methylsulfonimidoyl)pyridin-4-yl)-4-(trifluoromethyl)-1H-pyrazole-5-carboxamide;

86 3-cyclopropyl-1-((1-methyl-3-(trifluoromethyl)cyclobutyl)methyl)-N-(2-(S-methylsulfonimidoyl)pyridin-4-yl)-4-(trifluoromethyl)-1H-pyrazole-5-carboxamide;

87 3-cyclopropyl-1-((1-fluorospiro[2.3]hexan-5-yl)methyl)-N-(2-(S-methylsulfonimidoyl)pyridin-4-yl)-4-(trifluoromethyl)-1H-pyrazole-5-carboxamide;

88 3-cyclopropyl-N-(2-(S-methylsulfonimidoyl)pyridin-4-yl)-4-(trifluoromethyl)-1-((3-(trifluoromethyl)cyclobutyl)methyl)-1H-pyrazole-5-carboxamide;

89 3-cyclopropyl-1-((3,3-difluorocyclobutyl)methyl)-N-(2-(S-methylsulfonimidoyl)pyridin-4-yl)-4-(trifluoromethyl)-1H-pyrazole-5-carboxamide;

90 3-cyclopropyl-1-((5,5-difluorobicyclo[2.1.0]pentan-2-yl)methyl)-N-(2-(S-methylsulfonimidoyl)pyridin-4-yl)-4-(trifluoromethyl)-1H-pyrazole-5-carboxamide;

91 3-cyclopropyl-N-(2-(S-methylsulfonimidoyl)pyridin-4-yl)-1-(spiro[2.3]hexan-4-ylmethyl)-4-(trifluoromethyl)-1H-pyrazole-5-carboxamide;

92 3-cyclopropyl-1-((6,6-difluoro-4-methylspiro[2.3]hexan-4-yl)methyl)-N-(2-(S-methylsulfonimidoyl)pyridin-4-yl)-4-(trifluoromethyl)-1H-pyrazole-5-carboxamide;

93 3-cyclopropyl-N-(2-(S-methylsulfonimidoyl)pyridin-4-yl)-1-(spiro[3.3]heptan-1-ylmethyl)-4-(trifluoromethyl)-1H-pyrazole-5-carboxamide;

94 3-cyclopropyl-1-((2-methylbicyclo[2.2.0]hexan-2-yl)methyl)-N-(2-(S-methylsulfonimidoyl)pyridin-4-yl)-4-(trifluoromethyl)-1H-pyrazole-5-carboxamide;

95 3-cyclopropyl-1-((3,3-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide;

96 3-cyclopropyl-1-((4,4-difluorobicyclo[3.1.0]hexan-1-yl)methyl)-N-(2-(S-methylsulfonimidoyl)pyridin-4-yl)-4-(trifluoromethyl)-1H-pyrazole-5-carboxamide;

97 3-cyclopropyl-1-((5-fluorooctahydropentalen-2-yl)methyl)-N-(2-(S-methylsulfonimidoyl)pyridin-4-yl)-4-(trifluoromethyl)-1H-pyrazole-5-carboxamide;

98 3-cyclopropyl-N-(2-(S-methylsulfonimidoyl)pyridin-4-yl)-4-(trifluoromethyl)-1-((1-(trifluoromethyl)cyclopentyl)methyl)-1H-pyrazole-5-carboxamide;

99 3-cyclopropyl-1-((4,4-difluoro-2-methylcyclopentyl)methyl)-N-(2-(S-methylsulfonimidoyl)pyridin-4-yl)-4-(trifluoromethyl)-1H-pyrazole-5-carboxamide;

100 3-cyclopropyl-1-((4,4-difluoro-2-(trifluoromethyl)cyclopentyl)methyl)-N-(2-(S-methylsulfonimidoyl)pyridin-4-yl)-4-(trifluoromethyl)-1H-pyrazole-5-carboxamide;

101 3-cyclopropyl-1-((3,3-difluoro-5-methylbicyclo[3.1.0]hexan-1-yl)methyl)-N-(2-(S-methylsulfonimidoyl)pyridin-4-yl)-4-(trifluoromethyl)-1H-pyrazole-5-carboxamide;

102 3-cyclopropyl-1-((3,3-difluoro-5-(trifluoromethyl)bicyclo[3.1.0]hexan-1-yl)methyl)-N-(2-(S-methylsulfonimidoyl)pyridin-4-yl)-4-(trifluoromethyl)-1H-pyrazole-5-carboxamide;

103 3-cyclopropyl-1-((2,2-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide;

104 3-cyclopropyl-1-((3,3-difluorobicyclo[2.1.1]hexan-1-yl)methyl)-N-(2-(S-methylsulfonimidoyl)pyridin-4-yl)-4-(trifluoromethyl)-1H-pyrazole-5-carboxamide;

105 3-cyclopropyl-1-((4-fluorobicyclo[2.1.1]hexan-1-yl)methyl)-N-(2-(S-methylsulfonimidoyl)pyridin-4-yl)-4-(trifluoromethyl)-1H-pyrazole-5-carboxamide;

106 3-cyclopropyl-1-((4-fluorobicyclo[2.2.1]heptan-1-yl)methyl)-N-(2-(S-methylsulfonimidoyl)pyridin-4-yl)-4-(trifluoromethyl)-1H-pyrazole-5-carboxamide;

107 3-cyclopropyl-1-((4,4-difluorobicyclo[4.1.0]heptan-1-yl)methyl)-N-(2-(S-methylsulfonimidoyl)pyridin-4-yl)-4-(trifluoromethyl)-1H-pyrazole-5-carboxamide;

108 3-(bicyclo[1.1.1]pentan-1-yl)-1-((3,3-difluoro-1-methylcyclobutyl)methyl)-N-(3-(S-methylsulfonimidoyl)phenyl)-4-(trifluoromethyl)-1H-pyrazole-5-carboxamide;

109 1-((3,3-difluoro-1-methylcyclobutyl)methyl)-3-(1-fluorocyclopropyl)-N-(3-(S-methylsulfonimidoyl)phenyl)-4-(trifluoromethyl)-1H-pyrazole-5-carboxamide;

110 1-((3,3-difluoro-1-methylcyclobutyl)methyl)-3-(3-fluorobicyclo[1.1.1]pentan-1-yl)-N-(2-(S-methylsulfonimidoyl)pyridin-4-yl)-4-(trifluoromethyl)-1H-pyrazole-5-carboxamide;

111 1-((3,3-difluoro-1-methylcyclobutyl)methyl)-3-(3-fluorobicyclo[1.1.1]pentan-1-yl)-N-(3-(S-methylsulfonimidoyl)phenyl)-4-(trifluoromethyl)-1H-pyrazole-5-carboxamide;

112 1-((3,3-difluoro-1-methylcyclobutyl)methyl)-4-(difluoromethyl)-3-(3-fluorobicyclo[1.1.1]pentan-1-yl)-N-(2-(S-methylsulfonimidoyl)pyridin-4-yl)-1H-pyrazole-5-carboxamide;

113 1-((3,3-difluoro-1-methylcyclobutyl)methyl)-4-(difluoromethyl)-3-(3-fluorobicyclo[1.1.1]pentan-1-yl)-N-(3-(S-methylsulfonimidoyl)phenyl)-1H-pyrazole-5-carboxamide;

114 1-((3,3-difluoro-1-methylcyclobutyl)methyl)-3-(2,2-difluorobicyclo[1.1.1]pentan-1-yl)-N-(2-(S-methylsulfonimidoyl)pyridin-4-yl)-4-(trifluoromethyl)-1H-pyrazole-5-carboxamide;

115 1-((3,3-difluoro-1-methylcyclobutyl)methyl)-3-(2,2-difluorobicyclo[1.1.1]pentan-1-yl)-N-(3-(S-methylsulfonimidoyl)phenyl)-4-(trifluoromethyl)-1H-pyrazole-5-carboxamide;

116 1-((3,3-difluoro-1-methylcyclobutyl)methyl)-3-(2,2-difluorobicyclo[1.1.1]pentan-1-yl)-4-(difluoromethyl)-N-(2-(S-methylsulfonimidoyl)pyridin-4-yl)-1H-pyrazole-5-carboxamide;

117 1-((3,3-difluoro-1-methylcyclobutyl)methyl)-3-(2,2-difluorobicyclo[1.1.1]pentan-1-yl)-4-(difluoromethyl)-N-(3-(S-methylsulfonimidoyl)phenyl)-1H-pyrazole-5-carboxamide;

118 1-((3,3-difluoro-1-methylcyclobutyl)methyl)-N-(2-(S-methylsulfonimidoyl)pyridin-4-yl)-3-(2,2,3-trifluorobicyclo[1.1.1]pentan-1-yl)-4-(trifluoromethyl)-1H-pyrazole-5-carboxamide;

119 1-((3,3-difluoro-1-methylcyclobutyl)methyl)-N-(3-(S-methylsulfonimidoyl)phenyl)-3-(2,2,3-trifluorobicyclo[1.1.1]pentan-1-yl)-4-(trifluoromethyl)-1H-pyrazole-5-carboxamide;

120 1-((3,3-difluoro-1-methylcyclobutyl)methyl)-4-(difluoromethyl)-N-(2-(S-methylsulfonimidoyl)pyridin-4-yl)-3-(2,2,3-trifluorobicyclo[1.1.1]pentan-1-yl)-1H-pyrazole-5-carboxamide;

121 1-((3,3-difluoro-1-methylcyclobutyl)methyl)-4-(difluoromethyl)-N-(3-(S-methylsulfonimidoyl)phenyl)-3-(2,2,3-trifluorobicyclo[1.1.1]pentan-1-yl)-1H-pyrazole-5-carboxamide;

122 1-((3,3-difluoro-1-methylcyclobutyl)methyl)-3-(3-methoxybicyclo[1.1.1]pentan-1-yl)-N-(2-(S-methylsulfonimidoyl)pyridin-4-yl)-4-(trifluoromethyl)-1H-pyrazole-5-carboxamide;

123 1-((3,3-difluoro-1-methylcyclobutyl)methyl)-3-(3-methoxybicyclo[1.1.1]pentan-1-yl)-N-(3-(S-methylsulfonimidoyl)phenyl)-4-(trifluoromethyl)-1H-pyrazole-5-carboxamide;

124 1-((3,3-difluoro-1-methylcyclobutyl)methyl)-4-(difluoromethyl)-3-(3-methoxybicyclo[1.1.1]pentan-1-yl)-N-(2-(S-methylsulfonimidoyl)pyridin-4-yl)-1H-pyrazole-5-carboxamide;

125 1-((3,3-difluoro-1-methylcyclobutyl)methyl)-4-(difluoromethyl)-3-(3-methoxybicyclo[1.1.1]pentan-1-yl)-N-(3-(S-methylsulfonimidoyl)phenyl)-1H-pyrazole-5-carboxamide;

126 1-((3,3-difluoro-1-methylcyclobutyl)methyl)-N-(4-fluoro-3-(S-methylsulfonimidoyl)phenyl)-3-(1-fluorocyclopropyl)-4-(trifluoromethyl)-1H-pyrazole-5-carboxamide;

127 1-((3,3-difluoro-1-methylcyclobutyl)methyl)-N-(3-fluoro-5-(S-methylsulfonimidoyl)phenyl)-3-(1-fluorocyclopropyl)-4-(trifluoromethyl)-1H-pyrazole-5-carboxamide;

128 1-((3,3-difluoro-1-methylcyclobutyl)methyl)-N-(2-fluoro-5-(S-methylsulfonimidoyl)phenyl)-3-(1-fluorocyclopropyl)-4-(trifluoromethyl)-1H-pyrazole-5-carboxamide;

129 1-((3,3-difluoro-1-methylcyclobutyl)methyl)-N-(2-fluoro-3-(S-methylsulfonimidoyl)phenyl)-3-(1-fluorocyclopropyl)-4-(trifluoromethyl)-1H-pyrazole-5-carboxamide;

130 1-((3,3-difluoro-1-methylcyclobutyl)methyl)-N-(3-(S-(difluoromethyl)sulfonimidoyl)phenyl)-3-(1-fluorocyclopropyl)-4-(trifluoromethyl)-1H-pyrazole-5-carboxamide;

131 1-((3,3-difluoro-1-methylcyclobutyl)methyl)-3-(1-fluorocyclopropyl)-4-(trifluoromethyl)-N-(3-(S-(trifluoromethyl)sulfonimidoyl)phenyl)-1H-pyrazole-5-carboxamide;

132 3-cyclopropyl-1-((3,3-difluoro-1-methylcyclobutyl)methyl)-N-(4-fluoro-3-(S-methylsulfonimidoyl)phenyl)-4-(trifluoromethyl)-1H-pyrazole-5-carboxamide;

133 1-((3,3-difluoro-1-methylcyclobutyl)methyl)-4-(difluoromethyl)-N-(4-fluoro-3-(S-methylsulfonimidoyl)phenyl)-3-(1-fluorocyclopropyl)-1H-pyrazole-5-carboxamide;

134 3-(1-fluorocyclopropyl)-N-(3-(S-methylsulfonimidoyl)phenyl)-4-(trifluoromethyl)-1-((2-(trifluoromethyl)cyclopropyl)methyl)-1H-pyrazole-5-carboxamide;

135 1-((3,3-difluoro-1-methylcyclobutyl)methyl)-4-(difluoromethyl)-3-(1-fluorocyclopropyl)-N-(3-(S-methylsulfonimidoyl)phenyl)-1H-pyrazole-5-carboxamide;

136 3-cyclopropyl-1-((2,2-difluorospiro[2.3]hexan-1-yl)methyl)-N-(2-(S-methylsulfonimidoyl)pyridin-4-yl)-4-(trifluoromethyl)-1H-pyrazole-5-carboxamide;

137 3-(bicyclo[1.1.1]pentan-1-yl)-1-((3,3-difluoro-1-methylcyclobutyl)methyl)-4-(difluoromethyl)-N-(2-(S-methylsulfonimidoyl)pyridin-4-yl)-1H-pyrazole-5-carboxamide;

138 1-((3,3-difluoro-1-methylcyclobutyl)methyl)-4-(difluoromethyl)-N-(4-fluoro-3-(S-methylsulfonimidoyl)phenyl)-3-(3-fluorobicyclo[1.1.1]pentan-1-yl)-1H-pyrazole-5-carboxamide;

139 3-(bicyclo[1.1.1]pentan-1-yl)-1-((2-(difluoromethyl)cyclopropyl)methyl)-N-(3-(S-methylsulfonimidoyl)phenyl)-4-(trifluoromethyl)-1H-pyrazole-5-carboxamide;

141 1-((3,3-difluoro-1-methylcyclobutyl)methyl)-N-(4-fluoro-3-(S-methylsulfonimidoyl)phenyl)-3-(3-fluoro-bicyclo[1.1.1]pentan-1-yl)-4-(trifluoromethyl)-1H-pyrazole-5-carboxamide;

143 3-(tert-butyl)-1-((3,3-difluoro-1-methylcyclobutyl) methyl)-N-(2-(S-methylsulfonimidoyl)pyridin-4-yl)-4-(trifluoromethyl)-1H-pyrazole-5-carboxamide;

144 1-((3,3-difluoro-1-methylcyclobutyl)methyl)-N-(2-(S-methylsulfonimidoyl)pyridin-4-yl)-4-(trifluoromethyl)-3-(1-(trifluoromethyl)cyclopropyl)-1H-pyrazole-5-carboxamide;

145 1-((3,3-difluoro-1-methylcyclobutyl)methyl)-3-(1-(difluoromethyl)cyclopropyl)-N-(2-(S-methylsulfonimidoyl)pyridin-4-yl)-4-(trifluoromethyl)-1H-pyrazole-5-carboxamide;

146 3-(bicyclo[1.1.1]pentan-1-yl)-1-((2-(difluoromethyl) cyclopropyl)methyl)-N-(2-(S-methylsulfonimidoyl) pyridin-4-yl)-4-(trifluoromethyl)-1H-pyrazole-5-carboxamide;

147 3-(bicyclo[1.1.1]pentan-1-yl)-N-(2-(S-methylsulfonimidoyl)pyridin-4-yl)-4-(trifluoromethyl)-1-(((trans)-2-(trifluoromethyl)cyclopropyl)methyl)-1H-pyrazole-5-carboxamide, 148 1-((3,3-difluoro-1-methylcyclobutyl)methyl)-3-(2-fluoropropan-2-yl)-N-(2-(S-methylsulfonimidoyl)pyridin-4-yl)-4-(trifluoromethyl)-1H-pyrazole-5-carboxamide;

150 1-((3,3-difluoro-1-methylcyclobutyl)methyl)-3-(1-fluorocyclopropyl)-N-(3-(S-methyl-N-(oxetane-3-carbonyl)sulfonimidoyl)phenyl)-4-(trifluoromethyl)-1H-pyrazole-5-carboxamide;

151 1-((3,3-difluoro-1-methylcyclobutyl)methyl)-3-(1-fluorocyclopropyl)-N-(3-(N-(2-hydroxyacetyl)-S-methylsulfonimidoyl)phenyl)-4-(trifluoromethyl)-1H-pyrazole-5-carboxamide; and 152 3-cyclopropyl-1-((3,3-difluoro-1-methylcyclobutyl) methyl)-N-(2-(N-(2,3-dihydroxypropyl)-S-methylsulfonimidoyl)pyridin-4-yl)-4-(trifluoromethyl)-1H-pyrazole-5-carboxamide;

in the form of a free compound or a physiologically acceptable salt thereof.

20. A pharmaceutical composition comprising an amount effective to treat pain of at least one compound according to claim 1.

21. A pharmaceutical dosage form comprising at least one compound according to claim 1.

22. A method of treating pain in a subject in need thereof comprising administering to the subject an effective amount therefor of a compound according to claim 1.

23. A compound which is selected from the group consisting of:

140 1-((2-acetyl-2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide;

142 N-(2-N-cyano-S-methylsulfonimidoyl)pyridin-4-yl)-3-cyclopropyl-1-((3,3-difluoro-1-methylcyclobutyl) methyl)-4-(trifluoromethyl)-1H-pyrazole-5-carboxamide; and 153 1-((2-azaspiro[3.3]heptan-5-yl)methyl)-3-cyclopropyl-N-(2-(S-methylsulfonimidoyl)pyridin-4-yl)-4-(trifluoromethyl)-1H-pyrazole-5-carboxamide;

in the form of a free compound or a physiologically acceptable salt thereof.

* * * * *